US011266700B2

(12) United States Patent
Goodman et al.

(10) Patent No.: US 11,266,700 B2
(45) Date of Patent: Mar. 8, 2022

(54) **COMPOSITIONS AND METHODS FOR TREATING IMMUNE DISORDERS USING IMMUNE MODULATING *LACTOCOCCUS* BACTERIA STRAINS**

(71) Applicant: Evelo Biosciences, Inc., Cambridge, MA (US)

(72) Inventors: Brian Goodman, Jamaica Plain, MA (US); Holly Ponichtera, Cambridge, MA (US); Andrea Itano, Arlington, MA (US); Mark Bodmer, Boston, MA (US); Taylor A. Cormack, Dedham, MA (US); Maria Sizova, Roslindale, MA (US); Carolina Baez-Giangreco, Boston, MA (US); Duncan McHale, Kent (GB); Kritika Ramani, Cambridge, MA (US)

(73) Assignee: Evelo Biosciences, Inc., Cambridge, MA (US)

( * ) Notice: Subject to any disclaimer, the term of this patent is extended or adjusted under 35 U.S.C. 154(b) by 246 days.

(21) Appl. No.: 16/192,172

(22) Filed: Nov. 15, 2018

(65) Prior Publication Data

US 2019/0231829 A1 Aug. 1, 2019

Related U.S. Application Data

(60) Provisional application No. 62/721,941, filed on Aug. 23, 2018, provisional application No. 62/661,459, filed on Apr. 23, 2018, provisional application No. 62/660,693, filed on Apr. 20, 2018, provisional application No. 62/586,604, filed on Nov. 15, 2017.

(51) Int. Cl.

| | |
|---|---|
| ***A61K 35/744*** | (2015.01) |
| ***A61K 45/00*** | (2006.01) |
| ***A61K 35/00*** | (2006.01) |
| ***A61P 29/00*** | (2006.01) |
| ***A61P 17/06*** | (2006.01) |
| ***A61P 37/06*** | (2006.01) |
| ***C12N 1/20*** | (2006.01) |
| ***C12R 1/225*** | (2006.01) |

(52) U.S. Cl.

CPC ............ *A61K 35/744* (2013.01); *A61P 17/06* (2018.01); *A61P 29/00* (2018.01); *A61P 37/06* (2018.01); *C12N 1/20* (2013.01); *C12N 1/205* (2021.05); *A61K 45/05* (2013.01); *A61K 2035/115* (2013.01); *C12R 2001/225* (2021.05)

(58) Field of Classification Search

None

See application file for complete search history.

(56) References Cited

U.S. PATENT DOCUMENTS

| | | | | |
|---|---|---|---|---|
| 2003/0147857 A1* | 8/2003 | Monte | A61K 35/747 424/93.4 |
| 2015/0017208 A1 | 1/2015 | Tsai et al. | |

FOREIGN PATENT DOCUMENTS

| | | | |
|---|---|---|---|
| JP | 2015/145356 A | 8/2015 | |
| WO | WO-2016166104 A1 * | 10/2016 | A61K 38/19 |
| WO | WO-2019/006534 A1 | 1/2019 | |
| WO | WO-2019/099682 A1 | 5/2019 | |

OTHER PUBLICATIONS

Kimoto-Nira, H. et al. 2012. Oral intake of heat-killed cells of Lactococcus lactis strain H61 promotes skin health in women. Journal of Nutritional Science 1(18): 1-7. specif, pp. 1,2, 5, 6.*

Ayala-Fontanez, N. et al. Feb. 2016. Current knowledge on psoriasis and autoimmune diseases. Psoriasis: Targets and Therapy 6: 7-32. specif, pp. 7, 16.*

Lee, Y. et al. 2012. Changes in the transepidermal water loss and skin hydration according to expression of aquaporin-3 in psoriasis. Annals of Dermatology 24(2): 168-174. specif, p. 172.*

Muzes, G. et al. 2012. Changes of cytokine profile in inflammatory bowel diseases. World Journal of Gastroenterology 18(41): 5848-5861. specif. p. 5850.*

Miller, B.J. et al. 2011. Meta-analysis of cytokine alterations in schizophrenia: clinical status and antipsychotic effects. Biological Psychiatry 70: 663-671. specif. p. 663.*

Ozaki, A. et al. 2005. The control of allergic conjunctivitis by suppressor cytokine signaling (SOCS)3 and SOCS5 in murine model. Journal of Immunology 175: 5489-5497. specif. p. 5489.*

Gotoh et al., "Effect of orally administered exopolysaccharides produced by *Lactococcus lactis* subsp. *cremoris* FC on a mouse model of dermatitis induced by repeated exposure to 2,4,6-trinitro-1-chlorobenzene," Journal of Functional Foods, 35:43-50 (2017).

International Search Report and Written Opinion for International Application No. PCT/US2018/061297 dated Apr. 18, 2019, 21 pages.

Mei et al., "Immunomodulatory activity of *Lactococcus lactis* A17 from Taiwan fermented cabbage in OVA-sensitized BALB/c mice," Evidence-Based Complementary and Alternative Medicine, 2013:287803 (2012), 12 pages.

Sugimura et al., "Immunomodulatory effect of *Lactococcus lactis* JCM5805 on human plasmacytoid dendritic cells," Clinical Immunology, 149(3):509-518 (2013).

Yang et al., "A17, the First Sequenced Strain of *Lactococcus lactis* subsp. *cremoris* with Potential Immunomodulatory Functions," Genome Announcements, 3(1):1 (2015).

(Continued)

*Primary Examiner* — Renee Claytor
*Assistant Examiner* — Sharon M. Papciak
(74) *Attorney, Agent, or Firm* — Foley Hoag LLP; Brendan T. Jones; Mohanad Mossalam

(57) ABSTRACT

Provided herein are methods and compositions related to immune modulating *Lactococcus* strains useful as therapeutic agents. In certain embodiments, provided herein are methods of treating an immune disorder in a subject comprising administering to the subject a bacterial composition comprising *Lactococcus lactis cremoris* Strain A (ATCC Deposit Number PTA-125368).

13 Claims, 12 Drawing Sheets

Specification includes a Sequence Listing.

(56) References Cited

OTHER PUBLICATIONS

International Search Report and Written Opinion for International Application No. PCT/US2018/061297 dated May 16, 2019.

Kimoto-Nira et al., "Anti-ageing effect of a lactococcal strain: Analysis using senescence-accelerated mice," British Journal of Nutrition, 98: 1178-1186 (2007).

* cited by examiner

COMPOSITIONS AND METHODS FOR TREATING IMMUNE DISORDERS USING IMMUNE MODULATING *LACTOCOCCUS* BACTERIA STRAINS

RELATED APPLICATIONS

This application claims the benefit of priority to U.S. Provisional Patent Applications having Ser. Nos. 62/586,604, filed Nov. 15, 2017, 62/660,693, filed Apr. 20, 2018, 62/661,459, filed Apr. 23, 2018, and 62/721,941 filed Aug. 23, 2018, the contents of each of which are hereby incorporated herein by reference in their entirety.

SEQUENCE LISTING

The instant application contains a Sequence Listing which has been submitted electronically in ASCII format and is hereby incorporated by reference in its entirety. Said ASCII copy, created on Feb. 6, 2019, is named ETB-01701_SL.txt and is 482,494 bytes in size.

SUMMARY

In certain aspects, provided herein are methods and compositions (e.g., bacterial compositions, pharmaceutical compositions) related to the treatment and/or prevention of disease (e.g., cancer, autoimmune disease, inflammatory disease, metabolic disease), in a subject (e.g., a human subject) comprising administering a bacterial composition comprising *Lactococcus* bacteria and/or a product of such bacteria (e.g., extracellular vesicles (EVs) and/or pharmaceutically active biomasses (PhABs)). In certain aspects, provided herein are methods and compositions related to the treatment and/or prevention of an immune disorder in a subject (e.g., a human subject) comprising administering a bacterial (pharmaceutical) composition comprising immune modulating *Lactococcus* bacteria disclosed herein and/or a product of immune modulating *Lactococcus* bacteria disclosed herein (e.g., extracellular vesicles (EVs) and/or pharmaceutically active biomasses (PhABs)). Also provided herein are methods of making and/or identifying such a bacterium and/or bacterial product. In some embodiments, provided here are bioreactors comprising *Lactococcus* bacteria disclosed herein.

In certain embodiments, provided herein are immune modulating *Lactococcus* bacteria. In some embodiments the immune modulating *Lactococcus* bacteria is an immune modulating strain of *Lactococcus lactis cremoris*. In certain embodiments the immune modulating *Lactococcus* strain is *Lactococcus lactis cremoris* Strain A (ATCC Deposit Number PTA-125368). In some embodiments, the immune modulating bacteria is a strain of *Lactococcus* bacteria (e.g., a strain of *Lactococcus lactis cremoris*) comprising a protein listed in Table 1 and/or a gene encoding a protein listed in Table 1. In some embodiments, the immune modulating bacteria is a strain of *Lactococcus* bacteria (e.g., a strain of *Lactococcus lactis cremoris*) comprising a membrane associated protein listed in Table 2 and/or a gene encoding a membrane associated protein listed in Table 2. In some embodiments, the immune modulating bacteria is a strain of *Lactococcus* bacteria (e.g., a strain of *Lactococcus lactis cremoris*) free or substantially free of a protein listed in Table 3 and/or a gene encoding a protein listed in Table 3. In some embodiments, the immune modulating bacteria is a strain of *Lactococcus* bacteria (e.g., a strain of *Lactococcus lactis cremoris*) free or substantially free of an exopolysaccharide (EPS) synthesis protein listed in Table 4 and/or a gene encoding an EPS synthesis protein listed in Table 4. In some embodiments, the immune modulating bacteria is a strain of *Lactococcus* bacteria (e.g., a strain of *Lactococcus lactis cremoris*) free or substantially free of an EPS synthesized in whole or in part by a protein listed in Table 4. In some embodiments, the immune modulating bacteria is a strain of *Lactococcus* bacteria (e.g., a strain of *Lactococcus lactis cremoris*) free or substantially free of EPS. In some embodiments, the bacterial compositions provided herein comprise an immune modulating *Lactococcus* strain provided herein. In some embodiments, the immune modulating bacteria is a strain of *Lactococcus* bacteria (e.g., a strain of *Lactococcus lactis cremoris*) free or substantially free of a protein listed in Table 5 and/or a gene encoding a protein listed in Table 5. In some embodiments, the immune modulating bacteria is a strain of *Lactococcus* bacteria (e.g., a strain of *Lactococcus lactis cremoris*) comprising a protein listed in Table 6 and/or a gene encoding a protein listed in Table 6.

In some embodiments, provided herein are PhABs made from and/or comprising an immune modulating *Lactococcus* strain provided herein. In some embodiments, the PhABs comprise whole cells, fractions of cells, supernatant from fermentation, fractions of supernatant and/or extracellular vesicles made immune modulating bacteria described herein. In some embodiments, the bacterial compositions provided herein comprise an immune modulating *Lactococcus* strain PhAB provided herein.

In some embodiments, provided herein are EVs produced by and/or generated from and/or isolated from an immune modulating *Lactococcus* strain provided herein. In some embodiments, the bacterial compositions comprise both immune modulating *Lactococcus* strain EVs and whole immune modulating *Lactococcus* strain bacteria (e.g., live bacteria, killed bacteria, attenuated bacteria). In certain embodiments, provided herein are bacterial compositions comprising immune modulating *Lactococcus* strain bacteria (e.g., *Lactococcus lactis cremoris* Strain A) in the absence of immune modulating *Lactococcus* strain EVs. In some embodiments, the pharmaceutical compositions comprise immune modulating *Lactococcus* strain EVs in the absence of immune modulating *Lactococcus* strain bacteria.

In some embodiments, the immune modulating *Lactococcus* strain comprises at least 90%, at least 91%, at least 92%, at least 93%, at least 94%, at least 95%, at least 96%, at least 97%, at least 98%, or at least 99% sequence identity (e.g., at least 99.5% sequence identity, at least 99.6% sequence identity, at least 99.7% sequence identity, at least 99.8% sequence identity, at least 99.9% sequence identity) to the nucleotide sequence (e.g., genomic sequence, 16S sequence, CRISPR sequence) of the *Lactococcus lactis cremoris* Strain A. In some embodiments, the administration of the bacterial composition treats the immune disorder in the subject. In some embodiments, the immune disorder is an autoimmune disease. In some embodiments, the immune disorder is an inflammatory disease. In some embodiments, the immune disorder is an allergy.

In certain embodiments, provided herein are methods of treating a subject who has an immune disorder (e.g., an autoimmune disease, an inflammatory disease, an allergy), comprising administering to the subject a bacterial composition comprising immune modulating *Lactococcus* strain bacteria provided herein (e.g., a killed bacterium, a live bacterium, a pharmaceutically active biomass and/or an attenuated bacterium). In some embodiments, immune modulating *Lactococcus* strain is *Lactococcus lactis cremo-*

*ris* Strain A (ATCC Deposit Number PTA-125368). In some embodiments, immune modulating *Lactococcus* strain is a strain comprising at least 90%, at least 91%, at least 92%, at least 93%, at least 94%, at least 95%, at least 96%, at least 97%, at least 98%, or at least 99% sequence identity (e.g., genomic sequence identity, 16S sequence identity, CRISPR sequence identity) (e.g., at least 99.5% sequence identity, at least 99.6% sequence identity, at least 99.7% sequence identity, at least 99.8% sequence identity, at least 99.9% sequence identity) to the corresponding nucleotide sequence of the *Lactococcus lactis cremoris* Strain A (ATCC Deposit Number PTA-125368). In some embodiments, at least 50%, 60%, 70%, 80%, 85%, 90%, 90%, 91%, 92%, 93%, 94%, 95%, 96%, 97%, 98% or 99% of the bacteria in the bacterial composition are the immune modulating *Lactococcus* strain. In some embodiments, all or substantially all of the bacteria in the bacterial formulation are the immune modulating *Lactococcus* strain. In some embodiments, the bacterial formulation comprises at least $1\times10^5$, $5\times10^5$, $1\times10^6$, $2\times10^6$, $3\times10^6$, $4\times10^6$, $5\times10^6$, $6\times10^6$, $7\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$ or $1\times10^9$ colony forming units of the immune modulating *Lactococcus* strain. In some embodiments, the bacterial composition comprises EVs and/or PhABs (e.g., whole cells, fractions of cells, supernatant from fermentation, fractions of supernatant and/or extracellular vesicles) made from the immune modulating *Lactococcus* strain.

In certain embodiments, provided herein are bacterial compositions comprising an immune modulating *Lactococcus* strain provided herein (e.g., a killed bacterium, a live bacterium, a pharmaceutically active biomass and/or an attenuated bacterium). In some embodiments, immune modulating *Lactococcus* strain is *Lactococcus lactis cremoris* Strain A (ATCC Deposit Number PTA-125368). In some embodiments, immune modulating *Lactococcus* strain is a strain comprising at least 90%, at least 91%, at least 92%, at least 93%, at least 94%, at least 95%, at least 96%, at least 97%, at least 98%, or at least 99% sequence identity (e.g., genomic sequence identity, 16S sequence identity, CRISPR sequence identity) (e.g., at least 99.5% sequence identity, at least 99.6% sequence identity, at least 99.7% sequence identity, at least 99.8% sequence identity, at least 99.9% sequence identity) to the corresponding nucleotide sequence of the *Lactococcus lactis cremoris* Strain A (ATCC Deposit Number PTA-125368). In some embodiments, at least 50%, 60%, 70%, 80%, 85%, 90%, 90%, 91%, 92%, 93%, 94%, 95%, 96%, 97%, 98% or 99% of the bacteria in the bacterial composition are the immune modulating *Lactococcus* strain. In some embodiments, all or substantially all of the bacteria in the bacterial formulation are the immune modulating *Lactococcus* strain. In some embodiments, the bacterial formulation comprises at least $1\times10^5$, $5\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$ or $1\times10^9$ colony forming units of the immune modulating *Lactococcus* strain. In some embodiments, the bacterial composition comprises EVs and/or PhABs (e.g., whole cells, fractions of cells, supernatant from fermentation, fractions of supernatant and/or extracellular vesicles) made from the immune modulating *Lactococcus* strain.

In certain embodiments, the bacterial compositions provided herein comprise a specific ratio of immune modulating *Lactococcus* strain bacteria to immune modulating *Lactococcus* strain EV particles. For example, in some embodiments, the bacterial composition comprises at least 1 immune modulating *Lactococcus* strain bacterium for every 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 550, 600, 650, 700, 750, 800, 850, 900, 950, $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ immune modulating *Lactococcus* strain EV particles. In some embodiments, the bacterial composition comprises about 1 immune modulating *Lactococcus* strain bacterium for every 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 550, 600, 650, 700, 750, 800, 850, 900, 950, $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ immune modulating *Lactococcus* strain EV particles. In some embodiments, the bacterial composition comprises no more than 1 *Lactococcus lactis cremoris* bacterium for every 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 550, 600, 650, 700, 750, 800, 850, 900, 950, $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ immune modulating *Lactococcus* strain EV particles. In some embodiments, the bacterial composition comprises at least 1 immune modulating *Lactococcus* strain EV particle for every 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 550, 600, 650, 700, 750, 800, 850, 900, 950, $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ immune modulating *Lactococcus* strain bacteria. In some embodiments, the bacterial composition comprises about 1 immune modulating *Lactococcus* strain EV particle for every 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 550, 600, 650, 700, 750, 800, 850, 900, 950, $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ immune modulating *Lactococcus* strain bacteria. In some embodiments, the bacterial composition comprises no more than 1 immune modulating *Lactococcus* strain EV particle for every 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 550, 600, 650, 700, 750, 800, 850, 900, 950, $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ immune modulating *Lactococcus* strain bacteria.

In some embodiments, the bacterial composition is administered orally, intravenously, intratumorally, or subcutaneously. In some embodiments, the bacterial composition is administered in 2 or more (e.g., 3 or more, 4 or more or 5 or more doses). In some embodiments, the administration to the subject of the two or more doses are separated by at least 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days or 21 days. In some embodiments, a second bacterium is administered as part of an ecological consortium.

In some embodiments, the subject has mild to moderate atopic dermatitis. In some embodiments, the subject has mild atopic dermatitis. In some embodiments, the subject has moderate atopic dermatitis.

In some embodiments, the subject has mild to moderate psoriasis. In some embodiments, the subject has mild psoriasis. In some embodiments the subject has moderate psoriasis.

In some embodiments, the subject is administered a daily dose of between about 66 mg and about 3.3 g of an immune modulating *Lactococcus* strain provided herein (e.g., *Lactococcus lactis cremoris* Strain A (ATCC Deposit Number PTA-125368) or a strain comprising at least 99% sequence identity (e.g., genomic sequence identity, 16S sequence identity, CRISPR sequence identity) (e.g., at least 99.5% sequence identity, at least 99.6% sequence identity, at least 99.7% sequence identity, at least 99.8% sequence identity, at least 99.9% sequence identity) to the nucleotide sequence of the *Lactococcus lactis cremoris* Strain A (ATCC Deposit Number PTA-125368)). In some embodiments, the subject is administered a daily dose of about 66 mg of an immune modulating *Lactococcus* strain provided herein. In some embodiments, the subject is administered a daily dose of about 660 mg of an immune modulating *Lactococcus* strain provided herein. In some embodiments, the subject is administered a daily dose of about 3.3 g of an immune modulating *Lactococcus* strain provided herein. In some embodiments, the daily dose is formulated in a capsule. In some embodiments, the subject is administered the dose of an immune modulating *Lactococcus* strain provided herein for at least 2, 3, 4, 5, 6, 7, 8, 9, 10, 11, 12, 13, 14, 15, 16, 17, 18, 19, 20, 21, 22, 23, 24, 25, 26, 27, 28, 29 or 30 days.

In some embodiments, the subject has a body mass index of 18 kg/m2 to 35 kg/m2. In some embodiments, the subject has a confirmed diagnosis of mild to moderate plaque-type psoriasis for at least 6 months involving ≤5% of body surface area (BSA) (excluding the scalp). In some embodiments, the subject ha a minimum of 2 psoriatic lesions. In some embodiments, the subject has mild to moderate atopic dermatitis with a minimum of 3 to a maximum of 15% BSA involvement. In some embodiments, the subject has had a confirmed diagnosis of mild to moderate atopic dermatitis for at least 6 months with an IGA score of 2 or 3. In some embodiments, the subject has at least 2 atopic dermatitis lesions.

In some embodiments, the subject is not pregnant. In some embodiments, the subject is not breastfeeding. In some embodiments, the subject is not being treated with an anti-inflammatory drug. In some embodiments, the subject does not have an active infection (e.g., sepsis, pneumonia, abscess). In some embodiments, the subject does not have renal or liver impairment (e.g., for women a serum creatinine level≥125 μmol/L, for men a serum creatinine level of ≥125 μmol/L, an alanine aminotransferase (ALT) and aspartate aminotransferase (AST) ≥1.5× or 2× the upper limit of normal (ULN), alkaline phosphatase (ALP) and/or bilirubin>1.5×ULN.

In certain embodiments, the bacterial composition suppresses the immune response in delayed-type hypersensitivity (DTH). In certain embodiments, the bacterial composition induces a regulatory T cell or an anti-inflammatory response. In certain embodiments, the bacterial composition inhibits antigen-specific responses. In certain embodiments, the bacterial composition treats allergic contact dermatitis. In certain embodiments, the bacterial composition treats autoimmune myocarditis. In certain embodiments, the bacterial composition treats diabetes mellitus type 1. In certain embodiments, the bacterial composition treats granulomas. In certain embodiments, the bacterial composition treats peripheral neuropathies. In certain embodiments, the bacterial composition treats Hashimoto's thyroiditis. In certain embodiments, the bacterial composition treats multiple sclerosis. In certain embodiments, the bacterial composition treats rheumatoid arthritis.

In certain embodiments, the bacterial composition treats inflammation of the colon. In certain embodiments, the bacterial composition treats colitis. Colitis may be acute and self-limited or long-term. In certain embodiments, the bacterial composition treats ulcerative colitis. In certain embodiments, the bacterial composition treats digestive diseases. In certain embodiments, the bacterial composition treats Crohn's disease. In certain embodiments, the bacterial composition treats inflammatory bowel disease (IBD). In certain embodiments, the bacterial composition treats microscopic colitis. In certain embodiments, the bacterial composition treats collagenous colitis. In certain embodiments, the bacterial composition treats diversion colitis. In certain embodiments, the bacterial composition treats chemical colitis. In certain embodiments, the bacterial composition treats ischemic colitis. In certain embodiments, the bacterial composition treats indeterminate colitis. In certain embodiments, the bacterial composition treats atypical colitis. In some embodiments, the method further comprises administering to the subject an additional therapeutic (e.g., an antibiotic an immune suppressant, an anti-inflammatory agent). In some embodiments, the method further comprises administering to the subject is a second therapeutic bacterium.

In some embodiments, the subject is a mammal. In some embodiments, the subject is a human. In some embodiments, the subject is a non-human mammal (e.g., a dog, a cat, a cow, a horse, a pig, a donkey, a goat, a camel, a mouse, a rat, a guinea pig, a sheep, a llama, a monkey, a gorilla or a chimpanzee).

DETAILED DESCRIPTION

General

Figure 1:
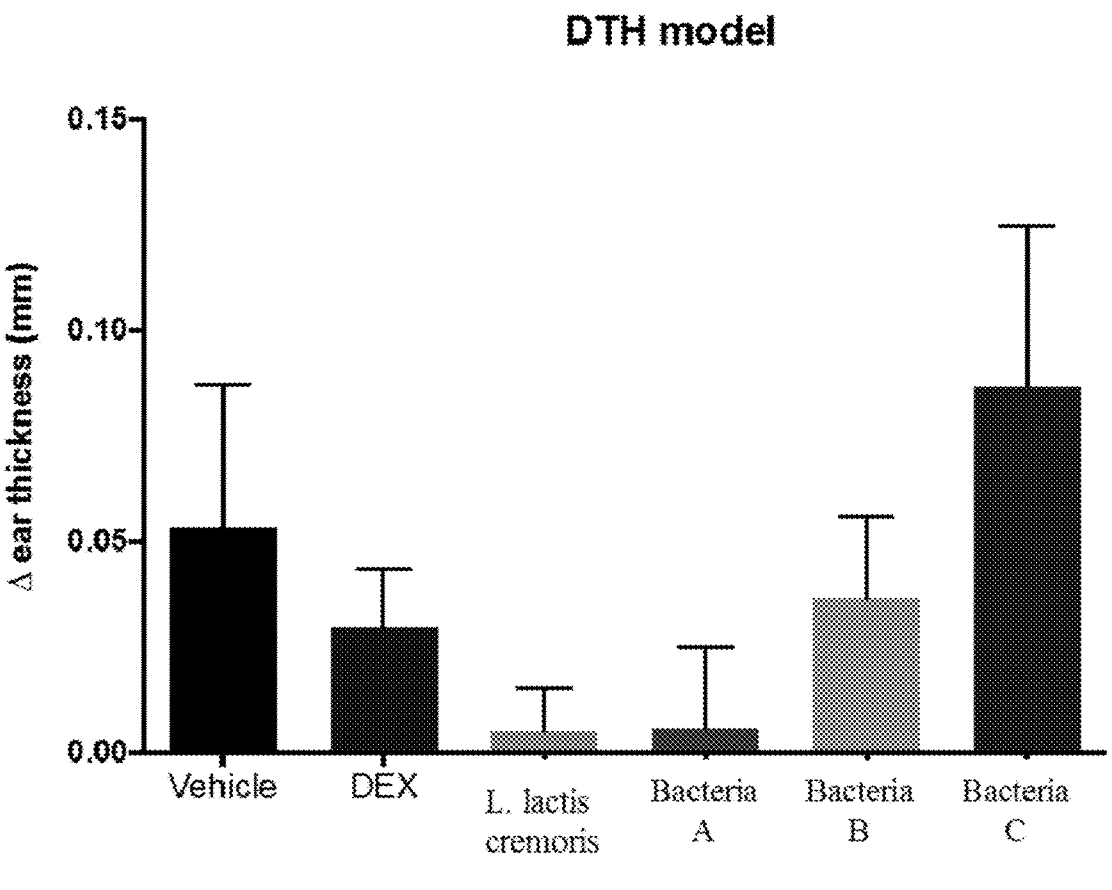
FIG. 1 shows the efficacy of orally administered *Lactococcus lactis cremoris* Strain A in reducing antigen-specific ear swelling (ear thickness) compared to vehicle (negative control), anti-inflammatory Dexamethasone (positive control), and Bacteria A, B, and C in a delayed type hypersensitivity mouse model.

In certain aspects, provided herein are methods and compositions (e.g., bacterial compositions, pharmaceutical compositions) related to the treatment and/or prevention of disease (e.g., cancer, autoimmune disease, inflammatory disease, metabolic disease), in a subject (e.g., a human subject) comprising administering a bacterial composition comprising *Lactococcus* bacteria and/or a product of such bacteria (e.g., extracellular vesicles (EVs) and/or pharmaceutically active biomasses (PhABs)). In certain aspects, also provided herein are methods of treating an immune disorder (e.g., an autoimmune disease, an inflammatory disease, an allergy) in a subject comprising administering to the subject a bacterial composition comprising an immune modulating *Lactococcus* strain provided herein, EVs generated by or isolated from an immune modulating *Lactococcus* strain provided herein and/or a PhAB made from or comprising an immune modulating *Lactococcus* strain provided herein.

Definitions

"Administration" broadly refers to a route of administration of a composition to a subject. Examples of routes of administration include oral administration, rectal administration, topical administration, inhalation (nasal) or injection. Administration by injection includes intravenous (IV), intramuscular (IM), intratumoral (IT) and subcutaneous (SC) administration. The pharmaceutical compositions described herein can be administered in any form by any effective route, including but not limited to intratumoral, oral, parenteral, enteral, intravenous, intraperitoneal, topical, transdermal (e.g., using any standard patch), intradermal, ophthalmic, (intra)nasally, local, non-oral, such as aerosol, inhalation, subcutaneous, intramuscular, buccal, sublingual, (trans)rectal, vaginal, intra-arterial, and intrathecal, transmucosal (e.g., sublingual, lingual, (trans)buccal, (trans)urethral, vaginal (e.g., trans- and perivaginally), intravesical, intrapulmonary, intraduodenal, intragastrical, and intrabronchial. In preferred embodiments, the pharmaceutical compositions described herein are administered orally, rectally, intratumorally, topically, intravesically, by injection into or adjacent to a draining lymph node, intravenously, by inhalation or aerosol, or subcutaneously.

As used herein, the term "antibody" may refer to both an intact antibody and an antigen binding fragment thereof. Intact antibodies are glycoproteins that include at least two heavy (H) chains and two light (L) chains inter-connected by disulfide bonds. Each heavy chain includes a heavy chain variable region (abbreviated herein as $V_H$) and a heavy chain constant region. Each light chain includes a light chain variable region (abbreviated herein as $V_L$) and a light chain constant region. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The term "antibody" includes, for example, monoclonal antibodies, polyclonal antibodies, chimeric antibodies, humanized antibodies, human antibodies, multispecific antibodies (e.g., bispecific antibodies), single-chain antibodies and antigen-binding antibody fragments.

The terms "antigen binding fragment" and "antigen-binding portion" of an antibody, as used herein, refers to one or more fragments of an antibody that retain the ability to bind to an antigen. Examples of binding fragments encompassed within the term "antigen-binding fragment" of an antibody include Fab, Fab', F(ab')2, Fv, scFv, disulfide linked Fv, Fd, diabodies, single-chain antibodies, NANOBODIES®, isolated CDRH3, and other antibody fragments that retain at least a portion of the variable region of an intact antibody. These antibody fragments can be obtained using conventional recombinant and/or enzymatic techniques and can be screened for antigen binding in the same manner as intact antibodies.

"Cellular augmentation" broadly refers to the influx of cells or expansion of cells in an environment that are not substantially present in the environment prior to administration of a composition and not present in the composition itself. Cells that augment the environment include immune cells, stromal cells, bacterial and fungal cells. Environments of particular interest are the microenvironments where cancer cells reside or locate. In some instances, the microenvironment is a tumor microenvironment or a tumor draining lymph node. In other instances, the microenvironment is a pre-cancerous tissue site or the site of local administration of a composition or a site where the composition will accumulate after remote administration.

"Clade" refers to the OTUs or members of a phylogenetic tree that are downstream of a statistically valid node in a phylogenetic tree. The clade comprises a set of terminal leaves in the phylogenetic tree that is a distinct monophyletic evolutionary unit and that share some extent of sequence similarity. "Operational taxonomic units," "OTU" (or plural; "OTUs") refer to a terminal leaf in a phylogenetic tree and is defined by a nucleic acid sequence, e.g., the entire genome, or a specific genetic sequence, and all sequences that share sequence identity to this nucleic acid sequence at the level of species. In some embodiments the specific genetic sequence may be the 16S sequence or a portion of the 16S sequence. In other embodiments, the entire genomes of two entities are sequenced and compared. In another embodiment, select regions such as multilocus sequence tags (MUST), specific genes, or sets of genes may be genetically compared. In 16S embodiments, OTUs that share ≥97% average nucleotide identity across the entire 16S or some variable region of the 16S are considered the same OTU (see e.g. Claesson M J, Wang Q, O'Sullivan O, Greene-Diniz R, Cole J R, Ros R P, and O'Toole P W. 2010. Comparison of two next-generation sequencing technologies for resolving highly complex microbiota composition using tandem variable 16S fRNA gene regions. *Nucleic Acid Res* 38: e200. Konstantinidis T, Ramette A, and Tiedje J M. 2006. The bacterial species definition in the genomic era. *Philos Trans R Soc Lond B Biol Sci* 361: 1929-1940.). In embodiments involving the complete genome, MLSTs, specific genes, or sets of genes OTUs that share ≥95% average nucleotide identity are considered the same OTU (see e.g. Achtman M, and Wagner M. 2008. Microbial diversity and the genetic nature of microbial species. *Nat. Rev. Microbiol.* 6: 431-440. Konstantinidis K T, Ramette A, and Tiedje J M. 2006. The bacterial species definition in the genomic era. *Philos Trans R Soc Lond B Biol Sci* 361: 1929-1940.). OTUs are frequently defined by comparing sequences between organisms. Generally, sequences with less than 95% sequence identity are not considered to form part of the same OTU. OTUs may also be characterized by any combination of nucleotide markers or genes, in particular highly conserved genes (e "house-keeping" genes), or a combination thereof. Such characterization employs, e.g., WGS data or a whole genome sequence.

A "combination" of two or more microbial strains includes the physical co-existence of the two microbial strains, either in the same material or product or in physically connected products, as well as the temporal co-administration or co-localization of the monoclonal microbial strains.

The term "decrease" or "deplete" means a change, such that the difference is, depending on circumstances, at least 10%, 20%, 30%, 40%, 50%, 60%, 70%, 80%, 90%, 1/100, 1/1000, 1/10,000, 1/100,000, 1/1,000,000 or undetectable after treatment when compared to a pre-treatment state.

The term "ecological consortium" is a group of bacteria which trades metabolites and positively co-regulates one another, in contrast to two bacteria which induce host synergy through activating complementary host pathways for improved efficacy.

The term "epitope" means a protein determinant capable of specific binding to an antibody. Epitopes usually consist of chemically active surface groupings of molecules such as amino acids or sugar side chains. Certain epitopes can be defined by a particular sequence of amino acids to which an antibody is capable of binding.

As used herein, "engineered bacteria" are any bacteria that have been genetically altered from their natural state by human intervention and the progeny of any such bacteria. Engineered bacteria include, for example, the products of targeted genetic modification, the products of random mutagenesis screens and the products of directed evolution.

As used herein, the term "extracellular vesicle" or "EV" or refers to a composition derived from a bacteria that comprises bacterial lipids, and bacterial proteins and/or bacterial nucleic acids and/or carbohydrate moieties contained in a nanoparticle. These EVs may contain 1, 2, 3, 4, 5, 10, or more than 10 different lipid species. EVs may contain 1, 2, 3, 4, 5, 10, or more than 10 different protein species. EVs may contain 1, 2, 3, 4, 5, 10, or more than 10 different nucleic acid species. EVs may contain 1, 2, 3, 4, 5, 10, or more than 10 different carbohydrate species.

The term "gene" is used broadly to refer to any nucleic acid associated with a biological function. The term "gene" applies to a specific genomic sequence, as well as to a cDNA or an mRNA encoded by that genomic sequence.

"Identity" as between nucleic acid sequences of two nucleic acid molecules can be determined as a percentage of identity using known computer algorithms such as the "FASTA" program, using for example, the default parameters as in Pearson et al. (1988) Proc. Natl. Acad. Sci. USA 85:2444 (other programs include the GCG program package (Devereux, J., et al., Nucleic Acids Research 12(I):387 (1984)), BLASTP, BLASTN, FASTA Atschul, S. F., et al., J Molec Biol 215:403 (1990); Guide to Huge Computers, Martin J. Bishop, ed., Academic Press, San Diego, 1994, and Carillo et al. (1988) SIAM J Applied Math 48:1073). For example, the BLAST function of the National Center for Biotechnology Information database can be used to determine identity. Other commercially or publicly available programs include, DNAStar "MegAlign" program (Madison, Wis.) and the University of Wisconsin Genetics Computer Group (UWG) "Gap" program (Madison Wis.)).

As used herein, the term "immune disorder" refers to any disease, disorder or disease symptom caused by an activity of the immune system, including autoimmune diseases, inflammatory diseases and allergies. Immune disorders include, but are not limited to, autoimmune diseases (e.g., Lupus, Scleroderma, hemolytic anemia, vasculitis, type one diabetes, Grave's disease, rheumatoid arthritis, multiple sclerosis, Goodpasture's syndrome, pernicious anemia and/or myopathy), inflammatory diseases (e.g., acne vulgaris, asthma, celiac disease, chronic prostatitis, glomerulonephritis, inflammatory bowel disease, pelvic inflammatory disease, reperfusion injury, rheumatoid arthritis, sarcoidosis, transplant rejection, vasculitis and/or interstitial cystitis), and/or an allergies (e.g., food allergies, drug allergies and/or environmental allergies).

The term "increase" means a change, such that the difference is, depending on circumstances, at least 10%, 20%, 30%, 40%, 50%, 60%, 70%, 80%, 90%, 2-fold, 4-fold, 10-fold, 100-fold, 10^3 fold, 10^4 fold, 10^5 fold, 10^6 fold, and/or 10^7 fold greater after treatment when compared to a pre-treatment state. Properties that may be increased include immune cells, bacterial cells, stromal cells, myeloid derived suppressor cells, fibroblasts, metabolites, and cytokines.

The "internal transcribed spacer" or "ITS" is a piece of non-functional RNA located between structural ribosomal RNAs (rRNA) on a common precursor transcript often used for identification of eukaryotic species in particular fungi. The rRNA of fungi that forms the core of the ribosome is transcribed as a signal gene and consists of the 8S, 5.8S and 28S regions with ITS4 and 5 between the 8S and 5.8S and 5.8S and 28S regions, respectively. These two intercistronic segments between the 18S and 5.8S and 5.8S and 28S regions are removed by splicing and contain significant variation between species for barcoding purposes as previously described (Schoch et al Nuclear ribosomal internal transcribed spacer (ITS) region as a universal DNA barcode marker for Fungi. PNAS 109:6241-6246, 2012). 18S rDNA is traditionally used for phylogenetic reconstruction however the ITS can serve this function as it is generally highly conserved but contains hypervariable regions that harbor sufficient nucleotide diversity to differentiate genera and species of most fungus.

The term "isolated" or "enriched" encompasses a microbe, bacteria or other entity or substance that has been (1) separated from at least some of the components with which it was associated when initially produced (whether in nature or in an experimental setting), and/or (2) produced, prepared, purified, and/or manufactured by the hand of man.

Isolated microbes may be separated from at least about 10%, about 20%, about 30%, about 40%, about 50%, about 60%, about 70%, about 80%, about 90%, or more of the other components with which they were initially associated. In some embodiments, isolated microbes are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. The terms "purify," "purifying" and "purified" refer to a microbe or other material that has been separated from at least some of the components with which it was associated either when initially produced or generated (e.g., whether in nature or in an experimental setting), or during any time after its initial production. A microbe or a microbial population may be considered purified if it is isolated at or after production, such as from a material or environment containing the microbe or microbial population, and a purified microbe or microbial population may contain other materials up to about 10%, about 20%, about 30%, about 40%, about 50%, about 60%, about 70%, about 80%, about 90%, or above about 90% and still be considered "isolated." In some embodiments, purified microbes or microbial population are more than about 80%, about 85%, about 90%, about 91%, about 92%, about 93%, about 94%, about 95%, about 96%, about 97%, about 98%, about 99%, or more than about 99% pure. In the instance of microbial compositions provided herein, the one or more microbial types present in the composition can be independently purified from one or more other microbes produced and/or present in the material or environment containing the microbial type. Microbial compositions and the microbial components thereof are generally purified from residual habitat products.

"Metabolite" as used herein refers to any and all molecular compounds, compositions, molecules, ions, co-factors, catalysts or nutrients used as substrates in any cellular or microbial metabolic reaction or resulting as product compounds, compositions, molecules, ions, co-factors, catalysts or nutrients from any cellular or microbial metabolic reaction.

"Microbe" refers to any natural or engineered organism characterized as a bacterium, fungus, microscopic alga, protozoan, and the stages of development or life cycle stages (e.g., vegetative, spore (including sporulation, dormancy, and germination), latent, biofilm) associated with the organism. Examples of gut microbes include: *Actinomyces graevenitzii, Actinomyces odontolyticus, Akkermansia muciniphila, Bacteroides caccae, Bacteroides fragilis, Bacteroides putredinis, Bacteroides thetaiotaomicron, Bacteroides vultagus, Bifidobacterium adolescentis, Bifidobacterium bifidum, Bilophila wadsworthia, Lactococcus lactis, Butyrivibrio, Campylobacter gracilis*, Clostridia cluster III, Clostridia cluster IV, Clostridia cluster IX (Acidaminococcaceae group), Clostridia cluster XI, Clostridia cluster XIII (*Peptostreptococcus* group), Clostridia cluster XIV, Clostridia cluster XV, *Collinsella aerofaciens, Coprococcus, Corynebacterium sunsvallense, Desulfomonas pigra, Dorea formicigenerans, Dorea longicatena, Escherichia coli, Eubacterium hadrum, Eubacterium rectale, Faecalibacteria prausnitzii, Gemella, Lactococcus, Lanchnospira*, Mollicutes cluster XVI, Mollicutes cluster XVIII, *Prevotella, Rothia mucilaginosa, Ruminococcus callidus, Ruminococcus gnavus, Ruminococcus torques*, and *Streptococcus.*

"Microbiome" broadly refers to the microbes residing on or in body site of a subject or patient. Microbes in a microbiome may include bacteria, viruses, eukaryotic microorganisms, and/or viruses. Individual microbes in a microbiome may be metabolically active, dormant, latent, or exist as spores, may exist planktonically or in biofilms, or may be present in the microbiome in sustainable or transient manner. The microbiome may be a commensal or healthy-state microbiome or a disease-state microbiome. The microbiome may be native to the subject or patient, or components of the microbiome may be modulated, introduced, or depleted due to changes in health state (e.g., precancerous or cancerous state) or treatment conditions (e.g., antibiotic treatment, exposure to different microbes). In some aspects, the microbiome occurs at a mucosal surface. In some aspects, the microbiome is a gut microbiome. In some aspects, the microbiome is a tumor microbiome.

A "microbiome profile" or a "microbiome signature" of a tissue or sample refers to an at least partial characterization of the bacterial makeup of a microbiome. In some embodiments, a microbiome profile indicates whether at least 2, 3, 4, 5, 6, 7, 8, 9, 10, 15, 20, 25, 30, 35, 40, 45, 50, 55, 60, 65, 70, 75, 80, 85, 90, 95, 100 or more bacterial strains are present or absent in a microbiome.

"Modified" in reference to a bacteria broadly refers to a bacteria that has undergone a change from its wild-type form. Examples of bacterial modifications include genetic modification, gene expression, phenotype modification, formulation, chemical modification, and dose or concentration. Examples of improved properties are described throughout this specification and include, e.g., attenuation, auxotrophy, homing, or antigenicity. Phenotype modification might include, by way of example, bacteria growth in media that modify the phenotype of a bacterium that increase or decrease virulence.

As used herein, a gene is "overexpressed" in a bacteria if it is expressed at a higher level in an engineered bacteria under at least some conditions than it is expressed by a wild-type bacteria of the same species under the same conditions. Similarly, a gene is "underexpressed" in a bacteria if it is expressed at a lower level in an engineered bacteria under at least some conditions than it is expressed by a wild-type bacteria of the same species under the same conditions.

The terms "polynucleotide" and "nucleic acid" are used interchangeably. They refer to a polymeric form of nucleotides of any length, either deoxyribonucleotides or ribonucleotides, or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleic acid sequences provided herein, U nucleotides are interchangeable with T nucleotides.

As used herein, a substance is "pure" if it is substantially free of other components. The terms "purify," "purifying" and "purified" refer to a EV or other material that has been separated from at least some of the components with which it was associated either when initially produced or generated (e.g., whether in nature or in an experimental setting), or during any time after its initial production. An EV may be considered purified if it is isolated at or after production, such as from one or more other bacterial components, and a purified microbe or microbial population may contain other materials up to about 10%, about 20%, about 30%, about 40%, about 50%, about 60%, about 70%, about 80%, about 90%, or above about 90% and still be considered "purified." In some embodiments, purified EVs are more than about 80%, about 85%, about 90%, about 91%, about 92%, about 93%, about 94%, about 95%, about 96%, about 97%, about 98%, about 99%, or more than about 99% pure. EV compositions and the microbial components thereof are, e.g., purified from residual habitat products.

As used herein, the term "purified EV composition" or "EV composition" refer to a preparation that includes EVs that have been separated from at least one associated substance found in a source material (e.g. separated from at least one other bacterial component) or any material associated with the EVs in any process used to produce the preparation. It also refers to a composition that has been significantly enriched or concentrated. In some embodiments the EVs are concentrated by 2 fold, 3-fold, 4-fold, 5-fold, 10-fold, 100-fold, 1000-fold, 10,000-fold or more than 10,000 fold.

"Operational taxonomic units" and "OTU(s)" refer to a terminal leaf in a phylogenetic tree and is defined by a nucleic acid sequence, e.g., the entire genome, or a specific genetic sequence, and all sequences that share sequence identity to this nucleic acid sequence at the level of species. In some embodiments the specific genetic sequence may be the 16S sequence or a portion of the 16S sequence. In other embodiments, the entire genomes of two entities are sequenced and compared. In another embodiment, select regions such as multilocus sequence tags (MLST), specific genes, or sets of genes may be genetically compared. For 16S, OTUs that share ≥97% average nucleotide identity across the entire 16S or some variable region of the 16S are considered the same OTU. See e.g. Claesson M J, Wang Q, O'Sullivan O, Greene-Diniz R, Cole J R, Ross R P, and O'Toole P W. 2010. Comparison of two next-generation sequencing technologies for resolving highly complex microbiota composition using tandem variable 16S rRNA gene regions. Nucleic Acids Res 38: e200. Konstantinidis K T, Ramette A, and Tiedje J M. 2006. The bacterial species definition in the genomic era. Philos Trans R Soc Lond B Biol Sci 361: 1929-1940. For complete genomes, MLSTs, specific genes, other than 16S, or sets of genes OTUs that share ≥95% average nucleotide identity are considered the same OTU. See e.g., Achtman M, and Wagner M. 2008. Microbial diversity and the genetic nature of microbial species. Nat. Rev. Microbiol. 6: 431-440. Konstantinidis K T, Ramette A, and Tiedje J M. 2006. The bacterial species definition in the genomic era. Philos Trans R Soc Lond B Biol Sci 361: 1929-1940. OTUs are frequently defined by comparing sequences between organisms. Generally, sequences with less than 95% sequence identity are not considered to form part of the same OTU. OTUs may also be characterized by any combination of nucleotide markers or genes, in particular highly conserved genes (e.g., "housekeeping" genes), or a combination thereof. Operational Taxonomic Units (OTUs) with taxonomic assignments made to, e.g., genus, species, and phylogenetic clade are provided herein.

As used herein, "specific binding" refers to the ability of an antibody to bind to a predetermined antigen or the ability of a polypeptide to bind to its predetermined binding partner. Typically, an antibody or polypeptide specifically binds to its predetermined antigen or binding partner with an affinity corresponding to a $K_D$ of about $10^{-7}$ M or less, and binds to the predetermined antigen/binding partner with an affinity (as expressed by $K_D$) that is at least 10 fold less, at least 100 fold less or at least 1000 fold less than its affinity for binding to a non-specific and unrelated antigen/binding partner (e.g., BSA, casein). Alternatively, specific binding applies more broadly to a two component system where one component is a protein, lipid, or carbohydrate or combination thereof and engages with the second component which is a protein, lipid, carbohydrate or combination thereof in a specific way.

The terms "subject" or "patient" refers to any animal. A subject or a patient described as "in need thereof" refers to one in need of a treatment for a disease. Mammals (i.e., mammalian animals) include humans, laboratory animals (e.g., primates, rats, mice), livestock (e.g., cows, sheep, goats, pigs), and household pets (e.g., dogs, cats, rodents). For example, the subject may be a non-human mammal including but not limited to of a dog, a cat, a cow, a horse, a pig, a donkey, a goat, a camel, a mouse, a rat, a guinea pig, a sheep, a llama, a monkey, a gorilla or a chimpanzee. The subject or patient may be healthy, or may be suffering from an immune disorder at any developmental stage.

"Strain" refers to a member of a bacterial species with a genetic signature such that it may be differentiated from closely-related members of the same bacterial species. The genetic signature may be the absence of all or part of at least one gene, the absence of all or part of at least on regulatory region (e.g., a promoter, a terminator, a riboswitch, a ribosome binding site), the absence ("curing") of at least one native plasmid, the presence of at least one recombinant gene, the presence of at least one mutated gene, the presence of at least one foreign gene (a gene derived from another species), the presence at least one mutated regulatory region (e.g., a promoter, a terminator, a riboswitch, a ribosome binding site), the presence of at least one non-native plasmid, the presence of at least one antibiotic resistance cassette, or a combination thereof. Genetic signatures between different strains may be identified by PCR amplification optionally followed by DNA sequencing of the genomic region(s) of interest or of the whole genome. In the case in which one strain (compared with another of the same species) has gained or lost antibiotic resistance or gained or lost a biosynthetic capability (such as an auxotrophic strain), strains may be differentiated by selection or counter-selection using an antibiotic or nutrient/metabolite, respectively.

As used herein, the term "treating" a disease in a subject or "treating" a subject having or suspected of having a disease refers to subjecting the subject to a pharmaceutical treatment, e.g., the administration of one or more agents, such that at least one symptom of the disease is decreased or prevented from worsening. Thus, in one embodiment, "treating" refers inter alia to delaying progression, expediting remission, inducing remission, augmenting remission, speeding recovery, increasing efficacy of or decreasing resistance to alternative therapeutics, or a combination thereof.

Bacteria

In certain aspects, provided herein are methods of using a bacterial composition comprising an immune modulating *Lactococcus* strain provided herein, EVs generated by or isolated from an immune modulating *Lactococcus* strain provided herein and/or a PhAB made from or comprising an immune modulating *Lactococcus* strain provided herein. In some embodiments, the immune modulating *Lactococcus* strain is a strain of *Lactococcus lactis cremoris*. In some embodiments, the immune modulating *Lactococcus* strain is *Lactococcus lactis cremoris* Strain A (ATCC Deposit Number PTA-125368). In some embodiments, the immune modulating *Lactococcus* strain is a strain comprising at least 90%, at least 91%, at least 92%, at least 93%, at least 94%, at least 95%, at least 96%, at least 97%, at least 98%, or at least 99% sequence identity (e.g., at least 99.5% sequence identity, at least 99.6% sequence identity, at least 99.7% sequence identity, at least 99.8% sequence identity, at least 99.9% sequence identity) to the nucleotide sequence (e.g., genomic, 16S or CRISPR nucleotide sequence) of the *Lactococcus lactis cremoris* Strain A (ATCC Deposit Number PTA-125368).

Under the terms of the Budapest Treaty on the International Recognition of the Deposit of Microorganisms for the Purpose of Patent Procedure, the *Lactococcus lactis cremoris* Strain A was deposited on Oct. 11, 2018, with the American Type Culture Collection (ATCC) of 10801 University Boulevard, Manassas, Va. 20110-2209 USA and was assigned ATCC Accession Number PTA-125368.

Applicant represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 U.S.C. 122. The deposited material will be maintained with all the care necessary to keep it viable and uncontaminated for a period of at least five years after the most recent request for the furnishing of a sample of the deposited plasmid, and in any case, for a period of at least thirty (30) years after the date of deposit or for the enforceable life of the patent, whichever period is longer. Applicant acknowledges its duty to replace the deposit should the depository be unable to furnish a sample when requested due to the condition of the deposit.

In some embodiments, the bacteria described herein are modified to improve colonization and/or engraftment in the mammalian gastrointestinal tract (e.g., modified metabolism, such as improved mucin degradation, enhanced competition profile, increased motility, increased adhesion to gut epithelial cells, modified chemotaxis). In some embodiments, the bacteria described herein are modified to enhance their immunomodulatory and/or therapeutic effect (e.g., either alone or in combination with another therapeutic agent). In some embodiments, the bacteria described herein are modified to enhance immune activation (e.g., through modified production of polysaccharides, pili, fimbriae, adhesins). In some embodiments, the bacteria described herein are modified to improve bacterial manufacturing (e.g., higher oxygen tolerance, improved freeze-thaw tolerance, shorter generation times).

*Lactococcus lactis cremoris* Strain A can be cultured according to methods known in the art. For example, *Lactococcus lactis cremoris* can be grown in ATCC Medium 2722, ATCC Medium 1490, or other medium using methods disclosed, for example in Caballero et al., 2017. "Cooperating Commensals Restore Colonization Resistance to Vancomycin-Resistant *Enterococcus faecium" Cell Host & Microbe* 21:592-602, which is hereby incorporated by reference in its entirety.

In some embodiments, the immune modulating *Lactococcus* bacteria is a strain of *Lactococcus* bacteria (e.g., a strain of *Lactococcus lactis cremoris*) comprising one or more (e.g., 1, 2, 3, 4, 5, 6, 7, 8, 9, 10, 11, 12, 13, 14, 15, 16, 17, 18, 19, 20, 21, 22, 23, 24, 25 or more) proteins listed in Table 1 and/or one or more (e.g., 1, 2, 3, 4, 5, 6, 7, 8, 9, 10, 11, 12, 13, 14, 15, 16, 17, 18, 19, 20, 21, 22, 23, 24, 25 or more) genes encoding proteins listed in Table 1. In some embodiments, the immune modulating bacteria comprises all of the proteins listed in Table 1 and/or all of the genes encoding the proteins listed in Table 1.

In some embodiments, the immune modulating *Lactococcus* bacteria is a strain of *Lactococcus* bacteria (e.g., a strain of *Lactococcus lactis cremoris*) comprising one or more (e.g., one, two or three) membrane associated proteins listed in Table 2 and/or one or more (e.g., one, two or three) genes encoding membrane associated proteins listed in Table 2. In some embodiments, the immune modulating bacteria comprises all of the proteins listed in Table 2 and/or all of the genes encoding the proteins listed in Table 2.

In some embodiments, the immune modulating *Lactococcus* bacteria is a strain of *Lactococcus* bacteria (e.g., a strain of *Lactococcus lactis cremoris*) free or substantially free of one or more (e.g., 1, 2, 3, 4, 5, 6, 7, 8, 9, 10, 11, 12, 13, 14, 15, 16, 17, 18, 19, 20, 21, 22, 23, 24, 25 or more) proteins listed in Table 3 and/or one or more (e.g., 1, 2, 3, 4, 5, 6, 7, 8, 9, 10, 11, 12, 13, 14, 15, 16, 17, 18, 19, 20, 21, 22, 23, 24, 25 or more) genes encoding proteins listed in Table 3. In some embodiments, the immune modulating bacteria is free of all of the proteins listed in Table 2 and/or all of the genes encoding the proteins listed in Table 2.

In some embodiments, the immune modulating *Lactococcus* bacteria is a strain of *Lactococcus* bacteria (e.g., a strain of *Lactococcus lactis cremoris*) free or substantially free of one or more (e.g., 1, 2, 3, 4, 5, 6, 7, 8, 9, 10, 11, 12, 13, 14, 15, 16, 17) exopolysaccharide (EPS) synthesis proteins listed in Table 4 and/or one or more (e.g., 1, 2, 3, 4, 5, 6, 7, 8, 9, 10, 11, 12, 13, 14, 15, 16, 17) genes encoding EPS synthesis proteins listed in Table 4. In some embodiments, the immune modulating bacteria is free of all of the proteins listed in Table 4 and/or all of the genes encoding the proteins listed in Table 4. In some embodiments, the immune modulating bacteria is a strain of *Lactococcus* bacteria (e.g., a strain of *Lactococcus lactis cremoris*) free or substantially free of an EPS synthesized in whole or in part by a protein listed in Table 4. In some embodiments, the immune modulating bacteria is a strain of *Lactococcus* bacteria (e.g., a strain of *Lactococcus lactis cremoris*) free or substantially free of EPS.

In certain aspects, the immune modulating *Lactococcus* strain bacteria described herein are substantially free of exopolysaccharides.

In some embodiments, the immune modulating *Lactococcus* bacteria is a strain of *Lactococcus* bacteria (e.g., a strain of *Lactococcus lactis cremoris*) comprising one or more (e.g., 1, 2, 3, 4, 5, 6, 7, 8, 9, 10, 11, 12, 13, 14, 15, 16, 17, 18, 19, 20, 21, 22, 23, 24, 25 or more) proteins listed in Table 6 and/or one or more (e.g., 1, 2, 3, 4, 5, 6, 7, 8, 9, 10, 11, 12, 13, 14, 15, 16, 17, 18, 19, 20, 21, 22, 23, 24, 25 or more) genes encoding proteins listed in Table 6. In some embodiments, the immune modulating bacteria comprises all of the proteins listed in Table 6 and/or all of the genes encoding the proteins listed in Table 6.

In some embodiments, the immune modulating *Lactococcus* bacteria is a strain of *Lactococcus* bacteria (e.g., a strain of *Lactococcus lactis cremoris*) free or substantially free of one or more (e.g., 1, 2, 3, 4, 5, 6, 7, or more) proteins listed in Table 5 and/or one or more (e.g., 1, 2, 3, 4, 5, 6, 7 or more) genes encoding proteins listed in Table 5. In some embodiments, the immune modulating bacteria is free of all of the proteins listed in Table 5 and/or all of the genes encoding the proteins listed in Table 5.

TABLE 1

Exemplary *Lactococcus lactis cremoris* Strain A Proteins

| SEQ ID NO. | name | uniprot_id | Protein Sequence |
|---|---|---|---|
| 1 | Cluster: Transposase for insertion sequence element IS905 | P35881 | MTQFTTELLNFLAQKQDIDEFFRTSLETAMNDLLQAE LSAFLGYEPYDKVGYNSGNSRNGSYSRQFETKYGTVQ LSIPRDRNGNFSPALLPAYGRRDDHLEEMVIKLYQTG VTTREISDIIERMYGHHYSPATISNISKATQENVATF HERSLEANYSVLFLDGTYLPLRRGTVSKECIHIALGI TPEGQKAVLGYEIAPNENNASWSTLLDKLQNQGIQQV SLVVTDGFKGLEQIISQAYPLAKQQRCLIHISRNLAS KVKRADRAVILEQFKTIYRAENLEMAVQALENFIAEW KPKYRKVMESLENTDNLLTFYQFPYQIWHSIYSTNLI ESLNKEIKRQTKKKVLFPNEEALERYLVTLFEDYNFK QSQRIHKGFGQCADTLESLFD |
| 2 | Cluster: Transposase of IS1077E | Q9CB06 | MKVTGFPKATYYYWVNCFERVNKDELIEKEMLKIRQE HANAGYRPMSELLKQRGYHVNHKKVQRLMKKLGLRVT SYWHKSRKYNSYKGKVGTVAKNKLHRRFRTSIPHQKI TTDTTEFKYYEDGIQKKCYLNPYIDLFNSEVISYHIS KQPSYQSIDIALNQALAVTSDCPYRRTFHSDQGWGYQ MRDYVSKLKSHRIFQSMSRKGNCHDNSVMENFFGLLK QEIYYGHIFSSFEELEQVIVIWIRYYNTKRIKQKLNW MSPIQFRLNYQNN |
| 3 | Cluster: Transposase IS256 | T0VLJ3 | MTQFTTELLNFLAQKQDIDEFFRTSLETAMNDLLQAE LSAFLGYEPYDKVGYNSGNSRNGSYSRQFETKYGTVQ LSIPRDRNGNFSPALLPAYGRRDDHLEEMGYQTLSNR CNDSRNL |
| 4 | Cluster: Uncharacterized protein | A2RKL1 | MTKYSFELKLKVVQDYDNGVGGCDYLAKKYHVTNEAI VRRWVKAYKELGAVGIQRKRQNTVYSTQFKLNAVNLY LTSEKSYRELAHELGMNNPPLLTRVVVSNYRKKGEFA FSNVQGRPRKESELLEISIKKAKDVVNETEQELARLQ NDNLNLRMEVEYLKGLRRLRQEQHKRENPEWSVNSDE NSSSHLSNS |
| 5 | Cluster: Transposase | S6EVX2 | MVCELRREFKFPLKQLLAISELSKATYYYWVNRFERP NKDEMIEQVMLEIRQEHTNAGYRPMVELLKQRGIYVN HKKVQRLMKKLGLRVTTFWHKSRKYNSYKGKVGTVAK NKLHRRFNTSIPHQKITTDTTEFKYYDKGVQKKLYLT PYLDLFNNEVISYEISKQPTYQAIATALQEALELTSD CLYRRTFHSDQGWAYQMKNYVFKLKSQKIIQSMSRKG NCHDNSVMENFFGLLKQEIYYGHVFNSFEELEQAITK WIHYYNTKRIKKKLNWMSPIQYRLTYSK |
| 6 | Cluster: PIL4_5 | G0WJR5 | MMINYQGEVFTETEFYGREILEAIQLTNKFPTPKKVL IDRLEEMIHEQLDLIDKEELNNYIHAKK |
| 7 | Cluster: Molybdopterin-guanine dinucleotide biosynthesis protein MobC | T0W7Q8 | MKIIENRERSIQKKFFVNEKENERIKLMMKKTGITNF SVFARRACCNKEIFTLDFSEYKNIISEISATKSELKR IGNNINQIAKHLNENKNNQTESLMSDYQNQLESLEEK IQKVVHYISEG |
| 8 | ESAT-6_secretion_accessory_factor_EsaA | Q2G188 | MMLKKEWQAILKHKFFIIVIIALALVPAIYNYIFLGS MWDPSGKLNDLPVAVVNLDKTSELNGKKFKLGDDVIT EMKKSKDLDYHFVSKDKASEGIKKGDYYMVITFPENF SENATTLMNKEPKTVQLDYQTTRGHNYISSKMSESAM NQLKSEVSKNITQTYTKTRIAS |
| 9 | Foldase_protein_PrsA | P0C2B5 | MKKKMRLKVLLASTATALLLLSGCQSNQTDQTVATYS GGKVTESSFYKELKQSPTTKTMLANMLIYRALNHAYG KSVSTKTVNDAYDSYKQQYGENFDAFLSQNGFSRSSF KESLRTNFLSEVALKKLKKVSESQLKAAWKTYQPKVT VQHILTSDEDTAKQVISDLAAGKDFAMLAKTDSIDTA TKDNGGKISFELNNKTLDATFKDAAYKLKNGDYTQTP VKVTDGYEVIKMINHPAKGTFTSSKKVLTASVYAKWS RDSSIMQRVISQVLKNQHVTIKDKDLADALDSYKKLA TTN |
| 10 | PIII-type_proteinase | P15292 | MQRKKKGLSFLLAGTVALGALAVLPVGEIQAKAAISQ QTKGSSLANTVTAATAKQAATDTTAATTNQAIATQLA AKGIDYNKLNKVQQQDIYVDVIVQMSAAPASENGTLR TDYSSTAEIQQETNKVIAAQASVKAAVEQVTQQTAGE SYGYVVNGFSTKVRVVDIPKLKQIAGVKTVTLAKVYY PTDAKANSMANVQAVWSNYKYKGEGTVVSVIDSGIDP THKDMRLSDDKDVKLTKSDVEKFTDTVKHGRYFNSKV |

TABLE 1-continued

Exemplary *Lactococcus lactis cremoris* Strain A Proteins

| SEQ ID NO. | name | uniprot_id | Protein Sequence |
|---|---|---|---|
| | | | PYGFNYADNNDTITDDKVDEQHGMHVAGIIGANGTGD<br>DPAKSVVGVAPEAQLLAMKVFTNSDTSATTGSDTLVS<br>AIEDSAKIGADVLNMSLGSDSGNQTLEDPEIAAVQNA<br>NESGTAAVISAGNSGTSGSATEGVNKDYYGLQDNEMV<br>GTPGTSRGATTVASAENTDVITQAVTITDGTGLQLGP<br>ETIQLSSNDFTGSFDQKKFYVVKDASGNLSKGKVADY<br>TADAKGKIAIVKRGELTFDDKQKYAQAAGAAGLIIVN<br>NDGTATPVTSMALTTTFPTFGLSSVTGQKLVDWVTAH<br>PDDSLGVKIALTLVPNQKYTEDKMSDFTSYGPVSNLS<br>FKPDITAPGGNIWSTQNNNGYTNMSGTSMASPFIAGS<br>QALLKQALNNKNNPFYAYYKQLKGTALTDFLKTVEMN<br>TAQPINDINYNNVIVSPRRQGAGLVDVKAAIDALEKN<br>PSTVVAENGYPAVELKDFTSTDKTFKLTFTNRTTHEL<br>TYQMDSNTDTNAVYTSATDPNSGVLYDKKIDGAAIKA<br>GSNITVPAGKTAQIEFTLSLPKSFDQQQFVEGFLNFK<br>GSDGSRLNLPYMGFFGDWNDGKIVDSLNGITYSPAGG<br>NFGTVPLLTNKNTGTQYYGGMVTDADGNQTVDDQAIA<br>FSSDKNALYNDISMKYYLLRNISNVQVDILDGQGNKV<br>TTLSSSTNLTKTYYNAHSQQYIYYHAPAWDGTYYDQR<br>DGNIKTADDGSYTYRISGVPEGGDKRQVFDVPFKLDS<br>KAPTVRHVALSAKTKNGKTQYYLTAEVKDDLSGLDAT<br>KSVKTAINEVTNLDATFTDAGTTADGYTKIETPLSDE<br>QAQALGNGDNSAELYLTDNASNATDQDASVQKPGSTS<br>FDLIVNGSGIPDKISSTTTGYEANTQGGGTYTFSGTY<br>PAAVDGTYTDAQGKKHDLNTTYDAATNSFTASMPVTN<br>ADYAAQVDLYADKAHTQLLKHFDTKVRLTAPTFTDLK<br>FNNGSDQTSEATIKVTGTVSADTKTVNVGDTVAALDA<br>QHHFSVDVPVNYGDNTIKVIATDEDGNTTTEQKTITS<br>SYDPDMLKNPVTFDQGVTFGSNEFNATSAKFYDPKTG<br>IATITGKVKHPTTTLQVDGKQIPIKDDLTFSFTLDLG<br>TLGQKPFGVVVGDTTQNKTFQEALTFILDAVAPTLSL<br>DSSTDAPVYTNDPNFQITGTATDNAQYLSLSINGSSV<br>ASQYADININSGKPGHMAIDQPVKLLEGKNVLTVAVT<br>DSEDNTTTKNITVYYEPKKTLAAPTVTPSTTEPAQTV<br>TLTANAAATGETVQYSADGGKTYQDVPAAGVTITANG<br>TFKFKSTDLYGNESPAVDYVVTNIKADDPAQLQAAKQ<br>ALTNLIASAKTLSASGKYDDATTTALAAATQKAQTAL<br>DQTNASVDSLTGANRDLQTAINQLAAKLPADKKTSLL<br>NQLQSVKDALGTDLGNQTDPSTGKTFTAALDDLVAQA<br>QAGTQTDDQLQATLAKILDEVLAKLAEGIKAATPAEV<br>GNAKDAATGKTWYADIADTLTSGQASADASDKLAHLQ<br>ALQSLKTKVAAAVEADKTVGKGDDTTGTSDKGSGQGT<br>PAPATGDTGKDKGDEGSQPSSGGNIPTNPATTTSTSA<br>DDTTDRNGQHTTGTSDKGGGQGTPAPATGDTGKDKGD<br>EGSQPSSGGNIPTNPATTTSTSADDTTDRNGQHTTGT<br>SDKGGGQGTPAPATGDTGKDKGDEGSQPSSGGNIPTN<br>PATTTSTSTDDTTDRNGQHTTGKGALPKTGETTERPA<br>FGFLGVIVVILMGVLGLKRKQREE |
| 11 | Cluster: Uncharacterized protein | T0V9Y4 | MRAAEGLFVYNKTNFHYLPQNIAFADFKSGKFATSGM<br>SMILIDSVNHRILDVMKDRGAGQLRAYFNQYSPSARA<br>AVKTITVDLFTPYRAMIKDLFPNANIVADRFHVVTQA<br>YRELNKVRISVMKQFGSDSKEYRQLKRFWKLLMKHEN<br>ALDYMTSKNRINFKHAYLTDKEVIDRLLALSDELRDA<br>YAFYQVIL |
| 12 | Cluster: Uncharacterized protein | T0UTW8 | MDNDIRILIGLTDLNIDFDAKAEQHFNETNLNGTAPI<br>TWNLLLTYATNCEKFGTPMVHNGIKMVTHKGPRIAFK<br>FQNYRIRKQKFL |
| 13 | Cluster: Uncharacterized protein | T0UZT2 | MIENTINIAYARKFYKTKDYHSFCNLIKGNKGLFGNK<br>TVNQKANISFVKSEGEKHTHIYLDYQETCKVAHPNFL<br>QLINLLKNYDPEFSEEKLPTFDLNDKIFGEYEIKVIP<br>ISKTKIVNTIDDVMNEIAKEIVLKYNQDMFKVTSKLG<br>EISLTPIQEKFDKLKDI |
| 14 | Cluster: RepB | Q9AIQ4 | MIIPEKQNKQKQVLTLNELEKRKVVEHNALIQSVAKM<br>QKTALKMFELAVSCIDTEEPPKNNTVYLSKSELFKFF<br>EVSSSSKHSQFKEAVNYMQKQAFFNIKADKKLGIEYE<br>SIVPIPYVKWNDYNDEVTIRFDQAIMPYLIDLKAEFT<br>QYKISELQKLNSKYSIILYRWLSMNYNQYEHYSVKGG<br>RRADQVEAYRTPSIKVKELREITDTINEHQHFPHFET<br>RVLKKAIEEINAHTSFNVTYEKVKKGRSIDSIVFHIE<br>KKRMADDNSYKLEDKVYQEDKARKAETEKDLVFQAMQ |

TABLE 1-continued

Exemplary *Lactococcus lactis cremoris* Strain A Proteins

| SEQ ID NO. | name | uniprot_id | Protein Sequence |
|---|---|---|---|
| | | | SPYTRLLIENMFLNVYETTDSQIMAGLQKNVYPLYDE LKELRGLNGVKDHLSYVSSKQEAYSKRNVAKYLKKAI EQYLPTVKRQDLNHE |
| 15 | Cluster: Uncharacterized protein | Q8BLH6 | MSEDLKTIKELADELGVSKSYVDKIIRILKLHTKLDK VGNKYVISKKQEKSIITRIENSKSTTETHTESTTQSH TKVDAEVDFLKEEIAYLKSNHDKQLTNKDKQIETLSN LLDQQQRLALQDKKWLEEYKAEINDLKALKMPSEDTK EEQSNYRSLEKEKDFVQTIQESYESEIKVLNQKLAEQ EEQIQEIQKEKETKEKKWFQFWK |
| 16 | Cluster: RecC | O05547 | MAQTFDRKILRALQDNGVREIRAYEVVSKRLTIFQTD RGTFKYSDSLYRLVAPRQELWRNCTTGFISEEKYHFY KK |
| 17 | Hypothetical protein | | MNHFKGKQFKKDVIIVAVGYYLRYNLSYREIQELLYD RGINVCHTTIYRWVQEYSKVLYHLWKKKNRQSFYSWK MDETYIKIKGRWHYLYRAIDADGLTLDIWLRKKRDTQ AAYAFLKRLHKQFGQPRVIVTDKAPSIGSAFRKLQSN GLYTKTEHRTVKYLNNLIEQDHRPIKRRNKFYRSLRT ASTTIKGMETIRGIYKKNRRNGTLFGFSVSTEIKVLM GILA |
| 18 | Cluster: Replication protein | Q52233 | MKEYFQGDEFKDISKNGKDRKWKERKINNLNLAKIFD SLDYPDSFIFNIKSCAEYLNFKRSSDGSLRLFQMYTC KNKQCAICSWRRSMKYQVQISKIVEEAMIRKPKGRFL FLTLTVENVSGEGLNNELSLLSEAFNRLMKYKKVSKN ILGFLRATEVTINESMDTYHPHIHVLLFISPTYFKNK NNYISQDEWTELWKKSAKLDYRPIVDVRSIKPKNEKT SDIRSAILETAKYPVKPMELNYDSAKVVDDLQKGLYR KRQIAFGGLFKQIKKELELDDIENGDLINIGDEENPI SDGEIISVLWNHERQNYYVR |
| 19 | Cluster: Uncharacterized protein | T0VLA4 | MINYQGEDFTETEFYGREILEAIQLTNKFPTPKKVLI DMLEEMIHEQLDFIDKEELNNYINAKKYVQTLTEDEV KNLCFEVKDLYEDVLKEFEIKL |
| 20 | Cluster: Uncharacterized protein (Fragment) | T0VQK1 | MTCSNLTIHLHAKNRSKLFGSKKYALQELEAESTAFV VANHLNIDTKDYSIGYLNSWGFDKISDEQLENVIKND KLSNNKIKGENE |

TABLE 2

Selected membrane associated *Lactococcus lactis cremoris* Strain A Proteins

| SEQ ID NO. | name | uniprot_id | Protein Sequence |
|---|---|---|---|
| 21 | ESAT-6_ secretion_ accessory_ factor_EsaA | Q2G188 | MMLKKEWQAILKHKFFIIVIIALALVPAIYNYIFLGS MWDPSGKLNDLPVAVVNLDKTSELNGKKFKLGDDVIT EMKKSKDLDYHFVSKDKASEGIKKGDYYMVITFPENF SENATTLMNKEPKTVQLDYQTTRGHNYISSKMSESAM NQLKSEVSKNITQTYTKTRIAS |
| 22 | Foldase_ protein_PrsA | P0C2B5 | MKKKMRLKVLLASTATALLLLSGCQSNQTDQTVATYS GGKVTESSFYKELKQSPTTKTMLANMLIYRALNHAYG KSVSTKTVNDAYDSYKQQYGENFDAFLSQNGFSRSSF KESLRTNFLSEVALKKLKKVSESQLKAAWKTYQPKVT VQHILTSDEDTAKQVISDLAAGKDFAMLAKTDSIDTA TKDNGGKISFELNNKTLDATFKDAAYKLKNGDYTQTP VKVTDGYEVIKMINHPAKGTFTSSKKVLTASVYAKWS RDSSIMQRVISQVLKNQHVTIKDKDLADALDSYKKLA TTN |
| 23 | PIII- type_proteinase | P15292 | MQRKKKGLSFLLAGTVALGALAVLPVGEIQAKAAISQ QTKGSSLANTVTAATAKQAATDTTAATTNQAIATQLA AKGIDYNKLNKVQQQDIYVDVIVQMSAAPASENGTLR TDYSSTAEIQQETNKVIAAQASVKAAVEQVTQQTAGE SYGYVVNGFSTKVRVVDIPKLKQIAGVKTVTLAKVYY PTDAKANSMANVQAVWSNYKYKGEGTVVSVIDSGIDP THKDMRLSDDKDVKLTKSDVEKFTDTVKHGRYFNSKV PYGFNYADNNDTITDDKVDEQHGMHVAGIIGANGTGD DPAKSVVGVAPEAQLLAMKVFTNSDTSATTGSDTLVS |

TABLE 2-continued

Selected membrane associated *Lactococcus lactis cremoris* Strain A Proteins

| SEQ ID NO. | name | uniprot_id | Protein Sequence |
|---|---|---|---|
| | | | AIEDSAKIGADVLNMSLGSDSGNQTLEDPEIAAVQNA<br>NESGTAAVISAGNSGTSGSATEGVNKDYYGLQDNEMV<br>GTPGTSRGATTVASAENTDVITQAVTITDGTGLQLGP<br>ETIQLSSNDFTGSFDQKKFYVVKDASGNLSKGKVADY<br>TADAKGKIAIVKRGELTFDDKQKYAQAAGAAGLIIVN<br>NDGTATPVTSMALTTTFPTFGLSSVTGQKLVDWVTAH<br>PDDSLGVKIALTLVPNQKYTEDKMSDFTSYGPVSNLS<br>FKPDITAPGGNIWSTQNNNGYTNMSGTSMASPFIAGS<br>QALLKQALNNKNNPFYAYYKQLKGTALTDFLKTVEMN<br>TAQPINDINYNNVIVSPRRQGAGLVDVKAAIDALEKN<br>PSTVVAENGYPAVELKDFTSTDKTFKLTFTNRTTHEL<br>TYQMDSNTDTNAVYTSATDPNSGVLYDKKIDGAAIKA<br>GSNITVPAGKTAQIEFTLSLPKSFDQQQFVEGFLNFK<br>GSDGSRLNLPYMGFFGDWNDGKIVDSLNGITYSPAGG<br>NFGTVPLLTNKNTGTQYYGGMVTDADGNQTVDDQAIA<br>FSSDKNALYNDISMKYYLLRNISNVQVDILDGQGNKV<br>TTLSSSTNLTKTYYNAHSQQYIYYHAPAWDGTYYDQR<br>DGNIKTADDGSYTYRISGVPEGGDKRQVFDVPFKLDS<br>KAPTVRHVALSAKTKNGKTQYYLTAEVKDDLSGLDAT<br>KSVKTAINEVTNLDATFTDAGTTADGYTKIETPLSDE<br>QAQALGNGDNSAELYLTDNASNATDQDASVQKPGSTS<br>FDLIVNGSGIPDKISSTTTGYEANTQGGGTYTFSGTY<br>PAAVDGTYTDAQGKKHDLNTTYDAATNSFTASMPVTN<br>ADYAAQVDLYADKAHTQLLKHFDTKVRLTAPTFTDLK<br>FNNGSDQTSEATIKVTGTVSADTKTVNVGDTVAALDA<br>QHHFSVDVPVNYGDNTIKVIATDEDGNTTTEQKTITS<br>SYDPDMLKNPVTFDQGVTFGSNEFNATSAKFYDPKTG<br>IATITGKVKHPTTTLQVDGKQIPIKDDLTFSFTLDLG<br>TLGQKPFGVVVGDTTQNKTFQEALTFILDAVAPTLSL<br>DSSTDAPVYTNDPNFQITGTATDNAQYLSLSINGSSV<br>ASQYADININSGKPGHMAIDQPVKLLEGKNVLTVAVT<br>DSEDNTTTKNITVYYEPKKTLAAPTVTPSTTEPAQTV<br>TLTANAAATGETVQYSADGGKTYQDVPAAGVTITANG<br>TFKFKSTDLYGNESPAVDYVVTNIKADDPAQLQAAKQ<br>ALTNLIASAKTLSASGKYDDATTTALAAATQKAQTAL<br>DQTNASVDSLTGANRDLQTAINQLAAKLPADKKTSLL<br>NQLQSVKDALGTDLGNQTDPSTGKTFTAALDDLVAQA<br>QAGTQTDDQLQATLAKILDEVLAKLAEGIKAATPAEV<br>GNAKDAATGKTWYADIADTLTSGQASADASDKLAHLQ<br>ALQSLKTKVAAAVEADKTVGKGDDTTGTSDKGSGQGT<br>PAPATGDTGKDKGDEGSQPSSGGNIPTNPATTTSTSA<br>DDTTDRNGQHTTGTSDKGGGQGTPAPATGDTGKDKGD<br>EGSQPSSGGNIPTNPATTTSTSADDTTDRNGQHTTGT<br>SDKGGGQGTPAPATGDTGKDKGDEGSQPSSGGNIPTN<br>PATTTSTSTDDTTDRNGQHTTGKGALPKTGETTERPA<br>FGFLGVIVVILMGVLGLKRKQREE |

TABLE 3

Exemplary *Lactococcus lactis cremoris* proteins not found in *Lactococcus lactis cremoris* Strain A

| SEQ ID NO. | name | uniprot_id | Protein Sequence |
|---|---|---|---|
| 24 | Cluster: Transposase | J7TTI4 | MTQFTTELLNFLAQKQDIDEFFRTSLETAMNDLLQA<br>ELSAFLGYEPYDKVGYNSGNSRNGSYSRQFETKYGT<br>VQLSIPRDRNGNFSPALLPAYGRRDDHLEEMVIKLY<br>QTGVTTREISDIIERMYGHHYSPATISNISKATQEN<br>VATFHERSLEANYSVLFLDGTYLPLRRGTVSKECIH<br>IAHLALHQKDRRLFLDMKSPQMKTMLLGPPC |
| 25 | Cluster: Transposase | T0USG6 | MQKRYSKEFKETLIVFYHSGQSVTQLSKEYDVAPAT<br>IYKWIDLYSKSNESSVSKADFLELKRQLAKVKEERD<br>ILKKY |
| 26 | Cluster: Transposase | A0A1V0NYX4 | MTYNSTLPKVFVYLLTTIETLYQTRVPLEVQNRKNV<br>HLATSDCLVIACYLWGVLHFSETLKAKHQLAQSLFP<br>NFLEYYRFVRRCNALLPSIQVIRQALVFKEVEGMSV<br>SIIDSFPIPLCQPIRNFRSKVLGDYANVGYNATKGQ<br>YFYGCKCHALVSESGYVIDYTITPASMADSSMTEEV<br>LNQFGTPTVLGDMGYLG |

TABLE 3-continued

Exemplary *Lactococcus lactis cremoris* proteins not found in *Lactococcus lactis cremoris* Strain A

| SEQ ID NO. | name | uniprot_id | Protein Sequence |
|---|---|---|---|
| 27 | Cluster: Transposase IS1077 (Fragment) | T0UZJ0 | MISYHISKQPSYQSIDIALNQALAVTSDCPYRRTFH SDQGWGYQMRDYVSKLKSHRIFQSMSRKGNCHDNSV MENFFGLLKQEIYYGHIFSSFEELEQVIVIWIRYYN TKRIKQKLNWMSPIQFRLNYQNN |
| 28 | Cluster: Penicillin-binding protein 2A | S6EVX7 | MPENKNFSRRSKKETGKKSLKIPKIRPKKQKNLKK |
| 29 | Cluster: Transposase | G8P734 | MKVTGFPKATYYYWVNCFERVNKDELIEKEMLKIRQ EHANAGYRPMSELLKQRGYHVNHKKVQPLMKKLGLR VTSYWHKSRKYNSYKGNVGTVAKNKLHRRFRTSIPH QKITTDTTEFKYYEDGIQKKCYLNPYIDLFNSEVIS YHISKQPSYQSIDIALNQALAVTSDCPYRRTFHSDQ GWGYQMRDYVSKLKSHRIF |
| 30 | Cluster: Transposase | A0A1V0PJ39 | MAKNKLHRRFNTSIPHQKITTDTTEFKYYDKGVQKK LYLTPYLDLFNNEVISYEISKQPTYQAIATALQEAL ELTSDCLYRRTFHSDQGWAYQMKNYVFKLKSQKIIQ SMSRKGNCHDNSVMENFFGLLKQEIYYGHVFNSFEE LEQAITKWIHYYNTKRIKKKLNWMSPIQYRLTYSK |
| 31 | Inner_member_ protein_YbiR | P75788 | MEHSATQRESQKIWTAIKNWFLVDKVFLISFIIAII AISLGGVTTRFFNYHVIVTVSGLMLVIGGFKETGLL QYLGQTLVKRSTTTRQLVRFTTLLTFFLAVFFTNDL TILTVLPLYLAITKEIKNRKSVYIGAALIVPACHIG SALLPQGNPHNLYLYSFYKVAAHHGGVPLTNLDFFK GTGALWILGLLILMIACQFIDNEPLVIETKVNQFNK VETSIFVVLMLLMAASVFGYVNFYLAGAVVALVVLI YRPRLFKGIDYHLLFTFIFFFLIVGNIANIHVLTDF ISNTLVGPQASFLGTVIMSQFISNIAAPILISPFTP HAVSLVLGADIGGIGTIVSSMATLIAYKVIRMNARG ETRGFVKYFIIVNAGFVLILTLIGLIIVTLVG |
| 32 | Cluster: Transposase | G8PA31 | MTYNSTLPKVFVYLLTTIDTLYQTRVPLEVQNRKNV HLATSDCLVIACYLWGVLHFSETLKAKHQLAQSLFP NFLEYSRFVRRCNALLPSIQVIRQALVFKEVEGMSV SIIDSFPIPLCQPIRNFRSKVLGDYANVGYNATKGQ YFYGCKCHALVTVNQAMS |
| 33 | Cluster: Transposase for insertion sequence element IS982B | A0A1V0PFP4 | MAQSLFPNFLEYYRFVRRCNALLPSIQVIRQALVFK EVEGISVSIIDNFPIPLCQPIRNFRSKVLGDYANVG YNATKGQYFYGCKCHALVTVNQAMS |
| 34 | Cluster: Transposase | A0A0E2QIB2 | MARRKFDKQFKNSAVKLILEEGYSVKEVSQELEVHA NSLYRWV |
| 35 | Cluster: Replication protein | G0WKP8 | MQSYDLLDELDSEDKFRKDIKYSRQLPEMFSTEDIN AASENITYAILGELRDRYNGSEPVTFSYQELAELGG LWVTRKNGVKSLYNGKRLQKIMYDLNEALKNFSYYQ VRETNDDGTPKSWKTINIFSVIDFDGTKKEVKLTIS NAQISSEQVDAKGHVIDKPLYVYDLINSKDWRTVKH LQYNRGINNSLPSKYSKRVYRFISEFRSFPKGTKMR IDDFDKKILKILKTQEDSFNTKEVFDLRKNRKKYLE TAVKEISELNTPEGTQIVKNLDYIYHTSGRRIQSIE FTYTPFNADLSGSNHISMNSRTSSPGTDSPFINEAR MVLEYFNYLSKVNFNLDENGIIKHLPNYYDIQFELD DIQLLQPIHKLLESGVAIDELLQVAEMKAIDWKLDS NQMINNFRPSVVFGNKFSEYRAFLTTYKAQNIHKLV FDSSSDFYVPMNGPWDSK |
| 36 | Cluster: Transposase for insertion sequence element IS982B | G0WKP9 | MTYNSTLPKVFVYLLTTIETLYQTKVPLEVQNRKNV HLATSDCLVIACYLWGVLHFSETLKAKHQLAQSLFP NFLEYSRFVRRCNALLLSIQLIRQALVFKEFEGIDV SIIDSFPIPLCQPIRNFRSKVLGDYANIGYNATKGQ YFYGCKCHALVSESGYVIDYVISPASIADSTMAEEV LSQFGTPIVLGDMGYLGQVLHDRLELKEIELITPVR MNMKKKDITFPNFSKRRKVIERVFSFLTNLGAERCK SRSSYGFLVKLEMTLLTYSLILKSAKTVNSMTLRYS TGYQVMAE |

TABLE 3-continued

Exemplary *Lactococcus lactis cremoris* proteins not found in *Lactococcus lactis cremoris* Strain A

| SEQ ID NO. | name | uniprot_id | Protein Sequence |
|---|---|---|---|
| 37 | Cluster: Uncharacterized protein | A0A0V8DWK8 | MEKVTDEIKNVVQRLLDDDENFSGWYIEKELEKIGIKVSRMTISNLRNKKTTLGNTKFETLEGLYHFAKTHENINKE |
| 38 | Sporulation_inhibitor protein_Soj | P37522 | MKTISLLNLKGGVAKTTTGGNIAKGLANRGFKTLLIDTDMQANATSIFLEDKRSKEDYKGFAELIVDEKLDDVDQYVYNVSENLDMIGSSLAVAESELKVRNSFNRNSSNIVKKVLKKLDSKYDYCIIDCAPTINLITLNIIIASDEIIIPIKIDKFALEGYRTTLKNINQIIDDYELDTEVTVLYTMVNRNNIDKQFIQEISGNRFETTIRHQAKPVTESALKNEVLIDSSKSSKVKDDYLNLIDEIVKRG |
| 39 | Nucleoid_occlusion_protein | MF_02015 | MSNSFGFTDLMNKDEHKRKKTNTKNIPIEEIKENENNNYDLVDIDKLADSIDELGLLQPVLVKQRDKYSYELIAGHRRFNAIKKLISENRLPEDYEVLAKKVDEDEDELVTRLKLHETNLQTRSLLKMPEEEKIAIIDDYMDILDKAKKQGLQINGKPVKGKTRDLIAERFGISHYTAQKLIRKAKEQGGEEEGAKISPQKKTAKKPITQLKKIETQLEKLEFEGTEEEQEIKKKLIELLMK |
| 40 | Cluster: Uncharacterized protein | Q2VHI9 | MSVDRSYSPYEVIRAYHDRGMMKWGAFATGELTEAQNTFEKEKKDDKVIQTLPHHVVLHLLNQSFSNQVQIKVKYQSKDKLTEVYGFVSEFINNQVRVKSTDKIYLISIEQIINIS |
| 41 | DNA_polymerase_IV_1 | P9WNT3 | MEQLKLNKYFDYSLEPRRAILFQDVKSNYASIECVQRNLNPLTTSLCVMSRADHSKGLTLASSPTFKKVFGMKNVSRASDLPFLIETRKFNYPQWYRTHTDIHGQRTEPTLQYVAFIESWAKRTWIVPPQMQLYVDYKIEVTDILTNYTSIDEIHSYSIDESFLDITESLNFFYPEIKNRYEQMNRIALDLQREIRDKLGLYVTVGMGDNPLLAKLAMDNYAKHNDNMRALIRYEDVPNKLWTIPKMTDFWGIGKRTEKRLNKLGITSIKELANADPLLLKQKLGTIGLQHFFHANGIDESNVREKYTPKSTSFSNSQILPRDYHKQREIELVIKEMAENLAIRLRKGGKLASNLSLYAGAASTSEYSSVKVSRNIEATQNTKELQDLAISLFREKYQGGAIRQIGISGNQLSDSSVKQLSLFESVQENQTNKKQESLQKAIDEIRETFDFLSIQKASSLSEGSRVIYRNKLIGGHAASQDKEEKDVS |
| 42 | Cluster: Uncharacterized protein | G8P9Y4 | MDKYIRRAYQRMNQMSFGGQALAWFLSIRLSDLVLKK |
| 43 | Cluster: HsdR type I restriction enzyme R protein | A0A1V0P5K1 | MAEAKFEAALIKKLEAEGVVTYRKDLSYVSIKVLEGHWREVLNENNAYKLNGKPLSDVEFGLVIQEVQRIKTPYDAQLLLVGAGGVGSIPITRDDGSNLEVWTNVKYLDTK |
| 44 | Cluster: Transposase TnpA | G8P9Y1 | MIFKLRNRTEIAINKRKPKEPIIFHSDHGSHFKSASFRKLLDEHQLLASYSKPGYPYGNAVTEVFFKYLKHREINRRTYHSIQEVQLSCFEYIEQFYNNYNPHSANNGLTPN |
| 45 | | nan | MKVTGFPKATYYYWVNCFERVNKDELVEKEMLKIRQEHANAGYRPMSELLKQRGYHVNNKKVQRLMKKLGLRVTSYWHKSRKYNSYKGNVGTVAKNKLHRRFRTSIPHQKITTDTTEFKYYEDGIQKKCYLNPYIDLFNSEVISYHISKHPSYQSIETALNQALAVTSDCPYRRTFHSDQGWGYQMRDYVSKLKSHRIFQSMSRKGNCHDNSVMENFFGLLKQEIYYGHIFSSFEELEQVIVIWIRYYNTKRIKQKLNWMSPIQFRLNYQNN |
| 46 | | nan | MVKYSIELKQRVIQDYLSGKGGSTYLAKLHNVGSSSQVRRWIRNYRAEGLHTAHSKVNKNYSMELKENAVQCYLTTDLTYEAVARKFEITNFTLLASWVNHFKIYGEVPISKKRGRRKKLESIASSMTQNPNDSQRIKELEQELRYAQIEVAYLKGLRRLEKNALMNKNQDSSTVSVKPSNSKKS |
| 47 | | nan | MKHHGKIKIKHAVKVLKVSRSGFYEYMHRRPSKQQVEREILSEKIKAVFHEHKGRYGAVRITKVLHNTGIMTNTKRVGKLMHLMGLYAKGSRYKYKHYNRKGASLSRPNLINQIFKATAPNKVWLGDMTYIPTKEGTLYLAVNIDVFSRKIVGWSMSSRMQDKLVRDCFLQACGKEHPQP |

TABLE 3-continued

Exemplary *Lactococcus lactis cremoris* proteins not found in *Lactococcus lactis cremoris* Strain A

| SEQ ID NO. | name | uniprot_id | Protein Sequence |
|---|---|---|---|
| | | | GLIVHTDQGSQYTSSRYQSTLRQVGAQSSMSRKGNP YDNAMMESFYKTLKRELINDAHFETRAEATQEIFKY IETYYNTKRMHSGLDYKSPKDFEKYNS |
| 48 | Cluster: Transposase | A0A1V0PDS7 | MNHFKGKQFKKDVIIVAVGYYLRYNLSYREVQELLY DRGINVCHTTIYRWVQEYSKVLYDLWKKKNRQSFYS WKMDETYIKIKGRGHYLYRAIDADGLTLDIWLRKKR DTQAAYAFLKRLHNQFGEPKAIVTDKAPSLGSAFRK LQSVGLYTKTEHRTVKYLNNLIEQDHRPIKRRNKFY QSLRTASSTIKGMETLRGIYKKNRRNGTLCSDPQNI DFSNLYFWKGYNKLDTKLREIVERFIMARRKFDKQF KNSAVKLILEEGYSVKEVSQELEVHANSLYRWVQEV EEYGESAFPGNGTALADAQHKIKLLEKENRYLQEEL ELLKKFRVFLKRSK |
| | tRNA-Met | nan | RNA |
| 49 | Cluster: Cold-shock protein | D2BMP1 | MKTGDKITLSNGEQATVVSGDINLYKYALIVELENH DVRVVDRETLTLAKENPHENLGNHKKINKF |
| 50 | Cold_shock-like_protein_CspLA | P0A355 | MNKGTINWFNADKGYGFIMADDMQDVFAYLLSIQGN DFKKYDEGQKVTFDIKMTSRGRYASNVHKR |
| 51 | Cold_shock_protein_2 | P96349 | MANGTVKWFNADKGFGFITSEEGKDLFAHFSAIQSD GFKTLDEGQKVEFDVEEGQRGPQAVNITKA |
| 52 | Cluster: Uncharacterized protein | Q2VHI5 | MARRKFDKQFKNSAVKLILEEGYSVKEVSQELEVHA NSLYRWVQEVEEYGESAFPGNGTALADAQHKIKLLE KENRYLQEELELLKKFRVFLKRSK |
| 53 | | nan | MKHHGKIKIKHAVKVLKVSRSGFYEYMHRRPSKQQV EREILSEKIKAVFHEHKGRYGAVRITKVLHNTGIMT NTKRVGKLMHLMGLYAKGSRYKYKHYNRKGASLSRP NLINQIFKATAPNKVWLGDMTYIPTKEGTLYLAVNI DVFSLKIVGWSMSSRMQDKLVRDCFLQACGKEHPQP GLIVHTDQGSQYTSSRYQSTLRQVGAQSSMSRKGNP YENAMMESFYKTLKRELINDAHFETRAEATQEIFKY IETYYNTKRMHSGLDYKSPKDFEKYNS |
| 54 | Cluster: DNA-directed DNA polymerase | A0A0V8EKB0 | MLENEYFVFTSTLTTMIRKQAQSIITGLKGHNQNSV TKNTTRLVTGYFPIDLIKGYRPSQKLSEAKQAEQRG QQIIMMTEKQFIDFLAQSFYLLSQGL |
| 55 | Cluster: Uncharacterized protein | A0A0V8EK89 | MKLREIIKEIPDDDWLEIIEQSSINYRSFIGRAPKK YIVGELLDYEALYIGEVKKNKNYQNHRFLVEDKFIE HSGR |
| 56 | Cluster: Uncharacterized protein | A0A1V0PE50 | MKKTIIFILHIPFILLLWLCITSPFFIKNSLLNSSF GHIFKGVENISHSGPLATVLLLFVIPLLSLISCLYL AFKKNQSGRKYVIYILMSLFSLVCLSVFSVIMIIGL GNYL |
| 57 | | nan | MNHFKGKQFKKDVIIVAVGYYLRYNLSYREVQELLY DCGINVCHTTIYRWVQEYSKVLYDLCKKKNRQSFYS WKMDESYIKIKGRGHYLYRAIDADGLTLDIWLRKKR DTQAAYAFLKRLHKQFGEPKAIVTDKAPSLGSAFRK LQSVGLYTKTEHRTVNYLNNLIEQDHRPIKRRNKFY QSLRTASSTIKGMETLRGIYKKNRRNGTLFGFSVST EIKVLMGITA |
| 58 | Cluster: Uncharacterized protein | G8P9W7 | MKTQELNLKQFVMLSEKELQEISGGGGWGSAFAGWL GGIGVNSGQTAQQVVNQLNGVTDFHAYNHNPYGSGG TPND |
| 59 | Cluster: Uncharacterized protein | Q2VHK7 | MFTLIFSNLTGGIIIKAIYKDKTVDVWEISKNNEQP DWVKNAFKENYLSWYDERLKILMNGIKPSAKSSLKL GIMGSVAGSLAGGLAGNNIYVMGEIGDYLDITNRKV VSKEKFLKKYSV |
| 60 | Cluster: Uncharacterized protein | Q2VHK6 | MKYFVTFLSPTQNMGILNWQTMILDDYLVDDSYWEN TKLELSKEVEWITQSELYKKVKRNDGSGNDIILSVP VSAVLETIKSFFILGHS |

TABLE 3-continued

Exemplary *Lactococcus lactis cremoris* proteins not found in *Lactococcus lactis cremoris* Strain A

| SEQ ID NO. | name | uniprot_id | Protein Sequence |
|---|---|---|---|
| 61 | Transcriptional_ regulator_ AcuR | Q3J6K8 | MRNTKEKILTATEQLIYKKGYTGTSINDILDETATG KGQFYYYFDSKKEACLAVIDNHVKIWQKHLLNGILS RDESPLANLKEMLDWIYSDHAQKKIYYGCPVGNLVI ELSALDEDFRKPLEQLFSDLQKKIAENLSGLTGLLV KQNLPAAHAIIAQIQGSLLLLKVTQDLNVLESNFDL LKTIFEKVGEK |
| 62 | Cluster: Uncharacterized protein | Q2VHK4 | MKKLDMIVIGPGPAPPTAVIRRKSLCQQLNLKKKSK LLQVDAIRREYTIADVQKRWQSCQTFIDVLRKGILK QLIAELS |
| 63 | Cluster: Transposase | A0A0D6E0F2 | MQNNYTSKGKHLTESERLLIERWHNKEKVSNREIAY RLGKAPQTIHNEIQRGTVQLKYKTKYSAKIAQESYK TLRTHSKRSTKLNAQLDDQISKAVKNKISLEVIHQE LKGVVCLRTLYNWISSGILSVAYHELLYPQYRKPKK QRVTQPKHMLGQSIEERPESVDERSEYGHWEIDTVL LTKEKGECLLTLTERKTRLEIIRLIPNKTTHSVNQA LRGIEFLALSVTSDNGREFAKLSEALDCPVYYCHAY ASHERGTNENHNRMIRRHLPKGTKKTTKQVVAYIEN WMNNYPRKMFNFKTPNQMLIESI |
| 64 | Isochorismatase_ family_ protein_ YecD | P0ADI7 | MFNNKNTAFVVTDPQVEFLKPKGAGYGLTKDILRKY HTTENLTELFKHAKAKGYKIFISPHYFYDHDQNWKF GGQGEQMMLNNKMFHREHQYQETVKGSGADFVEELK PYLDENTIITSPHKIFGPESNDLALQLRKNGIDTVI LAGMNANLCVDSHLRELVESGFHVHVAADATGAPGQ EAYDAAITNFGFVADRTMSTAKVLEEL |
| 65 | putative_ pyridine_ nucleotide- | P77212 | MKKIDVKNIVVGFGKGGKTLAKFLSGKGESVVVIEQ STLMYGGTCINIGCIPSKFLIVNGEKGLKFTEASEK KAMLTGNLNLKNYHMIADEATAEVIDGKAKFVSDHE IEVMDAEGEVIAQLIGERIFINTGATPVLPPIPGLV DSRNVVTSTELMDLKQLPEHLTIIGSGYIGLEFASM FASYGSKVTVLDIFDNFLPRDDEDISKLVRSDLESR GIIFKLGVKIDAITDNSVEIINKEGKKVSILSDKIL VATGRKPNTAGLGLENTNIQLGQRGEIVVNDKLETT VQNVWALGDVHGGLQFTYTSLDDFRIVSNNLYGDGK RSLSDRKNVPTSVFITPALSKVGLNEKDAKAAGIDY RLFKLAATAIPKSAVLNQSKGLLKALVDPETDKILG ITIYAEESYETINLVSLAIEVGLPYTLLRDKIYTHP TMTEALNDLFAAKNEVK |
| 66 | | nan | MELKENAVQCYLTTDLTYEAVARKFEITNFTLLASW VNHFKIYGEVPISKKRGWRKKLESIASSMTQNPNDS QRIKEPEQELRYAQIEVAYLKGLRRLEKNALMNKNQ DSSTVSVKPSNSKKS |
| 67 | Cluster: Transposase | G8P734 | MKVTGFPKATYYYWVNCFERVNKDELIEKEMLKIRQ EHANAGYRPMSELLKQRGYHVNHKKVQPLMKKLGLR VTSYWHKSRKYNSYKGNVGTVAKNKLHRRFRTSIPH QKITTDTTEFKYYEDGIQKKCYLNPYIDLFNSEVIS YHISKHPSYQSIDIALNQALAVTSDCPYRRTFHSDQ GWGYQMRDYVSKLKSHRIF |
| 68 | Cluster: Transposase | I7LSK3 | MSHKGNCQDNSVMENFFGLLKQEIYYGHIFSSFEEL EQVIVIWIRYYNTKRIKQKLNWMSPIQFRLNYQDN |
| 69 | | nan | MTYNSTLPKVFVYLLTTIETLYQTRVPLEVQNRKNV HLATSDCLVIACYLWGVLHFSETLKAKHQLAQSLFP NFLEYSRFVRRCNALLPIIQVIRQALVFKEVEGMSV SIIDSFPIPLCQPIRNFRSKVLGDYANVGYNATKGQ YFYGCKCHALVSESGYVIDYTITPASMADSSMTEEV LSQFGTPTVLGDMGYLGQSLHDRLELKEIDLMTPVR KNMKQKKILFPNFSKRRKVIERVFSFLTNLGAERCK SRSPQGFQLKLEMILLAYSLLLKSAKSLEPETLRYS IGYQVMAK |
| 70 | Putative_ phosphatase | Q5XD45 | MIKLVAIDLDGTLLDPNRQITAEVKTAVKKAKAAGV KIVITTGRPLPGVVDILKALELTDQSDYVITYNGGL VQQATGEEFIKETLSSEDWLDLDAAARKIGLPIHAI TREGIYTPNHDVGRYTVQEAQMVKMPLYIRQPEDIA ALEIAKVMMVDEPAALDDGIAYLPFEFFERYNVVKS TPFYLEFMNKKASKGSAVQHLAEKLSFDLDEVMAIG DEENDRSMLEVAVCSVVMENGKSKLKKIAKYVTKSN AKSGVAYAINEWVLKDYQD |

TABLE 3-continued

Exemplary *Lactococcus lactis cremoris* proteins not found in *Lactococcus lactis cremoris* Strain A

| SEQ ID NO. | name | uniprot_id | Protein Sequence |
|---|---|---|---|
| 71 | | nan | MKITFDEKTADKIKAFGDVDLVFDFDHTLSEVNTEV DACAGGISRYRIVAVEKGNVPEVFDASIDSEFGPIY YKGYGSYFFQDEMYTKINPSYNLIELHSTAELLSPN LLIVDFRGKQKAS |
| 72 | Cluster: Uncharacterized protein | T0SFW4 | MLSAGLLGIDPGHYIEHAFIGLVADKLRSFDLGVKI YESQEKTNPFYDI |
| 73 | Cluster: IS30 family transposase IS1062 | Q47803 | MTYTHLTSNELAMIEAYYNNHQSVAKTAVLLNRSRQ TIHKVYQFFKTGHNALDYFNQYKKNKTRCGRRPIVL SDEQTEYIQKRVVQGVVTPDVIVGRAEFSISCSMRT LYRMFKQGVFEVTHLPMKGKRKANGHKETRGKQSFR RSLRDRGNDYSKFNQEFGHLEGDTIVGKKHKSAVIT LVERLSKVIITLQPEGRRAIDIENRLNQWMQSVPKH LFKSMTFDCGKEFSNWKSISNINDIDIYFADPGTPS QRGLNENSNGLLRKDGLPKQMDFNEVDESFIQSIAS KRNNIPRKSLNYKTPIEVFLSHICKEELSNLI |
| 74 | Cold_shock-like_protein_CspLA | P0A355 | MANGTVKWFNATKGFGFITSEDGQDLFAHFSSIQSD GFKSLDEGQKVEFDVEEGQRGPQAVNITKA |
| 75 | | nan | MNYFKGKQFQKDVIIVAVGYYLRYNLSYREIQELLY DLGINVCHTTIYRWVQEYSKVLYHLWKKKNRPSFYS WKMDETYIKIKGRWHYLYRAIDADGLTLDIWLRKKR DTQAAYAFLKRLHKQFGQPRVIVTDKAPSIGSAFRK LQSNGLYTKTEHRTVKYLNNLIEQDHRPIKRRNKFY RSLRTASTTIKGMETIRGIYKKNRRNGTLFGFSVST EIKVLMGILA |
| 76 | Cluster: PIL7_11 | G0WKN9 | MVTYTDLLPKPTENQQAFILDHGKTEDDGQLKYADD AKSYGWNMRQYGKLKAGAVVLNRHPGKITKDRKWEI YGGGYVESVSDEDENGNVTAVITHAFTIEPPIKQGD SFIENFDWNTPNKKKRKKPNSWAYFWDQYGMNEISY TDFVGLIENRHLSPIDDTQSLPVEKDLTNAEVEEIE EASSKGFTVLVDEVGPNRPNGTQKRKFTGRHTDWER VNKAKQKTGALGEEIVLDFLIQKAEKNKTKLPEHVS KTEGDGHGYDIRAFDQSGNEIHIEVKASKTNFSDGF EMSANEVASSLEDTPYKIYFVHDLDVTSKVCKIKIY DGPFTEENFMMVPTNYKIFKK |
| 77 | Cluster: Uncharacterized protein | Q2VHL9 | MFWTNVKYLDAHILKQNEQLKYENPTEENKLKIKA LQLERKDLQAQYRKVIKKMKTYDAGQEIVQEKLKEK EINKEKTQDIPS |
| 78 | Cluster: Uncharacterized protein | S6EPX4 | MIYTIGYYIAVIGLVIMMFGFKSFYSQMNKWSRFGF IFLALGLAFPIVYDFIVGFINGLLKNVN |
| 79 | Aminodeoxy chorismate/ anthramilate_ synthase | P28819 | MKLLLIDNYDSFTYLLVQYFEELDCSVTVVNDQDKM SQKIRISPDFICENYDAITISPGPKTPKEAVFSRDV VQLYAGKIPMLGICLGQQVIAECFGGNVVLGERPMH GKISVIRHNCQGIFKGLPQNLKVARYHSLIVDKLPN DFEIDAQSEDGVIQAMHQPKLKLWALQFHPESLVTE YGHEMLNNFLKVV |
| 80 | Aminodeoxy chorismate_ synthase_ component_1 | P05041 | MKEFIIKNTDIWKIFLKYYRSDEEIVFLHSSQATEN EHYSILAHKPYKKVSKYKGQVFFNGEKKKFNFLDAV DLLKNEKVERPKNWPFYPELLGFVSYEQDPAYFAAY DEVLLFDHRTKRLRVVQFEQTDGQYWLTESEEIEVD SEIEFDGQNGIGAVFIDQTRQEYIASIKRLQDYMKA GDIYVANLTQQFEIWSDQKPIDVFKKTRNQIPAPFS SFLQYPEWKMTQISSSVERFVSIHDGALISKPIKGT IARGEDVVTDRLQKEILSNSIKERTELLMVTDLLRN DIARISQPFSLSVPKFAEIETFSHVHQLVTSIKSRI KEDLTFSEFMTALFPGGSITGTPKKRAMEIIKEVEK QPRGIYTGMQGWLSREMDLDMNIVIRTLVHDGEHYQ LGVGGGITFESEAEAEFSEILLKAKPFLDILGLKDV PSILFTTGLVKNGELLNLEGHVNRLKKQYHHPDLEE KLRKFAQNVTDGVLRVSTDGDSLNPEIRQLTHSNES YRVKLSSINDKPSPLSNFKLSGPDFQKVFRQEVLDV KKEGFQDILFHTDGLVSELSIGNFVAKKGNQYETPA KYALKGTFLDLFAKNHTLIYKDIAISDLKNYDCFYM TNAVRGLVEIKIDGISGSVAKFSKKSILV |

TABLE 3-continued

Exemplary *Lactococcus lactis cremoris* proteins not found in *Lactococcus lactis cremoris* Strain A

| SEQ ID NO. | name | uniprot_id | Protein Sequence |
|---|---|---|---|
| 81 | | nan | MNYFKGKQFQKDVIIVAVGYYLRYNLSYREIQELLYDRGINVCHTTIYRWVQEYSKVLYHLWKKKNRQSFYSWKMDETYIKIKGRWHYLYRAIDADGLTLDIWLRKKRDTQAAYAFLKRLHKQFGQPRVIVTDKAPSIGSAFRKLQSNGLYTKTEHRTVKYLNNLIEQDHRPIKRRNKFYRSLRTASTTIKGMETIRGIYKKNRRNGTLFGFSVSTEIKVLMGILA |
| 82 | Cluster: Uncharacterized protein | Q8GAR6 | MDNKDIELIQQMENKYDTFMPVLTNLIDSVEKFNSIYNNYIELRNFYGSEKWFEYMEIEKIPVKCGVLTEDQLFDMISDHNELLGVLLDLTSKMYKNF |
| 83 | Cluster: Integrase | Q7BLP2 | MVQDTLLDSFRAGRRNYTIFQVGKATLLRVSDVMKLKKTDVFNLDGTVKQTAFIHDQKTGKGNTLYLKPVQQDLMLYHAWLIQQNMNSEWLFPSTSRPYRPITEKQFYKIMARVGDLLGINYLGTHTMRKTGAYRVYTQSNYYWLSYAFIKPFK |
| 84 | | nan | MNHFKGKQFQQDVIIVAVGYYLRYNLSYREVQELLYDRGINVCHTTIYRWVKEYSKILYHLWKKKNKQSFYSWKMDETYIKIKGRWHYLYRAIDADGLTLDIWLRKKRDTQAAYAFLKRLHKQFGQPRVIVTDKAPSIGSAFRKLQRNGLYTKTEHRTVKYLNNLIEQDHRPIKRRNKFYRSLRTASSTIKGMETIRGIYKKNRRNGTLFGFSVSTEIKILMGIPA |
| 85 | Bis(5'-nucleosyl)-tetraphosphatase,_symmetrical | MF_00199 | MYNEVFVVSDIHGEYKKFKEILKYWDSNRQQLILLGDLCDRGLQSYECFYLAKYLCDNYGAILIKGNHEDLFLKFLNKTEDFKENYIKNGGLKTLESFGYSENNTFKDIVLDIKKNNDKLIEFLTYLPNFYEWNDYIFVHAGVNLKINNWKDTSIRDFMWIREDFHFTPNRLNKTIVFGHTETKILNKNNKYDIWIHDNKIGIDGGAVYGGYLYGVILDVHGIKDYVYV |
| 86 | Cluster: Uncharacterized protein | T0VLA4 | MINYQGEVFTETEFYGREILEAIQLTNKFPTPKKVLIDMLEEMIHEQLDLIDKEELNNYINAKKYVQTLTEDEVKNLCFEVKDLYEDVLKEFEIKL |
| 87 | Cluster: Molybdopterin-guanine dinucleotide biosynthesis protein MobC | T0V569 | MKKTGITNFSVFARRACCNKEIFTLDFSEYKNIISEISATKSELKRIGNNINQIAKHLNENKNNQTESLMSDYQNQLESLEEKIQKVVHYISEG |
| 88 | Cluster: Relaxase Mob DEI | Q9FB66 | MTVIYMPKQSNGTVHSAKDLKQLIDYVMNSEKTNDFEYVSGQNILDIHSTCDEMLATRTMANALKNKPQKNERFGYHFVQSFSPDDHLTPEQVHEIGCKTMKEYLGSSAEFIIATHTDKPHLHNVRPDRVLSQVV |
| 89 | Group_II_intron-encoded_protein_LtrA | P0A3U0 | MKPTMAILERISKNSQENIDEVFTRLYRYLLRPDIYYVAYQNLYSNKGASTKGILDDTADGFSEEKIKKIIQSLKDGTYYPQPVRRMYIAKKNSKKMRPLGIPTFTDKLIQEAVRIILESIYEPVFEDVSHGFRPQRSCHTALKTIKREFGGARWFVEGDIKGCFDNIDHVTLIGLINLKIKDMKMSQLIYKFLKAGYLENWQYHKTYSGTPQGGILSPLLANIYLHELDKFVLQLKMKFDRESPERITPEYRELHNEIKRISHRLKKLEGEEKAKVLLEYQEKRKRLPTLPCTSQTNKVLKYVRYADDFIISVKGSKEDCQWIKEQLKLFIHNKLKMELSEEKTLITHSSQPARFLGYDIRVRRSGTIKRSGKVKKRTLNGSVELLIPLQDKIRQFIFDKKIAIQKKDSSWFPVHRKYLIRSTDLEIITIYNSELRGICNYYGLASNFNQLNYFAYLMEYSCLKTIASKHKGTLSKTISMFKDGSGSWGIPYEIKQGKQRRYFANFSECKSPYQFTDKISQAPVLYGYARNTLENRLKAKCCELCGTSDENTSYEIHHVNKVKNLKGKEKWEMAMIAKQRKTLVVCFHCHRHVIHKHK |
| 90 | Cluster: Primosome assembly protein PriA | T0UZ98 | MKEISDNISKEYGCKIIVRPEQKLGNSHKNYLVYLAKNSYRKEIKNKLDFLMNHSHTWEDFKEKARALNLKVDDTKKYTTYLLEGSEQTKKIRDRSLKNDKFLKENLKERIEKNTIGYSVDEVVKLWKDKESIQEKGREKEIEILLEHWQVTKETEKDLVVTIDTAFDNEATIKIPARCVDKLENGQYKIFIKKGDRFSYLDKKSPANHKIMYGATVAKNLQRQSGNIPLYSDNVNIKLKQVFHEFDFLISQ |

TABLE 3-continued

Exemplary *Lactococcus lactis cremoris* proteins not found in *Lactococcus lactis cremoris* Strain A

| SEQ ID NO. | name | uniprot_id | Protein Sequence |
|---|---|---|---|
| | | | GLSFDRSFETIGEELKATYQETQHQLDKLDTKILEYVETTKTLPYEDTSIRDTIKNLTKERDDLRDTLYKVDKNIQYYQKSEQRLEAYQKNQSPKHKARDDDFEI |
| 91 | Cluster: Replication-associated protein RepX, RepB family | A0A1B1RSI6 | MSKNVKTIKELADELGTNKTRISRIINKNSIPTQKIKNKIVLEDNSVSLIRQYFKNETVSILRTELDKAHSHIEKLSNLSDQQQRLALQDKKLLEEYKAENDSLKALKMPTEGSQAEQANSQPKEEVKALKFEIRALQEELNKQKIHSQEEREKLKAELTTPKKWYQFWK |
| 92 | Cluster: Transposase | G0WJT7 | MSGFKRYDEDFKQSLVNLYQTGKTQTELCKDYGVSSSALAKWIKQYSQVRLEDNTVLTAKQIQELQKRNAQLEEENLILKKASAIFMQNSK |
| 93 | Cluster: Transposase | F9VEW3 | MKAKKRIGTRAFKIILLRDYGVNISEGRILRLLKSMTLPKMSTIKPRFKSNKSPVFSSDNLLKQEFNPNSPNQVWTTDFTYISIGPKRHVYLCAILDLYSRKCIAWKVSDKIDAQLACDTLEIALNKRKPKEPIIFHSDQGSQFKSASFRKLLDEHQLLASYSKPGYPYDNAVTEVFFKYLKQREINRRTYHSIQEVQLSCFEYIEQFYNNYNPHSANNGLTPN |
| 94 | Cluster: Putative transcriptional regulator | G0WKP7 | MRQLADALNVSFEYLTDTEILPIYQELSDDNKQQTINYAEDKLKSQKEQENIIHFRNSLIPYKQATEQALSAGLGEGYTDNIETCTVYWDKQVNYDIGIPIKGDSMEPEFHYGQTALIKYQSSPDYDGQVCAVDNVSMGNGFIKCVTVEEDGLLLQSLNIEEGQNGERKFPDIKLYWDDNPRIIGKVVAAFTPIEIDFLFKNLEL |
| 95 | Cluster: Exopolysaccharide biosynthesis protein EpsL | A0A218PFY7 | MERKKKKKENIWAIIVPILIIISLIGAWAYALRDSLIPNDYTKTNSSDQPTKTSVSNGYVEQKGVEAAVGSIALVDDAGVPEWVKVPSKVNLDKFTDLSTNNITIYRINNPEVLKTVTNRTDQRMKMSEVIAKYPNALIMNASAFDMQTGQVAGFQINNGKLIQDWSPGTTTQYAFVINKDGSCKIYDSSTPASTIIKNGGQQAYDFGTAIIRDGKIQPSDGSVDWKIHIFIANDKDNNLYAILSDTNAGYDNIMKSVSNLKLQNMLLLDSGGSSQLSVNGKTIVASQDDRAVPDYIVMK |
| 96 | hypothetical_ protein | | MAQTIQTLALNVRLSCQLLDVPESSYYERINRHPSKTQLRRQYLSLKISQLFNANRGIYGAPKIHHLLLKQGEKVGLKLVQKLMKQLQLKSVVIKKFKPGYSLSDHINRKNLIQTEPTKKNKVWSTDITYIPTQQGWAYLSTIMDRYTKKVIAWDLGKRMTVELVQRTLNKAIKSQDYPEAVILHSDQGSQYTSLEYEELLKYYGMTHSFSRRGYPYHNASLESWHGHLKREWVYQFKYKNFEEAYQSIFVVYIEAFYNSKRIHQSLGYLTPNQFEKVSA |
| 97 | Cluster: Polysaccharide pyruvyl transferase CsaB, csaB | A0A0M2ZR43 | MVDAYLDNNLGDDLMIRYFASYFYQHKIYLVESREHIRKTFYDIPNIYFYSEEDYKMNEYDFQLHVTIGGSMFILDDFKKLIRFRHRIKNSRKIKKRNIPSAIIGCNLGPFDKRNFGLKLAKFELKYKNLVTVRDKQSKELLLRGFKRKKINIKLFPDIIFSKVLYKSIPKYGLGMTLSQVFRVTNVEF |
| 98 | putative_ glycosyltransferase_ EpsJ | P71059 | MKNKFSIIVPVYNGESHIKKCIDTLLKQTYNDFEIIIINDGSTDDTKSVLTKFYAKNLKVKIVNTSNKGVSFARNLGINQSSGQYLLFVDSDDELSINALKYLSIMLNKKDRDLILFGFSLTGDNNRKNDTSILKSIANQNTDCKMNILKSILSTKNNILGYVWRAVYSLDFIKKNNIFFETHLKISEDYLFLLQSVEHSNNLFVITEEFYKYNLGETSMSNKFVPTLLNDMVWVNNWIESNILTVYPQFFVGFNCLVANTYIRYVQNAIRNKEENFMLKYREIKINKRKYNFQRSINQVIFHLDKFDFKSKIGVILFRIHLDIVYELLFNIKERKN |
| 99 | Cluster: EpsH | Q3ZK44 | MTNLNRKKFFINFQSLVFFILIIIYGLTTKNVMGGSGIFSIDSILKYGILFICISVEGYIFLKNGNERRETSENYNNFKYYFIIITFLSLFASFKQVHFSFRTVQSFIFIFIPMLYSYLILNNWTFRQINFSMKIALFLSVIEYLFSIRMGFSQIISSLASINYNNTNASALESSTFALLSLGFAAYFGYYKKNFLCKIVSLLFVIMTFKRVITLSGCILVILGILKIKNLRVNRFFLIVSTITLVSFSLIYYYSIQPQNILEISEKIGFSIRDFSTNRTDRLAWLSMTDFKSYGLGSTTDFMYKLWGVDLEMDIVQLILEVGA |

TABLE 3-continued

Exemplary *Lactococcus lactis cremoris* proteins not found in *Lactococcus lactis cremoris* Strain A

| SEQ ID NO. | name | uniprot_id | Protein Sequence |
|---|---|---|---|
| | | | FGVIVFIYFYLRFSKSNLYAFSFMALLLLNSILSSG MMSTFSWIIILIAMSTIMEYKEGM |
| 100 | Cluster: Transferase 2, rSAM/seleno domain-associated | A0A0M2ZW08 | MKKLKISVIIRTYNEVKHIGEVLKSLTDQTYLNHEI IIVDSGSVDGTLDIIERYPVKLVSINKEDFNYSYAS NVGVQNSSGDIVCFLSGHSVPVYKNYLEKINEIFQE TEIGACYGEVIALPDGSITEKIFNRIGYLKSKLSLN NKRFFLENKIHPGIFSCSNACARKKLLLKYPFKVEL GHGGEDVEVAYRIIQDGYFVAKSVELLVMHSHGSSL KKFIKEYKAWGKMYEDVLKFIKKNNDKSQ |
| 101 | Cluster: EpsF | Q3ZK46 | MIFVTVGTHEQPFNRLIQKIDELVRDGQIKDDVFMQ IGYSTYEPKYTKWASVIGYNDMTAYFNKADIVITHG GPSTYMQVLQHGKIPIVVPRQEKFGEHINDHQLRVS KQVIKKGYPLILCEDVSALKICIESSRIRTDEFIKS NNKNFISNFKKIIAFEE |
| 102 | Cluster: EpsE | Q9X491 | MKIALVGSSGGHLTHLYLLKKFWENEDRFWVTFDKT DAKSILKEERFYPCYYPTNRNVKNTIKNTILAFKIL RKEKPDLIISSGAAVAVPFFWIGKLFGAKTVYIEIF DRIDKPTLTGKLVYPVTDKFIVQWEELKKVYPKAIN LGGIF |
| 103 | putative_ sugar_ transferase_ EpsL | P71062 | MEFFEDASSPESEEPKLVELKNFSYRELIIKRAIDI LGGLAGSVLFLIAAALLYVPYKMSSKKDQGPMFYKQ KRYGKNGKIFYILKFRTMIFNAEQYLELNPDVKAAY HANGNKLENDPRVTKIGSFIRRHSIDELPQFINVLK GDMALVGPRPILLFEAKEYGERLSYLLMCKPGITGY WTTHGRSKVLFPQRADLELYYLQYHSTKNDIKLLSL TIVQSINGSDAY |
| 104 | Tyrosine- protein_ phosphatase_ YwqE | P96717 | MIDIHCHILPGIDDGAKTSGDTLTMLKSAIDEGITT ITATPHHNPQFNNESPLILKKVKEVQNIIDEHQLPI EVLPGQEVRIYGDLLKEFSEGKLLTAAGTSSYILIE FPSNHVPAYAKELFYNIKLEGLQPILVHPERNSGII ENPDILFDFIEQGVLSQITASSVTGHFGKKIQKLSF KMIENHLTHFVASDAHNVTSRAFKMKEAFEIIEDSY GSDVSRMFQNNAESVILNESFYQEKPTKIKTKKLLG LF |
| 105 | Tyrosine- protein_ kinase_YwqD | P96716 | MAKNKRSIDNNRYIITSVNPQSPISEQYRTIRTTID FKMADQGIKSFLVTSSEAAAGKSTVSANIAVAFAQQ GKKVLLIDGDLRKPTVNITFKVQNRVGLTNILMHQS SIEDAIQGTRLSENLTIITSGPIPPNPSELLASSAM KNLIDSVSDFFDVVLIDTPPLSAVTDAQILSSYVGG VVLVVRAYETKKESLAKTKKMLEQVNANILGVVLHG VDSSDSPSYYYYGVE |
| 106 | putative_ capsular_ polysaccharide_ biosynthesis | P96715 | MQETQEQTIDLRGIFKIIRKRLSLILFSALIVTILG SIYTFFIASPVYTASTQLVVKLPNSDNSDAYAGQVS GNIQMANTINQVIVSPVILDKVQSNLNLSDDSFQKQ VTAANQTNSQVITLTVKYSNPYIAQKIADETAKIFS SDAAKLLNVTNVNILSKAKAQTTPISPKPKLYLAIS VIAGLVLGLAIALLKELFDNKINKEEDIEALGLTVL GVTSLCSNE |
| 107 | Cluster: Polysaccharide biosynthesis protein | A9QSJ2 | MMKKGIFVITIVISIALIIGGFYSYNSRINNLSKAD KGKEVVKNSSEKNQIDLTYKKYYKNLPKSVQNKIDD ISSKNKEVTLTCIWQSDSVISEQFQQNLQKYYGNKF WNIKNITYNGETSEQLLAEKVQNQVLATNPDVVLYE APLFNDNQNIEATASVVTSNEQLITNLASTGAEVIV QPSPPIYGGVVYPVQEEQFKQSLSTKYPYIDYWASY PDKNSDEMKGLFSDDGVYRTLNASGNKVWLDYITKY FTAN |
| 108 | Cluster: EpsR | O06027 | MNNLFYHRLKELVESSGKSANQIERELGYPRNSLNN YKLGGEPSGTRLIGLSEYFNVSPKYLMGIIDEPNDS SAINLFKTLTQEEKKEMFIICQKWLFLEYQIEL |
| 109 | hypothetical_ protein | | MSVSIIDSFPIPLCQPIRNFRSKGLGDYANVGYNAT KGQYFYGCKCHALVSESGYVIDYTITPASMADSSMT EEVLSQFGTPTVLGDMGYLGQSLHDRLELKGIDLMT PVRKNMKQKKILFPNFSKRRKVIERVFSFLTNLGAE RCKSRSPQGFQLKLEMILLAYSLLLKSAKSLEPETL RYSIGYQVMAK |

TABLE 3-continued

Exemplary *Lactococcus lactis cremoris* proteins not found in *Lactococcus lactis cremoris* Strain A

| SEQ ID NO. | name | uniprot_id | Protein Sequence |
|---|---|---|---|
| 110 | Cluster: Signal transduction histidine kinase | A0A0B8QXZ2 | MTIKNKKDLSSSIEQLEKAINQQETILKKFDNEQLD FEQIKKLENLLIQEREKAKQVQIKINRSVLQNNSEN YKERKKRTRQLIQKGALLEKYLEAKHLTVDETEQLL QIFANMINKPELLVNFIGK |
| 111 | Cluster: Tyrosine recombinase | B1N0G0 | MVQQIVLPIKDSNILKMVQDTLLDSFRAGRRNYTIF QVGKATLLRVSDVMKLKKTDVFNSDGTVKQTAFIHD QKTGKANTLYLKPVQQDLVVYHDWMVQQNLNSEWLF PSTSRPDRPITEKQFYKIMARVGDLLSINYLGTHTM RKTGAYRVYTQSNYNIGLVIHLLNHSSEAMTLTYLG LDQASRETMLDQIDFG |
| 112 | Cluster: Uncharacterized protein | G1FE57 | MDQKEVSQNQTKYIQFRLSEEQYNKLKISGETYGLS PNLYAKKLAQKSHLKKPYLEHDQAKSLLLELSKQGT NLNQIAKKLNQFDRMDNQDKELIEALRYTYGVLAQA QKGYQELWQQLQK |
| 113 | Cluster: Mobilization protein | H2A9L4 | MATIAKISNGASAASALNYALGQDRPMHEKTEQWLQ DHQLERPVELTNCRAVAVGGTNGIDPFIAKEQFDVV RQLHNQTKESNQVMRITQSFALDELNPKVQKDWQKA NDLGVELAENLYPNHQSAVYTHLDGKNHVLHNHIIV NKVNLETGKKLREQKGESVQRAREMNDRLASRENWH ILEPPKERQTETEKELIAKNEYSYMDDLRERINKSL QDVSVSSYETFKERLSDNGVILSERGQTFSYAFLDA NNKQRRARETRLGSDFGKETILHELENRARQNEFSA VEQREPAITPLERDTQQRESEIVSLEQAIEPRKSEA LKRESKINRFIDTIKQFAGRVPELTQRVTRKLKQTK DKILDDFERRFSKDMKNYEQEQQKSLEKQANRDVQS EKKPTKDHDRGMSR |
| 114 | Cluster: Putative mobilization protein | S6EPU9 | MNKDEQLVVQVLNAYKNGKIDFSNVPELDRLVRQEV NKDFRDYQEKIEAVANQKIESAIQEQLHRLEAENLK ATILKDIQVEKQALLALKKELNEQKEQIKADRKREI VERYGILIANIVCLFCFLVVGILIGRWIYKGIWDGW GLHILYDTVMEIKPKHPYGAVILGLGGFGLIGAGIY GSFRLMYTASTWFDQRPKIFKRIFPKK |
| 115 | Adenosine_ monophosphate- transferase | Q7DDR9 | MVLDNKLGLTNSAELAKQEELLTKKRAKELFESGKI EDLEIGTFQGLSDIHQFLFQDIYDFAGKIREVNIAK GNFQFAPRIFLAQTLEYIDKLPQETFDEIIDKYSDM NVAHPFREGNGRATRIWLDLILKNKLHKIVDWNQID KDEYLNAMIRSTVSTNELKYLIQKALTDDLGKEQFF KGIDASYYYEGYYEIKTEDL |
| 116 | Cluster: RepB | O54680 | MSIITEFEKNQKQVKALNELSKRKVVEHNSLITSIA KMDKTPLKMFELAVSCINTEAPPKDHTVYLSKTELF AFFKVSDNDKHSRFKQAVENMQKQAFFKIQEKKEYG FEFENIVPIPYVKWADYHDEVTIRFSPEIMPYLINL KQNFTQHALSDIAELNSKYSIILYRWLSMNYNQYEH YSAKGGRREEQVETYRNPSISIRELREMTDTMKDYP RFQSLESYIIKNSLKEINEHTSFKVTYEKVKKGRSI NSIVFHITKKRRADDNSYKLEDKVYQKAKVQKEQKE NLLYAEAMQSKYTKLLLEHFLLSPYEMTNPATMAGL QRNVYPKYDELKDLMGIDGVKKHLSYIYDKQEPYSK GNIAKYLKKAIEQYLPTVKRRGL |
| 117 | Cluster: Replication- associated protein RepX | G0WJS1 | MSDNLKTIKELADELGVSKTAINKKVTDRERKLWFS KIGNKFVINEDGQKSIKRMFEGLTENQESQTENLEQ KPNSQTENFRNNNESNADIKYILDIIEYQKEQIKDL QNTKDEQFKQLSNMQNLLDQQQRLALQDKKLLEEYK SENDRLKVLKMPSQETKEEQANIQPQEELETLKEQT RALNDKIKGQEELNNKSSKKVVYQFWK |
| 118 | Cluster: Truncated peptidase E | G0WJS2 | MFSYIYI1LSYNTIKVKEVLKFEYRICTSFNWTSKF AEEMKTCFFNSGFKFKNFKGLDNRNAKEKSELISEA EVVILAGGHVPTQNIFFQQINLKNMSPVRIF |
| 119 | Putative_O- antigen_ transporter | P37746 | MQIAKNYLYNAIYQVFIIIVPLLTIPYLSRILGPSG IGINSYTNSIVQYFVLFGSIGVGLYGNRQIAFVRDN QVKMSKVFYEIFILRLFTICLAYFLFVAFLIINGQY HAYYLSQSIAIVAAAFDISWFFMGIENFKVTVLRNF IVKLLALFSIFLFVKSYNDLNIYILITVLSTLIGNL TFFPSLHRYLVKVNYRELRPIKHLKQSLVMFIPQIA |

TABLE 3-continued

| Exemplary *Lactococcus lactis cremoris* proteins not found in *Lactococcus lactis cremoris* Strain A | | | |
|---|---|---|---|
| SEQ ID NO. | name | uniprot_id | Protein Sequence |
| | | | VQIYVVVLNKTMLGSLDSVTSSGFFDQSDKIVKLVLAIATATGTVMLPRVANAFAHREYSKIKEYMYAGFSFVSAISIPMMFGLIAITPKFVPLFFTSQFSDVIPVLMIESIAIIFIAWSNAIGNQYLLPTNQNKSYTVSVIIGAIVNLMLNIPLIIYLGTVGASIATVISEMSVTVYQLFIIHKQLNLHTLFSDLSKYLIAGLVMFLIVFKISLLTPTSWIFILLEITVGIIIYVVLLIFLKAEIINKLKFIMHK |
| 120 | Cluster: Transposase | O50546 | MNLFGDSDYLEKLSSKGDPLERLEKVVDFECFRPTLNRIFKYDLKNKSHGGRPPYDLVLMLKILILQRLYNLSDDAMEYQMIDRISFRRFLKIDDKVPDAKTIWNFRNQLSKSNRGNWLFSAFQEKLESQGMIAHKGQIVDATFIEAPKQRNPKDENEL1KANRVPVNWTKNKRAQKDTAARWTIKGNERHYGYKNHIAIDTKSKFVKNYQTTPANVHDSQVIGVLVDPDEITLADSAYQNKATPKGAELFTFLKNTRSKSLKADDKMFNKIISKIRVRIEHVFGFVENSMHGSSLRSIGFDRAVLNTDLTNLTYNLLRHEQVKRLNLKTWR |
| 121 | Cluster: Orf14.9 | Q9CRJ9 | MRKYMIYLSSLLVTFILSYATITWLIMPVLTRYQSLARLINHFDYTALTLILLLTLIIWLFGIQYHLKHFSVIYLYLAFSVYLLLLFMVIFNKTTDFQAISLNPFDFIKADTRTIQEAVLNIIYFIPLGGLYCINTDFKQFVIISLVTLLGIETIQFIFYLGTFAISDIILNFLGCLIGYYCCWEIKKS |
| 122 | hypothetical_ protein | | MDETYIKIKGRGHYLYRTIDADGLTLDIWLRKKRDTQAAYAFLKRLHKQFGEPKAIVTDKAPSLGSAFRKLQSVGLYTKTEHRTVKYLNNLIEQDHRPIKRRNKFYQSLRTASSTIKGMETLRGIYKNNRRNGTLFGFSVSTEIKVLMGITA |
| 123 | Putative_ glycosyltransferase_ EpsH | P71057 | MKKNVLLSIIVPIYNVEKYIGSLVNSLVKQTNKNFEVIFIDDGSTDESMQILKEIIAGSEQEFSLKLLQQVNQGLSSARNIGILNATGEYIFFLDSDDEIEINFVETILTSCYKYSQPDTLIFDYSSIDEFGNALDSNYGHGSIYRQKDLCTSEQILTALYKDEIPITAWSFVTKRSVIEKHNLLFSVGKKFEDNNFTPKVFYFSKNIGVISLRLYRYRKRSGSIMSNHPEKFFSDDAIFVTYDLLDFYDQYKIRELGAVVGKLVMTRLAFFPDSKKLYNELNPIIKKVFKDYISIEKRHTKRIKMYVKMYVFSSYVGYKLYRLVKGKHWK |
| 124 | hypothetical_ protein | | MNHFKGKQFKKDVIIVAVGYYLRYNLSYREVQELLYDRGINVCHTTIYRVVVQEYSKVLYDLCKKKNRQSFYSWKMDETYIKIKGRWHYLYRAIDADGLTLDIWLQKKRDTQAAYAFLKRLHKQFGEPKAIVTDKAPSLGSAFRKLQSVGLYTKTEHRTVKYLNNLIEQDHWPIKRRNKFYQSLRTASSTIKGMETLRGIYKNNRRNGTLFGFSVSTEIKVLMGITA |
| 125 | Cluster: Transposase | H5SYB4 | MQQNLLKYYGMTHSFSRRGYPYHNASLESWHGHLKREWVYQFKYKNFEEAYQSIFWYIEAFYNSKRIHQSLGYLTPNQFEKVSA |
| 126 | Replication_ initiation_ protein | P03856 | MNDLEKRKVVEHNSLITSIAKMQKTALKMFELAVSCIDTENPPKDNIIYLSKKELFAFFDVSSASKHTRFKEAIELMQKQAFFQIKEVKDKGYEMTSIVPIPTVKWNSYNDDVMIQFNQFIMPYLIDLKAEFTQYKISELKELNSKYSIIILYRWLSMNYNQYEHYNVKGGRRAEQVENYRKPSISVKELREITDTVNEYKEIYDFEKRVLKKSLAEINAHTSFNVNYEKIKKGRSIDSIVFHIEKKRMADDNSYKLGDKDYQDDKKQKSRNEADLLKQAMESKYTRLLSENFLIGMNDIMDTTTMVGLQKNVYPLYDELKELRGLNGVKDHLSYVSSKREEYSKHNIAKYLKKAIEQYLPTVKRQDLENE |
| 127 | Cluster: RepX-like protein | A0A0D4CCQ1 | MNDNLKTIKEVADELGVSKKKIENKLSYIKKKGNTLGKVIGGVRYLNKQEIKILNISPETSKAPETSKVPETSKVPETSKVPETSKVPETSKAPETSEVPETSKVPDKHVFSSSFDLLREQTAYLLKELEEKNKHIEKLIDNEKSMQNLLDQQQRLALQDKKLLEEYKSEINELKALKMPQEDMKDDSSIRGEAQEEIVRLKAQLKLSEEERNKAKEKEPVKTESKKVWVQLWK |

TABLE 3-continued

Exemplary *Lactococcus lactis cremoris* proteins not found in *Lactococcus lactis cremoris* Strain A

| SEQ ID NO. | name | uniprot_id | Protein Sequence |
|---|---|---|---|
| 128 | Cluster: Uncharacterized protein | G6FEV8 | MNFGEVLQTKRKSMGLTQEDLADKLFVSSKTISNWE TNKTTPDIDNVIRISQLFDISLNNLLLEGSNMVENI KKKAEINNLKKYSYCTVITDLVFLFIILSSHYGAEL PISILIATCIGIGVNIAVMFYFLNRIKILEDKTKKQ QRKEIFITIILCILAFVVTILVSWFKH |
| 129 | Cluster: Uncharacterized protein | G6FEV7 | MIDLEEEGFLVLWGISIASSYTETISTLQQSGGSAI FTFLTYAIGLLFFILTVLPTNAVTTKSDNGFILFFL RAK |
| 130 | Cluster: Exosortase E/protease, VPEID-CTERM system, xrtE | A0A0B8R3X5 | MNYIKKFFIVLRLAILSQIGVAVYGGAKGFSLENGA HKLSLLAVLILIIFIVGNIYLLMYLGKKLGFLTLSK DFLTKKNIIYILVGTLIARTAGIGGTLLLNATGVTQ TANDETIGQLFTGENPLLIILLIGIAAPIMEEIVFR GGIVGYLFKDLPVVGIIVSSVLFGLMHSPTNIISFL IYGLIGLTCAIAYFKTRRLEVSIAIHFLNNILPALV LAFGIS |
| 131 | Cluster: Mobilization protein | S6FVR0 | MKKIKNRERIIQKKFFVNEKEDERIKLMMRKTGITN FSIFARRACCNKEIFSIDFSEYKNIISEISATKSEL KRIGNNINQIAKHLNENKNNQTKELMSDYQKQLENL EDKIQKVVHYISEG |
| 132 | Cluster: Replication protein | Q93T03 | MAKKQNYIWRNDRNFALDEYEQQQYYYVVESNDIIN KARHDLTARELKLMDFVISKIQPEDTQFNVIKTSMY ELTKVLNIKQNGKNYGDMAKAIGDLRKKEVLIYDDV HRTVTQTGWVQSAKYQENGQVEIKLNEDLAPHLLGL KTHYTQHLLIDTTKLKSRYSILLYKLMREADKDKGN SIAILQGTPEEFKEWLGAPKDYEYKDLKRNILKKAV EEINLKIDDMDLEILQGRCGRKVVQVEIHNNWTVQR AIEENSEYVESITTHDWLKGDSK |
| 133 | Cluster: Uncharacterized protein | G9ZK11 | MIYTSGYFIAFLGLIIMLFNFKDLYPKLNIWCRLGF ILLCLGLILPMLFGFITGFINNH |
| 134 | Cluster: Uncharacterized protein | O53072 | MAREKSDIEYQVVTVRFPKEIYQEYKKILKSEGKIP TYDLRNYIFSVVDEYEKGQR |
| 135 | hypothetical_ protein | | MNYFKGKQFQKDVIIVAVGYYLRYNLSYREIQELLY DRGINVCHTTIYRWVQEYSKVLYHLWKKKNRQSFYS WKMDETYIKIKGRWHYLYRAIDVDGLTLDIWLRKKR DTQAAYAFLKRLHKQFGQPRVIVKDKAPSIGSAFRK LQSNGLYTKTEHRTVKYLNNLIEQDHRPIKRRNKFY QSLRTASTTIKGMETIRGIYKKNRRNGTLFGFSVST EIKVLMGILA |
| 136 | Cluster: AraC family transcription regulator | A0A0E2UHK8 | MAGYNVLDDAKARNLGLDILEVKETEYAVVPVKGSV PDSIHQAWKYLLEEFFPENGYKHSGLPDFEVYTEND IHDPNYEMELWVPISKQ |
| 137 | Cluster: Transposase of IS 1216E, IS6 family | D2BRG5 | MIIVAVGYYLRYNLSYREVQDLLYDRGINVCHTTIY RWVQEYGKLLYQNGFYQGTEHRTIKYLNNLIEQDHR PVKRRNKFYRSLRTASPTIKGMEAIRGLYKKTRKEG TLFGFSVCTEIKVLLGIPA |
| 138 | Cluster: UPF0177 protein in abiGi 5′region | Q48724 | MIKNHWMKKLKYLSLFFLLFAIYWFPDVILAYPEVY LKSLVGYERQVVATWIFLGNMSISLFLGILICYKLG YYKNTISIFKIKNLLFLLITTIILFVIYFFSYTYYN SHFITPGIAKTQAAFSIQIVFPFVQFITIAICAPIF EEAAFRTTIYRFFKNDKIAYIVSCVGFAVVMHTGPN PILIVYLPMSIVLTSIYHRRRVLGESILVHGVFNAL LPIVIPLLQVITGLYYL |
| 139 | Cluster: Uncharacterized protein | A0A0M2ZU19 | MKYFVTTLSPSKNMGTMNWQTMILSDYCVNDSYWEK AKRELSEEVQWVTQSDLYKKIKWNHDSNDDIILSKP VSIILETVKSDFPHANVWVYQ |
| 140 | Cluster: Bacteriocin-type signal sequence | A0A0M2ZU05 | MEIQTNFQIISDEELSEIVGGGYPNNQSMNDVLHWL NGHNDGNPKQLPKVVMCGLG |

TABLE 3-continued

Exemplary *Lactococcus lactis cremoris* proteins not found in *Lactococcus lactis cremoris* Strain A

| SEQ ID NO. | name | uniprot_id | Protein Sequence |
|---|---|---|---|
| 141 | Cluster: Uncharacterized protein | A0A0M22V61 | MTKYIYPNLKDNQKYLLKIIDGILTSNNISSEEKKLFLIAKSNIEKGRNFDPQISELISSLQYLVHSDDVLVFFEEARKIMQINPGTGGSPYGWSNFESK |
| 142 | putative_ cadmium-transporting_ ATPase | Q60048 | MAKITLNFQKRLQQHSNHLVILSAILIVLGYLGKYGVNQIWIWNSTMIIASIIGFIPVAIHAYQAIKVKQISIDLLVSIAVIGALFIGEYEESAIVTFLFAFGGFLEKKTLEKTRSSIKELTNMAPRTALSADGEEMDIDEVEIGDKLLVKTGRQVPVDGRIYQGSGYVNEASITGESREIRKEAGTKVFAGSILENGTIYVEAEKVGEDTTFGKIIELVEEAQDTKSPAEKFIDRFAKYYTPAVLVIAAITVVVFSHNLELAITILVLGCPGALVIGAPVSNVAGIGNGAKRGVLIKGGDVMNTFSHIDTLLFDKTGTLTKGNTEVVVVKNYGASKELIDAVASAENESDHPLATAVVRMIGKFNPIKFEKTDVVKGQGIIADNLLIGNEKMMVVNHITISPEQKQDITEITDSGASVVLVAADNRLQLIYGIADEIRSGVKESLEELRHEGISRMIMLTGDNETTAKAVAAQLGIDEVRANLMPEEKAEVVKSLKNSGKKIAFIGDGVNDSPSLALANIGIAMGSGTDTAIETSDIVLMRSSFDELVHAYGLSKRTVANMTQNIVIAIVVVLFLLASLILGGTGLVPSFVNMGTGMFVHEASILIVIVNGMRLIRYREK |
| 143 | Cluster: Transposase | A0A0D6E0F2 | MQNNYTSKGKHLTESERLLIERWHNKEKVSNREIAYRLGKAPQTIHNEIQRGTVQLKYKTKYSAKIAQESYKTLRTHSKRSTKLNAQLDDQISKAVKNKISLEVIHQELKGVVCLRTLYNWISSGILSVAYHELLYPQYRKPKKQRVTQPKHMLGQSIEERPESVDERSEYGHWEIDTVLLTKEKGECLLTLTERKTRLEIIRLIPNKTTHSVNQALRGIEFLALSVTSDNGREFAKLSEALDCPVYYCHAYASHERGTNENHNRMIRRHLPKGTKKTTKQVVAYIENWMNNYPRKMFNFKTPNQMLIESI |
| 144 | Cluster: Transposase | P94884 | MNHFKGKQFQQDVIIVAVGYYLRYNLSYREVQEILYDRGINVSHTTIYRWVQEYGKLLYQIWKKKNKKSFYSWKMDETYIKIKGKWHYLYRAIDADGLTLDIWLRKKRDTQAAYAFLKRLVKQFDEPKVVVTDKAPSITSAFKKLKEYGFYQGTEHRTIKYLNNLIEQDHRPVKRRNKFYRSLRTASTTIKGMEAIRGLYKKTRKEGTLFGFSVCTEIKVLLGIPA |
| 145 | Alpha- acetolactate_ decarboxylase | Q8L208 | MNSRIFQHNTFTTLSIGFYKGTITLKEALTHGKVGIGTLDTANGEVTIIDGIAYHGDSENQVRLVEENETMPYVAMVEHQPIVKFTDNSVSNSEDFLSALTKRFPTANTAYTIVMTGQFKEVTVSSKPANNTRPYDEIMADQPYFTKENISGTMLGVWAPKHLTDLFGIGFHLHFVSEDKTFTAHVQNFITENLAIELGKITQIEQEFPDEDENFDQHLFQ |
| 146 | DNA- invertase_hin | P03013 | MNIGYARVSTGLQNLDLQKDSLKKYNCEKIFTDHMSGSKRERPGLKSAIEFSRPGDTIVVWRLDRLGRNMEDLINIVNSLNNKGVSFHSLQENITMDKSSSTGQLMFHLFAAFAEFERNLILERSAAGREAARARGRLGGRPEKFSEQDVKLLKTLVESGTPIKSIADSWGVSRTTIYRYINKF |
| 147 | Cluster: Uncharacterized protein | D2BPF3 | MKIITATLLLVISLLGILGTAFLYLGELTQGKGGGFLFILGCFLILGIQSFTWLEILFGKRQNGEVKKYDYFLFNILKVIFSIGALQLFIQRCFF |
| 148 | Nitrogen_ fixation_ regulation_ protein_FixK | P29286 | MSKYKHHFSHHEHHCVQLVPLFGLLSESELVQVEQVVNHKIFEKGETVISPFAVPQLAIVAHGTLKIYQLSSAGKEQLLRVIEPGGYAGEDALFGVMNDNLYGETLEETQICFLRQQDFKNLLLKYPELSLKLLETTVRRAAEMQYQAQFLMMEDVESRIANYLLQLVKVVDSNSVMIPMKMKDLATFIGTTPETISRKFKILEEKGFIERRGKIIKILDIDSLEDDYA |
| 149 | Cluster: specific DNA-binding | A0A161UM95 | MMTKLMIDEKYAKELDKAEIDHHKPTAGAMLGHVLSNLFIENIRLTQAGIYAKSPVKCEYLREIAQKEVEYFFKISDLLLDENEIVPSTTEEFLKYHKFITEDPKAKY |

TABLE 3-continued

| Exemplary *Lactococcus lactis cremoris* proteins not found in *Lactococcus lactis cremoris* Strain A | | | |
|---|---|---|---|
| SEQ ID NO. | name | uniprot_id | Protein Sequence |
| | protein Dps/ Iron-binding ferritin-like antioxidant protein/ Ferroxidase | | WTDEDLLESFIVDFQAQNMFITRAIKLANKEEKFALAAGVVELYGYNLQVIRNLAGDLGKSVADFHDEDEDNDN |
| 150 | Cluster: Copper ion binding protein | A0A0M2ZU22 | MSKVIMRLNELSCPSCMAKIEAAMTTTKGVANAKVLFNASKVKAEFDENVVSADELISKVEKLGYPVLSSKVTVV |
| 151 | Cluster: Transposase | P94884 | MNHFKGKQFQQDVIIVAVGYYLRYNLSYREVQEILYDRGINVSHTTIYRWVQEYGKLLYQIWKKKNKKSFYSWKMDETYIKIKGKWHYLYRAIDADGLTLDIWLRKKRDTQAAYAFLKRLVKQFDEPKVVVTDKAPSITSAFKKLKEYGFYQGTEHRTIKYLNNLIEQDHRPVKRRNKFYRSLRTASTTIKGMEAIRGLYKKTRKEGTLFGFSVCTEIKVLLGIPA |
| 152 | hypothetical_ protein | | MKMLRVQKPLLFKFSQIQVLQYTKTQDAVYKVNSNTICSVYKLSFTLVQLRL |
| 153 | Tyrosine_ recombinase_ XerC | MF_01808 | MTYIELNPVNNVVLPKHNSSVEDFEISENKTITYDELKIVLEYCHKHNKNQRLTLIIEFLFLTGLRLEELGGLQKSSVDFKKQTIKIKHVIDTKAIGDNSRKLYLPKTFASRREIYVNDRCIEILKWFFDNSLDDDFVFTTMIGTTVKQSATYLFVRNVCEASLGKQKNRKYNVHMLRHAHISLLAELDIPIKATMKRVGHSQESTTLRIYSHVSQKMNDSIMRKLNEI |
| 154 | Cluster: Transposase | P94884 | MNHFKGKQFQQDVIIVAVGYYLRYNLSYREVQEILYDRGINVSHTTIYRWVQEYGKLLYQIWKKKNKKSFYSWKMDETYIKIKGKWHYLYRAIDADGLTLDIWLRKKRDTQAAYAFLKRLVKQFDEPKVVVTDKAPSITSAFKKLKEYGFYQGTEHRTIKYLNNLIEQDHRPVKRRNKFYRSLRTASTTIKGMEAIRGLYKKTRKEGTLFGFSVCTEIKVLLGIPA |
| 155 | Replication_ protein_ RepB | P13921 | MKQKKREQRSNKWAFLIYQESVPEDYLNLLEELHVPFILSPWHDKDVNRTTGEFKKPHKHGVFFFESLKSYSQVSELISDKLNSPEHVEVVMSPKGMYDYFTHAENPEKSPYNIEDIESGAGFELDKFLAENNEDLLNQVYEVMRDSGIKEFADFTDLIAKQFPDLLYFVFSKSYFFKIYLDSKRYIEIKQKDDEDNHGK |
| 156 | hypothetical_ protein | | MENNYPYLLNREQASKFIGIRDDTFSVFFIVKIS |
| 157 | Na(+)/H(+)_ antiporter | P26235 | MEDIFQITIILFFSMLATLLSKKLKIPEVVGQMLIGIILAPSVLGLINGGHTIEVMSEIGVILLMFLAGLESDLEVLKKNLKPSILVVLLQSLKIKRALSELQIS |
| 158 | hypothetical_ protein | | MNHFKGKQFKKDVIIVAVGYYLRYNLSYREIQELLYDRGINVCHTTIYRWVQEYSKVLYHLWKKKNRQSFYSWKMDETYIKIKGRWHYLYRAIDADGLTLDIWLRKKRDTQAAYAFLKRLHKQFGQPRVIVTDKAPSIGSAFRKLQSNGLYTKTEHRTVKYLNNLIEQDHRPIKRRNKFYRSLRTASTTIKGMETIRGIYKKNRRNGTLFGFSVSTEIKVLMGIPA |
| 159 | Cluster: MobC mobilization protein | I6TH45 | MSEHLNMASIKKKQPNRKERKQISFRVSEPEYLNLERSAKVLNISVPAFVKKKAQGARVVAPKINPDDSKEMARQLAALGNNVNQLAKRVNQIEFADKDTQERLSADLRRTLHGLGEIWRQLT |
| 160 | Cluster: Relaxase/ Mobilization nuclease domain | A0A1V0PDY6 | MATTHIKRSNGASRLVNYAEKRAVQKDGYNLDIEYAKSELKQVREIYGNKGATQAYASRVAFSPKEFDPKNVKDQLKALEIAKEIYSTAYPNQQIAMYVHNDTDSLHVHAVIGAINLLTGKKMHGNWQEYRERLVKITDKVVEKHGLTVTVPHPRPEKRTMAELKMKARGQVTWKDKIRQAVDTTMREAHISDFKSFKEKLGELAVNVIERGRDLTYTLTGTDYKSRGAKLGEDYKKETIFYELDRRNQLQYGTSRQRQGRAWLEGRGERLEQEQRARQNLAKRAEDLQRRTLESTEQSIQPSHQRPQKSKERGLGGPSL |

TABLE 3-continued

Exemplary *Lactococcus lactis cremoris* proteins not found in *Lactococcus lactis cremoris* Strain A

| SEQ ID NO. | name | uniprot_id | Protein Sequence |
|---|---|---|---|
| 161 | Cluster: Replication initiator protein | A0A1V0PDZ8 | MVHEIVQYHNDFNTVPLRGFNERERRIVMALLHQVKNKDVEVVQLDFDTLRGLSGWNDTLAKSENSNAKFNRYLENLSDKIMTLRGTLRSEDGLQVVKFSLFPTFIIDGKNTMTLKVQINPTFKYLTNIFDMFTAFELDDYNRMNTSYGQELYRLLKQYRTSGFYRVKIEDLRHLLSVPESYTNAKMDQKVFSKTTVTDLTNAFPNFKIKQERGTGRGRPIIGYTFTFDKEAPNKYELDRKKQEQIAQFWKSNDPEPMPNAVAQTEYQNPELRKEKEELEKHNASFGDLLKGWFKK |
| 162 | Cluster: CAAX amino terminal protease family protein | A0A1V0PDX6 | MKFKKKNYTPQVDEKDCGCAALSMILKTYETEKSLASFLLNQRIKMHKVFEKIITIFFAFFLFFISQIPIYYVNYKNKENNLYGISNKISLPFIFIALFVIIIAVALGKKRGFYHHSKKTLEFKNIMLILVLVTISIILNILINRFIIFHHLGIMNNQINIDSILSSLSCLGKIFGIALLAPILEESIFRASIYQIFNNDKVSFLISSLLFAFLHSGYSWVFFTYLPVSLCMTFIYHRRKILTDSILFHSLFNLLVLGLNFLI |
| 163 | Cluster: Putative transporter | A0A1V0PES5 | MLDILNKARIHKKWFLFSYSIISFCITIIYIVFNHTFFKVNWAKYNSDDSYKNKVDEILKHGVFWINGNLTSISSPLLICLFLLGAFFSLTIFFLTWRNLSTRTWTPIISFLGFLIPFIHSDGNFINLLILSFILILFGAISSVPSLRYF |
| 164 | hypothetical_ protein | | MNHFKGKQFKKDVIIVAVGYYLRYNLSYREIQELLYDRGINVCHTTIYRWVQEYSKVLYHLWKKKNRQSFYSWKMDETYIKIKGRWHYLYRAIDADGLTLDIWLRKKRDTQAAYAFLKRLHKQFGQPRVIVTDKAPSIGSAFRKLQSNGLYTKTEHRTVKYLNNLIEQDHRPIKRRNKFYRSLRTASTTIKGMETIRGIYKKNRRNGTLFGFSVSTEIKVLMGIPA |
| 165 | Cluster: RepB | O54674 | MSIIPEKQNNQKQVLTLNELSKRKVVEHNSLITSIAKMDKTPLKMFELAVSCIDTEKPLEDNTVYLSKRDLFAFFKVSDNDKHSRFKQAVEKMQKQAFFQIKEEAGKGFKFKSIVPIPYVEWTDYNDEVKIEFHREIMPYLINLKKNFTQHALSDIAELNSKYSLILYRWLSMNYNQYEHYSVKGGRRAEQVEAYRNPSIKVKEMRLMTDTVNEYHKYNDWDRYILKNSLKEINAHTSFNVTYDKIKKGRSIDSIVFHIEKKRMADDNSYKLGDKDYQEDKARKAETEDMLTLQALKSPYTKLLMEHFLLSYLDLTDTKILSGLQAHVYPLYDELKDLRGLNGVKDHLSYVRAKREDYSKKNITKYLKKAIEQYLPTVKRQDL |
| 166 | Cluster: Replication-associated protein RepX | Q2VHR8 | MSEKLKTIKELADEIGVSKQAVWQKIKKESSIDLRQFTSKKGNTVYVDVDGQKVIKSAFF |
| 167 | Cluster: Replication protein X | G9BNK7 | MVKKLLRVLFFNKTSTKKRQQKVFVDDNVNNSVDGNPEGNEEILFLRNLVSELQSEKKDLHKLLDQQQRLALQDKKLLEEYKAENDSLKALKMPTEGSQAEQANSQPKEEVKALKFEIRTLQEELNKQKIHSQEEREKLKAELTTPKKWYQFWK |
| 168 | Cluster: Uncharacterized protein | A0A0H1RR04 | MNKLKKLQELEAKSDKQAELMGELEARLGLIENKQI |
| 169 | Cluster: Uncharacterized protein | G8P721 | MANTETVIWKSVKGFEGQYEVSNTGLVKSFKGKTERIDRFDSNVQEILKRLSYDDCRRYKR |
| 170 | Cluster: Uncharacterized protein | G8P722 | MNMKNKTNENFVQIPNKMFMNTNNDEKLVYVKLLQSQMIGYLDKDNRTTMTTVSLLVTLLGWSKGQYSNKKVVKALNGLKDKKYINFESIQDVFTVQINKWNDKEEHIVPVDWKQSGVKFSGHTQIRLSVIDNLLEGKDFTLYAYTEYRKMKTHQYRICYEEWGFVLRMTKDGAFKNVNSSEVIIKVSNGFDSDTKRRETNSYLTFDSVEDVKEVSLKPTYKAQSSKSVVKEQEPELVEDDFDNFEEEELSFKAEAKKPLIKEKKITKKQANELKDEINKFFGNTMEDNIFKKMASDKRITSVEQAMEIQDINKPMSLEMWKVVQDSDNFFVRESGNKKLKNKAWQKKFWSDLKEEIDKA |

TABLE 3-continued

Exemplary *Lactococcus lactis cremoris* proteins not found in *Lactococcus lactis cremoris* Strain A

| SEQ ID NO. | name | uniprot_id | Protein Sequence |
|---|---|---|---|
| | | | KELAYKTKFTSKYLYNTITEYYVDGGECVISSDKLY DYVHNRRVYSNDEYTYFTPTNMVPHLKFIKVTEKY |
| 171 | Cluster: Uncharacterized protein | A0A0V8EN50 | MYFCYSNKQKDFLNQKGIDSLFSARHAKTNKLFYVF YQSEELGQALTEFTEKKAEFFKNN |
| 172 | Carbon_ starvation_ protein_A | P15078 | MKDIGNSSNFTEDEELFLLRNKQGKIVGIKDLKQAN FQETMKDWKKHLPKPSLLSIIIWVAVALLGGLAWSL IALAQGETINAIWFVIAAVCSYLIGYRFYALYIQRK IMRPNDLRATPSESHNDGKEFDPTNRVVLFGHHFAS IAGAGPLVGPVLAAQMGYLPGTIWIIFGVIFAGGVQ DMLVLWYSHRRRAKSIGAMAHDEVGRFAGGLTSFIV FIMTMIVLAVLALICVTAMANSAWAVFSIGMTIPIA LLMGIYLKYIRPGHVNEISAIGFILLLVAIFGGRWV SESSFAHIFMLSPTALVWWVMGYTFIAAIIPAWILL TPRDYLSMFMKIGTIAVLAIAVVGVRPDVTIPALTN FAHNTDGPAFAGSLFPFLFVTIACGALSGFHVMMSS GTTPHLIAKESQTRMIGYGGMLFESFVAIMALVAAI SLNPGIYYSMNTPQASIQKLAASSYQADKSAEYNAA KAIPNVAMMPDGSKLSIDWEGTTGEKALEQVAKDVG EQSIVSRTGGAPTLAVSMSNILHKVPLIGGTNMMGF WYHFAIMFEALFILSAVSAATKSTRYLLNDALRGFK KLGRLGDDDWLPSKIITTAVIVGVWGALLLMGVSDP NGGIKIMYPLFGISNQLIAAVALAIVCVMVIRKGYL KWVWIPALPLVWDVCVTFAASWQKIFSNDVNIGYFA SYSAAKAQVASGKISGLALTNTQATMRNTMIQGSLS VIFLLCVAILLVICALKVAKILRTNEVGDKFSSEEV FEESNLFETSSFWPSKLEHKVLKSKVNE |
| 173 | hypothetical_ protein | | MNYFKGKQFQKDVIIVAVGYYLRYNLSYREIQELLY DRGINVCHTTIYRWVQEYSKVLYHLWKKKNRQSFYS WKMDETYIKIKGRWHYLYRAIDVDGLTLDIWLRKKR DTQAAYAFLKRLHKQFGQPRVIVKDKAPSIGSAFRK LQSNGLYTKTEHRTVKYLNNLIEQDHRPIKRRNKFY QSLRTASTTIKGMETIRGIYKKNRRNGTLFGFSVST EIKVLMGILA |
| 174 | Cluster: Putative competence protein/ transcription factor | G8PA25 | MKTLIHEDLRGKIIYLQEEIPFGQGRLIEQLRLPFL SQKLLTIPLIVDLKLAEFIRRQLYYCSPKWLKLQEK YYQRGENLLNLTFERSFIAPLGLNLLEVFDDEIPLH KFTQIKQNINLYYENFLINFQQNSFKAVYPPRFYAI MKKQKKDMNE |
| 175 | Oligoendopeptidase_ F,_plasmid | P54124 | MAKNRNEIPEKLTWDLTTIYKTDKEWEAELTRIKSE LSLVEETDPGHLLDSAESLLTITEKMLSISQQVEKL YVYASMKNDQDTREAKYQEYQSKATALYVKFGEVYA FYEPEFLKISKEVYNKWLGELQKLKNYDHMFERLFA KKAHILSQKEEKLLAAAGEIFESPSETFEIFDNADI KLPMVKNESDEMIQLTHGNYSSLMESKNRGVRKAAY KALYSNYEQYQHTYAKTLQTNVKVHNLNAQIRSYDS ARQAALANNFVPEKVYDVLMEAIHQHLPLLHRYIEL RKKILGITDLKMYDIYTPLSNLDYKFNYEDGVKKAE EVLAIFGKEYKGKVKAAFEQRWIDVEENIGKRSGAY SGGSYDTNAFMLLNWQETLDDLFTLVHETGHSMHSA FTRENQPYVYGNYPIFLAEIASTTNENILTETLLKE SKDDKERFALLNHWLDSFRGTVFRQSQFAEFEQKIH EADAAGEVLTSEYLNSLYGEINEKYYNLAVKENPEI QYEWARIPHFYYNFYVFQYATGFAAATFLAEKVVHG STEDRQKYLEYLKAGSSAYPLEVIAKAGVDMESTDY LDAAFELFENRLSELEKLVEKGVHL |
| 176 | Cluster: ORF4 protein | P94881 | MVETYKRTSNPMMNRPVVKAELVEVVMRSSQTQITG ELASLASVPVLTRLFPLV |
| 177 | Cluster: Insertion sequence IS981 | Q48667 | MQKRYSKEFKETLIAFYHSGQSVTQLSKEYDVAPAT IYKWIDLYSKSNESSVSKADFLELKRQLAKVKEERD ILKKVLTIFAEKKK |
| 178 | Serine_ recombinase_ PinR | P0ADI0 | MKIGYARVSTFEQKLESQIEVLKEAGAEEVFQEKFT GTTVERPQFNLVFKKLKDGDTLIVTKLDRLARNTRE VLEIVQSLFNRGIKVHILNIGLIDNTPTGQLIFTIF |

TABLE 3-continued

| Exemplary *Lactococcus lactis cremoris* proteins not found in *Lactococcus lactis cremoris* Strain A | | | |
|---|---|---|---|
| SEQ ID NO. | name | uniprot_id | Protein Sequence |
| | | | SAFAQFERDLIVTRTQEGKNFAKLHDPSFREGRPQKFTEEQIQFAYELKQQGMTYKMIERKTGISIATQKRRFIKAKNQAIDKDY |
| 179 | Cluster: Replication protein | Q52233 | MKEYFQGDEFKDISKNGKDRKWKERKINNLNLAKIFDSLDYPDSFIFNIKSCAEYLNFKRSSDGSLRLFQMYTCKNKQCAICSWRRSMKYQVQISKIVEEAMIRKPKGRFLFLTLTVENVSGEGLNNELSLLSEAFNRLMKYKKVSKNILGFLRATEVTINESMDTYHPHIHVLLFISPTYFKNKNNYISQDEWTELWKKSAKLDYRPIVDVRSIKPKNEKTSDIRSAILETAKYPVKPMELNYDSAKVVDDLQKGLYRKRQIAFGGLFKQIKKELELDDIENGDLINIGDEENPISDGEIISVLWNHERQNYYVR |
| 180 | Cluster: Uncharacterized protein (Fragment) | T0VQK1 | MTCSNLTIHLHAKNRSKLFGSKKYALQELEAESTAFVVANHLNIDTKDYSIGYLNSWGFDKISDEQLENVIKNDKLSNNKIKGENE |
| 181 | Cluster: Uncharacterized protein | T0VLA4 | MINYQGEDFTETEFYGREILEAIQLTNKFPTPKKVLIDMLEEMIHEQLDFIDKEELNNYINAKKYVQTLTEDEVKNLCFEVKDLYEDVLKEFEIKL |

TABLE 4

| Selected Exopolysaccharide producing *Lactococcus lactis cremoris* Proteins not found in *Lactococcus lactis cremoris* Strain A | | | |
|---|---|---|---|
| SEQ ID NO. | name | uniprot_id | Protein Sequence |
| | Cluster: Exopoly-saccharide biosynthesis protein EpsL | A0A218PFY7 | MERKKKKKENIWAIIVPILIIISLIGAWAYALRDSLIPNDYTKTNSSDQPTKTSVSNGYVEQKGVEAAVGSIALVDDAGVPEWVKVPSKVNLDKFTDLSTNNITIYRINNPEVLKTVTNRTDQRMKMSEVIAKYPNALIMNASAFDMQTGQVAGFQINNGKLIQDWSPGTTTQYAFVINKDGSCKIYDSSTPASTIIKNGGQQAYDFGTAIIRDGKIQPSDGSVDWKIHIFIANDKDNNLYAILSDTNAGYDNIMKSVSNLKLQNMLLLDSGGSSQLSVNGKTIVASQDDRAVPDYIVMK |
| | Cluster: Polysaccharide pyruvyl transferase CsaB, csaB | A0A0M2ZR43 | MVDAYLDNNLGDDLMIRYFASYFYQHKIYLVESREHIRKTFYDIPNIYFYSEEDYKMNEYDFQLHVTIGGSMFILDDFKKLIRFRHRIKNSRKIKKRNIPSAIIGCNLGPFDKRNFGLKLAKFELKYKNLVTVRDKQSKELLLRGFKRKKINIKLFPDIIFSKVLYKSIPKYGLGMTLSQVFRVTNVEF |
| | putative_glycosyl-transferase_EpsJ | P71059 | MKNKFSIIVPVYNGESHIKKCIDTLLKQTYNDFEIIIINDGSTDDTKSVLTKFYAKNLKVKIVNTSNKGVSFARNLGINQSSGQYLLFVDSDDELSINALKYLSIMLNKKDRDLILFGFSLTGDNNRKNDTSILKSIANQNTDCKMNILKSILSTKNNILGYVWRAVYSLDFIKKNNIFFETHLKISEDYLFLLQSVEHSNNLFVITEEFYKYNLGETSMSNKFVPTLLNDMVWVNNWIESNILTVYPQFFVGFNCLVANTYIRYVQNAIRNKEENFMLKYREIKINKRKYNFQRSINQVIFHLDKFDFKSKIGVILFRIHLDIVYELLFNIKERKN |
| | Cluster: EpsH | Q3ZK44 | MTNLNRKKFFINFQSLVFFILIIIYGLTTKNVMGGSGIFSIDSILKYGILFICISVEGYIFLKNGNERRETSENYNNFKYYFIIITFLSLFASFKQVHFSFRTVQSFIFIFIPMLYSYLILNNWTFRQINFSMKIALFLSVIEYLFSIRMGFSQIISSLASINYNNNTNASALESSTFALLSLGFAAYFGYYKKNFLCKIVSLLFVIMTFKRVITLSGCILVILGILKIKNLRVNRFFLIVSTITLVSFSLIYYYSIQPQNILEISEKIGFSIRDFSTNRTDRLAWLSMTDFKSYGLGSTTDFMYKLWGVDLEMDIVQLILEVGAFGVIVFIYFYLRFSKSNLYAFSFMALLLLNSILSSGMMSTFSWIIILIAMSTIMEYKEGM |
| | Cluster: EpsF | Q3ZK46 | MIFVTVGTHEQPFNRLIQKIDELVRDGQIKDDVFMQIGYSTYEPKYTKWASVIGYNDMTAYFNKADIVITHGGPSTYMQVLQHGKIPIVVPRQEKFGEHINDHQLRVSK |

TABLE 4-continued

| Selected Exopolysaccharide producing *Lactococcus lactis cremoris* Proteins not found in *Lactococcus lactis cremoris* Strain A | | | |
|---|---|---|---|
| SEQ ID NO. | name | uniprot_id | Protein Sequence |
| | | | QVIKKGYPLILCEDVSALKICIESSRIRTDEFIKSNNKN FISNFKKIIAFEE |
| | Cluster: EpsE | Q9X491 | MKIALVGSSGGHLTHLYLLKKFWENEDRFWVTFDKT DAKSILKEERFYPCYYPTNRNVKNTIKNTILAFKILRKE KPDLIISSGAAVAVPFFWIGKLFGAKTVYIEIFDRIDKP TLTGKLVYPVTDKFIVQWEELKKVYPKAINLGGIF |
| | putative_ sugar_ transferase_ EpsL | P71062 | MEFFEDASSPESEEPKLVELKNFSYRELIIKRAIDILG GLAGSVLFLIAAALLYVPYKMSSKKDQGPMFYKQKR YGKNGKIFYILKFRTMIFNAEQYLELNPDVKAAYHAN GNKLENDPRVTKIGSFIRRHSIDELPQFINVLKGDMAL VGPRPILLFEAKEYGERLSYLLMCKPGITGYWTTHG RSKVLFPQRADLELYYLQYHSTKNDIKLLSLTIVQSIN GSDAY |
| | Tyrosine- protein_ kinase_ YwqD | P96716 | MAKNKRSIDNNRYIITSVNPQSPISEQYRTIRTTIDFK MADQGIKSFLVTSSEAAAGKSTVSANIAVAFAQQGK KVLLIDGDLRKPTVNITFKVQNRVGLTNILMHQSSIED AIQGTRLSENLTIITSGPIPPNPSELLASSAMKNLIDSV SDFFDVVLIDTPPLSAVTDAQILSSYVGGVVLVVRAY ETKKESLAKTKKMLEQVNANILGVVLHGVDSSDSPS YYYYGVE |
| | putative_ capsular_ polysaccharide_ biosynthesis | P96715 | MQETQEQTIDLRGIFKIIRKRLSLILFSALIVTILGSIYTF FIASPVYTASTQLVVKLPNSDNSDAYAGQVSGNIQM ANTINQVIVSPVILDKVQSNLNLSDDSFQKQVTAANQ TNSQVITLTVKYSNPYIAQKIADETAKIFSSDAAKLLNV TNVNILSKAKAQTTPISPKPKLYLAISVIAGLVLGLAIAL LKELFDNKINKEEDIEALGLTVLGVTSLCSNE |
| | Cluster: Polysaccharide biosynthesis protein | A9QSJ2 | MMKKGIFVITIVISIALIIGGFYSYNSRINNLSKADKGKE VVKNSSEKNQIDLTYKKYYKNLPKSVQNKIDDISSKN KEVTLTCIWQSDSVISEQFQQNLQKYYGNKFWNIKNI TYNGETSEQLLAEKVQNQVLATNPDVVLYEAPLFND NQNIEATASWTSNEQLITNLASTGAEVIVQPSPPIYG GVVYPVQEEQFKQSLSTKYPYIDYWASYPDKNSDE MKGLFSDDGVYRTLNASGNKVWLDYITKYFTAN |
| | Cluster: EpsR | O06027 | MNNLFYHRLKELVESSGKSANQIERELGYPRNSLNN YKLGGEPSGTRLIGLSEYFNVSPKYLMGIIDEPNDSS AINLFKTLTQEEKKEMFIICQKWLFLEYQIEL |
| | Putative_ O-antigen_ transporter | P37746 | MQIAKNYLYNAIYQVFIIIVPLLTIPYLSRILGPSGIGINS YTNSIVQYFVLFGSIGVGLYGNRQIAFVRDNQVKMSK VFYEIFILRLFTICLAYFLFVAFLIINGQYHAYYLSQSIAI VAAAFDISWFFMGIENFKVTVLRNFIVKLLALFSIFLFV KSYNDLNIYILITVLSTLIGNLTFFPSLHRYLVKVNYRE LRPIKHLKQSLVMFIPQIAVQIYWVLNKTMLGSLDSVT SSGFFDQSDKIVKLVLAIATATGTVMLPRVANAFAHR EYSKIKEYMYAGFSFVSAISIPMMFGLIAITPKFVPLFF TSQFSDVIPVLMIESIAIIFIAWSNAIGNQYLLPTNQNK SYTVSVIIGAIVNLMLNIPLIIYLGTVGASIATVISEMSVT VYQLFIIHKQLNLHTLFSDLSKYLIAGLVMFLIVFKISLL TPTSWIFILLEITVGIIIYVVLLIFLKAEIINKLKFIMHK |
| | Putative_ glycosyl- transferase_ EpsH | P71057 | MKKNVLLSIIVPIYNVEKYIGSLVNSLVKQTNKNFEVIF IDDGSTDESMQILKEIIAGSEQEFSLKLLQQVNQGLS SARNIGILNATGEYIFFLDSDDEIEINFVETILTSCYKYS QPDTLIFDYSSIDEFGNALDSNYGHGSIYRQKDLCTS EQILTALYKDEIPITAWSFVTKRSVIEKHNLLFSVGKK FEDNNFTPKVFYFSKNIGVISLRLYRYRKRSGSIMSN HPEKFFSDDAIFVTYDLLDFYDQYKIRELGAVVGKLV MTRLAFFPDSKKLYNELNPIIKKVFKDYISIEKRHTKRI KMYVKMYVFSSYVGYKLYRLVKGKHWK |

TABLE 5

Select Proteins from 13kb plasmid of Lactococcus lactis cremoris Strain A

| SEQ ID NO. | name | uniprot_id | Protein Sequence |
|---|---|---|---|
| | Foldase_protein_ PrsA | P0C2B5 | MKKKMRLKVLLASTATALLLLSGCQSNQTDQT<br>VATYSGGKVTESSFYKELKQSPTTKTMLANMLI<br>YRALNHAYGKSVSTKTVNDAYDSYKQQYGENF<br>DAFLSQNGFSRSSFKESLRTNFLSEVALKKLKKV<br>SESQLKAAWKTYQPKVTVQHILTSDEDTAKQVI<br>SDLAAGKDFAMLAKTDSIDTATKDNGGKISFEL<br>NNKTLDATFKDAAYKLKNGDYTQTPVKVTDG<br>YEVIKMINHPAKGTFTSSKKVLTASVYAKWSRD<br>SSIMQRVISQVLKNQHVTIKDKDLADALDSYKK<br>LATTN |
| | PIII-type_proteinase | P15292 | MQRKKKGLSFLLAGTVALGALAVLPVGEIQAK<br>AAISQQTKGSSLANTVTAATAKQAATDTTAATT<br>NQAIATQLAAKGIDYNKLNKVQQQDIYVDVIVQ<br>MSAAPASENGTLRTDYSSTAEIQQETNKVIAAQ<br>ASVKAAVEQVTQQTAGESYGYVVNGFSTKVRV<br>VDIPKLKQIAGVKTVTLAKVYYPTDAKANSMA<br>NVQAVWSNYKYKGEGTVVSVIDSGIDPTHKDM<br>RLSDDKDVKLTKSDVEKFTDTVKHGRYFNSKV<br>PYGFNYADNNDTITDDKVDEQHGMHVAGIIGA<br>NGTGDDPAKSVVGVAPEAQLLAMKVFTNSDTS<br>ATTGSDTLVSAIEDSAKIGADVLNMSLGSDSGN<br>QTLEDPEIAAVQNANESGTAAVISAGNSGTSGS<br>ATEGVNKDYYGLQDNEMVGTPGTSRGATTVAS<br>AENTDVITQAVTITDGTGLQLGPETIQLSSNDFT<br>GSFDQKKFYVVKDASGNLSKGKVADYTADAK<br>GKIAIVKRGELTFDDKQKYAQAAGAAGLIIVNN<br>DGTATPVTSMALTTTFPTFGLSSVTGQKLVDWV<br>TAHPDDSLGVKIALTLVPNQKYTEDKMSDFTSY<br>GPVSNLSFKPDITAPGGNIWSTQNNNGYTNMSG<br>TSMASPFIAGSQALLKQALNNKNNPFYAYYKQL<br>KGTALTDFLKTVEMNTAQPINDINYNNVIVSPR<br>RQGAGLVDVKAAIDALEKNPSTVVAENGYPAV<br>ELKDFTSTDKTFKLTFTNRTTHELTYQMDSNTD<br>TNAVYTSATDPNSGVLYDKKIDGAAIKAGSNIT<br>VPAGKTAQIEFTLSLPKSFDQQQFVEGFLNFKGS<br>DGSRLNLPYMGFFGDWNDGKIVDSLNGITYSPA<br>GGNFGTVPLLTNKNTGTQYYGGMVTDADGNQ<br>TVDDQAIAFSSDKNALYNDISMKYYLLRNISNV<br>QVDILDGQGNKVTTLSSSTNLTKTYYNAHSQQY<br>IYYHAPAWDGTYYDQRDGNIKTADDGSYTYRIS<br>GVPEGGDKRQVFDVPFKLDSKAPTVRHVALSA<br>KTKNGKTQYYLTAEVKDDLSGLDATKSVKTAI<br>NEVTNLDATFTDAGTTADGYTKIETPLSDEQAQ<br>ALGNGDNSAELYLTDNASNATDQDASVQKPGS<br>TSFDLIVNGSGIPDKISSTTTGYEANTQGGGTYTF<br>SGTYPAAVDGTYTDAQGKKHDLNTTYDAATNS<br>FTASMPVTNADYAAQVDLYADKAHTQLLKHFD<br>TKVRLTAPTFTDLKFNNGSDQTSEATIKVTGTVS<br>ADTKTVNVGDTVAALDAQHHFSVDVPVNYGD<br>NTIKVIATDEDGNTTTEQKTITSSYDPDMLKNPV<br>TFDQGVTFGSNEFNATSAKFYDPKTGIATITGKV<br>KHPTTTLQVDGKQIPIKDDLTFSFTLDLGTLGQK<br>PFGVVVGDTTQNKTFQEALTFILDAVAPTLSLDS<br>STDAPVYTNDPNFQITGTATDNAQYLSLSINGSS<br>VASQYADININSGKPGHMAIDQPVKLLEGKNVL<br>TVAVTDSEDNTTTKNITVYYEPKKTLAAPTVTP<br>STTEPAQTVTLTANAAATGETVQYSADGGKTY<br>QDVPAAGVTITANGTFKFKSTDLYGNESPAVDY<br>VVTNIKADDPAQLQAAKQALTNLIASAKTLSAS<br>GKYDDATTTALAAATQKAQTALDQTNASVDSL<br>TGANRDLQTAINQLAAKLPADKKTSLLNQLQSV<br>KDALGTDLGNQTDPSTGKTFTAALDDLVAQAQ<br>AGTQTDDQLQATLAKILDEVLAKLAEGIKAATP<br>AEVGNAKDAATGKTWYADIADTLTSGQASADA<br>SDKLAHLQALQSLKTKVAAAVEADKTVGKGD<br>DTTGTSDKGSGQGTPAPATGDTGKDKGDEGSQ<br>PSSGGNIPTNPATTTSTSADDTTDRNGQHTTGTS<br>DKGGGQGTPAPATGDTGKDKGDEGSQPSSGGN<br>IPTNPATTTSTSADDTTDRNGQHTTGTSDKGGG<br>QGTPAPATGDTGKDKGDEGSQPSSGGNIPTNPA<br>TTTSTSTDDTTDRNGQHTTGKGALPKTGETTER<br>PAFGFLGVIVVILMGVLGLKRKQREE |

TABLE 5-continued

Select Proteins from 13kb plasmid of Lactococcus lactis cremoris Strain A

| SEQ ID NO. | name | uniprot_id | Protein Sequence |
|---|---|---|---|
| | Cluster: Uncharacterized protein | T0V9Y4 | MRAAEGLFVYNKTNFHYLPQNIAFADFKSGKFA<br>TSGMSMILIDSVNHRILDVMKDRGAGQLRAYFN<br>QYSPSARAAVKTITVDLFTPYRAMIKDLFPNANI<br>VADRFHVVTQAYRELNKVRISVMKQFGSDSKE<br>YRQLKRFWKLLMKHENALDYMTSKNRINFKHA<br>YLTDKEVIDRLLALSDELRDAYAFYQVIL |
| | Cluster: Uncharacterized protein | T0UTW8 | MDNDIRILIGLTDLNIDFDAKAEQHFNETNLNGT<br>APITWNLLLTYATNCEKFGTPMVHNGIKMVTH<br>KGPRIAFKFQNYRIRKQKFL |
| | Cluster: Uncharacterized protein | T0UZT2 | MIENTINIAYARKFYKTKDYHSFCNLIKGNKGLF<br>GNKTVNQKANISFVKSEGEKHTHIYLDYQETCK<br>VAHPNFLQLINLLKNYDPEFSEEKLPTFDLNDKI<br>FGEYEIKVIPISKTKIVNTIDDVMNEIAKEIVLKY<br>NQDMFKVTSKLGEISLTPIQEKFDKLKDI |
| | Cluster: RepB | Q9AIQ4 | MIIPEKQNKQKQVLTLNELEKRKVVEHNALIQS<br>VAKMQKTALKMFELAVSCIDTEEPPKNNTVYLS<br>KSELFKFFEVSSSSKHSQFKEAVNYMQKQAFFNI<br>KADKKLGIEYESIVPIPYVKWNDYNDEVTIRFDQ<br>AIMPYLIDLKAEFTQYKISELQKLNSKYSIILYRW<br>LSMNYNQYEHYSVKGGRRADQVEAYRTPSIKV<br>KELREITDTINEHQHFPHFETRVLKKAIEEINAHT<br>SFNVTYEKVKKGRSIDSIVFHIEKKRMADDNSY<br>KLEDKVYQEDKARKAETEKDLVFQAMQSPYTR<br>LLIENMFLNVYETTDSQIMAGLQKNVYPLYDEL<br>KELRGLNGVKDHLSYVSSKQEAYSKRNVAKYL<br>KKAIEQYLPTVKRQDLNHE |
| | Cluster: Uncharacterized protein | Q7BLH6 | MSEDLKTIKELADELGVSKSYVDKIIRILKLHTK<br>LDKVGNKYVISKKQEKSIITRIENSKSTTETHTES<br>TTQSHTKVDAEVDFLKEEIAYLKSNHDKQLTNK<br>DKQIETLSNLLDQQQRLALQDKKWLEEYKAEIN<br>DLKALKMPSEDTKEEQSNYRSLEKEKDFVQTIQ<br>ESYESEIKVLNQKLAEQEEQIQEIQKEKETKEKK<br>WFQFWK |
| | Cluster: RepC | O05547 | MAQTFDRKILRALQDNGVREIRAYEVVSKRLTI<br>FQTDRGTFKYSDSLYRLVAPRQELWRNCTTGFI<br>SEEKYHFYKK |
| | Cluster: Transposase | Q2VHJ0 | MNHFKGKQFKKDVIIVAVGYYLRYNLSYREIQE<br>LLYDRGINVCHTTIYRWVQEYSKVLYHLWKKK<br>NRQSFYSWKMDETYIKIKGRWHYLYRAIDADG<br>LTLDIWLRKKRDTQAAYAFLKRLHKQFGQPRVI<br>VTDKAPSIGSAFRKLQSNGLYTKTEHRTVKYLN<br>NLIEQDHRPIKRRNKFYRSLRTASTTIKGMETIR<br>GIYKKNRRNGTLFGFSVSTEIKVLMGILA |

TABLE 6

Select Proteins from 30 kb plasmid of Lactococcus lactis cremoris Strain B

| SEQ ID NO. | name | uniprot_id | Protein Sequence |
|---|---|---|---|
| | Cluster: Exopoly-saccharide biosynthesis protein EpsL | A0A218PFY7 | MERKKKKKENIWAIIVPILIIISLIGAWAYALRD<br>SLIPNDYTKTNSSDQPTKTSVSNGYVEQKGVEA<br>AVGSIALVDDAGVPEWVKVPSKVNLDKFTDLS<br>TNNITIYRINNPEVLKTVTNRTDQRMKMSEVIA<br>KYPNALIMNASAFDMQTGQVAGFQINNGKLIQ<br>DWSPGTTTQYAFVINKDGSCKIYDSSTPASTIIK<br>NGGQQAYDFGTAIIRDGKIQPSDGSVDWKIHIFI<br>ANDKDNNLYAILSDTNAGYDNIMKSVSNLKLQ<br>NMLLLDSGGSSQLSVNGKTIVASQDDRAVPDY<br>IVMK |
| | Cluster: Transposase B | A4VC87 | MAQTIQTLALNVRLSCQLLDVPESSYYERINRH<br>PSKTQLRRQYLSLKISQLFNANRGIYGAPKIHHL |

TABLE 6-continued

Select Proteins from 30 kb plasmid of Lactococcus lactis cremoris Strain B

| SEQ ID NO. | name | uniprot_id | Protein Sequence |
|---|---|---|---|
| | of IS981 | | LLKQGEKVGLKLVQKLMKQLQLKSVVIKKFKP GYSLSDHINRKNLIQTEPTKKNKVWSTDITYIPT QQGWAYLSTIMDRYTKKVIAWDLGKRMTVEL VQRTLNKAIKSQDYPEAVILHSDQGSQYTSLEY EELLKYYGMTHSFSRRGYPYHNASLESWHGHL KREWVYQFKYKNFEEAYQSIFWYIEAFYNSKRI HQSLGYLTPNQFEKVSA |
| | Cluster: Polysaccharide pyruvyl transferase CsaB, csaB | A0A0M2ZR43 | MVDAYLDNNLGDDLMIRYFASYFYQHKIYLVE SREHIRKTFYDIPNIYFYSEEDYKMNEYDFQLH VTIGGSMFILDDFKKLIRFRHRIKNSRKIKKRNIP SAIIGCNLGPFDKRNFGLKLAKFELKYKNLVTV RDKQSKELLLRGFKRKKINIKLFPDIIFSKVLYK SIPKYGLGMTLSQVFRVTNVEF |
| | putative_ glycosyl- transferase_ EpsJ | P71059 | MKNKFSITVPVYNGESHIKKCIDTLLKQTYNDF EIIIINDGSTDDTKSVLTKFYAKNLKVKIVNTSN KGVSFARNLGINQSSGQYLLFVDSDDELSINAL KYLSIMLNKKDRDLILFGFSLTGDNNRKNDTSI LKSIANQNTDCKMNILKSILSTKNNILGYVWRA VYSLDFIKKNNIFFETHLKISEDYLFLLQSVEHS NNLFVITEEFYKYNLGETSMSNKFVPTLLNDM VWVNNWIESNILTVYPQFFVGFNCLVANTYIR YVQNAIRNKEENFMLKYREIKINKRKYNFQRSI NQVIFHLDKFDFKSKIGVILFRIHLDIVYELLFNI KERKN |
| | Cluster: EpsH | Q3ZK44 | MTNLNRKKFFINFQSLVFFILIIIYGLTTKNVMG GSGIFSIDSILKYGILFICISVEGYIFLKNGNERRE TSENYNNFKYYFIIITFLSLFASFKQVHFSFRTVQ SFIFIFIPMLYSYLILNNWTFRQINFSMKIALFLS VIEYLFSIRMGFSQIISSLASINYNNTNASALESS TFALLSLGFAAYFGYYKKNFLCKIVSLLFVIMT FKRVITLSGCILVILGILKIKNLRVNRFFLIVSTIT LVSFSLIYYYSIQPQNILEISEKIGFSIRDFSTNRT DRLAWLSMTDFKSYGLGSTTDFMYKLWGVDL EMDIVQLILEVGAFGVIVFIYFYLRFSKSNLYAF SFMALLLLNSILSSGMMSTFSWIIILIAMSTIMEY KEGM |
| | Cluster: Transferase 2, rSAM/selenodo main-associated | A0A0M2ZW08 | MKKLKISVIIRTYNEVKHIGEVLKSLTDQTYLN HEIIIVDSGSVDGTLDIIERYPVKLVSINKEDFNY SYASNVGVQNSSGDIVCFLSGHSVPVYKNYLE KINEIFQETEIGACYGEVIALPDGSITEKIFNRIG YLKSKLSLNNKRFFLENKIHPGIFSCSNACARK KLLLKYPFKVELGHGGEDVEVAYRIIQDGYFV AKSVELLVMHSHGSSLKKFIKEYKAWGKMYE DVLKFIKKNNDKSQ |
| | Cluster: EpsF | Q3ZK46 | MIFVTVGTHEQPFNRLIQKIDELVRDGQIKDDV FMQIGYSTYEPKYTKWASVIGYNDMTAYFNK ADIVITHGGPSTYMQVLQHGKIPIVVPRQEKFG EHINDHQLRVSKQVIKKGYPLILCEDVSALKICI ESSRIRTDEFIKSNNKNFISNFKKIIAFEE |
| | Cluster: EpsE | Q9X491 | MKIALVGSSGGHLTHLYLLKKFWENEDRFWV TFDKTDAKSILKEERFYPCYYPTNRNVKNTIKN TILAFKILRKEKPDLIISSGAAVAVPFFWIGKLFG AKTVYIEIFDRIDKPTLTGKLVYPVTDKFIVQW EELKKVYPKAINLGGIF |
| | putative_sugar_ transferase_ EpsL | P71062 | MEFFEDASSPESEEPKLVELKNFSYRELIIKRAID ILGGLAGSVLFLIAAALLYVPYKMSSKKDQGP MFYKQKRYGKNGKIFYILKFRTMIFNAEQYLEL NPDVKAAYHANGNKLENDPRVTKIGSFIRRHSI DELPQFINVLKGDMALVGPRPILLFEAKEYGER LSYLLMCKPGITGYWTTHGRSKVLFPQRADLE LYYLQYHSTKNDIKLLSLTIVQSINGSDAY |
| | Tyrosine- protein_ phosphatase_ YwqE | P96717 | MIDIHCHILPGIDDGAKTSGDTLTMLKSAIDEGI TTITATPHHNPQFNNESPLILKKVKEVQNIIDEH QLPIEVLPGQEVRIYGDLLKEFSEGKLLTAAGTS SYILIEFPSNHVPAYAKELFYNIKLEGLQPILVHP ERNSGIIENPDILFDFIEQGVLSQITASSVTGHFG |

TABLE 6-continued

Select Proteins from 30 kb plasmid of Lactococcus lactis cremoris Strain B

| SEQ ID NO. | name | uniprot_id | Protein Sequence |
|---|---|---|---|
| | | | KKIQKLSFKMIENHLTHFVASDAHNVTSRAFK MKEAFEIIEDSYGSDVSRMFQNNAESVILNESF YQEKPTKIKTKKLLGLF |
| | Tyrosine-protein_kinase_YwqD | P96716 | MAKNKRSIDNNRYIITSVNPQSPISEQYRTIRTTI DFKMADQGIKSFLVTSSEAAAGKSTVSANIAV AFAQQGKKVLLIDGDLRKPTVNITFKVQNRVG LTNILMHQSSIEDAIQGTRLSENLTIITSGPIPPNP SELLASSAMKNLIDSVSDFFDVVLIDTPPLSAVT DAQILSSYVGGVVLVVRAYETKKESLAKTKKM LEQVNANILGVVLHGVDSSDSPSYYYYGVE |
| | putative_capsular_polysaccharide biosynthesis | P96715 | MQETQEQTIDLRGIFKIIRKRLSLILFSALIVTILG SIYTFFIASPVYTASTQLVVKLPNSDNSDAYAG QVSGNIQMANTINQVIVSPVILDKVQSNLNLSD DSFQKQVTAANQTNSQVITLTVKYSNPYIAQKI ADETAKIFSSDAAKLLNVTNVNILSKAKAQTTP ISPKPKLYLAISVIAGLVLGLAIALLKELFDNKIN KEEDIEALGLTVLGVTSLCSNE |
| | Cluster: Polysaccharide biosynthesis protein | A9QSJ2 | MMKKGIFVITIVISIALIIGGFYSYNSRINNLSKA DKGKEVVKNSSEKNQIDLTYKKYYKNLPKSVQ NKIDDISSKNKEVTLTCIWQSDSVISEQFQQNLQ KYYGNKFWNIKNITYNGETSEQLLAEKVQNQV LATNPDVVLYEAPLFNDNQNIEATASWTSNEQ LITNLASTGAEVIVQPSPPIYGGVVYPVQEEQFK QSLSTKYPYIDYWASYPDKNSDEMKGLFSDDG VYRTLNASGNKVWLDYITKYFTAN |
| | Cluster: EpsR | O06027 | MNNLFYHRLKELVESSGKSANQIERELGYPRNS LNNYKLGGEPSGTRLIGLSEYFNVSPKYLMGII DEPNDSSAINLFKTLTQEEKKEMFIICQKWLFLE YQIEL |
| | Cluster: Transposase A | Q2VHJ5 | MSVSIIDSFPIPLCQPIRNFRSKGLGDYANVGYN ATKGQYFYGCKCHALVSESGYVIDYTITPASM ADSSMTEEVLSQFGTPTVLGDMGYLGQSLHDR LELKGIDLMTPVRKNMKQKKILFPNFSKRRKVI ERVFSFLTNLGAERCKSRSPQGFQLKLEMILLA YSLLLKSAKSLEPETLRYSIGYQVMAK |
| | Cluster: Signal transduction histidine kinase | A0A0B8QXZ2 | MTIKNKKDLSSSIEQLEKAINQQETILKKFDNEQ LDFEQIKKLENLLIQEREKAKQVQIKINRSVLQN NSENYKERKKRTRQLIQKGALLEKYLEAKHLT VDETEQLLQIFANMINKPELLVNFIGK |
| | Cluster: Tyrosine recombinase | B1N0G0 | MVQQIVLPIKDSNILKMVQDTLLDSFRAGRRN YTIFQVGKATLLRVSDVMKLKKTDVFNSDGTV KQTAFIHDQKTGKANTLYLKPVQQDLVVYHD WMVQQNLNSEWLFPSTSRPDRPITEKQFYKIM ARVGDLLSINYLGTHTMRKTGAYRVYTQSNY NIGLVIHLLNHSSEAMTLTYLGLDQASRETMLD QIDFG |
| | Cluster: Uncharacterized protein | G1FE57 | MDQKEVSQNQTKYIQFRLSEEQYNKLKISGET YGLSPNLYAKKLAQKSHLKKPYLEHDQAKSLL LELSKQGTNLNQIAKKLNQFDRMDNQDKELIE ALRYTYGVLAQAQKGYQELWQQLQK |
| | Cluster: Mobilization protein | H2A9L4 | MATIAKISNGASAASALNYALGQDRPMHEKTE QWLQDHQLERPVELTNCRAVAVGGTNGIDPFI AKEQFDVVRQLHNQTKESNQVMRITQSFALDE LNPKVQKDWQKANDLGVELAENLYPNHQSAV YTHLDGKNHVLHNHIIVNKVNLETGKKLREQK GESVQRAREMNDRLASRENWHILEPPKERQTE TEKELIAKNEYSYMDDLRERINKSLQDVSVSSY ETFKERLSDNGVILSERGQTFSYAFLDANNKQR RARETRLGSDFGKETILHELENRARQNEFSAVE QREPAITPLERDTQQRESEIVSLEQAIEPRKSEAL KRESKINRFIDTIKQFAGRVPELTQRVTRKLKQT KDKILDDFERRFSKDMKNYEQEQQKSLEKQAN RDVQSEKKPTKDHDRGMSR |

TABLE 6-continued

Select Proteins from 30 kb plasmid of Lactococcus lactis cremoris Strain B

| SEQ ID NO. | name | uniprot_id | Protein Sequence |
|---|---|---|---|
| | Cluster: Putative mobilization protein | S6EPU9 | MNKDEQLVVQVLNAYKNGKIDFSNVPELDRLVRQEVNKDFRDYQEKIEAVANQKIESAIQEQLHRLEAENLKATILKDIQVEKQALLALKKELNEQKEQIKADRKREIVERYGILIANIVCLFCFLVVGILIGRWIYKGIWDGWGLHILYDTVMEIKPKHPYGAVILGLGGFGLIGAGIYGSFRLMYTASTWFDQRPKIFKRIFPKK |
| | Adenosine_monophosphate-protein_transferase | Q7DDR9 | MVLDNKLGLTNSAELAKQEELLTKKRAKELFESGKIEDLEIGTFQGLSDIHQFLFQDIYDFAGKIREVNIAKGNFQFAPRIFLAQTLEYIDKLPQETFDEIIDKYSDMNVAHPFREGNGRATRIWLDLILKNKLHKIVDWNQIDKDEYLNAMIRSTVSTNELKYLIQKALTDDLGKEQFFKGIDASYYYEGYYEIKTEDL |
| | Cluster: RepB | O54680 | MSIITEFEKNQKQVKALNELSKRKVVEHNSLITSIAKMDKTPLKMFELAVSCINTEAPPKDHTVYLSKTELFAFFKVSDNDKHSRFKQAVENMQKQAFFKIQEKKEYGFEFENIVPIPYVKWADYHDEVTIRFSPEIMPYLINLKQNFTQHALSDIAELNSKYSIILYRWLSMNYNQYEHYSAKGGRREEQVETYRNPSISIRELREMTDTMKDYPRFQSLESYBKNSLKEINEHTSFKVTYEKVKKGRSINSIVFHITKKRRADDNSYKLEDKVYQKAKVQKEQKENLLYAEAMQSKYTKLLLEHFLLSPYEMTNPATMAGLQRNVYPKYDELKDLMGIDGVKKHLSYIYDKQEPYSKGNIAKYLKKAIEQYLPTVKRRGL |
| | Cluster: Replication-associated protein RepX | G0WJS1 | MSDNLKTIKELADELGVSKTAINKKVTDRERKLWFSKIGNKFVINEDGQKSIKRMFEGLTENQESQTENLEQKPNSQTENFRNNNESNADIKYILDIIEYQKEQIKDLQNTKDEQFKQLSNMQNLLDQQQRLALQDKKLLEEYKSENDRLKVLKMPSQETKEEQANIQPQEELETLKEQTRALNDKIKGQEELNNKSSKKWYQFWK |
| | Cluster: Truncated peptidase E | G0WJS2 | IVIFSYIYIILSYNTIKVKEVLKFEYRICTSFNWTSKFAEEMKTCFFNSGFKFKNFKGLDNRNAKEKSELISEAEVVILAGGHVPTQNIFFQQINLKNMSPVRIF |
| | Putative_O-antigen_transporter | P37746 | MQIAKNYLYNAIYQVFIIIVPLLTIPYLSRILGPSGIGINSYTNSIVQYFVLFGSIGVGLYGNRQIAFVRDNQVKMSKVFYEIFILRLFTICLAYFLFVAFLIINGQYHAYYLSQSIAIVAAAFDISWFFMGIENFKVTVLRNFIVKLLALFSIFLFVKSYNDLNIYILITVLSTLIGNLTFFPSLHRYLVKVNYRELRPIKHLKQSLVMFIPQIAVQIYWVLNKTMLGSLDSVTSSGFFDQSDKIVKLVLAIATATGTVMLPRVANAFAHREYSKIKEYMYAGFSFVSAISIPMMFGLIAITPKFVPLFFTSQFSDVIPVLMIESIAIIFIAWSNAIGNQYLLPTNQNKSYTVSVIIGAIVNLMLNIPLIIYLGTVGASIATVISEMSVTVYQLFIIHKQLNLHTLFSDLSKYLIAGLVMFLIVFKISLLTPTSWIFILLEITVGIIIYVVLLIFLKAEIINKLKFIMHK |
| | Cluster: Transposase | O50546 | MNLFGDSDYLEKLSSKGDPLERLEKVVDFECFRPTLNRIFKYDLKNKSHGGRPPYDLVLMLKILILQRLYNLSDDAMEYQMIDRISFRRFLKIDDKVPDAKTIWNFRNQLSKSNRGNWLFSAFQEKLESQGMIAHKGQIVDATFIEAPKQRNPKDENELIKANRVPVNWTKNKRAQKDTAARWTIKGNERHYGYKNHIAIDTKSKFVKNYQTTPANVHDSQVIGVLVDPDEITLADSAYQNKATPKGAELFTFLKNTRSKSLKADDKMFNKIISKIRVRIEHVFGFVENSMHGSSLRSIGFDRAVLNTDLTNLTYNLLRHEQVKRLNLKTWR |
| | Cluster: Orf14.9 | Q9RCJ9 | MRKYMIYLSSLLVTFILSYATITWLIMPVLTRYQSLARLINHFDYTALTLILLLTLIIWLFGIQYHLKHFSVIYLYLAFSVYLLLLFMVIFNKTTDFQAISLNPFDFIKADTRTIQEAVLNIIYFIPLGGLYCINTDFKQFVIISLVTLLGIETIQFIFYLGTFAISDIILNFLGCLIGYYCCWEIKKS |

TABLE 6-continued

Select Proteins from 30 kb plasmid of Lactococcus lactis cremoris Strain B

| SEQ ID NO. | name | uniprot_id | Protein Sequence |
|---|---|---|---|
| | Cluster: Transposase | Q2VHJ0 | MDETYIKIKGRGHYLYRTIDADGLTLDIWLRK KRDTQAAYAFLKRLHKQFGEPKAIVTDKAPSL GSAFRKLQSVGLYTKTEHRTVKYLNNLIEQDH RPIKRRNKFYQSLRTASSTIKGMETLRGIYKNN RRNGTLFGFSVSTEIKVLMGITA |
| | Putative_ glycosyl- transferase_ EpsH | P71057 | MKKNVLLSIIVPIYNVEKYIGSLVNSLVKQTNK NFEVIFIDDGSTDESMQILKEIIAGSEQEFSLKLL QQVNQGLSSARNIGILNATGEYIFFLDSDDEIEI NFVETILTSCYKYSQPDTLIFDYSSIDEFGNALD SNYGHGSIYRQKDLCTSEQILTALYKDEIPITAW SFVTKRSVIEKHNLLFSVGKKFEDNNFTPKVFY FSKNIGVISLRLYRYRKRSGSIMSNHPEKFFSDD AIFVTYDLLDFYDQYKIRELGAVVGKLVMTRL AFFPDSKKLYNELNPIIKKVFKDYISIEKRHTKRI KMYVKMYVFSSYVGYKLYRLVKGKHWK |
| | Cluster: Transposase | Q2VHJ0 | MNHFKGKQFKKDVIIVAVGYYLRYNLSYREVQ ELLYDRGINVCHTTIYRWVQEYSKVLYDLCKK KNRQSFYSWKMDETYIKIKGRWHYLYRAIDAD GLTLDIWLQKKRDTQAAYAFLKRLHKQFGEPK AIVTDKAPSLGSAFRKLQSVGLYTKTEHRTVK YLNNLIEQDHWPIKRRNKFYQSLRTASSTIKGM ETLRGIYKNNRRNGTLFGFSVSTEIKVLMGITA |
| | Cluster: Transposase | H5SYB4 | MQQNLLKYYGMTHSFSRRGYPYHNASLESWH GHLKREWVYQFKYKNFEEAYQSIFWYIEAFYN SKRIHQSLGYLTPNQFEKVSA |

Production of Immune Modulating *Lactococcus* Strain EVs

In certain aspects, the immune modulating *Lactococcus* strain EVs described herein can be prepared using any method known in the art.

In some embodiments, the immune modulating *Lactococcus* strain EVs are prepared without an EV purification step. For example, in some embodiments, immune modulating *Lactococcus* strain bacteria comprising the EVs described herein are killed using a method that leaves the immune modulating *Lactococcus* strain bacterial EVs intact and the resulting bacterial components, including the EVs, are used in the methods and compositions described herein. In some embodiments, the immune modulating *Lactococcus* strain bacteria are killed using an antibiotic (e.g., using an antibiotic described herein). In some embodiments, the immune modulating *Lactococcus* strain bacteria are killed using UV irradiation.

In some embodiments, the EVs described herein are purified from one or more other bacterial components. Methods for purifying EVs from bacteria are known in the art. In some embodiments EVs are prepared from bacterial cultures using methods described in S. Bin Park, et al. PLoS ONE. 6(3):e17629 (2011) or G. Norheim, et al. PLoS ONE. 10(9): e0134353 (2015), each of which is hereby incorporated by reference in its entirety. In some embodiments, the bacteria are cultured to high optical density and then centrifuged to pellet bacteria (e.g., at 10,000×g for 30 min at 4° C.). In some embodiments, the culture supernatants are then passed through filter to exclude intact bacterial cells (e.g., a 0.22 μm filter). In some embodiments, filtered supernatants are centrifuged to pellet bacterial EVs (e.g., at 100,000-150,000×g for 1-3 hours at 4° C.). In some embodiments, the EVs are further purified by resuspending the resulting EV pellets (e.g., in PBS), and applying the resuspended EVs to sucrose gradient (e.g., a 30-60% discontinuous sucrose gradient), followed by centrifugation (e.g., at 200,000×g for 20 hours at 4° C.). EV bands can be collected, washed with (e.g., with PBS), and centrifuged to pellet the EVs (e.g., at 150,000×g for 3 hours at 4° C.). The purified EVs can be stored, for example, at −80° C. until use. In some embodiments, the EVs are further purified by treatment with DNase and/or proteinase K.

For example, in some embodiments, cultures of immune modulating *Lactococcus* strain bacteria disclosed herein can be centrifuged at 11,000×g for 20-40 min at 4° C. to pellet bacteria. Culture supernatants may be passed through a 0.22 μm filter to exclude intact bacterial cells. Filtered supernatants may then be concentrated using methods that may include, but are not limited to, ammonium sulfate precipitation, ultracentrifugation, or filtration. For example, for ammonium sulfate precipitation, 1.5-3 M ammonium sulfate can be added to filtered supernatant slowly, while stirring at 4° C. Precipitations can be incubated at 4° C. for 8-48 hours and then centrifuged at 11,000×g for 20-40 min at 4° C. The resulting pellets contain immune modulating *Lactococcus* strain EVs and other debris. Using ultracentrifugation, filtered supernatants can be centrifuged at 100,000-200,000×g for 1-16 hours at 4° C. The pellet of this centrifugation contains immune modulating *Lactococcus* strain EVs and other debris. In some embodiments, using a filtration technique, such as through the use of an Amicon Ultra spin filter or by tangential flow filtration, supernatants can be filtered so as to retain species of molecular weight >50 or 100 kDa.

Alternatively, EVs can be obtained from immune modulating *Lactococcus* strain bacterial cultures continuously during growth, or at selected time points during growth, by connecting a bioreactor to an alternating tangential flow (ATF) system (e.g., XCell ATF from Repligen). The ATF system retains intact cells (>0.22 um) in the bioreactor, and allows smaller components (e.g., EVs, free proteins) to pass through a filter for collection. For example, the system may be configured so that the <0.22 um filtrate is then passed through a second filter of 100 kDa, allowing species such as EVs between 0.22 um and 100 kDa to be collected, and species smaller than 100 kDa to be pumped back into the bioreactor. Alternatively, the system may be configured to allow for medium in the bioreactor to be replenished and/or modified during growth of the culture. EVs collected by this method may be further purified and/or concentrated by ultracentrifugation or filtration as described above for filtered supernatants.

EVs obtained by methods provided herein may be further purified by size based column chromatography, by affinity chromatography, and by gradient ultracentrifugation, using methods that may include, but are not limited to, use of a sucrose gradient or Optiprep gradient. Briefly, using a sucrose gradient method, if ammonium sulfate precipitation or ultracentrifugation were used to concentrate the filtered supernatants, pellets are resuspended in 60% sucrose, 30 mM Tris, pH 8.0. If filtration was used to concentrate the filtered supernatant, the concentrate is buffer exchanged into 60% sucrose, 30 mM Tris, pH 8.0, using an Amicon Ultra column. Samples are applied to a 35-60% discontinuous sucrose gradient and centrifuged at 200,000×g for 3-24 hours at 4° C. Briefly, using an Optiprep gradient method, if ammonium sulfate precipitation or ultracentrifugation were used to concentrate the filtered supernatants, pellets are resuspended in 35% Optiprep in PBS. In some embodiments, if filtration was used to concentrate the filtered supernatant, the concentrate is diluted using 60% Optiprep to a final concentration of 35% Optiprep. Samples are applied to a 35-60% discontinuous sucrose gradient and centrifuged at 200,000×g for 3-24 hours at 4° C.

In some embodiments, to confirm sterility and isolation of the EV preparations, EVs are serially diluted onto agar medium used for routine culture of the bacteria being tested, and incubated using routine conditions. Non-sterile preparations are passed through a 0.22 um filter to exclude intact cells. To further increase purity, isolated EVs may be DNase or proteinase K treated.

In some embodiments, for preparation of EVs used for in vivo injections, purified EVs are processed as described previously (G. Norheim, et al. PLoS ONE. 10(9): e0134353 (2015)). Briefly, after sucrose gradient centrifugation, bands containing EVs are resuspended to a final concentration of 50 μg/mL in a solution containing 3% sucrose or other solution suitable for in vivo injection known to one skilled in the art. This solution may also contain adjuvant, for example aluminum hydroxide at a concentration of 0-0.5% (w/v).

In certain embodiments, to make samples compatible with further testing (e.g. to remove sucrose prior to TEM imaging or in vitro assays), samples are buffer exchanged into PBS or 30 mM Tris, pH 8.0 using filtration (e.g. Amicon Ultra columns), dialysis, or ultracentrifugation (200,000×g, ≥3 hours, 4° C.) and resuspension.

In some embodiments, the sterility of the EV preparations can be confirmed by plating a portion of the EVs onto agar medium used for standard culture of the bacteria used in the generation of the EVs and incubating using standard conditions.

In some embodiments select EVs are isolated and enriched by chromatography and binding surface moieties on EVs. In other embodiments, select EVs are isolated and/or enriched by fluorescent cell sorting by methods using affinity reagents, chemical dyes, recombinant proteins or other methods known to one skilled in the art.

Bacterial Compositions

In certain aspects, provided herein are bacterial compositions comprising an immune modulating *Lactococcus* strain provided herein, an immune modulating *Lactococcus* strain EVs provided herein, and/or an immune modulating *Lactococcus* strain PhAB provided herein. In some embodiments, the bacterial formulation further comprises a pharmaceutically acceptable carrier.

In some embodiments, the bacterial composition comprises a killed bacterium, a live bacterium and/or an attenuated bacterium. Bacteria may be heat-killed by pasteurization, sterilization, high temperature treatment, spray cooking and/or spray drying (heat treatments can be performed at 50° C., 65° C., 85° C. or a variety of other temperatures and/or a varied amount of time). Bacteria may also be killed or inactivated using γ-irradiation (gamma irradiation), exposure to UV light, formalin-inactivation, and/or freezing methods, or a combination thereof. For example, the bacteria may be exposed to 1, 2, 3, 4, 5, 10, 15, 20, 25, 30, 35, 40, or 50 kGy of radiation prior to administration. In some embodiments, bacteria (e.g., *Lactococcus* strain) are killed using gamma irradiation. In some embodiments, the bacteria are killed or inactivated using electron irradiation (e.g., beta radiation) or x-ray irradiation.

In certain embodiments, at least 50%, 55%, 60%, 65%, 70%, 75%, 80%, 85%, 90%, 91%, 92%, 93%, 94%, 95%, 96%, 97%, 98% or 99% of the bacteria in the bacterial composition are the immune modulating *Lactococcus* strain. In certain embodiments, substantially all of the bacteria in the bacterial composition are the immune modulating *Lactococcus* strain. In certain embodiments, the bacterial composition comprises at least $1\times10^3$ colony forming units (CFUs), $1\times10^4$ colony forming units (CFUs), $1\times10^5$ colony forming units (CFUs), $5\times10^5$ colony forming units (CFUs), $1\times10^6$ colony forming units (CFUs), $2\times10^6$ colony forming units (CFUs), $3\times10^6$ colony forming units (CFUs), $4\times10^6$ colony forming units (CFUs), $5\times10^6$ colony forming units (CFUs), $6\times10^6$ colony forming units (CFUs), $7\times10^6$ colony forming units (CFUs), $8\times10^6$ colony forming units (CFUs), $9\times10^6$ colony forming units (CFUs), $1\times10^7$ colony forming units (CFUs), $2\times10^7$ colony forming units (CFUs), $3\times10^7$ colony forming units (CFUs), $4\times10^7$ colony forming units (CFUs), $5\times10^7$ colony forming units (CFUs), $6\times10^7$ colony forming units (CFUs), $7\times10^7$ colony forming units (CFUs), $8\times10^7$ colony forming units (CFUs), $9\times10^7$ colony forming units (CFUs), $1\times10^8$ colony forming units (CFUs), $2\times10^8$ colony forming units (CFUs), $3\times10^8$ colony forming units (CFUs), $4\times10^8$ colony forming units (CFUs), $5\times10^8$ colony forming units (CFUs), $6\times10^8$ colony forming units (CFUs), $7\times10^8$ colony forming units (CFUs), $8\times10^8$ colony forming units (CFUs), $9\times10^8$ colony forming units (CFUs), $1\times10^9$ colony forming units (CFUs), $5\times10^9$ colony forming units (CFUs), $1\times10^{10}$ colony forming units (CFUs) $5\times10^{10}$ colony forming units (CFUs), $1\times10^{11}$ colony forming units (CFUs) $5\times10^{11}$ colony forming units (CFUs), $1\times10^{12}$ colony forming units (CFUs) $5\times10^{12}$ colony forming units (CFUs), $1\times10^{13}$ colony forming units (CFUs) of the immune modulating *Lactococcus* strain.

In some embodiments, at least 10%, 15%, 20%, 25%, 30%, 35%, 40%, 45%, 50%, 55%, 60%, 65%, 70%, 75%, 80%, 85%, 90%, 95%, 96%, 97%, 98% or 99% of the bacteria in the composition are of the immune modulating *Lactococcus* strain. 10%, 15%, 20%, 25%, 30%, 35%, 40%, 45%, 50%, 55%, 60%, 65%, 70%, 75%, 80%, 85%, 90%, 95%, 96%, 97%, 98% or 99% of the bacteria in the composition are of the immune modulating *Lactococcus* strain.

In some embodiments, the compositions described herein may include only one strains of the immune modulating *Lactococcus* described herein. For example, 1, 2, 3, 4, 5, 6, 7, 8, 9, 10, 11, 12, 13, 14, 15, 16, 17, 18, 19 or 20 of the immune modulating *Lactococcus* strains described herein, in any combination, can be included in the compositions provided herein.

In some embodiments, the pharmaceutical compositions comprise immune modulating *Lactococcus* strain EVs substantially or entirely free of bacteria. In some embodiments, the pharmaceutical compositions comprise both immune modulating *Lactococcus* strain EVs and whole immune modulating *Lactococcus* strain bacteria (e.g., live bacteria, killed bacteria, attenuated bacteria). In certain embodiments, the pharmaceutical compositions comprise immune modulating *Lactococcus* strain bacteria that is substantially or entirely free of EVs.

In some embodiments, the pharmaceutical composition comprises at least 1 immune modulating *Lactococcus* strain bacterium for every 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 550, 600, 650, 700, 750, 800, 850, 900, 950, $1\times10^{3}$, $2\times10^{3}$, $3\times10^{3}$, $4\times10^{3}$, $5\times10^{3}$, $6\times10^{3}$, $7\times10^{3}$, $8\times10^{3}$, $9\times10^{3}$, $1\times10^{4}$, $2\times10^{4}$, $3\times10^{4}$, $4\times10^{4}$, $5\times10^{4}$, $6\times10^{4}$, $7\times10^{4}$, $8\times10^{4}$, $9\times10^{4}$, $1\times10^{5}$, $2\times10^{5}$, $3\times10^{5}$, $4\times10^{5}$, $5\times10^{5}$, $6\times10^{5}$, $7\times10^{5}$, $8\times10^{5}$, $9\times10^{5}$, $1\times10^{6}$, $2\times10^{6}$, $3\times10^{6}$, $4\times10^{6}$, $5\times10^{6}$, $6\times10^{6}$, $7\times10^{6}$, $8\times10^{6}$, $9\times10^{6}$, $1\times10^{7}$, $2\times10^{7}$, $3\times10^{7}$, $4\times10^{7}$, $5\times10^{7}$, $6\times10^{7}$, $7\times10^{7}$, $8\times10^{7}$, $9\times10^{7}$, $1\times10^{8}$, $2\times10^{8}$, $3\times10^{8}$, $4\times10^{8}$, $5\times10^{8}$, $6\times10^{8}$, $7\times10^{8}$, $8\times10^{8}$, $9\times10^{8}$, $1\times10^{9}$, $2\times10^{9}$, $3\times10^{9}$, $4\times10^{9}$, $5\times10^{9}$, $6\times10^{9}$, $7\times10^{9}$, $8\times10^{9}$, $9\times10^{9}$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ immune modulating *Lactococcus* strain EV particles.

In some embodiments, the pharmaceutical composition comprises about 1 immune modulating *Lactococcus* strain bacterium for every 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 550, 600, 650, 700, 750, 800, 850, 900, 950, $1\times10^{3}$, $2\times10^{3}$, $3\times10^{3}$, $4\times10^{3}$, $5\times10^{3}$, $6\times10^{3}$, $7\times10^{3}$, $8\times10^{3}$, $9\times10^{3}$, $1\times10^{4}$, $2\times10^{4}$, $3\times10^{4}$, $4\times10^{4}$, $5\times10^{4}$, $6\times10^{4}$, $7\times10^{4}$, $8\times10^{4}$, $9\times10^{4}$, $1\times10^{5}$, $2\times10^{5}$, $3\times10^{5}$, $4\times10^{5}$, $5\times10^{5}$, $6\times10^{5}$, $7\times10^{5}$, $8\times10^{5}$, $9\times10^{5}$, $1\times10^{6}$, $2\times10^{6}$, $3\times10^{6}$, $4\times10^{6}$, $5\times10^{6}$, $6\times10^{6}$, $7\times10^{6}$, $8\times10^{6}$, $9\times10^{6}$, $1\times10^{7}$, $2\times10^{7}$, $3\times10^{7}$, $4\times10^{7}$, $5\times10^{7}$, $6\times10^{7}$, $7\times10^{7}$, $8\times10^{7}$, $9\times10^{7}$, $1\times10^{8}$, $2\times10^{8}$, $3\times10^{8}$, $4\times10^{8}$, $5\times10^{8}$, $6\times10^{8}$, $7\times10^{8}$, $8\times10^{8}$, $9\times10^{8}$, $1\times10^{9}$, $2\times10^{9}$, $3\times10^{9}$, $4\times10^{9}$, $5\times10^{9}$, $6\times10^{9}$, $7\times10^{9}$, $8\times10^{9}$, $9\times10^{9}$ $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ immune modulating *Lactococcus* strain EV particles.

In certain embodiments, the pharmaceutical composition comprises a certain ratio of immune modulating *Lactococcus* strain bacteria particles to immune modulating *Lactococcus* strain EV particles. The number of immune modulating *Lactococcus* strain bacteria particles can be based on actual particle number or (if the bacteria is live) the number of CFUs. The particle number can be established by combining a set number of purified immune modulating *Lactococcus* strain EVs with a set number of purified immune modulating *Lactococcus* strain bacterium, by modifying the growth conditions under which the immune modulating *Lactococcus* strain bacteria are cultured, or by modifying the immune modulating *Lactococcus* strain bacteria itself to produce more or fewer immune modulating *Lactococcus* strain EVs.

In some embodiments, to quantify the numbers of immune modulating *Lactococcus* strain EVs and/or immune modulating *Lactococcus* strain bacteria present in a bacterial sample, electron microscopy (e.g., EM of ultrathin frozen sections) can be used to visualize the vesicles and bacteria and count their relative numbers. Alternatively, combinations of nanoparticle tracking analysis (NTA), Coulter counting, and dynamic light scattering (DLS) or a combination of these techniques can be used. NTA and the Coulter counter count particles and show their sizes. DLS gives the size distribution of particles, but not the concentration. Bacteria frequently have diameters of 1-2 um. The full range is 0.2-20 um. Combined results from Coulter counting and NTA can reveal the numbers of bacteria in a given sample. Coulter counting reveals the numbers of particles with diameters of 0.7-10 um. NTA reveals the numbers of particles with diameters of 50-1400 nm. For most bacterial samples, the Coulter counter alone can reveal the number of bacteria in a sample. EVs are 20-250 nm in diameter. NTA will allow us to count the numbers of particles that are 50-250 nm in diameter. DLS reveals the distribution of particles of different diameters within an approximate range of 1 nm-3 um.

In some embodiments, the pharmaceutical composition comprises no more than 1 immune modulating *Lactococcus* strain bacterium for every 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 550, 600, 650, 700, 750, 800, 850, 900, 950, $1\times10^{3}$, $2\times10^{3}$, $3\times10^{3}$, $4\times10^{3}$, $5\times10^{3}$, $6\times10^{3}$, $7\times10^{3}$, $8\times10^{3}$, $9\times10^{3}$, $1\times10^{4}$, $2\times10^{4}$, $3\times10^{4}$, $4\times10^{4}$, $5\times10^{4}$, $6\times10^{4}$, $7\times10^{4}$, $8\times10^{4}$, $9\times10^{4}$, $1\times10^{5}$, $2\times10^{5}$, $3\times10^{5}$, $4\times10^{5}$, $5\times10^{5}$, $6\times10^{5}$, $7\times10^{5}$, $8\times10^{5}$, $9\times10^{5}$, $1\times10^{6}$, $2\times10^{6}$, $3\times10^{6}$, $4\times10^{6}$, $5\times10^{6}$, $6\times10^{6}$, $7\times10^{6}$, $8\times10^{6}$, $9\times10^{6}$, $1\times10^{7}$, $2\times10^{7}$, $3\times10^{7}$, $4\times10^{7}$, $5\times10^{7}$, $6\times10^{7}$, $7\times10^{7}$, $8\times10^{7}$, $9\times10^{7}$, $1\times10^{8}$, $2\times10^{8}$, $3\times10^{8}$, $4\times10^{8}$, $5\times10^{8}$, $6\times10^{8}$, $7\times10^{8}$, $8\times10^{8}$, $9\times10^{8}$, $1\times10^{9}$, $2\times10^{9}$, $3\times10^{9}$, $4\times10^{9}$, $5\times10^{9}$, $6\times10^{9}$, $7\times10^{9}$, $8\times10^{9}$, $9\times10^{9}$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ immune modulating *Lactococcus* strain EV particles.

In some embodiments, the pharmaceutical composition comprises at least 1 immune modulating *Lactococcus* strain EV particle for every 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 550, 600, 650, 700, 750, 800, 850, 900, 950, $1\times10^{3}$, $2\times10^{3}$, $3\times10^{3}$, $4\times10^{3}$, $5\times10^{3}$, $6\times10^{3}$, $7\times10^{3}$, $8\times10^{3}$, $9\times10^{3}$, $1\times10^{4}$, $2\times10^{4}$, $3\times10^{4}$, $4\times10^{4}$, $5\times10^{4}$, $6\times10^{4}$, $7\times10^{4}$, $8\times10^{4}$, $9\times10^{4}$, $1\times10^{5}$, $2\times10^{5}$, $3\times10^{5}$, $4\times10^{5}$, $5\times10^{5}$, $6\times10^{5}$, $7\times10^{5}$, $8\times10^{5}$, $9\times10^{5}$, $1\times10^{6}$, $2\times10^{6}$, $3\times10^{6}$, $4\times10^{6}$, $5\times10^{6}$, $6\times10^{6}$, $7\times10^{6}$, $8\times10^{6}$, $9\times10^{6}$, $1\times10^{7}$, $2\times10^{7}$, $3\times10^{7}$, $4\times10^{7}$, $5\times10^{7}$, $6\times10^{7}$, $7\times10^{7}$, $8\times10^{7}$, $9\times10^{7}$, $1\times10^{8}$, $2\times10^{8}$, $3\times10^{8}$, $4\times10^{8}$, $5\times10^{8}$, $6\times10^{8}$, $7\times10^{8}$, $8\times10^{8}$, $9\times10^{8}$, $1\times10^{9}$, $2\times10^{9}$, $3\times10^{9}$, $4\times10^{9}$, $5\times10^{9}$, $6\times10^{9}$, $7\times10^{9}$, $8\times10^{9}$, $9\times10^{9}$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ immune modulating *Lactococcus* strain bacterium.

In some embodiments, the pharmaceutical composition comprises about 1 immune modulating *Lactococcus* strain EV particle for every 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 550, 600, 650, 700, 750, 800, 850, 900, 950, $1\times10^{3}$, $2\times10^{3}$, $3\times10^{3}$, $4\times10^{3}$, $5\times10^{3}$, $6\times10^{3}$, $7\times10^{3}$, $8\times10^{3}$, $9\times10^{3}$, $1\times10^{4}$, $2\times10^{4}$, $3\times10^{4}$, $4\times10^{4}$, $5\times10^{4}$, $6\times10^{4}$, $7\times10^{4}$, $8\times10^{4}$, $9\times10^{4}$, $1\times10^{5}$, $2\times10^{5}$, $3\times10^{5}$, $4\times10^{5}$, $5\times10^{5}$, $6\times10^{5}$, $7\times10^{5}$, $8\times10^{5}$, $9\times10^{5}$, $1\times10^{6}$, $2\times10^{6}$, $3\times10^{6}$, $4\times10^{6}$, $5\times10^{6}$, $6\times10^{6}$, $7\times10^{6}$, $8\times10^{6}$, $9\times10^{6}$, $1\times10^{7}$, $2\times10^{7}$, $3\times10^{7}$, $4\times10^{7}$, $5\times10^{7}$, $6\times10^{7}$, $7\times10^{7}$, $8\times10^{7}$, $9\times10^{7}$, $1\times10^{8}$, $2\times10^{8}$, $3\times10^{8}$, $4\times10^{8}$, $5\times10^{8}$, $6\times10^{8}$, $7\times10^{8}$, $8\times10^{8}$, $9\times10^{8}$, $1\times10^{9}$, $2\times10^{9}$, $3\times10^{9}$, $4\times10^{9}$, $5\times10^{9}$, $6\times10^{9}$, $7\times10^{9}$, $8\times10^{9}$, $9\times10^{9}$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ immune modulating *Lactococcus* strain bacterium. In some embodiments, the pharmaceutical composition comprises no more than 1 immune modulating *Lactococcus* strain EV particle for every 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 550, 600, 650, 700, 750, 800, 850, 900, 950, $1\times10^{3}$, $2\times10^{3}$, $3\times10^{3}$, $4\times10^{3}$, $5\times10^{3}$, $6\times10^{3}$, $7\times10^{3}$, $8\times10^{3}$, $9\times10^{3}$, $1\times10^{4}$, $2\times10^{4}$, $3\times10^{4}$, $4\times10^{4}$, $5\times10^{4}$, $6\times10^{4}$, $7\times10^{4}$, $8\times10^{4}$, $9\times10^{4}$, $1\times10^{5}$, $2\times10^{5}$, $3\times10^{5}$, $4\times10^{5}$, $5\times10^{5}$, $6\times10^{5}$, $7\times10^{5}$, $8\times10^{5}$, $9\times10^{5}$, $1\times10^{6}$, $2\times10^{6}$, $3\times10^{6}$, $4\times10^{6}$, $5\times10^{6}$, $6\times10^{6}$, $7\times10^{6}$, $8\times10^{6}$, $9\times10^{6}$, $1\times10^{7}$, $2\times10^{7}$, $3\times10^{7}$, $4\times10^{7}$, $5\times10^{7}$, $6\times10^{7}$, $7\times10^{7}$, $8\times10^{7}$, $9\times10^{7}$, $1\times10^{8}$, $2\times10^{8}$, $3\times10^{8}$, $4\times10^{8}$, $5\times10^{8}$, $6\times10^{8}$, $7\times10^{8}$, $8\times10^{8}$, $9\times10^{8}$, $1\times10^{9}$, $2\times10^{9}$, $3\times10^{9}$, $4\times10^{9}$, $5\times10^{9}$, $6\times10^{9}$, $7\times10^{9}$, $8\times10^{9}$, $9\times10^{9}$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ immune modulating *Lactococcus* strain bacterium.

In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the particles in the pharmaceutical composition are immune modulating *Lactococcus* strain EVs.

In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the particles in the pharmaceutical composition are immune modulating *Lactococcus* strain bacteria.

In some embodiments, no more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the particles in the pharmaceutical composition are immune modulating *Lactococcus* strain EVs.

In some embodiments, no more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the particles in the pharmaceutical composition are immune modulating *Lactococcus* strain bacteria.

In some embodiments, about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the particles in the pharmaceutical composition are immune modulating *Lactococcus* strain EVs.

In some embodiments, about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the particles in the pharmaceutical composition are immune modulating *Lactococcus* strain bacteria.

In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the protein in the pharmaceutical composition is immune modulating *Lactococcus* strain EV protein.

In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the protein in the pharmaceutical composition is immune modulating *Lactococcus* strain bacteria protein.

In some embodiments, no more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the protein in the pharmaceutical composition is immune modulating *Lactococcus* strain EV protein.

In some embodiments, no more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the protein in the pharmaceutical composition is immune modulating *Lactococcus* strain bacteria protein.

In some embodiments, about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the protein in the pharmaceutical composition is immune modulating *Lactococcus* strain EV protein.

In some embodiments, about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the protein in the pharmaceutical composition is immune modulating *Lactococcus* strain bacteria protein.

In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the lipids in the pharmaceutical composition are immune modulating *Lactococcus* strain EV lipids.

In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the lipids in the pharmaceutical composition are immune modulating *Lactococcus* strain bacteria lipids.

In some embodiments, no more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the lipids in the pharmaceutical composition are immune modulating *Lactococcus* strain EV lipids.

In some embodiments, no more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the lipids in the pharmaceutical composition are immune modulating *Lactococcus* strain bacteria lipids.

In some embodiments, about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the lipids in the pharmaceutical composition are immune modulating *Lactococcus* strain EV lipids.

In some embodiments, about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the lipids in the pharmaceutical composition are immune modulating *Lactococcus* strain bacteria lipids.

In some embodiments, the immune modulating *Lactococcus* strain EVs in the pharmaceutical composition are purified from one or more other bacterial components. In some embodiments, the pharmaceutical composition further comprises other bacterial components. In some embodiments, the pharmaceutical composition comprise bacteria cells.

As described in detail below, the pharmaceutical compositions disclosed herein may be specially formulated for administration in solid or liquid form, including those adapted for oral or rectal administration.

In some embodiments, the composition described herein may be a pharmaceutical composition, a dietary supplement, or a food product (e.g., a food or beverage). In some embodiments, the food product is an animal feed.

In certain embodiments, the pharmaceutical composition for oral administration described herein comprises an additional component that enables efficient delivery of the bacteria to the colon. In some embodiments, pharmaceutical preparation that enables the delivery of the bacteria to the colon can be used. Examples of such formulations include pH sensitive compositions, such as buffered sachet formulations or enteric polymers that release their contents when the pH becomes alkaline after the enteric polymers pass through the stomach. When a pH sensitive composition is used for formulating the pharmaceutical preparation, the pH sensitive composition can be a polymer whose pH threshold of the decomposition of the composition is between about 6.8 and about 7.5.

Another embodiment of a pharmaceutical composition useful for delivery of the bacteria to the colon is one that ensures the delivery to the colon by delaying the release of the bacteria by approximately 3 to 5 hours, which corresponds to the small intestinal transit time. In some embodiments, the pharmaceutical composition for delayed release includes a hydrogel shell. The hydrogel is hydrated and swells upon contact with gastrointestinal fluid, with the result that the contents are effectively released (released predominantly in the colon). Delayed release dosage units include bacteria-containing compositions having a material which coats or selectively coats the bacteria. Examples of such a selective coating material include in vivo degradable polymers, gradually hydrolyzable polymers, gradually water-soluble polymers, and/or enzyme degradable polymers. A wide variety of coating materials for efficiently delaying the release is available and includes, for example, cellulose-based polymers such as hydroxypropyl cellulose, acrylic acid polymers and copolymers such as methacrylic acid polymers and copolymers, and vinyl polymers and copolymers such as polyvinylpyrrolidone.

Examples of composition enabling the delivery to the colon further include bioadhesive compositions which specifically adhere to the colonic mucosal membrane (for example, a polymer described in the specification of U.S. Pat. No. 6,368,586, hereby incorporated by reference) and compositions into which a protease inhibitor is incorporated for protecting particularly a biopharmaceutical preparation in the gastrointestinal tracts from decomposition due to an activity of a protease.

An example of a system enabling the delivery to the colon is a system of delivering a composition to the colon by pressure change in such a way that the contents are released by utilizing pressure change caused by generation of gas in bacterial fermentation at a distal portion of the stomach. Such a system is not particularly limited, and a more specific example thereof is a capsule which has contents dispersed in a suppository base and which is coated with a hydrophobic polymer (for example, ethyl cellulose).

Another example of the system enabling the delivery to the colon is a system of delivering a composition to the colon, the system being specifically decomposed by an enzyme (for example, a carbohydrate hydrolase or a carbohydrate reductase) present in the colon. Such a system is not particularly limited, and more specific examples thereof include systems which use food components such as non-starch polysaccharides, amylose, xanthan gum, and azopolymers.

In some embodiments, Probiotic formulations are provided as encapsulated, enteric coated, or powder forms, with doses ranging up to $10^{11}$ cfu (e.g., up to $10^{10}$ cfu). In some embodiments, the composition comprises $5\times10^{11}$ cfu of immune modulating *Lactococcus* strain and 10% (w/w) corn starch in a capsule. The capsule is enteric coated for duodenal release at pH 5.5 In some embodiments, the capsule is enteric coated for duodenal release at pH 5.5. In some embodiments, the composition comprises a powder of freeze-dried immune modulating *Lactococcus* strain which is deemed "Qualified Presumption of Safety" (QPS) status. In some embodiments, the composition is stable at frozen or refrigerated temperature.

Methods for producing microbial compositions may include three main processing steps. The steps are: organism banking, organism production, and preservation. In certain embodiments, a sample that contains an abundance of immune modulating *Lactococcus* strain may be cultured by avoiding an isolation step.

For banking, the strains included in the microbial composition may be (1) isolated directly from a specimen or taken from a banked stock, (2) optionally cultured on a nutrient agar or broth that supports growth to generate viable biomass, and (3) the biomass optionally preserved in multiple aliquots in long-term storage.

In embodiments using a culturing step, the agar or broth may contain nutrients that provide essential elements and specific factors that enable growth. An example would be a medium composed of 20 g/L glucose, 10 g/L yeast extract, 10 g/L soy peptone, 2 g/L citric acid, 1.5 g/L sodium phosphate monobasic, 100 mg/L ferric ammonium citrate, 80 mg/L magnesium sulfate, 10 mg/L hemin chloride, 2 mg/L calcium chloride, 1 mg/L menadione. Another example would be a medium composed of 10 g/L beef extract, 10 g/L peptone, 5 g/L sodium chloride, 5 g/L dextrose, 3 g/L yeast extract, 3 g/L sodium acetate, 1 g/L soluble starch, and 0.5 g/L L-cysteine HCl, at pH 6.8. A variety of microbiological media and variations are well known in the art (e.g., R. M. Atlas, *Handbook of Microbiological Media* (2010) CRC Press). Culture media can be added to the culture at the start, may be added during the culture, or may be intermittently/continuously flowed through the culture. The strains in the bacterial composition may be cultivated alone, as a subset of the microbial composition, or as an entire collection comprising the microbial composition. As an example, a first strain may be cultivated together with a second strain in a mixed continuous culture, at a dilution rate lower than the maximum growth rate of either cell to prevent the culture from washing out of the cultivation.

The inoculated culture is incubated under favorable conditions for a time sufficient to build biomass. For microbial compositions for human use this is often at 37° C. temperature, pH, and other parameter with values similar to the normal human niche. The environment may be actively controlled, passively controlled (e.g., via buffers), or allowed to drift. For example, for anaerobic bacterial compositions, an anoxic/reducing environment may be employed. This can be accomplished by addition of reducing agents such as cysteine to the broth, and/or stripping it of oxygen. As an example, a culture of a bacterial composition may be grown at 37° C., pH 7, in the medium above, pre-reduced with 1 g/L cysteine-HCl.

When the culture has generated sufficient biomass, it may be preserved for banking. The organisms may be placed into a chemical milieu that protects from freezing (adding 'cryoprotectants'), drying ('lyoprotectants'), and/or osmotic shock ('osmoprotectants'), dispensing into multiple (optionally identical) containers to create a uniform bank, and then treating the culture for preservation. Containers are generally impermeable and have closures that assure isolation from the environment. Cryopreservation treatment is accomplished by freezing a liquid at ultra-low temperatures (e.g., at or below −80° C.). Dried preservation removes water from the culture by evaporation (in the case of spray drying or 'cool drying') or by sublimation (e.g., for freeze drying, spray freeze drying). Removal of water improves long-term microbial composition storage stability at temperatures elevated above cryogenic conditions. If the microbial composition comprises, for example, spore forming species and results in the production of spores, the final composition may be purified by additional means such as density gradient centrifugation and preserved using the techniques [?]described above[?]. Microbial composition banking may be done by culturing and preserving the strains individually, or by mixing the strains together to create a combined bank. As an example of cryopreservation, a microbial composition culture may be harvested by centrifugation to pellet the cells from the culture medium, the supernatant decanted and replaced with fresh culture broth containing 15% glycerol. The culture can then be aliquoted into 1 mL cryotubes, sealed, and placed at −80° C. for long-term viability retention. This procedure achieves acceptable viability upon recovery from frozen storage.

Microbial production may be conducted using similar culture steps to banking, including medium composition and culture conditions described above. It may be conducted at larger scales of operation, especially for clinical development or commercial production. At larger scales, there may be several subcultivations of the microbial composition prior to the final cultivation. At the end of cultivation, the culture is harvested to enable further formulation into a dosage form for administration. This can involve concentration, removal of undesirable medium components, and/or introduction into a chemical milieu that preserves the microbial composition and renders it acceptable for administration via the chosen route. For example, a microbial composition may be cultivated to a concentration of $10^{10}$ CFU/mL, then concentrated 20-fold by tangential flow microfiltration; the spent medium may be exchanged by diafiltering with a preservative medium consisting of 2% gelatin, 100 mM trehalose, and 10 mM sodium phosphate buffer. The suspension can then be freeze-dried to a powder and titrated.

After drying, the powder may be blended to an appropriate potency, and mixed with other cultures and/or a filler such as microcrystalline cellulose for consistency and ease of handling, and the bacterial composition formulated as provided herein.

In certain aspects, provided are bacterial compositions for administration subjects. In some embodiments, the bacterial compositions are combined with additional active and/or inactive materials in order to produce a final product, which may be in single dosage unit or in a multi-dose format.

In some embodiments, the composition comprises at least one carbohydrate. A "carbohydrate" refers to a sugar or polymer of sugars. The terms "saccharide," "polysaccharide," "carbohydrate," and "oligosaccharide" may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replaced with a fluorine, or N-acetylglucosamine, a nitrogen-containing form of glucose (e.g., 2'-fluororibose, deoxyribose, and hexose). Carbohydrates may exist in many different forms, for example, conformers, cyclic forms, acyclic forms, stereoisomers, tautomers, anomers, and isomers.

In some embodiments, the composition comprises at least one lipid. As used herein, a "lipid" includes fats, oils, triglycerides, cholesterol, phospholipids, fatty acids in any form including free fatty acids. Fats, oils and fatty acids can be saturated, unsaturated (cis or trans) or partially unsaturated (cis or trans). In some embodiments the lipid comprises at least one fatty acid selected from lauric acid (12:0), myristic acid (14:0), palmitic acid (16:0), palmitoleic acid (16:1), margaric acid (17:0), heptadecenoic acid (17:1), stearic acid (18:0), oleic acid (18:1), linoleic acid (18:2), linolenic acid (18:3), octadecatetraenoic acid (18:4), arachidic acid (20:0), eicosenoic acid (20:1), eicosadienoic acid (20:2), eicosatetraenoic acid (20:4), eicosapentaenoic acid (20:5) (EPA), docosanoic acid (22:0), docosenoic acid (22:1), docosapentaenoic acid (22:5), docosahexaenoic acid (22:6) (DHA), and tetracosanoic acid (24:0). In some embodiments the composition comprises at least one modified lipid, for example a lipid that has been modified by cooking.

In some embodiments, the composition comprises at least one supplemental mineral or mineral source. Examples of minerals include, without limitation: chloride, sodium, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and combinations thereof.

In some embodiments, the composition comprises at least one supplemental vitamin. The at least one vitamin can be fat-soluble or water soluble vitamins. Suitable vitamins include but are not limited to vitamin C, vitamin A, vitamin E, vitamin B12, vitamin K, riboflavin, niacin, vitamin D, vitamin B6, folic acid, pyridoxine, thiamine, pantothenic acid, and biotin. Suitable forms of any of the foregoing are salts of the vitamin, derivatives of the vitamin, compounds having the same or similar activity of the vitamin, and metabolites of the vitamin.

In some embodiments, the composition comprises an excipient. Non-limiting examples of suitable excipients include a buffering agent, a preservative, a stabilizer, a binder, a compaction agent, a lubricant, a dispersion enhancer, a disintegration agent, a flavoring agent, a sweetener, and a coloring agent.

In some embodiments, the excipient is a buffering agent. Non-limiting examples of suitable buffering agents include sodium citrate, magnesium carbonate, magnesium bicarbonate, calcium carbonate, and calcium bicarbonate.

In some embodiments, the excipient comprises a preservative. Non-limiting examples of suitable preservatives include antioxidants, such as alpha-tocopherol and ascorbate, and antimicrobials, such as parabens, chlorobutanol, and phenol.

In some embodiments, the composition comprises a binder as an excipient. Non-limiting examples of suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, and combinations thereof.

In some embodiments, the composition comprises a lubricant as an excipient. Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

In some embodiments, the composition comprises a dispersion enhancer as an excipient. Non-limiting examples of suitable dispersants include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In some embodiments, the composition comprises a disintegrant as an excipient. In some embodiments the disintegrant is a non-effervescent disintegrant. Non-limiting examples of suitable non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pectin, and tragacanth. In some embodiments the disintegrant is an effervescent disintegrant. Non-limiting examples of suitable effervescent disintegrants include sodium bicarbonate in combination with citric acid, and sodium bicarbonate in combination with tartaric acid.

In some embodiments, the bacterial formulation comprises an enteric coating or micro encapsulation. In certain embodiments, the enteric coating or micro encapsulation improves targeting to a desired region of the gastrointestinal tract. For example, in certain embodiments, the bacterial composition comprises an enteric coating and/or microcapsules that dissolves at a pH associated with a particular region of the gastrointestinal tract. In some embodiments, the enteric coating and/or microcapsules dissolve at a pH of about 5.5-6.2 to release in the duodenum, at a pH value of about 7.2-7.5 to release in the ileum, and/or at a pH value of about 5.6-6.2 to release in the colon. Exemplary enteric coatings and microcapsules are described, for example, in U.S. Pat. Pub. No. 2016/0022592, which is hereby incorporated by reference in its entirety.

In some embodiments, the composition is a food product (e.g., a food or beverage) such as a health food or beverage, a food or beverage for infants, a food or beverage for pregnant women, athletes, senior citizens or other specified group, a functional food, a beverage, a food or beverage for specified health use, a dietary supplement, a food or beverage for patients, or an animal feed. Specific examples of the foods and beverages include various beverages such as juices, refreshing beverages, tea beverages, drink preparations, jelly beverages, and functional beverages; alcoholic beverages such as beers; carbohydrate-containing foods such as rice food products, noodles, breads, and pastas; paste products such as fish hams, sausages, paste products of seafood; retort pouch products such as curries, food dressed with a thick starchy sauces, and Chinese soups; soups; dairy products such as milk, dairy beverages, ice creams, cheeses, and yogurts; fermented products such as fermented soybean pastes, yogurts, fermented beverages, and pickles; bean products; various confectionery products, including biscuits, cookies, and the like, candies, chewing gums, gummies, cold desserts including jellies, cream caramels, and frozen desserts; instant foods such as instant soups and instant soy-bean soups; microwavable foods; and the like. Further, the examples also include health foods and beverages prepared in the forms of powders, granules, tablets, capsules, liquids, pastes, and jellies.

In certain embodiments, the bacteria disclosed herein are administered in conjunction with a prebiotic to the subject. Prebiotics are carbohydrates which are generally indigestible by a host animal and are selectively fermented or metabolized by bacteria. Prebiotics may be short-chain carbohydrates (e.g., oligosaccharides) and/or simple sugars (e.g., mono- and di-saccharides) and/or mucins (heavily glycosylated proteins) that alter the composition or metabolism of a microbiome in the host. The short chain carbohydrates are also referred to as oligosaccharides, and usually contain from 2 or 3 and up to 8, 9, 10, 15 or more sugar moieties. When prebiotics are introduced to a host, the prebiotics affect the bacteria within the host and do not directly affect the host. In certain aspects, a prebiotic composition can selectively stimulate the growth and/or activity of one of a limited number of bacteria in a host. Prebiotics include oligosaccharides such as fructooligosaccharides (FOS) (including inulin), galactooligosaccharides (GOS), trans-galactooligosaccharides, xylooligosaccharides (XOS), chitooligosaccharides (COS), soy oligosaccharides (e.g., stachyose and raffinose) gentiooligosaccharides, isomaltooligosaccharides, mannooligosaccharides, maltooligosaccharides and mannanoligosaccharides. Oligosaccharides are not necessarily single components, and can be mixtures containing oligosaccharides with different degrees of oligomerization, sometimes including the parent disaccharide and the monomeric sugars. Various types of oligosaccharides are found as natural components in many common foods, including fruits, vegetables, milk, and honey. Specific examples of oligosaccharides are lactulose, lactosucrose, palatinose, glycosyl sucrose, guar gum, gum Arabic, tagalose, amylose, amylopectin, pectin, xylan, and cyclodextrins. Prebiotics may also be purified or chemically or enzymatically synthesized.

Production of PhABs

In certain aspects, the PhABs described herein can be prepared using any method known in the art.

In some embodiments, the PhABs described herein are prepared by fractionation. Bacterial cells and/or supernatants from cultured bacteria cells are fractionated into various pharmacologically active biomass (PhABs) and/or products derived therefrom. Bacterial cells and/or supernatants are fractionated using materials and methods known in the art (see e.g. Sandrini et al. Fractionation by ultracentrifugation of gram negative cytoplasmic and membrane proteins. 2014. Bio-Protocol. 4(21); Scholler et al. Protoplast and cytoplasmic membrane preparations from *Streptococcus sanguis* and *Streptococcus mutans.* 1983. J Gen Micro. 129: 3271-3279; Thein et al. Efficient subfractionation of gram-negative bacteria for proteomics studies. 2010. Am Chem Society. 9: 6135-6147; Hobb et al. Evaluation of procedures for outer membrane isolation from *Campylobacter jejuni.* 2009, 155(Pt. 3): 979-988).

Additionally, PhABs obtained by methods provided herein may be further purified by size based column chromatography, by affinity chromatography, and by gradient ultracentrifugation, using methods that may include, but are not limited to, use of a sucrose gradient or Optiprep gradient. Briefly, using a sucrose gradient method, if ammonium sulfate precipitation or ultracentrifugation were used to concentrate the filtered supernatants, pellets are resuspended in 60% sucrose, 30 mM Tris, pH 8.0. If filtration was used to concentrate the filtered supernatant, the concentrate is buffer exchanged into 60% sucrose, 30 mM Tris, pH 8.0, using an Amicon Ultra column. Samples are applied to a 35-60% discontinuous sucrose gradient and centrifuged at 200,000×g for 3-24 hours at 4° C. Briefly, using an Optiprep gradient method, if ammonium sulfate precipitation or ultracentrifugation were used to concentrate the filtered supernatants, pellets are resuspended in 35% Optiprep in PBS. In some embodiments, if filtration was used to concentrate the filtered supernatant, the concentrate is diluted using 60% Optiprep to a final concentration of 35% Optiprep. Samples are applied to a 35-60% discontinuous sucrose gradient and centrifuged at 200,000×g for 3-24 hours at 4° C.

In some embodiments, to confirm sterility and isolation of the PhAB preparations, PhABs are serially diluted onto agar medium used for routine culture of the bacteria being tested, and incubated using routine conditions. Non-sterile preparations are passed through a 0.22 um filter to exclude intact cells. To further increase purity, isolated PhABs may be DNase or proteinase K treated.

In some embodiments, for preparation of PhABs used for in vivo injections, purified PhABs are processed as described previously (G. Norheim, et al. *PLoS ONE.* 10(9): e0134353 (2015)). Briefly, after sucrose gradient centrifugation, bands containing PhABs are resuspended to a final concentration of 50 μg/mL in a solution containing 3% sucrose or other solution suitable for in vivo injection known to one skilled in the art. This solution may also contain adjuvant, for example aluminum hydroxide at a concentration of 0-0.5% (w/v).

In certain embodiments, to make samples compatible with further testing (e.g. to remove sucrose prior to TEM imaging or in vitro assays), samples are buffer exchanged into PBS or 30 mM Tris, pH 8.0 using filtration (e.g. Amicon Ultra columns), dialysis, or ultracentrifugation (200,000×g, ≥3 hours, 4° C.) and resuspension.

In some embodiments, the sterility of the PhAB preparations can be confirmed by plating a portion of the PhABs onto agar medium used for standard culture of the bacteria used in the generation of the PhABs and incubating using standard conditions.

In some embodiments select PhABs are isolated and enriched by chromatography and binding surface moieties on PhABs. In other embodiments, select PhABs are isolated and/or enriched by fluorescent cell sorting by methods using affinity reagents, chemical dyes, recombinant proteins or other methods known to one skilled in the art.

Administration

In certain aspects, provided herein is a method of delivering a bacterium and/or a bacterial composition described herein to a subject. In some embodiments of the methods provided herein, the bacteria are administered in conjunction with the administration of an additional therapeutic. In some embodiments, the bacteria is co-formulated in a pharmaceutical composition with the additional therapeutic. In some embodiments, the bacteria is co-administered with the additional therapeutic. In some embodiments, the additional therapeutic is administered to the subject before administration of the bacteria (e.g., about 1, 2, 3, 4, 5, 6, 7, 8, 9, 10, 15, 20, 25, 30, 35, 40, 45, 50 or 55 minutes before, about 1, 2, 3, 4, 5, 6, 7, 8, 9, 10, 11, 12, 13, 14, 15, 16, 17, 18, 19, 20, 21, 22 or 23 hours before, or about 1, 2, 3, 4, 5, 6, 7, 8, 9, 10, 11, 12, 13 or 14 days before). In some embodiments, the additional therapeutic is administered to the subject after administration of the bacteria (e.g., about 1, 2, 3, 4, 5, 6, 7, 8, 9, 10, 15, 20, 25, 30, 35, 40, 45, 50 or 55 minutes after, about 1, 2, 3, 4, 5, 6, 7, 8, 9, 10, 11, 12, 13, 14, 15, 16, 17, 18, 19, 20, 21, 22 or 23 hours after, or about 1, 2, 3, 4, 5, 6, 7, 8, 9, 10, 11, 12, 13 or 14 days after). In some embodiments, the same mode of delivery is used to deliver both the bacteria and the additional therapeutic. In some embodiments different modes of delivery are used to administer the bacteria and the additional therapeutic. For example, in some embodiments, the bacteria is administered orally while the additional therapeutic is administered via injection (e.g., an intravenous, intramuscular and/or intratumoral injection).

In certain embodiments, the pharmaceutical compositions, dosage forms, and kits described herein can be administered in conjunction with any other conventional anti-immune disorder treatment. These treatments may be applied as necessary and/or as indicated and may occur before, concurrent with or after administration of the pharmaceutical compositions, dosage forms, and kits described herein.

The dosage regimen can be any of a variety of methods and amounts, and can be determined by one skilled in the art according to known clinical factors. As is known in the medical arts, dosages for any one patient can depend on many factors, including the subject's species, size, body surface area, age, sex, immunocompetence, and general health, the particular microorganism to be administered, duration and route of administration, the kind and stage of the disease, for example, tumor size, and other compounds such as drugs being administered concurrently. In addition to the above factors, such levels can be affected by the infectivity of the microorganism, and the nature of the microorganism, as can be determined by one skilled in the art. In the present methods, appropriate minimum dosage levels of microorganisms can be levels sufficient for the microorganism to survive, grow and replicate. The methods of treatment described herein may be suitable for the treatment of an immune disorder (e.g., an autoimmune disease, an inflammatory disease, an allergy). The dose of the pharmaceutical compositions described herein may be appropriately set or adjusted in accordance with the dosage form, the route of administration, the degree or stage of a target disease, and the like. For example, the general effective dose of the agents may range between 0.01 mg/kg body weight/day and 1000 mg/kg body weight/day, between 0.1 mg/kg body weight/day and 1000 mg/kg body weight/day, 0.5 mg/kg body weight/day and 500 mg/kg body weight/day, 1 mg/kg body weight/day and 100 mg/kg body weight/day, or between 5 mg/kg body weight/day and 50 mg/kg body weight/day. The effective dose may be 0.01, 0.05, 0.1, 0.5, 1, 2, 3, 5, 10, 20, 30, 40, 50, 60, 70, 80, 90, 100, 200, 500, or 1000 mg/kg body weight/day or more, but the dose is not limited thereto.

In some embodiments, the dose administered to a subject is sufficient to prevent the immune disorder, delay its onset, or slow or stop its progression or prevent a relapse of the immune disorder. One skilled in the art will recognize that dosage will depend upon a variety of factors including the strength of the particular compound employed, as well as the age, species, condition, and body weight of the subject. The size of the dose will also be determined by the route, timing, and frequency of administration as well as the existence, nature, and extent of any adverse side-effects that might accompany the administration of a particular compound and the desired physiological effect.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. An effective dosage and treatment protocol can be determined by routine and conventional means, starting e.g., with a low dose in laboratory animals and then increasing the dosage while monitoring the effects, and systematically varying the dosage regimen as well. Animal studies are commonly used to determine the maximal tolerable dose ("MTD") of bioactive agent per kilogram weight. Those skilled in the art regularly extrapolate doses for efficacy, while avoiding toxicity, in other species, including humans.

In accordance with the above, in therapeutic applications, the dosages of the active agents used in accordance with the invention vary depending on the active agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the advancement of an immune disorder.

Separate administrations can include any number of two or more administrations (e.g., doses), including two, three, four, five or six administrations. One skilled in the art can readily determine the number of administrations to perform, or the desirability of performing one or more additional administrations, according to methods known in the art for monitoring therapeutic methods and other monitoring methods provided herein. In some embodiments, the doses may be separated by at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days or 1, 2, 3, or 4 weeks. Accordingly, the methods provided herein include methods of providing to the subject one or more administrations of a bacterium, where the number of administrations can be determined by monitoring the subject, and, based on the results of the monitoring, determining whether or not to provide one or more additional administrations. Deciding on whether or not to provide one or more additional administrations can be based on a variety of monitoring results, including, but not limited to, indication of tumor growth or inhibition of tumor growth, appearance of new metastases or inhibition of metastasis, the subject's anti-bacterium antibody titer, the subject's anti-tumor antibody titer, the overall health of the subject and/or the weight of the subject.

The time period between administrations can be any of a variety of time periods. The time period between administrations can be a function of any of a variety of factors, including monitoring steps, as described in relation to the number of administrations, the time period for a subject to mount an immune response and/or the time period for a subject to clear the bacteria from normal tissue. In one example, the time period can be a function of the time period for a subject to mount an immune response; for example, the time period can be more than the time period for a subject to mount an immune response, such as more than about one week, more than about ten days, more than about two weeks, or more than about a month; in another example, the time period can be less than the time period for a subject to mount an immune response, such as less than about one week, less than about ten days, less than about two weeks, or less than about a month. In another example, the time period can be a function of the time period for a subject to clear the bacteria from normal tissue; for example, the time period can be more than the time period for a subject to clear the bacteria from normal tissue, such as more than about a day, more than about two days, more than about three days, more than about five days, or more than about a week.

In some embodiments, the delivery of an immune disorder therapeutic in combination with the bacteria described herein reduces the adverse effects and/or improves the efficacy of the immune disorder therapeutic.

The effective dose of an immune disorder therapeutic described herein is the amount of the therapeutic agent that is effective to achieve the desired therapeutic response for a particular patient, composition, and mode of administration, with the least toxicity to the patient. The effective dosage level can be identified using the methods described herein and will depend upon a variety of pharmacokinetic factors including the activity of the particular compositions administered, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. In general, an effective dose of an immune disorder therapy will be the amount of the therapeutic agent, which is the lowest dose effective to produce a therapeutic effect. Such an effective dose will generally depend upon the factors described above.

The toxicity of an immune disorder therapy is the level of adverse effects experienced by the subject during and following treatment. Adverse events associated with immune disorder therapy toxicity include, but are not limited to, abdominal pain, acid indigestion, acid reflux, allergic reactions, alopecia, anaphylaxis, anemia, anxiety, lack of appetite, arthralgias, asthenia, ataxia, azotemia, loss of balance, bone pain, bleeding, blood clots, low blood pressure, elevated blood pressure, difficulty breathing, bronchitis, bruising, low white blood cell count, low red blood cell count, low platelet count, cardiotoxicity, cystitis, hemorrhagic cystitis, arrhythmias, heart valve disease, cardiomyopathy, coronary artery disease, cataracts, central neurotoxicity, cognitive impairment, confusion, conjunctivitis, constipation, coughing, cramping, cystitis, deep vein thrombosis, dehydration, depression, diarrhea, dizziness, dry mouth, dry skin, dyspepsia, dyspnea, edema, electrolyte imbalance, esophagitis, fatigue, loss of fertility, fever, flatulence, flushing, gastric reflux, gastroesophageal reflux disease, genital pain, granulocytopenia, gynecomastia, glaucoma, hair loss, hand-foot syndrome, headache, hearing loss, heart failure, heart palpitations, heartburn, hematoma, hemorrhagic cystitis, hepatotoxicity, hyperamylasemia, hypercalcemia, hyperchloremia, hyperglycemia, hyperkalemia, hyperlipasemia, hypermagnesemia, hypernatremia, hyperphosphatemia, hyperpigmentation, hypertriglyceridemia, hyperuricemia, hypoalbuminemia, hypocalcemia, hypochloremia, hypoglycemia, hypokalemia, hypomagnesemia, hyponatremia, hypophosphatemia, impotence, infection, injection site reactions, insomnia, iron deficiency, itching, joint pain, kidney failure, leukopenia, liver dysfunction, memory loss, menopause, mouth sores, mucositis, muscle pain, myalgias, myelosuppression, myocarditis, neutropenic fever, nausea, nephrotoxicity, neutropenia, nosebleeds, numbness, ototoxicity, pain, palmar-plantar erythrodysesthesia, pancytopenia, pericarditis, peripheral neuropathy, pharyngitis, photophobia, photosensitivity, pneumonia, pneumonitis, proteinuria, pulmonary embolus, pulmonary fibrosis, pulmonary toxicity, rash, rapid heart beat, rectal bleeding, restlessness, rhinitis, seizures, shortness of breath, sinusitis, thrombocytopenia, tinnitus, urinary tract infection, vaginal bleeding, vaginal dryness, vertigo, water retention, weakness, weight loss, weight gain, and xerostomia. In general, toxicity is acceptable if the benefits to the subject achieved through the therapy outweigh the adverse events experienced by the subject due to the therapy.

In some embodiments, the administration of the bacterial composition treats the immune disorder.

Therapeutic Agents

In certain aspects, the methods provided herein include the administration to a subject of a bacterium and/or a bacterial composition described herein (e.g., an immune modulating *Lactococcus* strain-containing bacterial composition) either alone or in combination with another therapeutic. In some embodiments, the bacterial composition and the other therapy can be administered to the subject in any order. In some embodiments, the bacterial composition and the other therapy are administered conjointly.

In some embodiments the bacterium is administered to the subject before the additional therapeutic is administered (e.g., at least 1, 2, 3, 4, 5, 6, 7, 8, 9, 10, 11, 12, 13, 14, 15, 16, 17, 18, 19, 20, 21, 22, 23 or 24 hours before or at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days before). In some embodiments the bacterium is administered to the subject after the additional therapeutic is administered (e.g., at least 1, 2, 3, 4, 5, 6, 7, 8, 9, 10, 11, 12, 13, 14, 15, 16, 17, 18, 19, 20, 21, 22, 23 or 24 hours after or at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days after). In some embodiments, the bacterium and the additional therapeutic are administered to the subject simultaneously or nearly simultaneously (e.g., administrations occur within an hour of each other). In some embodiments, the subject is administered an antibiotic before the bacterium is administered to the subject (e.g., at least 1, 2, 3, 4, 5, 6, 7, 8, 9, 10, 11, 12, 13, 14, 15, 16, 17, 18, 19, 20, 21, 22, 23 or 24 hours before or at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days before). In some embodiments, the subject is administered an antibiotic after the bacterium is administered to the subject (e.g., at least 1, 2, 3, 4, 5, 6, 7, 8, 9, 10, 11, 12, 13, 14, 15, 16, 17, 18, 19, 20, 21, 22, 23 or 24 hours before or at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days after). In some embodiments, the bacterium and the antibiotic are administered to the subject simultaneously or nearly simultaneously (e.g., administrations occur within an hour of each other).

In certain embodiments, the subject may undergo surgery. Types of surgery include but are not limited to preventative, diagnostic or staging, curative and palliative surgery.

In some embodiments, the additional therapeutic is an antibiotic. For example, if the presence of a immune-disorder-associated bacteria and/or an immune-disorder-associated microbiome profile is detected according to the methods provided herein, antibiotics can be administered to eliminate the immune-disorder-associated bacteria from the subject. "Antibiotics" broadly refers to compounds capable of inhibiting or preventing a bacterial infection. Antibiotics can be classified in a number of ways, including their use for specific infections, their mechanism of action, their bioavailability, or their spectrum of target microbe (e.g., Gram-negative vs. Gram-positive bacteria, aerobic vs. anaerobic bacteria, etc.) and these may be used to kill specific bacteria in specific areas of the host ("niches") (Leekha, et al 2011. General Principles of Antimicrobial Therapy. Mayo Clin Proc. 86(2): 156-167). In certain embodiments, antibiotics can be used to selectively target bacteria of a specific niche. In some embodiments, antibiotics known to treat a particular infection that includes an immune disorder niche may be used to target immune-disorder-associated microbes, including immune-disorder-associated bacteria in that niche. In other embodiments, antibiotics are administered after the bacterial treatment. In some embodiments, antibiotics are administered after the bacterial treatment to remove the engraftment.

In some aspects, antibiotics can be selected based on their bactericidal or bacteriostatic properties. Bactericidal antibiotics include mechanisms of action that disrupt the cell wall (e.g., β-lactams), the cell membrane (e.g., daptomycin), or bacterial DNA (e.g., fluoroquinolones). Bacteriostatic agents inhibit bacterial replication and include sulfonamides, tetracyclines, and macrolides, and act by inhibiting protein synthesis. Furthermore, while some drugs can be bactericidal in certain organisms and bacteriostatic in others, knowing the target organism allows one skilled in the art to select an antibiotic with the appropriate properties. In certain treatment conditions, bacteriostatic antibiotics inhibit the activity of bactericidal antibiotics. Thus, in certain embodiments, bactericidal and bacteriostatic antibiotics are not combined.

Antibiotics include, but are not limited to aminoglycosides, ansamycins, carbacephems, carbapenems, cephalosporins, glycopeptides, lincosamides, lipopeptides, macrolides, monobactams, nitrofurans, oxazolidonones, penicillins, polypeptide antibiotics, quinolones, fluoroquinolone, sulfonamides, tetracyclines, and anti-mycobacterial compounds, and combinations thereof.

Aminoglycosides include, but are not limited to Amikacin, Gentamicin, Kanamycin, Neomycin, Netilmicin, Tobramycin, Paromomycin, and Spectinomycin. Aminoglycosides are effective, e.g., against Gram-negative bacteria, such as *Escherichia coli, Klebsiella, Pseudomonas aeruginosa*, and *Francisella tularensis*, and against certain aerobic bacteria but less effective against obligate/facultative anaerobes. Aminoglycosides are believed to bind to the bacterial 30S or 50S ribosomal subunit thereby inhibiting bacterial protein synthesis.

Ansamycins include, but are not limited to, Geldanamycin, Herbimycin, Rifamycin, and Streptovaricin. Geldanamycin and Herbimycin are believed to inhibit or alter the function of Heat Shock Protein 90.

Carbacephems include, but are not limited to, Loracarbef. Carbacephems are believed to inhibit bacterial cell wall synthesis.

Carbapenems include, but are not limited to, Ertapenem, Doripenem, Imipenem/Cilastatin, and Meropenem. Carbapenems are bactericidal for both Gram-positive and Gram-negative bacteria as broad-spectrum antibiotics. Carbapenems are believed to inhibit bacterial cell wall synthesis.

Cephalosporins include, but are not limited to, Cefadroxil, Cefazolin, Cefalotin, Cefalothin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftaroline fosamil, and Ceftobiprole. Selected Cephalosporins are effective, e.g., against Gram-negative bacteria and against Gram-positive bacteria, including *Pseudomonas*, certain Cephalosporins are effective against methicillin-resistant *Staphylococcus aureus* (MRSA). Cephalosporins are believed to inhibit bacterial cell wall synthesis by disrupting synthesis of the peptidoglycan layer of bacterial cell walls.

Glycopeptides include, but are not limited to, Teicoplanin, Vancomycin, and Telavancin. Glycopeptides are effective, e.g., against aerobic and anaerobic Gram-positive bacteria including MRSA and *Clostridium difficile*. Glycopeptides are believed to inhibit bacterial cell wall synthesis by disrupting synthesis of the peptidoglycan layer of bacterial cell walls.

Lincosamides include, but are not limited to, Clindamycin and Lincomycin. Lincosamides are effective, e.g., against anaerobic bacteria, as well as *Staphylococcus*, and *Streptococcus*. Lincosamides are believed to bind to the bacterial 50S ribosomal subunit thereby inhibiting bacterial protein synthesis.

Lipopeptides include, but are not limited to, Daptomycin. Lipopeptides are effective, e.g., against Gram-positive bacteria. Lipopeptides are believed to bind to the bacterial membrane and cause rapid depolarization.

Macrolides include, but are not limited to, Azithromycin, Clarithromycin, Dirithromycin, Erythromycin, Roxithromycin, Troleandomycin, Telithromycin, and Spiramycin. Macrolides are effective, e.g., against *Streptococcus* and *Mycoplasma*. Macrolides are believed to bind to the bacterial or 50S ribosomal subunit, thereby inhibiting bacterial protein synthesis.

Monobactams include, but are not limited to, Aztreonam. Monobactams are effective, e.g., against Gram-negative bacteria. Monobactams are believed to inhibit bacterial cell wall synthesis by disrupting synthesis of the peptidoglycan layer of bacterial cell walls.

Nitrofurans include, but are not limited to, Furazolidone and Nitrofurantoin.

Oxazolidonones include, but are not limited to, Linezolid, Posizolid, Radezolid, and Torezolid. Oxazolidonones are believed to be protein synthesis inhibitors.

Penicillins include, but are not limited to, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Temocillin and Ticarcillin. Penicillins are effective, e.g., against Gram-positive bacteria, facultative anaerobes, e.g., *Streptococcus, Borrelia*, and *Treponema*. Penicillins are believed to inhibit bacterial cell wall synthesis by disrupting synthesis of the peptidoglycan layer of bacterial cell walls.

Penicillin combinations include, but are not limited to, Amoxicillin/clavulanate, Ampicillin/sulbactam, Piperacillin/tazobactam, and Ticarcillin/clavulanate.

Polypeptide antibiotics include, but are not limited to, Bacitracin, Colistin, and Polymyxin B and E. Polypeptide Antibiotics are effective, e.g., against Gram-negative bacteria. Certain polypeptide antibiotics are believed to inhibit isoprenyl pyrophosphate involved in synthesis of the peptidoglycan layer of bacterial cell walls, while others destabilize the bacterial outer membrane by displacing bacterial counter-ions.

Quinolones and Fluoroquinolone include, but are not limited to, Ciprofloxacin, Enoxacin, Gatifloxacin, Gemifloxacin, Levofloxacin, Lomefloxacin, Moxifloxacin, Nalidixic acid, Norfloxacin, Ofloxacin, Trovafloxacin, Grepafloxacin, Sparfloxacin, and Temafloxacin. Quinolones/Fluoroquinolone are effective, e.g., against *Streptococcus* and *Neisseria*. Quinolones/Fluoroquinolone are believed to inhibit the bacterial DNA gyrase or topoisomerase IV, thereby inhibiting DNA replication and transcription.

Sulfonamides include, but are not limited to, Mafenide, Sulfacetamide, Sulfadiazine, Silver sulfadiazine, Sulfadimethoxine, Sulfamethizole, Sulfamethoxazole, Sulfanilimide, Sulfasalazine, Sulfisoxazole, Trimethoprim-Sulfamethoxazole (Co-trimoxazole), and Sulfonamidochrysoidine. Sulfonamides are believed to inhibit folate synthesis by competitive inhibition of dihydropteroate synthetase, thereby inhibiting nucleic acid synthesis.

Tetracyclines include, but are not limited to, Demeclocycline, Doxycycline, Minocycline, Oxytetracycline, and Tetracycline. Tetracyclines are effective, e.g., against Gram-negative bacteria. Tetracyclines are believed to bind to the bacterial 30S ribosomal subunit thereby inhibiting bacterial protein synthesis.

Anti-mycobacterial compounds include, but are not limited to, Clofazimine, Dapsone, Capreomycin, Cycloserine, Ethambutol, Ethionamide, Isoniazid, Pyrazinamide, Rifampicin, Rifabutin, Rifapentine, and Streptomycin.

Suitable antibiotics also include arsphenamine, chloramphenicol, fosfomycin, fusidic acid, metronidazole, mupirocin, platensimycin, quinupristin/dalfopristin, tigecycline, tinidazole, trimethoprim amoxicillin/clavulanate, ampicillin/sulbactam, amphomycin ristocetin, azithromycin, bacitracin, buforin II, carbomycin, cecropin Pl, clarithromycin, erythromycins, furazolidone, fusidic acid, Na fusidate, gramicidin, imipenem, indolicidin, josamycin, magainan II, metronidazole, nitroimidazoles, mikamycin, mutacin B-Ny266, mutacin B-JHl 140, mutacin J-T8, nisin, nisin A, novobiocin, oleandomycin, ostreogrycin, piperacillin/tazobactam, pristinamycin, ramoplanin, ranalexin, reuterin, rifaximin, rosamicin, rosaramicin, spectinomycin, spiramycin, staphylomycin, streptogramin, streptogramin A, synergistin, taurolidine, teicoplanin, telithromycin, ticarcillin/clavulanic acid, triacetyloleandomycin, tylosin, tyrocidin, tyrothricin, vancomycin, vemamycin, and virginiamycin.

In some embodiments, the additional therapeutic is an immunosuppressive agent, a DMARD, a pain-control drug, a steroid, a non-steroidal antiinflammatory drug (NSAID), or a cytokine antagonist, and combinations thereof. Representative agents include, but are not limited to, cyclosporin, retinoids, corticosteroids, propionic acid derivative, acetic acid derivative, enolic acid derivatives, fenamic acid derivatives, Cox-2 inhibitors, lumiracoxib, ibuprophen, cholin magnesium salicylate, fenoprofen, salsalate, difunisal, tolmetin, ketoprofen, flurbiprofen, oxaprozin, indomethacin, sulindac, etodolac, ketorolac, nabumetone, naproxen, valdecoxib, etoricoxib, MK0966; rofecoxib, acetominophen, Celecoxib, Diclofenac, tramadol, piroxicam, meloxicam, tenoxicam, droxicam, lornoxicam, isoxicam, mefanamic acid, meclofenamic acid, flufenamic acid, tolfenamic, valdecoxib, parecoxib, etodolac, indomethacin, aspirin, ibuprophen, firocoxib, methotrexate (MTX), antimalarial drugs (e.g., hydroxychloroquine and chloroquine), sulfasalazine, Leflunomide, azathioprine, cyclosporin, gold salts, minocycline, cyclophosphamide, D-penicillamine, minocycline, auranofin, tacrolimus, myocrisin, chlorambucil, TNF alpha antagonists (e.g., TNF alpha antagonists or TNF alpha receptor antagonists), e.g., ADALIMUMAB (Humira®), ETANERCEPT (Enbrel®), INFLIXIMAB (Remicade®; TA-650), CERTOLIZUMAB PEGOL (Cimzia®; CDP870), GOLIMUMAB (Simpom®; CNTO 148), ANAKINRA (Kineret®), RITUXIMAB (Rituxan®; MabThera®), ABATACEPT (Orencia®), TOCILIZUMAB (RoActemra/Actemra®), integrin antagonists (TYSABRI® (natalizumab)), IL-1 antagonists (ACZ885 (Ilaris)), Anakinra (Kineret®)), CD4 antagonists, IL-23 antagonists, IL-20 antagonists, IL-6 antagonists, BLyS antagonists (e.g., Atacicept, Benlysta®/LymphoStat-B® (belimumab)), p38 Inhibitors, CD20 antagonists (Ocrelizumab, Ofatumumab (Arzerra®)), interferon gamma antagonists (Fontolizumab), prednisolone, Prednisone, dexamethasone, Cortisol, cortisone, hydrocortisone, methylprednisolone, betamethasone, triamcinolone, beclometasome, fludrocortisone, deoxycorticosterone, aldosterone, Doxycycline, vancomycin, pioglitazone, SBI-087, SCIO-469, Cura-100, Oncoxin+Viusid, TwHF, Methoxsalen, Vitamin D—ergocalciferol, Milnacipran, Paclitaxel, rosig tazone, Tacrolimus (Prograf®), RADOO1, rapamune, rapamycin, fostamatinib, Fentanyl, XOMA 052, Fostamatinib disodium, rosightazone, Curcumin (Longvida™) Rosuvastatin, Maraviroc, ramipnl, Milnacipran, Cobiprostone, somatropin, tgAAC94 gene therapy vector, MK0359, GW856553, esomeprazole, everolimus, trastuzumab, JAK1 and JAK2 inhibitors, pan JAK inhibitors, e.g., tetracyclic pyridone 6 (P6), 325, PF-956980, denosumab, IL-6 antagonists, CD20 antagonistis, CTLA4 antagonists, IL-8 antagonists, IL-21 antagonists, IL-22 antagonist, integrin antagonists (Tysarbri® (natalizumab)), VGEF antagnosits, CXCL antagonists, MMP antagonists, defensin antagonists, IL-1 antagonists (including IL-1 beta antagonsits), and IL-23 antagonists (e.g., receptor decoys, antagonistic antibodies, etc.).

In some embodiments, the agent is an immunosuppressive agent. Examples of immunosuppressive agents include, but are not limited to, corticosteroids, mesalazine, mesalamine, sulfasalazine, sulfasalazine derivatives, immunosuppressive drugs, cyclosporin A, mercaptopurine, azathiopurine, prednisone, methotrexate, antihistamines, glucocorticoids, epinephrine, theophylline, cromolyn sodium, anti-leukotrienes, anti-cholinergic drugs for rhinitis, TLR antagonists, inflammasome inhibitors, anti-cholinergic decongestants, mast-cell stabilizers, monoclonal anti-IgE antibodies, vaccines (e.g., vaccines used for vaccination where the amount of an allergen is gradually increased), cytokine inhibitors, such as anti-IL-6 antibodies, TNF inhibitors such as infliximab, adalimumab, certolizumab pegol, golimumab, or etanercept, and combinations thereof.

In some embodiments, the immune disorder therapy comprises administering a therapeutic bacteria and/or a therapeutic combination of bacteria to the subject so a healthy microbiome can be reconstituted in the subject. In some embodiments, the therapeutic bacteria is a non-immune-disorder-associated bacteria. In some embodiments the therapeutic bacteria is a probiotic bacteria.

In some embodiments, the additional therapeutic is a cancer therapeutic. In some embodiments, the cancer therapeutic is a chemotherapeutic agent. Examples of such chemotherapeutic agents include, but are not limited to, alkylating agents such as cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammalI and calicheamicin omegal1; dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylomithine (DMFO); retinoids such as retinoic acid; capecitabine; and pharmaceutically acceptable salts, acids or derivatives of any of the above.

In some embodiments, the cancer therapeutic is a cancer immunotherapy agent. Immunotherapy refers to a treatment that uses a subject's immune system to treat cancer, e.g., checkpoint inhibitors, cancer vaccines, cytokines, cell therapy, CAR-T cells, and dendritic cell therapy. Non-limiting examples of immunotherapies are checkpoint inhibitors include Nivolumab (BMS, anti-PD-1), Pembrolizumab (Merck, anti-PD-1), Ipilimumab (BMS, anti-CTLA-4), MEDI4736 (AstraZeneca, anti-PD-L1), and MPDL3280A (Roche, anti-PD-L1). Other immunotherapies may be tumor vaccines, such as Gardail, Cervarix, BCG, sipulencel-T, Gp100:209-217, AGS-003, DCVax-L, Algenpantucel-L, Tergenpantucel-L, TG4010, ProstAtak, Prostvac-V/R-TRICOM, Rindopepimul, E75 peptide acetate, IMA901, POL-103A, Belagenpumatucel-L, GSK1572932A, MDX-1279, GV1001, and Tecemotide. Immunotherapy may be administered via injection (e.g., intravenously, intratumorally, subcutaneously, or into lymph nodes), but may also be administered orally, topically, or via aerosol. Immunotherapies may comprise adjuvants such as cytokines.

In some embodiments, the immunotherapy agent is an immune checkpoint inhibitor. Immune checkpoint inhibition broadly refers to inhibiting the checkpoints that cancer cells can produce to prevent or downregulate an immune response. Examples of immune checkpoint proteins include, but are not limited to, CTLA4, PD-1, PD-L1, PD-L2, A2AR, B7-H3, B7-H4, BTLA, KIR, LAG3, TIM-3 or VISTA. Immune checkpoint inhibitors can be antibodies or antigen binding fragments thereof that bind to and inhibit an immune checkpoint protein. Examples of immune checkpoint inhibitors include, but are not limited to, nivolumab, pembrolizumab, pidilizumab, AMP-224, AMP-514, STI-A1110, TSR-042, RG-7446, BMS-936559, MEDI-4736, MSB-0020718C, AUR-012 and STI-A1010.

In some embodiments, the immunotherapy agent is an antibody or antigen binding fragment thereof that, for example, binds to a cancer-associated antigen. Examples of cancer-associated antigens include, but are not limited to, adipophilin, AIM-2, ALDH1A1, alpha-actinin-4, alpha-fetoprotein ("AFP"), ARTC1, B-RAF, BAGE-1, BCLX (L), BCR-ABL fusion protein b3a2, beta-catenin, BING-4, CA-125, CALCA, carcinoembryonic antigen ("CEA"), CASP-5, CASP-8, CD274, CD45, Cdc27, CDK12, CDK4, CDKN2A, CEA, CLPP, COA-1, CPSF, CSNK1A1, CTAG1, CTAG2, cyclin D1, Cyclin-A1, dek-can fusion protein, DKK1, EFTUD2, Elongation factor 2, ENAH (hMena), Ep-CAM, EpCAM, EphA3, epithelial tumor antigen ("ETA"), ETV6-AML1 fusion protein, EZH2, FGF5, FLT3-ITD, FN1, G250/MN/CAIX, GAGE-1,2,8, GAGE-3, 4,5,6,7, GAS7, glypican-3, GnTV, gp100/Pmel17, GPNMB, HAUS3, Hepsin, HER-2/neu, HERV-K-MEL, HLA-A11, HLA-A2, HLA-DOB, hsp70-2, IDO1, IGF2B3, IL13Ralpha2, Intestinal carboxyl esterase, K-ras, Kallikrein 4, KIF20A, KK-LC-1, KKLC1, KM-HN-1, KMHN1 also known as CCDC110, LAGE-1, LDLR-fucosyltransferaseAS fusion protein, Lengsin, M-CSF, MAGE-A1, MAGE-A10, MAGE-A12, MAGE-A2, MAGE-A3, MAGE-A4, MAGE-A6, MAGE-A9, MAGE-C1, MAGE-C2, malic enzyme, mammaglobin-A, MART2, MATN, MC1R, MCSP, mdm-2, ME1, Melan-A/MART-1, Meloe, Midkine, MMP-2, MMP-7, MUC1, MUCSAC, mucin, MUM-1, MUM-2, MUM-3, Myosin, Myosin class I, N-raw, NA88-A, neo-PAP, NFYC, NY-BR-1, NY-ESO-1/LAGE-2, OA1, OGT, OS-9, P polypeptide, p53, PAP, PAX5, PBF, pml-RARalpha fusion protein, polymorphic epithelial mucin ("PEM"), PPP1R3B, PRAME, PRDX5, PSA, PSMA, PTPRK, RAB38/NY-MEL-1, RAGE-1, RBAF600, RGS5, RhoC, RNF43, RU2AS, SAGE, secernin 1, SIRT2, SNRPD1, SOX10, Sp17, SPA17, SSX-2, SSX-4, STEAP1, survivin, SYT-SSX1 or -SSX2 fusion protein, TAG-1, TAG-2, Telomerase, TGF-betaRII, TPBG, TRAG-3, Triosephosphate isomerase, TRP-1/gp75, TRP-2, TRP2-INT2, tyrosinase, tyrosinase ("TYR"), VEGF, WT1, XAGE-1b/GAGED2a. In some embodiments, the antigen is a neo-antigen.

In some embodiments, the immunotherapy agent is a cancer vaccine and/or a component of a cancer vaccine (e.g., an antigenic peptide and/or protein). The cancer vaccine can be a protein vaccine, a nucleic acid vaccine or a combination thereof. For example, in some embodiments, the cancer vaccine comprises a polypeptide comprising an epitope of a cancer-associated antigen. In some embodiments, the cancer vaccine comprises a nucleic acid (e.g., DNA or RNA, such as mRNA) that encodes an epitope of a cancer-associated antigen. In some embodiments, the nucleic acid is a vector (e.g., a bacterial vector, viral vector). Examples of bacterial vectors include, but are not limited to, *Mycobacterium bovis* (BCG), *Salmonella Typhimurium* ssp., *Salmonella Typhi* ssp., *Clostridium* sp. spores, *Escherichia coli* Nissle 1917, *Escherichia coli* K-12/LLO, *Listeria monocytogenes*, and *Shigella flexneri*. Examples of viral vectors include, but are not limited to, vaccinia, adenovirus, RNA viruses, and replicationdefective avipox, replication-defective fowlpox, replication-defective canarypox, replicationdefective MVA and replication-defective adenovirus.

In some embodiments, the cancer immunotherapy comprises administration of an antigen presenting cell (APC) primed with a cancer-specific antigen. In some embodiments, the APC is a dendritic cell, a macrophage or a B cell.

Examples of cancer-associated antigens include, but are not limited to, adipophilin, AIM-2, ALDH1A1, alpha-actinin-4, alpha-fetoprotein ("AFP"), ARTC1, B-RAF, BAGE-1, BCLX (L), BCR-ABL fusion protein b3a2, beta-catenin, BING-4, CA-125, CALCA, carcinoembryonic antigen ("CEA"), CASP-5, CASP-8, CD274, CD45, Cdc27, CDK12, CDK4, CDKN2A, CEA, CLPP, COA-1, CPSF, CSNK1A1, CTAG1, CTAG2, cyclin D1, Cyclin-A1, dek-can fusion protein, DKK1, EFTUD2, Elongation factor 2, ENAH (hMena), Ep-CAM, EpCAM, EphA3, epithelial tumor antigen ("ETA"), ETV6-AML1 fusion protein, EZH2, FGF5, FLT3-ITD, FN1, G250/MN/CAIX, GAGE-1,2,8, GAGE-3,4,5,6,7, GAS7, glypican-3, GnTV, gp100/Pmel17, GPNMB, HAUS3, Hepsin, HER-2/neu, HERV-K-MEL, HLA-A11, HLA-A2, HLA-DOB, hsp70-2, IDO1, IGF2B3, IL13Ralpha2, Intestinal carboxyl esterase, K-ras, Kallikrein 4, KIF20A, KK-LC-1, KKLC1, KM-HN-1, KMHN1 also known as CCDC110, LAGE-1, LDLR-fucosyltransferaseAS fusion protein, Lengsin, M-CSF, MAGE-A1, MAGE-A10, MAGE-A12, MAGE-A2, MAGE-A3, MAGE-A4, MAGE-A6, MAGE-A9, MAGE-C1, MAGE-C2, malic enzyme, mammaglobin-A, MART2, MATN, MC1R, MCSP, mdm-2, ME1, Melan-A/MART-1, Meloe, Midkine, MMP-2, MMP-7, MUC1, MUC5AC, mucin, MUM-1, MUM-2, MUM-3, Myosin, Myosin class I, N-raw, NA88-A, neo-PAP, NFYC, NY-BR-1, NY-ESO-1/LAGE-2, OA1, OGT, OS-9, P polypeptide, p53, PAP, PAX5, PBF, pml-RARalpha fusion protein, polymorphic epithelial mucin ("PEM"), PPP1R3B, PRAME, PRDX5, PSA, PSMA, PTPRK, RAB38/NY-MEL-1, RAGE-1, RBAF600, RGS5, RhoC, RNF43, RU2AS, SAGE, secernin 1, SIRT2, SNRPD1, SOX10, Sp17, SPA17, SSX-2, SSX-4, STEAP1, survivin, SYT-SSX1 or -SSX2 fusion protein, TAG-1, TAG-2, Telomerase, TGF-betaRII, TPBG, TRAG-3, Triosephosphate isomerase, TRP-1/gp75, TRP-2, TRP2-INT2, tyrosinase, tyrosinase ("TYR"), VEGF, WT1, XAGE-1b/GAGED2a. In some embodiments, the antigen is a neo-antigen.

In some embodiments, the cancer immunotherapy comprises administration of a cancer-specific chimeric antigen receptor (CAR). In some embodiments, the CAR is administered on the surface of a T cell. In some embodiments, the CAR binds specifically to a cancer-associated antigen.

In some embodiments, the cancer immunotherapy comprises administration of a cancer-specific T cell to the subject. In some embodiments, the T cell is a CD4+ T cell. In some embodiments, the CD4+ T cell is a TH1 T cell, a TH2 T cell or a TH17 T cell. In some embodiments, the T cell expresses a T cell receptor specific for a cancer-associated antigen.

In some embodiments, the cancer vaccine is administered with an adjuvant. Examples of adjuvants include, but are not limited to, an immune modulatory protein, Adjuvant 65, α-GalCer, aluminum phosphate, aluminum hydroxide, calcium phosphate, β-Glucan Peptide, CpG ODN DNA, GPI-0100, lipid A, lipopolysaccharide, Lipovant, Montanide, N-acetyl-muramyl-L-alanyl-D-isoglutamine, Pam3CSK4, quil A, cholera toxin (CT) and heat-labile toxin from enterotoxigenic *Escherichia coli* (LT) including derivatives of these (CTB, mmCT, CTA1-DD, LTB, LTK63, LTR72, dmLT) and trehalose dimycolate.

In some embodiments, the immunotherapy agent is an immune modulating protein to the subject. In some embodiments, the immune modulatory protein is a cytokine or chemokine. Examples of immune modulating proteins include, but are not limited to, B lymphocyte chemoattractant ("BLC"), C—C motif chemokine 11 ("Eotaxin-1"), Eosinophil chemotactic protein 2 ("Eotaxin-2"), Granulocyte colony-stimulating factor ("G-CSF"), Granulocyte macrophage colony-stimulating factor ("GM-CSF"), 1-309, Intercellular Adhesion Molecule 1 ("ICAM-1"), Interferon alpha ("IFN-alpha"), Interferon beta ("IFN-beta") Interferon gamma ("IFN-gamma"), Interlukin-1 alpha ("IL-1 alpha"), Interlukin-1 beta ("IL-1 beta"), Interleukin 1 receptor antagonist ("IL-1 ra"), Interleukin-2 ("IL-2"), Interleukin-4 ("IL-4"), Interleukin-5 ("IL-5"), Interleukin-6 ("IL-6"), Interleukin-6 soluble receptor ("IL-6 sR"), Interleukin-7 ("IL-7"), Interleukin-8 ("IL-8"), Interleukin-10 ("IL-10"), Interleukin-11 ("IL-11"), Subunit beta of Interleukin-12 ("IL-12 p40" or "IL-12 p'70"), Interleukin-13 ("IL-13"), Interleukin-15 ("IL-15"), Interleukin-16 ("IL-16"), Interleukin-17A-F ("IL-17A-F"), Interleukin-18 ("IL-18"), Interleukin-21 ("IL-21"), Interleukin-22 ("IL-22"), Interleukin-23 ("IL-23"), Interleukin-33 ("IL-33"), Chemokine (C—C motif) Ligand 2 ("MCP-1"), Macrophage colony-stimulating factor ("M-CSF"), Monokine induced by gamma interferon ("MIG"), Chemokine (C—C motif) ligand 2 ("MIP-1 alpha"), Chemokine (C—C motif) ligand 4 ("MIP-1 beta"), Macrophage inflammatory protein-1-delta ("MIP-1 delta"), Platelet-derived growth factor subunit B ("PDGF-BB"), Chemokine (C—C motif) ligand 5, Regulated on Activation, Normal T cell Expressed and Secreted ("RANTES"), TIMP metallopeptidase inhibitor 1 ("TIMP-1"), TIMP metallopeptidase inhibitor 2 ("TIMP-2"), Tumor necrosis factor, lymphotoxin-alpha ("TNF alpha"), Tumor necrosis factor, lymphotoxin-beta ("TNF beta"), Soluble TNF receptor type 1 ("sTNFRI"), sTNFRIIAR, Brain-derived neurotrophic factor ("BDNF"), Basic fibroblast growth factor ("bFGF"), Bone morphogenetic protein 4 ('BMP-4"), Bone morphogenetic protein 5 ('BMP-5"), Bone morphogenetic protein 7 ("BMP-7"), Nerve growth factor ("b-NGF"), Epidermal growth factor ("EGF"), Epidermal growth factor receptor ("EGFR"), Endocrine-gland-derived vascular endothelial growth factor ("EG-VEGF"), Fibroblast growth factor 4 ("FGF-4"), Keratinocyte growth factor ("FGF-7"), Growth differentiation factor 15 ("GDF-15"), Glial cell-derived neurotrophic factor ("GDNF"), Growth Hormone, Heparin-binding EGF-like growth factor ("HB-EGF"), Hepatocyte growth factor ("HGF"), Insulin-like growth factor binding protein 1 ("IGFBP-1"), Insulin-like growth factor binding protein 2 ("IGFBP-2"), Insulin-like growth factor binding protein 3 ("IGFBP-3"), Insulin-like growth factor binding protein 4 ("IGFBP-4"), Insulin-like growth factor binding protein 6 ("IGFBP-6"), Insulin-like growth factor 1 ("IGF-1"), Insulin, Macrophage colony-stimulating factor ("M-CSF R"), Nerve growth factor receptor ("NGF R"), Neurotrophin-3 ("NT-3"), Neurotrophin-4 ("NT-4"), Osteoclastogenesis inhibitory factor ("Osteoprotegerin"), Platelet-derived growth factor receptors ("PDGF-AA"), Phosphatidylinositol-glycan biosynthesis ("PIGF"), Skp, Cullin, F-box containing comples ("SCF"), Stem cell factor receptor ("SCF R"), Transforming growth factor alpha ("TGFalpha"), Transforming growth factor beta-1 ("TGF beta 1"), Transforming growth factor beta-3 ("TGF beta 3"), Vascular endothelial growth factor ("VEGF"), Vascular endothelial growth factor receptor 2 ("VEGFR2"), Vascular endothelial growth factor receptor 3 ("VEGFR3"), VEGF-D 6Ckine, Tyrosine-protein kinase receptor UFO ("Axl"), Betacellulin ("BTC"), Mucosae-associated epithelial chemokine ("CCL28"), Chemokine (C—C motif) ligand 27 ("CTACK"), Chemokine (C—X—C motif) ligand 16 ("CXCL16"), C—X—C motif chemokine 5 ("ENA-78"), Chemokine (C—C motif) ligand 26 ("Eotaxin-3"), Granulocyte chemotactic protein 2 ("GCP-2"), GRO, Chemokine (C—C motif) ligand 14 ("HCC-1"), Chemokine (C—C motif) ligand 16 ("HCC-4"), Interleukin-9 ("IL-9"), Interleukin-17 F ("IL-17F"), Interleukin-18-binding protein ("IL-18 BPa"), Interleukin-28 A ("IL-28A"), Interleukin 29 ("IL-29"), Interleukin 31 ("IL-31"), C—X—C motif chemokine 10 ("IP-10"), Chemokine receptor CXCR3 ("I-TAC"), Leukemia inhibitory factor ("LIF"), Light, Chemokine (C motif) ligand ("Lymphotactin"), Monocyte chemoattractant protein 2 ("MCP-2"), Monocyte chemoattractant protein 3 ("MCP-3"), Monocyte chemoattractant protein 4 ("MCP-4"), Macrophage-derived chemokine ("MDC"), Macrophage migration inhibitory factor ("MIF"), Chemokine (C—C motif) ligand 20 ("MIP-3 alpha"), C—C motif chemokine 19 ("MIP-3 beta"), Chemokine (C—C motif) ligand 23 ("MPIF-1"), Macrophage stimulating protein alpha chain ("MSPalpha"), Nucleosome assembly protein 1-like 4 ("NAP-2"), Secreted phosphoprotein 1 ("Osteopontin"), Pulmonary and activation-regulated cytokine ("PARC"), Platelet factor 4 ("PF4"), Stroma cell-derived factor-1 alpha ("SDF-1 alpha"), Chemokine (C—C motif) ligand 17 ("TARC"), Thymus-expressed chemokine ("TECK"), Thymic stromal lymphopoietin ("TSLP 4-IBB"), CD 166 antigen ("ALCAM"), Cluster of Differentiation 80 ("B7-1"), Tumor necrosis factor receptor superfamily member 17 ("BCMA"), Cluster of Differentiation 14 ("CD14"), Cluster of Differentiation 30 ("CD30"), Cluster of Differentiation 40 ("CD40 Ligand"), Carcinoembryonic antigen-related cell adhesion molecule 1 (biliary glycoprotein) ("CEACAM-1"), Death Receptor 6 ("DR6"), Deoxythymidine kinase ("Dtk"), Type 1 membrane glycoprotein ("Endoglin"), Receptor tyrosine-protein kinase erbB-3 ("ErbB3"), Endothelial-leukocyte adhesion molecule 1 ("E-Selectin"), Apoptosis antigen 1 ("Fas"), Fms-like tyrosine kinase 3 ("Flt-3L"), Tumor necrosis factor receptor superfamily member 1 ("GITR"), Tumor necrosis factor receptor superfamily member 14 ("HVEM"), Intercellular adhesion molecule 3 ("ICAM-3"), IL-1 R4, IL-1 RI, IL-10 Rbeta, IL-17R, IL-2Rgamma, IL-21R, Lysosome membrane protein 2 ("LIMPII"), Neutrophil gelatinase-associated lipocalin ("Lipocalin-2"), CD62L ("L-Selectin"), Lymphatic endothelium ("LYVE-1"), MHC class I polypeptide-related sequence A ("MICA"), MHC class I polypeptide-related sequence B ("MICB"), NRG1-beta1, Beta-type platelet-derived growth factor receptor ("PDGF Rbeta"), Platelet endothelial cell adhesion molecule ("PECAM-1"), RAGE, Hepatitis A virus cellular receptor 1 ("TIM-1"), Tumor necrosis factor receptor superfamily member IOC ("TRAIL R3"), Trappin protein transglutaminase binding domain ("Trappin-2"), Urokinase receptor ("uPAR"), Vascular cell adhesion protein 1 ("VCAM-1"), XEDARActivin A, Agouti-related protein ("AgRP"), Ribonuclease 5 ("Angiogenin"), Angiopoietin 1, Angiostatin, Catheprin S, CD40, Cryptic family protein D3 ("Cripto-1"), DAN, Dickkopf-related protein 1 ("DKK-1"), E-Cadherin, Epithelial cell adhesion molecule ("EpCAM"), Fas Ligand (FasL or CD95L), Fcg RIIB/C, FoUistatin, Galectin-7, Intercellular adhesion molecule 2 ("ICAM-2"), IL-13 R1, IL-13R2, IL-17B, IL-2 Ra, IL-2 Rb, IL-23, LAP, Neuronal cell adhesion molecule ("NrCAM"), Plasminogen activator inhibitor-1 ("PAI-1"), Platelet derived growth factor receptors ("PDGF-AB"), Resistin, stromal cell-derived factor 1 ("SDF-1 beta"), sgp130, Secreted frizzled-related protein 2 ("ShhN"), Sialic acid-binding immunoglobulin-type lectins ("Siglec-5"), ST2, Transforming growth factor-beta 2 ("TGF beta 2"), Tie-2, Thrombopoietin ("TPO"), Tumor necrosis factor receptor superfamily member 10D ("TRAIL R4"), Triggering receptor expressed on myeloid cells 1 ("TREM-1"), Vascular endothelial growth factor C ("VEGF-C"), VEGFR1Adiponectin, Adipsin ("AND"), Alpha-fetoprotein ("AFP"), Angiopoietin-like 4 ("ANGPTL4"), Beta-2-microglobulin ("B2M"), Basal cell adhesion molecule ("BCAM"), Carbohydrate antigen 125 ("CA125"), Cancer Antigen 15-3 ("CA15-3"), Carcinoembryonic antigen ("CEA"), cAMP receptor protein ("CRP"), Human Epidermal Growth Factor Receptor 2 ("ErbB2"), Follistatin, Follicle-stimulating hormone ("FSH"), Chemokine (C—X—C motif) ligand 1 ("GRO alpha"), human chorionic gonadotropin ("beta HCG"), Insulin-like growth factor 1 receptor ("IGF-1 sR"), IL-1 sRII, IL-3, IL-18 Rb, IL-21, Leptin, Matrix metalloproteinase-1 ("MMP-1"), Matrix metalloproteinase-2 ("MMP-2"), Matrix metalloproteinase-3 ("MMP-3"), Matrix metalloproteinase-8 ("MMP-8"), Matrix metalloproteinase-9 ("MMP-9"), Matrix metalloproteinase-10 ("MMP-10"), Matrix metalloproteinase-13 ("MMP-13"), Neural Cell Adhesion Molecule ("NCAM-1"), Entactin ("Nidogen-1"), Neuron specific enolase ("NSE"), Oncostatin M ("OSM"), Procalcitonin, Prolactin, Prostate specific antigen ("PSA"), Sialic acid-binding Ig-like lectin 9 ("Siglec-9"), ADAM 17 endopeptidase ("TACE"), Thyroglobulin, Metalloproteinase inhibitor 4 ("TIMP-4"), TSH2B4, Disintegrin and metalloproteinase domain-containing protein 9 ("ADAM-9"), Angiopoietin 2, Tumor necrosis factor ligand superfamily member 13/Acidic leucine-rich nuclear phosphoprotein 32 family member B ("APRIL"), Bone morphogenetic protein 2 ("BMP-2"), Bone morphogenetic protein 9 ("BMP-9"), Complement component 5a ("C5a"), Cathepsin L, CD200, CD97, Chemerin, Tumor necrosis factor receptor superfamily member 6B ("DcR3"), Fatty acid-binding protein 2 ("FABP2"), Fibroblast activation protein, alpha ("FAP"), Fibroblast growth factor 19 ("FGF-19"), Galectin-3, Hepatocyte growth factor receptor ("HGF R"), IFN-gammalpha/beta R2, Insulin-like growth factor 2 ("IGF-2"), Insulin-like growth factor 2 receptor ("IGF-2 R"), Interleukin-1 receptor 6 ("IL-1R6"), Interleukin 24 ("IL-24"), Interleukin 33 ("IL-33", Kallikrein 14, Asparaginyl endopeptidase ("Legumain"), Oxidized low-density lipoprotein receptor 1 ("LOX-1"), Mannose-binding lectin ("MBL"), Neprilysin ("NEP"), Notch homolog 1, translocation-associated (*Drosophila*) ("Notch-1"), Nephroblastoma overexpressed ("NOV"), Osteoactivin, Programmed cell death protein 1 ("PD-1"), N-acetylmuramoyl-L-alanine amidase ("PGRP-5"), Serpin A4, Secreted frizzled related protein 3 ("sFRP-3"), Thrombomodulin, Tolllike receptor 2 ("TLR2"), Tumor necrosis factor receptor superfamily member 10A ("TRAIL R1"), Transferrin ("TRF"), WIF-1ACE-2, Albumin, AMICA, Angiopoietin 4, B-cell activating factor ("BAFF"), Carbohydrate antigen 19-9 ("CA19-9"), CD 163, Clusterin, CRT AM, Chemokine (C—X—C motif) ligand 14 ("CXCL14"), Cystatin C, Decorin ("DCN"), Dickkopf-related protein 3 ("Dkk-3"), Delta-like protein 1 ("DLL1"), Fetuin A, Heparin-binding growth factor 1 ("aFGF"), Folate receptor alpha ("FOLR1"), Furin, GPCR-associated sorting protein 1 ("GASP-1"), GPCR-associated sorting protein 2 ("GASP-2"), Granulocyte colony-stimulating factor receptor ("GCSF R"), Serine protease hepsin ("HAI-2"), Interleukin-17B Receptor ("IL-17B R"), Interleukin 27 ("IL-27"), Lymphocyte-activation gene 3 ("LAG-3"), Apolipoprotein A-V ("LDL R"), Pepsinogen I, Retinol binding protein 4 ("RBP4"), SOST, Heparan sulfate proteoglycan ("Syndecan-1"), Tumor necrosis factor receptor superfamily member 13B ("TACI"), Tissue factor pathway inhibitor ("TFPI"), TSP-1, Tumor necrosis factor receptor superfamily, member 10b ("TRAIL R2"), TRANCE, Troponin I, Urokinase Plasminogen Activator ("uPA"), Cadherin 5, type 2 or VE-cadherin (vascular endothelial) also known as CD144 ("VE-Cadherin"), WNT1-inducible-signaling pathway protein 1 ("WISP-1"), and Receptor Activator of Nuclear Factor κ B ("RANK").

In some embodiments, the cancer therapeutic agent is an anti-cancer compound. Exemplary anti-cancer compounds include, but are not limited to, Alemtuzumab (Campath®), Alitretinoin (Panretin®), Anastrozole (Arimidex®), Bevacizumab (Avastin®), Bexarotene (Targretin®), Bortezomib (Velcade®), Bosutinib (Bosulif®), Brentuximab vedotin (Adcetris®), Cabozantinib (Cometriq™), Carfilzomib (Kyprolis™), Cetuximab (Erbitux®), Crizotinib (Xalkori®), Dasatinib (Sprycel®), Denileukin diftitox (Ontak®), Erlotinib hydrochloride (Tarceva®), Everolimus (Afinitor®), Exemestane (Aromasin®), Fulvestrant (Faslodex®), Gefitinib (Iressa®), Ibritumomab tiuxetan (Zevalin®), Imatinib mesylate (Gleevec®), Ipilimumab (Yervoy™), Lapatinib ditosylate (Tykerb®), Letrozole (Femara®), Nilotinib (Tasigna®), Ofatumumab (Arzerra®), Panitumumab (Vectibix®), Pazopanib hydrochloride (Votrient®), Pertuzumab (Perjeta™), Pralatrexate (Folotyn®), Regorafenib (Stivarga®), Rituximab (Rituxan®), Romidepsin (Istodax®), Sorafenib tosylate (Nexavar®), Sunitinib malate (Sutent®), Tamoxifen, Temsirolimus (Torisel®), Toremifene (Fareston®), Tositumomab and 131I-tositumomab (Bexxar®), Trastuzumab (Herceptin®), Tretinoin (Vesanoid®), Vandetanib (Caprelsa®), Vemurafenib (Zelboraf®), Vorinostat (Zolinza®), and Ziv-aflibercept (Zaltrap®).

Exemplary anti-cancer compounds that modify the function of proteins that regulate gene expression and other cellular functions (e.g., HDAC inhibitors, retinoid receptor ligants) are Vorinostat (Zolinza®), Bexarotene (Targretin®) and Romidepsin (Istodax®), Alitretinoin (Panretin®), and Tretinoin (Vesanoid®).

Exemplary anti-cancer compounds that induce apoptosis (e.g., proteasome inhibitors, antifolates) are Bortezomib (Velcade®), Carfilzomib (Kyprolis™), and Pralatrexate (Folotyn®).

Exemplary anti-cancer compounds that increase anti-tumor immune response (e.g., anti CD20, anti CD52; anti-cytotoxic T-lymphocyte-associated antigen-4) are Rituximab (Rituxan®), Alemtuzumab (Campath®), Ofatumumab (Arzerra®), and Ipilimumab (Yervoy™).

Exemplary anti-cancer compounds that deliver toxic agents to cancer cells (e.g., anti-CD20-radionuclide fusions; IL-2-diphtheria toxin fusions; anti-CD30-monomethylauristatin E (MMAE)-fusions) are Tositumomab and 131I-tositumomab (Bexxar®) and Ibritumomab tiuxetan (Zevalin®), Denileukin diftitox (Ontak®), and Brentuximab vedotin (Adcetris®).

Other exemplary anti-cancer compounds are small molecule inhibitors and conjugates thereof of, e.g., Janus kinase, ALK, Bcl-2, PARP, PI3K, VEGF receptor, Braf, MEK, CDK, and HSP90.

Exemplary platinum-based anti-cancer compounds include, for example, cisplatin, carboplatin, oxaliplatin, satraplatin, picoplatin, Nedaplatin, Triplatin, and Lipoplatin. Other metal-based drugs suitable for treatment include, but are not limited to ruthenium-based compounds, ferrocene derivatives, titanium-based compounds, and gallium-based compounds.

In some embodiments, the cancer therapeutic is a radioactive moiety that comprises a radionuclide. Exemplary radionuclides include, but are not limited to Cr-51, Cs-131, Ce-134, Se-75, Ru-97, 1-125, Eu-149, Os-189m, Sb-119, 1-123, Ho-161, Sb-117, Ce-139, In-111, Rh-103m, Ga-67, T1-201, Pd-103, Au-195, Hg-197, Sr-87m, Pt-191, P-33, Er-169, Ru-103, Yb-169, Au-199, Sn-121, Tm-167, Yb-175, In-113m, Sn-113, Lu-177, Rh-105, Sn-117m, Cu-67, Sc-47, Pt-195m, Ce-141, 1-131, Tb-161, As-77, Pt-197, Sm-153, Gd-159, Tm-173, Pr-143, Au-198, Tm-170, Re-186, Ag-111, Pd-109, Ga-73, Dy-165, Pm-149, Sn-123, Sr-89, Ho-166, P-32, Re-188, Pr-142, Ir-194, In-114m/In-114, and Y-90.

Immune Disorders

In some embodiments, the methods and compositions described herein relate to the treatment or prevention of a disease or disorder associated with a pathological immune response, such as an autoimmune disease, an allergic reaction and/or an inflammatory disease. In some embodiments, the disease or disorder is an inflammatory bowel disease (e.g., Crohn's disease or ulcerative colitis). In some embodiments, the methods and compositions described herein relate to the treatment or prevention of delayed-type hypersensitivity, autoimmune myocarditis, granulomas, peripheral neuropathies, Hashimoto's thyroiditis, inflammation of the colon, colitis, microscopic colitis, collagenous colitis, diversion colitis, chemical colitis, ischemic colitis, indeterminate colitis, atypical colitis.

The methods described herein can be used to treat any subject in need thereof. As used herein, a "subject in need thereof" includes any subject that has a disease or disorder associated with a pathological immune response (e.g., an inflammatory bowel disease), as well as any subject with an increased likelihood of acquiring a such a disease or disorder.

The compositions described herein can be used, for example, as a pharmaceutical composition for preventing or treating (reducing, partially or completely, the adverse effects of) an autoimmune disease, such as chronic inflammatory bowel disease, systemic lupus erythematosus, psoriasis, muckle-wells syndrome, rheumatoid arthritis, multiple sclerosis, or Hashimoto's disease; an allergic disease, such as a food allergy, pollenosis, or asthma; an infectious disease, such as an infection with *Clostridium difficile*; an inflammatory disease such as a TNF-mediated inflammatory disease (e.g., an inflammatory disease of the gastrointestinal tract, such as pouchitis, a cardiovascular inflammatory condition, such as atherosclerosis, or an inflammatory lung disease, such as chronic obstructive pulmonary disease); a pharmaceutical composition for suppressing rejection in organ transplantation or other situations in which tissue rejection might occur; a supplement, food, or beverage for improving immune functions; or a reagent for suppressing the proliferation or function of immune cells.

In some embodiments, the methods provided herein are useful for the treatment of inflammation. In certain embodiments, the inflammation of any tissue and organs of the body, including musculoskeletal inflammation, vascular inflammation, neural inflammation, digestive system inflammation, ocular inflammation, inflammation of the reproductive system, and other inflammation, as discussed below.

Immune disorders of the musculoskeletal system include, but are not limited, to those conditions affecting skeletal joints, including joints of the hand, wrist, elbow, shoulder, jaw, spine, neck, hip, knew, ankle, and foot, and conditions affecting tissues connecting muscles to bones such as tendons. Examples of such immune disorders, which may be treated with the methods and compositions described herein include, but are not limited to, arthritis (including, for example, osteoarthritis, rheumatoid arthritis, psoriatic arthritis, ankylosing spondylitis, acute and chronic infectious arthritis, arthritis associated with gout and pseudogout, and juvenile idiopathic arthritis), tendonitis, synovitis, tenosynovitis, bursitis, fibrositis (fibromyalgia), epicondylitis, myositis, and osteitis (including, for example, Paget's disease, osteitis pubis, and osteitis fibrosa cystic).

Ocular immune disorders refers to an immune disorder that affects any structure of the eye, including the eye lids. Examples of ocular immune disorders which may be treated with the methods and compositions described herein include, but are not limited to, blepharitis, blepharochalasis, conjunctivitis, dacryoadenitis, keratitis, keratoconjunctivitis sicca (dry eye), scleritis, trichiasis, and uveitis Examples of nervous system immune disorders which may be treated with the methods and compositions described herein include, but are not limited to, encephalitis, Guillain-Barre syndrome, meningitis, neuromyotonia, narcolepsy, multiple sclerosis, myelitis and schizophrenia. Examples of inflammation of the vasculature or lymphatic system which may be treated with the methods and compositions described herein include, but are not limited to, arthrosclerosis, arthritis, phlebitis, vasculitis, and lymphangitis.

Examples of digestive system immune disorders which may be treated with the methods and compositions described herein include, but are not limited to, cholangitis, cholecystitis, enteritis, enterocolitis, gastritis, gastroenteritis, inflammatory bowel disease, ileitis, and proctitis. Inflammatory bowel diseases include, for example, certain art-recognized forms of a group of related conditions. Several major forms of inflammatory bowel diseases are known, with Crohn's disease (regional bowel disease, e.g., inactive and active forms) and ulcerative colitis (e.g., inactive and active forms) the most common of these disorders. In addition, the inflammatory bowel disease encompasses irritable bowel syndrome, microscopic colitis, lymphocytic-plasmocytic enteritis, coeliac disease, collagenous colitis, lymphocytic colitis and eosinophilic enterocolitis. Other less common forms of IBD include indeterminate colitis, pseudomembranous colitis (necrotizing colitis), ischemic inflammatory bowel disease, Behcet's disease, sarcoidosis, scleroderma, IBD-associated dysplasia, dysplasia associated masses or lesions, and primary sclerosing cholangitis.

Examples of reproductive system immune disorders which may be treated with the methods and compositions described herein include, but are not limited to, cervicitis, chorioamnionitis, endometritis, epididymitis, omphalitis, oophoritis, orchitis, salpingitis, tubo-ovarian abscess, urethritis, vaginitis, vulvitis, and vulvodynia.

The methods and compositions described herein may be used to treat autoimmune conditions having an inflammatory component. Such conditions include, but are not limited to, acute disseminated alopecia universalise, Behcet's disease, Chagas' disease, chronic fatigue syndrome, dysautonomia, encephalomyelitis, ankylosing spondylitis, aplastic anemia, hidradenitis suppurativa, autoimmune hepatitis, autoimmune oophoritis, celiac disease, Crohn's disease, diabetes mellitus type 1, giant cell arteritis, goodpasture's syndrome, Grave's disease, Guillain-Barre syndrome, Hashimoto's disease, Henoch-Schonlein purpura, Kawasaki's disease, lupus erythematosus, microscopic colitis, microscopic polyarteritis, mixed connective tissue disease, Muckle-Wells syndrome, multiple sclerosis, myasthenia gravis, opsoclonus myoclonus syndrome, optic neuritis, ord's thyroiditis, pemphigus, polyarteritis nodosa, polymyalgia, rheumatoid arthritis, Reiter's syndrome, Sjogren's syndrome, temporal arteritis, Wegener's granulomatosis, warm autoimmune haemolytic anemia, interstitial cystitis, Lyme disease, morphea, psoriasis, sarcoidosis, scleroderma, ulcerative colitis, and vitiligo.

The methods and compositions described herein may be used to treat T-cell mediated hypersensitivity diseases having an inflammatory component. Such conditions include, but are not limited to, contact hypersensitivity, contact dermatitis (including that due to poison ivy), uticaria, skin allergies, respiratory allergies (hay fever, allergic rhinitis, house dustmite allergy) and gluten-sensitive enteropathy (Celiac disease).

Other immune disorders which may be treated with the methods and compositions include, for example, appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, percarditis, peritonoitis, pharyngitis, pleuritis, pneumonitis, prostatistis, pyelonephritis, and stomatisi, transplant rejection (involving organs such as kidney, liver, heart, lung, pancreas (e.g., islet cells), bone marrow, cornea, small bowel, skin allografts, skin homografts, and heart valve xengrafts, sewrum sickness, and graft vs host disease), acute pancreatitis, chronic pancreatitis, acute respiratory distress syndrome, Sexary's syndrome, congenital adrenal hyperplasis, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensistivity reactions, allergic conjunctivitis, keratitis, herpes zoster ophthalmicus, iritis and oiridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) haemolytic anemia, leukaemia and lymphomas in adults, acute leukaemia of childhood, regional enteritis, autoimmune vasculitis, multiple sclerosis, chronic obstructive pulmonary disease, solid organ transplant rejection, sepsis. Preferred treatments include treatment of transplant rejection, rheumatoid arthritis, psoriatic arthritis, multiple sclerosis, Type 1 diabetes, asthma, inflammatory bowel disease, systemic lupus erythematosus, psoriasis, chronic obstructive pulmonary disease, and inflammation accompanying infectious conditions (e.g., sepsis).

The methods and compositions described herein may be used to treat metabolic disorders and metabolic syndromes. Such conditions include, but are not limited to, Type II Diabetes, Encephalopathy, Tay-Sachs disease, Krabbe disease, Galactosemia, Phenylketonuria (PKU), and Maple syrup urine disease.

The methods and compositions described herein may be used to treat neurodegenerative and neurological diseases. Such conditions include, but are not limited to, Parkinson's disease, Alzheimer's disease, prion disease, Huntington's disease, motor neurone diseases (MND), spinocerebellar ataxia, spinal muscular atrophy, dystonia, idiopathic intracranial hypertension, epilepsy, nervous system disease, central nervous system disease, movement disorders, multiple sclerosis, encephalopathy, and, post-operative cognitive dysfunction.

Cancer

In some embodiments, the methods and compositions described herein relate to the treatment of cancer. In some embodiments, any cancer can be treated using the methods described herein. Examples of cancers that may treated by methods and compositions described herein include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; plasmacytoma, colorectal cancer, rectal cancer, and hairy cell leukemia.

In some embodiments, the methods and compositions provided herein relate to the treatment of a leukemia. The term "leukemia" is meant broadly progressive, malignant diseases of the hematopoietic organs/systems and is generally characterized by a distorted proliferation and development of leukocytes and their precursors in the blood and bone marrow. Non-limiting examples of leukemia diseases include, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophilic leukemia, blast cell leukemia, bovine leukemia, chronic myelocytic leukemia, leukemia cutis, embryonal leukemia, eosinophilic leukemia, Gross' leukemia, Rieder cell leukemia, Schilling's leukemia, stem cell leukemia, subleukemic leukemia, undifferentiated cell leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, and promyelocytic leukemia.

In some embodiments, the methods and compositions provided herein relate to the treatment of a carcinoma. The term "carcinoma" refers to a malignant growth made up of epithelial cells tending to infiltrate the surrounding tissues, and/or resist physiological and non-physiological cell death signals and gives rise to metastases. Non-limiting exemplary types of carcinomas include, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, carcinoma villosum, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, merkel cell carcinoma, salivary gland carcinoma and carcinoma scroti.

In some embodiments, the methods and compositions provided herein relate to the treatment of a sarcoma. The term "sarcoma" generally refers to a tumor which is made up of a substance like the embryonic connective tissue and is generally composed of closely packed cells embedded in a fibrillar, heterogeneous, or homogeneous substance. Sarcomas include, but are not limited to, chondrosarcoma, fibrosarcoma, lymphosarcoma, melanosarcoma, myxosarcoma, osteosarcoma, endometrial sarcoma, stromal sarcoma, Ewing's sarcoma, fascial sarcoma, fibroblastic sarcoma, giant cell sarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

Additional exemplary neoplasias that can be treated using the methods and compositions described herein include Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, and adrenal cortical cancer.

In some embodiments, the cancer treated is a melanoma. The term "melanoma" is taken to mean a tumor arising from the melanocytic system of the skin and other organs. Non-limiting examples of melanomas are Harding-Passey melanoma, juvenile melanoma, lentigo maligna melanoma, malignant melanoma, acral-lentiginous melanoma, amelanotic melanoma, benign juvenile melanoma, Cloudman's melanoma, S91 melanoma, nodular melanoma subungal melanoma, and superficial spreading melanoma.

Particular categories of tumors that can be treated using methods and compositions described herein include lymphoproliferative disorders, breast cancer, ovarian cancer, prostate cancer, cervical cancer, endometrial cancer, bone cancer, liver cancer, stomach cancer, colon cancer, pancreatic cancer, cancer of the thyroid, head and neck cancer, cancer of the central nervous system, cancer of the peripheral nervous system, skin cancer, kidney cancer, as well as metastases of all the above. Particular types of tumors include hepatocellular carcinoma, hepatoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, pulmonary squamous cell carcinoma, basal cell carcinoma, adenocarcinoma (well differentiated, moderately differentiated, poorly differentiated or undifferentiated), bronchioloalveolar carcinoma, renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocyoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma.

Cancers treated in certain embodiments also include precancerous lesions, e.g., actinic keratosis (solar keratosis), moles (dysplastic nevi), acitinic chelitis (farmer's lip), cutaneous horns, Barrett's esophagus, atrophic gastritis, dyskeratosis congenita, sideropenic dysphagia, lichen planus, oral submucous fibrosis, actinic (solar) elastosis and cervical dysplasia.

Cancers treated in some embodiments include non-cancerous or benign tumors, e.g., of endodermal, ectodermal or mesenchymal origin, including, but not limited to cholangioma, colonic polyp, adenoma, papilloma, cystadenoma, liver cell adenoma, hydatidiform mole, renal tubular adenoma, squamous cell papilloma, gastric polyp, hemangioma, osteoma, chondroma, lipoma, fibroma, lymphangioma, leiomyoma, rhabdomyoma, astrocytoma, nevus, meningioma, and ganglioneuroma.

EXAMPLES

Example 1: Immune Modulation of Human Commensal Bacteria in a KLH-Based Delayed Type Hypersensitivity Model Delayed-type hypersensitivity (DTH) is an animal model of atopic dermatitis (or allergic contact dermatitis), as reviewed by Petersen et al. (In vivo pharmacological disease models for psoriasis and atopic dermatitis in drug discovery. Basic & Clinical Pharm & Toxicology. 2006, 99(2): 104-115; see also Irving C. Allen (ed.) Mouse Models of Innate Immunity: Methods and Protocols, Methods in Molecular Biology, 2013. vol. 1031, DOI 10.1007/978-1-62703-481-4_13). It can be induced in a variety of mouse and rat strains using various haptens or antigens, for example an antigen emulsified with an adjuvant. DTH is characterized by sensitization as well as an antigen-specific T cell-mediated reaction that results in erythema, edema, and cellular infiltration—especially infiltration of antigen presenting cells (APCs), eosinophils, activated CD4+ T cells, and cytokine-expressing Th2 cells.

The test formulations were prepared for KLH-based delayed type hypersensitivity model. The delayed-type hypersensitivity (DTH) model provides an in vivo mechanism to study the cell-mediated immune response, and resulting inflammation, following exposure to a specific antigen to which the mice have been sensitized. Several variations of the DTH model have been used and are well known in the art (Irving C. Allen (ed.). *Mouse Models of Innate Immunity: Methods and Protocols*, Methods in Molecular Biology. Vol. 1031, DOI 10.1007/978-1-62703-481-4_13, Springer Science+Business Media, LLC 2013). For example, the emulsion of Keyhole Limpet Hemocyanin (KLH) and Complete Freund's Adjuvant (CFA) are prepared freshly on the day of immunization (day 0). To this end, 8 mg of KLH powder is weighed and is thoroughly re-suspended in 16 mL saline. An emulsion is prepared by mixing the KLH/saline with an equal volume of CFA solution (e.g. 10 mL KLH/saline+10 mL CFA solution) using syringes and a luer lock connector. KLH and CFA is mixed vigorously for several minutes to form a white-colored emulsion to obtain maximum stability. A drop test is performed to check if a homogenous emulsion is obtained, mixing is continued until an intact drop remains visible in the water.

On day 0, C57Bl/6J female mice, approximately 7 weeks old, were primed with KLH antigen in CFA by subcutaneous immunization (4 sites, 50 μL per site).

Dexamethasone, a corticosteroid, is a known anti-inflammatory that ameliorates DTH reactions in mice, and serves as a positive control for suppressing inflammation in this model (Taube and Carlsten, Action of dexamethasone in the suppression of delayed-type hypersensitivity in reconstituted SCID mice. Inflamm Res. 2000, 49(10): 548-52). For the positive control group, a stock solution of 17 mg/mL of Dexamethasone was prepared on by diluting 6.8 mg Dexamethasone in 400 μL 96% ethanol. For each day of dosing, a working solution is prepared by diluting the stock solution 100× in sterile PBS to obtain a final concentration of 0.17 mg/mL in a septum vial for intraperitoneal dosing. Dexamethasone-treated mice received 100 μL Dexamethasone i.p. (5 mL/kg of a 0.17 mg/mL solution). Frozen sucrose served as the negative control (vehicle). *Lactococcus lactis cremoris* Strain A was dosed at 100 ul of bacterial cells at 1×10^10 CFU/ml p.o. daily. Dexamethasone (positive control), vehicle (negative control), and *Lactococcus lactis cremoris* Strain A were dosed daily.

On day 8, mice were challenged intradermally (i.d.) with 10 μg KLH in saline (in a volume of 10 μL) in the right ear and a control in the left ear. Inflammatory response were measured using methods known in the art. Ear pinna thickness was measured at 48 hours following antigen challenge (FIGS.FIGS, FIGS,1 and 3). As determined by ear thickness, *Lactococcus lactis cremoris* Strain A was as efficacious as Dexamethasone at suppressing inflammation compared to mice that received vehicle alone.

The efficacy of *Lactococcus lactis cremoris* Strain A may be studied further using varied timing and varied doses. For instance, treatment with *Lactococcus lactis cremoris* Strain A-containing bacterial composition may be initiated at some point, either around the time of priming or around the time of DTH challenge. For example, *Lactococcus lactis cremoris* strain A ($1\times10^9$ CFU per mouse per day) may be administered at the same time as the subcutaneous injections (day 0), or they may be administered prior to, or upon, intradermal injection. *Lactococcus lactis cremoris* strain A is administered at varied doses and at defined intervals. For example, some mice are intravenously injected with *Lactococcus lactis cremoris* strain A at a range of between $1\times10^4$ and $5\times10^9$ bacterial cells per mouse. While some mice will receive *Lactococcus lactis cremoris* strain A through i.v. injection, other mice may receive *Lactococcus lactis cremoris* strain A through intraperitoneal (i.p.) injection, subcutaneous (s.c.) injection, nasal route administration, oral gavage, topical administration, intradermal (i.d.) injection, or other means of administration. Some mice may receive *Lactococcus lactis cremoris* strain A every day (e.g. starting on day 0), while others may receive *Lactococcus lactis cremoris* strain A at alternative intervals (e.g. every other day, or once every three days). Additional groups of mice may receive some ratio of bacterial cells to *Lactococcus lactis cremoris* strain A. The bacterial cells may be live, dead, or weakened. The bacterial cells may be harvested fresh (or frozen) and administered, or they may be irradiated or heat-killed prior to administration.

For example, some groups of mice may receive between $1\times10^4$ and $5\times10^9$ bacterial cells in an administration separate from, or comingled with, the *Lactococcus lactis cremoris* strain A administration. As with the *Lactococcus lactis cremoris* strain A, bacterial cell administration may be varied by route of administration, dose, and schedule. This can include oral gavage, i.v. injection, i.p. injection, i.d. injection, topical administration, or nasal route administration.

Some groups of mice may be treated with anti-inflammatory agent(s) (e.g. anti-CD154, blockade of members of the TNF family, or other treatment), and/or an appropriate control (e.g. vehicle or control antibody) at various time points and at effective doses.

In addition, some mice are treated with antibiotics prior to treatment. For example, vancomycin (0.5 g/L), ampicillin (1.0 g/L), gentamicin (1.0 g/L) and amphotericin B (0.2 g/L) are added to the drinking water, and antibiotic treatment is halted at the time of treatment or a few days prior to treatment. Some immunized mice are treated without receiving antibiotics.

Study animals may be sacrificed by exsanguination from the orbital plexus under $CO_2/O_2$ anesthesia, followed by cervical dislocation on day 10. For serum preparation, the blood samples are allowed to clot before centrifuging. The sera are transferred into clean tubes, each animal in a separate tube. Following exsanguination, of all animals both ears (each ear in a separate vial), the spleen, the mesenteric lymph nodes (MLN), the entire small intestine, and the colon are collected in cryovials, snap frozen and stored at <−70° C.

Tissues may be dissociated using dissociation enzymes according to the manufacturer's instructions. Cells are stained for analysis by flow cytometry using techniques known in the art. Staining antibodies can include anti-CD11c (dendritic cells), anti-CD80, anti-CD86, anti-CD40, anti-MHCII, anti-CD8a, anti-CD4, and anti-CD103. Other markers that may be analyzed include pan-immune cell marker CD45, T cell markers (CD3, CD4, CD8, CD25, Foxp3, T-bet, Gata3, Roryt, Granzyme B, CD69, PD-1, CTLA-4), and macrophage/myeloid markers (CD11b, MHCII, CD206, CD40, CSF1R, PD-L1, Gr-1, F4/80). In addition to immunophenotyping, serum cytokines are analyzed including, but not limited to, TNFa, IL-17, IL-13, IL-12p70, IL12p40, IL-10, IL-6, IL-5, IL-4, IL-2, IL-1b, IFNy, GM-CSF, G-CSF, M-CSF, MIG, IP10, MIP1b, RANTES, and MCP-1. Cytokine analysis may be carried out on immune cells obtained from lymph nodes or other tissue, and/or on purified CD45+ infiltrated immune cells obtained ex vivo. Finally, immunohistochemistry is carried out on various tissue sections to measure T cells, macrophages, dendritic cells, and checkpoint molecule protein expression.

Example 2: An Evaluation of Test Articles in the Modulation of DSS-Induced Colitis in C57BL/6 Mice Dextran sulfate sodium (DSS)-induced colitis is a well-studied animal model of colitis, as reviewed by Randhawa et al. (A review on chemical-induced inflammatory bowel disease models in rodents. Korean J Physiol Pharmacol. 2014, 18(4): 279-288; see also Chassaing et al. Dextran sulfate sodium (DSS)-induced colitis in mice. Curr Protoc Immunol. 2014 Feb. 4; 104: Unit 15.25). In this model, mice are treated with DSS in drinking water, resulting in diarrhea and weight loss.

Figure 2:
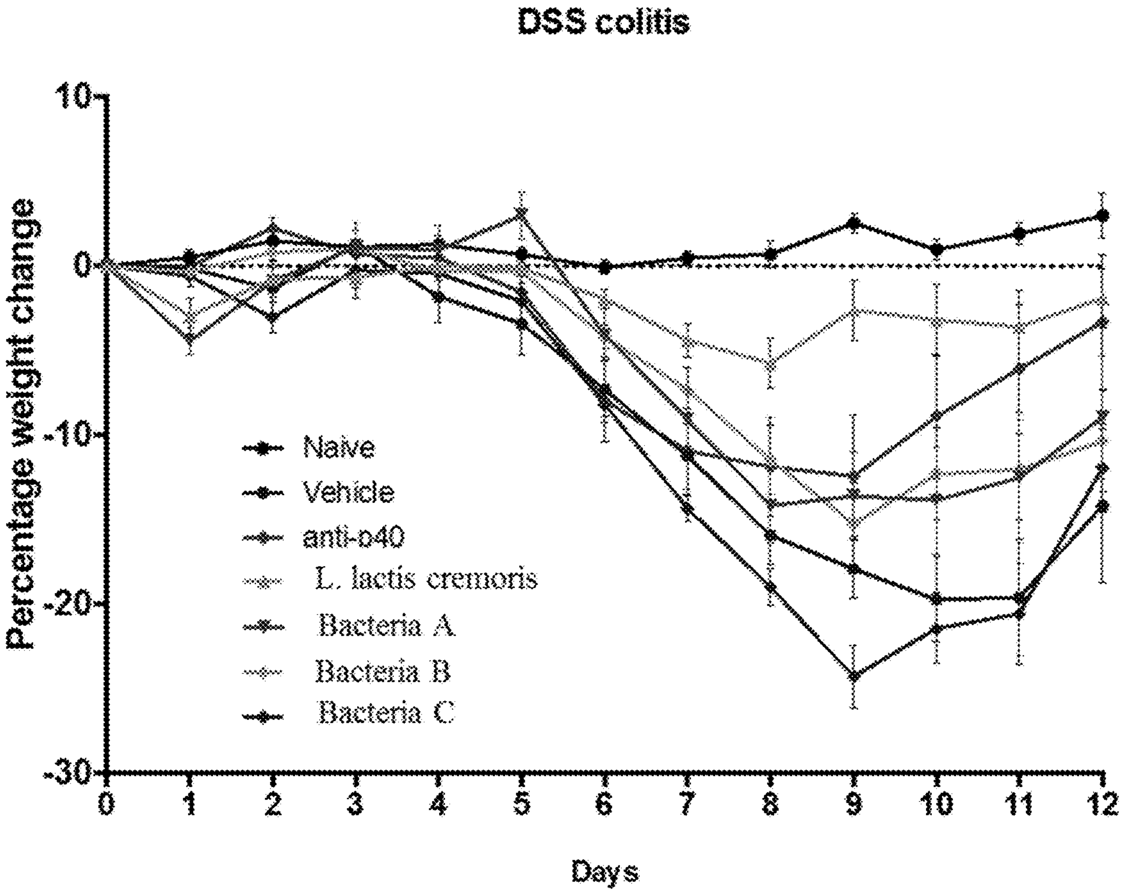
FIG. 2 is a line graphing showing percent weight change in acute DSS-induced colitis model over a 12 day period for *Lactococcus lactis cremoris* Strain A in comparison to Bacteria A, B, and C, positive control (anti-p40), and negative control (Sucrose vehicle). The *Lactococcus lactis cremoris* Strain A group showed less weight change than the anti-p40 antibody (positive control).
Figure 3A:
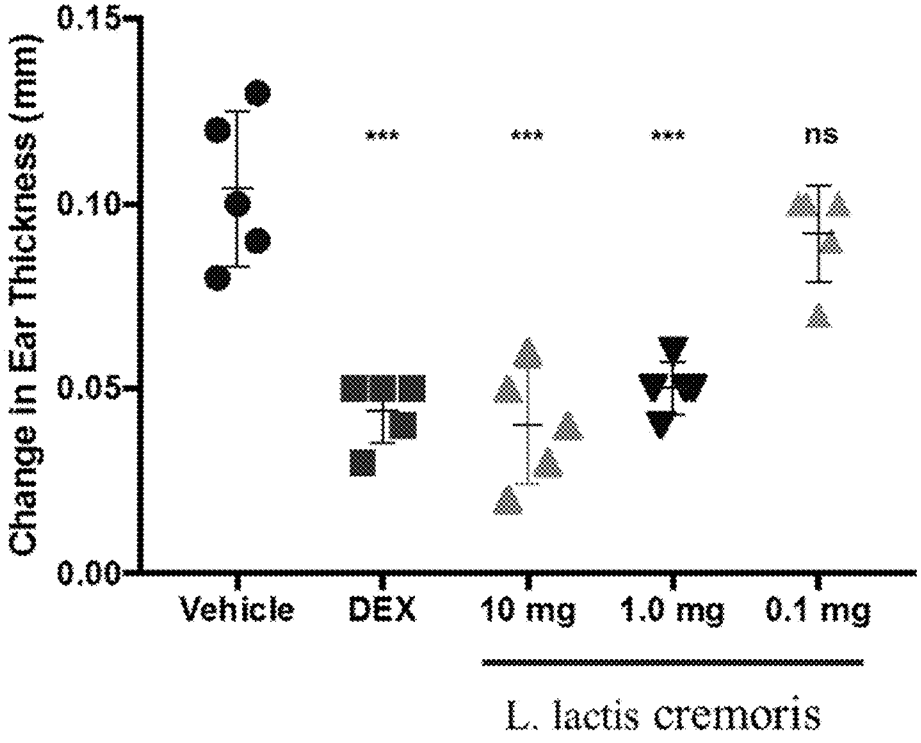
FIG. 3A and FIG. 3B are plots showing that orally administered *Lactococcus lactis cremoris* Strain A reduces antigen-specific ear swelling (ear thickness) compared to vehicle (negative control) and Dexamethasone (FIG. 3A) and Fingolimod (FIG. 3B).
Figure 3B:
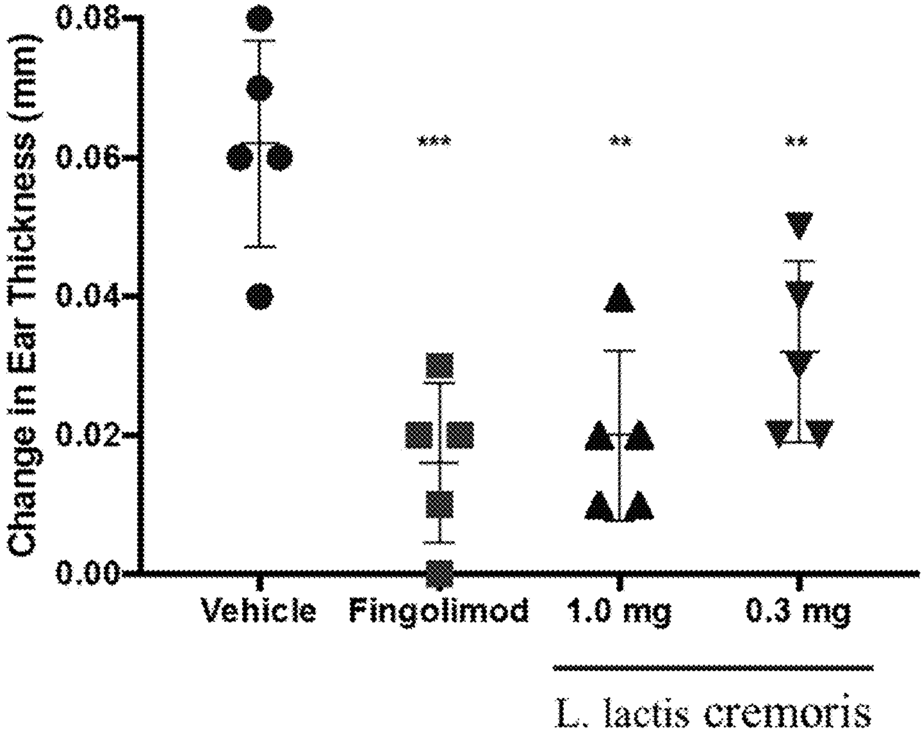

Groups of mice were treated with DSS to induce colitis as known in the art (Randhawa et al. 2014; Chassaing et al. 2014; see also Kim et al. Investigating intestinal inflammation in DSS-induced model of IBD. J Vis Exp. 2012, 60: 3678). For example, colitis was induced in mice by exposure to 3% DSS-treated drinking water from Day 0 to Day 5. One group did not receive DSS and served as naive controls. Animals were dosed with sucrose vehicle (negative control), *Lactococcus lactis cremoris* Strain A ($1\times10^9$ CFU per mouse per day), *Lactococcus lactis cremoris* Strain X ($1\times10^9$ CFU per mouse per day), or anti-p40 positive control (administered i.p. on days 0, 3, 7, and 10). All animals were weighed daily. As measured by decrease in weight loss, *Lactococcus lactis cremoris* Strain A was more efficacious than either anti-p40 (positive control), or Bacteria A, B, or C (FIG. 2).

In other studies, treatment with *Lactococcus lactis cremoris* Strain A-containing bacterial composition may be initiated at some point, either on day 1 of DSS administration, or sometime thereafter. For example, *Lactococcus lactis cremoris* strain A may be administered at the same time as DSS initiation (day 1), or they may be administered upon the first signs of disease (e.g. weight loss or diarrhea), or during the stages of severe colitis. Mice may be observed daily for weight, morbidity, survival, presence of diarrhea and/or bloody stool.

*Lactococcus lactis cremoris* strain A is administered at varied doses, varied intervals, and/or varied routes of administration. For example, some mice are intravenously injected with *Lactococcus lactis cremoris* strain A at a dose of between $1\times10^4$ and $5\times10^9$ bacterial cells per mouse. While some mice will receive *Lactococcus lactis cremoris* strain A through i.v. injection, other mice may receive *Lactococcus lactis cremoris* strain A through intraperitoneal (i.p.) injection, subcutaneous (s.c.) injection, nasal route administration, oral gavage, or other means of administration. Some mice may receive *Lactococcus lactis cremoris* strain A every day (e.g. starting on day 1), while others may receive *Lactococcus lactis cremoris* strain A at alternative intervals (e.g. every other day, or once every three days). Additional groups of mice may receive some ratio of bacterial cells to *Lactococcus lactis cremoris* strain A. The bacterial cells may be live, dead, or weakened. The bacterial cells may be harvested fresh (or frozen) and administered, or they may be irradiated or heat-killed prior to administration.

*Lactococcus lactis cremoris* Strain A-containing bacterial compositions may be tested for their efficacy in a mouse model of DSS-induced colitis, either alone or in combination with whole bacterial cells, with or without the addition of other anti-inflammatory agents.

For example, some groups of mice may receive between $1\times10^4$ and $5\times10^9$ bacterial cells in an administration separate from, or comingled with, the *Lactococcus lactis cremoris* strain A administration. As with the *Lactococcus lactis cremoris* strain A, bacterial cell administration may be varied by route of administration, dose, and schedule. This can include oral gavage, i.v. injection, i.p. injection, or nasal route administration.

Some groups of mice may be treated with additional anti-inflammatory agent(s) (e.g. anti-CD154, blockade of members of the TNF family, or other treatment), and/or an appropriate control (e.g. vehicle or control antibody) at various time points and at effective doses.

In addition, some mice are treated with antibiotics prior to treatment. For example, vancomycin (0.5 g/L), ampicillin (1.0 g/L), gentamicin (1.0 g/L) and amphotericin B (0.2 g/L) are added to the drinking water, and antibiotic treatment is halted at the time of treatment or a few days prior to treatment. Some mice receive DSS without receiving antibiotics beforehand.

At various time points, mice undergo video endoscopy using a small animal endoscope (Karl Storz Endoskipe, Germany) under isoflurane anesthesia. Still images and video will be recorded to evaluate the extent of colitis and the response to treatment. Colitis will be scored using criteria known in the art. Fecal material will be collected for study.

The gastrointestinal (GI) tract, lymph nodes, and/or other tissues may be removed for ex vivo histological, cytokine and/or flow cytometric analysis using methods known in the art. For example, tissues are harvested and may be dissociated using dissociation enzymes according to the manufacturer's instructions. Cells are stained for analysis by flow cytometry using techniques known in the art. Staining antibodies can include anti-CD11c (dendritic cells), anti-CD80, anti-CD86, anti-CD40, anti-MHCII, anti-CD8a, anti-CD4, and anti-CD103. Other markers that may be analyzed include pan-immune cell marker CD45, T cell markers (CD3, CD4, CD8, CD25, Foxp3, T-bet, Gata3, Roryt, Granzyme B, CD69, PD-1, CTLA-4), and macrophage/myeloid markers (CD11b, MHCII, CD206, CD40, CSF1R, PD-L1, Gr-1, F4/80). In addition to immunophenotyping, serum cytokines are analyzed including, but not limited to, TNFa, IL-17, IL-13, IL-12p70, IL12p40, IL-10, IL-6, IL-5, IL-4, IL-2, IL-1b, IFNy, GM-CSF, G-CSF, M-CSF, MIG, IP10, MIP1b, RANTES, and MCP-1. Cytokine analysis may be carried out on immune cells obtained from lymph nodes or other tissue, and/or on purified CD45+GI tract-infiltrated immune cells obtained ex vivo. Finally, immunohistochemistry is carried out on various tissue sections to measure T cells, macrophages, dendritic cells, and checkpoint molecule protein expression.

In order to examine the impact and longevity of disease protection, rather than being sacrificed, some mice may be rechallenged with a disease trigger. Mice will be analyzed for susceptibility to colitis severity following rechallenge.

Following sacrifice, the colon, small intestine, spleen, and mesenteric lymph nodes may be collected from all animals, and blood collected for analysis.

Example 3: *Lactococcus lactis cremoris* Strain A and/or EVs Derived from *Lactococcus lactis cremoris* Strain A in a Mouse Model of Experimental Autoimmune Encephalomyelitis (EAE)

EAE is a well-studied animal model of multiple sclerosis, as reviewed by Constantinescu et al. (Experimental autoimmune encephalomyelitis (EAE) as a model for multiple sclerosis (MS). Br J Pharmacol. 2011 October; 164(4): 1079-1106). It can be induced in a variety of mouse and rat strains using different myelin-associated peptides, by the adoptive transfer of activated encephalitogenic T cells, or the use of TCR transgenic mice susceptible to EAE, as discussed in Mangalam et al. (Two discreet subsets of CD8+ T cells modulate $PLP_{91-110}$ induced experimental autoimmune encephalomyelitis in HLA-DR3 transgenic mice. J Autoimmun. 2012 June; 38(4): 344-353).

*Lactococcus lactis cremoris* Strain A-containing bacterial compositions and/or EVs derived from *Lactococcus lactis cremoris* Strain A are tested for their efficacy in the rodent model of EAE, either alone or in combination with whole bacterial cells, with or without the addition of other anti-inflammatory treatments. For example, female 6-8 week old C57Bl/6 mice are obtained from Taconic (Germantown, N.Y.). Groups of mice will be administered two subcutaneous (s.c.) injections at two sites on the back (upper and lower) of 0.1 ml myelin oligodentrocyte glycoprotein 35-55 (MOG35-55; 100 ug per injection; 200 ug per mouse (total 0.2 ml per mouse)), emulsified in Complete Freund's Adjuvant (CFA; 2-5 mg killed *Mycobacterium tuberculosis* H37Ra/ml emulsion). Approximately 1-2 hours after the above, mice are intraperitoneally (i.p.) injected with 200 ng Pertussis toxin (PTx) in 0.1 ml PBS (2 ug/ml). An additional IP injection of PTx is administered on day 2. Alternatively, an appropriate amount of an alternative myelin peptide (e.g. proteolipid protein (PLP)) will be used to induce EAE. Some animals will serve as naïve controls. EAE severity will be assessed and a disability score will be assigned daily beginning on day 4 according to methods known in the art (Mangalam et al. 2012).

Treatment with *Lactococcus lactis cremoris* Strain A-containing bacterial composition and/or EVs derived from *Lactococcus lactis cremoris* Strain A is initiated at some point, either around the time of immunization or following EAE immunization. For example, *Lactococcus lactis cremoris* Strain A-containing bacterial and/or EVs derived from *Lactococcus lactis cremoris* Strain A composition may be administered at the same time as immunization (day 1), or they may be administered upon the first signs of disability (e.g. limp tail), or during severe EAE. *Lactococcus lactis cremoris* Strain A-containing bacterial compositions and/or EVs derived from *Lactococcus lactis cremoris* Strain A are administered at varied doses and at defined intervals. For example, some mice are intravenously injected with effective doses of *Lactococcus lactis cremoris* Strain A. For example, mice may receive between $1\times10^4$ and $5\times10^9$ bacterial cells per mouse. While some mice will receive *Lactococcus lactis cremoris* strain A and/or EVs derived from *Lactococcus lactis cremoris* Strain A through i.v. injection, other mice may receive *Lactococcus lactis cremoris* and/or EVs derived from *Lactococcus lactis cremoris* Strain A through intraperitoneal (i.p.) injection, subcutaneous (s.c.) injection, nasal route administration, oral gavage, or other means of administration. Some mice may receive *Lactococcus lactis cremoris* strain A and/or EVs derived from *Lactococcus lactis cremoris* Strain A every day (e.g. starting on day 1), while others may receive *Lactococcus lactis cremoris* strain A and/or EVs derived from *Lactococcus lactis cremoris* Strain A at alternative intervals (e.g. every other day, or once every three days). Additional groups of mice may receive some ratio of bacterial cells to *Lactococcus lactis cremoris* strain A. The bacterial cells may be live, dead, or weakened. The bacterial cells may be harvested fresh (or frozen) and administered, or they may be irradiated or heat-killed prior to administration.

For example, some groups of mice may receive between $1\times10^4$ and $5\times10^9$ bacterial cells in an administration separate from, or comingled with, the *Lactococcus lactis cremoris* strain A and/or EVs derived from *Lactococcus lactis cremoris* Strain A administration. As with the *Lactococcus lactis cremoris* strain A, bacterial cell administration may be varied by route of administration, dose, and schedule. This can include oral gavage, i.v. injection, i.p. injection, subcutaneous (s.c.) injection, or nasal route administration.

Some groups of mice may be treated with additional anti-inflammatory agent(s) or EAE therapeutic(s) (e.g. anti-CD154, blockade of members of the TNF family, Vitamin D, or other treatment), and/or an appropriate control (e.g. vehicle or control antibody) at various time points and at effective doses.

In addition, some mice are treated with antibiotics prior to treatment. For example, vancomycin (0.5 g/L), ampicillin (1.0 g/L), gentamicin (1.0 g/L) and amphotericin B (0.2 g/L) are added to the drinking water, and antibiotic treatment is halted at the time of treatment or a few days prior to treatment. Some immunized mice are treated without receiving antibiotics.

At various time points, mice are sacrificed and sites of inflammation (e.g. brain and spinal cord), lymph nodes, or other tissues may be removed for ex vivo histological, cytokine and/or flow cytometric analysis using methods known in the art. For example, tissues are dissociated using dissociation enzymes according to the manufacturer's instructions. Cells are stained for analysis by flow cytometry using techniques known in the art. Staining antibodies can include anti-CD11c (dendritic cells), anti-CD80, anti-CD86, anti-CD40, anti-MHCII, anti-CD8a, anti-CD4, and anti-CD103. Other markers that may be analyzed include pan-immune cell marker CD45, T cell markers (CD3, CD4, CD8, CD25, Foxp3, T-bet, Gata3, Roryt, Granzyme B, CD69, PD-1, CTLA-4), and macrophage/myeloid markers (CD11b, MHCII, CD206, CD40, CSF1R, PD-L1, Gr-1, F4/80). In addition to immunophenotyping, serum cytokines are analyzed including, but not limited to, TNFa, IL-17, IL-13, IL-12p70, IL12p40, IL-10, IL-6, IL-5, IL-4, IL-2, IL-1b, IFNy, GM-CSF, G-CSF, M-CSF, MIG, IP10, MIP1b, RANTES, and MCP-1. Cytokine analysis may be carried out on immune cells obtained from lymph nodes or other tissue, and/or on purified CD45+ central nervous system (CNS)-infiltrated immune cells obtained ex vivo. Finally, immunohistochemistry is carried out on various tissue sections to measure T cells, macrophages, dendritic cells, and checkpoint molecule protein expression.

In order to examine the impact and longevity of disease protection, rather than being sacrificed, some mice may be rechallenged with a disease trigger (e.g. activated encephalitogenic T cells or re-injection of EAE-inducing peptides).

Mice will be analyzed for susceptibility to disease and EAE severity following rechallenge.

Example 4: *Lactococcus lactis cremoris* Strain A and/or EVs Derived from *Lactococcus lactis cremoris* Strain A in a Mouse Model of Collagen-Induced Arthritis (CIA)

Collagen-induced arthritis (CIA) is an animal model commonly used to study rheumatoid arthritis (RA), as described by Caplazi et al. (Mouse models of rheumatoid arthritis. Veterinary Pathology. Sep. 1, 2015, 52(5): 819-826) (see also Brand et al. Collagen-induced arthritis. Nature Protocols. 2007, 2: 1269-1275; Pietrosimone et al. Collagen-induced arthritis: a model for murine autoimmune arthritis. Bio Protoc. 2015 Oct. 20; 5(20): e1626).

Among other versions of the CIA rodent model, one model involves immunizing HLA-DQ8 Tg mice with chick type II collagen as described by Taneja et al. (J. Immunology. 2007, 56: 69-78; see also Taneja et al. J. Immunology 2008, 181: 2869-2877; and Taneja et al. Arthritis Rheum., 2007, 56: 69-78). Purification of chick CII has been described by Taneja et al. (Arthritis Rheum., 2007, 56: 69-78). Mice are monitored for CIA disease onset and progression following immunization, and severity of disease is evaluated and "graded" as described by Wooley, J. Exp. Med. 1981, 154: 688-700.

Mice are immunized for CIA induction and separated into various treatment groups. *Lactococcus lactis cremoris* Strain A-containing bacterial compositions and/or EVs derived from *Lactococcus lactis cremoris* Strain A are tested for their efficacy in CIA, either alone or in combination with whole bacterial cells, with or without the addition of other anti-inflammatory treatments.

Treatment with *Lactococcus lactis cremoris* Strain A-containing bacterial composition and/or EVs derived from *Lactococcus lactis cremoris* Strain A is initiated either around the time of immunization with collagen or post-immunization. For example, in some groups, *Lactococcus lactis cremoris* strain A and/or EVs derived from *Lactococcus lactis cremoris* Strain A may be administered at the same time as immunization (day 1), or *Lactococcus lactis cremoris* strain A and/or EVs derived from *Lactococcus lactis cremoris* Strain A may be administered upon first signs of disease, or upon the onset of severe symptoms. *Lactococcus lactis cremoris* strain A and/or EVs derived from *Lactococcus lactis cremoris* Strain A is administered at varied doses and at defined intervals.

For example, some mice are intravenously injected with *Lactococcus lactis cremoris* strain A at a dose of between $1\times10^4$ and $5\times10^9$ bacterial cells per mouse. While some mice will receive *Lactococcus lactis cremoris* strain A and/or EVs derived from *Lactococcus lactis cremoris* Strain A through i.v. injection, other groups of mice may receive *Lactococcus lactis cremoris* strain A through intraperitoneal (i.p.) injection, subcutaneous (s.c.) injection, nasal route administration, oral gavage, or other means of administration. Some mice may receive *Lactococcus lactis cremoris* strain A and/or EVs derived from *Lactococcus lactis cremoris* Strain A every day (e.g. starting on day 1), while others may receive *Lactococcus lactis cremoris* strain A and/or EVs derived from *Lactococcus lactis cremoris* Strain A at alternative intervals (e.g. every other day, or once every three days). Additional groups of mice may receive some ratio of bacterial cells to *Lactococcus lactis cremoris* strain A and/or EVs derived from *Lactococcus lactis cremoris* Strain A. The bacterial cells may be live, dead, or weakened. The bacterial cells may be harvested fresh (or frozen) and administered, or they may be irradiated or heat-killed prior to administration.

For example, some groups of mice may receive between $1\times10^4$ and $5\times10^9$ bacterial cells in an administration separate from, or comingled with, the *Lactococcus lactis cremoris* strain A and/or EVs derived from *Lactococcus lactis cremoris* Strain A administration. As with the *Lactococcus lactis cremoris* strain A, bacterial cell administration may be varied by route of administration, dose, and schedule. This can include oral gavage, i.v. injection, i.p. injection, subcutaneous (s.c.) injection, intradermal (i.d.) injection, or nasal route administration.

Some groups of mice may be treated with additional anti-inflammatory agent(s) or CIA therapeutic(s) (e.g. anti-CD154, blockade of members of the TNF family, Vitamin D, or other treatment), and/or an appropriate control (e.g. vehicle or control antibody) at various time points and at effective doses.

In addition, some mice are treated with antibiotics prior to treatment. For example, vancomycin (0.5 g/L), ampicillin (1.0 g/L), gentamicin (1.0 g/L) and amphotericin B (0.2 g/L) are added to the drinking water, and antibiotic treatment is halted at the time of treatment or a few days prior to treatment. Some immunized mice are treated without receiving antibiotics.

At various time points, serum samples are obtained to assess levels of anti-chick and anti-mouse CII IgG antibodies using a standard ELISA (Batsalova et al. Comparative analysis of collagen type II-specific immune responses during development of collagen-induced arthritis in two B10 mouse strains. Arthritis Res Ther. 2012, 14(6): R237). Also, some mice are sacrificed and sites of inflammation (e.g. synovium), lymph nodes, or other tissues may be removed for ex vivo histological, cytokine and/or flow cytometric analysis using methods known in the art. The synovium and synovial fluid will be analyzed for plasma cell infiltration and the presence of antibodies using techniques known in the art. In addition, tissues are dissociated using dissociation enzymes according to the manufacturer's instructions to examine the profiles of the cellular infiltrates. Cells are stained for analysis by flow cytometry using techniques known in the art. Staining antibodies can include anti-CD11c (dendritic cells), anti-CD80, anti-CD86, anti-CD40, anti-MHCII, anti-CD8a, anti-CD4, and anti-CD103. Other markers that may be analyzed include pan-immune cell marker CD45, T cell markers (CD3, CD4, CD8, CD25, Foxp3, T-bet, Gata3, Roryt, Granzyme B, CD69, PD-1, CTLA-4), and macrophage/myeloid markers (CD11b, MHCII, CD206, CD40, CSF1R, PD-L1, Gr-1, F4/80). In addition to immunophenotyping, serum cytokines are analyzed including, but not limited to, TNFa, IL-17, IL-13, IL-12p70, IL12p40, IL-10, IL-6, IL-5, IL-4, IL-2, IL-1b, IFNy, GM-CSF, G-CSF, M-CSF, MIG, IP10, MIP1b, RANTES, and MCP-1. Cytokine analysis may be carried out on immune cells obtained from lymph nodes or other tissue, and/or on purified CD45+ synovium-infiltrated immune cells obtained ex vivo. Finally, immunohistochemistry is carried out on various tissue sections to measure T cells, macrophages, dendritic cells, and checkpoint molecule protein expression.

In order to examine the impact and longevity of disease protection, rather than being sacrificed, some mice may be rechallenged with a disease trigger (e.g. activated re-injection with CIA-inducing peptides). Mice will be analyzed for susceptibility to disease and CIA severity following rechallenge.

Example 5: *Lactococcus lactis cremoris* Strain A and/or EVs Derived from *Lactococcus lactis cremoris* Strain A in a Mouse Model of Type 1 Diabetes (T1D)

Type 1 diabetes (T1D) is an autoimmune disease in which the immune system targets the islets of Langerhans of the pancreas, thereby destroying the body's ability to produce insulin.

There are various models of animal models of T1D, as reviewed by Belle et al. (Mouse models for type 1 diabetes. Drug Discov Today Dis Models. 2009; 6(2): 41-45; see also Aileen J F King. The use of animal models in diabetes research. Br J Pharmacol. 2012 June; 166(3): 877-894. There are models for chemically-induced T1D, pathogen-induced T1D, as well as models in which the mice spontaneously develop T1D.

*Lactococcus lactis cremoris* Strain A-containing bacterial compositions and/or EVs derived from *Lactococcus lactis cremoris* Strain A are tested for their efficacy in a mouse model of T1D, either alone or in combination with whole bacterial cells, with or without the addition of other anti-inflammatory treatments.

Depending on the method of T1D induction and/or whether T1D development is spontaneous, treatment with *Lactococcus lactis cremoris* strain A and/or EVs derived from *Lactococcus lactis cremoris* Strain A is initiated at some point, either around the time of induction or following induction, or prior to the onset (or upon the onset) of spontaneously-occurring T1D. *Lactococcus lactis cremoris* strain A and/or EVs derived from *Lactococcus lactis cremoris* Strain A is administered at varied doses and at defined intervals. For example, some mice are intravenously injected with *Lactococcus lactis cremoris* strain A at a dose of between $1 \times 10^4$ and $5 \times 10^9$ bacterial cells per mouse. Other mice may receive 25, 50, or 100 mg of *Lactococcus lactis cremoris* strain A and/or EVs derived from *Lactococcus lactis cremoris* Strain A per mouse. While some mice will receive *Lactococcus lactis cremoris* strain A and/or EVs derived from *Lactococcus lactis cremoris* Strain A through i.v. injection, other mice may receive *Lactococcus lactis cremoris* strain A through intraperitoneal (i.p.) injection, subcutaneous (s.c.) injection, nasal route administration, oral gavage, or other means of administration. Some mice may receive *Lactococcus lactis cremoris* strain A and/or EVs derived from *Lactococcus lactis cremoris* Strain A every day, while others may receive *Lactococcus lactis cremoris* strain A at alternative intervals (e.g. every other day, or once every three days). Additional groups of mice may receive some ratio of bacterial cells to *Lactococcus lactis cremoris* strain A and/or EVs derived from *Lactococcus lactis cremoris* Strain A. The bacterial cells may be live, dead, or weakened. The bacterial cells may be harvested fresh (or frozen) and administered, or they may be irradiated or heat-killed prior to administration.

For example, some groups of mice may receive between $1 \times 10^4$ and $5 \times 10^9$ bacterial cells in an administration separate from, or comingled with, the *Lactococcus lactis cremoris* strain A and/or EVs derived from *Lactococcus lactis cremoris* Strain A administration. As with the *Lactococcus lactis cremoris* strain A, bacterial cell administration may be varied by route of administration, dose, and schedule. This can include oral gavage, i.v. injection, i.p. injection, or nasal route administration.

Some groups of mice may be treated with additional treatments and/or an appropriate control (e.g. vehicle or control antibody) at various time points and at effective doses.

In addition, some mice are treated with antibiotics prior to treatment. For example, vancomycin (0.5 g/L), ampicillin (1.0 g/L), gentamicin (1.0 g/L) and amphotericin B (0.2 g/L) are added to the drinking water, and antibiotic treatment is halted at the time of treatment or a few days prior to treatment. Some immunized mice are treated without receiving antibiotics.

Blood glucose is monitored biweekly prior to the start of the experiment. At various time points thereafter, nonfasting blood glucose is measured. At various time points, mice are sacrificed and site the pancreas, lymph nodes, or other tissues may be removed for ex vivo histological, cytokine and/or flow cytometric analysis using methods known in the art. For example, tissues are dissociated using dissociation enzymes according to the manufacturer's instructions. Cells are stained for analysis by flow cytometry using techniques known in the art. Staining antibodies can include anti-CD11c (dendritic cells), anti-CD80, anti-CD86, anti-CD40, anti-CD8a, anti-CD4, and anti-CD103. Other markers that may be analyzed include pan-immune cell marker CD45, T cell markers (CD3, CD4, CD8, CD25, Foxp3, T-bet, Gata3, Roryt, Granzyme B, CD69, PD-1, CTLA-4), and macrophage/myeloid markers (CD11b, MHCII, CD206, CD40, CSF1R, PD-L1, Gr-1, F4/80). In addition to immunophenotyping, serum cytokines are analyzed including, but not limited to, TNFa, IL-17, IL-13, IL-12p70, IL12p40, IL-10, IL-6, IL-5, IL-4, IL-2, IL-1b, IFNy, GM-CSF, G-CSF, M-CSF, MIG, IP10, MIP1b, RANTES, and MCP-1. Cytokine analysis may be carried out on immune cells obtained from lymph nodes or other tissue, and/or on purified tissue-infiltrating immune cells obtained ex vivo. Finally, immunohistochemistry is carried out on various tissue sections to measure T cells, macrophages, dendritic cells, and checkpoint molecule protein expression. Antibody production may also be assessed by ELISA.

In order to examine the impact and longevity of disease protection, rather than being sacrificed, some mice may be rechallenged with a disease trigger, or assessed for susceptibility to relapse. Mice will be analyzed for susceptibility to diabetes onset and severity following rechallenge (or spontaneously-occurring relapse).

Example 6: *Lactococcus lactis cremoris* Strain A and/or EVs Derived from *Lactococcus lactis cremoris* Strain A in a Mouse Model of Primary Sclerosing Cholangitis (PSC)

Primary Sclerosing Cholangitis (PSC) is a chronic liver disease that slowly damages the bile ducts and leads to end-stage cirrhosis. It is associated with inflammatory bowel disease (IBD).

There are various animal models for PSC, as reviewed by Fickert et al. (Characterization of animal models for primary sclerosing cholangitis (PSC). J Hepatol. 2014 June 60(6): 1290-1303; see also Pollheimer and Fickert. Animal models in primary biliary cirrhosis and primary sclerosing cholangitis. Clin Rev Allergy Immunol. 2015 June 48(2-3): 207-17). Induction of disease in PSC models includes chemical induction (e.g. 3,5-diethoxycarbonyl-1,4-dihydrocollidine (DDC)-induced cholangitis), pathogen-induced (e.g. *Cryptosporidium parvum*), experimental biliary obstruction (e.g. common bile duct ligation (CBDL)), and transgenic mouse model of antigen-driven biliary injury (e.g. Ova-Bil transgenic mice). For example, bile duct ligation is performed as described by Georgiev et al. (Characterization of time-related changes after experimental bile duct ligation. Br J Surg. 2008, 95(5): 646-56), or disease is induced by DCC exposure as described by Fickert et al. (A new xenobiotic-induced mouse model of sclerosing cholangitis and biliary fibrosis. Am J Path. Vol 171(2): 525-536.

*Lactococcus lactis cremoris* Strain A-containing bacterial compositions and/or EVs derived from *Lactococcus lactis cremoris* Strain A are tested for their efficacy in a mouse model of PSC, either alone or in combination with whole bacterial cells, with or without the addition of some other therapeutic agent.

DCC-Induced Cholangitis

For example, 6-8 week old C57bl/6 mice are obtained from Taconic or other vendor. Mice are fed a 0.1% DCC-supplemented diet for various durations. Some groups will receive DCC-supplement food for 1 week, others for 4 weeks, others for 8 weeks. Some groups of mice may receive a DCC-supplemented diet for a length of time and then be allowed to recover, thereafter receiving a normal diet. These mice may be studied for their ability to recover from disease and/or their susceptibility to relapse upon subsequent exposure to DCC. Treatment with *Lactococcus lactis cremoris* strain A and/or EVs derived from *Lactococcus lactis cremoris* Strain A is initiated at some point, either around the time of DCC-feeding or subsequent to initial exposure to DCC. For example, *Lactococcus lactis cremoris* strain A and/or EVs derived from *Lactococcus lactis cremoris* Strain A may be administered on day 1, or they may be administered sometime thereafter. *Lactococcus lactis cremoris* strain A and/or EVs derived from *Lactococcus lactis cremoris* Strain A is administered at varied doses and at defined intervals. For example, some mice are intravenously injected with *Lactococcus lactis cremoris* strain A at a range between $1 \times 10^4$ and $5 \times 10^9$ bacterial cells per mouse. Other mice may receive 25, 50, 100 mg of *Lactococcus lactis cremoris* strain A per mouse. While some mice will receive *Lactococcus lactis cremoris* strain A and/or EVs derived from *Lactococcus lactis cremoris* Strain A through i.v. injection, other mice may receive *Lactococcus lactis cremoris* strain A through i.p. injection, subcutaneous (s.c.) injection, nasal route administration, oral gavage, or other means of administration. Some mice may receive *Lactococcus lactis cremoris* strain A and/or EVs derived from *Lactococcus lactis cremoris* Strain A every day (e.g. starting on day 1), while others may receive *Lactococcus lactis cremoris* strain A and/or EVs derived from *Lactococcus lactis cremoris* Strain A at alternative intervals (e.g. every other day, or once every three days). Additional groups of mice may receive some ratio of bacterial cells to *Lactococcus lactis cremoris* strain A and/or EVs derived from *Lactococcus lactis cremoris* Strain A. The bacterial cells may be live, dead, or weakened. The bacterial cells may be harvested fresh (or frozen), and administered, or they may be irradiated or heat-killed prior to administration. For example, some groups of mice may receive between $1 \times 10^4$ and $5 \times 10^9$ bacterial cells in an administration separate from, or comingled with, the *Lactococcus lactis cremoris* strain A and/or EVs derived from *Lactococcus lactis cremoris* Strain A administration. As with *Lactococcus lactis cremoris* strain A and/or EVs derived from *Lactococcus lactis cremoris* Strain A, bacterial cell administration may be varied by route of administration, dose, and schedule. This can include oral gavage, i.v. injection, i.p. injection, or nasal route administration. Some groups of mice may be treated with additional agents and/or an appropriate control (e.g. vehicle or antibody) at various time points and at effective doses.

In addition, some mice are treated with antibiotics prior to treatment. For example, vancomycin (0.5 g/L), ampicillin (1.0 g/L), gentamicin (1.0 g/L) and amphotericin B (0.2 g/L) are added to the drinking water, and antibiotic treatment is halted at the time of treatment or a few days prior to treatment. Some immunized mice are treated without receiving antibiotics. At various time points, serum samples are analyzed for ALT, AP, bilirubin, and serum bile acid (BA) levels.

At various time points, mice are sacrificed, body and liver weight are recorded, and sites of inflammation (e.g. liver, small and large intestine, spleen), lymph nodes, or other tissues may be removed for ex vivo histolomorphological characterization, cytokine and/or flow cytometric analysis using methods known in the art (see Fickert et al. Characterization of animal models for primary sclerosing cholangitis (PSC)). J Hepatol. 2014, 60(6): 1290-1303). For example, bile ducts are stained for expression of ICAM-1, VCAM-1, MadCAM-1. Some tissues are stained for histological examination, while others are dissociated using dissociation enzymes according to the manufacturer's instructions. Cells are stained for analysis by flow cytometry using techniques known in the art. Staining antibodies can include anti-CD11c (dendritic cells), anti-CD80, anti-CD86, anti-CD40, anti-MHCII, anti-CD8a, anti-CD4, and anti-CD103. Other markers that may be analyzed include pan-immune cell marker CD45, T cell markers (CD3, CD4, CD8, CD25, Foxp3, T-bet, Gata3, Roryt, Granzyme B, CD69, PD-1, CTLA-4), and macrophage/myeloid markers (CD11b, MHCII, CD206, CD40, CSF1R, PD-L1, Gr-1, F4/80), as well as adhesion molecule expression (ICAM-1, VCAM-1, MadCAM-1). In addition to immunophenotyping, serum cytokines are analyzed including, but not limited to, TNFa, IL-17, IL-13, IL-12p70, IL12p40, IL-10, IL-6, IL-5, IL-4, IL-2, IL-1b, IFNy, GM-CSF, G-CSF, M-CSF, MIG, IP10, MIP1b, RANTES, and MCP-1. Cytokine analysis may be carried out on immune cells obtained from lymph nodes or other tissue, and/or on purified CD45+ bile duct-infiltrated immune cells obtained ex vivo.

Liver tissue is prepared for histological analysis, for example, using Sirius-red staining followed by quantification of the fibrotic area. At the end of the treatment, blood is collected for plasma analysis of liver enzymes, for example, AST or ALT, and to determine Bilirubin levels. The hepatic content of Hydroxyproline can be measured using established protocols. Hepatic gene expression analysis of inflammation and fibrosis markers may be performed by qRT-PCR using validated primers. These markers may include, but are not limited to, MCP-1, alpha-SMA, Col11a1, and TIMP-. Metabolite measurements may be performed in plasma, tissue and fecal samples using established metabolomics methods. Finally, immunohistochemistry is carried out on liver sections to measure neutrophils, T cells, macrophages, dendritic cells, or other immune cell infiltrates.

In order to examine the impact and longevity of disease protection, rather than being sacrificed, some mice may be rechallenged with DCC at a later time. Mice will be analyzed for susceptibility to cholangitis and cholangitis severity following rechallenge.

BDL-Induced Cholangitis

Alternatively, *Lactococcus lactis cremoris* Strain A-containing bacterial compositions and/or EVs derived from *Lactococcus lactis cremoris* Strain A are tested for their efficacy in BDL-induced cholangitis. For example, 6-8 week old C57Bl/6J mice are obtained from Taconic or other vendor. After an acclimation period the mice are subjected to a surgical procedure to perform a bile duct ligation (BDL). Some control animals receive a sham surgery. The BDL procedure leads to liver injury, inflammation and fibrosis within 7-21 days.

Treatment with *Lactococcus lactis cremoris* strain A and/or EVs derived from *Lactococcus lactis cremoris* Strain A is initiated at some point, either around the time of surgery or some time following the surgery. *Lactococcus lactis cremoris* strain A and/or EVs derived from *Lactococcus lactis cremoris* Strain A is administered at varied doses and at defined intervals. For example, some mice are intravenously injected with *Lactococcus lactis cremoris* strain A at a range between $1\times10^4$ and $5\times10^9$ bacterial cells per mouse. Other mice may receive 25, 50, or 100 mg of *Lactococcus lactis cremoris* strain A per mouse. While some mice will receive *Lactococcus lactis cremoris* strain A and/or EVs derived from *Lactococcus lactis cremoris* Strain A through i.v. injection, other mice may receive *Lactococcus lactis cremoris* strain A and/or EVs derived from *Lactococcus lactis cremoris* Strain A through i.p. injection, subcutaneous (s.c.) injection, nasal route administration, oral gavage, or other means of administration. Some mice receive *Lactococcus lactis cremoris* strain A and/or EVs derived from *Lactococcus lactis cremoris* Strain A every day (e.g. starting on day 1), while others may receive *Lactococcus lactis cremoris* strain A and/or EVs derived from *Lactococcus lactis cremoris* Strain A at alternative intervals (e.g. every other day, or once every three days). Additional groups of mice may receive some ratio of bacterial cells to *Lactococcus lactis cremoris* strain A and/or EVs derived from *Lactococcus lactis cremoris* Strain A. The bacterial cells may be live, dead, or weakened. They bacterial cells may be harvested fresh (or frozen), and administered, or they may be irradiated or heat-killed prior to administration. For example, some groups of mice may receive between $1\times10^4$ and $5\times10^9$ bacterial cells in an administration separate from, or comingled with, the *Lactococcus lactis cremoris* strain A and/or EVs derived from *Lactococcus lactis cremoris* Strain A administration. As with *Lactococcus lactis cremoris* strain A and/or EVs derived from *Lactococcus lactis cremoris* Strain A, bacterial cell administration may be varied by route of administration, dose, and schedule. This can include oral gavage, i.v. injection, i.p. injection, or nasal route administration. Some groups of mice may be treated with additional agents and/or an appropriate control (e.g. vehicle or antibody) at various time points and at effective doses.

In addition, some mice are treated with antibiotics prior to treatment. For example, vancomycin (0.5 g/L), ampicillin (1.0 g/L), gentamicin (1.0 g/L) and amphotericin B (0.2 g/L) are added to the drinking water, and antibiotic treatment is halted at the time of treatment or a few days prior to treatment. Some immunized mice are treated without receiving antibiotics. At various time points, serum samples are analyzed for ALT, AP, bilirubin, and serum bile acid (BA) levels.

At various time points, mice are sacrificed, body and liver weight are recorded, and sites of inflammation (e.g. liver, small and large intestine, spleen), lymph nodes, or other tissues may be removed for ex vivo histolomorphological characterization, cytokine and/or flow cytometric analysis using methods known in the art (see Fickert et al. Characterization of animal models for primary sclerosing cholangitis (PSC)). J Hepatol. 2014, 60(6): 1290-1303). For example, bile ducts are stained for expression of ICAM-1, VCAM-1, MadCAM-1. Some tissues are stained for histological examination, while others are dissociated using dissociation enzymes according to the manufacturer's instructions. Cells are stained for analysis by flow cytometry using techniques known in the art. Staining antibodies can include anti-CD11c (dendritic cells), anti-CD80, anti-CD86, anti-CD40, anti-MHCII, anti-CD8a, anti-CD4, and anti-CD103. Other markers that may be analyzed include pan-immune cell marker CD45, T cell markers (CD3, CD4, CD8, CD25, Foxp3, T-bet, Gata3, Rorγt, Granzyme B, CD69, PD-1, CTLA-4), and macrophage/myeloid markers (CD11b, MHCII, CD206, CD40, CSF1R, PD-L1, Gr-1, F4/80), as well as adhesion molecule expression (ICAM-1, VCAM-1, MadCAM-1). In addition to immunophenotyping, serum cytokines are analyzed including, but not limited to, TNFa, IL-17, IL-13, IL-12p70, IL12p40, IL-10, IL-6, IL-5, IL-4, IL-2, IL-1b, IFNy, GM-CSF, G-CSF, M-CSF, MIG, IP10, MIP1b, RANTES, and MCP-1. Cytokine analysis may be carried out on immune cells obtained from lymph nodes or other tissue, and/or on purified CD45+ bile duct-infiltrated immune cells obtained ex vivo.

Liver tissue is prepared for histological analysis, for example, using Sirius-red staining followed by quantification of the fibrotic area. At the end of the treatment, blood is collected for plasma analysis of liver enzymes, for example, AST or ALT, and to determine Bilirubin levels. The hepatic content of Hydroxyproline can be measured using established protocols. Hepatic gene expression analysis of inflammation and fibrosis markers may be performed by qRT-PCR using validated primers. These markers may include, but are not limited to, MCP-1, alpha-SMA, Coll1a1, and TIMP-. Metabolite measurements may be performed in plasma, tissue and fecal samples using established metabolomics methods. Finally, immunohistochemistry is carried out on liver sections to measure neutrophils, T cells, macrophages, dendritic cells, or other immune cell infiltrates.

In order to examine the impact and longevity of disease protection, rather than being sacrificed, some mice may be analyzed for recovery.

Example 7: *Lactococcus lactis cremoris* Strain A and/or EVs Derived from *Lactococcus lactis cremoris* Strain A in a Mouse Model of Nonalcoholic Steatohepatitis (NASH)

Nonalcoholic Steatohepattiis (NASH) is a severe form of Nonalcoholic Fatty Liver Disease (NAFLD), where buildup of hepatic fat (steatosis) and inflammation lead to liver injury and hepatocyte cell death (ballooning).

There are various animal models of NASH, as reviewed by Ibrahim et al. (Animal models of nonalcoholic steatohepatitis: Eat, Delete, and Inflame. Dig Dis Sci. 2016 May. 61(5): 1325-1336; see also Lau et al. Animal models of non-alcoholic fatty liver disease: current perspectives and recent advances 2017 January 241(1): 36-44).

*Lactococcus lactis cremoris* Strain A-containing bacterial compositions are tested for their efficacy in a mouse model of NASH, either alone or in combination with whole bacterial cells, with or without the addition of another therapeutic agent. For example, 8-10 week old C57Bl/6J mice, obtained from Taconic (Germantown, N.Y.), or other vendor, are placed on a methionine choline deficient (MCD) diet for a period of 4-8 weeks during which NASH features will develop, including steatosis, inflammation, ballooning and fibrosis.

Treatment with *Lactococcus lactis cremoris* strain A and/or EVs derived from *Lactococcus lactis cremoris* Strain A is initiated at some point, either at the beginning of the diet, or at some point following diet initiation (for example, one week after). For example, *Lactococcus lactis cremoris* strain A and/or EVs derived from *Lactococcus lactis cremoris* Strain A may be administered starting in the same day as the initiation of the MCD diet. *Lactococcus lactis cremoris* strain A and/or EVs derived from *Lactococcus lactis cremoris* Strain A is administered at varied doses and at defined intervals. For example, some mice are intravenously injected with *Lactococcus lactis cremoris* strain A at doses between $1\times10^4$ and $5\times10^9$ bacterial cells per mouse. Other mice may receive 25, 50, or 100 mg of *Lactococcus lactis cremoris* strain A and/or EVs derived from *Lactococcus lactis cremoris* Strain A per mouse. While some mice will receive *Lactococcus lactis cremoris* strain A and/or EVs derived from *Lactococcus lactis cremoris* Strain A through i.v. injection, other mice may receive *Lactococcus lactis cremoris* strain A and/or EVs derived from *Lactococcus lactis cremoris* Strain A through intraperitoneal (i.p.) injection, subcutaneous (s.c.) injection, nasal route administration, oral gavage, or other means of administration. Some mice may receive *Lactococcus lactis cremoris* strain A and/or EVs derived from *Lactococcus lactis cremoris* Strain A every day (e.g. starting on day 1), while others may receive *Lactococcus lactis cremoris* strain A and/or EVs derived from *Lactococcus lactis cremoris* Strain A at alternative intervals (e.g. every other day, or once every three days). Additional groups of mice may receive some ratio of bacterial cells to *Lactococcus lactis cremoris* strain A and/or EVs derived from *Lactococcus lactis cremoris* Strain A. The bacterial cells may be live, dead, or weakened. The bacterial cells may be harvested fresh (or frozen) and administered, or they may be irradiated or heat-killed prior to administration.

For example, some groups of mice may receive between $1\times10^4$ and $5\times10^9$ bacterial cells in an administration separate from, or comingled with, the *Lactococcus lactis cremoris* strain A and/or EVs derived from *Lactococcus lactis cremoris* Strain A administration. As with the *Lactococcus lactis cremoris* strain A and/or EVs derived from *Lactococcus lactis cremoris* Strain A, bacterial cell administration may be varied by route of administration, dose, and schedule. This can include oral gavage, i.v. injection, i.p. injection, or nasal route administration. Some groups of mice may be treated with additional NASH therapeutic(s) (e.g., FXR agonists, PPAR agonists, CCR2/5 antagonists or other treatment) and/or appropriate control at various time points and effective doses.

At various time points and/or at the end of the treatment, mice are sacrificed and liver, intestine, blood, feces, or other tissues may be removed for ex vivo histological, biochemical, molecular or cytokine and/or flow cytometry analysis using methods known in the art. For example, liver tissues are weighed and prepared for histological analysis, which may comprise staining with H&E, Sirius Red, and determination of NASH activity score (NAS). At various time points, blood is collected for plasma analysis of liver enzymes, for example, AST or ALT, using standards assays. In addition, the hepatic content of cholesterol, triglycerides, or fatty acid acids can be measured using established protocols. Hepatic gene expression analysis of inflammation, fibrosis, steatosis, ER stress, or oxidative stress markers may be performed by qRT-PCR using validated primers. These markers may include, but are not limited to, IL-6, MCP-1, alpha-SMA, Coll1a1, CHOP, and NRF2. Metabolite measurements may be performed in plasma, tissue and fecal samples using established biochemical and mass-spectrometry-based metabolomics methods. Serum cytokines are analyzed including, but not limited to, TNFa, IL-17, IL-13, IL-12p70, IL12p40, IL-10, IL-6, IL-5, IL-4, IL-2, IL-1b, IFNy, GM-CSF, G-CSF, M-CSF, MIG, IP10, MIP1b, RANTES, and MCP-1. Cytokine analysis may be carried out on immune cells obtained from lymph nodes or other tissue, and/or on purified CD45+ bile duct-infiltrated immune cells obtained ex vivo. Finally, immunohistochemistry is carried out on liver or intestine sections to measure neutrophils, T cells, macrophages, dendritic cells, or other immune cell infiltrates.

In order to examine the impact and longevity of disease protection, rather than being sacrificed, some mice may be analyzed for recovery.

Example 8: *Lactococcus lactis cremoris* Strain A and/or EVs Derived from *Lactococcus lactis cremoris* Strain A in a Mouse Model of Psoriasis Psoriasis is a T-cell-mediated chronic inflammatory skin disease. So-called "plaque-type" psoriasis is the most common form of psoriasis and is typified by dry scales, red plaques, and thickening of the skin due to infiltration of immune cells into the dermis and epidermis. Several animal models have contributed to the understanding of this disease, as reviewed by Gudjonsson et al. (Mouse models of psoriasis. J Invest Derm. 2007, 127: 1292-1308; see also van der Fits et al. Imiquimod-induced psoriasis-like skin inflammation in mice is mediated via the IL-23/IL-17 axis. J. Immunol. 2009 May 1, 182(9): 5836-45).

Psoriasis can be induced in a variety of mouse models, including those that use transgenic, knockout, or xenograft models, as well as topical application of imiquimod (IMQ), a TLR7/8 ligand.

*Lactococcus lactis cremoris* Strain A-containing bacterial compositions and/or EVs derived from *Lactococcus lactis cremoris* Strain A are tested for their efficacy in the mouse model of psoriasis, either alone or in combination with whole bacterial cells, with or without the addition of other anti-inflammatory treatments. For example, 6-8 week old C57Bl/6 or Balb/c mice are obtained from Taconic (Germantown, N.Y.), or other vendor. Mice are shaved on the back and the right ear. Groups of mice receive a daily topical dose of 62.5 mg of commercially available IMQ cream (5%) (Aldara; 3M Pharmaceuticals). The dose is applied to the shaved areas for 5 or 6 consecutive days. At regular intervals, mice are scored for erythema, scaling, and thickening on a scale from 0 to 4, as described by van der Fits et al. (2009). Mice are monitored for ear thickness using a Mitutoyo micrometer.

Treatment with *Lactococcus lactis cremoris* strain A and/or EVs derived from *Lactococcus lactis cremoris* Strain A is initiated at some point, either around the time of the first application of IMQ, or something thereafter. For example, *Lactococcus lactis cremoris* strain A and/or EVs derived from *Lactococcus lactis cremoris* Strain A may be administered at the same time as the subcutaneous injections (day 0), or they may be administered prior to, or upon, application. *Lactococcus lactis cremoris* strain A and/or EVs derived from *Lactococcus lactis cremoris* Strain A is administered at varied doses and at defined intervals. For example, some mice are intravenously injected with *Lactococcus lactis cremoris* strain A at a dose of between $1\times10^4$ and $5\times10^9$ bacterial cells per mouse. Other mice may receive 25, 50, or 100 mg of *Lactococcus lactis cremoris* strain A per mouse. While some mice will receive *Lactococcus lactis* cremoris strain A and/or EVs derived from *Lactococcus lactis cremoris* Strain A through i.v. injection, other mice may receive *Lactococcus lactis cremoris* strain A and/or EVs derived from *Lactococcus lactis cremoris* Strain A through intraperitoneal (i.p.) injection, nasal route administration, oral gavage, topical administration, intradermal (i.d.) injection, subcutaneous (s.c.) injection, or other means of administration. Some mice may receive *Lactococcus lactis cremoris* strain A and/or EVs derived from *Lactococcus lactis cremoris* Strain A every day (e.g. starting on day 0), while others may receive *Lactococcus lactis cremoris* strain A and/or EVs derived from *Lactococcus lactis cremoris* Strain A at alternative intervals (e.g. every other day, or once every three days). Additional groups of mice may receive some ratio of bacterial cells to *Lactococcus lactis cremoris* strain A and/or EVs derived from *Lactococcus lactis cremoris* Strain A. The bacterial cells may be live, dead, or weakened. The bacterial cells may be harvested fresh (or frozen) and administered, or they may be irradiated or heat-killed prior to administration.

For example, some groups of mice may receive between $1 \times 10^4$ and $5 \times 10^9$ bacterial cells in an administration separate from, or comingled with, the *Lactococcus lactis cremoris* strain A and/or EVs derived from *Lactococcus lactis cremoris* Strain A administration. As with the *Lactococcus lactis cremoris* strain A and/or EVs derived from *Lactococcus lactis cremoris* Strain A, bacterial cell administration may be varied by route of administration, dose, and schedule. This can include oral gavage, i.v. injection, i.p. injection, i.d. injection, s.c. injection, topical administration, or nasal route administration.

Some groups of mice may be treated with anti-inflammatory agent(s) (e.g. anti-CD154, blockade of members of the TNF family, or other treatment), and/or an appropriate control (e.g. vehicle or control antibody) at various time points and at effective doses.

In addition, some mice are treated with antibiotics prior to treatment. For example, vancomycin (0.5 g/L), ampicillin (1.0 g/L), gentamicin (1.0 g/L) and amphotericin B (0.2 g/L) are added to the drinking water, and antibiotic treatment is halted at the time of treatment or a few days prior to treatment. Some immunized mice are treated without receiving antibiotics.

At various time points, samples from back and ear skin are taken for cryosection staining analysis using methods known in the art. Other groups of mice are sacrificed and lymph nodes, spleen, mesenteric lymph nodes (MLN), the small intestine, colon, and other tissues may be removed for histology studies, ex vivo histological, cytokine and/or flow cytometric analysis using methods known in the art. Some tissues may be dissociated using dissociation enzymes according to the manufacturer's instructions. Cryosection samples, tissue samples, or cells obtained ex vivo are stained for analysis by flow cytometry using techniques known in the art. Staining antibodies can include anti-CD11c (dendritic cells), anti-CD80, anti-CD86, anti-CD40, anti-CD8a, anti-CD4, and anti-CD103. Other markers that may be analyzed include pan-immune cell marker CD45, T cell markers (CD3, CD4, CD8, CD25, Foxp3, T-bet, Gata3, Roryt, Granzyme B, CD69, PD-1, CTLA-4), and macrophage/myeloid markers (CD11b, CD206, CD40, CSF1R, PD-L1, Gr-1, F4/80). In addition to immunophenotyping, serum cytokines are analyzed including, but not limited to, TNFa, IL-17, IL-13, IL-12p70, IL12p40, IL-10, IL-6, IL-5, IL-4, IL-2, IL-1b, IFNy, GM-CSF, G-CSF, M-CSF, MIG, IP10, MIP1b, RANTES, and MCP-1. Cytokine analysis may be carried out on immune cells obtained from lymph nodes or other tissue, and/or on purified CD45+ skin-infiltrated immune cells obtained ex vivo. Finally, immunohistochemistry is carried out on various tissue sections to measure T cells, macrophages, dendritic cells, and checkpoint molecule protein expression.

In order to examine the impact and longevity of psoriasis protection, rather than being sacrificed, some mice may be studied to assess recovery, or they may be rechallenged with IMQ. The groups of rechallenged mice will be analyzed for susceptibility to psoriasis and severity of response.

Example 9: A Study of the Safety, Tolerability and Efficacy of *Lactococcus lactis cremoris* Strain A as an Oral Therapeutic for the Treatment of Mild to Moderate Psoriasis or Atopic Dermatitis A single-center, Phase 1 clinical study in performed in which preliminary safety, tolerability, and pharmacodynamic effect of *Lactococcus lactis cremoris* strain A is determined in healthy participants and participants with mild to moderate psoriasis or atopic dermatitis, but who are otherwise well.

This is a randomized, placebo-controlled clinical study with dose escalations and dose expansions to assess preliminary safety, tolerability, and pharmacodynamic effect of *Lactococcus lactis cremoris* strain A, and is participant and investigator blind, sponsor unblinded, with single and multiple ascending doses. This investigation provides an opportunity to gain pharmacodynamic information using a range of tissue biopsies and composite clinical endpoints.

The study consists of six (6) cohorts and will test doses of *Lactococcus lactis cremoris* strain A versus placebo. The initial three (3) cohorts are in healthy volunteers and will establish the safety and tolerability of *Lactococcus lactis cremoris* strain A. Once this has been established, the safety and tolerability in participants with psoriasis or atopic dermatitis will be tested, alongside pharmacodynamic effects on the systemic immune system and observation of any clinical effects.

The treatment arms are described in Table 7, and optional additional cohorts may be added to include dose expansion studies.

TABLE 7

Arms and Interventions

| Cohort | Arms | Assigned Interventions |
|---|---|---|
| 1 | 12 healthy volunteers: 8 on *Lactococcus lactis cremoris* strain A, 4 on placebo Dose = 66 mg capsule, once daily for 15 days | *Lactococcus lactis cremoris* strain A is orally administered Drug: placebo oral capsule |
| 2 | 12 healthy volunteers: 8 on *Lactococcus lactis cremoris* strain A, 4 on placebo Dose = 660 mg capsule, once daily for 15 days | *Lactococcus lactis cremoris* strain A is orally administered Drug: placebo oral capsule |
| 3 | 12 healthy volunteers: 8 on *Lactococcus lactis cremoris* strain A, 4 on placebo Dose = 3.3 g capsule, once daily for 15 days | *Lactococcus lactis cremoris* strain A is orally administered Drug: placebo oral capsule |
| 4 | 12 subjects with mild to moderate psoriasis: 8 on *Lactococcus lactis cremoris* strain A, 4 on placebo | *Lactococcus lactis cremoris* strain A is orally administered Drug: placebo oral capsule |

TABLE 7-continued

| Arms and Interventions | | |
|---|---|---|
| Cohort | Arms | Assigned Interventions |
| | Dose = 660 mg, capsule, once daily, 29 days | |
| 5 | 24 subjects with mild to moderate psoriasis: 16 on *Lactococcus lactis cremoris* strain A, 8 on placebo Dose = 3.3 g, capsule, once daily, 29 days | *Lactococcus lactis cremoris* strain A is orally administered Drug: placebo oral capsule |
| 6 | 24 subjects with mild to moderate atopic dermatitis: 16 on *Lactococcus lactis cremoris* strain A, 8 on placebo Dose = 3.3 g capsule, once daily, 29 days | *Lactococcus lactis cremoris* strain A is orally administered Drug: placebo oral capsule |

The study has at least three (3) outcome measures: 1) safety and tolerability; 2) clinical improvement in subjects with mild to moderate psoriasis; and 3) clinical improvement in subjects with mild to moderate atopic dermatitis.

For (1) Safety and tolerability, serious adverse events (SAE), lab measurements, electrocardiogram (ECG) measurements, vital sign measurements, physical examination, Bristol stool scale, markers of GI integrity, and immune biomarkers are conducted and assessed; for (2) Clinical improvement in subjects with mild to moderate psoriasis, psoriasis activity scoring index (PASI), investigators' global assessment (IGA), and lesion severity score (LSS) are assessed over a period of 14 months; and for (3) Clinical improvement in subjects with mild to moderate atopic dermatitis, EASI, severity scoring of atopic dermatitis (SCORAD), LSS, and IGA are assessed over a period of 14 months.

Anti-psoriasis and anti-atopic dermatitis activities are assessed by the Investigator according to disease specific response criteria and described in terms of objective response rate, duration of response, progression-free time-periods, clinical benefit rate, and disease control rate. Investigators will look for improvement from baseline at or around day 28 of dosing using the PASI and eczema activity scoring index (EAST), both of which are known in the art.

Inclusion and Exclusion Criteria:

The inclusion criteria for all parts of the study include the following:

1. Participant has a body mass index of ≥18 kg/m2 to ≤35 kg/m2 at screening.
2. Participants who are overtly healthy as determined by medical evaluation including medical history, physical examination, laboratory tests, and cardia monitoring.
3. For patients with mild to moderate psoriasis:
   a. Participant has had a confirmed diagnosis of mild to moderate plaque-type psoriasis for at least 6 months involving ≤5% of body surface area (BSA) (excluding the scalp).
   b. Participant has a minimum of 2 psoriatic lesions with at least 1 plaque in a site suitable for biopsy.
4. For patients with mild to moderate atopic dermatitis:
   a. Participant has mild to moderate atopic dermatitis with a minimum of 3 to a maximum of 15% BSA involvement.
   b. Participant has had a confirmed diagnosis of mild to moderate atopic dermatitis for at least 6 months with IGA score of 2 or 3.
   c. Participant has a minimum of 2 atopic dermatitis lesions with at least 1 in a site suitable for biopsy.

The following categories of patient are excluded from the study:

1. Female participant who is pregnant or plans to become pregnant during the study, and/or female participant who is breastfeeding or is sexually active with child-bearing potential who is not using a medically accepted birth control method.
2. Participant has received live attenuated vaccination within 6 weeks prior to screening or intends to have such a vaccination during the course of the study.
3. Participant has received any investigational drug or experimental procedure within 90 days or 5 half-lives, whichever is longer, prior to study intervention administration.
4. Participant requires treatment with an anti-inflammatory drug during the study period. Paracetamol will be permitted for use as an antipyretic and/or analgesic (maximum of 2 grams/day in any 24 hour period).
5. Participant has an active infection (e.g. sepsis, pneumonia, abscess) or has had an infection requiring antibiotic treatment within 6 weeks prior to investigational medicinal product (IMP) administration. When in doubt, the investigator should confer with the Sponsor study physician.
6. Participant has renal or liver impairment, defined as:
   a. For healthy volunteers: i. for women, serum creatinine level ≥125 μmol/L; for men, ≥135 μmol/L, or ii: Alanine aminotransferase (ALT) and aspartate aminotransferase (AST) ≥1.5× upper limit of normal (ULN), or iii. Alkaline phosphatase (ALP) and/or bilirubin >1.5×ULN.
   b. For participants with mild to moderate atopic dermatitis, or psoriasis: i. For women, serum creatinine level ≥125 μmol/L; for men ≥135 μmol/L, or ii. ALT or AST >2×ULN and/or bilirubin >1.5×ULN.

Dose Escalation Study

Patients receive all *Lactococcus lactis cremoris* strain A doses during the treatment period, or have had a dose-limiting toxicity (DLT) within the treatment period, may be considered evaluable for dose escalation decisions. Dose escalation decisions occur when the cohort of patients has met these criteria.

A DLT is defined as an adverse event (AE) or abnormal laboratory value that occurs within the first 7 days of treatment with *Lactococcus lactis cremoris* strain A, except for those that are clearly and incontrovertibly due to underlying disease, disease progression, or extraneous causes. Dose escalation decisions occur when the cohort of patients has met these criteria.

To implement dose escalation decisions, the available toxicity information (i.e., all AEs and all laboratory abnormalities regardless of DLT assessment) is evaluated by the enrolling Investigators and Sponsor medical monitor at a dose decision meeting or teleconference. Decisions are based on an evaluation of all relevant data available from all dose cohorts evaluated in the ongoing study. Drug administration at the next higher dose cohort may not proceed until the Investigator receives written confirmation from Sponsor indicating that the results of the previous dose cohort were evaluated and that it is permissible to proceed to the next higher dose cohort.

Intra-patient dose escalations are permitted for all cohorts after the intended dose level has been shown to be safe (i.e., all patients treated at the intended dose level completed DLT assessments and ≤1 patient experienced a DLT).

Example 10—Evaluation of Gene Deletion in *Lactococcus lactis cremoris* Strains in a KLH-Based Delayed Type Hypersensitivity Model The efficacy of *L. lactis cremoris* Strains that lacked certain plasmids was evaluated. Knockout strains were created using electroporation techniques known in the art. Briefly, electrocompetent cells were prepared by growing strain overnight in M17 media (5 g Pancreatic digest of casein, 5 g soy peptone, 5 g beef extract, 2.5 g yeast extract, 0.5 g ascorbic acid, 0.25 g MgSO4, 19 g Disodium-β-glycerophosphate per L) that included 1% glucose. 2 mL of overnight culture was inoculated with 50 mL of M17 media and allowed to grow to an optical density at 600 nm of 0.5-0.7 (about 5-7 hrs). The culture was then cooled on ice for 10 min. Cells were spun down for 15 min at 3000 g and resuspended in electroporation buffer (0.5M Sucrose+10% glycerol) which was repeated 2 more times. Cells were then resuspended in 5004, of electroporation buffer and separated into 1004, aliquots and stored at −80° C. until electroporation.

Electroporation proceeded by defrosting cells on ice prior to transfer to an electroporation cuvette. Cell were then electroporated at 1.2 kV for in *Lactococcus lactis cremoris* Strain A and 2.5 kV for in *Lactococcus lactis cremoris* Strain B. 9004, of recovery solution (M17+0.5M(0.17 g)Sucrose+0.5%(15 μl)Glucose+20 mM(10 μl)MgCl2+0.2 mM(10 μl)CaCl2 per mL) was then immediately added. The cells were then kept on ice for 10 min. Electroporated cells were subcultuted 1:10 in M17 media and incubated for 20 min at 30° C. before diluting and plating. Cells were then screened for plasmid loss by PCR.

Figure 4:
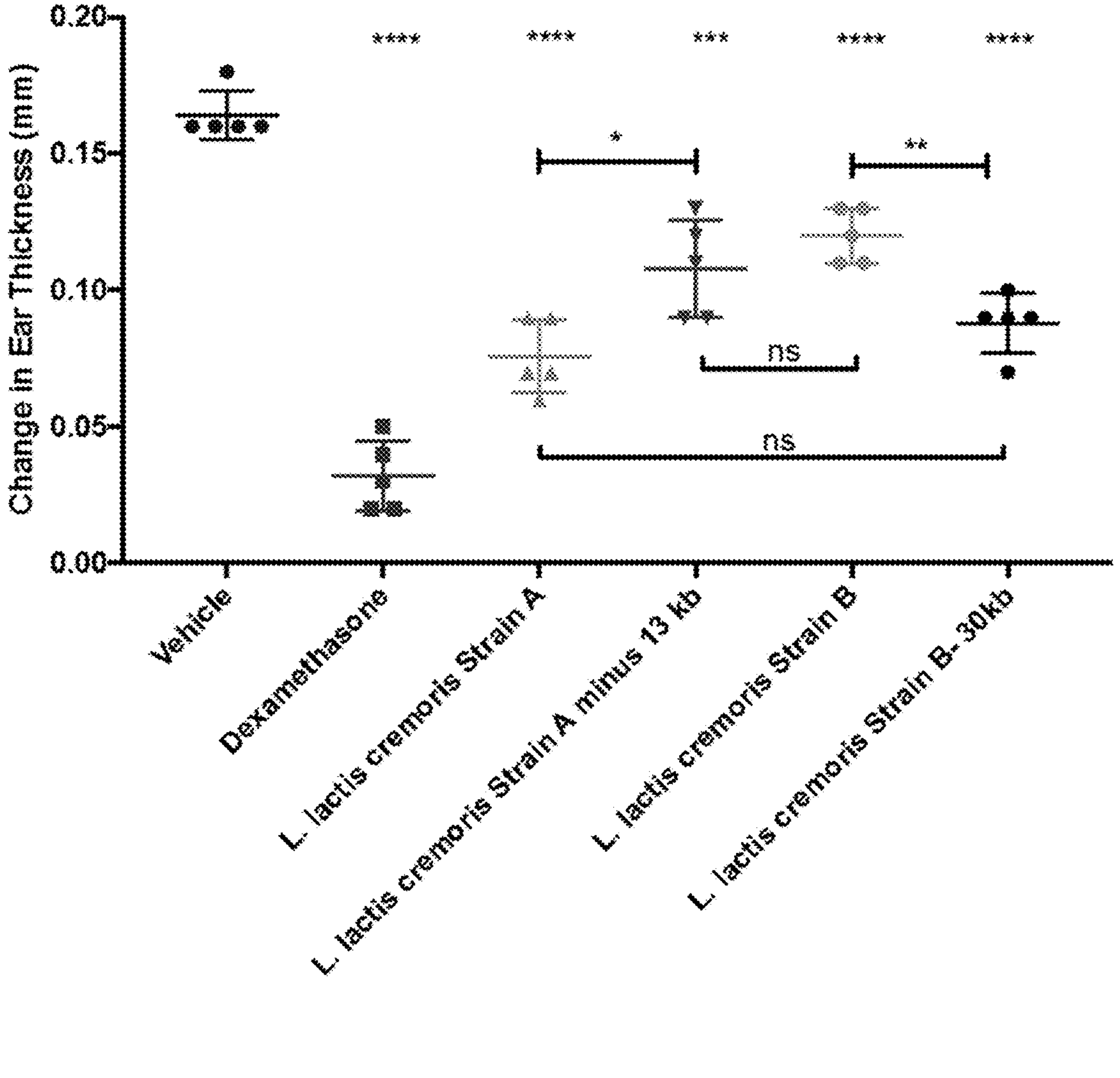
FIG. 4 is a plot showing the efficacy of *Lactococcus lactis cremoris* Strain A (with and without a 13 kb plasmid) and *Lactococcus lactis cremoris* Strain B (with and without a 30 kb plasmid) in reducing antigen-specific ear swelling (ear thickness) compared to vehicle and Dexamethasone in a KLH-based delayed type hypersensitivity mouse model. *Lactococcus lactis cremoris* Strain A without a 13 kb plasmid has reduced efficacy compared *Lactococcus lactis cremoris* Strain A with a 13 kb plasmid. Conversely, removal of a 30 kb plasmid from *L. lactis cremoris* Strain B enhances efficacy compared to *L. lactis cremoris* Strain B with the 30 kb plasmid.

To elucidate the effect of the strains without the plasmids, the *Lactococcus lactis cremoris* Strains A and B (both with and without plasmids) were evaluated in the mouse model of DTH. As noted above in Example 1, mice were injected with KLH and CFA i.d at 4 locations along the back (50 ug per mouse of KLH prepared in a 1:1 ratio with CFA in a total volume of 50 ul per site). Mice were dosed for 9 days with 1x10^9 viable cells per day as follows: 1) anaerobic PBS (vehicle); 2) *Lactococcus lactis cremoris* Strain A; 3) *Lactococcus lactis cremoris* Strain A minus a 13 kb plasmid; 4) *Lactococcus lactis cremoris* Strain B; 5) *Lactococcus lactis cremoris* Strains B minus a 30 kb plasmid; and 6) Dexamethasone (positive control). At 24 hours post-challenge, the removal of a 13 kb plasmid from *Lactococcus lactis cremoris* Strain A reduced the efficacy of the strain while the removal of a 30 kb plasmid from *Lactococcus lactis cremoris* Strain B improved the efficacy of the strain (FIG. 4).

The strains were then sequenced to determine the genes within the 13 kb plasmid from) *Lactococcus lactis cremoris* Strain A and the 30 kb plasmid from *Lactococcus lactis cremoris* Strain B. See Table 5 and Table 6.

Example 11: Manufacturing Conditions

Enriched media is used to grow and prepare the bacterium for in vitro and in vivo use. For example, media may contain sugar, yeast extracts, plant based peptones, buffers, salts, trace elements, surfactants, anti-foaming agents, and vitamins. Composition of complex components such as yeast extracts and peptones may be undefined or partially defined (including approximate concentrations of amino acids, sugars etc.). Microbial metabolism may be dependent on the availability of resources such as carbon and nitrogen. Various sugars or other carbon sources may be tested. Alternatively, media may be prepared and the selected bacterium grown as shown by Saarela et al., *J. Applied Microbiology.* 2005, 99: 1330-1339, which is hereby incorporated by reference. Influence of fermentation time, cryoprotectant and neutralization of cell concentrate on freeze-drying survival, storage stability, and acid and bile exposure of the selected bacterium produced without milk-based ingredients.

At large scale, the media is sterilized. Sterilization may be by Ultra High Temperature (UHT) processing. The UHT processing is performed at very high temperature for short periods of time. The UHT range may be from 135-180° C. For example, the medium may be sterilized from between 10 to 30 seconds at 135° C.

Inoculum can be prepared in flasks or in smaller bioreactors and growth is monitored. For example, the inoculum size may be between approximately 0.5 and 3% of the total bioreactor volume. Depending on the application and need for material, bioreactor volume can be at least 2 L, 10 L, 80 L, 100 L, 250 L, 1000 L, 2500 L, 5000 L, 10,000 L.

Before the inoculation, the bioreactor is prepared with medium at desired pH, temperature, and oxygen concentration. The initial pH of the culture medium may be different that the process set-point. pH stress may be detrimental at low cell centration; the initial pH could be between pH 7.5 and the process set-point. For example, pH may be set between 4.5 and 8.0. During the fermentation, the pH can be controlled through the use of sodium hydroxide, potassium hydroxide, or ammonium hydroxide. The temperature may be controlled from 25° C. to 45° C., for example at 37° C. Anaerobic conditions are created by reducing the level of oxygen in the culture broth from around 8 mg/L to 0 mg/L. For example, nitrogen or gas mixtures (N2, CO2, and H2) may be used in order to establish anaerobic conditions. Alternatively, no gases are used and anaerobic conditions are established by cells consuming remaining oxygen from the medium. Depending on strain and inoculum size, the bioreactor fermentation time can vary. For example, fermentation time can vary from approximately 5 hours to 48 hours.

Reviving microbes from a frozen state may require special considerations. Production medium may stress cells after a thaw; a specific thaw medium may be required to consistently start a seed train from thawed material. The kinetics of transfer or passage of seed material to fresh medium, for the purposes of increasing the seed volume or maintaining the microbial growth state, may be influenced by the current state of the microbes (ex. exponential growth, stationary growth, unstressed, stressed).

Inoculation of the production fermenter(s) can impact growth kinetics and cellular activity. The initial state of the bioreactor system must be optimized to facilitate successful and consistent production. The fraction of seed culture to total medium (e.g. a percentage) has a dramatic impact on growth kinetics. The range may be 1-5% of the fermenter's working volume. The initial pH of the culture medium may be different from the process set-point. pH stress may be detrimental at low cell concentration; the initial pH may be between pH 7.5 and the process set-point. Agitation and gas flow into the system during inoculation may be different from the process set-points. Physical and chemical stresses due to both conditions may be detrimental at low cell concentration.

Process conditions and control settings may influence the kinetics of microbial growth and cellular activity. Shifts in process conditions may change membrane composition, production of metabolites, growth rate, cellular stress, etc. Optimal temperature range for growth may vary with strain. The range may be 20-40° C. Optimal pH for cell growth and performance of downstream activity may vary with strain. The range may be pH 5-8. Gasses dissolved in the medium may be used by cells for metabolism. Adjusting concentrations of $O_2$, $CO_2$, and $N_2$ throughout the process may be required. Availability of nutrients may shift cellular growth. Microbes may have alternate kinetics when excess nutrients are available.

The state of microbes at the end of a fermentation and during harvesting may impact cell survival and activity. Microbes may be preconditioned shortly before harvest to better prepare them for the physical and chemical stresses involved in separation and downstream processing. A change in temperature (often reducing to 20-5° C.) may reduce cellular metabolism, slowing growth (and/or death) and physiological change when removed from the fermenter. Effectiveness of centrifugal concentration may be influenced by culture pH. Raising pH by 1-2 points can improve effectiveness of concentration but can also be detrimental to cells. Microbes may be stressed shortly before harvest by increasing the concentration of salts and/or sugars in the medium. Cells stressed in this way may better survive freezing and lyophilization during downstream.

Separation methods and technology may impact how efficiently microbes are separated from the culture medium. Solids may be removed using centrifugation techniques. Effectiveness of centrifugal concentration can be influenced by culture pH or by the use of flocculating agents. Raising pH by 1-2 points may improve effectiveness of concentration but can also be detrimental to cells. Microbes may be stressed shortly before harvest by increasing the concentration of salts and/or sugars in the medium. Cells stressed in this way may better survive freezing and lyophilization during downstream. Additionally, Microbes may also be separated via filtration. Filtration is superior to centrifugation techniques for purification if the cells require excessive g-minutes to successfully centrifuge. Excipients can be added before after separation. Excipients can be added for cryo protection or for protection during lyophilization. Excipients can include, but are not limited to, sucrose, trehalose, or lactose, and these may be alternatively mixed with buffer and anti-oxidants. Prior to lyophilization, droplets of cell pellets mixed with excipients are submerged in liquid nitrogen.

Harvesting can be performed by continuous centrifugation. Product may be resuspended with various excipients to a desired final concentration. Excipients can be added for cryo protection or for protection during lyophilization. Excipients can include, but are not limited to, sucrose, trehalose, or lactose, and these may be alternatively mixed with buffer and anti-oxidants. Prior to lyophilization, droplets of cell pellets mixed with excipients are submerged in liquid nitrogen.

Lyophilization of material, including live bacteria, begins with primary drying. During the primary drying phase, the ice is removed. Here, a vacuum is generated and an appropriate amount of heat is supplied to the material for the ice to sublime. During the secondary drying phase, product bound water molecules are removed. Here, the temperature is raised higher than in the primary drying phase to break any physico-chemical interactions that have formed between the water molecules and the product material. The pressure may also be lowered further to enhance desorption during this stage. After the freeze-drying process is complete, the chamber may be filled with an inert gas, such as nitrogen. The product may be sealed within the freeze dryer under dry conditions, preventing exposure to atmospheric water and contaminants.

Example 12: Adoptive Transfer Delayed-Type Hypersensitivity (AdDTH) Mouse Model Briefly, mice were purchased from Jackson Labs and allowed to acclimate in the vivarium for 1 week prior to start of experiment. Mice are housed 5 animals per cage, in individually ventilated cages with standard bedding and enrichment. Standard Purina rodent diet (5001) and autoclaved water is provided ad libitum and checked daily. Ventilated cages are changed once weekly. Animal housing rooms undergoes a lighting cycle consisting of 12 hours on and 12 hours off. Floors, walls, and ceilings are sanitized once a month and rooms maintain a humidity range between 30%-70%, and a temperature range between 68-79 degrees Fahrenheit. Animal health checks are done twice daily.

On day −1, recipient BALB/c mice were adoptively transferred with 1×10^8 D011. TCR Tg lymphocytes (i.p.).

On day 0, mice were anesthetized with isoflurane (one at a time) and their back was shaved. Mice were injected subcutaneously at 4 sites on the back with 50 μl of Ovalbumin in CFA emulsion (Hooke Labs catalog #EK-0301).

A dexamethasone stock solution (17 mg/ml) was created by resuspending 6.8 mg of dexamethasone in 400 μl of 96% ethanol. For each day of dosing, a working solution is prepared by diluting the stock solution 100× in sterile PBS to obtain a final concentration of 0.17 mg/mL in a septum vial for intraperitoneal dosing. Dexamethasone-treated mice received 100 μL Dexamethasone i.p. (5 mL/kg of a 0.17 mg/mL solution). Frozen sucrose served as the negative control (vehicle). *Lactococcus lactis cremoris* Strain A was dosed at 100 ul of bacterial cells at 1×10^10 CFU/ml daily. Dexamethasone (positive control), vehicle (negative control), and *Lactococcus lactis cremoris* Strain A were dosed daily.

On days 1-9 mice were orally gavaged (groups 1 and 3) or injected intraperitoneally (i.p. group 2).

Figure 5:
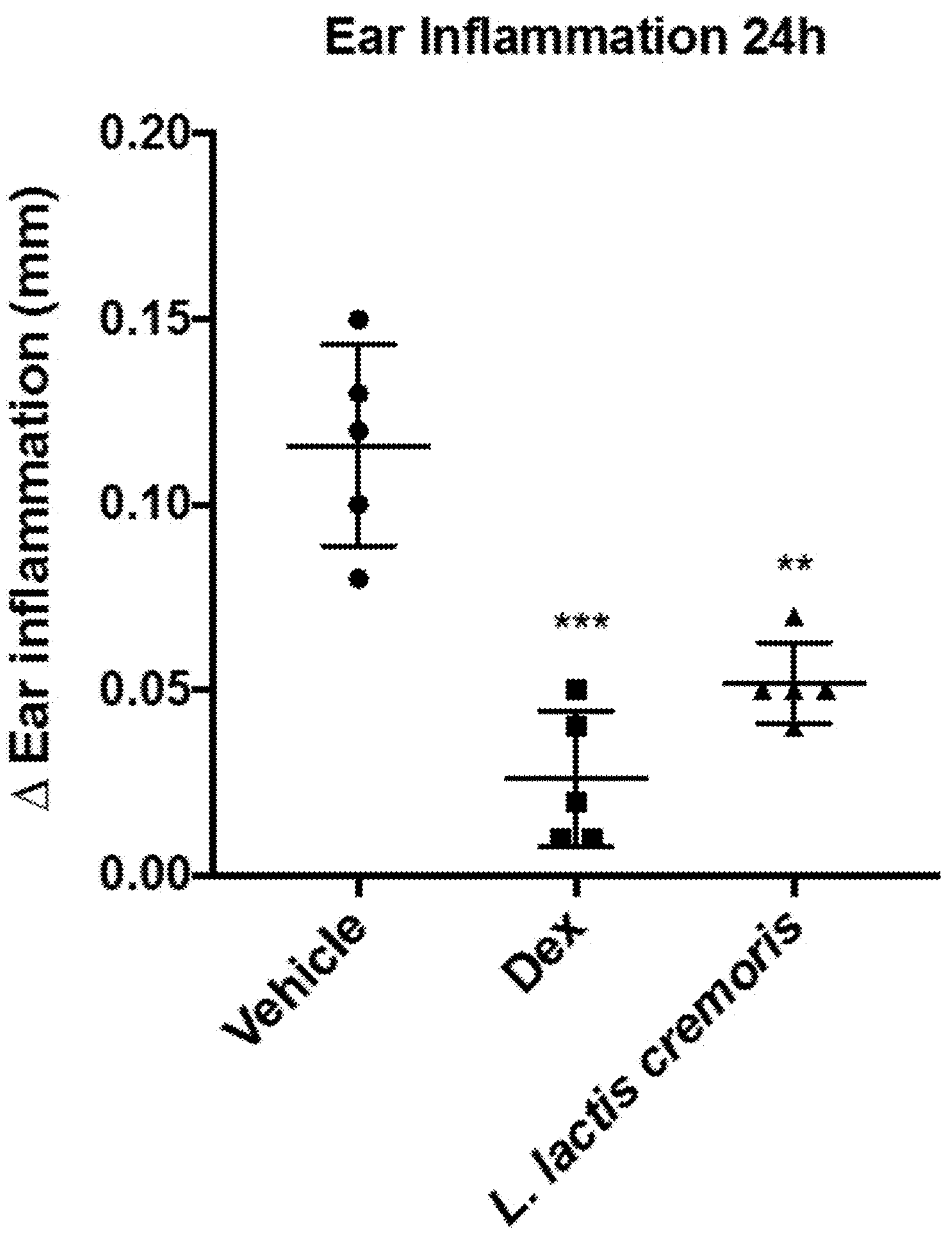
FIG. 5 shows the efficacy of *Lactococcus lactis cremoris* Strain A in reducing antigen-specific ear swelling (ear thickness) compared to vehicle (negative control), and anti-inflammatory Dexamethasone (positive control) in an OVA based adoptive transfer delayed-type hypersensitivity (AdDTH) Mouse Model.

On day 8, after all mice were gavaged, each mouse was anesthetized with isoflurane and a baseline left ear measurement was obtained using Fowler calipers. Then 10 μl of OVA323-339 (Invivogen) (dissolved in sterile PBS to a concentration of 1 mg/ml) was injected intradermally in the left ear. As shown in FIG. 5, *Lactococcus lactis cremoris* Strain A reduces antigen-specific ear swelling (ear thickness) compared to vehicle (negative control), and anti-inflammatory Dexamethasone (positive control) in an OVA based adoptive transfer delayed-type hypersensitivity (AdDTH) Mouse Model.

On day 9, a 24-hour ear measurement was obtained using Fowler calipers and mice were euthanized and tissues like spleen, draining cervical lymph nodes and mesenteric lymph nodes were collected for ex vivo processing.

Single cell suspensions of tissues were prepared, counted and plated to 200,000 cells/well and restimulated with LPS and PMA/Ionomycin for 48 hours or with OVA323-339 peptide or left unstimulated for 72 hours. Supernatants were collected at the end of stimulations and used for downstream MSD or Luminex analyses.

Figure 6A:
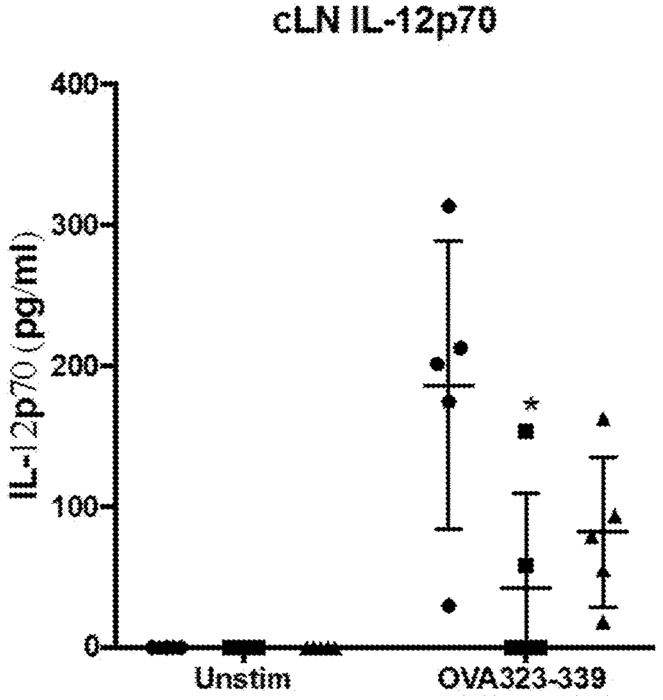
FIGS. 6A, 6B, and 6C show the ability of *Lactococcus lactis cremoris* Strain A in reducing expression of IL-12p70 (FIG. 6A), IL-22 (FIG. 6B), and KC (FIG. 6C) in an Adoptive Transfer Delayed-Type Hypersensitivity (AdDTH) Mouse Model. Circle represents vehicle, square represents dexamethasone, and triangle represents *Lactococcus lactis cremoris* Strain A.
Figure 6B:
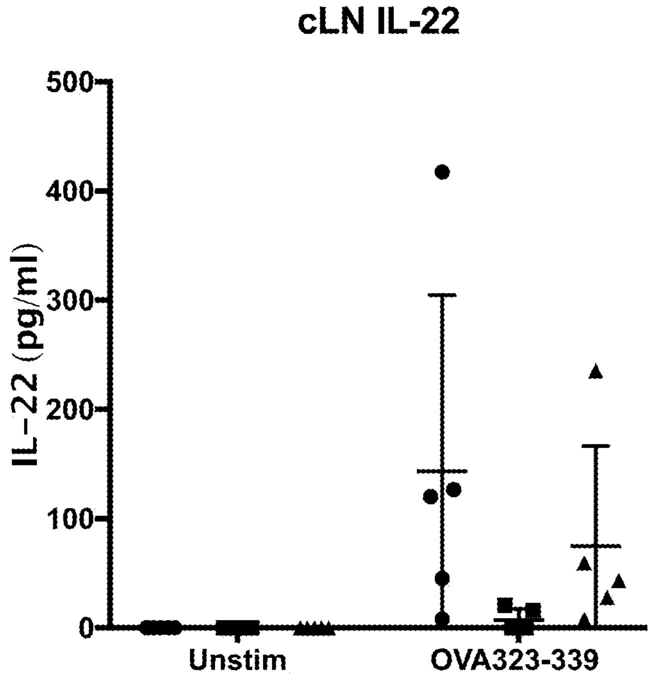
Figure 6C:
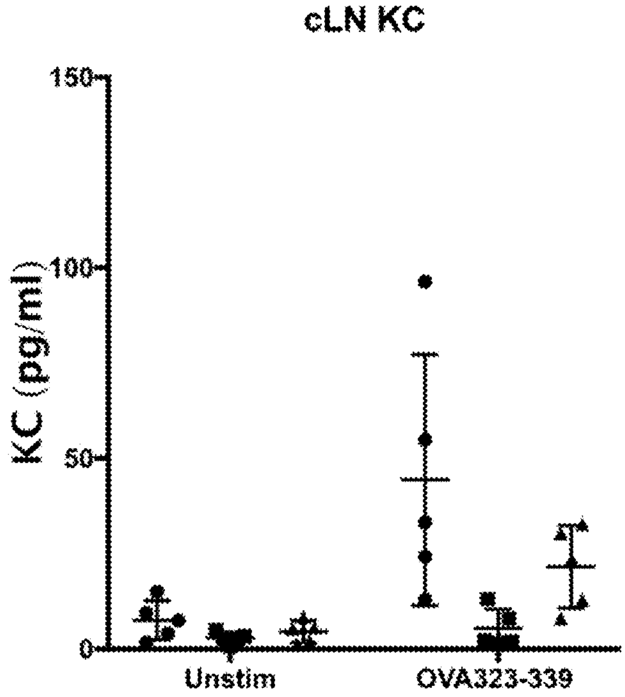

As shown in FIGS. 6A, 6B, and 6C, *Lactococcus lactis cremoris* Strain A reduces expression of IL-12p70 (FIG. 6A), IL-22 (FIG. 6B), and KC (FIG. 6C) in an Adoptive Transfer Delayed-Type Hypersensitivity (AdDTH) Mouse Model. Circle represents vehicle, square represents dexamethasone, and triangle represents *Lactococcus lactis cremoris* Strain A.

Example 13: Imiquimod Mouse Model of Psoriasis

Imiquimod driven psoriasis model is a Th17 driven skin inflammation model. Mice develop flakiness of the skin and erythema which mimics some of the pathology associated with human psoriasis that is scored on a scale of 0-4. Additionally, an ear inflammation may be assessed similar to the DTH.

Briefly, mice were purchased from Taconic Labs and allowed to acclimate in the vivarium for 1 week prior to start of experiment. Mice are housed 5 animals per cage, in individually ventilated cages with standard bedding and enrichment. Standard Purina rodent diet (5001) and autoclaved water is provided ad libitum and checked daily. Ventilated cages are changed once weekly. Animal housing rooms undergoes a lighting cycle consisting of 12 hours on and 12 hours off. Floors, walls, and ceilings are sanitized once a month and rooms maintain a humidity range between 30%-70%, and a temperature range between 68-79 degrees Fahrenheit. Animal health checks are done twice daily.

A dexamethasone stock solution (17 mg/ml) was created by resuspending 6.8 mg of dexamethasone in 400 μl of 96% ethanol. For each day of dosing, a working solution is prepared by diluting the stock solution 100× in sterile PBS to obtain a final concentration of 0.17 mg/mL in a septum vial for intraperitoneal dosing. Dexamethasone-treated mice received 100 μL Dexamethasone i.p. (5 mL/kg of a 0.17 mg/mL solution). Frozen sucrose served as the negative control (vehicle). *Lactococcus lactis cremoris* Strain A was dosed at 100 ul of bacterial cells at 1×10ˆ10 CFU/ml p.o. daily. Dexamethasone (positive control), vehicle (negative control), and *Lactococcus lactis cremoris* Strain A were dosed daily.

On Day 0, the backs of mice were shaved and the depilated with Nair (~25 sec). The Nair is then wiped off and backs of mice washed with warm water (2×).

On Days 1-7, Aldara (5% Imiquimod 62.5 mg per mouse) or control cream is applied on the backs of mice. The cream is re-spread to ensure uniform application. Every day an inflammation skin score is recorded.

Figure 7:
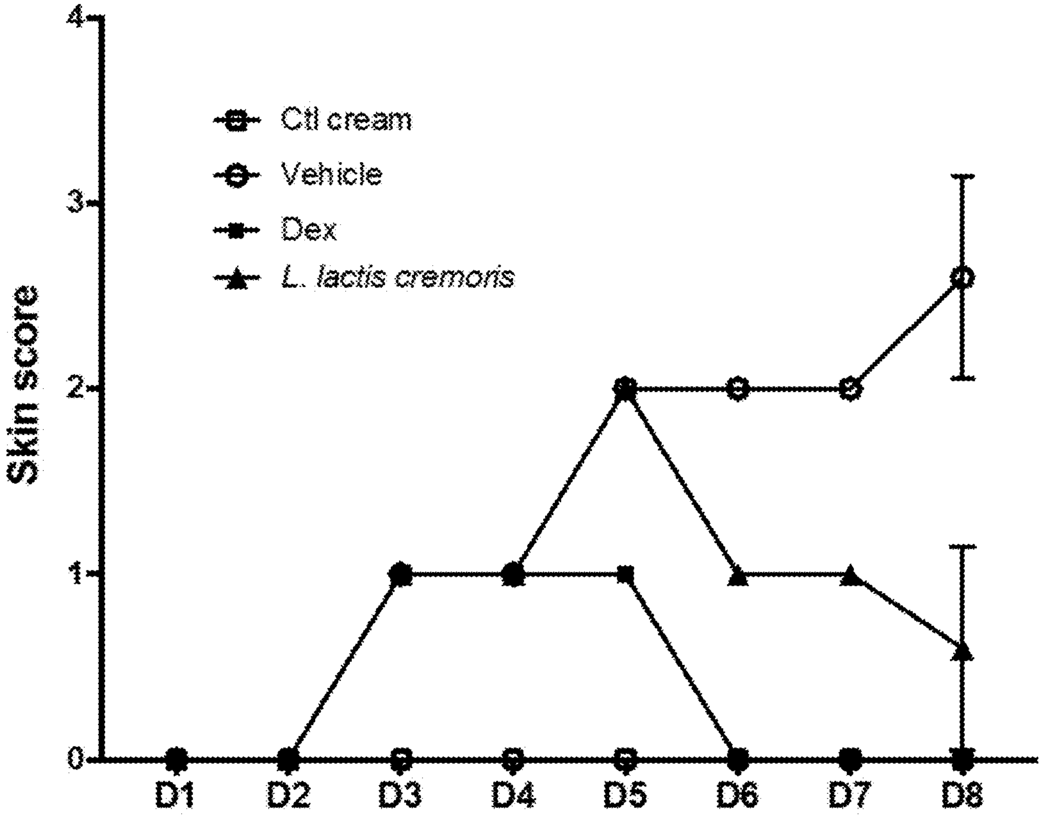
FIG. 7 shows the efficacy of *Lactococcus lactis cremoris* Strain A in improving the skin inflammation scores in an imiquimod model of psoriasis compared to control cream, vehicle, and dexamethasone.
Figure 8:
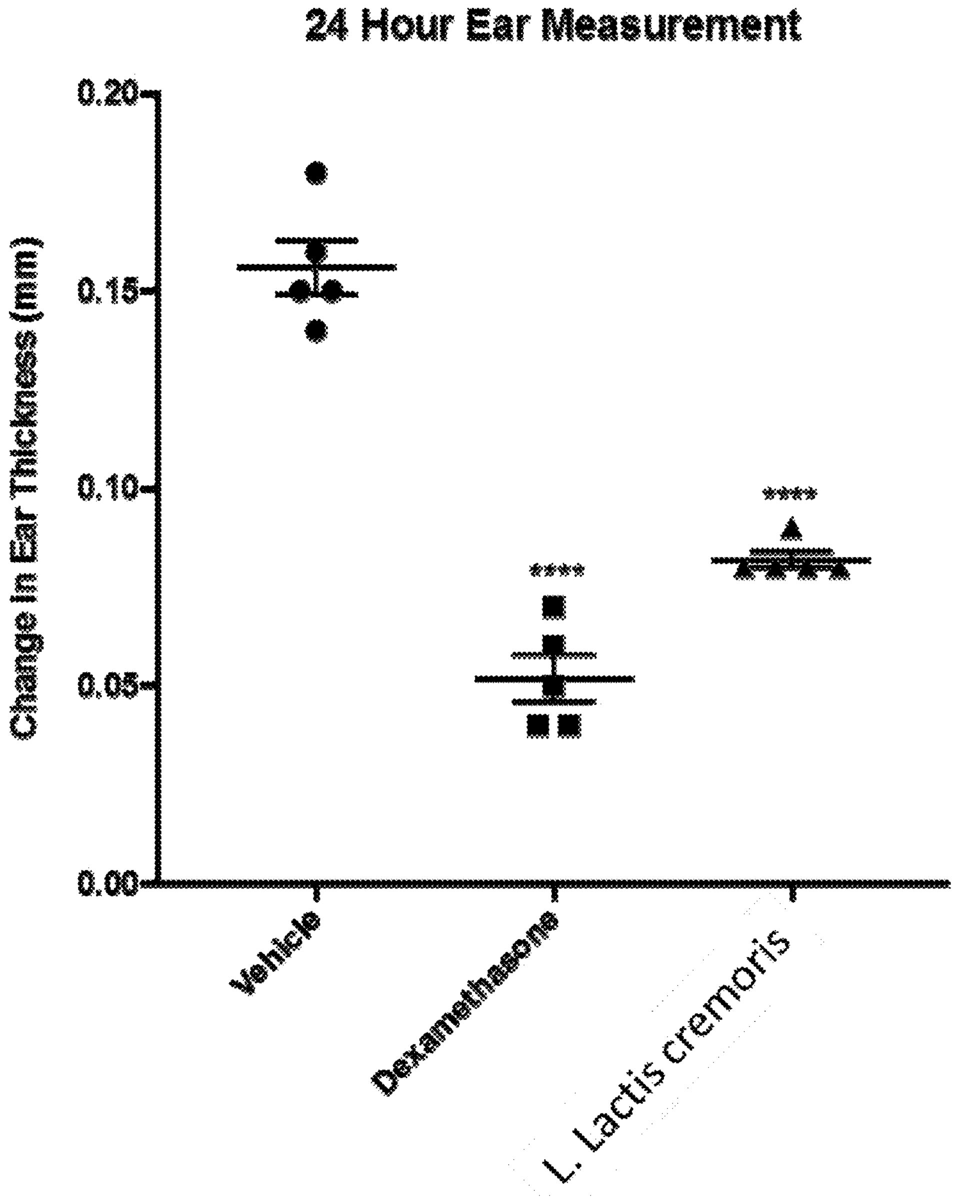
FIG. 8 shows the efficacy of gamma-irradiated *Lactococcus lactis cremoris* Strain A in reducing antigen-specific ear swelling (ear thickness) at 24 hours compared to vehicle (negative control) and anti-inflammatory Dexamethasone (positive control) in a KLH-based delayed type hypersensitivity mouse model. As shown, gamma-irradiated *Lactococcus lactis cremoris* Strain A retains efficacy.
Figure 9A:
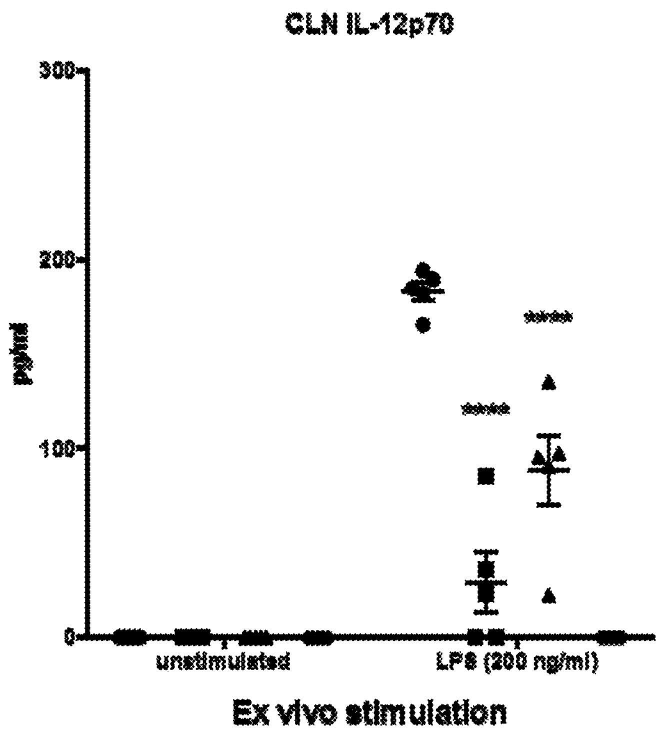
FIGS. 9A, 9B, 9C, and 9D show the ability of gamma-irradiated *Lactococcus lactis cremoris* Strain A to reduce expression of IL-12p70 (FIG. 9A), TNF (FIG. 9B), IL-6 (FIG. 9C), and IL-13 (FIG. 9D) in a KLH-based delayed type hypersensitivity mouse model. Circle represents vehicle, square represents dexamethasone, and triangle represents gamma-irradiated *Lactococcus lactis cremoris* Strain A. Gamma-irradiated *Lactococcus lactis cremoris* Strain A decreases pro-inflammatory cytokine responses in leukocytes from the site-draining lymph node. Circle represents vehicle, square represents dexamethasone, and triangle represents *Lactococcus lactis cremoris* Strain A.
Figure 9B:
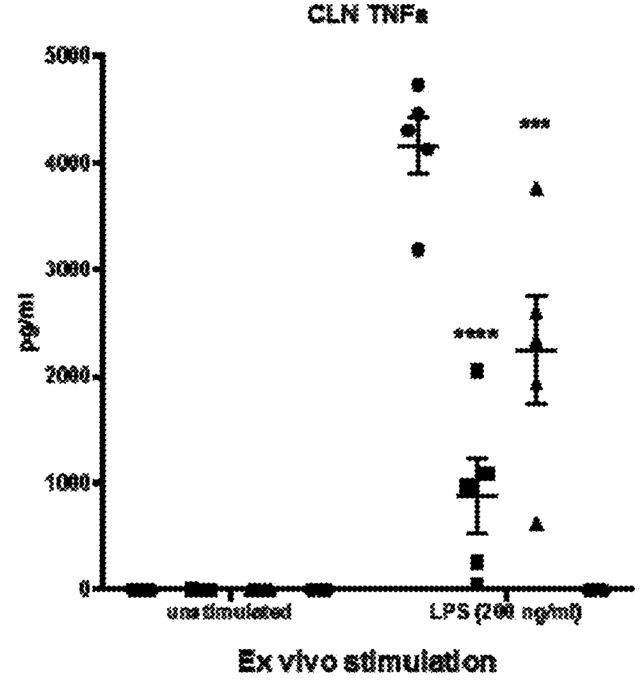
Figure 9C:
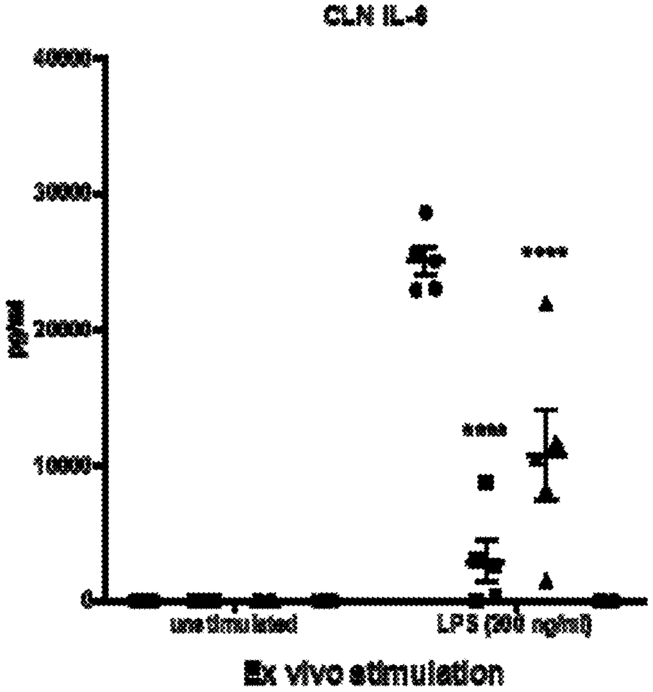
Figure 9D:
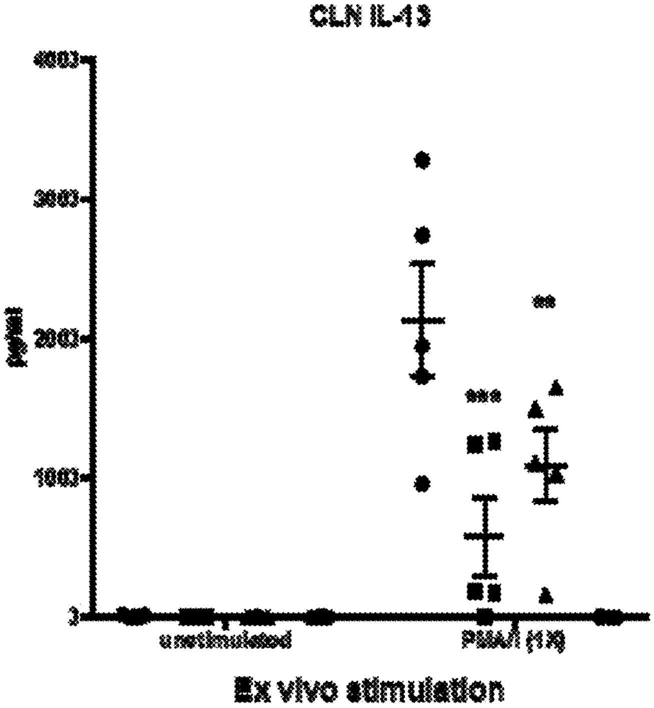
Figure 10A:
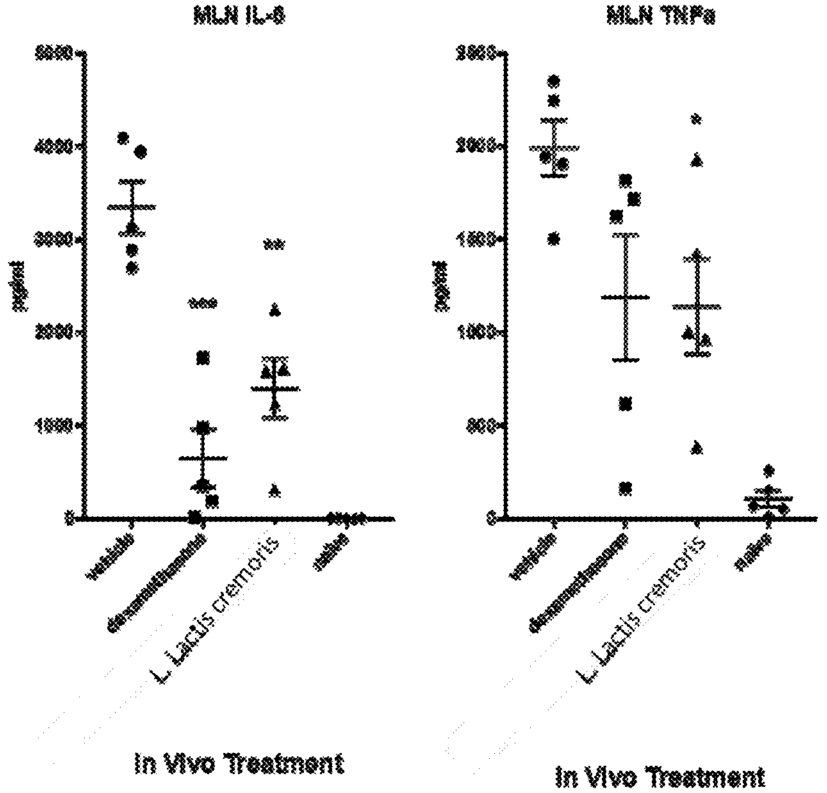
FIGS. 10A and 10B show the ability of gamma-irradiated *Lactococcus lactis cremoris* Strain A to reduce the secretion of pro-inflammatory cytokines (IL-6 and TNFa) from gut-draining lymph nodes (FIG. 10A), while gamma-irradiated *Lactococcus lactis cremoris* Strain A induces peripheral immune cells to secrete more IL-10 (FIG. 10B).
Figure 10B:
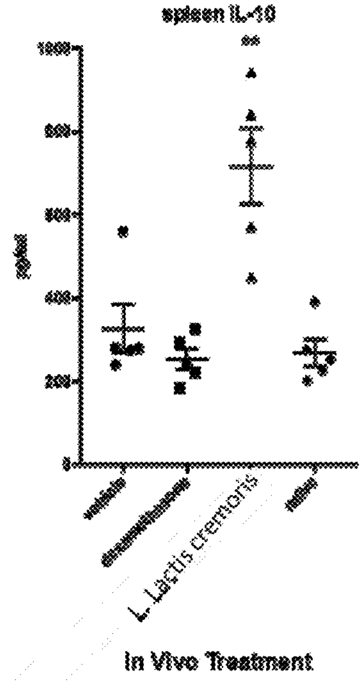

On Day 8, back skin punches are collected for downstream RNA analyses. Skin inflammation scores are evaluated based on the following scale: 0—normal, no reaction; 1—slight erythema; 2—moderate to severe erythema and some plaques; 3—marked erythema and plaques; 4—very marked erythema and plaques. As depicted in FIG. 7, *Lactococcus lactis cremoris* Strain A improved the skin inflammation scores in an imiquimod model of psoriasis compared to control cream, vehicle, and dexamethasone.

INCORPORATION BY REFERENCE

All publications patent applications mentioned herein are hereby incorporated by reference in their entirety as if each individual publication or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating psoriasis in a subject comprising administering to the subject a therapeutically effective dose of a bacterial composition comprising *Lactococcus lactis cremoris* Strain A (ATCC Deposit Number PTA-125368).

2. The method of claim 1, wherein the bacterial composition is administered orally.

3. The method of claim 1, wherein at least 50% of the bacteria in the bacterial composition are *Lactococcus lactis cremoris* Strain A (ATCC Deposit Number PTA-125368).

4. The method of claim 1, wherein at least 99% of the bacteria in the bacterial composition are *Lactococcus lactis cremoris* Strain A (ATCC Deposit Number PTA-125368).

5. The method of claim 1, wherein the bacterial composition comprises at least $1\times10^6$ colony forming units (CFUs) of *Lactococcus lactis cremoris* Strain A (ATCC Deposit Number PTA-125368).

6. The method of claim 1, wherein the bacterial composition comprises live bacteria, attenuated bacteria and/or killed bacteria.

7. The method of claim 1, wherein the method further comprises administering to the subject an additional therapeutic.

8. The method of claim 7, wherein the additional therapeutic is selected from the group consisting of an immunosuppressive agent, a DMARD, a pain-control drug, a steroid, a non-steroidal antiinflammatory drug (NSAID), a cytokine antagonist, cyclosporin, retinoids, corticosteroids, propionic acid derivative, acetic acid derivative, enolic acid derivatives, fenamic acid derivatives, Cox-2 inhibitors, lumiracoxib, ibuprofen, cholin magnesium salicylate, fenoprofen, salsalate, difunisal, tolmetin, ketoprofen, flurbiprofen, oxaprozin, indomethacin, sulindac, etodolac, ketorolac, nabumetone, naproxen, valdecoxib, etoricoxib, MK0966; rofecoxib, acetaminophen, Celecoxib, Diclofenac, tramadol, piroxicam, meloxicam, tenoxicam, droxicam, lornoxicam, isoxicam, mefanamic acid, meclofenamic acid, flufenamic acid, tolfenamic, valdecoxib, parecoxib, etodolac, indomethacin, aspirin, ibuprophen, firocoxib, methotrexate (MTX), antimalarial drugs, hydroxychloroquine, chloroquine, sulfasalazine, Leflunomide, azathioprine, gold salts, minocycline, cyclophosphamide, D-penicillamine, auranofin, tacrolimus, myocrisin, chlorambucil, TNF alpha antagonists, TNF alpha receptor antagonists, adalimumab, etanercept, infliximab, certolizumab pegol, golimumab, anakinra, rituximab, abatacept, tocilizumab, integrin antagonists, natalizumab, IL-1 antagonists, ACZ885, CD4 antagonists, IL-23 antagonists, IL-20 antagonists, IL-6 antagonists, BLyS antagonists, atacicept, belimumab, p38 inhibitors, CD20 antagonists, ocrelizumab, ofatumumab, interferon gamma antagonists, fontolizumab, prednisolone, prednisone, dexamethasone, cortisol, cortisone, hydrocortisone, methylprednisolone, betamethasone, triamcinolone, beclometasome, fludrocortisone, deoxycorticosterone, aldosterone, doxycycline, vancomycin, pioglitazone, SBI-087, SCIO-469, Cura-100, Oncoxin+Viusid, TwHF, methoxsalen, Vitamin D, ergocalciferol, Milnacipran, Paclitaxel, rosiglitazone, rapamune, rapamycin, fostamatinib, Fentanyl, XOMA 052, Fostamatinib disodium, rosightazone, Curcumin, Rosuvastatin, Maraviroc, ramipnl, Cobiprostone, somatropin, tgAAC94 gene therapy vector, MK0359, GW856553, esomeprazole, everolimus, trastuzumab, JAK1 and JAK2 inhibitors, pan JAK inhibitors, tetracyclic pyridone 6 (P6), PF-956980, denosumab, CD20 antagonistis, CTLA4 antagonists, IL-8 antagonists, IL-21 antagonists, IL-22 antagonist, VGEF antagnosits, CXCL antagonists, MMP antagonists, defensin antagonists, IL-1 beta antagonsits, receptor decoys, antagonistic antibodies, mesalazine, mesalamine, sulfasalazine derivatives, immunosuppressive drugs, cyclosporin A, mercaptopurine, azathiopurine, antihistamines, glucocorticoids, epinephrine, theophylline, cromolyn sodium, anti-leukotrienes, anti-cholinergic drugs for rhinitis, TLR antagonists, inflammasome inhibitors, anticholinergic decongestants, mast-cell stabilizers, monoclonal anti-IgE antibodies, vaccines, cytokine inhibitors, anti-IL-6 antibodies, and TNF inhibitors.

9. The method of claim 7, wherein the additional therapeutic is an antibiotic.

10. The method of claim 1, wherein the method further comprises administering a prebiotic to the subject.

11. The method of claim 1, wherein the bacterial composition is formulated for administration in solid form.

12. The method of claim 1, wherein the bacterial composition is formulated with an enteric coating or micro encapsulation.

13. The method of claim 1, wherein the bacterial composition is formulated in a capsule.

* * * * *

SEQUENCE LISTING

```
<160> NUMBER OF SEQ ID NOS: 234

<210> SEQ ID NO 1
<211> LENGTH: 391
<212> TYPE: PRT
<213> ORGANISM: Lactococcus lactis

<400> SEQUENCE: 1

Met Thr Gln Phe Thr Thr Glu Leu Leu Asn Phe Leu Ala Gln Lys Gln
1               5                   10                  15

Asp Ile Asp Glu Phe Phe Arg Thr Ser Leu Glu Thr Ala Met Asn Asp
            20                  25                  30

Leu Leu Gln Ala Glu Leu Ser Ala Phe Leu Gly Tyr Glu Pro Tyr Asp
        35                  40                  45

Lys Val Gly Tyr Asn Ser Gly Asn Ser Arg Asn Gly Ser Tyr Ser Arg
    50                  55                  60

Gln Phe Glu Thr Lys Tyr Gly Thr Val Gln Leu Ser Ile Pro Arg Asp
65                  70                  75                  80

Arg Asn Gly Asn Phe Ser Pro Ala Leu Leu Pro Ala Tyr Gly Arg Arg
                85                  90                  95

Asp Asp His Leu Glu Glu Met Val Ile Lys Leu Tyr Gln Thr Gly Val
            100                 105                 110

Thr Thr Arg Glu Ile Ser Asp Ile Ile Glu Arg Met Tyr Gly His His
        115                 120                 125

Tyr Ser Pro Ala Thr Ile Ser Asn Ile Ser Lys Ala Thr Gln Glu Asn
    130                 135                 140

Val Ala Thr Phe His Glu Arg Ser Leu Glu Ala Asn Tyr Ser Val Leu
145                 150                 155                 160
```

Phe Leu Asp Gly Thr Tyr Leu Pro Leu Arg Arg Gly Thr Val Ser Lys
165 170 175

Glu Cys Ile His Ile Ala Leu Gly Ile Thr Pro Glu Gly Gln Lys Ala
180 185 190

Val Leu Gly Tyr Glu Ile Ala Pro Asn Glu Asn Asn Ala Ser Trp Ser
195 200 205

Thr Leu Leu Asp Lys Leu Gln Asn Gln Gly Ile Gln Gln Val Ser Leu
210 215 220

Val Val Thr Asp Gly Phe Lys Gly Leu Glu Gln Ile Ile Ser Gln Ala
225 230 235 240

Tyr Pro Leu Ala Lys Gln Gln Arg Cys Leu Ile His Ile Ser Arg Asn
245 250 255

Leu Ala Ser Lys Val Lys Arg Ala Asp Arg Ala Val Ile Leu Glu Gln
260 265 270

Phe Lys Thr Ile Tyr Arg Ala Glu Asn Leu Glu Met Ala Val Gln Ala
275 280 285

Leu Glu Asn Phe Ile Ala Glu Trp Lys Pro Lys Tyr Arg Lys Val Met
290 295 300

Glu Ser Leu Glu Asn Thr Asp Asn Leu Leu Thr Phe Tyr Gln Phe Pro
305 310 315 320

Tyr Gln Ile Trp His Ser Ile Tyr Ser Thr Asn Leu Ile Glu Ser Leu
325 330 335

Asn Lys Glu Ile Lys Arg Gln Thr Lys Lys Lys Val Leu Phe Pro Asn
340 345 350

Glu Glu Ala Leu Glu Arg Tyr Leu Val Thr Leu Phe Glu Asp Tyr Asn
355 360 365

Phe Lys Gln Ser Gln Arg Ile His Lys Gly Phe Gly Gln Cys Ala Asp
370 375 380

Thr Leu Glu Ser Leu Phe Asp
385 390

<210> SEQ ID NO 2
<211> LENGTH: 272
<212> TYPE: PRT
<213> ORGANISM: Lactococcus lactis

<400> SEQUENCE: 2

Met Lys Val Thr Gly Phe Pro Lys Ala Thr Tyr Tyr Tyr Trp Val Asn
1 5 10 15

Cys Phe Glu Arg Val Asn Lys Asp Glu Leu Ile Glu Lys Glu Met Leu
20 25 30

Lys Ile Arg Gln Glu His Ala Asn Ala Gly Tyr Arg Pro Met Ser Glu
35 40 45

Leu Leu Lys Gln Arg Gly Tyr His Val Asn His Lys Lys Val Gln Arg
50 55 60

Leu Met Lys Lys Leu Gly Leu Arg Val Thr Ser Tyr Trp His Lys Ser
65 70 75 80

Arg Lys Tyr Asn Ser Tyr Lys Gly Lys Val Gly Thr Val Ala Lys Asn
85 90 95

Lys Leu His Arg Arg Phe Arg Thr Ser Ile Pro His Gln Lys Ile Thr
100 105 110

Thr Asp Thr Thr Glu Phe Lys Tyr Tyr Glu Asp Gly Ile Gln Lys Lys
115 120 125

Cys Tyr Leu Asn Pro Tyr Ile Asp Leu Phe Asn Ser Glu Val Ile Ser

-continued

```
    130                 135                 140

Tyr His Ile Ser Lys Gln Pro Ser Tyr Gln Ser Ile Asp Ile Ala Leu
145                 150                 155                 160

Asn Gln Ala Leu Ala Val Thr Ser Asp Cys Pro Tyr Arg Arg Thr Phe
                165                 170                 175

His Ser Asp Gln Gly Trp Gly Tyr Gln Met Arg Asp Tyr Val Ser Lys
            180                 185                 190

Leu Lys Ser His Arg Ile Phe Gln Ser Met Ser Arg Lys Gly Asn Cys
        195                 200                 205

His Asp Asn Ser Val Met Glu Asn Phe Phe Gly Leu Leu Lys Gln Glu
    210                 215                 220

Ile Tyr Tyr Gly His Ile Phe Ser Ser Phe Glu Glu Leu Glu Gln Val
225                 230                 235                 240

Ile Val Ile Trp Ile Arg Tyr Tyr Asn Thr Lys Arg Ile Lys Gln Lys
                245                 250                 255

Leu Asn Trp Met Ser Pro Ile Gln Phe Arg Leu Asn Tyr Gln Asn Asn
            260                 265                 270


<210> SEQ ID NO 3
<211> LENGTH: 118
<212> TYPE: PRT
<213> ORGANISM: Lactococcus lactis

<400> SEQUENCE: 3

Met Thr Gln Phe Thr Thr Glu Leu Leu Asn Phe Leu Ala Gln Lys Gln
1               5                   10                  15

Asp Ile Asp Glu Phe Phe Arg Thr Ser Leu Glu Thr Ala Met Asn Asp
            20                  25                  30

Leu Leu Gln Ala Glu Leu Ser Ala Phe Leu Gly Tyr Glu Pro Tyr Asp
        35                  40                  45

Lys Val Gly Tyr Asn Ser Gly Asn Ser Arg Asn Gly Ser Tyr Ser Arg
    50                  55                  60

Gln Phe Glu Thr Lys Tyr Gly Thr Val Gln Leu Ser Ile Pro Arg Asp
65                  70                  75                  80

Arg Asn Gly Asn Phe Ser Pro Ala Leu Leu Pro Ala Tyr Gly Arg Arg
                85                  90                  95

Asp Asp His Leu Glu Glu Met Gly Tyr Gln Thr Leu Ser Asn Arg Cys
            100                 105                 110

Asn Asp Ser Arg Asn Leu
        115


<210> SEQ ID NO 4
<211> LENGTH: 193
<212> TYPE: PRT
<213> ORGANISM: Lactococcus lactis

<400> SEQUENCE: 4

Met Thr Lys Tyr Ser Phe Glu Leu Lys Leu Lys Val Val Gln Asp Tyr
1               5                   10                  15

Asp Asn Gly Val Gly Gly Cys Asp Tyr Leu Ala Lys Lys Tyr His Val
            20                  25                  30

Thr Asn Glu Ala Ile Val Arg Arg Trp Val Lys Ala Tyr Lys Glu Leu
        35                  40                  45

Gly Ala Val Gly Ile Gln Arg Lys Arg Gln Asn Thr Val Tyr Ser Thr
    50                  55                  60

Gln Phe Lys Leu Asn Ala Val Asn Leu Tyr Leu Thr Ser Glu Lys Ser
```

65 70 75 80

Tyr Arg Glu Leu Ala His Glu Leu Gly Met Asn Asn Pro Pro Leu Leu
85 90 95

Thr Arg Trp Val Ser Asn Tyr Arg Lys Lys Gly Glu Phe Ala Phe Ser
100 105 110

Asn Val Gln Gly Arg Pro Arg Lys Glu Ser Glu Leu Leu Glu Ile Ser
115 120 125

Ile Lys Lys Ala Lys Asp Val Val Asn Glu Thr Glu Gln Glu Leu Ala
130 135 140

Arg Leu Gln Asn Asp Asn Leu Asn Leu Arg Met Glu Val Glu Tyr Leu
145 150 155 160

Lys Gly Leu Arg Arg Leu Arg Gln Glu Gln His Lys Arg Glu Asn Pro
165 170 175

Glu Trp Ser Val Asn Ser Asp Glu Asn Ser Ser Ser His Leu Ser Asn
180 185 190

Ser

<210> SEQ ID NO 5
<211> LENGTH: 287
<212> TYPE: PRT
<213> ORGANISM: Lactococcus lactis

<400> SEQUENCE: 5

Met Val Cys Glu Leu Arg Arg Glu Phe Lys Phe Pro Leu Lys Gln Leu
1 5 10 15

Leu Ala Ile Ser Glu Leu Ser Lys Ala Thr Tyr Tyr Tyr Trp Val Asn
20 25 30

Arg Phe Glu Arg Pro Asn Lys Asp Glu Met Ile Glu Gln Val Met Leu
35 40 45

Glu Ile Arg Gln Glu His Thr Asn Ala Gly Tyr Arg Pro Met Val Glu
50 55 60

Leu Leu Lys Gln Arg Gly Ile Tyr Val Asn His Lys Lys Val Gln Arg
65 70 75 80

Leu Met Lys Lys Leu Gly Leu Arg Val Thr Thr Phe Trp His Lys Ser
85 90 95

Arg Lys Tyr Asn Ser Tyr Lys Gly Lys Val Gly Thr Val Ala Lys Asn
100 105 110

Lys Leu His Arg Arg Phe Asn Thr Ser Ile Pro His Gln Lys Ile Thr
115 120 125

Thr Asp Thr Thr Glu Phe Lys Tyr Tyr Asp Lys Gly Val Gln Lys Lys
130 135 140

Leu Tyr Leu Thr Pro Tyr Leu Asp Leu Phe Asn Asn Glu Val Ile Ser
145 150 155 160

Tyr Glu Ile Ser Lys Gln Pro Thr Tyr Gln Ala Ile Ala Thr Ala Leu
165 170 175

Gln Glu Ala Leu Glu Leu Thr Ser Asp Cys Leu Tyr Arg Arg Thr Phe
180 185 190

His Ser Asp Gln Gly Trp Ala Tyr Gln Met Lys Asn Tyr Val Phe Lys
195 200 205

Leu Lys Ser Gln Lys Ile Ile Gln Ser Met Ser Arg Lys Gly Asn Cys
210 215 220

His Asp Asn Ser Val Met Glu Asn Phe Phe Gly Leu Leu Lys Gln Glu
225 230 235 240

Ile Tyr Tyr Gly His Val Phe Asn Ser Phe Glu Glu Leu Glu Gln Ala

```
                245                 250                 255

Ile Thr Lys Trp Ile His Tyr Tyr Asn Thr Lys Arg Ile Lys Lys Lys
            260                 265                 270

Leu Asn Trp Met Ser Pro Ile Gln Tyr Arg Leu Thr Tyr Ser Lys
        275                 280                 285


<210> SEQ ID NO 6
<211> LENGTH: 65
<212> TYPE: PRT
<213> ORGANISM: Lactococcus lactis

<400> SEQUENCE: 6

Met Met Ile Asn Tyr Gln Gly Glu Val Phe Thr Glu Thr Glu Phe Tyr
1               5                   10                  15

Gly Arg Glu Ile Leu Glu Ala Ile Gln Leu Thr Asn Lys Phe Pro Thr
            20                  25                  30

Pro Lys Lys Val Leu Ile Asp Arg Leu Glu Glu Met Ile His Glu Gln
        35                  40                  45

Leu Asp Leu Ile Asp Lys Glu Glu Leu Asn Asn Tyr Ile His Ala Lys
    50                  55                  60

Lys
65


<210> SEQ ID NO 7
<211> LENGTH: 122
<212> TYPE: PRT
<213> ORGANISM: Lactococcus lactis

<400> SEQUENCE: 7

Met Lys Ile Ile Glu Asn Arg Glu Arg Ser Ile Gln Lys Lys Phe Phe
1               5                   10                  15

Val Asn Glu Lys Glu Asn Glu Arg Ile Lys Leu Met Met Lys Lys Thr
            20                  25                  30

Gly Ile Thr Asn Phe Ser Val Phe Ala Arg Arg Ala Cys Cys Asn Lys
        35                  40                  45

Glu Ile Phe Thr Leu Asp Phe Ser Glu Tyr Lys Asn Ile Ile Ser Glu
    50                  55                  60

Ile Ser Ala Thr Lys Ser Glu Leu Lys Arg Ile Gly Asn Asn Ile Asn
65                  70                  75                  80

Gln Ile Ala Lys His Leu Asn Glu Asn Lys Asn Asn Gln Thr Glu Ser
                85                  90                  95

Leu Met Ser Asp Tyr Gln Asn Gln Leu Glu Ser Leu Glu Glu Lys Ile
            100                 105                 110

Gln Lys Val Val His Tyr Ile Ser Glu Gly
        115                 120


<210> SEQ ID NO 8
<211> LENGTH: 170
<212> TYPE: PRT
<213> ORGANISM: Lactococcus lactis

<400> SEQUENCE: 8

Met Met Leu Lys Lys Glu Trp Gln Ala Ile Leu Lys His Lys Phe Phe
1               5                   10                  15

Ile Ile Val Ile Ile Ala Leu Ala Leu Val Pro Ala Ile Tyr Asn Tyr
            20                  25                  30

Ile Phe Leu Gly Ser Met Trp Asp Pro Ser Gly Lys Leu Asn Asp Leu
        35                  40                  45
```

```
Pro Val Ala Val Val Asn Leu Asp Lys Thr Ser Glu Leu Asn Gly Lys
    50                  55                  60

Lys Phe Lys Leu Gly Asp Asp Val Ile Thr Glu Met Lys Lys Ser Lys
65                  70                  75                  80

Asp Leu Asp Tyr His Phe Val Ser Lys Asp Lys Ala Ser Glu Gly Ile
                85                  90                  95

Lys Lys Gly Asp Tyr Tyr Met Val Ile Thr Phe Pro Glu Asn Phe Ser
            100                 105                 110

Glu Asn Ala Thr Thr Leu Met Asn Lys Glu Pro Lys Thr Val Gln Leu
        115                 120                 125

Asp Tyr Gln Thr Thr Arg Gly His Asn Tyr Ile Ser Ser Lys Met Ser
    130                 135                 140

Glu Ser Ala Met Asn Gln Leu Lys Ser Glu Val Ser Lys Asn Ile Thr
145                 150                 155                 160

Gln Thr Tyr Thr Lys Thr Arg Ile Ala Ser
                165                 170
```

<210> SEQ ID NO 9
<211> LENGTH: 299
<212> TYPE: PRT
<213> ORGANISM: Lactococcus lactis

<400> SEQUENCE: 9

```
Met Lys Lys Lys Met Arg Leu Lys Val Leu Leu Ala Ser Thr Ala Thr
1               5                   10                  15

Ala Leu Leu Leu Leu Ser Gly Cys Gln Ser Asn Gln Thr Asp Gln Thr
            20                  25                  30

Val Ala Thr Tyr Ser Gly Gly Lys Val Thr Glu Ser Ser Phe Tyr Lys
        35                  40                  45

Glu Leu Lys Gln Ser Pro Thr Thr Lys Thr Met Leu Ala Asn Met Leu
    50                  55                  60

Ile Tyr Arg Ala Leu Asn His Ala Tyr Gly Lys Ser Val Ser Thr Lys
65                  70                  75                  80

Thr Val Asn Asp Ala Tyr Asp Ser Tyr Lys Gln Gln Tyr Gly Glu Asn
                85                  90                  95

Phe Asp Ala Phe Leu Ser Gln Asn Gly Phe Ser Arg Ser Ser Phe Lys
            100                 105                 110

Glu Ser Leu Arg Thr Asn Phe Leu Ser Glu Val Ala Leu Lys Lys Leu
        115                 120                 125

Lys Lys Val Ser Glu Ser Gln Leu Lys Ala Ala Trp Lys Thr Tyr Gln
    130                 135                 140

Pro Lys Val Thr Val Gln His Ile Leu Thr Ser Asp Glu Asp Thr Ala
145                 150                 155                 160

Lys Gln Val Ile Ser Asp Leu Ala Ala Gly Lys Asp Phe Ala Met Leu
                165                 170                 175

Ala Lys Thr Asp Ser Ile Asp Thr Ala Thr Lys Asp Asn Gly Gly Lys
            180                 185                 190

Ile Ser Phe Glu Leu Asn Asn Lys Thr Leu Asp Ala Thr Phe Lys Asp
        195                 200                 205

Ala Ala Tyr Lys Leu Lys Asn Gly Asp Tyr Thr Gln Thr Pro Val Lys
    210                 215                 220

Val Thr Asp Gly Tyr Glu Val Ile Lys Met Ile Asn His Pro Ala Lys
225                 230                 235                 240

Gly Thr Phe Thr Ser Ser Lys Lys Val Leu Thr Ala Ser Val Tyr Ala
```

-continued

```
                245                 250                 255

Lys Trp Ser Arg Asp Ser Ser Ile Met Gln Arg Val Ile Ser Gln Val
            260                 265                 270

Leu Lys Asn Gln His Val Thr Ile Lys Asp Lys Asp Leu Ala Asp Ala
        275                 280                 285

Leu Asp Ser Tyr Lys Lys Leu Ala Thr Thr Asn
    290                 295


<210> SEQ ID NO 10
<211> LENGTH: 2022
<212> TYPE: PRT
<213> ORGANISM: Lactococcus lactis

<400> SEQUENCE: 10

Met Gln Arg Lys Lys Lys Gly Leu Ser Phe Leu Leu Ala Gly Thr Val
1               5                   10                  15

Ala Leu Gly Ala Leu Ala Val Leu Pro Val Gly Glu Ile Gln Ala Lys
            20                  25                  30

Ala Ala Ile Ser Gln Gln Thr Lys Gly Ser Ser Leu Ala Asn Thr Val
        35                  40                  45

Thr Ala Ala Thr Ala Lys Gln Ala Ala Thr Asp Thr Thr Ala Ala Thr
    50                  55                  60

Thr Asn Gln Ala Ile Ala Thr Gln Leu Ala Ala Lys Gly Ile Asp Tyr
65                  70                  75                  80

Asn Lys Leu Asn Lys Val Gln Gln Gln Asp Ile Tyr Val Asp Val Ile
                85                  90                  95

Val Gln Met Ser Ala Ala Pro Ala Ser Glu Asn Gly Thr Leu Arg Thr
            100                 105                 110

Asp Tyr Ser Ser Thr Ala Glu Ile Gln Gln Glu Thr Asn Lys Val Ile
        115                 120                 125

Ala Ala Gln Ala Ser Val Lys Ala Ala Val Glu Gln Val Thr Gln Gln
    130                 135                 140

Thr Ala Gly Glu Ser Tyr Gly Tyr Val Val Asn Gly Phe Ser Thr Lys
145                 150                 155                 160

Val Arg Val Val Asp Ile Pro Lys Leu Lys Gln Ile Ala Gly Val Lys
                165                 170                 175

Thr Val Thr Leu Ala Lys Val Tyr Tyr Pro Thr Asp Ala Lys Ala Asn
            180                 185                 190

Ser Met Ala Asn Val Gln Ala Val Trp Ser Asn Tyr Lys Tyr Lys Gly
        195                 200                 205

Glu Gly Thr Val Val Ser Val Ile Asp Ser Gly Ile Asp Pro Thr His
    210                 215                 220

Lys Asp Met Arg Leu Ser Asp Asp Lys Asp Val Lys Leu Thr Lys Ser
225                 230                 235                 240

Asp Val Glu Lys Phe Thr Asp Thr Val Lys His Gly Arg Tyr Phe Asn
                245                 250                 255

Ser Lys Val Pro Tyr Gly Phe Asn Tyr Ala Asp Asn Asn Asp Thr Ile
            260                 265                 270

Thr Asp Asp Lys Val Asp Glu Gln His Gly Met His Val Ala Gly Ile
        275                 280                 285

Ile Gly Ala Asn Gly Thr Gly Asp Asp Pro Ala Lys Ser Val Val Gly
    290                 295                 300

Val Ala Pro Glu Ala Gln Leu Leu Ala Met Lys Val Phe Thr Asn Ser
305                 310                 315                 320
```

```
Asp Thr Ser Ala Thr Thr Gly Ser Asp Thr Leu Val Ser Ala Ile Glu
                325                 330                 335

Asp Ser Ala Lys Ile Gly Ala Asp Val Leu Asn Met Ser Leu Gly Ser
            340                 345                 350

Asp Ser Gly Asn Gln Thr Leu Glu Asp Pro Glu Ile Ala Ala Val Gln
        355                 360                 365

Asn Ala Asn Glu Ser Gly Thr Ala Ala Val Ile Ser Ala Gly Asn Ser
    370                 375                 380

Gly Thr Ser Gly Ser Ala Thr Glu Gly Val Asn Lys Asp Tyr Tyr Gly
385                 390                 395                 400

Leu Gln Asp Asn Glu Met Val Gly Thr Pro Gly Thr Ser Arg Gly Ala
                405                 410                 415

Thr Thr Val Ala Ser Ala Glu Asn Thr Asp Val Ile Thr Gln Ala Val
            420                 425                 430

Thr Ile Thr Asp Gly Thr Gly Leu Gln Leu Gly Pro Glu Thr Ile Gln
        435                 440                 445

Leu Ser Ser Asn Asp Phe Thr Gly Ser Phe Asp Gln Lys Lys Phe Tyr
    450                 455                 460

Val Val Lys Asp Ala Ser Gly Asn Leu Ser Lys Gly Lys Val Ala Asp
465                 470                 475                 480

Tyr Thr Ala Asp Ala Lys Gly Lys Ile Ala Ile Val Lys Arg Gly Glu
                485                 490                 495

Leu Thr Phe Asp Asp Lys Gln Lys Tyr Ala Gln Ala Ala Gly Ala Ala
            500                 505                 510

Gly Leu Ile Ile Val Asn Asn Asp Gly Thr Ala Thr Pro Val Thr Ser
        515                 520                 525

Met Ala Leu Thr Thr Thr Phe Pro Thr Phe Gly Leu Ser Ser Val Thr
    530                 535                 540

Gly Gln Lys Leu Val Asp Trp Val Thr Ala His Pro Asp Asp Ser Leu
545                 550                 555                 560

Gly Val Lys Ile Ala Leu Thr Leu Val Pro Asn Gln Lys Tyr Thr Glu
                565                 570                 575

Asp Lys Met Ser Asp Phe Thr Ser Tyr Gly Pro Val Ser Asn Leu Ser
            580                 585                 590

Phe Lys Pro Asp Ile Thr Ala Pro Gly Gly Asn Ile Trp Ser Thr Gln
        595                 600                 605

Asn Asn Asn Gly Tyr Thr Asn Met Ser Gly Thr Ser Met Ala Ser Pro
    610                 615                 620

Phe Ile Ala Gly Ser Gln Ala Leu Leu Lys Gln Ala Leu Asn Asn Lys
625                 630                 635                 640

Asn Asn Pro Phe Tyr Ala Tyr Tyr Lys Gln Leu Lys Gly Thr Ala Leu
                645                 650                 655

Thr Asp Phe Leu Lys Thr Val Glu Met Asn Thr Ala Gln Pro Ile Asn
            660                 665                 670

Asp Ile Asn Tyr Asn Asn Val Ile Val Ser Pro Arg Arg Gln Gly Ala
        675                 680                 685

Gly Leu Val Asp Val Lys Ala Ala Ile Asp Ala Leu Glu Lys Asn Pro
    690                 695                 700

Ser Thr Val Val Ala Glu Asn Gly Tyr Pro Ala Val Glu Leu Lys Asp
705                 710                 715                 720

Phe Thr Ser Thr Asp Lys Thr Phe Lys Leu Thr Phe Thr Asn Arg Thr
                725                 730                 735

Thr His Glu Leu Thr Tyr Gln Met Asp Ser Asn Thr Asp Thr Asn Ala
```

```
            740                 745                 750

Val Tyr Thr Ser Ala Thr Asp Pro Asn Ser Gly Val Leu Tyr Asp Lys
        755                 760                 765

Lys Ile Asp Gly Ala Ala Ile Lys Ala Gly Ser Asn Ile Thr Val Pro
    770                 775                 780

Ala Gly Lys Thr Ala Gln Ile Glu Phe Thr Leu Ser Leu Pro Lys Ser
785                 790                 795                 800

Phe Asp Gln Gln Gln Phe Val Glu Gly Phe Leu Asn Phe Lys Gly Ser
                805                 810                 815

Asp Gly Ser Arg Leu Asn Leu Pro Tyr Met Gly Phe Phe Gly Asp Trp
            820                 825                 830

Asn Asp Gly Lys Ile Val Asp Ser Leu Asn Gly Ile Thr Tyr Ser Pro
        835                 840                 845

Ala Gly Gly Asn Phe Gly Thr Val Pro Leu Leu Thr Asn Lys Asn Thr
    850                 855                 860

Gly Thr Gln Tyr Tyr Gly Gly Met Val Thr Asp Ala Asp Gly Asn Gln
865                 870                 875                 880

Thr Val Asp Asp Gln Ala Ile Ala Phe Ser Ser Asp Lys Asn Ala Leu
                885                 890                 895

Tyr Asn Asp Ile Ser Met Lys Tyr Tyr Leu Leu Arg Asn Ile Ser Asn
            900                 905                 910

Val Gln Val Asp Ile Leu Asp Gly Gln Gly Asn Lys Val Thr Thr Leu
        915                 920                 925

Ser Ser Ser Thr Asn Leu Thr Lys Thr Tyr Tyr Asn Ala His Ser Gln
    930                 935                 940

Gln Tyr Ile Tyr Tyr His Ala Pro Ala Trp Asp Gly Thr Tyr Tyr Asp
945                 950                 955                 960

Gln Arg Asp Gly Asn Ile Lys Thr Ala Asp Asp Gly Ser Tyr Thr Tyr
                965                 970                 975

Arg Ile Ser Gly Val Pro Glu Gly Gly Asp Lys Arg Gln Val Phe Asp
            980                 985                 990

Val Pro Phe Lys Leu Asp Ser Lys  Ala Pro Thr Val Arg  His Val Ala
        995                 1000                1005

Leu Ser  Ala Lys Thr Lys Asn  Gly Lys Thr Gln Tyr  Tyr Leu Thr
    1010                1015                1020

Ala Glu  Val Lys Asp Asp Leu  Ser Gly Leu Asp Ala  Thr Lys Ser
    1025                1030                1035

Val Lys  Thr Ala Ile Asn Glu  Val Thr Asn Leu Asp  Ala Thr Phe
    1040                1045                1050

Thr Asp  Ala Gly Thr Thr Ala  Asp Gly Tyr Thr Lys  Ile Glu Thr
    1055                1060                1065

Pro Leu  Ser Asp Glu Gln Ala  Gln Ala Leu Gly Asn  Gly Asp Asn
    1070                1075                1080

Ser Ala  Glu Leu Tyr Leu Thr  Asp Asn Ala Ser Asn  Ala Thr Asp
    1085                1090                1095

Gln Asp  Ala Ser Val Gln Lys  Pro Gly Ser Thr Ser  Phe Asp Leu
    1100                1105                1110

Ile Val  Asn Gly Ser Gly Ile  Pro Asp Lys Ile Ser  Ser Thr Thr
    1115                1120                1125

Thr Gly  Tyr Glu Ala Asn Thr  Gln Gly Gly Gly Thr  Tyr Thr Phe
    1130                1135                1140

Ser Gly  Thr Tyr Pro Ala Ala  Val Asp Gly Thr Tyr  Thr Asp Ala
    1145                1150                1155
```

```
Gln Gly  Lys Lys His Asp Leu  Asn Thr Thr Tyr Asp  Ala Ala Thr
    1160                 1165                 1170

Asn Ser  Phe Thr Ala Ser Met  Pro Val Thr Asn Ala  Asp Tyr Ala
    1175                 1180                 1185

Ala Gln  Val Asp Leu Tyr Ala  Asp Lys Ala His Thr  Gln Leu Leu
    1190                 1195                 1200

Lys His  Phe Asp Thr Lys Val  Arg Leu Thr Ala Pro  Thr Phe Thr
    1205                 1210                 1215

Asp Leu  Lys Phe Asn Asn Gly  Ser Asp Gln Thr Ser  Glu Ala Thr
    1220                 1225                 1230

Ile Lys  Val Thr Gly Thr Val  Ser Ala Asp Thr Lys  Thr Val Asn
    1235                 1240                 1245

Val Gly  Asp Thr Val Ala Ala  Leu Asp Ala Gln His  His Phe Ser
    1250                 1255                 1260

Val Asp  Val Pro Val Asn Tyr  Gly Asp Asn Thr Ile  Lys Val Ile
    1265                 1270                 1275

Ala Thr  Asp Glu Asp Gly Asn  Thr Thr Thr Glu Gln  Lys Thr Ile
    1280                 1285                 1290

Thr Ser  Ser Tyr Asp Pro Asp  Met Leu Lys Asn Pro  Val Thr Phe
    1295                 1300                 1305

Asp Gln  Gly Val Thr Phe Gly  Ser Asn Glu Phe Asn  Ala Thr Ser
    1310                 1315                 1320

Ala Lys  Phe Tyr Asp Pro Lys  Thr Gly Ile Ala Thr  Ile Thr Gly
    1325                 1330                 1335

Lys Val  Lys His Pro Thr Thr  Thr Leu Gln Val Asp  Gly Lys Gln
    1340                 1345                 1350

Ile Pro  Ile Lys Asp Asp Leu  Thr Phe Ser Phe Thr  Leu Asp Leu
    1355                 1360                 1365

Gly Thr  Leu Gly Gln Lys Pro  Phe Gly Val Val Val  Gly Asp Thr
    1370                 1375                 1380

Thr Gln  Asn Lys Thr Phe Gln  Glu Ala Leu Thr Phe  Ile Leu Asp
    1385                 1390                 1395

Ala Val  Ala Pro Thr Leu Ser  Leu Asp Ser Ser Thr  Asp Ala Pro
    1400                 1405                 1410

Val Tyr  Thr Asn Asp Pro Asn  Phe Gln Ile Thr Gly  Thr Ala Thr
    1415                 1420                 1425

Asp Asn  Ala Gln Tyr Leu Ser  Leu Ser Ile Asn Gly  Ser Ser Val
    1430                 1435                 1440

Ala Ser  Gln Tyr Ala Asp Ile  Asn Ile Asn Ser Gly  Lys Pro Gly
    1445                 1450                 1455

His Met  Ala Ile Asp Gln Pro  Val Lys Leu Leu Glu  Gly Lys Asn
    1460                 1465                 1470

Val Leu  Thr Val Ala Val Thr  Asp Ser Glu Asp Asn  Thr Thr Thr
    1475                 1480                 1485

Lys Asn  Ile Thr Val Tyr Tyr  Glu Pro Lys Lys Thr  Leu Ala Ala
    1490                 1495                 1500

Pro Thr  Val Thr Pro Ser Thr  Thr Glu Pro Ala Gln  Thr Val Thr
    1505                 1510                 1515

Leu Thr  Ala Asn Ala Ala Ala  Thr Gly Glu Thr Val  Gln Tyr Ser
    1520                 1525                 1530

Ala Asp  Gly Gly Lys Thr Tyr  Gln Asp Val Pro Ala  Ala Gly Val
    1535                 1540                 1545
```

-continued

```
Thr Ile  Thr Ala Asn Gly Thr  Phe Lys Phe Lys Ser  Thr Asp Leu
    1550                 1555                 1560

Tyr Gly  Asn Glu Ser Pro Ala  Val Asp Tyr Val Val  Thr Asn Ile
    1565                 1570                 1575

Lys Ala  Asp Asp Pro Ala Gln  Leu Gln Ala Ala Lys  Gln Ala Leu
    1580                 1585                 1590

Thr Asn  Leu Ile Ala Ser Ala  Lys Thr Leu Ser Ala  Ser Gly Lys
    1595                 1600                 1605

Tyr Asp  Asp Ala Thr Thr Thr  Ala Leu Ala Ala Ala  Thr Gln Lys
    1610                 1615                 1620

Ala Gln  Thr Ala Leu Asp Gln  Thr Asn Ala Ser Val  Asp Ser Leu
    1625                 1630                 1635

Thr Gly  Ala Asn Arg Asp Leu  Gln Thr Ala Ile Asn  Gln Leu Ala
    1640                 1645                 1650

Ala Lys  Leu Pro Ala Asp Lys  Lys Thr Ser Leu Leu  Asn Gln Leu
    1655                 1660                 1665

Gln Ser  Val Lys Asp Ala Leu  Gly Thr Asp Leu Gly  Asn Gln Thr
    1670                 1675                 1680

Asp Pro  Ser Thr Gly Lys Thr  Phe Thr Ala Ala Leu  Asp Asp Leu
    1685                 1690                 1695

Val Ala  Gln Ala Gln Ala Gly  Thr Gln Thr Asp Asp  Gln Leu Gln
    1700                 1705                 1710

Ala Thr  Leu Ala Lys Ile Leu  Asp Glu Val Leu Ala  Lys Leu Ala
    1715                 1720                 1725

Glu Gly  Ile Lys Ala Ala Thr  Pro Ala Glu Val Gly  Asn Ala Lys
    1730                 1735                 1740

Asp Ala  Ala Thr Gly Lys Thr  Trp Tyr Ala Asp Ile  Ala Asp Thr
    1745                 1750                 1755

Leu Thr  Ser Gly Gln Ala Ser  Ala Asp Ala Ser Asp  Lys Leu Ala
    1760                 1765                 1770

His Leu  Gln Ala Leu Gln Ser  Leu Lys Thr Lys Val  Ala Ala Ala
    1775                 1780                 1785

Val Glu  Ala Asp Lys Thr Val  Gly Lys Gly Asp Asp  Thr Thr Gly
    1790                 1795                 1800

Thr Ser  Asp Lys Gly Ser Gly  Gln Gly Thr Pro Ala  Pro Ala Thr
    1805                 1810                 1815

Gly Asp  Thr Gly Lys Asp Lys  Gly Asp Glu Gly Ser  Gln Pro Ser
    1820                 1825                 1830

Ser Gly  Gly Asn Ile Pro Thr  Asn Pro Ala Thr Thr  Thr Ser Thr
    1835                 1840                 1845

Ser Ala  Asp Asp Thr Thr Asp  Arg Asn Gly Gln His  Thr Thr Gly
    1850                 1855                 1860

Thr Ser  Asp Lys Gly Gly Gly  Gln Gly Thr Pro Ala  Pro Ala Thr
    1865                 1870                 1875

Gly Asp  Thr Gly Lys Asp Lys  Gly Asp Glu Gly Ser  Gln Pro Ser
    1880                 1885                 1890

Ser Gly  Gly Asn Ile Pro Thr  Asn Pro Ala Thr Thr  Thr Ser Thr
    1895                 1900                 1905

Ser Ala  Asp Asp Thr Thr Asp  Arg Asn Gly Gln His  Thr Thr Gly
    1910                 1915                 1920

Thr Ser  Asp Lys Gly Gly Gly  Gln Gly Thr Pro Ala  Pro Ala Thr
    1925                 1930                 1935

Gly Asp  Thr Gly Lys Asp Lys  Gly Asp Glu Gly Ser  Gln Pro Ser
```

```
    1940                1945                1950

Ser Gly  Gly Asn Ile Pro Thr  Asn Pro Ala Thr Thr  Thr Ser Thr
    1955                1960                1965

Ser Thr  Asp Asp Thr Thr Asp  Arg Asn Gly Gln His  Thr Thr Gly
    1970                1975                1980

Lys Gly  Ala Leu Pro Lys Thr  Gly Glu Thr Thr Glu  Arg Pro Ala
    1985                1990                1995

Phe Gly  Phe Leu Gly Val Ile  Val Val Ile Leu Met  Gly Val Leu
    2000                2005                2010

Gly Leu  Lys Arg Lys Gln Arg  Glu Glu
    2015                2020
```

<210> SEQ ID NO 11
<211> LENGTH: 193
<212> TYPE: PRT
<213> ORGANISM: Lactococcus lactis

<400> SEQUENCE: 11

```
Met Arg Ala Ala Glu Gly Leu Phe Val Tyr Asn Lys Thr Asn Phe His
1               5                   10                  15

Tyr Leu Pro Gln Asn Ile Ala Phe Ala Asp Phe Lys Ser Gly Lys Phe
            20                  25                  30

Ala Thr Ser Gly Met Ser Met Ile Leu Ile Asp Ser Val Asn His Arg
        35                  40                  45

Ile Leu Asp Val Met Lys Asp Arg Gly Ala Gly Gln Leu Arg Ala Tyr
    50                  55                  60

Phe Asn Gln Tyr Ser Pro Ser Ala Arg Ala Ala Val Lys Thr Ile Thr
65                  70                  75                  80

Val Asp Leu Phe Thr Pro Tyr Arg Ala Met Ile Lys Asp Leu Phe Pro
                85                  90                  95

Asn Ala Asn Ile Val Ala Asp Arg Phe His Val Val Thr Gln Ala Tyr
            100                 105                 110

Arg Glu Leu Asn Lys Val Arg Ile Ser Val Met Lys Gln Phe Gly Ser
        115                 120                 125

Asp Ser Lys Glu Tyr Arg Gln Leu Lys Arg Phe Trp Lys Leu Leu Met
    130                 135                 140

Lys His Glu Asn Ala Leu Asp Tyr Met Thr Ser Lys Asn Arg Ile Asn
145                 150                 155                 160

Phe Lys His Ala Tyr Leu Thr Asp Lys Glu Val Ile Asp Arg Leu Leu
                165                 170                 175

Ala Leu Ser Asp Glu Leu Arg Asp Ala Tyr Ala Phe Tyr Gln Val Ile
            180                 185                 190

Leu
```

<210> SEQ ID NO 12
<211> LENGTH: 86
<212> TYPE: PRT
<213> ORGANISM: Lactococcus lactis

<400> SEQUENCE: 12

```
Met Asp Asn Asp Ile Arg Ile Leu Ile Gly Leu Thr Asp Leu Asn Ile
1               5                   10                  15

Asp Phe Asp Ala Lys Ala Glu Gln His Phe Asn Glu Thr Asn Leu Asn
            20                  25                  30

Gly Thr Ala Pro Ile Thr Trp Asn Leu Leu Leu Thr Tyr Ala Thr Asn
        35                  40                  45
```

```
Cys Glu Lys Phe Gly Thr Pro Met Val His Asn Gly Ile Lys Met Val
    50                  55                  60

Thr His Lys Gly Pro Arg Ile Ala Phe Lys Phe Gln Asn Tyr Arg Ile
65                  70                  75                  80

Arg Lys Gln Lys Phe Leu
                85


<210> SEQ ID NO 13
<211> LENGTH: 165
<212> TYPE: PRT
<213> ORGANISM: Lactococcus lactis

<400> SEQUENCE: 13

Met Ile Glu Asn Thr Ile Asn Ile Ala Tyr Ala Arg Lys Phe Tyr Lys
1               5                   10                  15

Thr Lys Asp Tyr His Ser Phe Cys Asn Leu Ile Lys Gly Asn Lys Gly
            20                  25                  30

Leu Phe Gly Asn Lys Thr Val Asn Gln Lys Ala Asn Ile Ser Phe Val
        35                  40                  45

Lys Ser Glu Gly Glu Lys His Thr His Ile Tyr Leu Asp Tyr Gln Glu
    50                  55                  60

Thr Cys Lys Val Ala His Pro Asn Phe Leu Gln Leu Ile Asn Leu Leu
65                  70                  75                  80

Lys Asn Tyr Asp Pro Glu Phe Ser Glu Glu Lys Leu Pro Thr Phe Asp
                85                  90                  95

Leu Asn Asp Lys Ile Phe Gly Glu Tyr Glu Ile Lys Val Ile Pro Ile
            100                 105                 110

Ser Lys Thr Lys Ile Val Asn Thr Ile Asp Asp Val Met Asn Glu Ile
        115                 120                 125

Ala Lys Glu Ile Val Leu Lys Tyr Asn Gln Asp Met Phe Lys Val Thr
    130                 135                 140

Ser Lys Leu Gly Glu Ile Ser Leu Thr Pro Ile Gln Glu Lys Phe Asp
145                 150                 155                 160

Lys Leu Lys Asp Ile
                165


<210> SEQ ID NO 14
<211> LENGTH: 385
<212> TYPE: PRT
<213> ORGANISM: Lactococcus lactis

<400> SEQUENCE: 14

Met Ile Ile Pro Glu Lys Gln Asn Lys Gln Lys Gln Val Leu Thr Leu
1               5                   10                  15

Asn Glu Leu Glu Lys Arg Lys Val Val Glu His Asn Ala Leu Ile Gln
            20                  25                  30

Ser Val Ala Lys Met Gln Lys Thr Ala Leu Lys Met Phe Glu Leu Ala
        35                  40                  45

Val Ser Cys Ile Asp Thr Glu Glu Pro Pro Lys Asn Asn Thr Val Tyr
    50                  55                  60

Leu Ser Lys Ser Glu Leu Phe Lys Phe Phe Glu Val Ser Ser Ser Ser
65                  70                  75                  80

Lys His Ser Gln Phe Lys Glu Ala Val Asn Tyr Met Gln Lys Gln Ala
                85                  90                  95

Phe Phe Asn Ile Lys Ala Asp Lys Lys Leu Gly Ile Glu Tyr Glu Ser
            100                 105                 110
```

```
Ile Val Pro Ile Pro Tyr Val Lys Trp Asn Asp Tyr Asn Asp Glu Val
        115                 120                 125

Thr Ile Arg Phe Asp Gln Ala Ile Met Pro Tyr Leu Ile Asp Leu Lys
    130                 135                 140

Ala Glu Phe Thr Gln Tyr Lys Ile Ser Glu Leu Gln Lys Leu Asn Ser
145                 150                 155                 160

Lys Tyr Ser Ile Ile Leu Tyr Arg Trp Leu Ser Met Asn Tyr Asn Gln
                165                 170                 175

Tyr Glu His Tyr Ser Val Lys Gly Gly Arg Arg Ala Asp Gln Val Glu
            180                 185                 190

Ala Tyr Arg Thr Pro Ser Ile Lys Val Lys Glu Leu Arg Glu Ile Thr
        195                 200                 205

Asp Thr Ile Asn Glu His Gln His Phe Pro His Phe Glu Thr Arg Val
    210                 215                 220

Leu Lys Lys Ala Ile Glu Glu Ile Asn Ala His Thr Ser Phe Asn Val
225                 230                 235                 240

Thr Tyr Glu Lys Val Lys Lys Gly Arg Ser Ile Asp Ser Ile Val Phe
                245                 250                 255

His Ile Glu Lys Lys Arg Met Ala Asp Asp Asn Ser Tyr Lys Leu Glu
            260                 265                 270

Asp Lys Val Tyr Gln Glu Asp Lys Ala Arg Lys Ala Glu Thr Glu Lys
        275                 280                 285

Asp Leu Val Phe Gln Ala Met Gln Ser Pro Tyr Thr Arg Leu Leu Ile
    290                 295                 300

Glu Asn Met Phe Leu Asn Val Tyr Glu Thr Thr Asp Ser Gln Ile Met
305                 310                 315                 320

Ala Gly Leu Gln Lys Asn Val Tyr Pro Leu Tyr Asp Glu Leu Lys Glu
                325                 330                 335

Leu Arg Gly Leu Asn Gly Val Lys Asp His Leu Ser Tyr Val Ser Ser
            340                 345                 350

Lys Gln Glu Ala Tyr Ser Lys Arg Asn Val Ala Lys Tyr Leu Lys Lys
        355                 360                 365

Ala Ile Glu Gln Tyr Leu Pro Thr Val Lys Arg Gln Asp Leu Asn His
    370                 375                 380

Glu
385


<210> SEQ ID NO 15
<211> LENGTH: 208
<212> TYPE: PRT
<213> ORGANISM: Lactococcus lactis

<400> SEQUENCE: 15

Met Ser Glu Asp Leu Lys Thr Ile Lys Glu Leu Ala Asp Glu Leu Gly
1               5                   10                  15

Val Ser Lys Ser Tyr Val Asp Lys Ile Ile Arg Ile Leu Lys Leu His
            20                  25                  30

Thr Lys Leu Asp Lys Val Gly Asn Lys Tyr Val Ile Ser Lys Lys Gln
        35                  40                  45

Glu Lys Ser Ile Ile Thr Arg Ile Glu Asn Ser Lys Ser Thr Thr Glu
    50                  55                  60

Thr His Thr Glu Ser Thr Thr Gln Ser His Thr Lys Val Asp Ala Glu
65                  70                  75                  80

Val Asp Phe Leu Lys Glu Glu Ile Ala Tyr Leu Lys Ser Asn His Asp
```

```
                85                  90                  95

Lys Gln Leu Thr Asn Lys Asp Lys Gln Ile Glu Thr Leu Ser Asn Leu
            100                 105                 110

Leu Asp Gln Gln Gln Arg Leu Ala Leu Gln Asp Lys Lys Trp Leu Glu
        115                 120                 125

Glu Tyr Lys Ala Glu Ile Asn Asp Leu Lys Ala Leu Lys Met Pro Ser
    130                 135                 140

Glu Asp Thr Lys Glu Glu Gln Ser Asn Tyr Arg Ser Leu Glu Lys Glu
145                 150                 155                 160

Lys Asp Phe Val Gln Thr Ile Gln Glu Ser Tyr Glu Ser Glu Ile Lys
                165                 170                 175

Val Leu Asn Gln Lys Leu Ala Glu Gln Glu Glu Gln Ile Gln Glu Ile
            180                 185                 190

Gln Lys Glu Lys Glu Thr Lys Glu Lys Lys Trp Phe Gln Phe Trp Lys
        195                 200                 205


<210> SEQ ID NO 16
<211> LENGTH: 76
<212> TYPE: PRT
<213> ORGANISM: Lactococcus lactis

<400> SEQUENCE: 16

Met Ala Gln Thr Phe Asp Arg Lys Ile Leu Arg Ala Leu Gln Asp Asn
1               5                   10                  15

Gly Val Arg Glu Ile Arg Ala Tyr Glu Val Val Ser Lys Arg Leu Thr
            20                  25                  30

Ile Phe Gln Thr Asp Arg Gly Thr Phe Lys Tyr Ser Asp Ser Leu Tyr
        35                  40                  45

Arg Leu Val Ala Pro Arg Gln Glu Leu Trp Arg Asn Cys Thr Thr Gly
    50                  55                  60

Phe Ile Ser Glu Glu Lys Tyr His Phe Tyr Lys Lys
65                  70                  75


<210> SEQ ID NO 17
<211> LENGTH: 226
<212> TYPE: PRT
<213> ORGANISM: Lactococcus lactis

<400> SEQUENCE: 17

Met Asn His Phe Lys Gly Lys Gln Phe Lys Lys Asp Val Ile Ile Val
1               5                   10                  15

Ala Val Gly Tyr Tyr Leu Arg Tyr Asn Leu Ser Tyr Arg Glu Ile Gln
            20                  25                  30

Glu Leu Leu Tyr Asp Arg Gly Ile Asn Val Cys His Thr Thr Ile Tyr
        35                  40                  45

Arg Trp Val Gln Glu Tyr Ser Lys Val Leu Tyr His Leu Trp Lys Lys
    50                  55                  60

Lys Asn Arg Gln Ser Phe Tyr Ser Trp Lys Met Asp Glu Thr Tyr Ile
65                  70                  75                  80

Lys Ile Lys Gly Arg Trp His Tyr Leu Tyr Arg Ala Ile Asp Ala Asp
                85                  90                  95

Gly Leu Thr Leu Asp Ile Trp Leu Arg Lys Lys Arg Asp Thr Gln Ala
            100                 105                 110

Ala Tyr Ala Phe Leu Lys Arg Leu His Lys Gln Phe Gly Gln Pro Arg
        115                 120                 125

Val Ile Val Thr Asp Lys Ala Pro Ser Ile Gly Ser Ala Phe Arg Lys
```

```
    130                 135                 140

Leu Gln Ser Asn Gly Leu Tyr Thr Lys Thr Glu His Arg Thr Val Lys
145                 150                 155                 160

Tyr Leu Asn Asn Leu Ile Glu Gln Asp His Arg Pro Ile Lys Arg Arg
                165                 170                 175

Asn Lys Phe Tyr Arg Ser Leu Arg Thr Ala Ser Thr Thr Ile Lys Gly
            180                 185                 190

Met Glu Thr Ile Arg Gly Ile Tyr Lys Lys Asn Arg Arg Asn Gly Thr
        195                 200                 205

Leu Phe Gly Phe Ser Val Ser Thr Glu Ile Lys Val Leu Met Gly Ile
    210                 215                 220

Leu Ala
225


<210> SEQ ID NO 18
<211> LENGTH: 316
<212> TYPE: PRT
<213> ORGANISM: Lactococcus lactis

<400> SEQUENCE: 18

Met Lys Glu Tyr Phe Gln Gly Asp Glu Phe Lys Asp Ile Ser Lys Asn
1               5                   10                  15

Gly Lys Asp Arg Lys Trp Lys Glu Arg Lys Ile Asn Asn Leu Asn Leu
            20                  25                  30

Ala Lys Ile Phe Asp Ser Leu Asp Tyr Pro Asp Ser Phe Ile Phe Asn
        35                  40                  45

Ile Lys Ser Cys Ala Glu Tyr Leu Asn Phe Lys Arg Ser Ser Asp Gly
    50                  55                  60

Ser Leu Arg Leu Phe Gln Met Tyr Thr Cys Lys Asn Lys Gln Cys Ala
65                  70                  75                  80

Ile Cys Ser Trp Arg Arg Ser Met Lys Tyr Gln Val Gln Ile Ser Lys
                85                  90                  95

Ile Val Glu Glu Ala Met Ile Arg Lys Pro Lys Gly Arg Phe Leu Phe
            100                 105                 110

Leu Thr Leu Thr Val Glu Asn Val Ser Gly Glu Gly Leu Asn Asn Glu
        115                 120                 125

Leu Ser Leu Leu Ser Glu Ala Phe Asn Arg Leu Met Lys Tyr Lys Lys
    130                 135                 140

Val Ser Lys Asn Ile Leu Gly Phe Leu Arg Ala Thr Glu Val Thr Ile
145                 150                 155                 160

Asn Glu Ser Met Asp Thr Tyr His Pro His Ile His Val Leu Leu Phe
                165                 170                 175

Ile Ser Pro Thr Tyr Phe Lys Asn Lys Asn Asn Tyr Ile Ser Gln Asp
            180                 185                 190

Glu Trp Thr Glu Leu Trp Lys Lys Ser Ala Lys Leu Asp Tyr Arg Pro
        195                 200                 205

Ile Val Asp Val Arg Ser Ile Lys Pro Lys Asn Glu Lys Thr Ser Asp
    210                 215                 220

Ile Arg Ser Ala Ile Leu Glu Thr Ala Lys Tyr Pro Val Lys Pro Met
225                 230                 235                 240

Glu Leu Asn Tyr Asp Ser Ala Lys Val Val Asp Asp Leu Gln Lys Gly
                245                 250                 255

Leu Tyr Arg Lys Arg Gln Ile Ala Phe Gly Gly Leu Phe Lys Gln Ile
            260                 265                 270
```

-continued

```
Lys Lys Glu Leu Glu Leu Asp Asp Ile Glu Asn Gly Asp Leu Ile Asn
        275                 280                 285

Ile Gly Asp Glu Glu Asn Pro Ile Ser Asp Gly Glu Ile Ile Ser Val
    290                 295                 300

Leu Trp Asn His Glu Arg Gln Asn Tyr Tyr Val Arg
305                 310                 315


<210> SEQ ID NO 19
<211> LENGTH: 96
<212> TYPE: PRT
<213> ORGANISM: Lactococcus lactis

<400> SEQUENCE: 19

Met Ile Asn Tyr Gln Gly Glu Asp Phe Thr Glu Thr Glu Phe Tyr Gly
1               5                   10                  15

Arg Glu Ile Leu Glu Ala Ile Gln Leu Thr Asn Lys Phe Pro Thr Pro
            20                  25                  30

Lys Lys Val Leu Ile Asp Met Leu Glu Glu Met Ile His Glu Gln Leu
        35                  40                  45

Asp Phe Ile Asp Lys Glu Glu Leu Asn Asn Tyr Ile Asn Ala Lys Lys
    50                  55                  60

Tyr Val Gln Thr Leu Thr Glu Asp Glu Val Lys Asn Leu Cys Phe Glu
65                  70                  75                  80

Val Lys Asp Leu Tyr Glu Asp Val Leu Lys Glu Phe Glu Ile Lys Leu
                85                  90                  95


<210> SEQ ID NO 20
<211> LENGTH: 86
<212> TYPE: PRT
<213> ORGANISM: Lactococcus lactis

<400> SEQUENCE: 20

Met Thr Cys Ser Asn Leu Thr Ile His Leu His Ala Lys Asn Arg Ser
1               5                   10                  15

Lys Leu Phe Gly Ser Lys Lys Tyr Ala Leu Gln Glu Leu Glu Ala Glu
            20                  25                  30

Ser Thr Ala Phe Val Val Ala Asn His Leu Asn Ile Asp Thr Lys Asp
        35                  40                  45

Tyr Ser Ile Gly Tyr Leu Asn Ser Trp Gly Phe Asp Lys Ile Ser Asp
    50                  55                  60

Glu Gln Leu Glu Asn Val Ile Lys Asn Asp Lys Leu Ser Asn Asn Lys
65                  70                  75                  80

Ile Lys Gly Glu Asn Glu
                85


<210> SEQ ID NO 21
<211> LENGTH: 170
<212> TYPE: PRT
<213> ORGANISM: Lactococcus lactis

<400> SEQUENCE: 21

Met Met Leu Lys Lys Glu Trp Gln Ala Ile Leu Lys His Lys Phe Phe
1               5                   10                  15

Ile Ile Val Ile Ile Ala Leu Ala Leu Val Pro Ala Ile Tyr Asn Tyr
            20                  25                  30

Ile Phe Leu Gly Ser Met Trp Asp Pro Ser Gly Lys Leu Asn Asp Leu
        35                  40                  45

Pro Val Ala Val Val Asn Leu Asp Lys Thr Ser Glu Leu Asn Gly Lys
```

```
    50                  55                  60

Lys Phe Lys Leu Gly Asp Asp Val Ile Thr Glu Met Lys Lys Ser Lys
65                  70                  75                  80

Asp Leu Asp Tyr His Phe Val Ser Lys Asp Lys Ala Ser Glu Gly Ile
                85                  90                  95

Lys Lys Gly Asp Tyr Tyr Met Val Ile Thr Phe Pro Glu Asn Phe Ser
            100                 105                 110

Glu Asn Ala Thr Thr Leu Met Asn Lys Glu Pro Lys Thr Val Gln Leu
        115                 120                 125

Asp Tyr Gln Thr Thr Arg Gly His Asn Tyr Ile Ser Ser Lys Met Ser
    130                 135                 140

Glu Ser Ala Met Asn Gln Leu Lys Ser Glu Val Ser Lys Asn Ile Thr
145                 150                 155                 160

Gln Thr Tyr Thr Lys Thr Arg Ile Ala Ser
                165                 170


<210> SEQ ID NO 22
<211> LENGTH: 299
<212> TYPE: PRT
<213> ORGANISM: Lactococcus lactis

<400> SEQUENCE: 22

Met Lys Lys Lys Met Arg Leu Lys Val Leu Leu Ala Ser Thr Ala Thr
1               5                   10                  15

Ala Leu Leu Leu Leu Ser Gly Cys Gln Ser Asn Gln Thr Asp Gln Thr
            20                  25                  30

Val Ala Thr Tyr Ser Gly Gly Lys Val Thr Glu Ser Ser Phe Tyr Lys
        35                  40                  45

Glu Leu Lys Gln Ser Pro Thr Thr Lys Thr Met Leu Ala Asn Met Leu
    50                  55                  60

Ile Tyr Arg Ala Leu Asn His Ala Tyr Gly Lys Ser Val Ser Thr Lys
65                  70                  75                  80

Thr Val Asn Asp Ala Tyr Asp Ser Tyr Lys Gln Gln Tyr Gly Glu Asn
                85                  90                  95

Phe Asp Ala Phe Leu Ser Gln Asn Gly Phe Ser Arg Ser Ser Phe Lys
            100                 105                 110

Glu Ser Leu Arg Thr Asn Phe Leu Ser Glu Val Ala Leu Lys Lys Leu
        115                 120                 125

Lys Lys Val Ser Glu Ser Gln Leu Lys Ala Ala Trp Lys Thr Tyr Gln
    130                 135                 140

Pro Lys Val Thr Val Gln His Ile Leu Thr Ser Asp Glu Asp Thr Ala
145                 150                 155                 160

Lys Gln Val Ile Ser Asp Leu Ala Ala Gly Lys Asp Phe Ala Met Leu
                165                 170                 175

Ala Lys Thr Asp Ser Ile Asp Thr Ala Thr Lys Asp Asn Gly Gly Lys
            180                 185                 190

Ile Ser Phe Glu Leu Asn Asn Lys Thr Leu Asp Ala Thr Phe Lys Asp
        195                 200                 205

Ala Ala Tyr Lys Leu Lys Asn Gly Asp Tyr Thr Gln Thr Pro Val Lys
    210                 215                 220

Val Thr Asp Gly Tyr Glu Val Ile Lys Met Ile Asn His Pro Ala Lys
225                 230                 235                 240

Gly Thr Phe Thr Ser Ser Lys Lys Val Leu Thr Ala Ser Val Tyr Ala
                245                 250                 255
```

-continued

```
Lys Trp Ser Arg Asp Ser Ser Ile Met Gln Arg Val Ile Ser Gln Val
            260                 265                 270

Leu Lys Asn Gln His Val Thr Ile Lys Asp Lys Asp Leu Ala Asp Ala
        275                 280                 285

Leu Asp Ser Tyr Lys Lys Leu Ala Thr Thr Asn
    290                 295


<210> SEQ ID NO 23
<211> LENGTH: 2022
<212> TYPE: PRT
<213> ORGANISM: Lactococcus lactis

<400> SEQUENCE: 23

Met Gln Arg Lys Lys Lys Gly Leu Ser Phe Leu Leu Ala Gly Thr Val
1               5                   10                  15

Ala Leu Gly Ala Leu Ala Val Leu Pro Val Gly Glu Ile Gln Ala Lys
            20                  25                  30

Ala Ala Ile Ser Gln Gln Thr Lys Gly Ser Ser Leu Ala Asn Thr Val
        35                  40                  45

Thr Ala Ala Thr Ala Lys Gln Ala Ala Thr Asp Thr Thr Ala Ala Thr
    50                  55                  60

Thr Asn Gln Ala Ile Ala Thr Gln Leu Ala Ala Lys Gly Ile Asp Tyr
65                  70                  75                  80

Asn Lys Leu Asn Lys Val Gln Gln Gln Asp Ile Tyr Val Asp Val Ile
                85                  90                  95

Val Gln Met Ser Ala Ala Pro Ala Ser Glu Asn Gly Thr Leu Arg Thr
            100                 105                 110

Asp Tyr Ser Ser Thr Ala Glu Ile Gln Gln Glu Thr Asn Lys Val Ile
        115                 120                 125

Ala Ala Gln Ala Ser Val Lys Ala Ala Val Glu Gln Val Thr Gln Gln
    130                 135                 140

Thr Ala Gly Glu Ser Tyr Gly Tyr Val Val Asn Gly Phe Ser Thr Lys
145                 150                 155                 160

Val Arg Val Val Asp Ile Pro Lys Leu Lys Gln Ile Ala Gly Val Lys
                165                 170                 175

Thr Val Thr Leu Ala Lys Val Tyr Tyr Pro Thr Asp Ala Lys Ala Asn
            180                 185                 190

Ser Met Ala Asn Val Gln Ala Val Trp Ser Asn Tyr Lys Tyr Lys Gly
        195                 200                 205

Glu Gly Thr Val Val Ser Val Ile Asp Ser Gly Ile Asp Pro Thr His
    210                 215                 220

Lys Asp Met Arg Leu Ser Asp Asp Lys Asp Val Lys Leu Thr Lys Ser
225                 230                 235                 240

Asp Val Glu Lys Phe Thr Asp Thr Val Lys His Gly Arg Tyr Phe Asn
                245                 250                 255

Ser Lys Val Pro Tyr Gly Phe Asn Tyr Ala Asp Asn Asn Asp Thr Ile
            260                 265                 270

Thr Asp Asp Lys Val Asp Glu Gln His Gly Met His Val Ala Gly Ile
        275                 280                 285

Ile Gly Ala Asn Gly Thr Gly Asp Asp Pro Ala Lys Ser Val Val Gly
    290                 295                 300

Val Ala Pro Glu Ala Gln Leu Leu Ala Met Lys Val Phe Thr Asn Ser
305                 310                 315                 320

Asp Thr Ser Ala Thr Thr Gly Ser Asp Thr Leu Val Ser Ala Ile Glu
                325                 330                 335
```

```
Asp Ser Ala Lys Ile Gly Ala Asp Val Leu Asn Met Ser Leu Gly Ser
            340                 345                 350

Asp Ser Gly Asn Gln Thr Leu Glu Asp Pro Glu Ile Ala Ala Val Gln
        355                 360                 365

Asn Ala Asn Glu Ser Gly Thr Ala Ala Val Ile Ser Ala Gly Asn Ser
    370                 375                 380

Gly Thr Ser Gly Ser Ala Thr Glu Gly Val Asn Lys Asp Tyr Tyr Gly
385                 390                 395                 400

Leu Gln Asp Asn Glu Met Val Gly Thr Pro Gly Thr Ser Arg Gly Ala
                405                 410                 415

Thr Thr Val Ala Ser Ala Glu Asn Thr Asp Val Ile Thr Gln Ala Val
            420                 425                 430

Thr Ile Thr Asp Gly Thr Gly Leu Gln Leu Gly Pro Glu Thr Ile Gln
        435                 440                 445

Leu Ser Ser Asn Asp Phe Thr Gly Ser Phe Asp Gln Lys Lys Phe Tyr
    450                 455                 460

Val Val Lys Asp Ala Ser Gly Asn Leu Ser Lys Gly Lys Val Ala Asp
465                 470                 475                 480

Tyr Thr Ala Asp Ala Lys Gly Lys Ile Ala Ile Val Lys Arg Gly Glu
                485                 490                 495

Leu Thr Phe Asp Asp Lys Gln Lys Tyr Ala Gln Ala Ala Gly Ala Ala
            500                 505                 510

Gly Leu Ile Ile Val Asn Asn Asp Gly Thr Ala Thr Pro Val Thr Ser
        515                 520                 525

Met Ala Leu Thr Thr Thr Phe Pro Thr Phe Gly Leu Ser Ser Val Thr
    530                 535                 540

Gly Gln Lys Leu Val Asp Trp Val Thr Ala His Pro Asp Asp Ser Leu
545                 550                 555                 560

Gly Val Lys Ile Ala Leu Thr Leu Val Pro Asn Gln Lys Tyr Thr Glu
                565                 570                 575

Asp Lys Met Ser Asp Phe Thr Ser Tyr Gly Pro Val Ser Asn Leu Ser
            580                 585                 590

Phe Lys Pro Asp Ile Thr Ala Pro Gly Gly Asn Ile Trp Ser Thr Gln
        595                 600                 605

Asn Asn Asn Gly Tyr Thr Asn Met Ser Gly Thr Ser Met Ala Ser Pro
    610                 615                 620

Phe Ile Ala Gly Ser Gln Ala Leu Leu Lys Gln Ala Leu Asn Asn Lys
625                 630                 635                 640

Asn Asn Pro Phe Tyr Ala Tyr Tyr Lys Gln Leu Lys Gly Thr Ala Leu
                645                 650                 655

Thr Asp Phe Leu Lys Thr Val Glu Met Asn Thr Ala Gln Pro Ile Asn
            660                 665                 670

Asp Ile Asn Tyr Asn Asn Val Ile Val Ser Pro Arg Arg Gln Gly Ala
        675                 680                 685

Gly Leu Val Asp Val Lys Ala Ala Ile Asp Ala Leu Glu Lys Asn Pro
    690                 695                 700

Ser Thr Val Val Ala Glu Asn Gly Tyr Pro Ala Val Glu Leu Lys Asp
705                 710                 715                 720

Phe Thr Ser Thr Asp Lys Thr Phe Lys Leu Thr Phe Thr Asn Arg Thr
                725                 730                 735

Thr His Glu Leu Thr Tyr Gln Met Asp Ser Asn Thr Asp Thr Asn Ala
            740                 745                 750
```

-continued

```
Val Tyr Thr Ser Ala Thr Asp Pro Asn Ser Gly Val Leu Tyr Asp Lys
        755                 760                 765

Lys Ile Asp Gly Ala Ala Ile Lys Ala Gly Ser Asn Ile Thr Val Pro
    770                 775                 780

Ala Gly Lys Thr Ala Gln Ile Glu Phe Thr Leu Ser Leu Pro Lys Ser
785                 790                 795                 800

Phe Asp Gln Gln Gln Phe Val Glu Gly Phe Leu Asn Phe Lys Gly Ser
                805                 810                 815

Asp Gly Ser Arg Leu Asn Leu Pro Tyr Met Gly Phe Phe Gly Asp Trp
            820                 825                 830

Asn Asp Gly Lys Ile Val Asp Ser Leu Asn Gly Ile Thr Tyr Ser Pro
        835                 840                 845

Ala Gly Gly Asn Phe Gly Thr Val Pro Leu Leu Thr Asn Lys Asn Thr
    850                 855                 860

Gly Thr Gln Tyr Tyr Gly Gly Met Val Thr Asp Ala Asp Gly Asn Gln
865                 870                 875                 880

Thr Val Asp Asp Gln Ala Ile Ala Phe Ser Ser Asp Lys Asn Ala Leu
                885                 890                 895

Tyr Asn Asp Ile Ser Met Lys Tyr Tyr Leu Leu Arg Asn Ile Ser Asn
            900                 905                 910

Val Gln Val Asp Ile Leu Asp Gly Gln Gly Asn Lys Val Thr Thr Leu
        915                 920                 925

Ser Ser Ser Thr Asn Leu Thr Lys Thr Tyr Tyr Asn Ala His Ser Gln
    930                 935                 940

Gln Tyr Ile Tyr Tyr His Ala Pro Ala Trp Asp Gly Thr Tyr Tyr Asp
945                 950                 955                 960

Gln Arg Asp Gly Asn Ile Lys Thr Ala Asp Asp Gly Ser Tyr Thr Tyr
                965                 970                 975

Arg Ile Ser Gly Val Pro Glu Gly Gly Asp Lys Arg Gln Val Phe Asp
            980                 985                 990

Val Pro Phe Lys Leu Asp Ser Lys  Ala Pro Thr Val Arg  His Val Ala
        995                 1000                1005

Leu Ser  Ala Lys Thr Lys Asn  Gly Lys Thr Gln Tyr  Tyr Leu Thr
    1010                1015                1020

Ala Glu  Val Lys Asp Asp Leu  Ser Gly Leu Asp Ala  Thr Lys Ser
    1025                1030                1035

Val Lys  Thr Ala Ile Asn Glu  Val Thr Asn Leu Asp  Ala Thr Phe
    1040                1045                1050

Thr Asp  Ala Gly Thr Thr Ala  Asp Gly Tyr Thr Lys  Ile Glu Thr
    1055                1060                1065

Pro Leu  Ser Asp Glu Gln Ala  Gln Ala Leu Gly Asn  Gly Asp Asn
    1070                1075                1080

Ser Ala  Glu Leu Tyr Leu Thr  Asp Asn Ala Ser Asn  Ala Thr Asp
    1085                1090                1095

Gln Asp  Ala Ser Val Gln Lys  Pro Gly Ser Thr Ser  Phe Asp Leu
    1100                1105                1110

Ile Val  Asn Gly Ser Gly Ile  Pro Asp Lys Ile Ser  Ser Thr Thr
    1115                1120                1125

Thr Gly  Tyr Glu Ala Asn Thr  Gln Gly Gly Gly Thr  Tyr Thr Phe
    1130                1135                1140

Ser Gly  Thr Tyr Pro Ala Ala  Val Asp Gly Thr Tyr  Thr Asp Ala
    1145                1150                1155

Gln Gly  Lys Lys His Asp Leu  Asn Thr Thr Tyr Asp  Ala Ala Thr
```

```
    1160                1165                1170

Asn Ser  Phe Thr Ala Ser Met  Pro Val Thr Asn Ala  Asp Tyr Ala
    1175                1180                1185

Ala Gln  Val Asp Leu Tyr Ala  Asp Lys Ala His Thr  Gln Leu Leu
    1190                1195                1200

Lys His  Phe Asp Thr Lys Val  Arg Leu Thr Ala Pro  Thr Phe Thr
    1205                1210                1215

Asp Leu  Lys Phe Asn Asn Gly  Ser Asp Gln Thr Ser  Glu Ala Thr
    1220                1225                1230

Ile Lys  Val Thr Gly Thr Val  Ser Ala Asp Thr Lys  Thr Val Asn
    1235                1240                1245

Val Gly  Asp Thr Val Ala Ala  Leu Asp Ala Gln His  His Phe Ser
    1250                1255                1260

Val Asp  Val Pro Val Asn Tyr  Gly Asp Asn Thr Ile  Lys Val Ile
    1265                1270                1275

Ala Thr  Asp Glu Asp Gly Asn  Thr Thr Thr Glu Gln  Lys Thr Ile
    1280                1285                1290

Thr Ser  Ser Tyr Asp Pro Asp  Met Leu Lys Asn Pro  Val Thr Phe
    1295                1300                1305

Asp Gln  Gly Val Thr Phe Gly  Ser Asn Glu Phe Asn  Ala Thr Ser
    1310                1315                1320

Ala Lys  Phe Tyr Asp Pro Lys  Thr Gly Ile Ala Thr  Ile Thr Gly
    1325                1330                1335

Lys Val  Lys His Pro Thr Thr  Thr Leu Gln Val Asp  Gly Lys Gln
    1340                1345                1350

Ile Pro  Ile Lys Asp Asp Leu  Thr Phe Ser Phe Thr  Leu Asp Leu
    1355                1360                1365

Gly Thr  Leu Gly Gln Lys Pro  Phe Gly Val Val Val  Gly Asp Thr
    1370                1375                1380

Thr Gln  Asn Lys Thr Phe Gln  Glu Ala Leu Thr Phe  Ile Leu Asp
    1385                1390                1395

Ala Val  Ala Pro Thr Leu Ser  Leu Asp Ser Ser Thr  Asp Ala Pro
    1400                1405                1410

Val Tyr  Thr Asn Asp Pro Asn  Phe Gln Ile Thr Gly  Thr Ala Thr
    1415                1420                1425

Asp Asn  Ala Gln Tyr Leu Ser  Leu Ser Ile Asn Gly  Ser Ser Val
    1430                1435                1440

Ala Ser  Gln Tyr Ala Asp Ile  Asn Ile Asn Ser Gly  Lys Pro Gly
    1445                1450                1455

His Met  Ala Ile Asp Gln Pro  Val Lys Leu Leu Glu  Gly Lys Asn
    1460                1465                1470

Val Leu  Thr Val Ala Val Thr  Asp Ser Glu Asp Asn  Thr Thr Thr
    1475                1480                1485

Lys Asn  Ile Thr Val Tyr Tyr  Glu Pro Lys Lys Thr  Leu Ala Ala
    1490                1495                1500

Pro Thr  Val Thr Pro Ser Thr  Thr Glu Pro Ala Gln  Thr Val Thr
    1505                1510                1515

Leu Thr  Ala Asn Ala Ala Ala  Thr Gly Glu Thr Val  Gln Tyr Ser
    1520                1525                1530

Ala Asp  Gly Gly Lys Thr Tyr  Gln Asp Val Pro Ala  Ala Gly Val
    1535                1540                1545

Thr Ile  Thr Ala Asn Gly Thr  Phe Lys Phe Lys Ser  Thr Asp Leu
    1550                1555                1560
```

Tyr Gly Asn Glu Ser Pro Ala Val Asp Tyr Val Val Thr Asn Ile
1565 1570 1575

Lys Ala Asp Asp Pro Ala Gln Leu Gln Ala Ala Lys Gln Ala Leu
1580 1585 1590

Thr Asn Leu Ile Ala Ser Ala Lys Thr Leu Ser Ala Ser Gly Lys
1595 1600 1605

Tyr Asp Asp Ala Thr Thr Thr Ala Leu Ala Ala Ala Thr Gln Lys
1610 1615 1620

Ala Gln Thr Ala Leu Asp Gln Thr Asn Ala Ser Val Asp Ser Leu
1625 1630 1635

Thr Gly Ala Asn Arg Asp Leu Gln Thr Ala Ile Asn Gln Leu Ala
1640 1645 1650

Ala Lys Leu Pro Ala Asp Lys Lys Thr Ser Leu Leu Asn Gln Leu
1655 1660 1665

Gln Ser Val Lys Asp Ala Leu Gly Thr Asp Leu Gly Asn Gln Thr
1670 1675 1680

Asp Pro Ser Thr Gly Lys Thr Phe Thr Ala Ala Leu Asp Asp Leu
1685 1690 1695

Val Ala Gln Ala Gln Ala Gly Thr Gln Thr Asp Asp Gln Leu Gln
1700 1705 1710

Ala Thr Leu Ala Lys Ile Leu Asp Glu Val Leu Ala Lys Leu Ala
1715 1720 1725

Glu Gly Ile Lys Ala Ala Thr Pro Ala Glu Val Gly Asn Ala Lys
1730 1735 1740

Asp Ala Ala Thr Gly Lys Thr Trp Tyr Ala Asp Ile Ala Asp Thr
1745 1750 1755

Leu Thr Ser Gly Gln Ala Ser Ala Asp Ala Ser Asp Lys Leu Ala
1760 1765 1770

His Leu Gln Ala Leu Gln Ser Leu Lys Thr Lys Val Ala Ala Ala
1775 1780 1785

Val Glu Ala Asp Lys Thr Val Gly Lys Gly Asp Asp Thr Thr Gly
1790 1795 1800

Thr Ser Asp Lys Gly Ser Gly Gln Gly Thr Pro Ala Pro Ala Thr
1805 1810 1815

Gly Asp Thr Gly Lys Asp Lys Gly Asp Glu Gly Ser Gln Pro Ser
1820 1825 1830

Ser Gly Gly Asn Ile Pro Thr Asn Pro Ala Thr Thr Thr Ser Thr
1835 1840 1845

Ser Ala Asp Asp Thr Thr Asp Arg Asn Gly Gln His Thr Thr Gly
1850 1855 1860

Thr Ser Asp Lys Gly Gly Gly Gln Gly Thr Pro Ala Pro Ala Thr
1865 1870 1875

Gly Asp Thr Gly Lys Asp Lys Gly Asp Glu Gly Ser Gln Pro Ser
1880 1885 1890

Ser Gly Gly Asn Ile Pro Thr Asn Pro Ala Thr Thr Thr Ser Thr
1895 1900 1905

Ser Ala Asp Asp Thr Thr Asp Arg Asn Gly Gln His Thr Thr Gly
1910 1915 1920

Thr Ser Asp Lys Gly Gly Gly Gln Gly Thr Pro Ala Pro Ala Thr
1925 1930 1935

Gly Asp Thr Gly Lys Asp Lys Gly Asp Glu Gly Ser Gln Pro Ser
1940 1945 1950

```
Ser Gly  Gly Asn Ile Pro Thr  Asn Pro Ala Thr Thr  Thr Ser Thr
    1955                1960                1965

Ser Thr  Asp Asp Thr Thr Asp  Arg Asn Gly Gln His  Thr Thr Gly
    1970                1975                1980

Lys Gly  Ala Leu Pro Lys Thr  Gly Glu Thr Thr Glu  Arg Pro Ala
    1985                1990                1995

Phe Gly  Phe Leu Gly Val Ile  Val Val Ile Leu Met  Gly Val Leu
    2000                2005                2010

Gly Leu  Lys Arg Lys Gln Arg  Glu Glu
    2015                2020
```

<210> SEQ ID NO 24
<211> LENGTH: 211
<212> TYPE: PRT
<213> ORGANISM: Lactococcus lactis

<400> SEQUENCE: 24

```
Met Thr Gln Phe Thr Thr Glu Leu Leu Asn Phe Leu Ala Gln Lys Gln
1               5                   10                  15

Asp Ile Asp Glu Phe Phe Arg Thr Ser Leu Glu Thr Ala Met Asn Asp
            20                  25                  30

Leu Leu Gln Ala Glu Leu Ser Ala Phe Leu Gly Tyr Glu Pro Tyr Asp
        35                  40                  45

Lys Val Gly Tyr Asn Ser Gly Asn Ser Arg Asn Gly Ser Tyr Ser Arg
    50                  55                  60

Gln Phe Glu Thr Lys Tyr Gly Thr Val Gln Leu Ser Ile Pro Arg Asp
65                  70                  75                  80

Arg Asn Gly Asn Phe Ser Pro Ala Leu Leu Pro Ala Tyr Gly Arg Arg
                85                  90                  95

Asp Asp His Leu Glu Glu Met Val Ile Lys Leu Tyr Gln Thr Gly Val
            100                 105                 110

Thr Thr Arg Glu Ile Ser Asp Ile Ile Glu Arg Met Tyr Gly His His
        115                 120                 125

Tyr Ser Pro Ala Thr Ile Ser Asn Ile Ser Lys Ala Thr Gln Glu Asn
    130                 135                 140

Val Ala Thr Phe His Glu Arg Ser Leu Glu Ala Asn Tyr Ser Val Leu
145                 150                 155                 160

Phe Leu Asp Gly Thr Tyr Leu Pro Leu Arg Arg Gly Thr Val Ser Lys
                165                 170                 175

Glu Cys Ile His Ile Ala His Leu Ala Leu His Gln Lys Asp Arg Arg
            180                 185                 190

Leu Phe Leu Asp Met Lys Ser Pro Gln Met Lys Thr Met Leu Leu Gly
        195                 200                 205

Pro Pro Cys
    210
```

<210> SEQ ID NO 25
<211> LENGTH: 77
<212> TYPE: PRT
<213> ORGANISM: Lactococcus lactis

<400> SEQUENCE: 25

```
Met Gln Lys Arg Tyr Ser Lys Glu Phe Lys Glu Thr Leu Ile Val Phe
1               5                   10                  15

Tyr His Ser Gly Gln Ser Val Thr Gln Leu Ser Lys Glu Tyr Asp Val
            20                  25                  30
```

```
Ala Pro Ala Thr Ile Tyr Lys Trp Ile Asp Leu Tyr Ser Lys Ser Asn
        35                  40                  45

Glu Ser Ser Val Ser Lys Ala Asp Phe Leu Glu Leu Lys Arg Gln Leu
    50                  55                  60

Ala Lys Val Lys Glu Glu Arg Asp Ile Leu Lys Lys Tyr
65                  70                  75


<210> SEQ ID NO 26
<211> LENGTH: 197
<212> TYPE: PRT
<213> ORGANISM: Lactococcus lactis

<400> SEQUENCE: 26

Met Thr Tyr Asn Ser Thr Leu Pro Lys Val Phe Val Tyr Leu Leu Thr
1               5                   10                  15

Thr Ile Glu Thr Leu Tyr Gln Thr Arg Val Pro Leu Glu Val Gln Asn
            20                  25                  30

Arg Lys Asn Val His Leu Ala Thr Ser Asp Cys Leu Val Ile Ala Cys
        35                  40                  45

Tyr Leu Trp Gly Val Leu His Phe Ser Glu Thr Leu Lys Ala Lys His
    50                  55                  60

Gln Leu Ala Gln Ser Leu Phe Pro Asn Phe Leu Glu Tyr Tyr Arg Phe
65                  70                  75                  80

Val Arg Arg Cys Asn Ala Leu Leu Pro Ser Ile Gln Val Ile Arg Gln
                85                  90                  95

Ala Leu Val Phe Lys Glu Val Glu Gly Met Ser Val Ser Ile Ile Asp
            100                 105                 110

Ser Phe Pro Ile Pro Leu Cys Gln Pro Ile Arg Asn Phe Arg Ser Lys
        115                 120                 125

Val Leu Gly Asp Tyr Ala Asn Val Gly Tyr Asn Ala Thr Lys Gly Gln
    130                 135                 140

Tyr Phe Tyr Gly Cys Lys Cys His Ala Leu Val Ser Glu Ser Gly Tyr
145                 150                 155                 160

Val Ile Asp Tyr Thr Ile Thr Pro Ala Ser Met Ala Asp Ser Ser Met
                165                 170                 175

Thr Glu Glu Val Leu Asn Gln Phe Gly Thr Pro Thr Val Leu Gly Asp
            180                 185                 190

Met Gly Tyr Leu Gly
        195


<210> SEQ ID NO 27
<211> LENGTH: 131
<212> TYPE: PRT
<213> ORGANISM: Lactococcus lactis

<400> SEQUENCE: 27

Met Ile Ser Tyr His Ile Ser Lys Gln Pro Ser Tyr Gln Ser Ile Asp
1               5                   10                  15

Ile Ala Leu Asn Gln Ala Leu Ala Val Thr Ser Asp Cys Pro Tyr Arg
            20                  25                  30

Arg Thr Phe His Ser Asp Gln Gly Trp Gly Tyr Gln Met Arg Asp Tyr
        35                  40                  45

Val Ser Lys Leu Lys Ser His Arg Ile Phe Gln Ser Met Ser Arg Lys
    50                  55                  60

Gly Asn Cys His Asp Asn Ser Val Met Glu Asn Phe Phe Gly Leu Leu
65                  70                  75                  80
```

```
Lys Gln Glu Ile Tyr Tyr Gly His Ile Phe Ser Ser Phe Glu Glu Leu
                85                  90                  95

Glu Gln Val Ile Val Ile Trp Ile Arg Tyr Tyr Asn Thr Lys Arg Ile
            100                 105                 110

Lys Gln Lys Leu Asn Trp Met Ser Pro Ile Gln Phe Arg Leu Asn Tyr
        115                 120                 125

Gln Asn Asn
    130


<210> SEQ ID NO 28
<211> LENGTH: 35
<212> TYPE: PRT
<213> ORGANISM: Lactococcus lactis

<400> SEQUENCE: 28

Met Pro Glu Asn Lys Asn Phe Ser Arg Arg Ser Lys Lys Glu Thr Gly
1               5                   10                  15

Lys Lys Ser Leu Lys Ile Pro Lys Ile Arg Pro Lys Lys Gln Lys Asn
            20                  25                  30

Leu Lys Lys
        35


<210> SEQ ID NO 29
<211> LENGTH: 199
<212> TYPE: PRT
<213> ORGANISM: Lactococcus lactis

<400> SEQUENCE: 29

Met Lys Val Thr Gly Phe Pro Lys Ala Thr Tyr Tyr Tyr Trp Val Asn
1               5                   10                  15

Cys Phe Glu Arg Val Asn Lys Asp Glu Leu Ile Glu Lys Glu Met Leu
            20                  25                  30

Lys Ile Arg Gln Glu His Ala Asn Ala Gly Tyr Arg Pro Met Ser Glu
        35                  40                  45

Leu Leu Lys Gln Arg Gly Tyr His Val Asn His Lys Lys Val Gln Pro
    50                  55                  60

Leu Met Lys Lys Leu Gly Leu Arg Val Thr Ser Tyr Trp His Lys Ser
65                  70                  75                  80

Arg Lys Tyr Asn Ser Tyr Lys Gly Asn Val Gly Thr Val Ala Lys Asn
                85                  90                  95

Lys Leu His Arg Arg Phe Arg Thr Ser Ile Pro His Gln Lys Ile Thr
            100                 105                 110

Thr Asp Thr Thr Glu Phe Lys Tyr Tyr Glu Asp Gly Ile Gln Lys Lys
        115                 120                 125

Cys Tyr Leu Asn Pro Tyr Ile Asp Leu Phe Asn Ser Glu Val Ile Ser
    130                 135                 140

Tyr His Ile Ser Lys Gln Pro Ser Tyr Gln Ser Ile Asp Ile Ala Leu
145                 150                 155                 160

Asn Gln Ala Leu Ala Val Thr Ser Asp Cys Pro Tyr Arg Arg Thr Phe
                165                 170                 175

His Ser Asp Gln Gly Trp Gly Tyr Gln Met Arg Asp Tyr Val Ser Lys
            180                 185                 190

Leu Lys Ser His Arg Ile Phe
        195


<210> SEQ ID NO 30
<211> LENGTH: 179
```

<212> TYPE: PRT
<213> ORGANISM: Lactococcus lactis

<400> SEQUENCE: 30

Met Ala Lys Asn Lys Leu His Arg Arg Phe Asn Thr Ser Ile Pro His
1               5                   10                  15

Gln Lys Ile Thr Thr Asp Thr Thr Glu Phe Lys Tyr Tyr Asp Lys Gly
            20                  25                  30

Val Gln Lys Lys Leu Tyr Leu Thr Pro Tyr Leu Asp Leu Phe Asn Asn
        35                  40                  45

Glu Val Ile Ser Tyr Glu Ile Ser Lys Gln Pro Thr Tyr Gln Ala Ile
    50                  55                  60

Ala Thr Ala Leu Gln Glu Ala Leu Glu Leu Thr Ser Asp Cys Leu Tyr
65                  70                  75                  80

Arg Arg Thr Phe His Ser Asp Gln Gly Trp Ala Tyr Gln Met Lys Asn
                85                  90                  95

Tyr Val Phe Lys Leu Lys Ser Gln Lys Ile Ile Gln Ser Met Ser Arg
            100                 105                 110

Lys Gly Asn Cys His Asp Asn Ser Val Met Glu Asn Phe Phe Gly Leu
        115                 120                 125

Leu Lys Gln Glu Ile Tyr Tyr Gly His Val Phe Asn Ser Phe Glu Glu
    130                 135                 140

Leu Glu Gln Ala Ile Thr Lys Trp Ile His Tyr Tyr Asn Thr Lys Arg
145                 150                 155                 160

Ile Lys Lys Lys Leu Asn Trp Met Ser Pro Ile Gln Tyr Arg Leu Thr
                165                 170                 175

Tyr Ser Lys

<210> SEQ ID NO 31
<211> LENGTH: 392
<212> TYPE: PRT
<213> ORGANISM: Lactococcus lactis

<400> SEQUENCE: 31

Met Glu His Ser Ala Thr Gln Arg Glu Ser Gln Lys Ile Trp Thr Ala
1               5                   10                  15

Ile Lys Asn Trp Phe Leu Val Asp Lys Val Phe Leu Ile Ser Phe Ile
            20                  25                  30

Ile Ala Ile Ile Ala Ile Ser Leu Gly Gly Val Thr Thr Arg Phe Phe
        35                  40                  45

Asn Tyr His Val Ile Val Thr Val Ser Gly Leu Met Leu Val Ile Gly
    50                  55                  60

Gly Phe Lys Glu Thr Gly Leu Leu Gln Tyr Leu Gly Gln Thr Leu Val
65                  70                  75                  80

Lys Arg Ser Thr Thr Thr Arg Gln Leu Val Arg Phe Thr Thr Leu Leu
                85                  90                  95

Thr Phe Phe Leu Ala Val Phe Phe Thr Asn Asp Leu Thr Ile Leu Thr
            100                 105                 110

Val Leu Pro Leu Tyr Leu Ala Ile Thr Lys Glu Ile Lys Asn Arg Lys
        115                 120                 125

Ser Val Tyr Ile Gly Ala Ala Leu Ile Val Pro Ala Cys His Ile Gly
    130                 135                 140

Ser Ala Leu Leu Pro Gln Gly Asn Pro His Asn Leu Tyr Leu Tyr Ser
145                 150                 155                 160

Phe Tyr Lys Val Ala Ala His His Gly Gly Val Pro Leu Thr Asn Leu

-continued

```
                165                 170                 175

Asp Phe Phe Lys Gly Thr Gly Ala Leu Trp Ile Leu Gly Leu Leu Ile
            180                 185                 190

Leu Met Ile Ala Cys Gln Phe Ile Asp Asn Glu Pro Leu Val Ile Glu
        195                 200                 205

Thr Lys Val Asn Gln Phe Asn Lys Val Glu Thr Ser Ile Phe Val Val
    210                 215                 220

Leu Met Leu Leu Met Ala Ala Ser Val Phe Gly Tyr Val Asn Phe Tyr
225                 230                 235                 240

Leu Ala Gly Ala Val Val Ala Leu Val Val Leu Ile Tyr Arg Pro Arg
                245                 250                 255

Leu Phe Lys Gly Ile Asp Tyr His Leu Leu Phe Thr Phe Ile Phe Phe
            260                 265                 270

Phe Leu Ile Val Gly Asn Ile Ala Asn Ile His Val Leu Thr Asp Phe
        275                 280                 285

Ile Ser Asn Thr Leu Val Gly Pro Gln Ala Ser Phe Leu Gly Thr Val
    290                 295                 300

Ile Met Ser Gln Phe Ile Ser Asn Ile Ala Ala Pro Ile Leu Ile Ser
305                 310                 315                 320

Pro Phe Thr Pro His Ala Val Ser Leu Val Leu Gly Ala Asp Ile Gly
                325                 330                 335

Gly Ile Gly Thr Ile Val Ser Ser Met Ala Thr Leu Ile Ala Tyr Lys
            340                 345                 350

Val Ile Arg Met Asn Ala Arg Gly Glu Thr Arg Gly Phe Val Lys Tyr
        355                 360                 365

Phe Ile Ile Val Asn Ala Gly Phe Val Leu Ile Leu Thr Leu Ile Gly
    370                 375                 380

Leu Ile Ile Val Thr Leu Val Gly
385                 390
```

<210> SEQ ID NO 32
<211> LENGTH: 162
<212> TYPE: PRT
<213> ORGANISM: Lactococcus lactis

<400> SEQUENCE: 32

```
Met Thr Tyr Asn Ser Thr Leu Pro Lys Val Phe Val Tyr Leu Leu Thr
1               5                   10                  15

Thr Ile Asp Thr Leu Tyr Gln Thr Arg Val Pro Leu Glu Val Gln Asn
            20                  25                  30

Arg Lys Asn Val His Leu Ala Thr Ser Asp Cys Leu Val Ile Ala Cys
        35                  40                  45

Tyr Leu Trp Gly Val Leu His Phe Ser Glu Thr Leu Lys Ala Lys His
    50                  55                  60

Gln Leu Ala Gln Ser Leu Phe Pro Asn Phe Leu Glu Tyr Ser Arg Phe
65                  70                  75                  80

Val Arg Arg Cys Asn Ala Leu Leu Pro Ser Ile Gln Val Ile Arg Gln
                85                  90                  95

Ala Leu Val Phe Lys Glu Val Glu Gly Met Ser Val Ser Ile Ile Asp
            100                 105                 110

Ser Phe Pro Ile Pro Leu Cys Gln Pro Ile Arg Asn Phe Arg Ser Lys
        115                 120                 125

Val Leu Gly Asp Tyr Ala Asn Val Gly Tyr Asn Ala Thr Lys Gly Gln
    130                 135                 140
```

Tyr Phe Tyr Gly Cys Lys Cys His Ala Leu Val Thr Val Asn Gln Ala
145 150 155 160

Met Ser

<210> SEQ ID NO 33
<211> LENGTH: 97
<212> TYPE: PRT
<213> ORGANISM: Lactococcus lactis

<400> SEQUENCE: 33

Met Ala Gln Ser Leu Phe Pro Asn Phe Leu Glu Tyr Tyr Arg Phe Val
1 5 10 15

Arg Arg Cys Asn Ala Leu Leu Pro Ser Ile Gln Val Ile Arg Gln Ala
20 25 30

Leu Val Phe Lys Glu Val Glu Gly Ile Ser Val Ser Ile Ile Asp Asn
35 40 45

Phe Pro Ile Pro Leu Cys Gln Pro Ile Arg Asn Phe Arg Ser Lys Val
50 55 60

Leu Gly Asp Tyr Ala Asn Val Gly Tyr Asn Ala Thr Lys Gly Gln Tyr
65 70 75 80

Phe Tyr Gly Cys Lys Cys His Ala Leu Val Thr Val Asn Gln Ala Met
85 90 95

Ser

<210> SEQ ID NO 34
<211> LENGTH: 43
<212> TYPE: PRT
<213> ORGANISM: Lactococcus lactis

<400> SEQUENCE: 34

Met Ala Arg Arg Lys Phe Asp Lys Gln Phe Lys Asn Ser Ala Val Lys
1 5 10 15

Leu Ile Leu Glu Glu Gly Tyr Ser Val Lys Glu Val Ser Gln Glu Leu
20 25 30

Glu Val His Ala Asn Ser Leu Tyr Arg Trp Val
35 40

<210> SEQ ID NO 35
<211> LENGTH: 450
<212> TYPE: PRT
<213> ORGANISM: Lactococcus lactis

<400> SEQUENCE: 35

Met Gln Ser Tyr Asp Leu Leu Asp Glu Leu Asp Ser Glu Asp Lys Phe
1 5 10 15

Arg Lys Asp Ile Lys Tyr Ser Arg Gln Leu Pro Glu Met Phe Ser Thr
20 25 30

Glu Asp Ile Asn Ala Ala Ser Glu Asn Ile Thr Tyr Ala Ile Leu Gly
35 40 45

Glu Leu Arg Asp Arg Tyr Asn Gly Ser Glu Pro Val Thr Phe Ser Tyr
50 55 60

Gln Glu Leu Ala Glu Leu Gly Gly Leu Trp Val Thr Arg Lys Asn Gly
65 70 75 80

Val Lys Ser Leu Tyr Asn Gly Lys Arg Leu Gln Lys Ile Met Tyr Asp
85 90 95

Leu Asn Glu Ala Leu Lys Asn Phe Ser Tyr Tyr Gln Val Arg Glu Thr
100 105 110

-continued

```
Asn Asp Asp Gly Thr Pro Lys Ser Trp Lys Thr Ile Asn Ile Phe Ser
        115                 120                 125

Val Ile Asp Phe Asp Gly Thr Lys Lys Glu Val Lys Leu Thr Ile Ser
    130                 135                 140

Asn Ala Gln Ile Ser Ser Glu Gln Val Asp Ala Lys Gly His Val Ile
145                 150                 155                 160

Asp Lys Pro Leu Tyr Val Tyr Asp Leu Ile Asn Ser Lys Asp Trp Arg
                165                 170                 175

Thr Val Lys His Leu Gln Tyr Asn Arg Gly Ile Asn Asn Ser Leu Pro
            180                 185                 190

Ser Lys Tyr Ser Lys Arg Val Tyr Arg Phe Ile Ser Glu Phe Arg Ser
        195                 200                 205

Phe Pro Lys Gly Thr Lys Met Arg Ile Asp Asp Phe Asp Lys Lys Ile
    210                 215                 220

Leu Lys Ile Leu Lys Thr Gln Glu Asp Ser Phe Asn Thr Lys Glu Val
225                 230                 235                 240

Phe Asp Leu Arg Lys Asn Arg Lys Lys Tyr Leu Glu Thr Ala Val Lys
                245                 250                 255

Glu Ile Ser Glu Leu Asn Thr Pro Glu Gly Thr Gln Ile Val Lys Asn
            260                 265                 270

Leu Asp Tyr Ile Tyr His Thr Ser Gly Arg Arg Ile Gln Ser Ile Glu
        275                 280                 285

Phe Thr Tyr Thr Pro Phe Asn Ala Asp Leu Ser Gly Ser Asn His Ile
    290                 295                 300

Ser Met Asn Ser Arg Thr Ser Ser Pro Gly Thr Asp Ser Pro Phe Ile
305                 310                 315                 320

Asn Glu Ala Arg Met Val Leu Glu Tyr Phe Asn Tyr Leu Ser Lys Val
                325                 330                 335

Asn Phe Asn Leu Asp Glu Asn Gly Ile Ile Lys His Leu Pro Asn Tyr
            340                 345                 350

Tyr Asp Ile Gln Phe Glu Leu Asp Asp Ile Gln Leu Leu Gln Pro Ile
        355                 360                 365

His Lys Leu Leu Glu Ser Gly Val Ala Ile Asp Glu Leu Leu Gln Val
    370                 375                 380

Ala Glu Met Lys Ala Ile Asp Trp Lys Leu Asp Ser Asn Gln Met Ile
385                 390                 395                 400

Asn Asn Phe Arg Pro Ser Val Val Phe Gly Asn Lys Phe Ser Glu Tyr
                405                 410                 415

Arg Ala Phe Leu Thr Thr Tyr Lys Ala Gln Asn Ile His Lys Leu Val
            420                 425                 430

Phe Asp Ser Ser Ser Asp Phe Tyr Val Pro Met Asn Gly Pro Trp Asp
        435                 440                 445

Ser Lys
    450


<210> SEQ ID NO 36
<211> LENGTH: 296
<212> TYPE: PRT
<213> ORGANISM: Lactococcus lactis

<400> SEQUENCE: 36

Met Thr Tyr Asn Ser Thr Leu Pro Lys Val Phe Val Tyr Leu Leu Thr
1               5                   10                  15

Thr Ile Glu Thr Leu Tyr Gln Thr Lys Val Pro Leu Glu Val Gln Asn
            20                  25                  30
```

-continued

```
Arg Lys Asn Val His Leu Ala Thr Ser Asp Cys Leu Val Ile Ala Cys
        35                  40                  45

Tyr Leu Trp Gly Val Leu His Phe Ser Glu Thr Leu Lys Ala Lys His
    50                  55                  60

Gln Leu Ala Gln Ser Leu Phe Pro Asn Phe Leu Glu Tyr Ser Arg Phe
65                  70                  75                  80

Val Arg Arg Cys Asn Ala Leu Leu Leu Ser Ile Gln Leu Ile Arg Gln
                85                  90                  95

Ala Leu Val Phe Lys Glu Phe Glu Gly Ile Asp Val Ser Ile Ile Asp
            100                 105                 110

Ser Phe Pro Ile Pro Leu Cys Gln Pro Ile Arg Asn Phe Arg Ser Lys
        115                 120                 125

Val Leu Gly Asp Tyr Ala Asn Ile Gly Tyr Asn Ala Thr Lys Gly Gln
    130                 135                 140

Tyr Phe Tyr Gly Cys Lys Cys His Ala Leu Val Ser Glu Ser Gly Tyr
145                 150                 155                 160

Val Ile Asp Tyr Val Ile Ser Pro Ala Ser Ile Ala Asp Ser Thr Met
                165                 170                 175

Ala Glu Glu Val Leu Ser Gln Phe Gly Thr Pro Ile Val Leu Gly Asp
            180                 185                 190

Met Gly Tyr Leu Gly Gln Val Leu His Asp Arg Leu Glu Leu Lys Glu
        195                 200                 205

Ile Glu Leu Ile Thr Pro Val Arg Met Asn Met Lys Lys Lys Asp Ile
    210                 215                 220

Thr Phe Pro Asn Phe Ser Lys Arg Arg Lys Val Ile Glu Arg Val Phe
225                 230                 235                 240

Ser Phe Leu Thr Asn Leu Gly Ala Glu Arg Cys Lys Ser Arg Ser Ser
                245                 250                 255

Tyr Gly Phe Leu Val Lys Leu Glu Met Thr Leu Leu Thr Tyr Ser Leu
            260                 265                 270

Ile Leu Lys Ser Ala Lys Thr Val Asn Ser Met Thr Leu Arg Tyr Ser
        275                 280                 285

Thr Gly Tyr Gln Val Met Ala Glu
    290                 295


<210> SEQ ID NO 37
<211> LENGTH: 77
<212> TYPE: PRT
<213> ORGANISM: Lactococcus lactis

<400> SEQUENCE: 37

Met Glu Lys Val Thr Asp Glu Ile Lys Asn Val Val Gln Arg Leu Leu
1               5                   10                  15

Asp Asp Asp Glu Asn Phe Ser Gly Trp Tyr Ile Glu Lys Glu Leu Glu
            20                  25                  30

Lys Ile Gly Ile Lys Val Ser Arg Met Thr Ile Ser Asn Leu Arg Asn
        35                  40                  45

Lys Lys Thr Thr Leu Gly Asn Thr Lys Phe Glu Thr Leu Glu Gly Leu
    50                  55                  60

Tyr His Phe Ala Lys Thr His Glu Asn Ile Asn Lys Glu
65                  70                  75


<210> SEQ ID NO 38
<211> LENGTH: 252
<212> TYPE: PRT
```

-continued

<213> ORGANISM: Lactococcus lactis

<400> SEQUENCE: 38

Met Lys Thr Ile Ser Leu Leu Asn Leu Lys Gly Gly Val Ala Lys Thr
1 5 10 15

Thr Thr Gly Gly Asn Ile Ala Lys Gly Leu Ala Asn Arg Gly Phe Lys
20 25 30

Thr Leu Leu Ile Asp Thr Asp Met Gln Ala Asn Ala Thr Ser Ile Phe
35 40 45

Leu Glu Asp Lys Arg Ser Lys Glu Asp Tyr Lys Gly Phe Ala Glu Leu
50 55 60

Ile Val Asp Glu Lys Leu Asp Asp Val Asp Gln Tyr Val Tyr Asn Val
65 70 75 80

Ser Glu Asn Leu Asp Met Ile Gly Ser Ser Leu Ala Val Ala Glu Ser
85 90 95

Glu Leu Lys Val Arg Asn Ser Phe Asn Arg Asn Ser Ser Asn Ile Val
100 105 110

Lys Lys Val Leu Lys Lys Leu Asp Ser Lys Tyr Asp Tyr Cys Ile Ile
115 120 125

Asp Cys Ala Pro Thr Ile Asn Leu Ile Thr Leu Asn Ile Ile Ile Ala
130 135 140

Ser Asp Glu Ile Ile Ile Pro Ile Lys Ile Asp Lys Phe Ala Leu Glu
145 150 155 160

Gly Tyr Arg Thr Thr Leu Lys Asn Ile Asn Gln Ile Ile Asp Asp Tyr
165 170 175

Glu Leu Asp Thr Glu Val Thr Val Leu Tyr Thr Met Val Asn Arg Asn
180 185 190

Asn Ile Asp Lys Gln Phe Ile Gln Glu Ile Ser Gly Asn Arg Phe Glu
195 200 205

Thr Thr Ile Arg His Gln Ala Lys Pro Val Thr Glu Ser Ala Leu Lys
210 215 220

Asn Glu Val Leu Ile Asp Ser Ser Lys Ser Ser Lys Val Lys Asp Asp
225 230 235 240

Tyr Leu Asn Leu Ile Asp Glu Ile Val Lys Arg Gly
245 250

<210> SEQ ID NO 39
<211> LENGTH: 242
<212> TYPE: PRT
<213> ORGANISM: Lactococcus lactis

<400> SEQUENCE: 39

Met Ser Asn Ser Phe Gly Phe Thr Asp Leu Met Asn Lys Asp Glu His
1 5 10 15

Lys Arg Lys Lys Thr Asn Thr Lys Asn Ile Pro Ile Glu Glu Ile Lys
20 25 30

Glu Asn Glu Asn Asn Asn Tyr Asp Leu Val Asp Ile Asp Lys Leu Ala
35 40 45

Asp Ser Ile Asp Glu Leu Gly Leu Leu Gln Pro Val Leu Val Lys Gln
50 55 60

Arg Asp Lys Tyr Ser Tyr Glu Leu Ile Ala Gly His Arg Arg Phe Asn
65 70 75 80

Ala Ile Lys Lys Leu Ile Ser Glu Asn Arg Leu Pro Glu Asp Tyr Glu
85 90 95

Val Leu Ala Lys Lys Val Asp Glu Asp Glu Asp Glu Leu Val Thr Arg

-continued

```
            100                 105                 110

Leu Lys Leu His Glu Thr Asn Leu Gln Thr Arg Ser Leu Leu Lys Met
        115                 120                 125

Pro Glu Glu Glu Lys Ile Ala Ile Ile Asp Asp Tyr Met Asp Ile Leu
    130                 135                 140

Asp Lys Ala Lys Lys Gln Gly Leu Gln Ile Asn Gly Lys Pro Val Lys
145                 150                 155                 160

Gly Lys Thr Arg Asp Leu Ile Ala Glu Arg Phe Gly Ile Ser His Tyr
                165                 170                 175

Thr Ala Gln Lys Leu Ile Arg Lys Ala Lys Glu Gln Gly Gly Glu Glu
            180                 185                 190

Glu Gly Ala Lys Ile Ser Pro Gln Lys Lys Thr Ala Lys Lys Pro Ile
        195                 200                 205

Thr Gln Leu Lys Lys Ile Glu Thr Gln Leu Glu Lys Leu Glu Phe Glu
    210                 215                 220

Gly Thr Glu Glu Glu Gln Glu Ile Lys Lys Lys Leu Ile Glu Leu Leu
225                 230                 235                 240

Met Lys


<210> SEQ ID NO 40
<211> LENGTH: 116
<212> TYPE: PRT
<213> ORGANISM: Lactococcus lactis

<400> SEQUENCE: 40

Met Ser Val Asp Arg Ser Tyr Ser Pro Tyr Glu Val Ile Arg Ala Tyr
1               5                   10                  15

His Asp Arg Gly Met Met Lys Trp Gly Ala Phe Ala Thr Gly Glu Leu
            20                  25                  30

Thr Glu Ala Gln Asn Thr Phe Glu Lys Glu Lys Lys Asp Asp Lys Val
        35                  40                  45

Ile Gln Thr Leu Pro His His Val Val Leu His Leu Leu Asn Gln Ser
    50                  55                  60

Phe Ser Asn Gln Val Gln Ile Lys Val Lys Tyr Gln Ser Lys Asp Lys
65                  70                  75                  80

Leu Thr Glu Val Tyr Gly Phe Val Ser Glu Phe Ile Asn Asn Gln Val
                85                  90                  95

Arg Val Lys Ser Thr Asp Lys Ile Tyr Leu Ile Ser Ile Glu Gln Ile
            100                 105                 110

Ile Asn Ile Ser
        115


<210> SEQ ID NO 41
<211> LENGTH: 488
<212> TYPE: PRT
<213> ORGANISM: Lactococcus lactis

<400> SEQUENCE: 41

Met Glu Gln Leu Lys Leu Asn Lys Tyr Phe Asp Tyr Ser Leu Glu Pro
1               5                   10                  15

Arg Arg Ala Ile Leu Phe Gln Asp Val Lys Ser Asn Tyr Ala Ser Ile
            20                  25                  30

Glu Cys Val Gln Arg Asn Leu Asn Pro Leu Thr Thr Ser Leu Cys Val
        35                  40                  45

Met Ser Arg Ala Asp His Ser Lys Gly Leu Thr Leu Ala Ser Ser Pro
    50                  55                  60
```

```
Thr Phe Lys Lys Val Phe Gly Met Lys Asn Val Ser Arg Ala Ser Asp
65                  70                  75                  80

Leu Pro Phe Leu Ile Glu Thr Arg Lys Phe Asn Tyr Pro Gln Trp Tyr
                85                  90                  95

Arg Thr His Thr Asp Ile His Gly Gln Arg Thr Glu Pro Thr Leu Gln
            100                 105                 110

Tyr Val Ala Phe Ile Glu Ser Trp Ala Lys Arg Thr Trp Ile Val Pro
        115                 120                 125

Pro Gln Met Gln Leu Tyr Val Asp Tyr Lys Ile Glu Val Thr Asp Ile
    130                 135                 140

Leu Thr Asn Tyr Thr Ser Ile Asp Glu Ile His Ser Tyr Ser Ile Asp
145                 150                 155                 160

Glu Ser Phe Leu Asp Ile Thr Glu Ser Leu Asn Phe Phe Tyr Pro Glu
                165                 170                 175

Ile Lys Asn Arg Tyr Glu Gln Met Asn Arg Ile Ala Leu Asp Leu Gln
            180                 185                 190

Arg Glu Ile Arg Asp Lys Leu Gly Leu Tyr Val Thr Val Gly Met Gly
        195                 200                 205

Asp Asn Pro Leu Leu Ala Lys Leu Ala Met Asp Asn Tyr Ala Lys His
    210                 215                 220

Asn Asp Asn Met Arg Ala Leu Ile Arg Tyr Glu Asp Val Pro Asn Lys
225                 230                 235                 240

Leu Trp Thr Ile Pro Lys Met Thr Asp Phe Trp Gly Ile Gly Lys Arg
                245                 250                 255

Thr Glu Lys Arg Leu Asn Lys Leu Gly Ile Thr Ser Ile Lys Glu Leu
            260                 265                 270

Ala Asn Ala Asp Pro Leu Leu Leu Lys Gln Lys Leu Gly Thr Ile Gly
        275                 280                 285

Leu Gln His Phe Phe His Ala Asn Gly Ile Asp Glu Ser Asn Val Arg
    290                 295                 300

Glu Lys Tyr Thr Pro Lys Ser Thr Ser Phe Ser Asn Ser Gln Ile Leu
305                 310                 315                 320

Pro Arg Asp Tyr His Lys Gln Arg Glu Ile Glu Leu Val Ile Lys Glu
                325                 330                 335

Met Ala Glu Asn Leu Ala Ile Arg Leu Arg Lys Gly Gly Lys Leu Ala
            340                 345                 350

Ser Asn Leu Ser Leu Tyr Ala Gly Ala Ala Ser Thr Ser Glu Tyr Ser
        355                 360                 365

Ser Val Lys Val Ser Arg Asn Ile Glu Ala Thr Gln Asn Thr Lys Glu
    370                 375                 380

Leu Gln Asp Leu Ala Ile Ser Leu Phe Arg Glu Lys Tyr Gln Gly Gly
385                 390                 395                 400

Ala Ile Arg Gln Ile Gly Ile Ser Gly Asn Gln Leu Ser Asp Ser Ser
                405                 410                 415

Val Lys Gln Leu Ser Leu Phe Glu Ser Val Gln Glu Asn Gln Thr Asn
            420                 425                 430

Lys Lys Gln Glu Ser Leu Gln Lys Ala Ile Asp Glu Ile Arg Glu Thr
        435                 440                 445

Phe Asp Phe Leu Ser Ile Gln Lys Ala Ser Ser Leu Ser Glu Gly Ser
    450                 455                 460

Arg Val Ile Tyr Arg Asn Lys Leu Ile Gly Gly His Ala Ala Ser Gln
465                 470                 475                 480
```

Asp Lys Glu Glu Lys Asp Val Ser
                485

<210> SEQ ID NO 42
<211> LENGTH: 37
<212> TYPE: PRT
<213> ORGANISM: Lactococcus lactis

<400> SEQUENCE: 42

Met Asp Lys Tyr Ile Arg Arg Ala Tyr Gln Arg Met Asn Gln Met Ser
1               5                   10                  15

Phe Gly Gly Gln Ala Leu Ala Trp Phe Leu Ser Ile Arg Leu Ser Asp
            20                  25                  30

Leu Val Leu Lys Lys
        35

<210> SEQ ID NO 43
<211> LENGTH: 110
<212> TYPE: PRT
<213> ORGANISM: Lactococcus lactis

<400> SEQUENCE: 43

Met Ala Glu Ala Lys Phe Glu Ala Ala Leu Ile Lys Lys Leu Glu Ala
1               5                   10                  15

Glu Gly Trp Thr Tyr Arg Lys Asp Leu Ser Tyr Val Ser Ile Lys Val
            20                  25                  30

Leu Glu Gly His Trp Arg Glu Val Leu Asn Glu Asn Asn Ala Tyr Lys
        35                  40                  45

Leu Asn Gly Lys Pro Leu Ser Asp Val Glu Phe Gly Leu Val Ile Gln
    50                  55                  60

Glu Val Gln Arg Ile Lys Thr Pro Tyr Asp Ala Gln Leu Leu Leu Val
65                  70                  75                  80

Gly Ala Gly Gly Val Gly Ser Ile Pro Ile Thr Arg Asp Asp Gly Ser
                85                  90                  95

Asn Leu Glu Val Trp Thr Asn Val Lys Tyr Leu Asp Thr Lys
            100                 105                 110

<210> SEQ ID NO 44
<211> LENGTH: 112
<212> TYPE: PRT
<213> ORGANISM: Lactococcus lactis

<400> SEQUENCE: 44

Met Ile Phe Lys Leu Arg Asn Arg Thr Glu Ile Ala Ile Asn Lys Arg
1               5                   10                  15

Lys Pro Lys Glu Pro Ile Ile Phe His Ser Asp His Gly Ser His Phe
            20                  25                  30

Lys Ser Ala Ser Phe Arg Lys Leu Leu Asp Glu His Gln Leu Leu Ala
        35                  40                  45

Ser Tyr Ser Lys Pro Gly Tyr Pro Tyr Gly Asn Ala Val Thr Glu Val
    50                  55                  60

Phe Phe Lys Tyr Leu Lys His Arg Glu Ile Asn Arg Arg Thr Tyr His
65                  70                  75                  80

Ser Ile Gln Glu Val Gln Leu Ser Cys Phe Glu Tyr Ile Glu Gln Phe
                85                  90                  95

Tyr Asn Asn Tyr Asn Pro His Ser Ala Asn Asn Gly Leu Thr Pro Asn
            100                 105                 110

<210> SEQ ID NO 45
<211> LENGTH: 272
<212> TYPE: PRT
<213> ORGANISM: Lactococcus lactis

<400> SEQUENCE: 45

Met Lys Val Thr Gly Phe Pro Lys Ala Thr Tyr Tyr Tyr Trp Val Asn
1 5 10 15

Cys Phe Glu Arg Val Asn Lys Asp Glu Leu Val Glu Lys Glu Met Leu
20 25 30

Lys Ile Arg Gln Glu His Ala Asn Ala Gly Tyr Arg Pro Met Ser Glu
35 40 45

Leu Leu Lys Gln Arg Gly Tyr His Val Asn Asn Lys Lys Val Gln Arg
50 55 60

Leu Met Lys Lys Leu Gly Leu Arg Val Thr Ser Tyr Trp His Lys Ser
65 70 75 80

Arg Lys Tyr Asn Ser Tyr Lys Gly Asn Val Gly Thr Val Ala Lys Asn
85 90 95

Lys Leu His Arg Arg Phe Arg Thr Ser Ile Pro His Gln Lys Ile Thr
100 105 110

Thr Asp Thr Thr Glu Phe Lys Tyr Tyr Glu Asp Gly Ile Gln Lys Lys
115 120 125

Cys Tyr Leu Asn Pro Tyr Ile Asp Leu Phe Asn Ser Glu Val Ile Ser
130 135 140

Tyr His Ile Ser Lys His Pro Ser Tyr Gln Ser Ile Glu Thr Ala Leu
145 150 155 160

Asn Gln Ala Leu Ala Val Thr Ser Asp Cys Pro Tyr Arg Arg Thr Phe
165 170 175

His Ser Asp Gln Gly Trp Gly Tyr Gln Met Arg Asp Tyr Val Ser Lys
180 185 190

Leu Lys Ser His Arg Ile Phe Gln Ser Met Ser Arg Lys Gly Asn Cys
195 200 205

His Asp Asn Ser Val Met Glu Asn Phe Phe Gly Leu Leu Lys Gln Glu
210 215 220

Ile Tyr Tyr Gly His Ile Phe Ser Ser Phe Glu Glu Leu Glu Gln Val
225 230 235 240

Ile Val Ile Trp Ile Arg Tyr Tyr Asn Thr Lys Arg Ile Lys Gln Lys
245 250 255

Leu Asn Trp Met Ser Pro Ile Gln Phe Arg Leu Asn Tyr Gln Asn Asn
260 265 270

<210> SEQ ID NO 46
<211> LENGTH: 185
<212> TYPE: PRT
<213> ORGANISM: Lactococcus lactis

<400> SEQUENCE: 46

Met Val Lys Tyr Ser Ile Glu Leu Lys Gln Arg Val Ile Gln Asp Tyr
1 5 10 15

Leu Ser Gly Lys Gly Gly Ser Thr Tyr Leu Ala Lys Leu His Asn Val
20 25 30

Gly Ser Ser Ser Gln Val Arg Arg Trp Ile Arg Asn Tyr Arg Ala Glu
35 40 45

Gly Leu His Thr Ala His Ser Lys Val Asn Lys Asn Tyr Ser Met Glu
50 55 60

Leu Lys Glu Asn Ala Val Gln Cys Tyr Leu Thr Thr Asp Leu Thr Tyr

-continued

```
65                  70                  75                  80

Glu Ala Val Ala Arg Lys Phe Glu Ile Thr Asn Phe Thr Leu Leu Ala
                85                  90                  95

Ser Trp Val Asn His Phe Lys Ile Tyr Gly Glu Val Pro Ile Ser Lys
            100                 105                 110

Lys Arg Gly Arg Arg Lys Lys Leu Glu Ser Ile Ala Ser Ser Met Thr
        115                 120                 125

Gln Asn Pro Asn Asp Ser Gln Arg Ile Lys Glu Leu Glu Gln Glu Leu
    130                 135                 140

Arg Tyr Ala Gln Ile Glu Val Ala Tyr Leu Lys Gly Leu Arg Arg Leu
145                 150                 155                 160

Glu Lys Asn Ala Leu Met Asn Lys Asn Gln Asp Ser Ser Thr Val Ser
                165                 170                 175

Val Lys Pro Ser Asn Ser Lys Lys Ser
            180                 185


<210> SEQ ID NO 47
<211> LENGTH: 279
<212> TYPE: PRT
<213> ORGANISM: Lactococcus lactis

<400> SEQUENCE: 47

Met Lys His His Gly Lys Ile Lys Ile Lys His Ala Val Lys Val Leu
1               5                   10                  15

Lys Val Ser Arg Ser Gly Phe Tyr Glu Tyr Met His Arg Arg Pro Ser
            20                  25                  30

Lys Gln Gln Val Glu Arg Glu Ile Leu Ser Glu Lys Ile Lys Ala Val
        35                  40                  45

Phe His Glu His Lys Gly Arg Tyr Gly Ala Val Arg Ile Thr Lys Val
    50                  55                  60

Leu His Asn Thr Gly Ile Met Thr Asn Thr Lys Arg Val Gly Lys Leu
65                  70                  75                  80

Met His Leu Met Gly Leu Tyr Ala Lys Gly Ser Arg Tyr Lys Tyr Lys
                85                  90                  95

His Tyr Asn Arg Lys Gly Ala Ser Leu Ser Arg Pro Asn Leu Ile Asn
            100                 105                 110

Gln Ile Phe Lys Ala Thr Ala Pro Asn Lys Val Trp Leu Gly Asp Met
        115                 120                 125

Thr Tyr Ile Pro Thr Lys Glu Gly Thr Leu Tyr Leu Ala Val Asn Ile
    130                 135                 140

Asp Val Phe Ser Arg Lys Ile Val Gly Trp Ser Met Ser Ser Arg Met
145                 150                 155                 160

Gln Asp Lys Leu Val Arg Asp Cys Phe Leu Gln Ala Cys Gly Lys Glu
                165                 170                 175

His Pro Gln Pro Gly Leu Ile Val His Thr Asp Gln Gly Ser Gln Tyr
            180                 185                 190

Thr Ser Ser Arg Tyr Gln Ser Thr Leu Arg Gln Val Gly Ala Gln Ser
        195                 200                 205

Ser Met Ser Arg Lys Gly Asn Pro Tyr Asp Asn Ala Met Met Glu Ser
    210                 215                 220

Phe Tyr Lys Thr Leu Lys Arg Glu Leu Ile Asn Asp Ala His Phe Glu
225                 230                 235                 240

Thr Arg Ala Glu Ala Thr Gln Glu Ile Phe Lys Tyr Ile Glu Thr Tyr
                245                 250                 255
```

```
Tyr Asn Thr Lys Arg Met His Ser Gly Leu Asp Tyr Lys Ser Pro Lys
            260                 265                 270

Asp Phe Glu Lys Tyr Asn Ser
        275


<210> SEQ ID NO 48
<211> LENGTH: 338
<212> TYPE: PRT
<213> ORGANISM: Lactococcus lactis

<400> SEQUENCE: 48

Met Asn His Phe Lys Gly Lys Gln Phe Lys Lys Asp Val Ile Ile Val
1               5                   10                  15

Ala Val Gly Tyr Tyr Leu Arg Tyr Asn Leu Ser Tyr Arg Glu Val Gln
            20                  25                  30

Glu Leu Leu Tyr Asp Arg Gly Ile Asn Val Cys His Thr Thr Ile Tyr
        35                  40                  45

Arg Trp Val Gln Glu Tyr Ser Lys Val Leu Tyr Asp Leu Trp Lys Lys
    50                  55                  60

Lys Asn Arg Gln Ser Phe Tyr Ser Trp Lys Met Asp Glu Thr Tyr Ile
65                  70                  75                  80

Lys Ile Lys Gly Arg Gly His Tyr Leu Tyr Arg Ala Ile Asp Ala Asp
                85                  90                  95

Gly Leu Thr Leu Asp Ile Trp Leu Arg Lys Lys Arg Asp Thr Gln Ala
            100                 105                 110

Ala Tyr Ala Phe Leu Lys Arg Leu His Asn Gln Phe Gly Glu Pro Lys
        115                 120                 125

Ala Ile Val Thr Asp Lys Ala Pro Ser Leu Gly Ser Ala Phe Arg Lys
    130                 135                 140

Leu Gln Ser Val Gly Leu Tyr Thr Lys Thr Glu His Arg Thr Val Lys
145                 150                 155                 160

Tyr Leu Asn Asn Leu Ile Glu Gln Asp His Arg Pro Ile Lys Arg Arg
                165                 170                 175

Asn Lys Phe Tyr Gln Ser Leu Arg Thr Ala Ser Ser Thr Ile Lys Gly
            180                 185                 190

Met Glu Thr Leu Arg Gly Ile Tyr Lys Lys Asn Arg Arg Asn Gly Thr
        195                 200                 205

Leu Cys Ser Asp Pro Gln Asn Ile Asp Phe Ser Asn Leu Tyr Phe Trp
    210                 215                 220

Lys Gly Tyr Asn Lys Leu Asp Thr Lys Leu Arg Glu Ile Val Glu Arg
225                 230                 235                 240

Phe Ile Met Ala Arg Arg Lys Phe Asp Lys Gln Phe Lys Asn Ser Ala
                245                 250                 255

Val Lys Leu Ile Leu Glu Glu Gly Tyr Ser Val Lys Glu Val Ser Gln
            260                 265                 270

Glu Leu Glu Val His Ala Asn Ser Leu Tyr Arg Trp Val Gln Glu Val
        275                 280                 285

Glu Glu Tyr Gly Glu Ser Ala Phe Pro Gly Asn Gly Thr Ala Leu Ala
    290                 295                 300

Asp Ala Gln His Lys Ile Lys Leu Leu Glu Lys Glu Asn Arg Tyr Leu
305                 310                 315                 320

Gln Glu Glu Leu Glu Leu Leu Lys Lys Phe Arg Val Phe Leu Lys Arg
                325                 330                 335

Ser Lys
```

<210> SEQ ID NO 49
<211> LENGTH: 66
<212> TYPE: PRT
<213> ORGANISM: Lactococcus lactis

<400> SEQUENCE: 49

```
Met Lys Thr Gly Asp Lys Ile Thr Leu Ser Asn Gly Glu Gln Ala Thr
1               5                   10                  15

Val Val Ser Gly Asp Ile Asn Leu Tyr Lys Tyr Ala Leu Ile Val Glu
            20                  25                  30

Leu Glu Asn His Asp Val Arg Val Val Asp Arg Glu Thr Leu Thr Leu
        35                  40                  45

Ala Lys Glu Asn Pro His Glu Asn Leu Gly Asn His Lys Lys Ile Asn
    50                  55                  60

Lys Phe
65
```

<210> SEQ ID NO 50
<211> LENGTH: 66
<212> TYPE: PRT
<213> ORGANISM: Lactococcus lactis

<400> SEQUENCE: 50

```
Met Asn Lys Gly Thr Ile Asn Trp Phe Asn Ala Asp Lys Gly Tyr Gly
1               5                   10                  15

Phe Ile Met Ala Asp Asp Met Gln Asp Val Phe Ala Tyr Leu Leu Ser
            20                  25                  30

Ile Gln Gly Asn Asp Phe Lys Lys Tyr Asp Glu Gly Gln Lys Val Thr
        35                  40                  45

Phe Asp Ile Lys Met Thr Ser Arg Gly Arg Tyr Ala Ser Asn Val His
    50                  55                  60

Lys Arg
65
```

<210> SEQ ID NO 51
<211> LENGTH: 66
<212> TYPE: PRT
<213> ORGANISM: Lactococcus lactis

<400> SEQUENCE: 51

```
Met Ala Asn Gly Thr Val Lys Trp Phe Asn Ala Asp Lys Gly Phe Gly
1               5                   10                  15

Phe Ile Thr Ser Glu Glu Gly Lys Asp Leu Phe Ala His Phe Ser Ala
            20                  25                  30

Ile Gln Ser Asp Gly Phe Lys Thr Leu Asp Glu Gly Gln Lys Val Glu
        35                  40                  45

Phe Asp Val Glu Glu Gly Gln Arg Gly Pro Gln Ala Val Asn Ile Thr
    50                  55                  60

Lys Ala
65
```

<210> SEQ ID NO 52
<211> LENGTH: 96
<212> TYPE: PRT
<213> ORGANISM: Lactococcus lactis

<400> SEQUENCE: 52

```
Met Ala Arg Arg Lys Phe Asp Lys Gln Phe Lys Asn Ser Ala Val Lys
1               5                   10                  15
```

```
Leu Ile Leu Glu Glu Gly Tyr Ser Val Lys Glu Val Ser Gln Glu Leu
            20                  25                  30

Glu Val His Ala Asn Ser Leu Tyr Arg Trp Val Gln Glu Val Glu Glu
        35                  40                  45

Tyr Gly Glu Ser Ala Phe Pro Gly Asn Gly Thr Ala Leu Ala Asp Ala
    50                  55                  60

Gln His Lys Ile Lys Leu Leu Glu Lys Glu Asn Arg Tyr Leu Gln Glu
65                  70                  75                  80

Glu Leu Glu Leu Leu Lys Lys Phe Arg Val Phe Leu Lys Arg Ser Lys
                85                  90                  95


<210> SEQ ID NO 53
<211> LENGTH: 279
<212> TYPE: PRT
<213> ORGANISM: Lactococcus lactis

<400> SEQUENCE: 53

Met Lys His His Gly Lys Ile Lys Ile Lys His Ala Val Lys Val Leu
1               5                   10                  15

Lys Val Ser Arg Ser Gly Phe Tyr Glu Tyr Met His Arg Arg Pro Ser
            20                  25                  30

Lys Gln Gln Val Glu Arg Glu Ile Leu Ser Glu Lys Ile Lys Ala Val
        35                  40                  45

Phe His Glu His Lys Gly Arg Tyr Gly Ala Val Arg Ile Thr Lys Val
    50                  55                  60

Leu His Asn Thr Gly Ile Met Thr Asn Thr Lys Arg Val Gly Lys Leu
65                  70                  75                  80

Met His Leu Met Gly Leu Tyr Ala Lys Gly Ser Arg Tyr Lys Tyr Lys
                85                  90                  95

His Tyr Asn Arg Lys Gly Ala Ser Leu Ser Arg Pro Asn Leu Ile Asn
            100                 105                 110

Gln Ile Phe Lys Ala Thr Ala Pro Asn Lys Val Trp Leu Gly Asp Met
        115                 120                 125

Thr Tyr Ile Pro Thr Lys Glu Gly Thr Leu Tyr Leu Ala Val Asn Ile
    130                 135                 140

Asp Val Phe Ser Leu Lys Ile Val Gly Trp Ser Met Ser Ser Arg Met
145                 150                 155                 160

Gln Asp Lys Leu Val Arg Asp Cys Phe Leu Gln Ala Cys Gly Lys Glu
                165                 170                 175

His Pro Gln Pro Gly Leu Ile Val His Thr Asp Gln Gly Ser Gln Tyr
            180                 185                 190

Thr Ser Ser Arg Tyr Gln Ser Thr Leu Arg Gln Val Gly Ala Gln Ser
        195                 200                 205

Ser Met Ser Arg Lys Gly Asn Pro Tyr Glu Asn Ala Met Met Glu Ser
    210                 215                 220

Phe Tyr Lys Thr Leu Lys Arg Glu Leu Ile Asn Asp Ala His Phe Glu
225                 230                 235                 240

Thr Arg Ala Glu Ala Thr Gln Glu Ile Phe Lys Tyr Ile Glu Thr Tyr
                245                 250                 255

Tyr Asn Thr Lys Arg Met His Ser Gly Leu Asp Tyr Lys Ser Pro Lys
            260                 265                 270

Asp Phe Glu Lys Tyr Asn Ser
        275
```

<210> SEQ ID NO 54
<211> LENGTH: 98
<212> TYPE: PRT
<213> ORGANISM: Lactococcus lactis

<400> SEQUENCE: 54

Met Leu Glu Asn Glu Tyr Phe Val Phe Thr Ser Thr Leu Thr Thr Met
1 5 10 15

Ile Arg Lys Gln Ala Gln Ser Ile Ile Thr Gly Leu Lys Gly His Asn
20 25 30

Gln Asn Ser Val Thr Lys Asn Thr Thr Arg Leu Val Thr Gly Tyr Phe
35 40 45

Pro Ile Asp Leu Ile Lys Gly Tyr Arg Pro Ser Gln Lys Leu Ser Glu
50 55 60

Ala Lys Gln Ala Glu Gln Arg Gly Gln Gln Ile Ile Met Met Thr Glu
65 70 75 80

Lys Gln Phe Ile Asp Phe Leu Ala Gln Ser Phe Tyr Leu Leu Ser Gln
85 90 95

Gly Leu

<210> SEQ ID NO 55
<211> LENGTH: 76
<212> TYPE: PRT
<213> ORGANISM: Lactococcus lactis

<400> SEQUENCE: 55

Met Lys Leu Arg Glu Ile Ile Lys Glu Ile Pro Asp Asp Asp Trp Leu
1 5 10 15

Glu Ile Ile Glu Gln Ser Ser Ile Asn Tyr Arg Ser Phe Ile Gly Arg
20 25 30

Ala Pro Lys Lys Tyr Ile Val Gly Glu Leu Leu Asp Tyr Glu Ala Leu
35 40 45

Tyr Ile Gly Glu Val Lys Lys Asn Lys Asn Tyr Gln Asn His Arg Phe
50 55 60

Leu Val Glu Asp Lys Phe Ile Glu His Ser Gly Arg
65 70 75

<210> SEQ ID NO 56
<211> LENGTH: 112
<212> TYPE: PRT
<213> ORGANISM: Lactococcus lactis

<400> SEQUENCE: 56

Met Lys Lys Thr Ile Ile Phe Ile Leu His Ile Pro Phe Ile Leu Leu
1 5 10 15

Leu Trp Leu Cys Ile Thr Ser Pro Phe Phe Ile Lys Asn Ser Leu Leu
20 25 30

Asn Ser Ser Phe Gly His Ile Phe Lys Gly Val Glu Asn Ile Ser His
35 40 45

Ser Gly Pro Leu Ala Thr Val Leu Leu Leu Phe Val Ile Pro Leu Leu
50 55 60

Ser Leu Ile Ser Cys Leu Tyr Leu Ala Phe Lys Lys Asn Gln Ser Gly
65 70 75 80

Arg Lys Tyr Val Ile Tyr Ile Leu Met Ser Leu Phe Ser Leu Val Cys
85 90 95

Leu Ser Val Phe Ser Val Ile Met Ile Ile Gly Leu Gly Asn Tyr Leu
100 105 110

<210> SEQ ID NO 57
<211> LENGTH: 226
<212> TYPE: PRT
<213> ORGANISM: Lactococcus lactis

<400> SEQUENCE: 57

Met Asn His Phe Lys Gly Lys Gln Phe Lys Lys Asp Val Ile Ile Val
1               5                   10                  15

Ala Val Gly Tyr Tyr Leu Arg Tyr Asn Leu Ser Tyr Arg Glu Val Gln
            20                  25                  30

Glu Leu Leu Tyr Asp Cys Gly Ile Asn Val Cys His Thr Thr Ile Tyr
        35                  40                  45

Arg Trp Val Gln Glu Tyr Ser Lys Val Leu Tyr Asp Leu Cys Lys Lys
    50                  55                  60

Lys Asn Arg Gln Ser Phe Tyr Ser Trp Lys Met Asp Glu Ser Tyr Ile
65                  70                  75                  80

Lys Ile Lys Gly Arg Gly His Tyr Leu Tyr Arg Ala Ile Asp Ala Asp
                85                  90                  95

Gly Leu Thr Leu Asp Ile Trp Leu Arg Lys Lys Arg Asp Thr Gln Ala
            100                 105                 110

Ala Tyr Ala Phe Leu Lys Arg Leu His Lys Gln Phe Gly Glu Pro Lys
        115                 120                 125

Ala Ile Val Thr Asp Lys Ala Pro Ser Leu Gly Ser Ala Phe Arg Lys
    130                 135                 140

Leu Gln Ser Val Gly Leu Tyr Thr Lys Thr Glu His Arg Thr Val Asn
145                 150                 155                 160

Tyr Leu Asn Asn Leu Ile Glu Gln Asp His Arg Pro Ile Lys Arg Arg
                165                 170                 175

Asn Lys Phe Tyr Gln Ser Leu Arg Thr Ala Ser Ser Thr Ile Lys Gly
            180                 185                 190

Met Glu Thr Leu Arg Gly Ile Tyr Lys Lys Asn Arg Arg Asn Gly Thr
        195                 200                 205

Leu Phe Gly Phe Ser Val Ser Thr Glu Ile Lys Val Leu Met Gly Ile
    210                 215                 220

Thr Ala
225

<210> SEQ ID NO 58
<211> LENGTH: 76
<212> TYPE: PRT
<213> ORGANISM: Lactococcus lactis

<400> SEQUENCE: 58

Met Lys Thr Gln Glu Leu Asn Leu Lys Gln Phe Val Met Leu Ser Glu
1               5                   10                  15

Lys Glu Leu Gln Glu Ile Ser Gly Gly Gly Gly Trp Gly Ser Ala Phe
            20                  25                  30

Ala Gly Trp Leu Gly Gly Ile Gly Val Asn Ser Gly Gln Thr Ala Gln
        35                  40                  45

Gln Val Val Asn Gln Leu Asn Gly Val Thr Asp Phe His Ala Tyr Asn
    50                  55                  60

His Asn Pro Tyr Gly Ser Gly Gly Thr Pro Asn Asp
65                  70                  75

<210> SEQ ID NO 59
<211> LENGTH: 120

<212> TYPE: PRT
<213> ORGANISM: Lactococcus lactis

<400> SEQUENCE: 59

Met Phe Thr Leu Ile Phe Ser Asn Leu Thr Gly Gly Ile Ile Ile Lys
1 5 10 15

Ala Ile Tyr Lys Asp Lys Thr Val Asp Val Trp Glu Ile Ser Lys Asn
20 25 30

Asn Glu Gln Pro Asp Trp Val Lys Asn Ala Phe Lys Glu Asn Tyr Leu
35 40 45

Ser Trp Tyr Asp Glu Arg Leu Lys Ile Leu Met Asn Gly Ile Lys Pro
50 55 60

Ser Ala Lys Ser Ser Leu Lys Leu Gly Ile Met Gly Ser Val Ala Gly
65 70 75 80

Ser Leu Ala Gly Gly Leu Ala Gly Asn Asn Ile Tyr Val Met Gly Glu
85 90 95

Ile Gly Asp Tyr Leu Asp Ile Thr Asn Arg Lys Val Val Ser Lys Glu
100 105 110

Lys Phe Leu Lys Lys Tyr Ser Val
115 120

<210> SEQ ID NO 60
<211> LENGTH: 89
<212> TYPE: PRT
<213> ORGANISM: Lactococcus lactis

<400> SEQUENCE: 60

Met Lys Tyr Phe Val Thr Phe Leu Ser Pro Thr Gln Asn Met Gly Ile
1 5 10 15

Leu Asn Trp Gln Thr Met Ile Leu Asp Asp Tyr Leu Val Asp Asp Ser
20 25 30

Tyr Trp Glu Asn Thr Lys Leu Glu Leu Ser Lys Glu Val Glu Trp Ile
35 40 45

Thr Gln Ser Glu Leu Tyr Lys Lys Val Lys Arg Asn Asp Gly Ser Gly
50 55 60

Asn Asp Ile Ile Leu Ser Val Pro Val Ser Ala Val Leu Glu Thr Ile
65 70 75 80

Lys Ser Phe Phe Ile Leu Gly His Ser
85

<210> SEQ ID NO 61
<211> LENGTH: 191
<212> TYPE: PRT
<213> ORGANISM: Lactococcus lactis

<400> SEQUENCE: 61

Met Arg Asn Thr Lys Glu Lys Ile Leu Thr Ala Thr Glu Gln Leu Ile
1 5 10 15

Tyr Lys Lys Gly Tyr Thr Gly Thr Ser Ile Asn Asp Ile Leu Asp Glu
20 25 30

Thr Ala Thr Gly Lys Gly Gln Phe Tyr Tyr Tyr Phe Asp Ser Lys Lys
35 40 45

Glu Ala Cys Leu Ala Val Ile Asp Asn His Val Lys Ile Trp Gln Lys
50 55 60

His Leu Leu Asn Gly Ile Leu Ser Arg Asp Glu Ser Pro Leu Ala Asn
65 70 75 80

Leu Lys Glu Met Leu Asp Trp Ile Tyr Ser Asp His Ala Gln Lys Lys

```
                85                  90                  95

Ile Tyr Tyr Gly Cys Pro Val Gly Asn Leu Val Ile Glu Leu Ser Ala
            100                 105                 110

Leu Asp Glu Asp Phe Arg Lys Pro Leu Glu Gln Leu Phe Ser Asp Leu
        115                 120                 125

Gln Lys Lys Ile Ala Glu Asn Leu Ser Gly Leu Thr Gly Leu Leu Val
    130                 135                 140

Lys Gln Asn Leu Pro Ala Ala His Ala Ile Ile Ala Gln Ile Gln Gly
145                 150                 155                 160

Ser Leu Leu Leu Leu Lys Val Thr Gln Asp Leu Asn Val Leu Glu Ser
                165                 170                 175

Asn Phe Asp Leu Leu Lys Thr Ile Phe Glu Lys Val Gly Glu Lys
            180                 185                 190


<210> SEQ ID NO 62
<211> LENGTH: 79
<212> TYPE: PRT
<213> ORGANISM: Lactococcus lactis

<400> SEQUENCE: 62

Met Lys Lys Leu Asp Met Ile Val Ile Gly Pro Gly Pro Ala Pro Pro
1               5                   10                  15

Thr Ala Val Ile Arg Arg Lys Ser Leu Cys Gln Gln Leu Asn Leu Lys
            20                  25                  30

Lys Lys Ser Lys Leu Leu Gln Val Asp Ala Ile Arg Arg Glu Tyr Thr
        35                  40                  45

Ile Ala Asp Val Gln Lys Arg Trp Gln Ser Cys Gln Thr Phe Ile Asp
    50                  55                  60

Val Leu Arg Lys Gly Ile Leu Lys Gln Leu Ile Ala Glu Leu Ser
65                  70                  75


<210> SEQ ID NO 63
<211> LENGTH: 311
<212> TYPE: PRT
<213> ORGANISM: Lactococcus lactis

<400> SEQUENCE: 63

Met Gln Asn Asn Tyr Thr Ser Lys Gly Lys His Leu Thr Glu Ser Glu
1               5                   10                  15

Arg Leu Leu Ile Glu Arg Trp His Asn Lys Glu Lys Val Ser Asn Arg
            20                  25                  30

Glu Ile Ala Tyr Arg Leu Gly Lys Ala Pro Gln Thr Ile His Asn Glu
        35                  40                  45

Ile Gln Arg Gly Thr Val Gln Leu Lys Tyr Lys Thr Lys Tyr Ser Ala
    50                  55                  60

Lys Ile Ala Gln Glu Ser Tyr Lys Thr Leu Arg Thr His Ser Lys Arg
65                  70                  75                  80

Ser Thr Lys Leu Asn Ala Gln Leu Asp Asp Gln Ile Ser Lys Ala Val
                85                  90                  95

Lys Asn Lys Ile Ser Leu Glu Val Ile His Gln Glu Leu Lys Gly Val
            100                 105                 110

Val Cys Leu Arg Thr Leu Tyr Asn Trp Ile Ser Ser Gly Ile Leu Ser
        115                 120                 125

Val Ala Tyr His Glu Leu Leu Tyr Pro Gln Tyr Arg Lys Pro Lys Lys
    130                 135                 140

Gln Arg Val Thr Gln Pro Lys His Met Leu Gly Gln Ser Ile Glu Glu
```

-continued 145 150 155 160

Arg Pro Glu Ser Val Asp Glu Arg Ser Glu Tyr Gly His Trp Glu Ile
165 170 175

Asp Thr Val Leu Leu Thr Lys Glu Lys Gly Glu Cys Leu Leu Thr Leu
180 185 190

Thr Glu Arg Lys Thr Arg Leu Glu Ile Ile Arg Leu Ile Pro Asn Lys
195 200 205

Thr Thr His Ser Val Asn Gln Ala Leu Arg Gly Ile Glu Phe Leu Ala
210 215 220

Leu Ser Val Thr Ser Asp Asn Gly Arg Glu Phe Ala Lys Leu Ser Glu
225 230 235 240

Ala Leu Asp Cys Pro Val Tyr Tyr Cys His Ala Tyr Ala Ser His Glu
245 250 255

Arg Gly Thr Asn Glu Asn His Asn Arg Met Ile Arg Arg His Leu Pro
260 265 270

Lys Gly Thr Lys Lys Thr Thr Lys Gln Val Val Ala Tyr Ile Glu Asn
275 280 285

Trp Met Asn Asn Tyr Pro Arg Lys Met Phe Asn Phe Lys Thr Pro Asn
290 295 300

Gln Met Leu Ile Glu Ser Ile
305 310

<210> SEQ ID NO 64
<211> LENGTH: 207
<212> TYPE: PRT
<213> ORGANISM: Lactococcus lactis

<400> SEQUENCE: 64

Met Phe Asn Asn Lys Asn Thr Ala Phe Val Val Thr Asp Pro Gln Val
1 5 10 15

Glu Phe Leu Lys Pro Lys Gly Ala Gly Tyr Gly Leu Thr Lys Asp Ile
20 25 30

Leu Arg Lys Tyr His Thr Thr Glu Asn Leu Thr Glu Leu Phe Lys His
35 40 45

Ala Lys Ala Lys Gly Tyr Lys Ile Phe Ile Ser Pro His Tyr Phe Tyr
50 55 60

Asp His Asp Gln Asn Trp Lys Phe Gly Gly Gln Gly Glu Gln Met Met
65 70 75 80

Leu Asn Asn Lys Met Phe His Arg Glu His Gln Tyr Gln Glu Thr Val
85 90 95

Lys Gly Ser Gly Ala Asp Phe Val Glu Glu Leu Lys Pro Tyr Leu Asp
100 105 110

Glu Asn Thr Ile Ile Thr Ser Pro His Lys Ile Phe Gly Pro Glu Ser
115 120 125

Asn Asp Leu Ala Leu Gln Leu Arg Lys Asn Gly Ile Asp Thr Val Ile
130 135 140

Leu Ala Gly Met Asn Ala Asn Leu Cys Val Asp Ser His Leu Arg Glu
145 150 155 160

Leu Val Glu Ser Gly Phe His Val His Val Ala Ala Asp Ala Thr Gly
165 170 175

Ala Pro Gly Gln Glu Ala Tyr Asp Ala Ala Ile Thr Asn Phe Gly Phe
180 185 190

Val Ala Asp Arg Thr Met Ser Thr Ala Lys Val Leu Glu Glu Leu
195 200 205

<210> SEQ ID NO 65
<211> LENGTH: 449
<212> TYPE: PRT
<213> ORGANISM: Lactococcus lactis

<400> SEQUENCE: 65

```
Met Lys Lys Ile Asp Val Lys Asn Ile Val Val Gly Phe Gly Lys Gly
1               5                   10                  15

Gly Lys Thr Leu Ala Lys Phe Leu Ser Gly Lys Gly Glu Ser Val Val
            20                  25                  30

Val Ile Glu Gln Ser Thr Leu Met Tyr Gly Gly Thr Cys Ile Asn Ile
        35                  40                  45

Gly Cys Ile Pro Ser Lys Phe Leu Ile Val Asn Gly Glu Lys Gly Leu
    50                  55                  60

Lys Phe Thr Glu Ala Ser Glu Lys Lys Ala Met Leu Thr Gly Asn Leu
65                  70                  75                  80

Asn Leu Lys Asn Tyr His Met Ile Ala Asp Glu Ala Thr Ala Glu Val
                85                  90                  95

Ile Asp Gly Lys Ala Lys Phe Val Ser Asp His Glu Ile Glu Val Met
            100                 105                 110

Asp Ala Glu Gly Glu Val Ile Ala Gln Leu Ile Gly Glu Arg Ile Phe
        115                 120                 125

Ile Asn Thr Gly Ala Thr Pro Val Leu Pro Pro Ile Pro Gly Leu Val
    130                 135                 140

Asp Ser Arg Asn Val Val Thr Ser Thr Glu Leu Met Asp Leu Lys Gln
145                 150                 155                 160

Leu Pro Glu His Leu Thr Ile Ile Gly Ser Gly Tyr Ile Gly Leu Glu
                165                 170                 175

Phe Ala Ser Met Phe Ala Ser Tyr Gly Ser Lys Val Thr Val Leu Asp
            180                 185                 190

Ile Phe Asp Asn Phe Leu Pro Arg Asp Asp Glu Asp Ile Ser Lys Leu
        195                 200                 205

Val Arg Ser Asp Leu Glu Ser Arg Gly Ile Ile Phe Lys Leu Gly Val
    210                 215                 220

Lys Ile Asp Ala Ile Thr Asp Asn Ser Val Glu Ile Ile Asn Lys Glu
225                 230                 235                 240

Gly Lys Lys Val Ser Ile Leu Ser Asp Lys Ile Leu Val Ala Thr Gly
                245                 250                 255

Arg Lys Pro Asn Thr Ala Gly Leu Gly Leu Glu Asn Thr Asn Ile Gln
            260                 265                 270

Leu Gly Gln Arg Gly Glu Ile Val Val Asn Asp Lys Leu Glu Thr Thr
        275                 280                 285

Val Gln Asn Val Trp Ala Leu Gly Asp Val His Gly Gly Leu Gln Phe
    290                 295                 300

Thr Tyr Thr Ser Leu Asp Asp Phe Arg Ile Val Ser Asn Asn Leu Tyr
305                 310                 315                 320

Gly Asp Gly Lys Arg Ser Leu Ser Asp Arg Lys Asn Val Pro Thr Ser
                325                 330                 335

Val Phe Ile Thr Pro Ala Leu Ser Lys Val Gly Leu Asn Glu Lys Asp
            340                 345                 350

Ala Lys Ala Ala Gly Ile Asp Tyr Arg Leu Phe Lys Leu Ala Ala Thr
        355                 360                 365

Ala Ile Pro Lys Ser Ala Val Leu Asn Gln Ser Lys Gly Leu Leu Lys
    370                 375                 380
```

Ala Leu Val Asp Pro Glu Thr Asp Lys Ile Leu Gly Ile Thr Ile Tyr
385 390 395 400

Ala Glu Glu Ser Tyr Glu Thr Ile Asn Leu Val Ser Leu Ala Ile Glu
405 410 415

Val Gly Leu Pro Tyr Thr Leu Leu Arg Asp Lys Ile Tyr Thr His Pro
420 425 430

Thr Met Thr Glu Ala Leu Asn Asp Leu Phe Ala Ala Lys Asn Glu Val
435 440 445

Lys

<210> SEQ ID NO 66
<211> LENGTH: 123
<212> TYPE: PRT
<213> ORGANISM: Lactococcus lactis

<400> SEQUENCE: 66

Met Glu Leu Lys Glu Asn Ala Val Gln Cys Tyr Leu Thr Thr Asp Leu
1 5 10 15

Thr Tyr Glu Ala Val Ala Arg Lys Phe Glu Ile Thr Asn Phe Thr Leu
20 25 30

Leu Ala Ser Trp Val Asn His Phe Lys Ile Tyr Gly Glu Val Pro Ile
35 40 45

Ser Lys Lys Arg Gly Trp Arg Lys Lys Leu Glu Ser Ile Ala Ser Ser
50 55 60

Met Thr Gln Asn Pro Asn Asp Ser Gln Arg Ile Lys Glu Pro Glu Gln
65 70 75 80

Glu Leu Arg Tyr Ala Gln Ile Glu Val Ala Tyr Leu Lys Gly Leu Arg
85 90 95

Arg Leu Glu Lys Asn Ala Leu Met Asn Lys Asn Gln Asp Ser Ser Thr
100 105 110

Val Ser Val Lys Pro Ser Asn Ser Lys Lys Ser
115 120

<210> SEQ ID NO 67
<211> LENGTH: 199
<212> TYPE: PRT
<213> ORGANISM: Lactococcus lactis

<400> SEQUENCE: 67

Met Lys Val Thr Gly Phe Pro Lys Ala Thr Tyr Tyr Tyr Trp Val Asn
1 5 10 15

Cys Phe Glu Arg Val Asn Lys Asp Glu Leu Ile Glu Lys Glu Met Leu
20 25 30

Lys Ile Arg Gln Glu His Ala Asn Ala Gly Tyr Arg Pro Met Ser Glu
35 40 45

Leu Leu Lys Gln Arg Gly Tyr His Val Asn His Lys Lys Val Gln Pro
50 55 60

Leu Met Lys Lys Leu Gly Leu Arg Val Thr Ser Tyr Trp His Lys Ser
65 70 75 80

Arg Lys Tyr Asn Ser Tyr Lys Gly Asn Val Gly Thr Val Ala Lys Asn
85 90 95

Lys Leu His Arg Arg Phe Arg Thr Ser Ile Pro His Gln Lys Ile Thr
100 105 110

Thr Asp Thr Thr Glu Phe Lys Tyr Tyr Glu Asp Gly Ile Gln Lys Lys
115 120 125

Cys Tyr Leu Asn Pro Tyr Ile Asp Leu Phe Asn Ser Glu Val Ile Ser
130 135 140

Tyr His Ile Ser Lys His Pro Ser Tyr Gln Ser Ile Asp Ile Ala Leu
145 150 155 160

Asn Gln Ala Leu Ala Val Thr Ser Asp Cys Pro Tyr Arg Arg Thr Phe
165 170 175

His Ser Asp Gln Gly Trp Gly Tyr Gln Met Arg Asp Tyr Val Ser Lys
180 185 190

Leu Lys Ser His Arg Ile Phe
195

<210> SEQ ID NO 68
<211> LENGTH: 71
<212> TYPE: PRT
<213> ORGANISM: Lactococcus lactis

<400> SEQUENCE: 68

Met Ser His Lys Gly Asn Cys Gln Asp Asn Ser Val Met Glu Asn Phe
1 5 10 15

Phe Gly Leu Leu Lys Gln Glu Ile Tyr Tyr Gly His Ile Phe Ser Ser
20 25 30

Phe Glu Glu Leu Glu Gln Val Ile Val Ile Trp Ile Arg Tyr Tyr Asn
35 40 45

Thr Lys Arg Ile Lys Gln Lys Leu Asn Trp Met Ser Pro Ile Gln Phe
50 55 60

Arg Leu Asn Tyr Gln Asp Asn
65 70

<210> SEQ ID NO 69
<211> LENGTH: 296
<212> TYPE: PRT
<213> ORGANISM: Lactococcus lactis

<400> SEQUENCE: 69

Met Thr Tyr Asn Ser Thr Leu Pro Lys Val Phe Val Tyr Leu Leu Thr
1 5 10 15

Thr Ile Glu Thr Leu Tyr Gln Thr Arg Val Pro Leu Glu Val Gln Asn
20 25 30

Arg Lys Asn Val His Leu Ala Thr Ser Asp Cys Leu Val Ile Ala Cys
35 40 45

Tyr Leu Trp Gly Val Leu His Phe Ser Glu Thr Leu Lys Ala Lys His
50 55 60

Gln Leu Ala Gln Ser Leu Phe Pro Asn Phe Leu Glu Tyr Ser Arg Phe
65 70 75 80

Val Arg Arg Cys Asn Ala Leu Leu Pro Ile Ile Gln Val Ile Arg Gln
85 90 95

Ala Leu Val Phe Lys Glu Val Glu Gly Met Ser Val Ser Ile Ile Asp
100 105 110

Ser Phe Pro Ile Pro Leu Cys Gln Pro Ile Arg Asn Phe Arg Ser Lys
115 120 125

Val Leu Gly Asp Tyr Ala Asn Val Gly Tyr Asn Ala Thr Lys Gly Gln
130 135 140

Tyr Phe Tyr Gly Cys Lys Cys His Ala Leu Val Ser Glu Ser Gly Tyr
145 150 155 160

Val Ile Asp Tyr Thr Ile Thr Pro Ala Ser Met Ala Asp Ser Ser Met
165 170 175

-continued

Thr Glu Glu Val Leu Ser Gln Phe Gly Thr Pro Thr Val Leu Gly Asp
180 185 190

Met Gly Tyr Leu Gly Gln Ser Leu His Asp Arg Leu Glu Leu Lys Glu
195 200 205

Ile Asp Leu Met Thr Pro Val Arg Lys Asn Met Lys Gln Lys Lys Ile
210 215 220

Leu Phe Pro Asn Phe Ser Lys Arg Arg Lys Val Ile Glu Arg Val Phe
225 230 235 240

Ser Phe Leu Thr Asn Leu Gly Ala Glu Arg Cys Lys Ser Arg Ser Pro
245 250 255

Gln Gly Phe Gln Leu Lys Leu Glu Met Ile Leu Leu Ala Tyr Ser Leu
260 265 270

Leu Leu Lys Ser Ala Lys Ser Leu Glu Pro Glu Thr Leu Arg Tyr Ser
275 280 285

Ile Gly Tyr Gln Val Met Ala Lys
290 295

<210> SEQ ID NO 70
<211> LENGTH: 271
<212> TYPE: PRT
<213> ORGANISM: Lactococcus lactis

<400> SEQUENCE: 70

Met Ile Lys Leu Val Ala Ile Asp Leu Asp Gly Thr Leu Leu Asp Pro
1 5 10 15

Asn Arg Gln Ile Thr Ala Glu Val Lys Thr Ala Val Lys Lys Ala Lys
20 25 30

Ala Ala Gly Val Lys Ile Val Ile Thr Thr Gly Arg Pro Leu Pro Gly
35 40 45

Val Val Asp Ile Leu Lys Ala Leu Glu Leu Thr Asp Gln Ser Asp Tyr
50 55 60

Val Ile Thr Tyr Asn Gly Gly Leu Val Gln Gln Ala Thr Gly Glu Glu
65 70 75 80

Phe Ile Lys Glu Thr Leu Ser Ser Glu Asp Trp Leu Asp Leu Asp Ala
85 90 95

Ala Ala Arg Lys Ile Gly Leu Pro Ile His Ala Ile Thr Arg Glu Gly
100 105 110

Ile Tyr Thr Pro Asn His Asp Val Gly Arg Tyr Thr Val Gln Glu Ala
115 120 125

Gln Met Val Lys Met Pro Leu Tyr Ile Arg Gln Pro Glu Asp Ile Ala
130 135 140

Ala Leu Glu Ile Ala Lys Val Met Met Val Asp Glu Pro Ala Ala Leu
145 150 155 160

Asp Asp Gly Ile Ala Tyr Leu Pro Phe Glu Phe Phe Glu Arg Tyr Asn
165 170 175

Val Val Lys Ser Thr Pro Phe Tyr Leu Glu Phe Met Asn Lys Lys Ala
180 185 190

Ser Lys Gly Ser Ala Val Gln His Leu Ala Glu Lys Leu Ser Phe Asp
195 200 205

Leu Asp Glu Val Met Ala Ile Gly Asp Glu Glu Asn Asp Arg Ser Met
210 215 220

Leu Glu Val Ala Val Cys Ser Val Val Met Glu Asn Gly Lys Ser Lys
225 230 235 240

Leu Lys Lys Ile Ala Lys Tyr Val Thr Lys Ser Asn Ala Lys Ser Gly
245 250 255

-continued

```
Val Ala Tyr Ala Ile Asn Glu Trp Val Leu Lys Asp Tyr Gln Asp
            260                 265                 270


<210> SEQ ID NO 71
<211> LENGTH: 121
<212> TYPE: PRT
<213> ORGANISM: Lactococcus lactis

<400> SEQUENCE: 71

Met Lys Ile Thr Phe Asp Glu Lys Thr Ala Asp Lys Ile Lys Ala Phe
1               5                   10                  15

Gly Asp Val Asp Leu Val Phe Asp Phe Asp His Thr Leu Ser Glu Val
            20                  25                  30

Asn Thr Glu Val Asp Ala Cys Ala Gly Gly Ile Ser Arg Tyr Arg Ile
        35                  40                  45

Val Ala Val Glu Lys Gly Asn Val Pro Glu Val Phe Asp Ala Ser Ile
    50                  55                  60

Asp Ser Glu Phe Gly Pro Ile Tyr Tyr Lys Gly Tyr Gly Ser Tyr Phe
65                  70                  75                  80

Phe Gln Asp Glu Met Tyr Thr Lys Ile Asn Pro Ser Tyr Asn Leu Ile
                85                  90                  95

Glu Leu His Ser Thr Ala Glu Leu Leu Ser Pro Asn Leu Leu Ile Val
            100                 105                 110

Asp Phe Arg Gly Lys Gln Lys Ala Ser
        115                 120


<210> SEQ ID NO 72
<211> LENGTH: 49
<212> TYPE: PRT
<213> ORGANISM: Lactococcus lactis

<400> SEQUENCE: 72

Met Leu Ser Ala Gly Leu Leu Gly Ile Asp Pro Gly His Tyr Ile Glu
1               5                   10                  15

His Ala Phe Ile Gly Leu Val Ala Asp Lys Leu Arg Ser Phe Asp Leu
            20                  25                  30

Gly Val Lys Ile Tyr Glu Ser Gln Glu Lys Thr Asn Pro Phe Tyr Asp
        35                  40                  45

Ile


<210> SEQ ID NO 73
<211> LENGTH: 319
<212> TYPE: PRT
<213> ORGANISM: Lactococcus lactis

<400> SEQUENCE: 73

Met Thr Tyr Thr His Leu Thr Ser Asn Glu Leu Ala Met Ile Glu Ala
1               5                   10                  15

Tyr Tyr Asn Asn His Gln Ser Val Ala Lys Thr Ala Val Leu Leu Asn
            20                  25                  30

Arg Ser Arg Gln Thr Ile His Lys Val Tyr Gln Phe Phe Lys Thr Gly
        35                  40                  45

His Asn Ala Leu Asp Tyr Phe Asn Gln Tyr Lys Lys Asn Lys Thr Arg
    50                  55                  60

Cys Gly Arg Arg Pro Ile Val Leu Ser Asp Glu Gln Thr Glu Tyr Ile
65                  70                  75                  80

Gln Lys Arg Val Val Gln Gly Trp Thr Pro Asp Val Ile Val Gly Arg
```

-continued

```
                85                  90                  95

Ala Glu Phe Ser Ile Ser Cys Ser Met Arg Thr Leu Tyr Arg Met Phe
            100                 105                 110

Lys Gln Gly Val Phe Glu Val Thr His Leu Pro Met Lys Gly Lys Arg
        115                 120                 125

Lys Ala Asn Gly His Lys Glu Thr Arg Gly Lys Gln Ser Phe Arg Arg
    130                 135                 140

Ser Leu Arg Asp Arg Gly Asn Asp Tyr Ser Lys Phe Asn Gln Glu Phe
145                 150                 155                 160

Gly His Leu Glu Gly Asp Thr Ile Val Gly Lys Lys His Lys Ser Ala
                165                 170                 175

Val Ile Thr Leu Val Glu Arg Leu Ser Lys Val Ile Ile Thr Leu Gln
            180                 185                 190

Pro Glu Gly Arg Arg Ala Ile Asp Ile Glu Asn Arg Leu Asn Gln Trp
        195                 200                 205

Met Gln Ser Val Pro Lys His Leu Phe Lys Ser Met Thr Phe Asp Cys
    210                 215                 220

Gly Lys Glu Phe Ser Asn Trp Lys Ser Ile Ser Asn Ile Asn Asp Ile
225                 230                 235                 240

Asp Ile Tyr Phe Ala Asp Pro Gly Thr Pro Ser Gln Arg Gly Leu Asn
                245                 250                 255

Glu Asn Ser Asn Gly Leu Leu Arg Lys Asp Gly Leu Pro Lys Gln Met
            260                 265                 270

Asp Phe Asn Glu Val Asp Glu Ser Phe Ile Gln Ser Ile Ala Ser Lys
        275                 280                 285

Arg Asn Asn Ile Pro Arg Lys Ser Leu Asn Tyr Lys Thr Pro Ile Glu
    290                 295                 300

Val Phe Leu Ser His Ile Cys Lys Glu Glu Leu Ser Asn Leu Ile
305                 310                 315


<210> SEQ ID NO 74
<211> LENGTH: 66
<212> TYPE: PRT
<213> ORGANISM: Lactococcus lactis

<400> SEQUENCE: 74

Met Ala Asn Gly Thr Val Lys Trp Phe Asn Ala Thr Lys Gly Phe Gly
1               5                   10                  15

Phe Ile Thr Ser Glu Asp Gly Gln Asp Leu Phe Ala His Phe Ser Ser
            20                  25                  30

Ile Gln Ser Asp Gly Phe Lys Ser Leu Asp Glu Gly Gln Lys Val Glu
        35                  40                  45

Phe Asp Val Glu Glu Gly Gln Arg Gly Pro Gln Ala Val Asn Ile Thr
    50                  55                  60

Lys Ala
65


<210> SEQ ID NO 75
<211> LENGTH: 226
<212> TYPE: PRT
<213> ORGANISM: Lactococcus lactis

<400> SEQUENCE: 75

Met Asn Tyr Phe Lys Gly Lys Gln Phe Gln Lys Asp Val Ile Ile Val
1               5                   10                  15

Ala Val Gly Tyr Tyr Leu Arg Tyr Asn Leu Ser Tyr Arg Glu Ile Gln
```

```
            20                  25                  30

Glu Leu Leu Tyr Asp Leu Gly Ile Asn Val Cys His Thr Thr Ile Tyr
        35                  40                  45

Arg Trp Val Gln Glu Tyr Ser Lys Val Leu Tyr His Leu Trp Lys Lys
    50                  55                  60

Lys Asn Arg Pro Ser Phe Tyr Ser Trp Lys Met Asp Glu Thr Tyr Ile
65                  70                  75                  80

Lys Ile Lys Gly Arg Trp His Tyr Leu Tyr Arg Ala Ile Asp Ala Asp
                85                  90                  95

Gly Leu Thr Leu Asp Ile Trp Leu Arg Lys Lys Arg Asp Thr Gln Ala
            100                 105                 110

Ala Tyr Ala Phe Leu Lys Arg Leu His Lys Gln Phe Gly Gln Pro Arg
        115                 120                 125

Val Ile Val Thr Asp Lys Ala Pro Ser Ile Gly Ser Ala Phe Arg Lys
    130                 135                 140

Leu Gln Ser Asn Gly Leu Tyr Thr Lys Thr Glu His Arg Thr Val Lys
145                 150                 155                 160

Tyr Leu Asn Asn Leu Ile Glu Gln Asp His Arg Pro Ile Lys Arg Arg
                165                 170                 175

Asn Lys Phe Tyr Arg Ser Leu Arg Thr Ala Ser Thr Thr Ile Lys Gly
            180                 185                 190

Met Glu Thr Ile Arg Gly Ile Tyr Lys Lys Asn Arg Arg Asn Gly Thr
        195                 200                 205

Leu Phe Gly Phe Ser Val Ser Thr Glu Ile Lys Val Leu Met Gly Ile
    210                 215                 220

Leu Ala
225
```

<210> SEQ ID NO 76
<211> LENGTH: 345
<212> TYPE: PRT
<213> ORGANISM: Lactococcus lactis

<400> SEQUENCE: 76

```
Met Val Thr Tyr Thr Asp Leu Leu Pro Lys Pro Thr Glu Asn Gln Gln
1               5                   10                  15

Ala Phe Ile Leu Asp His Gly Lys Thr Glu Asp Asp Gly Gln Leu Lys
            20                  25                  30

Tyr Ala Asp Asp Ala Lys Ser Tyr Gly Trp Asn Met Arg Gln Tyr Gly
        35                  40                  45

Lys Leu Lys Ala Gly Ala Val Val Leu Asn Arg His Pro Gly Lys Ile
    50                  55                  60

Thr Lys Asp Arg Lys Trp Glu Ile Tyr Gly Gly Gly Tyr Val Glu Ser
65                  70                  75                  80

Val Ser Asp Glu Asp Glu Asn Gly Asn Val Thr Ala Val Ile Thr His
                85                  90                  95

Ala Phe Thr Ile Glu Pro Pro Ile Lys Gln Gly Asp Ser Phe Ile Glu
            100                 105                 110

Asn Phe Asp Trp Asn Thr Pro Asn Lys Lys Lys Arg Lys Lys Pro Asn
        115                 120                 125

Ser Trp Ala Tyr Phe Trp Asp Gln Tyr Gly Met Asn Glu Ile Ser Tyr
    130                 135                 140

Thr Asp Phe Val Gly Leu Ile Glu Asn Arg His Leu Ser Pro Ile Asp
145                 150                 155                 160
```

```
Asp Thr Gln Ser Leu Pro Val Glu Lys Asp Leu Thr Asn Ala Glu Val
            165                 170                 175

Glu Glu Ile Glu Glu Ala Ser Ser Lys Gly Phe Thr Val Leu Val Asp
            180                 185                 190

Glu Val Gly Pro Asn Arg Pro Asn Gly Thr Gln Lys Arg Lys Phe Thr
        195                 200                 205

Gly Arg His Thr Asp Trp Glu Arg Val Asn Lys Ala Lys Gln Lys Thr
    210                 215                 220

Gly Ala Leu Gly Glu Glu Ile Val Leu Asp Phe Leu Ile Gln Lys Ala
225                 230                 235                 240

Glu Lys Asn Lys Thr Lys Leu Pro Glu His Val Ser Lys Thr Glu Gly
            245                 250                 255

Asp Gly His Gly Tyr Asp Ile Arg Ala Phe Asp Gln Ser Gly Asn Glu
            260                 265                 270

Ile His Ile Glu Val Lys Ala Ser Lys Thr Asn Phe Ser Asp Gly Phe
        275                 280                 285

Glu Met Ser Ala Asn Glu Val Ala Ser Ser Leu Glu Asp Thr Pro Tyr
    290                 295                 300

Lys Ile Tyr Phe Val His Asp Leu Asp Val Thr Ser Lys Val Cys Lys
305                 310                 315                 320

Ile Lys Ile Tyr Asp Gly Pro Phe Thr Glu Glu Asn Phe Met Met Val
            325                 330                 335

Pro Thr Asn Tyr Lys Ile Phe Lys Lys
            340                 345


<210> SEQ ID NO 77
<211> LENGTH: 83
<212> TYPE: PRT
<213> ORGANISM: Lactococcus lactis

<400> SEQUENCE: 77

Met Phe Trp Thr Asn Val Lys Tyr Leu Asp Ala His Ile Leu Lys Gln
1               5                   10                  15

Asn Glu Gln Leu Lys Tyr Glu Asn Pro Thr Glu Glu Asn Lys Leu Lys
            20                  25                  30

Ile Lys Ala Leu Gln Leu Glu Arg Lys Asp Leu Gln Ala Gln Tyr Arg
        35                  40                  45

Lys Val Ile Lys Lys Met Lys Thr Tyr Asp Ala Gly Gln Glu Ile Val
    50                  55                  60

Gln Glu Lys Leu Lys Glu Lys Glu Ile Asn Lys Glu Lys Thr Gln Asp
65                  70                  75                  80

Ile Pro Ser


<210> SEQ ID NO 78
<211> LENGTH: 64
<212> TYPE: PRT
<213> ORGANISM: Lactococcus lactis

<400> SEQUENCE: 78

Met Ile Tyr Thr Ile Gly Tyr Tyr Ile Ala Val Ile Gly Leu Val Ile
1               5                   10                  15

Met Met Phe Gly Phe Lys Ser Phe Tyr Ser Gln Met Asn Lys Trp Ser
            20                  25                  30

Arg Phe Gly Phe Ile Phe Leu Ala Leu Gly Leu Ala Phe Pro Ile Val
        35                  40                  45

Tyr Asp Phe Ile Val Gly Phe Ile Asn Gly Leu Leu Lys Asn Val Asn
```

50 55 60

<210> SEQ ID NO 79
<211> LENGTH: 193
<212> TYPE: PRT
<213> ORGANISM: Lactococcus lactis

<400> SEQUENCE: 79

Met Lys Leu Leu Leu Ile Asp Asn Tyr Asp Ser Phe Thr Tyr Leu Leu
1 5 10 15

Val Gln Tyr Phe Glu Glu Leu Asp Cys Ser Val Thr Val Val Asn Asp
20 25 30

Gln Asp Lys Met Ser Gln Lys Ile Arg Ile Ser Pro Asp Phe Ile Cys
35 40 45

Glu Asn Tyr Asp Ala Ile Thr Ile Ser Pro Gly Pro Lys Thr Pro Lys
50 55 60

Glu Ala Val Phe Ser Arg Asp Val Val Gln Leu Tyr Ala Gly Lys Ile
65 70 75 80

Pro Met Leu Gly Ile Cys Leu Gly Gln Gln Val Ile Ala Glu Cys Phe
85 90 95

Gly Gly Asn Val Val Leu Gly Glu Arg Pro Met His Gly Lys Ile Ser
100 105 110

Val Ile Arg His Asn Cys Gln Gly Ile Phe Lys Gly Leu Pro Gln Asn
115 120 125

Leu Lys Val Ala Arg Tyr His Ser Leu Ile Val Asp Lys Leu Pro Asn
130 135 140

Asp Phe Glu Ile Asp Ala Gln Ser Glu Asp Gly Val Ile Gln Ala Met
145 150 155 160

His Gln Pro Lys Leu Lys Leu Trp Ala Leu Gln Phe His Pro Glu Ser
165 170 175

Leu Val Thr Glu Tyr Gly His Glu Met Leu Asn Asn Phe Leu Lys Val
180 185 190

Val

<210> SEQ ID NO 80
<211> LENGTH: 641
<212> TYPE: PRT
<213> ORGANISM: Lactococcus lactis

<400> SEQUENCE: 80

Met Lys Glu Phe Ile Ile Lys Asn Thr Asp Ile Trp Lys Ile Phe Leu
1 5 10 15

Lys Tyr Tyr Arg Ser Asp Glu Glu Ile Val Phe Leu His Ser Ser Gln
20 25 30

Ala Thr Glu Asn Glu His Tyr Ser Ile Leu Ala His Lys Pro Tyr Lys
35 40 45

Lys Val Ser Lys Tyr Lys Gly Gln Val Phe Phe Asn Gly Glu Lys Lys
50 55 60

Lys Phe Asn Phe Leu Asp Ala Val Asp Leu Leu Lys Asn Glu Lys Val
65 70 75 80

Glu Arg Pro Lys Asn Trp Pro Phe Tyr Pro Glu Leu Leu Gly Phe Val
85 90 95

Ser Tyr Glu Gln Asp Pro Ala Tyr Phe Ala Ala Tyr Asp Glu Val Leu
100 105 110

Leu Phe Asp His Arg Thr Lys Arg Leu Arg Val Val Gln Phe Glu Gln
115 120 125

Thr Asp Gly Gln Tyr Trp Leu Thr Glu Ser Glu Glu Ile Glu Val Asp
    130                 135                 140

Ser Glu Ile Glu Phe Asp Gly Gln Asn Gly Ile Gly Ala Val Phe Ile
145                 150                 155                 160

Asp Gln Thr Arg Gln Glu Tyr Ile Ala Ser Ile Lys Arg Leu Gln Asp
                165                 170                 175

Tyr Met Lys Ala Gly Asp Ile Tyr Val Ala Asn Leu Thr Gln Gln Phe
            180                 185                 190

Glu Ile Trp Ser Asp Gln Lys Pro Ile Asp Val Phe Lys Lys Thr Arg
        195                 200                 205

Asn Gln Ile Pro Ala Pro Phe Ser Ser Phe Leu Gln Tyr Pro Glu Trp
    210                 215                 220

Lys Met Thr Gln Ile Ser Ser Ser Val Glu Arg Phe Val Ser Ile His
225                 230                 235                 240

Asp Gly Ala Leu Ile Ser Lys Pro Ile Lys Gly Thr Ile Ala Arg Gly
                245                 250                 255

Glu Asp Val Val Thr Asp Arg Leu Gln Lys Glu Ile Leu Ser Asn Ser
            260                 265                 270

Ile Lys Glu Arg Thr Glu Leu Leu Met Val Thr Asp Leu Leu Arg Asn
        275                 280                 285

Asp Ile Ala Arg Ile Ser Gln Pro Phe Ser Leu Ser Val Pro Lys Phe
    290                 295                 300

Ala Glu Ile Glu Thr Phe Ser His Val His Gln Leu Val Thr Ser Ile
305                 310                 315                 320

Lys Ser Arg Ile Lys Glu Asp Leu Thr Phe Ser Glu Phe Met Thr Ala
                325                 330                 335

Leu Phe Pro Gly Gly Ser Ile Thr Gly Thr Pro Lys Lys Arg Ala Met
            340                 345                 350

Glu Ile Ile Lys Glu Val Glu Lys Gln Pro Arg Gly Ile Tyr Thr Gly
        355                 360                 365

Met Gln Gly Trp Leu Ser Arg Glu Met Asp Leu Asp Met Asn Ile Val
    370                 375                 380

Ile Arg Thr Leu Val His Asp Gly Glu His Tyr Gln Leu Gly Val Gly
385                 390                 395                 400

Gly Gly Ile Thr Phe Glu Ser Glu Ala Glu Ala Glu Phe Ser Glu Ile
                405                 410                 415

Leu Leu Lys Ala Lys Pro Phe Leu Asp Ile Leu Gly Leu Lys Asp Val
            420                 425                 430

Pro Ser Ile Leu Phe Thr Thr Gly Leu Val Lys Asn Gly Glu Leu Leu
        435                 440                 445

Asn Leu Glu Gly His Val Asn Arg Leu Lys Lys Gln Tyr His His Pro
    450                 455                 460

Asp Leu Glu Glu Lys Leu Arg Lys Phe Ala Gln Asn Val Thr Asp Gly
465                 470                 475                 480

Val Leu Arg Val Ser Thr Asp Gly Asp Ser Leu Asn Pro Glu Ile Arg
                485                 490                 495

Gln Leu Thr His Ser Asn Glu Ser Tyr Arg Val Lys Leu Ser Ser Ile
            500                 505                 510

Asn Asp Lys Pro Ser Pro Leu Ser Asn Phe Lys Leu Ser Gly Pro Asp
        515                 520                 525

Phe Gln Lys Val Phe Arg Gln Glu Val Leu Asp Val Lys Lys Glu Gly
    530                 535                 540

```
Phe Gln Asp Ile Leu Phe His Thr Asp Gly Leu Val Ser Glu Leu Ser
545                 550                 555                 560

Ile Gly Asn Phe Val Ala Lys Lys Gly Asn Gln Tyr Glu Thr Pro Ala
                565                 570                 575

Lys Tyr Ala Leu Lys Gly Thr Phe Leu Asp Leu Phe Ala Lys Asn His
            580                 585                 590

Thr Leu Ile Tyr Lys Asp Ile Ala Ile Ser Asp Leu Lys Asn Tyr Asp
        595                 600                 605

Cys Phe Tyr Met Thr Asn Ala Val Arg Gly Leu Val Glu Ile Lys Ile
    610                 615                 620

Asp Gly Ile Ser Gly Ser Val Ala Lys Phe Ser Lys Lys Ser Ile Leu
625                 630                 635                 640

Val


<210> SEQ ID NO 81
<211> LENGTH: 226
<212> TYPE: PRT
<213> ORGANISM: Lactococcus lactis

<400> SEQUENCE: 81

Met Asn Tyr Phe Lys Gly Lys Gln Phe Gln Lys Asp Val Ile Ile Val
1               5                   10                  15

Ala Val Gly Tyr Tyr Leu Arg Tyr Asn Leu Ser Tyr Arg Glu Ile Gln
            20                  25                  30

Glu Leu Leu Tyr Asp Arg Gly Ile Asn Val Cys His Thr Thr Ile Tyr
        35                  40                  45

Arg Trp Val Gln Glu Tyr Ser Lys Val Leu Tyr His Leu Trp Lys Lys
    50                  55                  60

Lys Asn Arg Gln Ser Phe Tyr Ser Trp Lys Met Asp Glu Thr Tyr Ile
65                  70                  75                  80

Lys Ile Lys Gly Arg Trp His Tyr Leu Tyr Arg Ala Ile Asp Ala Asp
                85                  90                  95

Gly Leu Thr Leu Asp Ile Trp Leu Arg Lys Lys Arg Asp Thr Gln Ala
            100                 105                 110

Ala Tyr Ala Phe Leu Lys Arg Leu His Lys Gln Phe Gly Gln Pro Arg
        115                 120                 125

Val Ile Val Thr Asp Lys Ala Pro Ser Ile Gly Ser Ala Phe Arg Lys
    130                 135                 140

Leu Gln Ser Asn Gly Leu Tyr Thr Lys Thr Glu His Arg Thr Val Lys
145                 150                 155                 160

Tyr Leu Asn Asn Leu Ile Glu Gln Asp His Arg Pro Ile Lys Arg Arg
                165                 170                 175

Asn Lys Phe Tyr Arg Ser Leu Arg Thr Ala Ser Thr Thr Ile Lys Gly
            180                 185                 190

Met Glu Thr Ile Arg Gly Ile Tyr Lys Lys Asn Arg Arg Asn Gly Thr
        195                 200                 205

Leu Phe Gly Phe Ser Val Ser Thr Glu Ile Lys Val Leu Met Gly Ile
    210                 215                 220

Leu Ala
225


<210> SEQ ID NO 82
<211> LENGTH: 98
<212> TYPE: PRT
<213> ORGANISM: Lactococcus lactis
```

<400> SEQUENCE: 82

Met Asp Asn Lys Asp Ile Glu Leu Ile Gln Gln Met Glu Asn Lys Tyr
1 5 10 15

Asp Thr Phe Met Pro Val Leu Thr Asn Leu Ile Asp Ser Val Glu Lys
20 25 30

Phe Asn Ser Ile Tyr Asn Asn Tyr Ile Glu Leu Arg Asn Phe Tyr Gly
35 40 45

Ser Glu Lys Trp Phe Glu Tyr Met Glu Ile Glu Lys Ile Pro Val Lys
50 55 60

Cys Gly Val Leu Thr Glu Asp Gln Leu Phe Asp Met Ile Ser Asp His
65 70 75 80

Asn Glu Leu Leu Gly Val Leu Leu Asp Leu Thr Ser Lys Met Tyr Lys
85 90 95

Asn Phe

<210> SEQ ID NO 83
<211> LENGTH: 154
<212> TYPE: PRT
<213> ORGANISM: Lactococcus lactis

<400> SEQUENCE: 83

Met Val Gln Asp Thr Leu Leu Asp Ser Phe Arg Ala Gly Arg Arg Asn
1 5 10 15

Tyr Thr Ile Phe Gln Val Gly Lys Ala Thr Leu Leu Arg Val Ser Asp
20 25 30

Val Met Lys Leu Lys Lys Thr Asp Val Phe Asn Leu Asp Gly Thr Val
35 40 45

Lys Gln Thr Ala Phe Ile His Asp Gln Lys Thr Gly Lys Gly Asn Thr
50 55 60

Leu Tyr Leu Lys Pro Val Gln Gln Asp Leu Met Leu Tyr His Ala Trp
65 70 75 80

Leu Ile Gln Gln Asn Met Asn Ser Glu Trp Leu Phe Pro Ser Thr Ser
85 90 95

Arg Pro Tyr Arg Pro Ile Thr Glu Lys Gln Phe Tyr Lys Ile Met Ala
100 105 110

Arg Val Gly Asp Leu Leu Gly Ile Asn Tyr Leu Gly Thr His Thr Met
115 120 125

Arg Lys Thr Gly Ala Tyr Arg Val Tyr Thr Gln Ser Asn Tyr Tyr Trp
130 135 140

Leu Ser Tyr Ala Phe Ile Lys Pro Phe Lys
145 150

<210> SEQ ID NO 84
<211> LENGTH: 226
<212> TYPE: PRT
<213> ORGANISM: Lactococcus lactis

<400> SEQUENCE: 84

Met Asn His Phe Lys Gly Lys Gln Phe Gln Gln Asp Val Ile Ile Val
1 5 10 15

Ala Val Gly Tyr Tyr Leu Arg Tyr Asn Leu Ser Tyr Arg Glu Val Gln
20 25 30

Glu Leu Leu Tyr Asp Arg Gly Ile Asn Val Cys His Thr Thr Ile Tyr
35 40 45

Arg Trp Val Lys Glu Tyr Ser Lys Ile Leu Tyr His Leu Trp Lys Lys
50 55 60

```
Lys Asn Lys Gln Ser Phe Tyr Ser Trp Lys Met Asp Glu Thr Tyr Ile
65                  70                  75                  80

Lys Ile Lys Gly Arg Trp His Tyr Leu Tyr Arg Ala Ile Asp Ala Asp
                85                  90                  95

Gly Leu Thr Leu Asp Ile Trp Leu Arg Lys Lys Arg Asp Thr Gln Ala
            100                 105                 110

Ala Tyr Ala Phe Leu Lys Arg Leu His Lys Gln Phe Gly Gln Pro Arg
        115                 120                 125

Val Ile Val Thr Asp Lys Ala Pro Ser Ile Gly Ser Ala Phe Arg Lys
    130                 135                 140

Leu Gln Arg Asn Gly Leu Tyr Thr Lys Thr Glu His Arg Thr Val Lys
145                 150                 155                 160

Tyr Leu Asn Asn Leu Ile Glu Gln Asp His Arg Pro Ile Lys Arg Arg
                165                 170                 175

Asn Lys Phe Tyr Arg Ser Leu Arg Thr Ala Ser Ser Thr Ile Lys Gly
            180                 185                 190

Met Glu Thr Ile Arg Gly Ile Tyr Lys Lys Asn Arg Arg Asn Gly Thr
        195                 200                 205

Leu Phe Gly Phe Ser Val Ser Thr Glu Ile Lys Ile Leu Met Gly Ile
    210                 215                 220

Pro Ala
225


<210> SEQ ID NO 85
<211> LENGTH: 229
<212> TYPE: PRT
<213> ORGANISM: Lactococcus lactis

<400> SEQUENCE: 85

Met Tyr Asn Glu Val Phe Val Val Ser Asp Ile His Gly Glu Tyr Lys
1               5                   10                  15

Lys Phe Lys Glu Ile Leu Lys Tyr Trp Asp Ser Asn Arg Gln Gln Leu
            20                  25                  30

Ile Leu Leu Gly Asp Leu Cys Asp Arg Gly Leu Gln Ser Tyr Glu Cys
        35                  40                  45

Phe Tyr Leu Ala Lys Tyr Leu Cys Asp Asn Tyr Gly Ala Ile Leu Ile
    50                  55                  60

Lys Gly Asn His Glu Asp Leu Phe Leu Lys Phe Leu Asn Lys Thr Glu
65                  70                  75                  80

Asp Phe Lys Glu Asn Tyr Ile Lys Asn Gly Gly Leu Lys Thr Leu Glu
                85                  90                  95

Ser Phe Gly Tyr Ser Glu Asn Asn Thr Phe Lys Asp Ile Val Leu Asp
            100                 105                 110

Ile Lys Lys Asn Asn Asp Lys Leu Ile Glu Phe Leu Thr Tyr Leu Pro
        115                 120                 125

Asn Phe Tyr Glu Trp Asn Asp Tyr Ile Phe Val His Ala Gly Val Asn
    130                 135                 140

Leu Lys Ile Asn Asn Trp Lys Asp Thr Ser Ile Arg Asp Phe Met Trp
145                 150                 155                 160

Ile Arg Glu Asp Phe His Phe Thr Pro Asn Arg Leu Asn Lys Thr Ile
                165                 170                 175

Val Phe Gly His Thr Glu Thr Lys Ile Leu Asn Lys Asn Asn Lys Tyr
            180                 185                 190

Asp Ile Trp Ile His Asp Asn Lys Ile Gly Ile Asp Gly Gly Ala Val
```

```
        195                 200                 205

Tyr Gly Gly Tyr Leu Tyr Gly Val Ile Leu Asp Val His Gly Ile Lys
    210                 215                 220

Asp Tyr Val Tyr Val
225


<210> SEQ ID NO 86
<211> LENGTH: 96
<212> TYPE: PRT
<213> ORGANISM: Lactococcus lactis

<400> SEQUENCE: 86

Met Ile Asn Tyr Gln Gly Glu Val Phe Thr Glu Thr Glu Phe Tyr Gly
1               5                   10                  15

Arg Glu Ile Leu Glu Ala Ile Gln Leu Thr Asn Lys Phe Pro Thr Pro
            20                  25                  30

Lys Lys Val Leu Ile Asp Met Leu Glu Glu Met Ile His Glu Gln Leu
        35                  40                  45

Asp Leu Ile Asp Lys Glu Glu Leu Asn Asn Tyr Ile Asn Ala Lys Lys
    50                  55                  60

Tyr Val Gln Thr Leu Thr Glu Asp Glu Val Lys Asn Leu Cys Phe Glu
65                  70                  75                  80

Val Lys Asp Leu Tyr Glu Asp Val Leu Lys Glu Phe Glu Ile Lys Leu
                85                  90                  95


<210> SEQ ID NO 87
<211> LENGTH: 94
<212> TYPE: PRT
<213> ORGANISM: Lactococcus lactis

<400> SEQUENCE: 87

Met Lys Lys Thr Gly Ile Thr Asn Phe Ser Val Phe Ala Arg Arg Ala
1               5                   10                  15

Cys Cys Asn Lys Glu Ile Phe Thr Leu Asp Phe Ser Glu Tyr Lys Asn
            20                  25                  30

Ile Ile Ser Glu Ile Ser Ala Thr Lys Ser Glu Leu Lys Arg Ile Gly
        35                  40                  45

Asn Asn Ile Asn Gln Ile Ala Lys His Leu Asn Glu Asn Lys Asn Asn
    50                  55                  60

Gln Thr Glu Ser Leu Met Ser Asp Tyr Gln Asn Gln Leu Glu Ser Leu
65                  70                  75                  80

Glu Glu Lys Ile Gln Lys Val Val His Tyr Ile Ser Glu Gly
                85                  90


<210> SEQ ID NO 88
<211> LENGTH: 135
<212> TYPE: PRT
<213> ORGANISM: Lactococcus lactis

<400> SEQUENCE: 88

Met Thr Val Ile Tyr Met Pro Lys Gln Ser Asn Gly Thr Val His Ser
1               5                   10                  15

Ala Lys Asp Leu Lys Gln Leu Ile Asp Tyr Val Met Asn Ser Glu Lys
            20                  25                  30

Thr Asn Asp Phe Glu Tyr Val Ser Gly Gln Asn Ile Leu Asp Ile His
        35                  40                  45

Ser Thr Cys Asp Glu Met Leu Ala Thr Arg Thr Met Ala Asn Ala Leu
    50                  55                  60
```

Lys Asn Lys Pro Gln Lys Asn Glu Arg Phe Gly Tyr His Phe Val Gln
65 70 75 80

Ser Phe Ser Pro Asp Asp His Leu Thr Pro Glu Gln Val His Glu Ile
85 90 95

Gly Cys Lys Thr Met Lys Glu Tyr Leu Gly Ser Ser Ala Glu Phe Ile
100 105 110

Ile Ala Thr His Thr Asp Lys Pro His Leu His Asn Val Arg Pro Asp
115 120 125

Arg Val Leu Ser Gln Val Val
130 135

<210> SEQ ID NO 89
<211> LENGTH: 599
<212> TYPE: PRT
<213> ORGANISM: Lactococcus lactis

<400> SEQUENCE: 89

Met Lys Pro Thr Met Ala Ile Leu Glu Arg Ile Ser Lys Asn Ser Gln
1 5 10 15

Glu Asn Ile Asp Glu Val Phe Thr Arg Leu Tyr Arg Tyr Leu Leu Arg
20 25 30

Pro Asp Ile Tyr Tyr Val Ala Tyr Gln Asn Leu Tyr Ser Asn Lys Gly
35 40 45

Ala Ser Thr Lys Gly Ile Leu Asp Asp Thr Ala Asp Gly Phe Ser Glu
50 55 60

Glu Lys Ile Lys Lys Ile Ile Gln Ser Leu Lys Asp Gly Thr Tyr Tyr
65 70 75 80

Pro Gln Pro Val Arg Arg Met Tyr Ile Ala Lys Lys Asn Ser Lys Lys
85 90 95

Met Arg Pro Leu Gly Ile Pro Thr Phe Thr Asp Lys Leu Ile Gln Glu
100 105 110

Ala Val Arg Ile Ile Leu Glu Ser Ile Tyr Glu Pro Val Phe Glu Asp
115 120 125

Val Ser His Gly Phe Arg Pro Gln Arg Ser Cys His Thr Ala Leu Lys
130 135 140

Thr Ile Lys Arg Glu Phe Gly Gly Ala Arg Trp Phe Val Glu Gly Asp
145 150 155 160

Ile Lys Gly Cys Phe Asp Asn Ile Asp His Val Thr Leu Ile Gly Leu
165 170 175

Ile Asn Leu Lys Ile Lys Asp Met Lys Met Ser Gln Leu Ile Tyr Lys
180 185 190

Phe Leu Lys Ala Gly Tyr Leu Glu Asn Trp Gln Tyr His Lys Thr Tyr
195 200 205

Ser Gly Thr Pro Gln Gly Gly Ile Leu Ser Pro Leu Leu Ala Asn Ile
210 215 220

Tyr Leu His Glu Leu Asp Lys Phe Val Leu Gln Leu Lys Met Lys Phe
225 230 235 240

Asp Arg Glu Ser Pro Glu Arg Ile Thr Pro Glu Tyr Arg Glu Leu His
245 250 255

Asn Glu Ile Lys Arg Ile Ser His Arg Leu Lys Lys Leu Glu Gly Glu
260 265 270

Glu Lys Ala Lys Val Leu Leu Glu Tyr Gln Glu Lys Arg Lys Arg Leu
275 280 285

Pro Thr Leu Pro Cys Thr Ser Gln Thr Asn Lys Val Leu Lys Tyr Val

```
    290                 295                 300

Arg Tyr Ala Asp Asp Phe Ile Ile Ser Val Lys Gly Ser Lys Glu Asp
305                 310                 315                 320

Cys Gln Trp Ile Lys Glu Gln Leu Lys Leu Phe Ile His Asn Lys Leu
                325                 330                 335

Lys Met Glu Leu Ser Glu Glu Lys Thr Leu Ile Thr His Ser Ser Gln
            340                 345                 350

Pro Ala Arg Phe Leu Gly Tyr Asp Ile Arg Val Arg Arg Ser Gly Thr
        355                 360                 365

Ile Lys Arg Ser Gly Lys Val Lys Lys Arg Thr Leu Asn Gly Ser Val
    370                 375                 380

Glu Leu Leu Ile Pro Leu Gln Asp Lys Ile Arg Gln Phe Ile Phe Asp
385                 390                 395                 400

Lys Lys Ile Ala Ile Gln Lys Lys Asp Ser Ser Trp Phe Pro Val His
                405                 410                 415

Arg Lys Tyr Leu Ile Arg Ser Thr Asp Leu Glu Ile Ile Thr Ile Tyr
            420                 425                 430

Asn Ser Glu Leu Arg Gly Ile Cys Asn Tyr Tyr Gly Leu Ala Ser Asn
        435                 440                 445

Phe Asn Gln Leu Asn Tyr Phe Ala Tyr Leu Met Glu Tyr Ser Cys Leu
    450                 455                 460

Lys Thr Ile Ala Ser Lys His Lys Gly Thr Leu Ser Lys Thr Ile Ser
465                 470                 475                 480

Met Phe Lys Asp Gly Ser Gly Ser Trp Gly Ile Pro Tyr Glu Ile Lys
                485                 490                 495

Gln Gly Lys Gln Arg Arg Tyr Phe Ala Asn Phe Ser Glu Cys Lys Ser
            500                 505                 510

Pro Tyr Gln Phe Thr Asp Lys Ile Ser Gln Ala Pro Val Leu Tyr Gly
        515                 520                 525

Tyr Ala Arg Asn Thr Leu Glu Asn Arg Leu Lys Ala Lys Cys Cys Glu
    530                 535                 540

Leu Cys Gly Thr Ser Asp Glu Asn Thr Ser Tyr Glu Ile His His Val
545                 550                 555                 560

Asn Lys Val Lys Asn Leu Lys Gly Lys Glu Lys Trp Glu Met Ala Met
                565                 570                 575

Ile Ala Lys Gln Arg Lys Thr Leu Val Val Cys Phe His Cys His Arg
            580                 585                 590

His Val Ile His Lys His Lys
        595


<210> SEQ ID NO 90
<211> LENGTH: 357
<212> TYPE: PRT
<213> ORGANISM: Lactococcus lactis

<400> SEQUENCE: 90

Met Lys Glu Ile Ser Asp Asn Ile Ser Lys Glu Tyr Gly Cys Lys Ile
1               5                   10                  15

Ile Val Arg Pro Glu Gln Lys Leu Gly Asn Ser His Lys Asn Tyr Leu
            20                  25                  30

Val Tyr Leu Ala Lys Asn Ser Tyr Arg Lys Glu Ile Lys Asn Lys Leu
        35                  40                  45

Asp Phe Leu Met Asn His Ser His Thr Trp Glu Asp Phe Lys Glu Lys
    50                  55                  60
```

-continued

```
Ala Arg Ala Leu Asn Leu Lys Val Asp Asp Thr Lys Lys Tyr Thr Thr
65                  70                  75                  80

Tyr Leu Leu Glu Gly Ser Glu Gln Thr Lys Lys Ile Arg Asp Arg Ser
                85                  90                  95

Leu Lys Asn Asp Lys Phe Leu Lys Glu Asn Leu Lys Glu Arg Ile Glu
            100                 105                 110

Lys Asn Thr Ile Gly Tyr Ser Val Asp Glu Val Val Lys Leu Trp Lys
        115                 120                 125

Asp Lys Glu Ser Ile Gln Glu Lys Gly Arg Glu Lys Glu Ile Glu Ile
    130                 135                 140

Leu Leu Glu His Trp Gln Val Thr Lys Glu Thr Glu Lys Asp Leu Val
145                 150                 155                 160

Val Thr Ile Asp Thr Ala Phe Asp Asn Glu Ala Thr Ile Lys Ile Pro
                165                 170                 175

Ala Arg Cys Val Asp Lys Leu Glu Asn Gly Gln Tyr Lys Ile Phe Ile
            180                 185                 190

Lys Lys Gly Asp Arg Phe Ser Tyr Leu Asp Lys Lys Ser Pro Ala Asn
        195                 200                 205

His Lys Ile Met Tyr Gly Ala Thr Val Ala Lys Asn Leu Gln Arg Gln
    210                 215                 220

Ser Gly Asn Ile Pro Leu Tyr Ser Asp Asn Val Asn Ile Lys Leu Lys
225                 230                 235                 240

Gln Val Phe His Glu Phe Asp Phe Leu Ile Ser Gln Gly Leu Ser Phe
                245                 250                 255

Asp Arg Ser Phe Glu Thr Ile Gly Glu Glu Leu Lys Ala Thr Tyr Gln
            260                 265                 270

Glu Thr Gln His Gln Leu Asp Lys Leu Asp Thr Lys Ile Leu Glu Tyr
        275                 280                 285

Val Glu Thr Thr Lys Thr Leu Pro Tyr Glu Asp Thr Ser Ile Arg Asp
    290                 295                 300

Thr Ile Lys Asn Leu Thr Lys Glu Arg Asp Asp Leu Arg Asp Thr Leu
305                 310                 315                 320

Tyr Lys Val Asp Lys Asn Ile Gln Tyr Tyr Gln Lys Ser Glu Gln Arg
                325                 330                 335

Leu Glu Ala Tyr Gln Lys Asn Gln Ser Pro Lys His Lys Ala Arg Asp
            340                 345                 350

Asp Asp Phe Glu Ile
        355
```

```
<210> SEQ ID NO 91
<211> LENGTH: 170
<212> TYPE: PRT
<213> ORGANISM: Lactococcus lactis

<400> SEQUENCE: 91

Met Ser Lys Asn Val Lys Thr Ile Lys Glu Leu Ala Asp Glu Leu Gly
1               5                   10                  15

Thr Asn Lys Thr Arg Ile Ser Arg Ile Ile Asn Lys Asn Ser Ile Pro
            20                  25                  30

Thr Gln Lys Ile Lys Asn Lys Ile Val Leu Glu Asp Asn Ser Val Ser
        35                  40                  45

Leu Ile Arg Gln Tyr Phe Lys Asn Glu Thr Val Ser Ile Leu Arg Thr
    50                  55                  60

Glu Leu Asp Lys Ala His Ser His Ile Glu Lys Leu Ser Asn Leu Ser
65                  70                  75                  80
```

Asp Gln Gln Gln Arg Leu Ala Leu Gln Asp Lys Lys Leu Leu Glu Glu
85 90 95

Tyr Lys Ala Glu Asn Asp Ser Leu Lys Ala Leu Lys Met Pro Thr Glu
100 105 110

Gly Ser Gln Ala Glu Gln Ala Asn Ser Gln Pro Lys Glu Glu Val Lys
115 120 125

Ala Leu Lys Phe Glu Ile Arg Ala Leu Gln Glu Glu Leu Asn Lys Gln
130 135 140

Lys Ile His Ser Gln Glu Glu Arg Glu Lys Leu Lys Ala Glu Leu Thr
145 150 155 160

Thr Pro Lys Lys Trp Tyr Gln Phe Trp Lys
165 170

<210> SEQ ID NO 92
<211> LENGTH: 91
<212> TYPE: PRT
<213> ORGANISM: Lactococcus lactis

<400> SEQUENCE: 92

Met Ser Gly Phe Lys Arg Tyr Asp Glu Asp Phe Lys Gln Ser Leu Val
1 5 10 15

Asn Leu Tyr Gln Thr Gly Lys Thr Gln Thr Glu Leu Cys Lys Asp Tyr
20 25 30

Gly Val Ser Ser Ser Ala Leu Ala Lys Trp Ile Lys Gln Tyr Ser Gln
35 40 45

Val Arg Leu Glu Asp Asn Thr Val Leu Thr Ala Lys Gln Ile Gln Glu
50 55 60

Leu Gln Lys Arg Asn Ala Gln Leu Glu Glu Glu Asn Leu Ile Leu Lys
65 70 75 80

Lys Ala Ser Ala Ile Phe Met Gln Asn Ser Lys
85 90

<210> SEQ ID NO 93
<211> LENGTH: 224
<212> TYPE: PRT
<213> ORGANISM: Lactococcus lactis

<400> SEQUENCE: 93

Met Lys Ala Lys Lys Arg Ile Gly Thr Arg Ala Phe Lys Ile Ile Leu
1 5 10 15

Leu Arg Asp Tyr Gly Val Asn Ile Ser Glu Gly Arg Ile Leu Arg Leu
20 25 30

Leu Lys Ser Met Thr Leu Pro Lys Met Ser Thr Ile Lys Pro Arg Phe
35 40 45

Lys Ser Asn Lys Ser Pro Val Phe Ser Ser Asp Asn Leu Leu Lys Gln
50 55 60

Glu Phe Asn Pro Asn Ser Pro Asn Gln Val Trp Thr Thr Asp Phe Thr
65 70 75 80

Tyr Ile Ser Ile Gly Pro Lys Arg His Val Tyr Leu Cys Ala Ile Leu
85 90 95

Asp Leu Tyr Ser Arg Lys Cys Ile Ala Trp Lys Val Ser Asp Lys Ile
100 105 110

Asp Ala Gln Leu Ala Cys Asp Thr Leu Glu Ile Ala Leu Asn Lys Arg
115 120 125

Lys Pro Lys Glu Pro Ile Ile Phe His Ser Asp Gln Gly Ser Gln Phe
130 135 140

Lys Ser Ala Ser Phe Arg Lys Leu Leu Asp Glu His Gln Leu Leu Ala
145 150 155 160

Ser Tyr Ser Lys Pro Gly Tyr Pro Tyr Asp Asn Ala Val Thr Glu Val
165 170 175

Phe Phe Lys Tyr Leu Lys Gln Arg Glu Ile Asn Arg Arg Thr Tyr His
180 185 190

Ser Ile Gln Glu Val Gln Leu Ser Cys Phe Glu Tyr Ile Glu Gln Phe
195 200 205

Tyr Asn Asn Tyr Asn Pro His Ser Ala Asn Asn Gly Leu Thr Pro Asn
210 215 220

<210> SEQ ID NO 94
<211> LENGTH: 205
<212> TYPE: PRT
<213> ORGANISM: Lactococcus lactis

<400> SEQUENCE: 94

Met Arg Gln Leu Ala Asp Ala Leu Asn Val Ser Phe Glu Tyr Leu Thr
1 5 10 15

Asp Thr Glu Ile Leu Pro Ile Tyr Gln Glu Leu Ser Asp Asp Asn Lys
20 25 30

Gln Gln Thr Ile Asn Tyr Ala Glu Asp Lys Leu Lys Ser Gln Lys Glu
35 40 45

Gln Glu Asn Ile Ile His Phe Arg Asn Ser Leu Ile Pro Tyr Lys Gln
50 55 60

Ala Thr Glu Gln Ala Leu Ser Ala Gly Leu Gly Glu Gly Tyr Thr Asp
65 70 75 80

Asn Ile Glu Thr Cys Thr Val Tyr Trp Asp Lys Gln Val Asn Tyr Asp
85 90 95

Ile Gly Ile Pro Ile Lys Gly Asp Ser Met Glu Pro Glu Phe His Tyr
100 105 110

Gly Gln Thr Ala Leu Ile Lys Tyr Gln Ser Ser Pro Asp Tyr Asp Gly
115 120 125

Gln Val Cys Ala Val Asp Asn Val Ser Met Gly Asn Gly Phe Ile Lys
130 135 140

Cys Val Thr Val Glu Glu Asp Gly Leu Leu Leu Gln Ser Leu Asn Ile
145 150 155 160

Glu Glu Gly Gln Asn Gly Glu Arg Lys Phe Pro Asp Ile Lys Leu Tyr
165 170 175

Trp Asp Asp Asn Pro Arg Ile Ile Gly Lys Val Val Ala Ala Phe Thr
180 185 190

Pro Ile Glu Ile Asp Phe Leu Phe Lys Asn Leu Glu Leu
195 200 205

<210> SEQ ID NO 95
<211> LENGTH: 300
<212> TYPE: PRT
<213> ORGANISM: Lactococcus lactis

<400> SEQUENCE: 95

Met Glu Arg Lys Lys Lys Lys Lys Glu Asn Ile Trp Ala Ile Ile Val
1 5 10 15

Pro Ile Leu Ile Ile Ile Ser Leu Ile Gly Ala Trp Ala Tyr Ala Leu
20 25 30

Arg Asp Ser Leu Ile Pro Asn Asp Tyr Thr Lys Thr Asn Ser Ser Asp
35 40 45

```
Gln Pro Thr Lys Thr Ser Val Ser Asn Gly Tyr Val Glu Gln Lys Gly
    50                  55                  60

Val Glu Ala Ala Val Gly Ser Ile Ala Leu Val Asp Asp Ala Gly Val
65                  70                  75                  80

Pro Glu Trp Val Lys Val Pro Ser Lys Val Asn Leu Asp Lys Phe Thr
                85                  90                  95

Asp Leu Ser Thr Asn Asn Ile Thr Ile Tyr Arg Ile Asn Asn Pro Glu
            100                 105                 110

Val Leu Lys Thr Val Thr Asn Arg Thr Asp Gln Arg Met Lys Met Ser
        115                 120                 125

Glu Val Ile Ala Lys Tyr Pro Asn Ala Leu Ile Met Asn Ala Ser Ala
    130                 135                 140

Phe Asp Met Gln Thr Gly Gln Val Ala Gly Phe Gln Ile Asn Asn Gly
145                 150                 155                 160

Lys Leu Ile Gln Asp Trp Ser Pro Gly Thr Thr Thr Gln Tyr Ala Phe
                165                 170                 175

Val Ile Asn Lys Asp Gly Ser Cys Lys Ile Tyr Asp Ser Ser Thr Pro
            180                 185                 190

Ala Ser Thr Ile Ile Lys Asn Gly Gly Gln Gln Ala Tyr Asp Phe Gly
        195                 200                 205

Thr Ala Ile Ile Arg Asp Gly Lys Ile Gln Pro Ser Asp Gly Ser Val
    210                 215                 220

Asp Trp Lys Ile His Ile Phe Ile Ala Asn Asp Lys Asp Asn Asn Leu
225                 230                 235                 240

Tyr Ala Ile Leu Ser Asp Thr Asn Ala Gly Tyr Asp Asn Ile Met Lys
                245                 250                 255

Ser Val Ser Asn Leu Lys Leu Gln Asn Met Leu Leu Leu Asp Ser Gly
            260                 265                 270

Gly Ser Ser Gln Leu Ser Val Asn Gly Lys Thr Ile Val Ala Ser Gln
        275                 280                 285

Asp Asp Arg Ala Val Pro Asp Tyr Ile Val Met Lys
    290                 295                 300
```

<210> SEQ ID NO 96
<211> LENGTH: 279
<212> TYPE: PRT
<213> ORGANISM: Lactococcus lactis

<400> SEQUENCE: 96

```
Met Ala Gln Thr Ile Gln Thr Leu Ala Leu Asn Val Arg Leu Ser Cys
1               5                   10                  15

Gln Leu Leu Asp Val Pro Glu Ser Ser Tyr Tyr Glu Arg Ile Asn Arg
            20                  25                  30

His Pro Ser Lys Thr Gln Leu Arg Arg Gln Tyr Leu Ser Leu Lys Ile
        35                  40                  45

Ser Gln Leu Phe Asn Ala Asn Arg Gly Ile Tyr Gly Ala Pro Lys Ile
    50                  55                  60

His His Leu Leu Leu Lys Gln Gly Glu Lys Val Gly Leu Lys Leu Val
65                  70                  75                  80

Gln Lys Leu Met Lys Gln Leu Gln Leu Lys Ser Val Val Ile Lys Lys
                85                  90                  95

Phe Lys Pro Gly Tyr Ser Leu Ser Asp His Ile Asn Arg Lys Asn Leu
            100                 105                 110

Ile Gln Thr Glu Pro Thr Lys Lys Asn Lys Val Trp Ser Thr Asp Ile
```

```
        115                 120                 125

Thr Tyr Ile Pro Thr Gln Gln Gly Trp Ala Tyr Leu Ser Thr Ile Met
    130                 135                 140

Asp Arg Tyr Thr Lys Lys Val Ile Ala Trp Asp Leu Gly Lys Arg Met
145                 150                 155                 160

Thr Val Glu Leu Val Gln Arg Thr Leu Asn Lys Ala Ile Lys Ser Gln
                165                 170                 175

Asp Tyr Pro Glu Ala Val Ile Leu His Ser Asp Gln Gly Ser Gln Tyr
            180                 185                 190

Thr Ser Leu Glu Tyr Glu Glu Leu Leu Lys Tyr Tyr Gly Met Thr His
        195                 200                 205

Ser Phe Ser Arg Arg Gly Tyr Pro Tyr His Asn Ala Ser Leu Glu Ser
    210                 215                 220

Trp His Gly His Leu Lys Arg Glu Trp Val Tyr Gln Phe Lys Tyr Lys
225                 230                 235                 240

Asn Phe Glu Glu Ala Tyr Gln Ser Ile Phe Trp Tyr Ile Glu Ala Phe
                245                 250                 255

Tyr Asn Ser Lys Arg Ile His Gln Ser Leu Gly Tyr Leu Thr Pro Asn
            260                 265                 270

Gln Phe Glu Lys Val Ser Ala
        275


<210> SEQ ID NO 97
<211> LENGTH: 189
<212> TYPE: PRT
<213> ORGANISM: Lactococcus lactis

<400> SEQUENCE: 97

Met Val Asp Ala Tyr Leu Asp Asn Asn Leu Gly Asp Asp Leu Met Ile
1               5                   10                  15

Arg Tyr Phe Ala Ser Tyr Phe Tyr Gln His Lys Ile Tyr Leu Val Glu
            20                  25                  30

Ser Arg Glu His Ile Arg Lys Thr Phe Tyr Asp Ile Pro Asn Ile Tyr
        35                  40                  45

Phe Tyr Ser Glu Glu Asp Tyr Lys Met Asn Glu Tyr Asp Phe Gln Leu
    50                  55                  60

His Val Thr Ile Gly Gly Ser Met Phe Ile Leu Asp Asp Phe Lys Lys
65                  70                  75                  80

Leu Ile Arg Phe Arg His Arg Ile Lys Asn Ser Arg Lys Ile Lys Lys
                85                  90                  95

Arg Asn Ile Pro Ser Ala Ile Ile Gly Cys Asn Leu Gly Pro Phe Asp
            100                 105                 110

Lys Arg Asn Phe Gly Leu Lys Leu Ala Lys Phe Glu Leu Lys Tyr Lys
        115                 120                 125

Asn Leu Val Thr Val Arg Asp Lys Gln Ser Lys Glu Leu Leu Leu Arg
    130                 135                 140

Gly Phe Lys Arg Lys Lys Ile Asn Ile Lys Leu Phe Pro Asp Ile Ile
145                 150                 155                 160

Phe Ser Lys Val Leu Tyr Lys Ser Ile Pro Lys Tyr Gly Leu Gly Met
                165                 170                 175

Thr Leu Ser Gln Val Phe Arg Val Thr Asn Val Glu Phe
            180                 185


<210> SEQ ID NO 98
<211> LENGTH: 337
```

<212> TYPE: PRT
<213> ORGANISM: Lactococcus lactis

<400> SEQUENCE: 98

```
Met Lys Asn Lys Phe Ser Ile Ile Val Pro Val Tyr Asn Gly Glu Ser
1               5                   10                  15

His Ile Lys Lys Cys Ile Asp Thr Leu Leu Lys Gln Thr Tyr Asn Asp
            20                  25                  30

Phe Glu Ile Ile Ile Ile Asn Asp Gly Ser Thr Asp Asp Thr Lys Ser
        35                  40                  45

Val Leu Thr Lys Phe Tyr Ala Lys Asn Leu Lys Val Lys Ile Val Asn
    50                  55                  60

Thr Ser Asn Lys Gly Val Ser Phe Ala Arg Asn Leu Gly Ile Asn Gln
65                  70                  75                  80

Ser Ser Gly Gln Tyr Leu Leu Phe Val Asp Ser Asp Asp Glu Leu Ser
                85                  90                  95

Ile Asn Ala Leu Lys Tyr Leu Ser Ile Met Leu Asn Lys Lys Asp Arg
            100                 105                 110

Asp Leu Ile Leu Phe Gly Phe Ser Leu Thr Gly Asp Asn Asn Arg Lys
        115                 120                 125

Asn Asp Thr Ser Ile Leu Lys Ser Ile Ala Asn Gln Asn Thr Asp Cys
    130                 135                 140

Lys Met Asn Ile Leu Lys Ser Ile Leu Ser Thr Lys Asn Asn Ile Leu
145                 150                 155                 160

Gly Tyr Val Trp Arg Ala Val Tyr Ser Leu Asp Phe Ile Lys Lys Asn
                165                 170                 175

Asn Ile Phe Phe Glu Thr His Leu Lys Ile Ser Glu Asp Tyr Leu Phe
            180                 185                 190

Leu Leu Gln Ser Val Glu His Ser Asn Asn Leu Phe Val Ile Thr Glu
        195                 200                 205

Glu Phe Tyr Lys Tyr Asn Leu Gly Glu Thr Ser Met Ser Asn Lys Phe
    210                 215                 220

Val Pro Thr Leu Leu Asn Asp Met Val Trp Val Asn Asn Trp Ile Glu
225                 230                 235                 240

Ser Asn Ile Leu Thr Val Tyr Pro Gln Phe Phe Val Gly Phe Asn Cys
                245                 250                 255

Leu Val Ala Asn Thr Tyr Ile Arg Tyr Val Gln Asn Ala Ile Arg Asn
            260                 265                 270

Lys Glu Glu Asn Phe Met Leu Lys Tyr Arg Glu Ile Lys Ile Asn Lys
        275                 280                 285

Arg Lys Tyr Asn Phe Gln Arg Ser Ile Asn Gln Val Ile Phe His Leu
    290                 295                 300

Asp Lys Phe Asp Phe Lys Ser Lys Ile Gly Val Ile Leu Phe Arg Ile
305                 310                 315                 320

His Leu Asp Ile Val Tyr Glu Leu Leu Phe Asn Ile Lys Glu Arg Lys
                325                 330                 335

Asn
```

<210> SEQ ID NO 99
<211> LENGTH: 384
<212> TYPE: PRT
<213> ORGANISM: Lactococcus lactis

<400> SEQUENCE: 99

```
Met Thr Asn Leu Asn Arg Lys Lys Phe Phe Ile Asn Phe Gln Ser Leu
```

-continued

```
1               5                   10                  15

Val Phe Phe Ile Leu Ile Ile Ile Tyr Gly Leu Thr Thr Lys Asn Val
            20                  25                  30

Met Gly Gly Ser Gly Ile Phe Ser Ile Asp Ser Ile Leu Lys Tyr Gly
        35                  40                  45

Ile Leu Phe Ile Cys Ile Ser Val Glu Gly Tyr Ile Phe Leu Lys Asn
    50                  55                  60

Gly Asn Glu Arg Arg Glu Thr Ser Glu Asn Tyr Asn Asn Phe Lys Tyr
65                  70                  75                  80

Tyr Phe Ile Ile Ile Thr Phe Leu Ser Leu Phe Ala Ser Phe Lys Gln
                85                  90                  95

Val His Phe Ser Phe Arg Thr Val Gln Ser Phe Ile Phe Ile Phe Ile
            100                 105                 110

Pro Met Leu Tyr Ser Tyr Leu Ile Leu Asn Asn Trp Thr Phe Arg Gln
        115                 120                 125

Ile Asn Phe Ser Met Lys Ile Ala Leu Phe Leu Ser Val Ile Glu Tyr
    130                 135                 140

Leu Phe Ser Ile Arg Met Gly Phe Ser Gln Ile Ile Ser Ser Leu Ala
145                 150                 155                 160

Ser Ile Asn Tyr Asn Asn Thr Asn Ala Ser Ala Leu Glu Ser Ser Thr
                165                 170                 175

Phe Ala Leu Leu Ser Leu Gly Phe Ala Ala Tyr Phe Gly Tyr Tyr Lys
            180                 185                 190

Lys Asn Phe Leu Cys Lys Ile Val Ser Leu Leu Phe Val Ile Met Thr
        195                 200                 205

Phe Lys Arg Val Ile Thr Leu Ser Gly Cys Ile Leu Val Ile Leu Gly
    210                 215                 220

Ile Leu Lys Ile Lys Asn Leu Arg Val Asn Arg Phe Phe Leu Ile Val
225                 230                 235                 240

Ser Thr Ile Thr Leu Val Ser Phe Ser Leu Ile Tyr Tyr Tyr Ser Ile
                245                 250                 255

Gln Pro Gln Asn Ile Leu Glu Ile Ser Glu Lys Ile Gly Phe Ser Ile
            260                 265                 270

Arg Asp Phe Ser Thr Asn Arg Thr Asp Arg Leu Ala Trp Leu Ser Met
        275                 280                 285

Thr Asp Phe Lys Ser Tyr Gly Leu Gly Ser Thr Thr Asp Phe Met Tyr
    290                 295                 300

Lys Leu Trp Gly Val Asp Leu Glu Met Asp Ile Val Gln Leu Ile Leu
305                 310                 315                 320

Glu Val Gly Ala Phe Gly Val Ile Val Phe Ile Tyr Phe Tyr Leu Arg
                325                 330                 335

Phe Ser Lys Ser Asn Leu Tyr Ala Phe Ser Phe Met Ala Leu Leu Leu
            340                 345                 350

Leu Asn Ser Ile Leu Ser Ser Gly Met Met Ser Thr Phe Ser Trp Ile
        355                 360                 365

Ile Ile Leu Ile Ala Met Ser Thr Ile Met Glu Tyr Lys Glu Gly Met
    370                 375                 380
```

<210> SEQ ID NO 100
<211> LENGTH: 245
<212> TYPE: PRT
<213> ORGANISM: Lactococcus lactis

<400> SEQUENCE: 100

```
Met Lys Lys Leu Lys Ile Ser Val Ile Ile Arg Thr Tyr Asn Glu Val
1               5                   10                  15

Lys His Ile Gly Glu Val Leu Lys Ser Leu Thr Asp Gln Thr Tyr Leu
            20                  25                  30

Asn His Glu Ile Ile Ile Val Asp Ser Gly Ser Val Asp Gly Thr Leu
        35                  40                  45

Asp Ile Ile Glu Arg Tyr Pro Val Lys Leu Val Ser Ile Asn Lys Glu
    50                  55                  60

Asp Phe Asn Tyr Ser Tyr Ala Ser Asn Val Gly Val Gln Asn Ser Ser
65                  70                  75                  80

Gly Asp Ile Val Cys Phe Leu Ser Gly His Ser Val Pro Val Tyr Lys
                85                  90                  95

Asn Tyr Leu Glu Lys Ile Asn Glu Ile Phe Gln Glu Thr Glu Ile Gly
            100                 105                 110

Ala Cys Tyr Gly Glu Val Ile Ala Leu Pro Asp Gly Ser Ile Thr Glu
        115                 120                 125

Lys Ile Phe Asn Arg Ile Gly Tyr Leu Lys Ser Lys Leu Ser Leu Asn
    130                 135                 140

Asn Lys Arg Phe Phe Leu Glu Asn Lys Ile His Pro Gly Ile Phe Ser
145                 150                 155                 160

Cys Ser Asn Ala Cys Ala Arg Lys Lys Leu Leu Leu Lys Tyr Pro Phe
                165                 170                 175

Lys Val Glu Leu Gly His Gly Gly Glu Asp Val Glu Val Ala Tyr Arg
            180                 185                 190

Ile Ile Gln Asp Gly Tyr Phe Val Ala Lys Ser Val Glu Leu Leu Val
        195                 200                 205

Met His Ser His Gly Ser Ser Leu Lys Lys Phe Ile Lys Glu Tyr Lys
    210                 215                 220

Ala Trp Gly Lys Met Tyr Glu Asp Val Leu Lys Phe Ile Lys Lys Asn
225                 230                 235                 240

Asn Asp Lys Ser Gln
                245


<210> SEQ ID NO 101
<211> LENGTH: 161
<212> TYPE: PRT
<213> ORGANISM: Lactococcus lactis

<400> SEQUENCE: 101

Met Ile Phe Val Thr Val Gly Thr His Glu Gln Pro Phe Asn Arg Leu
1               5                   10                  15

Ile Gln Lys Ile Asp Glu Leu Val Arg Asp Gly Gln Ile Lys Asp Asp
            20                  25                  30

Val Phe Met Gln Ile Gly Tyr Ser Thr Tyr Glu Pro Lys Tyr Thr Lys
        35                  40                  45

Trp Ala Ser Val Ile Gly Tyr Asn Asp Met Thr Ala Tyr Phe Asn Lys
    50                  55                  60

Ala Asp Ile Val Ile Thr His Gly Gly Pro Ser Thr Tyr Met Gln Val
65                  70                  75                  80

Leu Gln His Gly Lys Ile Pro Ile Val Val Pro Arg Gln Glu Lys Phe
                85                  90                  95

Gly Glu His Ile Asn Asp His Gln Leu Arg Val Ser Lys Gln Val Ile
            100                 105                 110

Lys Lys Gly Tyr Pro Leu Ile Leu Cys Glu Asp Val Ser Ala Leu Lys
        115                 120                 125
```

Ile Cys Ile Glu Ser Ser Arg Ile Arg Thr Asp Glu Phe Ile Lys Ser
130 135 140

Asn Asn Lys Asn Phe Ile Ser Asn Phe Lys Lys Ile Ile Ala Phe Glu
145 150 155 160

Glu

<210> SEQ ID NO 102
<211> LENGTH: 149
<212> TYPE: PRT
<213> ORGANISM: Lactococcus lactis

<400> SEQUENCE: 102

Met Lys Ile Ala Leu Val Gly Ser Ser Gly Gly His Leu Thr His Leu
1 5 10 15

Tyr Leu Leu Lys Lys Phe Trp Glu Asn Glu Asp Arg Phe Trp Val Thr
20 25 30

Phe Asp Lys Thr Asp Ala Lys Ser Ile Leu Lys Glu Glu Arg Phe Tyr
35 40 45

Pro Cys Tyr Tyr Pro Thr Asn Arg Asn Val Lys Asn Thr Ile Lys Asn
50 55 60

Thr Ile Leu Ala Phe Lys Ile Leu Arg Lys Glu Lys Pro Asp Leu Ile
65 70 75 80

Ile Ser Ser Gly Ala Ala Val Ala Val Pro Phe Phe Trp Ile Gly Lys
85 90 95

Leu Phe Gly Ala Lys Thr Val Tyr Ile Glu Ile Phe Asp Arg Ile Asp
100 105 110

Lys Pro Thr Leu Thr Gly Lys Leu Val Tyr Pro Val Thr Asp Lys Phe
115 120 125

Ile Val Gln Trp Glu Glu Leu Lys Lys Val Tyr Pro Lys Ala Ile Asn
130 135 140

Leu Gly Gly Ile Phe
145

<210> SEQ ID NO 103
<211> LENGTH: 228
<212> TYPE: PRT
<213> ORGANISM: Lactococcus lactis

<400> SEQUENCE: 103

Met Glu Phe Phe Glu Asp Ala Ser Ser Pro Glu Ser Glu Glu Pro Lys
1 5 10 15

Leu Val Glu Leu Lys Asn Phe Ser Tyr Arg Glu Leu Ile Ile Lys Arg
20 25 30

Ala Ile Asp Ile Leu Gly Gly Leu Ala Gly Ser Val Leu Phe Leu Ile
35 40 45

Ala Ala Ala Leu Leu Tyr Val Pro Tyr Lys Met Ser Ser Lys Lys Asp
50 55 60

Gln Gly Pro Met Phe Tyr Lys Gln Lys Arg Tyr Gly Lys Asn Gly Lys
65 70 75 80

Ile Phe Tyr Ile Leu Lys Phe Arg Thr Met Ile Phe Asn Ala Glu Gln
85 90 95

Tyr Leu Glu Leu Asn Pro Asp Val Lys Ala Ala Tyr His Ala Asn Gly
100 105 110

Asn Lys Leu Glu Asn Asp Pro Arg Val Thr Lys Ile Gly Ser Phe Ile
115 120 125

```
Arg Arg His Ser Ile Asp Glu Leu Pro Gln Phe Ile Asn Val Leu Lys
    130                 135                 140

Gly Asp Met Ala Leu Val Gly Pro Arg Pro Ile Leu Leu Phe Glu Ala
145                 150                 155                 160

Lys Glu Tyr Gly Glu Arg Leu Ser Tyr Leu Leu Met Cys Lys Pro Gly
                165                 170                 175

Ile Thr Gly Tyr Trp Thr Thr His Gly Arg Ser Lys Val Leu Phe Pro
            180                 185                 190

Gln Arg Ala Asp Leu Glu Leu Tyr Tyr Leu Gln Tyr His Ser Thr Lys
        195                 200                 205

Asn Asp Ile Lys Leu Leu Ser Leu Thr Ile Val Gln Ser Ile Asn Gly
    210                 215                 220

Ser Asp Ala Tyr
225
```

<210> SEQ ID NO 104
<211> LENGTH: 254
<212> TYPE: PRT
<213> ORGANISM: Lactococcus lactis

<400> SEQUENCE: 104

```
Met Ile Asp Ile His Cys His Ile Leu Pro Gly Ile Asp Asp Gly Ala
1               5                   10                  15

Lys Thr Ser Gly Asp Thr Leu Thr Met Leu Lys Ser Ala Ile Asp Glu
            20                  25                  30

Gly Ile Thr Thr Ile Thr Ala Thr Pro His His Asn Pro Gln Phe Asn
        35                  40                  45

Asn Glu Ser Pro Leu Ile Leu Lys Lys Val Lys Glu Val Gln Asn Ile
    50                  55                  60

Ile Asp Glu His Gln Leu Pro Ile Glu Val Leu Pro Gly Gln Glu Val
65                  70                  75                  80

Arg Ile Tyr Gly Asp Leu Leu Lys Glu Phe Ser Glu Gly Lys Leu Leu
                85                  90                  95

Thr Ala Ala Gly Thr Ser Ser Tyr Ile Leu Ile Glu Phe Pro Ser Asn
            100                 105                 110

His Val Pro Ala Tyr Ala Lys Glu Leu Phe Tyr Asn Ile Lys Leu Glu
        115                 120                 125

Gly Leu Gln Pro Ile Leu Val His Pro Glu Arg Asn Ser Gly Ile Ile
    130                 135                 140

Glu Asn Pro Asp Ile Leu Phe Asp Phe Ile Glu Gln Gly Val Leu Ser
145                 150                 155                 160

Gln Ile Thr Ala Ser Ser Val Thr Gly His Phe Gly Lys Lys Ile Gln
                165                 170                 175

Lys Leu Ser Phe Lys Met Ile Glu Asn His Leu Thr His Phe Val Ala
            180                 185                 190

Ser Asp Ala His Asn Val Thr Ser Arg Ala Phe Lys Met Lys Glu Ala
        195                 200                 205

Phe Glu Ile Ile Glu Asp Ser Tyr Gly Ser Asp Val Ser Arg Met Phe
    210                 215                 220

Gln Asn Asn Ala Glu Ser Val Ile Leu Asn Glu Ser Phe Tyr Gln Glu
225                 230                 235                 240

Lys Pro Thr Lys Ile Lys Thr Lys Lys Leu Leu Gly Leu Phe
                245                 250
```

<210> SEQ ID NO 105

<211> LENGTH: 231
<212> TYPE: PRT
<213> ORGANISM: Lactococcus lactis

<400> SEQUENCE: 105

Met Ala Lys Asn Lys Arg Ser Ile Asp Asn Asn Arg Tyr Ile Ile Thr
1 5 10 15

Ser Val Asn Pro Gln Ser Pro Ile Ser Glu Gln Tyr Arg Thr Ile Arg
20 25 30

Thr Thr Ile Asp Phe Lys Met Ala Asp Gln Gly Ile Lys Ser Phe Leu
35 40 45

Val Thr Ser Ser Glu Ala Ala Ala Gly Lys Ser Thr Val Ser Ala Asn
50 55 60

Ile Ala Val Ala Phe Ala Gln Gln Gly Lys Lys Val Leu Leu Ile Asp
65 70 75 80

Gly Asp Leu Arg Lys Pro Thr Val Asn Ile Thr Phe Lys Val Gln Asn
85 90 95

Arg Val Gly Leu Thr Asn Ile Leu Met His Gln Ser Ser Ile Glu Asp
100 105 110

Ala Ile Gln Gly Thr Arg Leu Ser Glu Asn Leu Thr Ile Ile Thr Ser
115 120 125

Gly Pro Ile Pro Pro Asn Pro Ser Glu Leu Leu Ala Ser Ser Ala Met
130 135 140

Lys Asn Leu Ile Asp Ser Val Ser Asp Phe Phe Asp Val Val Leu Ile
145 150 155 160

Asp Thr Pro Pro Leu Ser Ala Val Thr Asp Ala Gln Ile Leu Ser Ser
165 170 175

Tyr Val Gly Gly Val Val Leu Val Val Arg Ala Tyr Glu Thr Lys Lys
180 185 190

Glu Ser Leu Ala Lys Thr Lys Lys Met Leu Glu Gln Val Asn Ala Asn
195 200 205

Ile Leu Gly Val Val Leu His Gly Val Asp Ser Ser Asp Ser Pro Ser
210 215 220

Tyr Tyr Tyr Tyr Gly Val Glu
225 230

<210> SEQ ID NO 106
<211> LENGTH: 225
<212> TYPE: PRT
<213> ORGANISM: Lactococcus lactis

<400> SEQUENCE: 106

Met Gln Glu Thr Gln Glu Gln Thr Ile Asp Leu Arg Gly Ile Phe Lys
1 5 10 15

Ile Ile Arg Lys Arg Leu Ser Leu Ile Leu Phe Ser Ala Leu Ile Val
20 25 30

Thr Ile Leu Gly Ser Ile Tyr Thr Phe Phe Ile Ala Ser Pro Val Tyr
35 40 45

Thr Ala Ser Thr Gln Leu Val Val Lys Leu Pro Asn Ser Asp Asn Ser
50 55 60

Asp Ala Tyr Ala Gly Gln Val Ser Gly Asn Ile Gln Met Ala Asn Thr
65 70 75 80

Ile Asn Gln Val Ile Val Ser Pro Val Ile Leu Asp Lys Val Gln Ser
85 90 95

Asn Leu Asn Leu Ser Asp Asp Ser Phe Gln Lys Gln Val Thr Ala Ala
100 105 110

```
Asn Gln Thr Asn Ser Gln Val Ile Thr Leu Thr Val Lys Tyr Ser Asn
        115                 120                 125

Pro Tyr Ile Ala Gln Lys Ile Ala Asp Glu Thr Ala Lys Ile Phe Ser
    130                 135                 140

Ser Asp Ala Ala Lys Leu Leu Asn Val Thr Asn Val Asn Ile Leu Ser
145                 150                 155                 160

Lys Ala Lys Ala Gln Thr Thr Pro Ile Ser Pro Lys Pro Lys Leu Tyr
                165                 170                 175

Leu Ala Ile Ser Val Ile Ala Gly Leu Val Leu Gly Leu Ala Ile Ala
            180                 185                 190

Leu Leu Lys Glu Leu Phe Asp Asn Lys Ile Asn Lys Glu Glu Asp Ile
        195                 200                 205

Glu Ala Leu Gly Leu Thr Val Leu Gly Val Thr Ser Leu Cys Ser Asn
    210                 215                 220

Glu
225


<210> SEQ ID NO 107
<211> LENGTH: 255
<212> TYPE: PRT
<213> ORGANISM: Lactococcus lactis

<400> SEQUENCE: 107

Met Met Lys Lys Gly Ile Phe Val Ile Thr Ile Val Ile Ser Ile Ala
1               5                   10                  15

Leu Ile Ile Gly Gly Phe Tyr Ser Tyr Asn Ser Arg Ile Asn Asn Leu
            20                  25                  30

Ser Lys Ala Asp Lys Gly Lys Glu Val Val Lys Asn Ser Ser Glu Lys
        35                  40                  45

Asn Gln Ile Asp Leu Thr Tyr Lys Lys Tyr Tyr Lys Asn Leu Pro Lys
    50                  55                  60

Ser Val Gln Asn Lys Ile Asp Asp Ile Ser Ser Lys Asn Lys Glu Val
65                  70                  75                  80

Thr Leu Thr Cys Ile Trp Gln Ser Asp Ser Val Ile Ser Glu Gln Phe
                85                  90                  95

Gln Gln Asn Leu Gln Lys Tyr Tyr Gly Asn Lys Phe Trp Asn Ile Lys
            100                 105                 110

Asn Ile Thr Tyr Asn Gly Glu Thr Ser Glu Gln Leu Leu Ala Glu Lys
        115                 120                 125

Val Gln Asn Gln Val Leu Ala Thr Asn Pro Asp Val Val Leu Tyr Glu
    130                 135                 140

Ala Pro Leu Phe Asn Asp Asn Gln Asn Ile Glu Ala Thr Ala Ser Trp
145                 150                 155                 160

Thr Ser Asn Glu Gln Leu Ile Thr Asn Leu Ala Ser Thr Gly Ala Glu
                165                 170                 175

Val Ile Val Gln Pro Ser Pro Pro Ile Tyr Gly Gly Val Val Tyr Pro
            180                 185                 190

Val Gln Glu Glu Gln Phe Lys Gln Ser Leu Ser Thr Lys Tyr Pro Tyr
        195                 200                 205

Ile Asp Tyr Trp Ala Ser Tyr Pro Asp Lys Asn Ser Asp Glu Met Lys
    210                 215                 220

Gly Leu Phe Ser Asp Asp Gly Val Tyr Arg Thr Leu Asn Ala Ser Gly
225                 230                 235                 240

Asn Lys Val Trp Leu Asp Tyr Ile Thr Lys Tyr Phe Thr Ala Asn
```

245 250 255

<210> SEQ ID NO 108
<211> LENGTH: 105
<212> TYPE: PRT
<213> ORGANISM: Lactococcus lactis

<400> SEQUENCE: 108

Met Asn Asn Leu Phe Tyr His Arg Leu Lys Glu Leu Val Glu Ser Ser
1 5 10 15

Gly Lys Ser Ala Asn Gln Ile Glu Arg Glu Leu Gly Tyr Pro Arg Asn
20 25 30

Ser Leu Asn Asn Tyr Lys Leu Gly Gly Glu Pro Ser Gly Thr Arg Leu
35 40 45

Ile Gly Leu Ser Glu Tyr Phe Asn Val Ser Pro Lys Tyr Leu Met Gly
50 55 60

Ile Ile Asp Glu Pro Asn Asp Ser Ser Ala Ile Asn Leu Phe Lys Thr
65 70 75 80

Leu Thr Gln Glu Glu Lys Lys Glu Met Phe Ile Ile Cys Gln Lys Trp
85 90 95

Leu Phe Leu Glu Tyr Gln Ile Glu Leu
100 105

<210> SEQ ID NO 109
<211> LENGTH: 191
<212> TYPE: PRT
<213> ORGANISM: Lactococcus lactis

<400> SEQUENCE: 109

Met Ser Val Ser Ile Ile Asp Ser Phe Pro Ile Pro Leu Cys Gln Pro
1 5 10 15

Ile Arg Asn Phe Arg Ser Lys Gly Leu Gly Asp Tyr Ala Asn Val Gly
20 25 30

Tyr Asn Ala Thr Lys Gly Gln Tyr Phe Tyr Gly Cys Lys Cys His Ala
35 40 45

Leu Val Ser Glu Ser Gly Tyr Val Ile Asp Tyr Thr Ile Thr Pro Ala
50 55 60

Ser Met Ala Asp Ser Ser Met Thr Glu Glu Val Leu Ser Gln Phe Gly
65 70 75 80

Thr Pro Thr Val Leu Gly Asp Met Gly Tyr Leu Gly Gln Ser Leu His
85 90 95

Asp Arg Leu Glu Leu Lys Gly Ile Asp Leu Met Thr Pro Val Arg Lys
100 105 110

Asn Met Lys Gln Lys Lys Ile Leu Phe Pro Asn Phe Ser Lys Arg Arg
115 120 125

Lys Val Ile Glu Arg Val Phe Ser Phe Leu Thr Asn Leu Gly Ala Glu
130 135 140

Arg Cys Lys Ser Arg Ser Pro Gln Gly Phe Gln Leu Lys Leu Glu Met
145 150 155 160

Ile Leu Leu Ala Tyr Ser Leu Leu Leu Lys Ser Ala Lys Ser Leu Glu
165 170 175

Pro Glu Thr Leu Arg Tyr Ser Ile Gly Tyr Gln Val Met Ala Lys
180 185 190

<210> SEQ ID NO 110
<211> LENGTH: 127
<212> TYPE: PRT

<213> ORGANISM: Lactococcus lactis

<400> SEQUENCE: 110

Met Thr Ile Lys Asn Lys Lys Asp Leu Ser Ser Ser Ile Glu Gln Leu
1 5 10 15

Glu Lys Ala Ile Asn Gln Gln Glu Thr Ile Leu Lys Lys Phe Asp Asn
20 25 30

Glu Gln Leu Asp Phe Glu Gln Ile Lys Lys Leu Glu Asn Leu Leu Ile
35 40 45

Gln Glu Arg Glu Lys Ala Lys Gln Val Gln Ile Lys Ile Asn Arg Ser
50 55 60

Val Leu Gln Asn Asn Ser Glu Asn Tyr Lys Glu Arg Lys Lys Arg Thr
65 70 75 80

Arg Gln Leu Ile Gln Lys Gly Ala Leu Leu Glu Lys Tyr Leu Glu Ala
85 90 95

Lys His Leu Thr Val Asp Glu Thr Glu Gln Leu Leu Gln Ile Phe Ala
100 105 110

Asn Met Ile Asn Lys Pro Glu Leu Leu Val Asn Phe Ile Gly Lys
115 120 125

<210> SEQ ID NO 111
<211> LENGTH: 196
<212> TYPE: PRT
<213> ORGANISM: Lactococcus lactis

<400> SEQUENCE: 111

Met Val Gln Gln Ile Val Leu Pro Ile Lys Asp Ser Asn Ile Leu Lys
1 5 10 15

Met Val Gln Asp Thr Leu Leu Asp Ser Phe Arg Ala Gly Arg Arg Asn
20 25 30

Tyr Thr Ile Phe Gln Val Gly Lys Ala Thr Leu Leu Arg Val Ser Asp
35 40 45

Val Met Lys Leu Lys Lys Thr Asp Val Phe Asn Ser Asp Gly Thr Val
50 55 60

Lys Gln Thr Ala Phe Ile His Asp Gln Lys Thr Gly Lys Ala Asn Thr
65 70 75 80

Leu Tyr Leu Lys Pro Val Gln Gln Asp Leu Val Val Tyr His Asp Trp
85 90 95

Met Val Gln Gln Asn Leu Asn Ser Glu Trp Leu Phe Pro Ser Thr Ser
100 105 110

Arg Pro Asp Arg Pro Ile Thr Glu Lys Gln Phe Tyr Lys Ile Met Ala
115 120 125

Arg Val Gly Asp Leu Leu Ser Ile Asn Tyr Leu Gly Thr His Thr Met
130 135 140

Arg Lys Thr Gly Ala Tyr Arg Val Tyr Thr Gln Ser Asn Tyr Asn Ile
145 150 155 160

Gly Leu Val Ile His Leu Leu Asn His Ser Ser Glu Ala Met Thr Leu
165 170 175

Thr Tyr Leu Gly Leu Asp Gln Ala Ser Arg Glu Thr Met Leu Asp Gln
180 185 190

Ile Asp Phe Gly
195

<210> SEQ ID NO 112
<211> LENGTH: 121
<212> TYPE: PRT

<213> ORGANISM: Lactococcus lactis

<400> SEQUENCE: 112

Met Asp Gln Lys Glu Val Ser Gln Asn Gln Thr Lys Tyr Ile Gln Phe
1 5 10 15

Arg Leu Ser Glu Glu Gln Tyr Asn Lys Leu Lys Ile Ser Gly Glu Thr
20 25 30

Tyr Gly Leu Ser Pro Asn Leu Tyr Ala Lys Lys Leu Ala Gln Lys Ser
35 40 45

His Leu Lys Lys Pro Tyr Leu Glu His Asp Gln Ala Lys Ser Leu Leu
50 55 60

Leu Glu Leu Ser Lys Gln Gly Thr Asn Leu Asn Gln Ile Ala Lys Lys
65 70 75 80

Leu Asn Gln Phe Asp Arg Met Asp Asn Gln Asp Lys Glu Leu Ile Glu
85 90 95

Ala Leu Arg Tyr Thr Tyr Gly Val Leu Ala Gln Ala Gln Lys Gly Tyr
100 105 110

Gln Glu Leu Trp Gln Gln Leu Gln Lys
115 120

<210> SEQ ID NO 113
<211> LENGTH: 410
<212> TYPE: PRT
<213> ORGANISM: Lactococcus lactis

<400> SEQUENCE: 113

Met Ala Thr Ile Ala Lys Ile Ser Asn Gly Ala Ser Ala Ala Ser Ala
1 5 10 15

Leu Asn Tyr Ala Leu Gly Gln Asp Arg Pro Met His Glu Lys Thr Glu
20 25 30

Gln Trp Leu Gln Asp His Gln Leu Glu Arg Pro Val Glu Leu Thr Asn
35 40 45

Cys Arg Ala Val Ala Val Gly Gly Thr Asn Gly Ile Asp Pro Phe Ile
50 55 60

Ala Lys Glu Gln Phe Asp Val Val Arg Gln Leu His Asn Gln Thr Lys
65 70 75 80

Glu Ser Asn Gln Val Met Arg Ile Thr Gln Ser Phe Ala Leu Asp Glu
85 90 95

Leu Asn Pro Lys Val Gln Lys Asp Trp Gln Lys Ala Asn Asp Leu Gly
100 105 110

Val Glu Leu Ala Glu Asn Leu Tyr Pro Asn His Gln Ser Ala Val Tyr
115 120 125

Thr His Leu Asp Gly Lys Asn His Val Leu His Asn His Ile Ile Val
130 135 140

Asn Lys Val Asn Leu Glu Thr Gly Lys Lys Leu Arg Glu Gln Lys Gly
145 150 155 160

Glu Ser Val Gln Arg Ala Arg Glu Met Asn Asp Arg Leu Ala Ser Arg
165 170 175

Glu Asn Trp His Ile Leu Glu Pro Pro Lys Glu Arg Gln Thr Glu Thr
180 185 190

Glu Lys Glu Leu Ile Ala Lys Asn Glu Tyr Ser Tyr Met Asp Asp Leu
195 200 205

Arg Glu Arg Ile Asn Lys Ser Leu Gln Asp Val Ser Val Ser Ser Tyr
210 215 220

Glu Thr Phe Lys Glu Arg Leu Ser Asp Asn Gly Val Ile Leu Ser Glu 225 230 235 240

Arg Gly Gln Thr Phe Ser Tyr Ala Phe Leu Asp Ala Asn Asn Lys Gln
245 250 255

Arg Arg Ala Arg Glu Thr Arg Leu Gly Ser Asp Phe Gly Lys Glu Thr
260 265 270

Ile Leu His Glu Leu Glu Asn Arg Ala Arg Gln Asn Glu Phe Ser Ala
275 280 285

Val Glu Gln Arg Glu Pro Ala Ile Thr Pro Leu Glu Arg Asp Thr Gln
290 295 300

Gln Arg Glu Ser Glu Ile Val Ser Leu Glu Gln Ala Ile Glu Pro Arg
305 310 315 320

Lys Ser Glu Ala Leu Lys Arg Glu Ser Lys Ile Asn Arg Phe Ile Asp
325 330 335

Thr Ile Lys Gln Phe Ala Gly Arg Val Pro Glu Leu Thr Gln Arg Val
340 345 350

Thr Arg Lys Leu Lys Gln Thr Lys Asp Lys Ile Leu Asp Asp Phe Glu
355 360 365

Arg Arg Phe Ser Lys Asp Met Lys Asn Tyr Glu Gln Glu Gln Gln Lys
370 375 380

Ser Leu Glu Lys Gln Ala Asn Arg Asp Val Gln Ser Glu Lys Lys Pro
385 390 395 400

Thr Lys Asp His Asp Arg Gly Met Ser Arg
405 410

<210> SEQ ID NO 114
<211> LENGTH: 207
<212> TYPE: PRT
<213> ORGANISM: Lactococcus lactis

<400> SEQUENCE: 114

Met Asn Lys Asp Glu Gln Leu Val Val Gln Val Leu Asn Ala Tyr Lys
1 5 10 15

Asn Gly Lys Ile Asp Phe Ser Asn Val Pro Glu Leu Asp Arg Leu Val
20 25 30

Arg Gln Glu Val Asn Lys Asp Phe Arg Asp Tyr Gln Glu Lys Ile Glu
35 40 45

Ala Val Ala Asn Gln Lys Ile Glu Ser Ala Ile Gln Glu Gln Leu His
50 55 60

Arg Leu Glu Ala Glu Asn Leu Lys Ala Thr Ile Leu Lys Asp Ile Gln
65 70 75 80

Val Glu Lys Gln Ala Leu Leu Ala Leu Lys Lys Glu Leu Asn Glu Gln
85 90 95

Lys Glu Gln Ile Lys Ala Asp Arg Lys Arg Glu Ile Val Glu Arg Tyr
100 105 110

Gly Ile Leu Ile Ala Asn Ile Val Cys Leu Phe Cys Phe Leu Val Val
115 120 125

Gly Ile Leu Ile Gly Arg Trp Ile Tyr Lys Gly Ile Trp Asp Gly Trp
130 135 140

Gly Leu His Ile Leu Tyr Asp Thr Val Met Glu Ile Lys Pro Lys His
145 150 155 160

Pro Tyr Gly Ala Val Ile Leu Gly Leu Gly Gly Phe Gly Leu Ile Gly
165 170 175

Ala Gly Ile Tyr Gly Ser Phe Arg Leu Met Tyr Thr Ala Ser Thr Trp
180 185 190

-continued

Phe Asp Gln Arg Pro Lys Ile Phe Lys Arg Ile Phe Pro Lys Lys
195 200 205

<210> SEQ ID NO 115
<211> LENGTH: 200
<212> TYPE: PRT
<213> ORGANISM: Lactococcus lactis

<400> SEQUENCE: 115

Met Val Leu Asp Asn Lys Leu Gly Leu Thr Asn Ser Ala Glu Leu Ala
1 5 10 15

Lys Gln Glu Glu Leu Leu Thr Lys Lys Arg Ala Lys Glu Leu Phe Glu
20 25 30

Ser Gly Lys Ile Glu Asp Leu Glu Ile Gly Thr Phe Gln Gly Leu Ser
35 40 45

Asp Ile His Gln Phe Leu Phe Gln Asp Ile Tyr Asp Phe Ala Gly Lys
50 55 60

Ile Arg Glu Val Asn Ile Ala Lys Gly Asn Phe Gln Phe Ala Pro Arg
65 70 75 80

Ile Phe Leu Ala Gln Thr Leu Glu Tyr Ile Asp Lys Leu Pro Gln Glu
85 90 95

Thr Phe Asp Glu Ile Ile Asp Lys Tyr Ser Asp Met Asn Val Ala His
100 105 110

Pro Phe Arg Glu Gly Asn Gly Arg Ala Thr Arg Ile Trp Leu Asp Leu
115 120 125

Ile Leu Lys Asn Lys Leu His Lys Ile Val Asp Trp Asn Gln Ile Asp
130 135 140

Lys Asp Glu Tyr Leu Asn Ala Met Ile Arg Ser Thr Val Ser Thr Asn
145 150 155 160

Glu Leu Lys Tyr Leu Ile Gln Lys Ala Leu Thr Asp Asp Leu Gly Lys
165 170 175

Glu Gln Phe Phe Lys Gly Ile Asp Ala Ser Tyr Tyr Tyr Glu Gly Tyr
180 185 190

Tyr Glu Ile Lys Thr Glu Asp Leu
195 200

<210> SEQ ID NO 116
<211> LENGTH: 383
<212> TYPE: PRT
<213> ORGANISM: Lactococcus lactis

<400> SEQUENCE: 116

Met Ser Ile Ile Thr Glu Phe Glu Lys Asn Gln Lys Gln Val Lys Ala
1 5 10 15

Leu Asn Glu Leu Ser Lys Arg Lys Val Val Glu His Asn Ser Leu Ile
20 25 30

Thr Ser Ile Ala Lys Met Asp Lys Thr Pro Leu Lys Met Phe Glu Leu
35 40 45

Ala Val Ser Cys Ile Asn Thr Glu Ala Pro Pro Lys Asp His Thr Val
50 55 60

Tyr Leu Ser Lys Thr Glu Leu Phe Ala Phe Phe Lys Val Ser Asp Asn
65 70 75 80

Asp Lys His Ser Arg Phe Lys Gln Ala Val Glu Asn Met Gln Lys Gln
85 90 95

Ala Phe Phe Lys Ile Gln Glu Lys Lys Glu Tyr Gly Phe Glu Phe Glu
100 105 110

-continued

```
Asn Ile Val Pro Ile Pro Tyr Val Lys Trp Ala Asp Tyr His Asp Glu
        115                 120                 125

Val Thr Ile Arg Phe Ser Pro Glu Ile Met Pro Tyr Leu Ile Asn Leu
    130                 135                 140

Lys Gln Asn Phe Thr Gln His Ala Leu Ser Asp Ile Ala Glu Leu Asn
145                 150                 155                 160

Ser Lys Tyr Ser Ile Ile Leu Tyr Arg Trp Leu Ser Met Asn Tyr Asn
                165                 170                 175

Gln Tyr Glu His Tyr Ser Ala Lys Gly Gly Arg Arg Glu Glu Gln Val
            180                 185                 190

Glu Thr Tyr Arg Asn Pro Ser Ile Ser Ile Arg Glu Leu Arg Glu Met
        195                 200                 205

Thr Asp Thr Met Lys Asp Tyr Pro Arg Phe Gln Ser Leu Glu Ser Tyr
    210                 215                 220

Ile Ile Lys Asn Ser Leu Lys Glu Ile Asn Glu His Thr Ser Phe Lys
225                 230                 235                 240

Val Thr Tyr Glu Lys Val Lys Lys Gly Arg Ser Ile Asn Ser Ile Val
                245                 250                 255

Phe His Ile Thr Lys Lys Arg Arg Ala Asp Asp Asn Ser Tyr Lys Leu
            260                 265                 270

Glu Asp Lys Val Tyr Gln Lys Ala Lys Val Gln Lys Glu Gln Lys Glu
        275                 280                 285

Asn Leu Leu Tyr Ala Glu Ala Met Gln Ser Lys Tyr Thr Lys Leu Leu
    290                 295                 300

Leu Glu His Phe Leu Leu Ser Pro Tyr Glu Met Thr Asn Pro Ala Thr
305                 310                 315                 320

Met Ala Gly Leu Gln Arg Asn Val Tyr Pro Lys Tyr Asp Glu Leu Lys
                325                 330                 335

Asp Leu Met Gly Ile Asp Gly Val Lys Lys His Leu Ser Tyr Ile Tyr
            340                 345                 350

Asp Lys Gln Glu Pro Tyr Ser Lys Gly Asn Ile Ala Lys Tyr Leu Lys
        355                 360                 365

Lys Ala Ile Glu Gln Tyr Leu Pro Thr Val Lys Arg Arg Gly Leu
    370                 375                 380
```

<210> SEQ ID NO 117
<211> LENGTH: 206
<212> TYPE: PRT
<213> ORGANISM: Lactococcus lactis

<400> SEQUENCE: 117

```
Met Ser Asp Asn Leu Lys Thr Ile Lys Glu Leu Ala Asp Glu Leu Gly
1               5                   10                  15

Val Ser Lys Thr Ala Ile Asn Lys Lys Val Thr Asp Arg Glu Arg Lys
            20                  25                  30

Leu Trp Phe Ser Lys Ile Gly Asn Lys Phe Val Ile Asn Glu Asp Gly
        35                  40                  45

Gln Lys Ser Ile Lys Arg Met Phe Glu Gly Leu Thr Glu Asn Gln Glu
    50                  55                  60

Ser Gln Thr Glu Asn Leu Glu Gln Lys Pro Asn Ser Gln Thr Glu Asn
65                  70                  75                  80

Phe Arg Asn Asn Asn Glu Ser Asn Ala Asp Ile Lys Tyr Ile Leu Asp
                85                  90                  95

Ile Ile Glu Tyr Gln Lys Glu Gln Ile Lys Asp Leu Gln Asn Thr Lys
            100                 105                 110
```

```
Asp Glu Gln Phe Lys Gln Leu Ser Asn Met Gln Asn Leu Leu Asp Gln
        115                 120                 125

Gln Gln Arg Leu Ala Leu Gln Asp Lys Lys Leu Leu Glu Glu Tyr Lys
    130                 135                 140

Ser Glu Asn Asp Arg Leu Lys Val Leu Lys Met Pro Ser Gln Glu Thr
145                 150                 155                 160

Lys Glu Glu Gln Ala Asn Ile Gln Pro Gln Glu Glu Leu Glu Thr Leu
                165                 170                 175

Lys Glu Gln Thr Arg Ala Leu Asn Asp Lys Ile Lys Gly Gln Glu Glu
            180                 185                 190

Leu Asn Asn Lys Ser Ser Lys Lys Trp Tyr Gln Phe Trp Lys
        195                 200                 205


<210> SEQ ID NO 118
<211> LENGTH: 103
<212> TYPE: PRT
<213> ORGANISM: Lactococcus lactis

<400> SEQUENCE: 118

Met Phe Ser Tyr Ile Tyr Ile Ile Leu Ser Tyr Asn Thr Ile Lys Val
1               5                   10                  15

Lys Glu Val Leu Lys Phe Glu Tyr Arg Ile Cys Thr Ser Phe Asn Trp
            20                  25                  30

Thr Ser Lys Phe Ala Glu Glu Met Lys Thr Cys Phe Phe Asn Ser Gly
        35                  40                  45

Phe Lys Phe Lys Asn Phe Lys Gly Leu Asp Asn Arg Asn Ala Lys Glu
    50                  55                  60

Lys Ser Glu Leu Ile Ser Glu Ala Glu Val Val Ile Leu Ala Gly Gly
65                  70                  75                  80

His Val Pro Thr Gln Asn Ile Phe Phe Gln Gln Ile Asn Leu Lys Asn
                85                  90                  95

Met Ser Pro Val Arg Ile Phe
            100


<210> SEQ ID NO 119
<211> LENGTH: 471
<212> TYPE: PRT
<213> ORGANISM: Lactococcus lactis

<400> SEQUENCE: 119

Met Gln Ile Ala Lys Asn Tyr Leu Tyr Asn Ala Ile Tyr Gln Val Phe
1               5                   10                  15

Ile Ile Ile Val Pro Leu Leu Thr Ile Pro Tyr Leu Ser Arg Ile Leu
            20                  25                  30

Gly Pro Ser Gly Ile Gly Ile Asn Ser Tyr Thr Asn Ser Ile Val Gln
        35                  40                  45

Tyr Phe Val Leu Phe Gly Ser Ile Gly Val Gly Leu Tyr Gly Asn Arg
    50                  55                  60

Gln Ile Ala Phe Val Arg Asp Asn Gln Val Lys Met Ser Lys Val Phe
65                  70                  75                  80

Tyr Glu Ile Phe Ile Leu Arg Leu Phe Thr Ile Cys Leu Ala Tyr Phe
                85                  90                  95

Leu Phe Val Ala Phe Leu Ile Ile Asn Gly Gln Tyr His Ala Tyr Tyr
            100                 105                 110

Leu Ser Gln Ser Ile Ala Ile Val Ala Ala Ala Phe Asp Ile Ser Trp
        115                 120                 125
```

Phe Phe Met Gly Ile Glu Asn Phe Lys Val Thr Val Leu Arg Asn Phe
    130                 135                 140

Ile Val Lys Leu Leu Ala Leu Phe Ser Ile Phe Leu Phe Val Lys Ser
145                 150                 155                 160

Tyr Asn Asp Leu Asn Ile Tyr Ile Leu Ile Thr Val Leu Ser Thr Leu
                165                 170                 175

Ile Gly Asn Leu Thr Phe Phe Pro Ser Leu His Arg Tyr Leu Val Lys
            180                 185                 190

Val Asn Tyr Arg Glu Leu Arg Pro Ile Lys His Leu Lys Gln Ser Leu
        195                 200                 205

Val Met Phe Ile Pro Gln Ile Ala Val Gln Ile Tyr Trp Val Leu Asn
    210                 215                 220

Lys Thr Met Leu Gly Ser Leu Asp Ser Val Thr Ser Ser Gly Phe Phe
225                 230                 235                 240

Asp Gln Ser Asp Lys Ile Val Lys Leu Val Leu Ala Ile Ala Thr Ala
                245                 250                 255

Thr Gly Thr Val Met Leu Pro Arg Val Ala Asn Ala Phe Ala His Arg
            260                 265                 270

Glu Tyr Ser Lys Ile Lys Glu Tyr Met Tyr Ala Gly Phe Ser Phe Val
        275                 280                 285

Ser Ala Ile Ser Ile Pro Met Met Phe Gly Leu Ile Ala Ile Thr Pro
    290                 295                 300

Lys Phe Val Pro Leu Phe Phe Thr Ser Gln Phe Ser Asp Val Ile Pro
305                 310                 315                 320

Val Leu Met Ile Glu Ser Ile Ala Ile Ile Phe Ile Ala Trp Ser Asn
                325                 330                 335

Ala Ile Gly Asn Gln Tyr Leu Leu Pro Thr Asn Gln Asn Lys Ser Tyr
            340                 345                 350

Thr Val Ser Val Ile Ile Gly Ala Ile Val Asn Leu Met Leu Asn Ile
        355                 360                 365

Pro Leu Ile Ile Tyr Leu Gly Thr Val Gly Ala Ser Ile Ala Thr Val
    370                 375                 380

Ile Ser Glu Met Ser Val Thr Val Tyr Gln Leu Phe Ile Ile His Lys
385                 390                 395                 400

Gln Leu Asn Leu His Thr Leu Phe Ser Asp Leu Ser Lys Tyr Leu Ile
                405                 410                 415

Ala Gly Leu Val Met Phe Leu Ile Val Phe Lys Ile Ser Leu Leu Thr
            420                 425                 430

Pro Thr Ser Trp Ile Phe Ile Leu Leu Glu Ile Thr Val Gly Ile Ile
        435                 440                 445

Ile Tyr Val Val Leu Leu Ile Phe Leu Lys Ala Glu Ile Ile Asn Lys
    450                 455                 460

Leu Lys Phe Ile Met His Lys
465                 470

<210> SEQ ID NO 120
<211> LENGTH: 332
<212> TYPE: PRT
<213> ORGANISM: Lactococcus lactis

<400> SEQUENCE: 120

Met Asn Leu Phe Gly Asp Ser Asp Tyr Leu Glu Lys Leu Ser Ser Lys
1               5                   10                  15

Gly Asp Pro Leu Glu Arg Leu Glu Lys Val Val Asp Phe Glu Cys Phe

```
            20                  25                  30

Arg Pro Thr Leu Asn Arg Ile Phe Lys Tyr Asp Leu Lys Asn Lys Ser
        35                  40                  45

His Gly Gly Arg Pro Pro Tyr Asp Leu Val Leu Met Leu Lys Ile Leu
    50                  55                  60

Ile Leu Gln Arg Leu Tyr Asn Leu Ser Asp Asp Ala Met Glu Tyr Gln
65                  70                  75                  80

Met Ile Asp Arg Ile Ser Phe Arg Arg Phe Leu Lys Ile Asp Asp Lys
                85                  90                  95

Val Pro Asp Ala Lys Thr Ile Trp Asn Phe Arg Asn Gln Leu Ser Lys
            100                 105                 110

Ser Asn Arg Gly Asn Trp Leu Phe Ser Ala Phe Gln Glu Lys Leu Glu
        115                 120                 125

Ser Gln Gly Met Ile Ala His Lys Gly Gln Ile Val Asp Ala Thr Phe
    130                 135                 140

Ile Glu Ala Pro Lys Gln Arg Asn Pro Lys Asp Glu Asn Glu Leu Ile
145                 150                 155                 160

Lys Ala Asn Arg Val Pro Val Asn Trp Thr Lys Asn Lys Arg Ala Gln
                165                 170                 175

Lys Asp Thr Ala Ala Arg Trp Thr Ile Lys Gly Asn Glu Arg His Tyr
            180                 185                 190

Gly Tyr Lys Asn His Ile Ala Ile Asp Thr Lys Ser Lys Phe Val Lys
        195                 200                 205

Asn Tyr Gln Thr Thr Pro Ala Asn Val His Asp Ser Gln Val Ile Gly
    210                 215                 220

Val Leu Val Asp Pro Asp Glu Ile Thr Leu Ala Asp Ser Ala Tyr Gln
225                 230                 235                 240

Asn Lys Ala Thr Pro Lys Gly Ala Glu Leu Phe Thr Phe Leu Lys Asn
                245                 250                 255

Thr Arg Ser Lys Ser Leu Lys Ala Asp Asp Lys Met Phe Asn Lys Ile
            260                 265                 270

Ile Ser Lys Ile Arg Val Arg Ile Glu His Val Phe Gly Phe Val Glu
        275                 280                 285

Asn Ser Met His Gly Ser Ser Leu Arg Ser Ile Gly Phe Asp Arg Ala
    290                 295                 300

Val Leu Asn Thr Asp Leu Thr Asn Leu Thr Tyr Asn Leu Leu Arg His
305                 310                 315                 320

Glu Gln Val Lys Arg Leu Asn Leu Lys Thr Trp Arg
                325                 330


<210> SEQ ID NO 121
<211> LENGTH: 189
<212> TYPE: PRT
<213> ORGANISM: Lactococcus lactis

<400> SEQUENCE: 121

Met Arg Lys Tyr Met Ile Tyr Leu Ser Ser Leu Leu Val Thr Phe Ile
1               5                   10                  15

Leu Ser Tyr Ala Thr Ile Thr Trp Leu Ile Met Pro Val Leu Thr Arg
            20                  25                  30

Tyr Gln Ser Leu Ala Arg Leu Ile Asn His Phe Asp Tyr Thr Ala Leu
        35                  40                  45

Thr Leu Ile Leu Leu Leu Thr Leu Ile Ile Trp Leu Phe Gly Ile Gln
    50                  55                  60
```

```
Tyr His Leu Lys His Phe Ser Val Ile Tyr Leu Tyr Leu Ala Phe Ser
65                  70                  75                  80

Val Tyr Leu Leu Leu Leu Phe Met Val Ile Phe Asn Lys Thr Thr Asp
                85                  90                  95

Phe Gln Ala Ile Ser Leu Asn Pro Phe Asp Phe Ile Lys Ala Asp Thr
            100                 105                 110

Arg Thr Ile Gln Glu Ala Val Leu Asn Ile Ile Tyr Phe Ile Pro Leu
        115                 120                 125

Gly Gly Leu Tyr Cys Ile Asn Thr Asp Phe Lys Gln Phe Val Ile Ile
    130                 135                 140

Ser Leu Val Thr Leu Leu Gly Ile Glu Thr Ile Gln Phe Ile Phe Tyr
145                 150                 155                 160

Leu Gly Thr Phe Ala Ile Ser Asp Ile Ile Leu Asn Phe Leu Gly Cys
                165                 170                 175

Leu Ile Gly Tyr Tyr Cys Cys Trp Glu Ile Lys Lys Ser
            180                 185


<210> SEQ ID NO 122
<211> LENGTH: 152
<212> TYPE: PRT
<213> ORGANISM: Lactococcus lactis

<400> SEQUENCE: 122

Met Asp Glu Thr Tyr Ile Lys Ile Lys Gly Arg Gly His Tyr Leu Tyr
1               5                   10                  15

Arg Thr Ile Asp Ala Asp Gly Leu Thr Leu Asp Ile Trp Leu Arg Lys
            20                  25                  30

Lys Arg Asp Thr Gln Ala Ala Tyr Ala Phe Leu Lys Arg Leu His Lys
        35                  40                  45

Gln Phe Gly Glu Pro Lys Ala Ile Val Thr Asp Lys Ala Pro Ser Leu
    50                  55                  60

Gly Ser Ala Phe Arg Lys Leu Gln Ser Val Gly Leu Tyr Thr Lys Thr
65                  70                  75                  80

Glu His Arg Thr Val Lys Tyr Leu Asn Asn Leu Ile Glu Gln Asp His
                85                  90                  95

Arg Pro Ile Lys Arg Arg Asn Lys Phe Tyr Gln Ser Leu Arg Thr Ala
            100                 105                 110

Ser Ser Thr Ile Lys Gly Met Glu Thr Leu Arg Gly Ile Tyr Lys Asn
        115                 120                 125

Asn Arg Arg Asn Gly Thr Leu Phe Gly Phe Ser Val Ser Thr Glu Ile
    130                 135                 140

Lys Val Leu Met Gly Ile Thr Ala
145                 150


<210> SEQ ID NO 123
<211> LENGTH: 331
<212> TYPE: PRT
<213> ORGANISM: Lactococcus lactis

<400> SEQUENCE: 123

Met Lys Lys Asn Val Leu Leu Ser Ile Ile Val Pro Ile Tyr Asn Val
1               5                   10                  15

Glu Lys Tyr Ile Gly Ser Leu Val Asn Ser Leu Val Lys Gln Thr Asn
            20                  25                  30

Lys Asn Phe Glu Val Ile Phe Ile Asp Asp Gly Ser Thr Asp Glu Ser
        35                  40                  45
```

Met Gln Ile Leu Lys Glu Ile Ile Ala Gly Ser Glu Gln Glu Phe Ser
50 55 60

Leu Lys Leu Leu Gln Gln Val Asn Gln Gly Leu Ser Ser Ala Arg Asn
65 70 75 80

Ile Gly Ile Leu Asn Ala Thr Gly Glu Tyr Ile Phe Phe Leu Asp Ser
85 90 95

Asp Asp Glu Ile Glu Ile Asn Phe Val Glu Thr Ile Leu Thr Ser Cys
100 105 110

Tyr Lys Tyr Ser Gln Pro Asp Thr Leu Ile Phe Asp Tyr Ser Ser Ile
115 120 125

Asp Glu Phe Gly Asn Ala Leu Asp Ser Asn Tyr Gly His Gly Ser Ile
130 135 140

Tyr Arg Gln Lys Asp Leu Cys Thr Ser Glu Gln Ile Leu Thr Ala Leu
145 150 155 160

Tyr Lys Asp Glu Ile Pro Ile Thr Ala Trp Ser Phe Val Thr Lys Arg
165 170 175

Ser Val Ile Glu Lys His Asn Leu Leu Phe Ser Val Gly Lys Lys Phe
180 185 190

Glu Asp Asn Asn Phe Thr Pro Lys Val Phe Tyr Phe Ser Lys Asn Ile
195 200 205

Gly Val Ile Ser Leu Arg Leu Tyr Arg Tyr Arg Lys Arg Ser Gly Ser
210 215 220

Ile Met Ser Asn His Pro Glu Lys Phe Phe Ser Asp Asp Ala Ile Phe
225 230 235 240

Val Thr Tyr Asp Leu Leu Asp Phe Tyr Asp Gln Tyr Lys Ile Arg Glu
245 250 255

Leu Gly Ala Val Val Gly Lys Leu Val Met Thr Arg Leu Ala Phe Phe
260 265 270

Pro Asp Ser Lys Lys Leu Tyr Asn Glu Leu Asn Pro Ile Ile Lys Lys
275 280 285

Val Phe Lys Asp Tyr Ile Ser Ile Glu Lys Arg His Thr Lys Arg Ile
290 295 300

Lys Met Tyr Val Lys Met Tyr Val Phe Ser Ser Tyr Val Gly Tyr Lys
305 310 315 320

Leu Tyr Arg Leu Val Lys Gly Lys His Trp Lys
325 330

<210> SEQ ID NO 124
<211> LENGTH: 226
<212> TYPE: PRT
<213> ORGANISM: Lactococcus lactis

<400> SEQUENCE: 124

Met Asn His Phe Lys Gly Lys Gln Phe Lys Lys Asp Val Ile Ile Val
1 5 10 15

Ala Val Gly Tyr Tyr Leu Arg Tyr Asn Leu Ser Tyr Arg Glu Val Gln
20 25 30

Glu Leu Leu Tyr Asp Arg Gly Ile Asn Val Cys His Thr Thr Ile Tyr
35 40 45

Arg Trp Val Gln Glu Tyr Ser Lys Val Leu Tyr Asp Leu Cys Lys Lys
50 55 60

Lys Asn Arg Gln Ser Phe Tyr Ser Trp Lys Met Asp Glu Thr Tyr Ile
65 70 75 80

Lys Ile Lys Gly Arg Trp His Tyr Leu Tyr Arg Ala Ile Asp Ala Asp
85 90 95

Gly Leu Thr Leu Asp Ile Trp Leu Gln Lys Lys Arg Asp Thr Gln Ala
100 105 110

Ala Tyr Ala Phe Leu Lys Arg Leu His Lys Gln Phe Gly Glu Pro Lys
115 120 125

Ala Ile Val Thr Asp Lys Ala Pro Ser Leu Gly Ser Ala Phe Arg Lys
130 135 140

Leu Gln Ser Val Gly Leu Tyr Thr Lys Thr Glu His Arg Thr Val Lys
145 150 155 160

Tyr Leu Asn Asn Leu Ile Glu Gln Asp His Trp Pro Ile Lys Arg Arg
165 170 175

Asn Lys Phe Tyr Gln Ser Leu Arg Thr Ala Ser Ser Thr Ile Lys Gly
180 185 190

Met Glu Thr Leu Arg Gly Ile Tyr Lys Asn Asn Arg Arg Asn Gly Thr
195 200 205

Leu Phe Gly Phe Ser Val Ser Thr Glu Ile Lys Val Leu Met Gly Ile
210 215 220

Thr Ala
225

<210> SEQ ID NO 125
<211> LENGTH: 84
<212> TYPE: PRT
<213> ORGANISM: Lactococcus lactis

<400> SEQUENCE: 125

Met Gln Gln Asn Leu Leu Lys Tyr Tyr Gly Met Thr His Ser Phe Ser
1 5 10 15

Arg Arg Gly Tyr Pro Tyr His Asn Ala Ser Leu Glu Ser Trp His Gly
20 25 30

His Leu Lys Arg Glu Trp Val Tyr Gln Phe Lys Tyr Lys Asn Phe Glu
35 40 45

Glu Ala Tyr Gln Ser Ile Phe Trp Tyr Ile Glu Ala Phe Tyr Asn Ser
50 55 60

Lys Arg Ile His Gln Ser Leu Gly Tyr Leu Thr Pro Asn Gln Phe Glu
65 70 75 80

Lys Val Ser Ala

<210> SEQ ID NO 126
<211> LENGTH: 370
<212> TYPE: PRT
<213> ORGANISM: Lactococcus lactis

<400> SEQUENCE: 126

Met Asn Asp Leu Glu Lys Arg Lys Val Val Glu His Asn Ser Leu Ile
1 5 10 15

Thr Ser Ile Ala Lys Met Gln Lys Thr Ala Leu Lys Met Phe Glu Leu
20 25 30

Ala Val Ser Cys Ile Asp Thr Glu Asn Pro Pro Lys Asp Asn Ile Ile
35 40 45

Tyr Leu Ser Lys Lys Glu Leu Phe Ala Phe Phe Asp Val Ser Ser Ala
50 55 60

Ser Lys His Thr Arg Phe Lys Glu Ala Ile Glu Leu Met Gln Lys Gln
65 70 75 80

Ala Phe Phe Gln Ile Lys Glu Val Lys Asp Lys Gly Tyr Glu Met Thr
85 90 95

```
Ser Ile Val Pro Ile Pro Thr Val Lys Trp Asn Ser Tyr Asn Asp Asp
            100                 105                 110

Val Met Ile Gln Phe Asn Gln Phe Ile Met Pro Tyr Leu Ile Asp Leu
        115                 120                 125

Lys Ala Glu Phe Thr Gln Tyr Lys Ile Ser Glu Leu Lys Glu Leu Asn
    130                 135                 140

Ser Lys Tyr Ser Ile Ile Leu Tyr Arg Trp Leu Ser Met Asn Tyr Asn
145                 150                 155                 160

Gln Tyr Glu His Tyr Asn Val Lys Gly Gly Arg Arg Ala Glu Gln Val
                165                 170                 175

Glu Asn Tyr Arg Lys Pro Ser Ile Ser Val Lys Glu Leu Arg Glu Ile
            180                 185                 190

Thr Asp Thr Val Asn Glu Tyr Lys Glu Ile Tyr Asp Phe Glu Lys Arg
        195                 200                 205

Val Leu Lys Lys Ser Leu Ala Glu Ile Asn Ala His Thr Ser Phe Asn
    210                 215                 220

Val Asn Tyr Glu Lys Ile Lys Lys Gly Arg Ser Ile Asp Ser Ile Val
225                 230                 235                 240

Phe His Ile Glu Lys Lys Arg Met Ala Asp Asp Asn Ser Tyr Lys Leu
                245                 250                 255

Gly Asp Lys Asp Tyr Gln Asp Asp Lys Lys Gln Lys Ser Arg Asn Glu
            260                 265                 270

Ala Asp Leu Leu Lys Gln Ala Met Glu Ser Lys Tyr Thr Arg Leu Leu
        275                 280                 285

Ser Glu Asn Phe Leu Ile Gly Met Asn Asp Ile Met Asp Thr Thr Thr
    290                 295                 300

Met Val Gly Leu Gln Lys Asn Val Tyr Pro Leu Tyr Asp Glu Leu Lys
305                 310                 315                 320

Glu Leu Arg Gly Leu Asn Gly Val Lys Asp His Leu Ser Tyr Val Ser
                325                 330                 335

Ser Lys Arg Glu Glu Tyr Ser Lys His Asn Ile Ala Lys Tyr Leu Lys
            340                 345                 350

Lys Ala Ile Glu Gln Tyr Leu Pro Thr Val Lys Arg Gln Asp Leu Glu
        355                 360                 365

Asn Glu
    370


<210> SEQ ID NO 127
<211> LENGTH: 233
<212> TYPE: PRT
<213> ORGANISM: Lactococcus lactis

<400> SEQUENCE: 127

Met Asn Asp Asn Leu Lys Thr Ile Lys Glu Val Ala Asp Glu Leu Gly
1               5                   10                  15

Val Ser Lys Lys Lys Ile Glu Asn Lys Leu Ser Tyr Ile Lys Lys Lys
            20                  25                  30

Gly Asn Thr Leu Gly Lys Val Ile Gly Gly Val Arg Tyr Leu Asn Lys
        35                  40                  45

Gln Glu Ile Lys Ile Leu Asn Ile Ser Pro Glu Thr Ser Lys Ala Pro
    50                  55                  60

Glu Thr Ser Lys Val Pro Glu Thr Ser Lys Val Pro Glu Thr Ser Lys
65                  70                  75                  80

Val Pro Glu Thr Ser Lys Val Pro Glu Thr Ser Lys Ala Pro Glu Thr
                85                  90                  95
```

```
Ser Glu Val Pro Glu Thr Ser Lys Val Pro Asp Lys His Val Phe Ser
            100                 105                 110

Ser Ser Phe Asp Leu Leu Arg Glu Gln Thr Ala Tyr Leu Leu Lys Glu
        115                 120                 125

Leu Glu Glu Lys Asn Lys His Ile Glu Lys Leu Ile Asp Asn Glu Lys
    130                 135                 140

Ser Met Gln Asn Leu Leu Asp Gln Gln Gln Arg Leu Ala Leu Gln Asp
145                 150                 155                 160

Lys Lys Leu Leu Glu Glu Tyr Lys Ser Glu Ile Asn Glu Leu Lys Ala
                165                 170                 175

Leu Lys Met Pro Gln Glu Asp Met Lys Asp Asp Ser Ser Ile Arg Gly
            180                 185                 190

Glu Ala Gln Glu Glu Ile Val Arg Leu Lys Ala Gln Leu Lys Leu Ser
        195                 200                 205

Glu Glu Glu Arg Asn Lys Ala Lys Glu Lys Glu Pro Val Lys Thr Glu
    210                 215                 220

Ser Lys Lys Trp Trp Gln Leu Trp Lys
225                 230


<210> SEQ ID NO 128
<211> LENGTH: 171
<212> TYPE: PRT
<213> ORGANISM: Lactococcus lactis

<400> SEQUENCE: 128

Met Asn Phe Gly Glu Val Leu Gln Thr Lys Arg Lys Ser Met Gly Leu
1               5                   10                  15

Thr Gln Glu Asp Leu Ala Asp Lys Leu Phe Val Ser Ser Lys Thr Ile
            20                  25                  30

Ser Asn Trp Glu Thr Asn Lys Thr Thr Pro Asp Ile Asp Asn Val Ile
        35                  40                  45

Arg Ile Ser Gln Leu Phe Asp Ile Ser Leu Asn Asn Leu Leu Leu Glu
    50                  55                  60

Gly Ser Asn Met Val Glu Asn Ile Lys Lys Lys Ala Glu Ile Asn Asn
65                  70                  75                  80

Leu Lys Lys Tyr Ser Tyr Cys Thr Val Ile Thr Asp Leu Val Phe Leu
                85                  90                  95

Phe Ile Ile Leu Ser Ser His Tyr Gly Ala Glu Leu Pro Ile Ser Ile
            100                 105                 110

Leu Ile Ala Thr Cys Ile Gly Ile Gly Val Asn Ile Ala Val Met Phe
        115                 120                 125

Tyr Phe Leu Asn Arg Ile Lys Ile Leu Glu Asp Lys Thr Lys Lys Gln
    130                 135                 140

Gln Arg Lys Glu Ile Phe Ile Thr Ile Ile Leu Cys Ile Leu Ala Phe
145                 150                 155                 160

Val Val Thr Ile Leu Val Ser Trp Phe Lys His
                165                 170


<210> SEQ ID NO 129
<211> LENGTH: 75
<212> TYPE: PRT
<213> ORGANISM: Lactococcus lactis

<400> SEQUENCE: 129

Met Ile Asp Leu Glu Glu Glu Gly Phe Leu Val Leu Trp Gly Ile Ser
1               5                   10                  15
```

```
Ile Ala Ser Ser Tyr Thr Glu Thr Ile Ser Thr Leu Gln Gln Ser Gly
            20                  25                  30

Gly Ser Ala Ile Phe Thr Phe Leu Thr Tyr Ala Ile Gly Leu Leu Phe
        35                  40                  45

Phe Ile Leu Thr Val Leu Pro Thr Asn Ala Val Thr Thr Lys Ser Asp
    50                  55                  60

Asn Gly Phe Ile Leu Phe Phe Leu Arg Ala Lys
65                  70                  75
```

<210> SEQ ID NO 130
<211> LENGTH: 222
<212> TYPE: PRT
<213> ORGANISM: Lactococcus lactis

<400> SEQUENCE: 130

```
Met Asn Tyr Ile Lys Lys Phe Phe Ile Val Leu Arg Leu Ala Ile Leu
1               5                   10                  15

Ser Gln Ile Gly Val Ala Val Tyr Gly Gly Ala Lys Gly Phe Ser Leu
            20                  25                  30

Glu Asn Gly Ala His Lys Leu Ser Leu Leu Ala Val Leu Ile Leu Ile
        35                  40                  45

Ile Phe Ile Val Gly Asn Ile Tyr Leu Leu Met Tyr Leu Gly Lys Lys
    50                  55                  60

Leu Gly Phe Leu Thr Leu Ser Lys Asp Phe Leu Thr Lys Lys Asn Ile
65                  70                  75                  80

Ile Tyr Ile Leu Val Gly Thr Leu Ile Ala Arg Thr Ala Gly Ile Gly
                85                  90                  95

Gly Thr Leu Leu Leu Asn Ala Thr Gly Val Thr Gln Thr Ala Asn Asp
            100                 105                 110

Glu Thr Ile Gly Gln Leu Phe Thr Gly Glu Asn Pro Leu Leu Ile Ile
        115                 120                 125

Leu Leu Ile Gly Ile Ala Ala Pro Ile Met Glu Glu Ile Val Phe Arg
    130                 135                 140

Gly Gly Ile Val Gly Tyr Leu Phe Lys Asp Leu Pro Val Val Gly Ile
145                 150                 155                 160

Ile Val Ser Ser Val Leu Phe Gly Leu Met His Ser Pro Thr Asn Ile
                165                 170                 175

Ile Ser Phe Leu Ile Tyr Gly Leu Ile Gly Leu Thr Cys Ala Ile Ala
            180                 185                 190

Tyr Phe Lys Thr Arg Arg Leu Glu Val Ser Ile Ala Ile His Phe Leu
        195                 200                 205

Asn Asn Ile Leu Pro Ala Leu Val Leu Ala Phe Gly Ile Ser
    210                 215                 220
```

<210> SEQ ID NO 131
<211> LENGTH: 122
<212> TYPE: PRT
<213> ORGANISM: Lactococcus lactis

<400> SEQUENCE: 131

```
Met Lys Lys Ile Lys Asn Arg Glu Arg Ile Ile Gln Lys Lys Phe Phe
1               5                   10                  15

Val Asn Glu Lys Glu Asp Glu Arg Ile Lys Leu Met Met Arg Lys Thr
            20                  25                  30

Gly Ile Thr Asn Phe Ser Ile Phe Ala Arg Arg Ala Cys Cys Asn Lys
        35                  40                  45
```

```
Glu Ile Phe Ser Ile Asp Phe Ser Glu Tyr Lys Asn Ile Ile Ser Glu
    50                  55                  60

Ile Ser Ala Thr Lys Ser Glu Leu Lys Arg Ile Gly Asn Asn Ile Asn
65                  70                  75                  80

Gln Ile Ala Lys His Leu Asn Glu Asn Lys Asn Asn Gln Thr Lys Glu
                85                  90                  95

Leu Met Ser Asp Tyr Gln Lys Gln Leu Glu Asn Leu Glu Asp Lys Ile
            100                 105                 110

Gln Lys Val Val His Tyr Ile Ser Glu Gly
        115                 120


<210> SEQ ID NO 132
<211> LENGTH: 275
<212> TYPE: PRT
<213> ORGANISM: Lactococcus lactis

<400> SEQUENCE: 132

Met Ala Lys Lys Gln Asn Tyr Ile Trp Arg Asn Asp Arg Asn Phe Ala
1               5                   10                  15

Leu Asp Glu Tyr Glu Gln Gln Gln Tyr Tyr Tyr Val Val Glu Ser Asn
            20                  25                  30

Asp Ile Ile Asn Lys Ala Arg His Asp Leu Thr Ala Arg Glu Leu Lys
        35                  40                  45

Leu Met Asp Phe Val Ile Ser Lys Ile Gln Pro Glu Asp Thr Gln Phe
    50                  55                  60

Asn Val Ile Lys Thr Ser Met Tyr Glu Leu Thr Lys Val Leu Asn Ile
65                  70                  75                  80

Lys Gln Asn Gly Lys Asn Tyr Gly Asp Met Ala Lys Ala Ile Gly Asp
                85                  90                  95

Leu Arg Lys Lys Glu Val Leu Ile Tyr Asp Asp Val His Arg Thr Val
            100                 105                 110

Thr Gln Thr Gly Trp Val Gln Ser Ala Lys Tyr Gln Glu Asn Gly Gln
        115                 120                 125

Val Glu Ile Lys Leu Asn Glu Asp Leu Ala Pro His Leu Leu Gly Leu
    130                 135                 140

Lys Thr His Tyr Thr Gln His Leu Leu Ile Asp Thr Thr Lys Leu Lys
145                 150                 155                 160

Ser Arg Tyr Ser Ile Leu Leu Tyr Lys Leu Met Arg Glu Ala Asp Lys
                165                 170                 175

Asp Lys Gly Asn Ser Ile Ala Ile Leu Gln Gly Thr Pro Glu Glu Phe
            180                 185                 190

Lys Glu Trp Leu Gly Ala Pro Lys Asp Tyr Glu Tyr Lys Asp Leu Lys
        195                 200                 205

Arg Asn Ile Leu Lys Lys Ala Val Glu Glu Ile Asn Leu Lys Ile Asp
    210                 215                 220

Asp Met Asp Leu Glu Ile Leu Gln Gly Arg Cys Gly Arg Lys Val Val
225                 230                 235                 240

Gln Val Glu Ile His Asn Asn Trp Thr Val Gln Arg Ala Ile Glu Glu
                245                 250                 255

Asn Ser Glu Tyr Val Glu Ser Ile Thr Thr His Asp Trp Leu Lys Gly
            260                 265                 270

Asp Ser Lys
        275
```

<210> SEQ ID NO 133
<211> LENGTH: 59
<212> TYPE: PRT
<213> ORGANISM: Lactococcus lactis

<400> SEQUENCE: 133

```
Met Ile Tyr Thr Ser Gly Tyr Phe Ile Ala Phe Leu Gly Leu Ile Ile
1               5                   10                  15

Met Leu Phe Asn Phe Lys Asp Leu Tyr Pro Lys Leu Asn Ile Trp Cys
            20                  25                  30

Arg Leu Gly Phe Ile Leu Leu Cys Leu Gly Leu Ile Leu Pro Met Leu
        35                  40                  45

Phe Gly Phe Ile Thr Gly Phe Ile Asn Asn His
    50                  55
```

<210> SEQ ID NO 134
<211> LENGTH: 56
<212> TYPE: PRT
<213> ORGANISM: Lactococcus lactis

<400> SEQUENCE: 134

```
Met Ala Arg Glu Lys Ser Asp Ile Glu Tyr Gln Val Val Thr Val Arg
1               5                   10                  15

Phe Pro Lys Glu Ile Tyr Gln Glu Tyr Lys Lys Ile Leu Lys Ser Glu
            20                  25                  30

Gly Lys Ile Pro Thr Tyr Asp Leu Arg Asn Tyr Ile Phe Ser Val Val
        35                  40                  45

Asp Glu Tyr Glu Lys Gly Gln Arg
    50                  55
```

<210> SEQ ID NO 135
<211> LENGTH: 226
<212> TYPE: PRT
<213> ORGANISM: Lactococcus lactis

<400> SEQUENCE: 135

```
Met Asn Tyr Phe Lys Gly Lys Gln Phe Gln Lys Asp Val Ile Ile Val
1               5                   10                  15

Ala Val Gly Tyr Tyr Leu Arg Tyr Asn Leu Ser Tyr Arg Glu Ile Gln
            20                  25                  30

Glu Leu Leu Tyr Asp Arg Gly Ile Asn Val Cys His Thr Thr Ile Tyr
        35                  40                  45

Arg Trp Val Gln Glu Tyr Ser Lys Val Leu Tyr His Leu Trp Lys Lys
    50                  55                  60

Lys Asn Arg Gln Ser Phe Tyr Ser Trp Lys Met Asp Glu Thr Tyr Ile
65                  70                  75                  80

Lys Ile Lys Gly Arg Trp His Tyr Leu Tyr Arg Ala Ile Asp Val Asp
                85                  90                  95

Gly Leu Thr Leu Asp Ile Trp Leu Arg Lys Lys Arg Asp Thr Gln Ala
            100                 105                 110

Ala Tyr Ala Phe Leu Lys Arg Leu His Lys Gln Phe Gly Gln Pro Arg
        115                 120                 125

Val Ile Val Lys Asp Lys Ala Pro Ser Ile Gly Ser Ala Phe Arg Lys
    130                 135                 140

Leu Gln Ser Asn Gly Leu Tyr Thr Lys Thr Glu His Arg Thr Val Lys
145                 150                 155                 160

Tyr Leu Asn Asn Leu Ile Glu Gln Asp His Arg Pro Ile Lys Arg Arg
                165                 170                 175
```

Asn Lys Phe Tyr Gln Ser Leu Arg Thr Ala Ser Thr Thr Ile Lys Gly
180 185 190

Met Glu Thr Ile Arg Gly Ile Tyr Lys Lys Asn Arg Arg Asn Gly Thr
195 200 205

Leu Phe Gly Phe Ser Val Ser Thr Glu Ile Lys Val Leu Met Gly Ile
210 215 220

Leu Ala
225

<210> SEQ ID NO 136
<211> LENGTH: 89
<212> TYPE: PRT
<213> ORGANISM: Lactococcus lactis

<400> SEQUENCE: 136

Met Ala Gly Tyr Asn Val Leu Asp Asp Ala Lys Ala Arg Asn Leu Gly
1 5 10 15

Leu Asp Ile Leu Glu Val Lys Glu Thr Glu Tyr Ala Val Val Pro Val
20 25 30

Lys Gly Ser Val Pro Asp Ser Ile His Gln Ala Trp Lys Tyr Leu Leu
35 40 45

Glu Glu Phe Phe Pro Glu Asn Gly Tyr Lys His Ser Gly Leu Pro Asp
50 55 60

Phe Glu Val Tyr Thr Glu Asn Asp Ile His Asp Pro Asn Tyr Glu Met
65 70 75 80

Glu Leu Trp Val Pro Ile Ser Lys Gln
85

<210> SEQ ID NO 137
<211> LENGTH: 127
<212> TYPE: PRT
<213> ORGANISM: Lactococcus lactis

<400> SEQUENCE: 137

Met Ile Ile Val Ala Val Gly Tyr Tyr Leu Arg Tyr Asn Leu Ser Tyr
1 5 10 15

Arg Glu Val Gln Asp Leu Leu Tyr Asp Arg Gly Ile Asn Val Cys His
20 25 30

Thr Thr Ile Tyr Arg Trp Val Gln Glu Tyr Gly Lys Leu Leu Tyr Gln
35 40 45

Asn Gly Phe Tyr Gln Gly Thr Glu His Arg Thr Ile Lys Tyr Leu Asn
50 55 60

Asn Leu Ile Glu Gln Asp His Arg Pro Val Lys Arg Arg Asn Lys Phe
65 70 75 80

Tyr Arg Ser Leu Arg Thr Ala Ser Pro Thr Ile Lys Gly Met Glu Ala
85 90 95

Ile Arg Gly Leu Tyr Lys Lys Thr Arg Lys Glu Gly Thr Leu Phe Gly
100 105 110

Phe Ser Val Cys Thr Glu Ile Lys Val Leu Leu Gly Ile Pro Ala
115 120 125

<210> SEQ ID NO 138
<211> LENGTH: 232
<212> TYPE: PRT
<213> ORGANISM: Lactococcus lactis

<400> SEQUENCE: 138

-continued

Met Ile Lys Asn His Trp Met Lys Lys Leu Lys Tyr Leu Ser Leu Phe
1 5 10 15

Phe Leu Leu Phe Ala Ile Tyr Trp Phe Pro Asp Val Ile Leu Ala Tyr
20 25 30

Pro Glu Val Tyr Leu Lys Ser Leu Val Gly Tyr Glu Arg Gln Val Val
35 40 45

Ala Thr Trp Ile Phe Leu Gly Asn Met Ser Ile Ser Leu Phe Leu Gly
50 55 60

Ile Leu Ile Cys Tyr Lys Leu Gly Tyr Tyr Lys Asn Thr Ile Ser Ile
65 70 75 80

Phe Lys Ile Lys Asn Leu Leu Phe Leu Leu Ile Thr Thr Ile Ile Leu
85 90 95

Phe Val Ile Tyr Phe Phe Ser Tyr Thr Tyr Tyr Asn Ser His Phe Ile
100 105 110

Thr Pro Gly Ile Ala Lys Thr Gln Ala Ala Phe Ser Ile Gln Ile Val
115 120 125

Phe Pro Phe Val Gln Phe Ile Thr Ile Ala Ile Cys Ala Pro Ile Phe
130 135 140

Glu Glu Ala Ala Phe Arg Thr Thr Ile Tyr Arg Phe Phe Lys Asn Asp
145 150 155 160

Lys Ile Ala Tyr Ile Val Ser Cys Val Gly Phe Ala Trp Met His Thr
165 170 175

Gly Pro Asn Pro Ile Leu Ile Val Tyr Leu Pro Met Ser Ile Val Leu
180 185 190

Thr Ser Ile Tyr His Arg Arg Arg Val Leu Gly Glu Ser Ile Leu Val
195 200 205

His Gly Val Phe Asn Ala Leu Leu Pro Ile Val Ile Pro Leu Leu Gln
210 215 220

Val Ile Thr Gly Leu Tyr Tyr Leu
225 230

<210> SEQ ID NO 139
<211> LENGTH: 93
<212> TYPE: PRT
<213> ORGANISM: Lactococcus lactis

<400> SEQUENCE: 139

Met Lys Tyr Phe Val Thr Thr Leu Ser Pro Ser Lys Asn Met Gly Thr
1 5 10 15

Met Asn Trp Gln Thr Met Ile Leu Ser Asp Tyr Cys Val Asn Asp Ser
20 25 30

Tyr Trp Glu Lys Ala Lys Arg Glu Leu Ser Glu Glu Val Gln Trp Val
35 40 45

Thr Gln Ser Asp Leu Tyr Lys Lys Ile Lys Trp Asn His Asp Ser Asn
50 55 60

Asp Asp Ile Ile Leu Ser Lys Pro Val Ser Ile Ile Leu Glu Thr Val
65 70 75 80

Lys Ser Asp Phe Pro His Ala Asn Val Trp Val Tyr Gln
85 90

<210> SEQ ID NO 140
<211> LENGTH: 55
<212> TYPE: PRT
<213> ORGANISM: Lactococcus lactis

<400> SEQUENCE: 140

```
Met Glu Ile Gln Thr Asn Phe Gln Ile Ile Ser Asp Glu Glu Leu Ser
1               5                   10                  15

Glu Ile Val Gly Gly Gly Tyr Pro Asn Asn Gln Ser Met Asn Asp Val
            20                  25                  30

Leu His Trp Leu Asn Gly His Asn Asp Gly Asn Pro Lys Gln Leu Pro
        35                  40                  45

Lys Trp Met Cys Gly Leu Gly
    50                  55


<210> SEQ ID NO 141
<211> LENGTH: 100
<212> TYPE: PRT
<213> ORGANISM: Lactococcus lactis

<400> SEQUENCE: 141

Met Thr Lys Tyr Ile Tyr Pro Asn Leu Lys Asp Asn Gln Lys Tyr Leu
1               5                   10                  15

Leu Lys Ile Ile Asp Gly Ile Leu Thr Ser Asn Asn Ile Ser Ser Glu
            20                  25                  30

Glu Lys Lys Leu Phe Leu Ile Ala Lys Ser Asn Ile Glu Lys Gly Arg
        35                  40                  45

Asn Phe Asp Pro Gln Ile Ser Glu Leu Ile Ser Ser Leu Gln Tyr Leu
    50                  55                  60

Val His Ser Asp Asp Val Leu Val Phe Phe Glu Glu Ala Arg Lys Ile
65                  70                  75                  80

Met Gln Ile Asn Pro Gly Thr Gly Gly Ser Pro Tyr Gly Trp Ser Asn
                85                  90                  95

Phe Glu Ser Lys
            100


<210> SEQ ID NO 142
<211> LENGTH: 620
<212> TYPE: PRT
<213> ORGANISM: Lactococcus lactis

<400> SEQUENCE: 142

Met Ala Lys Ile Thr Leu Asn Phe Gln Lys Arg Leu Gln Gln His Ser
1               5                   10                  15

Asn His Leu Val Ile Leu Ser Ala Ile Leu Ile Val Leu Gly Tyr Leu
            20                  25                  30

Gly Lys Tyr Gly Val Asn Gln Ile Trp Ile Trp Asn Ser Thr Met Ile
        35                  40                  45

Ile Ala Ser Ile Ile Gly Phe Ile Pro Val Ala Ile His Ala Tyr Gln
    50                  55                  60

Ala Ile Lys Val Lys Gln Ile Ser Ile Asp Leu Leu Val Ser Ile Ala
65                  70                  75                  80

Val Ile Gly Ala Leu Phe Ile Gly Glu Tyr Glu Glu Ser Ala Ile Val
                85                  90                  95

Thr Phe Leu Phe Ala Phe Gly Gly Phe Leu Glu Lys Lys Thr Leu Glu
            100                 105                 110

Lys Thr Arg Ser Ser Ile Lys Glu Leu Thr Asn Met Ala Pro Arg Thr
        115                 120                 125

Ala Leu Ser Ala Asp Gly Glu Glu Met Asp Ile Asp Glu Val Glu Ile
    130                 135                 140

Gly Asp Lys Leu Leu Val Lys Thr Gly Arg Gln Val Pro Val Asp Gly
145                 150                 155                 160
```

-continued

```
Arg Ile Tyr Gln Gly Ser Gly Tyr Val Asn Glu Ala Ser Ile Thr Gly
                165                 170                 175

Glu Ser Arg Glu Ile Arg Lys Glu Ala Gly Thr Lys Val Phe Ala Gly
            180                 185                 190

Ser Ile Leu Glu Asn Gly Thr Ile Tyr Val Glu Ala Glu Lys Val Gly
        195                 200                 205

Glu Asp Thr Thr Phe Gly Lys Ile Ile Glu Leu Val Glu Glu Ala Gln
    210                 215                 220

Asp Thr Lys Ser Pro Ala Glu Lys Phe Ile Asp Arg Phe Ala Lys Tyr
225                 230                 235                 240

Tyr Thr Pro Ala Val Leu Val Ile Ala Ala Ile Thr Trp Val Phe Ser
                245                 250                 255

His Asn Leu Glu Leu Ala Ile Thr Ile Leu Val Leu Gly Cys Pro Gly
            260                 265                 270

Ala Leu Val Ile Gly Ala Pro Val Ser Asn Val Ala Gly Ile Gly Asn
        275                 280                 285

Gly Ala Lys Arg Gly Val Leu Ile Lys Gly Gly Asp Val Met Asn Thr
    290                 295                 300

Phe Ser His Ile Asp Thr Leu Leu Phe Asp Lys Thr Gly Thr Leu Thr
305                 310                 315                 320

Lys Gly Asn Thr Glu Val Val Val Val Lys Asn Tyr Gly Ala Ser Lys
                325                 330                 335

Glu Leu Ile Asp Ala Val Ala Ser Ala Glu Asn Glu Ser Asp His Pro
            340                 345                 350

Leu Ala Thr Ala Val Val Arg Met Ile Gly Lys Phe Asn Pro Ile Lys
        355                 360                 365

Phe Glu Lys Thr Asp Val Val Lys Gly Gln Gly Ile Ile Ala Asp Asn
    370                 375                 380

Leu Leu Ile Gly Asn Glu Lys Met Met Val Val Asn His Ile Thr Ile
385                 390                 395                 400

Ser Pro Glu Gln Lys Gln Asp Ile Thr Glu Ile Thr Asp Ser Gly Ala
                405                 410                 415

Ser Val Val Leu Val Ala Ala Asp Asn Arg Leu Gln Leu Ile Tyr Gly
            420                 425                 430

Ile Ala Asp Glu Ile Arg Ser Gly Val Lys Glu Ser Leu Glu Glu Leu
        435                 440                 445

Arg His Glu Gly Ile Ser Arg Met Ile Met Leu Thr Gly Asp Asn Glu
    450                 455                 460

Thr Thr Ala Lys Ala Val Ala Ala Gln Leu Gly Ile Asp Glu Val Arg
465                 470                 475                 480

Ala Asn Leu Met Pro Glu Glu Lys Ala Glu Val Val Lys Ser Leu Lys
                485                 490                 495

Asn Ser Gly Lys Lys Ile Ala Phe Ile Gly Asp Gly Val Asn Asp Ser
            500                 505                 510

Pro Ser Leu Ala Leu Ala Asn Ile Gly Ile Ala Met Gly Ser Gly Thr
        515                 520                 525

Asp Thr Ala Ile Glu Thr Ser Asp Ile Val Leu Met Arg Ser Ser Phe
    530                 535                 540

Asp Glu Leu Val His Ala Tyr Gly Leu Ser Lys Arg Thr Val Ala Asn
545                 550                 555                 560

Met Thr Gln Asn Ile Val Ile Ala Ile Val Val Val Leu Phe Leu Leu
                565                 570                 575

Ala Ser Leu Ile Leu Gly Gly Thr Gly Leu Val Pro Ser Phe Val Asn
```

```
            580                 585                 590

Met Gly Thr Gly Met Phe Val His Glu Ala Ser Ile Leu Ile Val Ile
        595                 600                 605

Val Asn Gly Met Arg Leu Ile Arg Tyr Arg Glu Lys
    610                 615                 620


<210> SEQ ID NO 143
<211> LENGTH: 311
<212> TYPE: PRT
<213> ORGANISM: Lactococcus lactis

<400> SEQUENCE: 143

Met Gln Asn Asn Tyr Thr Ser Lys Gly Lys His Leu Thr Glu Ser Glu
1               5                   10                  15

Arg Leu Leu Ile Glu Arg Trp His Asn Lys Glu Lys Val Ser Asn Arg
            20                  25                  30

Glu Ile Ala Tyr Arg Leu Gly Lys Ala Pro Gln Thr Ile His Asn Glu
        35                  40                  45

Ile Gln Arg Gly Thr Val Gln Leu Lys Tyr Lys Thr Lys Tyr Ser Ala
    50                  55                  60

Lys Ile Ala Gln Glu Ser Tyr Lys Thr Leu Arg Thr His Ser Lys Arg
65                  70                  75                  80

Ser Thr Lys Leu Asn Ala Gln Leu Asp Asp Gln Ile Ser Lys Ala Val
                85                  90                  95

Lys Asn Lys Ile Ser Leu Glu Val Ile His Gln Glu Leu Lys Gly Val
            100                 105                 110

Val Cys Leu Arg Thr Leu Tyr Asn Trp Ile Ser Ser Gly Ile Leu Ser
        115                 120                 125

Val Ala Tyr His Glu Leu Leu Tyr Pro Gln Tyr Arg Lys Pro Lys Lys
    130                 135                 140

Gln Arg Val Thr Gln Pro Lys His Met Leu Gly Gln Ser Ile Glu Glu
145                 150                 155                 160

Arg Pro Glu Ser Val Asp Glu Arg Ser Glu Tyr Gly His Trp Glu Ile
                165                 170                 175

Asp Thr Val Leu Leu Thr Lys Glu Lys Gly Glu Cys Leu Leu Thr Leu
            180                 185                 190

Thr Glu Arg Lys Thr Arg Leu Glu Ile Ile Arg Leu Ile Pro Asn Lys
        195                 200                 205

Thr Thr His Ser Val Asn Gln Ala Leu Arg Gly Ile Glu Phe Leu Ala
    210                 215                 220

Leu Ser Val Thr Ser Asp Asn Gly Arg Glu Phe Ala Lys Leu Ser Glu
225                 230                 235                 240

Ala Leu Asp Cys Pro Val Tyr Tyr Cys His Ala Tyr Ala Ser His Glu
                245                 250                 255

Arg Gly Thr Asn Glu Asn His Asn Arg Met Ile Arg Arg His Leu Pro
            260                 265                 270

Lys Gly Thr Lys Lys Thr Thr Lys Gln Val Val Ala Tyr Ile Glu Asn
        275                 280                 285

Trp Met Asn Asn Tyr Pro Arg Lys Met Phe Asn Phe Lys Thr Pro Asn
    290                 295                 300

Gln Met Leu Ile Glu Ser Ile
305                 310


<210> SEQ ID NO 144
<211> LENGTH: 226
```

<212> TYPE: PRT
<213> ORGANISM: Lactococcus lactis

<400> SEQUENCE: 144

Met Asn His Phe Lys Gly Lys Gln Phe Gln Gln Asp Val Ile Ile Val
1               5                   10                  15

Ala Val Gly Tyr Tyr Leu Arg Tyr Asn Leu Ser Tyr Arg Glu Val Gln
            20                  25                  30

Glu Ile Leu Tyr Asp Arg Gly Ile Asn Val Ser His Thr Thr Ile Tyr
        35                  40                  45

Arg Trp Val Gln Glu Tyr Gly Lys Leu Leu Tyr Gln Ile Trp Lys Lys
    50                  55                  60

Lys Asn Lys Lys Ser Phe Tyr Ser Trp Lys Met Asp Glu Thr Tyr Ile
65                  70                  75                  80

Lys Ile Lys Gly Lys Trp His Tyr Leu Tyr Arg Ala Ile Asp Ala Asp
                85                  90                  95

Gly Leu Thr Leu Asp Ile Trp Leu Arg Lys Lys Arg Asp Thr Gln Ala
            100                 105                 110

Ala Tyr Ala Phe Leu Lys Arg Leu Val Lys Gln Phe Asp Glu Pro Lys
        115                 120                 125

Val Val Val Thr Asp Lys Ala Pro Ser Ile Thr Ser Ala Phe Lys Lys
    130                 135                 140

Leu Lys Glu Tyr Gly Phe Tyr Gln Gly Thr Glu His Arg Thr Ile Lys
145                 150                 155                 160

Tyr Leu Asn Asn Leu Ile Glu Gln Asp His Arg Pro Val Lys Arg Arg
                165                 170                 175

Asn Lys Phe Tyr Arg Ser Leu Arg Thr Ala Ser Thr Thr Ile Lys Gly
            180                 185                 190

Met Glu Ala Ile Arg Gly Leu Tyr Lys Lys Thr Arg Lys Glu Gly Thr
        195                 200                 205

Leu Phe Gly Phe Ser Val Cys Thr Glu Ile Lys Val Leu Leu Gly Ile
    210                 215                 220

Pro Ala
225

<210> SEQ ID NO 145
<211> LENGTH: 221
<212> TYPE: PRT
<213> ORGANISM: Lactococcus lactis

<400> SEQUENCE: 145

Met Asn Ser Arg Ile Phe Gln His Asn Thr Phe Thr Thr Leu Ser Ile
1               5                   10                  15

Gly Phe Tyr Lys Gly Thr Ile Thr Leu Lys Glu Ala Leu Thr His Gly
            20                  25                  30

Lys Val Gly Ile Gly Thr Leu Asp Thr Ala Asn Gly Glu Val Thr Ile
        35                  40                  45

Ile Asp Gly Ile Ala Tyr His Gly Asp Ser Glu Asn Gln Val Arg Leu
    50                  55                  60

Val Glu Glu Asn Glu Thr Met Pro Tyr Val Ala Met Val Glu His Gln
65                  70                  75                  80

Pro Ile Val Lys Phe Thr Asp Asn Ser Val Ser Asn Ser Glu Asp Phe
                85                  90                  95

Leu Ser Ala Leu Thr Lys Arg Phe Pro Thr Ala Asn Thr Ala Tyr Thr
            100                 105                 110

Ile Val Met Thr Gly Gln Phe Lys Glu Val Thr Val Ser Ser Lys Pro
115 120 125

Ala Asn Asn Thr Arg Pro Tyr Asp Glu Ile Met Ala Asp Gln Pro Tyr
130 135 140

Phe Thr Lys Glu Asn Ile Ser Gly Thr Met Leu Gly Val Trp Ala Pro
145 150 155 160

Lys His Leu Thr Asp Leu Phe Gly Ile Gly Phe His Leu His Phe Val
165 170 175

Ser Glu Asp Lys Thr Phe Thr Ala His Val Gln Asn Phe Ile Thr Glu
180 185 190

Asn Leu Ala Ile Glu Leu Gly Lys Ile Thr Gln Ile Glu Gln Glu Phe
195 200 205

Pro Asp Glu Asp Glu Asn Phe Asp Gln His Leu Phe Gln
210 215 220

<210> SEQ ID NO 146
<211> LENGTH: 184
<212> TYPE: PRT
<213> ORGANISM: Lactococcus lactis

<400> SEQUENCE: 146

Met Asn Ile Gly Tyr Ala Arg Val Ser Thr Gly Leu Gln Asn Leu Asp
1 5 10 15

Leu Gln Lys Asp Ser Leu Lys Lys Tyr Asn Cys Glu Lys Ile Phe Thr
20 25 30

Asp His Met Ser Gly Ser Lys Arg Glu Arg Pro Gly Leu Lys Ser Ala
35 40 45

Ile Glu Phe Ser Arg Pro Gly Asp Thr Ile Val Val Trp Arg Leu Asp
50 55 60

Arg Leu Gly Arg Asn Met Glu Asp Leu Ile Asn Ile Val Asn Ser Leu
65 70 75 80

Asn Asn Lys Gly Val Ser Phe His Ser Leu Gln Glu Asn Ile Thr Met
85 90 95

Asp Lys Ser Ser Ser Thr Gly Gln Leu Met Phe His Leu Phe Ala Ala
100 105 110

Phe Ala Glu Phe Glu Arg Asn Leu Ile Leu Glu Arg Ser Ala Ala Gly
115 120 125

Arg Glu Ala Ala Arg Ala Arg Gly Arg Leu Gly Gly Arg Pro Glu Lys
130 135 140

Phe Ser Glu Gln Asp Val Lys Leu Leu Lys Thr Leu Val Glu Ser Gly
145 150 155 160

Thr Pro Ile Lys Ser Ile Ala Asp Ser Trp Gly Val Ser Arg Thr Thr
165 170 175

Ile Tyr Arg Tyr Ile Asn Lys Phe
180

<210> SEQ ID NO 147
<211> LENGTH: 95
<212> TYPE: PRT
<213> ORGANISM: Lactococcus lactis

<400> SEQUENCE: 147

Met Lys Ile Ile Thr Ala Thr Leu Leu Leu Val Ile Ser Leu Leu Gly
1 5 10 15

Ile Leu Gly Thr Ala Phe Leu Tyr Leu Gly Glu Leu Thr Gln Gly Lys
20 25 30

```
Gly Gly Gly Phe Leu Phe Ile Leu Gly Cys Phe Leu Ile Leu Gly Ile
        35                  40                  45

Gln Ser Phe Thr Trp Leu Glu Ile Leu Phe Gly Lys Arg Gln Asn Gly
    50                  55                  60

Glu Val Lys Lys Tyr Asp Tyr Phe Leu Phe Asn Ile Leu Lys Val Ile
65                  70                  75                  80

Phe Ser Ile Gly Ala Leu Gln Leu Phe Ile Gln Arg Cys Phe Phe
                85                  90                  95


<210> SEQ ID NO 148
<211> LENGTH: 229
<212> TYPE: PRT
<213> ORGANISM: Lactococcus lactis

<400> SEQUENCE: 148

Met Ser Lys Tyr Lys His His Phe Ser His His Glu His His Cys Val
1               5                   10                  15

Gln Leu Val Pro Leu Phe Gly Leu Leu Ser Glu Ser Glu Leu Val Gln
            20                  25                  30

Val Glu Gln Val Val Asn His Lys Ile Phe Glu Lys Gly Glu Thr Val
        35                  40                  45

Ile Ser Pro Phe Ala Val Pro Gln Leu Ala Ile Val Ala His Gly Thr
    50                  55                  60

Leu Lys Ile Tyr Gln Leu Ser Ser Ala Gly Lys Glu Gln Leu Leu Arg
65                  70                  75                  80

Val Ile Glu Pro Gly Gly Tyr Ala Gly Glu Asp Ala Leu Phe Gly Val
                85                  90                  95

Met Asn Asp Asn Leu Tyr Gly Glu Thr Leu Glu Glu Thr Gln Ile Cys
            100                 105                 110

Phe Leu Arg Gln Gln Asp Phe Lys Asn Leu Leu Leu Lys Tyr Pro Glu
        115                 120                 125

Leu Ser Leu Lys Leu Leu Glu Thr Thr Val Arg Arg Ala Ala Glu Met
    130                 135                 140

Gln Tyr Gln Ala Gln Phe Leu Met Met Glu Asp Val Glu Ser Arg Ile
145                 150                 155                 160

Ala Asn Tyr Leu Leu Gln Leu Val Lys Val Val Asp Ser Asn Ser Val
                165                 170                 175

Met Ile Pro Met Lys Met Lys Asp Leu Ala Thr Phe Ile Gly Thr Thr
            180                 185                 190

Pro Glu Thr Ile Ser Arg Lys Phe Lys Ile Leu Glu Glu Lys Gly Phe
        195                 200                 205

Ile Glu Arg Arg Gly Lys Ile Ile Lys Ile Leu Asp Ile Asp Ser Leu
    210                 215                 220

Glu Asp Asp Tyr Ala
225


<210> SEQ ID NO 149
<211> LENGTH: 182
<212> TYPE: PRT
<213> ORGANISM: Lactococcus lactis

<400> SEQUENCE: 149

Met Met Thr Lys Leu Met Ile Asp Glu Lys Tyr Ala Lys Glu Leu Asp
1               5                   10                  15

Lys Ala Glu Ile Asp His His Lys Pro Thr Ala Gly Ala Met Leu Gly
            20                  25                  30
```

```
His Val Leu Ser Asn Leu Phe Ile Glu Asn Ile Arg Leu Thr Gln Ala
        35                  40                  45

Gly Ile Tyr Ala Lys Ser Pro Val Lys Cys Glu Tyr Leu Arg Glu Ile
    50                  55                  60

Ala Gln Lys Glu Val Glu Tyr Phe Phe Lys Ile Ser Asp Leu Leu Leu
65                  70                  75                  80

Asp Glu Asn Glu Ile Val Pro Ser Thr Thr Glu Glu Phe Leu Lys Tyr
                85                  90                  95

His Lys Phe Ile Thr Glu Asp Pro Lys Ala Lys Tyr Trp Thr Asp Glu
            100                 105                 110

Asp Leu Leu Glu Ser Phe Ile Val Asp Phe Gln Ala Gln Asn Met Phe
        115                 120                 125

Ile Thr Arg Ala Ile Lys Leu Ala Asn Lys Glu Glu Lys Phe Ala Leu
    130                 135                 140

Ala Ala Gly Val Val Glu Leu Tyr Gly Tyr Asn Leu Gln Val Ile Arg
145                 150                 155                 160

Asn Leu Ala Gly Asp Leu Gly Lys Ser Val Ala Asp Phe His Asp Glu
                165                 170                 175

Asp Glu Asp Asn Asp Asn
            180


<210> SEQ ID NO 150
<211> LENGTH: 75
<212> TYPE: PRT
<213> ORGANISM: Lactococcus lactis

<400> SEQUENCE: 150

Met Ser Lys Val Ile Met Arg Leu Asn Glu Leu Ser Cys Pro Ser Cys
1               5                   10                  15

Met Ala Lys Ile Glu Ala Ala Met Thr Thr Thr Lys Gly Val Ala Asn
            20                  25                  30

Ala Lys Val Leu Phe Asn Ala Ser Lys Val Lys Ala Glu Phe Asp Glu
        35                  40                  45

Asn Val Val Ser Ala Asp Glu Leu Ile Ser Lys Val Glu Lys Leu Gly
    50                  55                  60

Tyr Pro Val Leu Ser Ser Lys Val Thr Val Val
65                  70                  75


<210> SEQ ID NO 151
<211> LENGTH: 226
<212> TYPE: PRT
<213> ORGANISM: Lactococcus lactis

<400> SEQUENCE: 151

Met Asn His Phe Lys Gly Lys Gln Phe Gln Gln Asp Val Ile Ile Val
1               5                   10                  15

Ala Val Gly Tyr Tyr Leu Arg Tyr Asn Leu Ser Tyr Arg Glu Val Gln
            20                  25                  30

Glu Ile Leu Tyr Asp Arg Gly Ile Asn Val Ser His Thr Thr Ile Tyr
        35                  40                  45

Arg Trp Val Gln Glu Tyr Gly Lys Leu Leu Tyr Gln Ile Trp Lys Lys
    50                  55                  60

Lys Asn Lys Lys Ser Phe Tyr Ser Trp Lys Met Asp Glu Thr Tyr Ile
65                  70                  75                  80

Lys Ile Lys Gly Lys Trp His Tyr Leu Tyr Arg Ala Ile Asp Ala Asp
                85                  90                  95
```

```
Gly Leu Thr Leu Asp Ile Trp Leu Arg Lys Lys Arg Asp Thr Gln Ala
            100                 105                 110

Ala Tyr Ala Phe Leu Lys Arg Leu Val Lys Gln Phe Asp Glu Pro Lys
        115                 120                 125

Val Val Val Thr Asp Lys Ala Pro Ser Ile Thr Ser Ala Phe Lys Lys
    130                 135                 140

Leu Lys Glu Tyr Gly Phe Tyr Gln Gly Thr Glu His Arg Thr Ile Lys
145                 150                 155                 160

Tyr Leu Asn Asn Leu Ile Glu Gln Asp His Arg Pro Val Lys Arg Arg
                165                 170                 175

Asn Lys Phe Tyr Arg Ser Leu Arg Thr Ala Ser Thr Thr Ile Lys Gly
            180                 185                 190

Met Glu Ala Ile Arg Gly Leu Tyr Lys Lys Thr Arg Lys Glu Gly Thr
        195                 200                 205

Leu Phe Gly Phe Ser Val Cys Thr Glu Ile Lys Val Leu Leu Gly Ile
    210                 215                 220

Pro Ala
225


<210> SEQ ID NO 152
<211> LENGTH: 52
<212> TYPE: PRT
<213> ORGANISM: Lactococcus lactis

<400> SEQUENCE: 152

Met Lys Met Leu Arg Val Gln Lys Pro Leu Leu Phe Lys Phe Ser Gln
1               5                   10                  15

Ile Gln Val Leu Gln Tyr Thr Lys Thr Gln Asp Ala Val Tyr Lys Val
            20                  25                  30

Asn Ser Asn Thr Ile Cys Ser Val Tyr Lys Leu Ser Phe Thr Leu Val
        35                  40                  45

Gln Leu Arg Leu
    50


<210> SEQ ID NO 153
<211> LENGTH: 229
<212> TYPE: PRT
<213> ORGANISM: Lactococcus lactis

<400> SEQUENCE: 153

Met Thr Tyr Ile Glu Leu Asn Pro Val Asn Asn Val Val Leu Pro Lys
1               5                   10                  15

His Asn Ser Ser Val Glu Asp Phe Glu Ile Ser Glu Asn Lys Thr Ile
            20                  25                  30

Thr Tyr Asp Glu Leu Lys Ile Val Leu Glu Tyr Cys His Lys His Asn
        35                  40                  45

Lys Asn Gln Arg Leu Thr Leu Ile Ile Glu Phe Leu Phe Leu Thr Gly
    50                  55                  60

Leu Arg Leu Glu Glu Leu Gly Gly Leu Gln Lys Ser Ser Val Asp Phe
65                  70                  75                  80

Lys Lys Gln Thr Ile Lys Ile Lys His Val Ile Asp Thr Lys Ala Ile
                85                  90                  95

Gly Asp Asn Ser Arg Lys Leu Tyr Leu Pro Lys Thr Phe Ala Ser Arg
            100                 105                 110

Arg Glu Ile Tyr Val Asn Asp Arg Cys Ile Glu Ile Leu Lys Trp Phe
        115                 120                 125
```

```
Phe Asp Asn Ser Leu Asp Asp Asp Phe Val Phe Thr Thr Met Ile Gly
    130                 135                 140

Thr Thr Val Lys Gln Ser Ala Thr Tyr Leu Phe Val Arg Asn Val Cys
145                 150                 155                 160

Glu Ala Ser Leu Gly Lys Gln Lys Asn Arg Lys Tyr Asn Val His Met
                165                 170                 175

Leu Arg His Ala His Ile Ser Leu Leu Ala Glu Leu Asp Ile Pro Ile
            180                 185                 190

Lys Ala Thr Met Lys Arg Val Gly His Ser Gln Glu Ser Thr Thr Leu
        195                 200                 205

Arg Ile Tyr Ser His Val Ser Gln Lys Met Asn Asp Ser Ile Met Arg
    210                 215                 220

Lys Leu Asn Glu Ile
225


<210> SEQ ID NO 154
<211> LENGTH: 226
<212> TYPE: PRT
<213> ORGANISM: Lactococcus lactis

<400> SEQUENCE: 154

Met Asn His Phe Lys Gly Lys Gln Phe Gln Gln Asp Val Ile Ile Val
1               5                   10                  15

Ala Val Gly Tyr Tyr Leu Arg Tyr Asn Leu Ser Tyr Arg Glu Val Gln
            20                  25                  30

Glu Ile Leu Tyr Asp Arg Gly Ile Asn Val Ser His Thr Thr Ile Tyr
        35                  40                  45

Arg Trp Val Gln Glu Tyr Gly Lys Leu Leu Tyr Gln Ile Trp Lys Lys
    50                  55                  60

Lys Asn Lys Lys Ser Phe Tyr Ser Trp Lys Met Asp Glu Thr Tyr Ile
65                  70                  75                  80

Lys Ile Lys Gly Lys Trp His Tyr Leu Tyr Arg Ala Ile Asp Ala Asp
                85                  90                  95

Gly Leu Thr Leu Asp Ile Trp Leu Arg Lys Lys Arg Asp Thr Gln Ala
            100                 105                 110

Ala Tyr Ala Phe Leu Lys Arg Leu Val Lys Gln Phe Asp Glu Pro Lys
        115                 120                 125

Val Val Val Thr Asp Lys Ala Pro Ser Ile Thr Ser Ala Phe Lys Lys
    130                 135                 140

Leu Lys Glu Tyr Gly Phe Tyr Gln Gly Thr Glu His Arg Thr Ile Lys
145                 150                 155                 160

Tyr Leu Asn Asn Leu Ile Glu Gln Asp His Arg Pro Val Lys Arg Arg
                165                 170                 175

Asn Lys Phe Tyr Arg Ser Leu Arg Thr Ala Ser Thr Thr Ile Lys Gly
            180                 185                 190

Met Glu Ala Ile Arg Gly Leu Tyr Lys Lys Thr Arg Lys Glu Gly Thr
        195                 200                 205

Leu Phe Gly Phe Ser Val Cys Thr Glu Ile Lys Val Leu Leu Gly Ile
    210                 215                 220

Pro Ala
225


<210> SEQ ID NO 155
<211> LENGTH: 200
<212> TYPE: PRT
<213> ORGANISM: Lactococcus lactis
```

<400> SEQUENCE: 155

Met Lys Gln Lys Lys Arg Glu Gln Arg Ser Asn Lys Trp Ala Phe Leu
1               5                   10                  15

Ile Tyr Gln Glu Ser Val Pro Glu Asp Tyr Leu Asn Leu Leu Glu Glu
            20                  25                  30

Leu His Val Pro Phe Ile Leu Ser Pro Trp His Asp Lys Asp Val Asn
        35                  40                  45

Arg Thr Thr Gly Glu Phe Lys Lys Pro His Lys His Gly Val Phe Phe
    50                  55                  60

Phe Glu Ser Leu Lys Ser Tyr Ser Gln Val Ser Glu Leu Ile Ser Asp
65                  70                  75                  80

Lys Leu Asn Ser Pro Glu His Val Glu Val Val Met Ser Pro Lys Gly
                85                  90                  95

Met Tyr Asp Tyr Phe Thr His Ala Glu Asn Pro Glu Lys Ser Pro Tyr
            100                 105                 110

Asn Ile Glu Asp Ile Glu Ser Gly Ala Gly Phe Glu Leu Asp Lys Phe
        115                 120                 125

Leu Ala Glu Asn Asn Glu Asp Leu Leu Asn Gln Val Tyr Glu Val Met
    130                 135                 140

Arg Asp Ser Gly Ile Lys Glu Phe Ala Asp Phe Thr Asp Leu Ile Ala
145                 150                 155                 160

Lys Gln Phe Pro Asp Leu Leu Tyr Phe Val Phe Ser Lys Ser Tyr Phe
                165                 170                 175

Phe Lys Ile Tyr Leu Asp Ser Lys Arg Tyr Ile Glu Ile Lys Gln Lys
            180                 185                 190

Asp Asp Glu Asp Asn His Gly Lys
        195                 200

<210> SEQ ID NO 156
<211> LENGTH: 34
<212> TYPE: PRT
<213> ORGANISM: Lactococcus lactis

<400> SEQUENCE: 156

Met Glu Asn Asn Tyr Pro Tyr Leu Leu Asn Arg Glu Gln Ala Ser Lys
1               5                   10                  15

Phe Ile Gly Ile Arg Asp Asp Thr Phe Ser Val Phe Phe Ile Val Lys
            20                  25                  30

Ile Ser

<210> SEQ ID NO 157
<211> LENGTH: 105
<212> TYPE: PRT
<213> ORGANISM: Lactococcus lactis

<400> SEQUENCE: 157

Met Glu Asp Ile Phe Gln Ile Thr Ile Ile Leu Phe Phe Ser Met Leu
1               5                   10                  15

Ala Thr Leu Leu Ser Lys Lys Leu Lys Ile Pro Glu Val Val Gly Gln
            20                  25                  30

Met Leu Ile Gly Ile Ile Leu Ala Pro Ser Val Leu Gly Leu Ile Asn
        35                  40                  45

Gly Gly His Thr Ile Glu Val Met Ser Glu Ile Gly Val Ile Leu Leu
    50                  55                  60

Met Phe Leu Ala Gly Leu Glu Ser Asp Leu Glu Val Leu Lys Lys Asn

```
65                  70                  75                  80

Leu Lys Pro Ser Ile Leu Val Val Leu Leu Gln Ser Leu Lys Ile Lys
                85                  90                  95

Arg Ala Leu Ser Glu Leu Gln Ile Ser
            100                 105
```

<210> SEQ ID NO 158
<211> LENGTH: 226
<212> TYPE: PRT
<213> ORGANISM: Lactococcus lactis

<400> SEQUENCE: 158

```
Met Asn His Phe Lys Gly Lys Gln Phe Lys Lys Asp Val Ile Ile Val
1               5                   10                  15

Ala Val Gly Tyr Tyr Leu Arg Tyr Asn Leu Ser Tyr Arg Glu Ile Gln
            20                  25                  30

Glu Leu Leu Tyr Asp Arg Gly Ile Asn Val Cys His Thr Thr Ile Tyr
        35                  40                  45

Arg Trp Val Gln Glu Tyr Ser Lys Val Leu Tyr His Leu Trp Lys Lys
    50                  55                  60

Lys Asn Arg Gln Ser Phe Tyr Ser Trp Lys Met Asp Glu Thr Tyr Ile
65                  70                  75                  80

Lys Ile Lys Gly Arg Trp His Tyr Leu Tyr Arg Ala Ile Asp Ala Asp
                85                  90                  95

Gly Leu Thr Leu Asp Ile Trp Leu Arg Lys Lys Arg Asp Thr Gln Ala
            100                 105                 110

Ala Tyr Ala Phe Leu Lys Arg Leu His Lys Gln Phe Gly Gln Pro Arg
        115                 120                 125

Val Ile Val Thr Asp Lys Ala Pro Ser Ile Gly Ser Ala Phe Arg Lys
    130                 135                 140

Leu Gln Ser Asn Gly Leu Tyr Thr Lys Thr Glu His Arg Thr Val Lys
145                 150                 155                 160

Tyr Leu Asn Asn Leu Ile Glu Gln Asp His Arg Pro Ile Lys Arg Arg
                165                 170                 175

Asn Lys Phe Tyr Arg Ser Leu Arg Thr Ala Ser Thr Thr Ile Lys Gly
            180                 185                 190

Met Glu Thr Ile Arg Gly Ile Tyr Lys Lys Asn Arg Arg Asn Gly Thr
        195                 200                 205

Leu Phe Gly Phe Ser Val Ser Thr Glu Ile Lys Val Leu Met Gly Ile
    210                 215                 220

Pro Ala
225
```

<210> SEQ ID NO 159
<211> LENGTH: 123
<212> TYPE: PRT
<213> ORGANISM: Lactococcus lactis

<400> SEQUENCE: 159

```
Met Ser Glu His Leu Asn Met Ala Ser Ile Lys Lys Lys Gln Pro Asn
1               5                   10                  15

Arg Lys Glu Arg Lys Gln Ile Ser Phe Arg Val Ser Glu Pro Glu Tyr
            20                  25                  30

Leu Asn Leu Glu Arg Ser Ala Lys Val Leu Asn Ile Ser Val Pro Ala
        35                  40                  45

Phe Val Lys Lys Lys Ala Gln Gly Ala Arg Val Val Ala Pro Lys Ile
```

```
    50                  55                  60

Asn Pro Asp Asp Ser Lys Glu Met Ala Arg Gln Leu Ala Ala Leu Gly
65                  70                  75                  80

Asn Asn Val Asn Gln Leu Ala Lys Arg Val Asn Gln Ile Glu Phe Ala
                85                  90                  95

Asp Lys Asp Thr Gln Glu Arg Leu Ser Ala Asp Leu Arg Arg Thr Leu
            100                 105                 110

His Gly Leu Gly Glu Ile Trp Arg Gln Leu Thr
        115                 120


<210> SEQ ID NO 160
<211> LENGTH: 320
<212> TYPE: PRT
<213> ORGANISM: Lactococcus lactis

<400> SEQUENCE: 160

Met Ala Thr Thr His Ile Lys Arg Ser Asn Gly Ala Ser Arg Leu Val
1               5                   10                  15

Asn Tyr Ala Glu Lys Arg Ala Val Gln Lys Asp Gly Tyr Asn Leu Asp
            20                  25                  30

Ile Glu Tyr Ala Lys Ser Glu Leu Lys Gln Val Arg Glu Ile Tyr Gly
        35                  40                  45

Asn Lys Gly Ala Thr Gln Ala Tyr Ala Ser Arg Val Ala Phe Ser Pro
    50                  55                  60

Lys Glu Phe Asp Pro Lys Asn Val Lys Asp Gln Leu Lys Ala Leu Glu
65                  70                  75                  80

Ile Ala Lys Glu Ile Tyr Ser Thr Ala Tyr Pro Asn Gln Gln Ile Ala
                85                  90                  95

Met Tyr Val His Asn Asp Thr Asp Ser Leu His Val His Ala Val Ile
            100                 105                 110

Gly Ala Ile Asn Leu Leu Thr Gly Lys Lys Met His Gly Asn Trp Gln
        115                 120                 125

Glu Tyr Arg Glu Arg Leu Val Lys Ile Thr Asp Lys Val Val Glu Lys
    130                 135                 140

His Gly Leu Thr Val Thr Val Pro His Pro Arg Pro Glu Lys Arg Thr
145                 150                 155                 160

Met Ala Glu Leu Lys Met Lys Ala Arg Gly Gln Val Thr Trp Lys Asp
                165                 170                 175

Lys Ile Arg Gln Ala Val Asp Thr Thr Met Arg Glu Ala His Ile Ser
            180                 185                 190

Asp Phe Lys Ser Phe Lys Glu Lys Leu Gly Glu Leu Ala Val Asn Val
        195                 200                 205

Ile Glu Arg Gly Arg Asp Leu Thr Tyr Thr Leu Thr Gly Thr Asp Tyr
    210                 215                 220

Lys Ser Arg Gly Ala Lys Leu Gly Glu Asp Tyr Lys Lys Glu Thr Ile
225                 230                 235                 240

Phe Tyr Glu Leu Asp Arg Arg Asn Gln Leu Gln Tyr Gly Thr Ser Arg
                245                 250                 255

Gln Arg Gln Gly Arg Ala Trp Leu Glu Gly Arg Gly Glu Arg Leu Glu
            260                 265                 270

Gln Glu Gln Arg Ala Arg Gln Asn Leu Ala Lys Arg Ala Glu Asp Leu
        275                 280                 285

Gln Arg Arg Thr Leu Glu Ser Thr Glu Gln Ser Ile Gln Pro Ser His
    290                 295                 300
```

Gln Arg Pro Gln Lys Ser Lys Glu Arg Gly Leu Gly Gly Pro Ser Leu
305 310 315 320

<210> SEQ ID NO 161
<211> LENGTH: 296
<212> TYPE: PRT
<213> ORGANISM: Lactococcus lactis

<400> SEQUENCE: 161

Met Val His Glu Ile Val Gln Tyr His Asn Asp Phe Asn Thr Val Pro
1 5 10 15

Leu Arg Gly Phe Asn Glu Arg Glu Arg Arg Ile Val Met Ala Leu Leu
20 25 30

His Gln Val Lys Asn Lys Asp Val Glu Val Val Gln Leu Asp Phe Asp
35 40 45

Thr Leu Arg Gly Leu Ser Gly Trp Asn Asp Thr Leu Ala Lys Ser Glu
50 55 60

Asn Ser Asn Ala Lys Phe Asn Arg Tyr Leu Glu Asn Leu Ser Asp Lys
65 70 75 80

Ile Met Thr Leu Arg Gly Thr Leu Arg Ser Glu Asp Gly Leu Gln Val
85 90 95

Val Lys Phe Ser Leu Phe Pro Thr Phe Ile Ile Asp Gly Lys Asn Thr
100 105 110

Met Thr Leu Lys Val Gln Ile Asn Pro Thr Phe Lys Tyr Leu Thr Asn
115 120 125

Ile Phe Asp Met Phe Thr Ala Phe Glu Leu Asp Asp Tyr Asn Arg Met
130 135 140

Asn Thr Ser Tyr Gly Gln Glu Leu Tyr Arg Leu Leu Lys Gln Tyr Arg
145 150 155 160

Thr Ser Gly Phe Tyr Arg Val Lys Ile Glu Asp Leu Arg His Leu Leu
165 170 175

Ser Val Pro Glu Ser Tyr Thr Asn Ala Lys Met Asp Gln Lys Val Phe
180 185 190

Ser Lys Thr Thr Val Thr Asp Leu Thr Asn Ala Phe Pro Asn Phe Lys
195 200 205

Ile Lys Gln Glu Arg Gly Thr Gly Arg Gly Arg Pro Ile Ile Gly Tyr
210 215 220

Thr Phe Thr Phe Asp Lys Glu Ala Pro Asn Lys Tyr Glu Leu Asp Arg
225 230 235 240

Lys Lys Gln Glu Gln Ile Ala Gln Phe Trp Lys Ser Asn Asp Pro Glu
245 250 255

Pro Met Pro Asn Ala Val Ala Gln Thr Glu Tyr Gln Asn Pro Glu Leu
260 265 270

Arg Lys Glu Lys Glu Glu Leu Glu Lys His Asn Ala Ser Phe Gly Asp
275 280 285

Leu Leu Lys Gly Trp Phe Lys Lys
290 295

<210> SEQ ID NO 162
<211> LENGTH: 263
<212> TYPE: PRT
<213> ORGANISM: Lactococcus lactis

<400> SEQUENCE: 162

Met Lys Phe Lys Lys Lys Asn Tyr Thr Pro Gln Val Asp Glu Lys Asp
1 5 10 15

```
Cys Gly Cys Ala Ala Leu Ser Met Ile Leu Lys Thr Tyr Glu Thr Glu
            20                  25                  30

Lys Ser Leu Ala Ser Phe Leu Leu Asn Gln Arg Ile Lys Met His Lys
        35                  40                  45

Val Phe Glu Lys Ile Ile Thr Ile Phe Phe Ala Phe Phe Leu Phe Phe
    50                  55                  60

Ile Ser Gln Ile Pro Ile Tyr Tyr Val Asn Tyr Lys Asn Lys Glu Asn
65                  70                  75                  80

Asn Leu Tyr Gly Ile Ser Asn Lys Ile Ser Leu Pro Phe Ile Phe Ile
                85                  90                  95

Ala Leu Phe Val Ile Ile Ile Ala Val Ala Leu Gly Lys Lys Arg Gly
            100                 105                 110

Phe Tyr His His Ser Lys Lys Thr Leu Glu Phe Lys Asn Ile Met Leu
        115                 120                 125

Ile Leu Val Leu Val Thr Ile Ser Ile Ile Leu Asn Ile Leu Ile Asn
    130                 135                 140

Arg Phe Ile Ile Phe His His Leu Gly Ile Met Asn Asn Gln Ile Asn
145                 150                 155                 160

Ile Asp Ser Ile Leu Ser Ser Leu Ser Cys Leu Gly Lys Ile Phe Gly
                165                 170                 175

Ile Ala Leu Leu Ala Pro Ile Leu Glu Glu Ser Ile Phe Arg Ala Ser
            180                 185                 190

Ile Tyr Gln Ile Phe Asn Asn Asp Lys Val Ser Phe Leu Ile Ser Ser
        195                 200                 205

Leu Leu Phe Ala Phe Leu His Ser Gly Tyr Ser Trp Val Phe Phe Thr
    210                 215                 220

Tyr Leu Pro Val Ser Leu Cys Met Thr Phe Ile Tyr His Arg Arg Lys
225                 230                 235                 240

Ile Leu Thr Asp Ser Ile Leu Phe His Ser Leu Phe Asn Leu Leu Val
                245                 250                 255

Leu Gly Leu Asn Phe Leu Ile
            260


<210> SEQ ID NO 163
<211> LENGTH: 150
<212> TYPE: PRT
<213> ORGANISM: Lactococcus lactis

<400> SEQUENCE: 163

Met Leu Asp Ile Leu Asn Lys Ala Arg Ile His Lys Lys Trp Phe Leu
1               5                   10                  15

Phe Ser Tyr Ser Ile Ile Ser Phe Cys Ile Thr Ile Ile Tyr Ile Val
            20                  25                  30

Phe Asn His Thr Phe Phe Lys Val Asn Trp Ala Lys Tyr Asn Ser Asp
        35                  40                  45

Asp Ser Tyr Lys Asn Lys Val Asp Glu Ile Leu Lys His Gly Val Phe
    50                  55                  60

Trp Ile Asn Gly Asn Leu Thr Ser Ile Ser Ser Pro Leu Leu Ile Cys
65                  70                  75                  80

Leu Phe Leu Leu Gly Ala Phe Phe Ser Leu Thr Ile Phe Phe Leu Thr
                85                  90                  95

Trp Arg Asn Leu Ser Thr Arg Thr Trp Thr Pro Ile Ile Ser Phe Leu
            100                 105                 110

Gly Phe Leu Ile Pro Phe Ile His Ser Asp Gly Asn Phe Ile Asn Leu
        115                 120                 125
```

Leu Ile Leu Ser Phe Ile Leu Ile Leu Phe Gly Ala Ile Ser Ser Val
    130                 135                 140

Pro Ser Leu Arg Tyr Phe
145                 150

<210> SEQ ID NO 164
<211> LENGTH: 226
<212> TYPE: PRT
<213> ORGANISM: Lactococcus lactis

<400> SEQUENCE: 164

Met Asn His Phe Lys Gly Lys Gln Phe Lys Lys Asp Val Ile Ile Val
1               5                   10                  15

Ala Val Gly Tyr Tyr Leu Arg Tyr Asn Leu Ser Tyr Arg Glu Ile Gln
            20                  25                  30

Glu Leu Leu Tyr Asp Arg Gly Ile Asn Val Cys His Thr Thr Ile Tyr
        35                  40                  45

Arg Trp Val Gln Glu Tyr Ser Lys Val Leu Tyr His Leu Trp Lys Lys
    50                  55                  60

Lys Asn Arg Gln Ser Phe Tyr Ser Trp Lys Met Asp Glu Thr Tyr Ile
65                  70                  75                  80

Lys Ile Lys Gly Arg Trp His Tyr Leu Tyr Arg Ala Ile Asp Ala Asp
                85                  90                  95

Gly Leu Thr Leu Asp Ile Trp Leu Arg Lys Lys Arg Asp Thr Gln Ala
            100                 105                 110

Ala Tyr Ala Phe Leu Lys Arg Leu His Lys Gln Phe Gly Gln Pro Arg
        115                 120                 125

Val Ile Val Thr Asp Lys Ala Pro Ser Ile Gly Ser Ala Phe Arg Lys
    130                 135                 140

Leu Gln Ser Asn Gly Leu Tyr Thr Lys Thr Glu His Arg Thr Val Lys
145                 150                 155                 160

Tyr Leu Asn Asn Leu Ile Glu Gln Asp His Arg Pro Ile Lys Arg Arg
                165                 170                 175

Asn Lys Phe Tyr Arg Ser Leu Arg Thr Ala Ser Thr Thr Ile Lys Gly
            180                 185                 190

Met Glu Thr Ile Arg Gly Ile Tyr Lys Lys Asn Arg Arg Asn Gly Thr
        195                 200                 205

Leu Phe Gly Phe Ser Val Ser Thr Glu Ile Lys Val Leu Met Gly Ile
    210                 215                 220

Pro Ala
225

<210> SEQ ID NO 165
<211> LENGTH: 383
<212> TYPE: PRT
<213> ORGANISM: Lactococcus lactis

<400> SEQUENCE: 165

Met Ser Ile Ile Pro Glu Lys Gln Asn Asn Gln Lys Gln Val Leu Thr
1               5                   10                  15

Leu Asn Glu Leu Ser Lys Arg Lys Val Val Glu His Asn Ser Leu Ile
            20                  25                  30

Thr Ser Ile Ala Lys Met Asp Lys Thr Pro Leu Lys Met Phe Glu Leu
        35                  40                  45

Ala Val Ser Cys Ile Asp Thr Glu Lys Pro Leu Glu Asp Asn Thr Val
    50                  55                  60

Tyr Leu Ser Lys Arg Asp Leu Phe Ala Phe Phe Lys Val Ser Asp Asn
65 70 75 80

Asp Lys His Ser Arg Phe Lys Gln Ala Val Glu Lys Met Gln Lys Gln
85 90 95

Ala Phe Phe Gln Ile Lys Glu Glu Ala Gly Lys Gly Phe Lys Phe Lys
100 105 110

Ser Ile Val Pro Ile Pro Tyr Val Glu Trp Thr Asp Tyr Asn Asp Glu
115 120 125

Val Lys Ile Glu Phe His Arg Glu Ile Met Pro Tyr Leu Ile Asn Leu
130 135 140

Lys Lys Asn Phe Thr Gln His Ala Leu Ser Asp Ile Ala Glu Leu Asn
145 150 155 160

Ser Lys Tyr Ser Leu Ile Leu Tyr Arg Trp Leu Ser Met Asn Tyr Asn
165 170 175

Gln Tyr Glu His Tyr Ser Val Lys Gly Gly Arg Arg Ala Glu Gln Val
180 185 190

Glu Ala Tyr Arg Asn Pro Ser Ile Lys Val Lys Glu Met Arg Leu Met
195 200 205

Thr Asp Thr Val Asn Glu Tyr His Lys Tyr Asn Asp Trp Asp Arg Tyr
210 215 220

Ile Leu Lys Asn Ser Leu Lys Glu Ile Asn Ala His Thr Ser Phe Asn
225 230 235 240

Val Thr Tyr Asp Lys Ile Lys Lys Gly Arg Ser Ile Asp Ser Ile Val
245 250 255

Phe His Ile Glu Lys Lys Arg Met Ala Asp Asp Asn Ser Tyr Lys Leu
260 265 270

Gly Asp Lys Asp Tyr Gln Glu Asp Lys Ala Arg Lys Ala Glu Thr Glu
275 280 285

Asp Met Leu Thr Leu Gln Ala Leu Lys Ser Pro Tyr Thr Lys Leu Leu
290 295 300

Met Glu His Phe Leu Leu Ser Tyr Leu Asp Leu Thr Asp Thr Lys Ile
305 310 315 320

Leu Ser Gly Leu Gln Ala His Val Tyr Pro Leu Tyr Asp Glu Leu Lys
325 330 335

Asp Leu Arg Gly Leu Asn Gly Val Lys Asp His Leu Ser Tyr Val Arg
340 345 350

Ala Lys Arg Glu Asp Tyr Ser Lys Lys Asn Ile Thr Lys Tyr Leu Lys
355 360 365

Lys Ala Ile Glu Gln Tyr Leu Pro Thr Val Lys Arg Gln Asp Leu
370 375 380

<210> SEQ ID NO 166
<211> LENGTH: 60
<212> TYPE: PRT
<213> ORGANISM: Lactococcus lactis

<400> SEQUENCE: 166

Met Ser Glu Lys Leu Lys Thr Ile Lys Glu Leu Ala Asp Glu Ile Gly
1 5 10 15

Val Ser Lys Gln Ala Val Trp Gln Lys Ile Lys Lys Glu Ser Ser Ile
20 25 30

Asp Leu Arg Gln Phe Thr Ser Lys Lys Gly Asn Thr Val Tyr Val Asp
35 40 45

Val Asp Gly Gln Lys Val Ile Lys Ser Ala Phe Phe 50 55 60

<210> SEQ ID NO 167
<211> LENGTH: 154
<212> TYPE: PRT
<213> ORGANISM: Lactococcus lactis

<400> SEQUENCE: 167

Met Val Lys Lys Leu Leu Arg Val Leu Phe Phe Asn Lys Thr Ser Thr
1 5 10 15

Lys Lys Arg Gln Gln Lys Val Phe Val Asp Asp Asn Val Asn Asn Ser
20 25 30

Val Asp Gly Asn Pro Glu Gly Asn Glu Glu Ile Leu Phe Leu Arg Asn
35 40 45

Leu Val Ser Glu Leu Gln Ser Glu Lys Lys Asp Leu His Lys Leu Leu
50 55 60

Asp Gln Gln Gln Arg Leu Ala Leu Gln Asp Lys Lys Leu Leu Glu Glu
65 70 75 80

Tyr Lys Ala Glu Asn Asp Ser Leu Lys Ala Leu Lys Met Pro Thr Glu
85 90 95

Gly Ser Gln Ala Glu Gln Ala Asn Ser Gln Pro Lys Glu Glu Val Lys
100 105 110

Ala Leu Lys Phe Glu Ile Arg Thr Leu Gln Glu Glu Leu Asn Lys Gln
115 120 125

Lys Ile His Ser Gln Glu Glu Arg Glu Lys Leu Lys Ala Glu Leu Thr
130 135 140

Thr Pro Lys Lys Trp Tyr Gln Phe Trp Lys
145 150

<210> SEQ ID NO 168
<211> LENGTH: 36
<212> TYPE: PRT
<213> ORGANISM: Lactococcus lactis

<400> SEQUENCE: 168

Met Asn Lys Leu Lys Lys Leu Gln Glu Leu Glu Ala Lys Ser Asp Lys
1 5 10 15

Gln Ala Glu Leu Met Gly Glu Leu Glu Ala Arg Leu Gly Leu Ile Glu
20 25 30

Asn Lys Gln Ile
35

<210> SEQ ID NO 169
<211> LENGTH: 61
<212> TYPE: PRT
<213> ORGANISM: Lactococcus lactis

<400> SEQUENCE: 169

Met Ala Asn Thr Glu Thr Val Ile Trp Lys Ser Val Lys Gly Phe Glu
1 5 10 15

Gly Gln Tyr Glu Val Ser Asn Thr Gly Leu Val Lys Ser Phe Lys Gly
20 25 30

Lys Thr Glu Arg Ile Asp Arg Phe Asp Ser Asn Val Gln Glu Ile Leu
35 40 45

Lys Arg Leu Ser Tyr Asp Asp Cys Arg Arg Tyr Lys Arg
50 55 60

<210> SEQ ID NO 170

```
<211> LENGTH: 431
<212> TYPE: PRT
<213> ORGANISM: Lactococcus lactis

<400> SEQUENCE: 170

Met Asn Met Lys Asn Lys Thr Asn Glu Asn Phe Val Gln Ile Pro Asn
1               5                   10                  15

Lys Met Phe Met Asn Thr Asn Asn Asp Glu Lys Leu Val Tyr Val Lys
            20                  25                  30

Leu Leu Gln Ser Gln Met Ile Gly Tyr Leu Asp Lys Asp Asn Arg Thr
        35                  40                  45

Thr Met Thr Thr Val Ser Leu Leu Val Thr Leu Leu Gly Trp Ser Lys
    50                  55                  60

Gly Gln Tyr Ser Asn Lys Lys Val Val Lys Ala Leu Asn Gly Leu Lys
65                  70                  75                  80

Asp Lys Lys Tyr Ile Asn Phe Glu Ser Ile Gln Asp Val Phe Thr Val
                85                  90                  95

Gln Ile Asn Lys Trp Asn Asp Lys Glu Glu His Ile Val Pro Val Asp
            100                 105                 110

Trp Lys Gln Ser Gly Val Lys Phe Ser Gly His Thr Gln Ile Arg Leu
        115                 120                 125

Ser Val Ile Asp Asn Leu Leu Glu Gly Lys Asp Phe Thr Leu Tyr Ala
    130                 135                 140

Tyr Thr Glu Tyr Arg Lys Met Lys Thr His Gln Tyr Arg Ile Cys Tyr
145                 150                 155                 160

Glu Glu Trp Gly Phe Val Leu Arg Met Thr Lys Asp Gly Ala Phe Lys
                165                 170                 175

Asn Val Asn Ser Ser Glu Val Ile Ile Lys Val Ser Asn Gly Phe Asp
            180                 185                 190

Ser Asp Thr Lys Arg Arg Glu Thr Asn Ser Tyr Leu Thr Phe Asp Ser
        195                 200                 205

Val Glu Asp Val Lys Glu Val Ser Leu Lys Pro Thr Tyr Lys Ala Gln
    210                 215                 220

Ser Ser Lys Ser Val Val Lys Glu Gln Glu Pro Glu Leu Val Glu Asp
225                 230                 235                 240

Asp Phe Asp Asn Phe Glu Glu Glu Glu Leu Ser Phe Lys Ala Glu Ala
                245                 250                 255

Lys Lys Pro Leu Ile Lys Glu Lys Lys Ile Thr Lys Lys Gln Ala Asn
            260                 265                 270

Glu Leu Lys Asp Glu Ile Asn Lys Phe Phe Gly Asn Thr Met Glu Asp
        275                 280                 285

Asn Ile Phe Lys Lys Met Ala Ser Asp Lys Arg Ile Thr Ser Val Glu
    290                 295                 300

Gln Ala Met Glu Ile Gln Asp Ile Asn Lys Pro Met Ser Leu Glu Met
305                 310                 315                 320

Trp Lys Val Val Gln Asp Ser Asp Asn Phe Phe Val Arg Glu Ser Gly
                325                 330                 335

Asn Lys Lys Leu Lys Asn Lys Ala Trp Gln Lys Lys Phe Trp Ser Asp
            340                 345                 350

Leu Lys Glu Glu Ile Asp Lys Ala Lys Glu Leu Ala Tyr Lys Thr Lys
        355                 360                 365

Phe Thr Ser Lys Tyr Leu Tyr Asn Thr Ile Thr Glu Tyr Tyr Val Asp
    370                 375                 380

Gly Gly Glu Cys Val Ile Ser Ser Asp Lys Leu Tyr Asp Tyr Val His
```

```
385                 390                 395                 400

Asn Arg Arg Val Tyr Ser Asn Asp Glu Tyr Thr Tyr Phe Thr Pro Thr
                405                 410                 415

Asn Met Val Pro His Leu Lys Phe Ile Lys Val Thr Glu Lys Tyr
            420                 425                 430


<210> SEQ ID NO 171
<211> LENGTH: 60
<212> TYPE: PRT
<213> ORGANISM: Lactococcus lactis

<400> SEQUENCE: 171

Met Tyr Phe Cys Tyr Ser Asn Lys Gln Lys Asp Phe Leu Asn Gln Lys
1               5                   10                  15

Gly Ile Asp Ser Leu Phe Ser Ala Arg His Ala Lys Thr Asn Lys Leu
            20                  25                  30

Phe Tyr Val Phe Tyr Gln Ser Glu Glu Leu Gly Gln Ala Leu Thr Glu
        35                  40                  45

Phe Thr Glu Lys Lys Ala Glu Phe Phe Lys Asn Asn
    50                  55                  60


<210> SEQ ID NO 172
<211> LENGTH: 784
<212> TYPE: PRT
<213> ORGANISM: Lactococcus lactis

<400> SEQUENCE: 172

Met Lys Asp Ile Gly Asn Ser Ser Asn Phe Thr Glu Asp Glu Glu Leu
1               5                   10                  15

Phe Leu Leu Arg Asn Lys Gln Gly Lys Ile Val Gly Ile Lys Asp Leu
            20                  25                  30

Lys Gln Ala Asn Phe Gln Glu Thr Met Lys Asp Trp Lys Lys His Leu
        35                  40                  45

Pro Lys Pro Ser Leu Leu Ser Ile Ile Ile Trp Val Ala Val Ala Leu
    50                  55                  60

Leu Gly Gly Leu Ala Trp Ser Leu Ile Ala Leu Ala Gln Gly Glu Thr
65                  70                  75                  80

Ile Asn Ala Ile Trp Phe Val Ile Ala Ala Val Cys Ser Tyr Leu Ile
                85                  90                  95

Gly Tyr Arg Phe Tyr Ala Leu Tyr Ile Gln Arg Lys Ile Met Arg Pro
            100                 105                 110

Asn Asp Leu Arg Ala Thr Pro Ser Glu Ser His Asn Asp Gly Lys Glu
        115                 120                 125

Phe Asp Pro Thr Asn Arg Val Val Leu Phe Gly His His Phe Ala Ser
    130                 135                 140

Ile Ala Gly Ala Gly Pro Leu Val Gly Pro Val Leu Ala Ala Gln Met
145                 150                 155                 160

Gly Tyr Leu Pro Gly Thr Ile Trp Ile Ile Phe Gly Val Ile Phe Ala
                165                 170                 175

Gly Gly Val Gln Asp Met Leu Val Leu Trp Tyr Ser His Arg Arg Arg
            180                 185                 190

Ala Lys Ser Ile Gly Ala Met Ala His Asp Glu Val Gly Arg Phe Ala
        195                 200                 205

Gly Gly Leu Thr Ser Phe Ile Val Phe Ile Met Thr Met Ile Val Leu
    210                 215                 220

Ala Val Leu Ala Leu Ile Cys Val Thr Ala Met Ala Asn Ser Ala Trp
```

-continued

```
225                 230                 235                 240

Ala Val Phe Ser Ile Gly Met Thr Ile Pro Ile Ala Leu Leu Met Gly
                245                 250                 255

Ile Tyr Leu Lys Tyr Ile Arg Pro Gly His Val Asn Glu Ile Ser Ala
            260                 265                 270

Ile Gly Phe Ile Leu Leu Leu Val Ala Ile Phe Gly Gly Arg Trp Val
        275                 280                 285

Ser Glu Ser Ser Phe Ala His Ile Phe Met Leu Ser Pro Thr Ala Leu
    290                 295                 300

Val Trp Trp Val Met Gly Tyr Thr Phe Ile Ala Ala Ile Ile Pro Ala
305                 310                 315                 320

Trp Ile Leu Leu Thr Pro Arg Asp Tyr Leu Ser Met Phe Met Lys Ile
                325                 330                 335

Gly Thr Ile Ala Val Leu Ala Ile Ala Val Val Gly Val Arg Pro Asp
            340                 345                 350

Val Thr Ile Pro Ala Leu Thr Asn Phe Ala His Asn Thr Asp Gly Pro
        355                 360                 365

Ala Phe Ala Gly Ser Leu Phe Pro Phe Leu Phe Val Thr Ile Ala Cys
    370                 375                 380

Gly Ala Leu Ser Gly Phe His Val Met Met Ser Ser Gly Thr Thr Pro
385                 390                 395                 400

His Leu Ile Ala Lys Glu Ser Gln Thr Arg Met Ile Gly Tyr Gly Gly
                405                 410                 415

Met Leu Phe Glu Ser Phe Val Ala Ile Met Ala Leu Val Ala Ala Ile
            420                 425                 430

Ser Leu Asn Pro Gly Ile Tyr Tyr Ser Met Asn Thr Pro Gln Ala Ser
        435                 440                 445

Ile Gln Lys Leu Ala Ala Ser Ser Tyr Gln Ala Asp Lys Ser Ala Glu
    450                 455                 460

Tyr Asn Ala Ala Lys Ala Ile Pro Asn Val Ala Met Met Pro Asp Gly
465                 470                 475                 480

Ser Lys Leu Ser Ile Asp Trp Glu Gly Thr Thr Gly Glu Lys Ala Leu
                485                 490                 495

Glu Gln Val Ala Lys Asp Val Gly Glu Gln Ser Ile Val Ser Arg Thr
            500                 505                 510

Gly Gly Ala Pro Thr Leu Ala Val Ser Met Ser Asn Ile Leu His Lys
        515                 520                 525

Val Pro Leu Ile Gly Gly Thr Asn Met Met Gly Phe Trp Tyr His Phe
    530                 535                 540

Ala Ile Met Phe Glu Ala Leu Phe Ile Leu Ser Ala Val Ser Ala Ala
545                 550                 555                 560

Thr Lys Ser Thr Arg Tyr Leu Leu Asn Asp Ala Leu Arg Gly Phe Lys
                565                 570                 575

Lys Leu Gly Arg Leu Gly Asp Asp Asp Trp Leu Pro Ser Lys Ile Ile
            580                 585                 590

Thr Thr Ala Val Ile Val Gly Val Trp Gly Ala Leu Leu Leu Met Gly
        595                 600                 605

Val Ser Asp Pro Asn Gly Gly Ile Lys Ile Met Tyr Pro Leu Phe Gly
    610                 615                 620

Ile Ser Asn Gln Leu Ile Ala Ala Val Ala Leu Ala Ile Val Cys Val
625                 630                 635                 640

Met Val Ile Arg Lys Gly Tyr Leu Lys Trp Val Trp Ile Pro Ala Leu
                645                 650                 655
```

```
Pro Leu Val Trp Asp Val Cys Val Thr Phe Ala Ala Ser Trp Gln Lys
            660                 665                 670

Ile Phe Ser Asn Asp Val Asn Ile Gly Tyr Phe Ala Ser Tyr Ser Ala
        675                 680                 685

Ala Lys Ala Gln Val Ala Ser Gly Lys Ile Ser Gly Leu Ala Leu Thr
    690                 695                 700

Asn Thr Gln Ala Thr Met Arg Asn Thr Met Ile Gln Gly Ser Leu Ser
705                 710                 715                 720

Val Ile Phe Leu Leu Cys Val Ala Ile Leu Leu Val Ile Cys Ala Leu
                725                 730                 735

Lys Val Ala Lys Ile Leu Arg Thr Asn Glu Val Gly Asp Lys Phe Ser
            740                 745                 750

Ser Glu Glu Val Phe Glu Glu Ser Asn Leu Phe Glu Thr Ser Ser Phe
        755                 760                 765

Trp Pro Ser Lys Leu Glu His Lys Val Leu Lys Ser Lys Val Asn Glu
    770                 775                 780


<210> SEQ ID NO 173
<211> LENGTH: 226
<212> TYPE: PRT
<213> ORGANISM: Lactococcus lactis

<400> SEQUENCE: 173

Met Asn Tyr Phe Lys Gly Lys Gln Phe Gln Lys Asp Val Ile Ile Val
1               5                   10                  15

Ala Val Gly Tyr Tyr Leu Arg Tyr Asn Leu Ser Tyr Arg Glu Ile Gln
            20                  25                  30

Glu Leu Leu Tyr Asp Arg Gly Ile Asn Val Cys His Thr Thr Ile Tyr
        35                  40                  45

Arg Trp Val Gln Glu Tyr Ser Lys Val Leu Tyr His Leu Trp Lys Lys
    50                  55                  60

Lys Asn Arg Gln Ser Phe Tyr Ser Trp Lys Met Asp Glu Thr Tyr Ile
65                  70                  75                  80

Lys Ile Lys Gly Arg Trp His Tyr Leu Tyr Arg Ala Ile Asp Val Asp
                85                  90                  95

Gly Leu Thr Leu Asp Ile Trp Leu Arg Lys Lys Arg Asp Thr Gln Ala
            100                 105                 110

Ala Tyr Ala Phe Leu Lys Arg Leu His Lys Gln Phe Gly Gln Pro Arg
        115                 120                 125

Val Ile Val Lys Asp Lys Ala Pro Ser Ile Gly Ser Ala Phe Arg Lys
    130                 135                 140

Leu Gln Ser Asn Gly Leu Tyr Thr Lys Thr Glu His Arg Thr Val Lys
145                 150                 155                 160

Tyr Leu Asn Asn Leu Ile Glu Gln Asp His Arg Pro Ile Lys Arg Arg
                165                 170                 175

Asn Lys Phe Tyr Gln Ser Leu Arg Thr Ala Ser Thr Thr Ile Lys Gly
            180                 185                 190

Met Glu Thr Ile Arg Gly Ile Tyr Lys Lys Asn Arg Arg Asn Gly Thr
        195                 200                 205

Leu Phe Gly Phe Ser Val Ser Thr Glu Ile Lys Val Leu Met Gly Ile
    210                 215                 220

Leu Ala
225
```

<210> SEQ ID NO 174
<211> LENGTH: 154
<212> TYPE: PRT
<213> ORGANISM: Lactococcus lactis

<400> SEQUENCE: 174

Met Lys Thr Leu Ile His Glu Asp Leu Arg Gly Lys Ile Ile Tyr Leu
1 5 10 15

Gln Glu Glu Ile Pro Phe Gly Gln Gly Arg Leu Ile Glu Gln Leu Arg
20 25 30

Leu Pro Phe Leu Ser Gln Lys Leu Leu Thr Ile Pro Leu Ile Val Asp
35 40 45

Leu Lys Leu Ala Glu Phe Ile Arg Arg Gln Leu Tyr Tyr Cys Ser Pro
50 55 60

Lys Trp Leu Lys Leu Gln Glu Lys Tyr Tyr Gln Arg Gly Glu Asn Leu
65 70 75 80

Leu Asn Leu Thr Phe Glu Arg Ser Phe Ile Ala Pro Leu Gly Leu Asn
85 90 95

Leu Leu Glu Val Phe Asp Asp Glu Ile Pro Leu His Lys Phe Thr Gln
100 105 110

Ile Lys Gln Asn Ile Asn Leu Tyr Tyr Glu Asn Phe Leu Ile Asn Phe
115 120 125

Gln Gln Asn Ser Phe Lys Ala Val Tyr Pro Pro Arg Phe Tyr Ala Ile
130 135 140

Met Lys Lys Gln Lys Lys Asp Met Asn Glu
145 150

<210> SEQ ID NO 175
<211> LENGTH: 601
<212> TYPE: PRT
<213> ORGANISM: Lactococcus lactis

<400> SEQUENCE: 175

Met Ala Lys Asn Arg Asn Glu Ile Pro Glu Lys Leu Thr Trp Asp Leu
1 5 10 15

Thr Thr Ile Tyr Lys Thr Asp Lys Glu Trp Glu Ala Glu Leu Thr Arg
20 25 30

Ile Lys Ser Glu Leu Ser Leu Val Glu Glu Thr Asp Pro Gly His Leu
35 40 45

Leu Asp Ser Ala Glu Ser Leu Leu Thr Ile Thr Glu Lys Met Leu Ser
50 55 60

Ile Ser Gln Gln Val Glu Lys Leu Tyr Val Tyr Ala Ser Met Lys Asn
65 70 75 80

Asp Gln Asp Thr Arg Glu Ala Lys Tyr Gln Glu Tyr Gln Ser Lys Ala
85 90 95

Thr Ala Leu Tyr Val Lys Phe Gly Glu Val Tyr Ala Phe Tyr Glu Pro
100 105 110

Glu Phe Leu Lys Ile Ser Lys Glu Val Tyr Asn Lys Trp Leu Gly Glu
115 120 125

Leu Gln Lys Leu Lys Asn Tyr Asp His Met Phe Glu Arg Leu Phe Ala
130 135 140

Lys Lys Ala His Ile Leu Ser Gln Lys Glu Glu Lys Leu Leu Ala Ala
145 150 155 160

Ala Gly Glu Ile Phe Glu Ser Pro Ser Glu Thr Phe Glu Ile Phe Asp
165 170 175

Asn Ala Asp Ile Lys Leu Pro Met Val Lys Asn Glu Ser Asp Glu Met

-continued

```
            180                 185                 190

Ile Gln Leu Thr His Gly Asn Tyr Ser Ser Leu Met Glu Ser Lys Asn
        195                 200                 205

Arg Gly Val Arg Lys Ala Ala Tyr Lys Ala Leu Tyr Ser Asn Tyr Glu
    210                 215                 220

Gln Tyr Gln His Thr Tyr Ala Lys Thr Leu Gln Thr Asn Val Lys Val
225                 230                 235                 240

His Asn Leu Asn Ala Gln Ile Arg Ser Tyr Asp Ser Ala Arg Gln Ala
                245                 250                 255

Ala Leu Ala Asn Asn Phe Val Pro Glu Lys Val Tyr Asp Val Leu Met
            260                 265                 270

Glu Ala Ile His Gln His Leu Pro Leu Leu His Arg Tyr Ile Glu Leu
        275                 280                 285

Arg Lys Lys Ile Leu Gly Ile Thr Asp Leu Lys Met Tyr Asp Ile Tyr
    290                 295                 300

Thr Pro Leu Ser Asn Leu Asp Tyr Lys Phe Asn Tyr Glu Asp Gly Val
305                 310                 315                 320

Lys Lys Ala Glu Glu Val Leu Ala Ile Phe Gly Lys Glu Tyr Lys Gly
                325                 330                 335

Lys Val Lys Ala Ala Phe Glu Gln Arg Trp Ile Asp Val Glu Glu Asn
            340                 345                 350

Ile Gly Lys Arg Ser Gly Ala Tyr Ser Gly Gly Ser Tyr Asp Thr Asn
        355                 360                 365

Ala Phe Met Leu Leu Asn Trp Gln Glu Thr Leu Asp Asp Leu Phe Thr
    370                 375                 380

Leu Val His Glu Thr Gly His Ser Met His Ser Ala Phe Thr Arg Glu
385                 390                 395                 400

Asn Gln Pro Tyr Val Tyr Gly Asn Tyr Pro Ile Phe Leu Ala Glu Ile
                405                 410                 415

Ala Ser Thr Thr Asn Glu Asn Ile Leu Thr Glu Thr Leu Leu Lys Glu
            420                 425                 430

Ser Lys Asp Asp Lys Glu Arg Phe Ala Leu Leu Asn His Trp Leu Asp
        435                 440                 445

Ser Phe Arg Gly Thr Val Phe Arg Gln Ser Gln Phe Ala Glu Phe Glu
    450                 455                 460

Gln Lys Ile His Glu Ala Asp Ala Ala Gly Glu Val Leu Thr Ser Glu
465                 470                 475                 480

Tyr Leu Asn Ser Leu Tyr Gly Glu Ile Asn Glu Lys Tyr Tyr Asn Leu
                485                 490                 495

Ala Val Lys Glu Asn Pro Glu Ile Gln Tyr Glu Trp Ala Arg Ile Pro
            500                 505                 510

His Phe Tyr Tyr Asn Phe Tyr Val Phe Gln Tyr Ala Thr Gly Phe Ala
        515                 520                 525

Ala Ala Thr Phe Leu Ala Glu Lys Val Val His Gly Ser Thr Glu Asp
    530                 535                 540

Arg Gln Lys Tyr Leu Glu Tyr Leu Lys Ala Gly Ser Ser Ala Tyr Pro
545                 550                 555                 560

Leu Glu Val Ile Ala Lys Ala Gly Val Asp Met Glu Ser Thr Asp Tyr
                565                 570                 575

Leu Asp Ala Ala Phe Glu Leu Phe Glu Asn Arg Leu Ser Glu Leu Glu
            580                 585                 590

Lys Leu Val Glu Lys Gly Val His Leu
        595                 600
```

<210> SEQ ID NO 176
<211> LENGTH: 53
<212> TYPE: PRT
<213> ORGANISM: Lactococcus lactis

<400> SEQUENCE: 176

Met Val Glu Thr Tyr Lys Arg Thr Ser Asn Pro Met Met Asn Arg Pro
1 5 10 15

Val Val Lys Ala Glu Leu Val Glu Trp Met Arg Ser Ser Gln Thr Gln
20 25 30

Ile Thr Gly Glu Leu Ala Ser Leu Ala Ser Val Pro Val Leu Thr Arg
35 40 45

Leu Phe Pro Leu Val
50

<210> SEQ ID NO 177
<211> LENGTH: 86
<212> TYPE: PRT
<213> ORGANISM: Lactococcus lactis

<400> SEQUENCE: 177

Met Gln Lys Arg Tyr Ser Lys Glu Phe Lys Glu Thr Leu Ile Ala Phe
1 5 10 15

Tyr His Ser Gly Gln Ser Val Thr Gln Leu Ser Lys Glu Tyr Asp Val
20 25 30

Ala Pro Ala Thr Ile Tyr Lys Trp Ile Asp Leu Tyr Ser Lys Ser Asn
35 40 45

Glu Ser Ser Val Ser Lys Ala Asp Phe Leu Glu Leu Lys Arg Gln Leu
50 55 60

Ala Lys Val Lys Glu Glu Arg Asp Ile Leu Lys Lys Val Leu Thr Ile
65 70 75 80

Phe Ala Glu Lys Lys Lys
85

<210> SEQ ID NO 178
<211> LENGTH: 193
<212> TYPE: PRT
<213> ORGANISM: Lactococcus lactis

<400> SEQUENCE: 178

Met Lys Ile Gly Tyr Ala Arg Val Ser Thr Phe Glu Gln Lys Leu Glu
1 5 10 15

Ser Gln Ile Glu Val Leu Lys Glu Ala Gly Ala Glu Glu Val Phe Gln
20 25 30

Glu Lys Phe Thr Gly Thr Thr Val Glu Arg Pro Gln Phe Asn Leu Val
35 40 45

Phe Lys Lys Leu Lys Asp Gly Asp Thr Leu Ile Val Thr Lys Leu Asp
50 55 60

Arg Leu Ala Arg Asn Thr Arg Glu Val Leu Glu Ile Val Gln Ser Leu
65 70 75 80

Phe Asn Arg Gly Ile Lys Val His Ile Leu Asn Ile Gly Leu Ile Asp
85 90 95

Asn Thr Pro Thr Gly Gln Leu Ile Phe Thr Ile Phe Ser Ala Phe Ala
100 105 110

Gln Phe Glu Arg Asp Leu Ile Val Thr Arg Thr Gln Glu Gly Lys Asn
115 120 125

```
Phe Ala Lys Leu His Asp Pro Ser Phe Arg Glu Gly Arg Pro Gln Lys
    130                 135                 140

Phe Thr Glu Glu Gln Ile Gln Phe Ala Tyr Glu Leu Lys Gln Gln Gly
145                 150                 155                 160

Met Thr Tyr Lys Met Ile Glu Arg Lys Thr Gly Ile Ser Ile Ala Thr
                165                 170                 175

Gln Lys Arg Arg Phe Ile Lys Ala Lys Asn Gln Ala Ile Asp Lys Asp
            180                 185                 190

Tyr
```

<210> SEQ ID NO 179
<211> LENGTH: 316
<212> TYPE: PRT
<213> ORGANISM: Lactococcus lactis

<400> SEQUENCE: 179

```
Met Lys Glu Tyr Phe Gln Gly Asp Glu Phe Lys Asp Ile Ser Lys Asn
1               5                   10                  15

Gly Lys Asp Arg Lys Trp Lys Glu Arg Lys Ile Asn Asn Leu Asn Leu
            20                  25                  30

Ala Lys Ile Phe Asp Ser Leu Asp Tyr Pro Asp Ser Phe Ile Phe Asn
        35                  40                  45

Ile Lys Ser Cys Ala Glu Tyr Leu Asn Phe Lys Arg Ser Ser Asp Gly
    50                  55                  60

Ser Leu Arg Leu Phe Gln Met Tyr Thr Cys Lys Asn Lys Gln Cys Ala
65                  70                  75                  80

Ile Cys Ser Trp Arg Arg Ser Met Lys Tyr Gln Val Gln Ile Ser Lys
                85                  90                  95

Ile Val Glu Glu Ala Met Ile Arg Lys Pro Lys Gly Arg Phe Leu Phe
            100                 105                 110

Leu Thr Leu Thr Val Glu Asn Val Ser Gly Glu Gly Leu Asn Asn Glu
        115                 120                 125

Leu Ser Leu Leu Ser Glu Ala Phe Asn Arg Leu Met Lys Tyr Lys Lys
    130                 135                 140

Val Ser Lys Asn Ile Leu Gly Phe Leu Arg Ala Thr Glu Val Thr Ile
145                 150                 155                 160

Asn Glu Ser Met Asp Thr Tyr His Pro His Ile His Val Leu Leu Phe
                165                 170                 175

Ile Ser Pro Thr Tyr Phe Lys Asn Lys Asn Asn Tyr Ile Ser Gln Asp
            180                 185                 190

Glu Trp Thr Glu Leu Trp Lys Lys Ser Ala Lys Leu Asp Tyr Arg Pro
        195                 200                 205

Ile Val Asp Val Arg Ser Ile Lys Pro Lys Asn Glu Lys Thr Ser Asp
    210                 215                 220

Ile Arg Ser Ala Ile Leu Glu Thr Ala Lys Tyr Pro Val Lys Pro Met
225                 230                 235                 240

Glu Leu Asn Tyr Asp Ser Ala Lys Val Val Asp Asp Leu Gln Lys Gly
                245                 250                 255

Leu Tyr Arg Lys Arg Gln Ile Ala Phe Gly Gly Leu Phe Lys Gln Ile
            260                 265                 270

Lys Lys Glu Leu Glu Leu Asp Asp Ile Glu Asn Gly Asp Leu Ile Asn
        275                 280                 285

Ile Gly Asp Glu Glu Asn Pro Ile Ser Asp Gly Glu Ile Ile Ser Val
    290                 295                 300
```

-continued

Leu Trp Asn His Glu Arg Gln Asn Tyr Tyr Val Arg
305 310 315

<210> SEQ ID NO 180
<211> LENGTH: 86
<212> TYPE: PRT
<213> ORGANISM: Lactococcus lactis

<400> SEQUENCE: 180

Met Thr Cys Ser Asn Leu Thr Ile His Leu His Ala Lys Asn Arg Ser
1 5 10 15

Lys Leu Phe Gly Ser Lys Lys Tyr Ala Leu Gln Glu Leu Glu Ala Glu
20 25 30

Ser Thr Ala Phe Val Val Ala Asn His Leu Asn Ile Asp Thr Lys Asp
35 40 45

Tyr Ser Ile Gly Tyr Leu Asn Ser Trp Gly Phe Asp Lys Ile Ser Asp
50 55 60

Glu Gln Leu Glu Asn Val Ile Lys Asn Asp Lys Leu Ser Asn Asn Lys
65 70 75 80

Ile Lys Gly Glu Asn Glu
85

<210> SEQ ID NO 181
<211> LENGTH: 96
<212> TYPE: PRT
<213> ORGANISM: Lactococcus lactis

<400> SEQUENCE: 181

Met Ile Asn Tyr Gln Gly Glu Asp Phe Thr Glu Thr Glu Phe Tyr Gly
1 5 10 15

Arg Glu Ile Leu Glu Ala Ile Gln Leu Thr Asn Lys Phe Pro Thr Pro
20 25 30

Lys Lys Val Leu Ile Asp Met Leu Glu Glu Met Ile His Glu Gln Leu
35 40 45

Asp Phe Ile Asp Lys Glu Glu Leu Asn Asn Tyr Ile Asn Ala Lys Lys
50 55 60

Tyr Val Gln Thr Leu Thr Glu Asp Glu Val Lys Asn Leu Cys Phe Glu
65 70 75 80

Val Lys Asp Leu Tyr Glu Asp Val Leu Lys Glu Phe Glu Ile Lys Leu
85 90 95

<210> SEQ ID NO 182
<211> LENGTH: 300
<212> TYPE: PRT
<213> ORGANISM: Lactococcus lactis

<400> SEQUENCE: 182

Met Glu Arg Lys Lys Lys Lys Lys Glu Asn Ile Trp Ala Ile Ile Val
1 5 10 15

Pro Ile Leu Ile Ile Ile Ser Leu Ile Gly Ala Trp Ala Tyr Ala Leu
20 25 30

Arg Asp Ser Leu Ile Pro Asn Asp Tyr Thr Lys Thr Asn Ser Ser Asp
35 40 45

Gln Pro Thr Lys Thr Ser Val Ser Asn Gly Tyr Val Glu Gln Lys Gly
50 55 60

Val Glu Ala Ala Val Gly Ser Ile Ala Leu Val Asp Asp Ala Gly Val
65 70 75 80

Pro Glu Trp Val Lys Val Pro Ser Lys Val Asn Leu Asp Lys Phe Thr

```
                85                  90                  95

Asp Leu Ser Thr Asn Asn Ile Thr Ile Tyr Arg Ile Asn Asn Pro Glu
            100                 105                 110

Val Leu Lys Thr Val Thr Asn Arg Thr Asp Gln Arg Met Lys Met Ser
        115                 120                 125

Glu Val Ile Ala Lys Tyr Pro Asn Ala Leu Ile Met Asn Ala Ser Ala
    130                 135                 140

Phe Asp Met Gln Thr Gly Gln Val Ala Gly Phe Gln Ile Asn Asn Gly
145                 150                 155                 160

Lys Leu Ile Gln Asp Trp Ser Pro Gly Thr Thr Thr Gln Tyr Ala Phe
                165                 170                 175

Val Ile Asn Lys Asp Gly Ser Cys Lys Ile Tyr Asp Ser Ser Thr Pro
            180                 185                 190

Ala Ser Thr Ile Ile Lys Asn Gly Gly Gln Gln Ala Tyr Asp Phe Gly
        195                 200                 205

Thr Ala Ile Ile Arg Asp Gly Lys Ile Gln Pro Ser Asp Gly Ser Val
    210                 215                 220

Asp Trp Lys Ile His Ile Phe Ile Ala Asn Asp Lys Asp Asn Asn Leu
225                 230                 235                 240

Tyr Ala Ile Leu Ser Asp Thr Asn Ala Gly Tyr Asp Asn Ile Met Lys
                245                 250                 255

Ser Val Ser Asn Leu Lys Leu Gln Asn Met Leu Leu Leu Asp Ser Gly
            260                 265                 270

Gly Ser Ser Gln Leu Ser Val Asn Gly Lys Thr Ile Val Ala Ser Gln
        275                 280                 285

Asp Asp Arg Ala Val Pro Asp Tyr Ile Val Met Lys
    290                 295                 300


<210> SEQ ID NO 183
<211> LENGTH: 189
<212> TYPE: PRT
<213> ORGANISM: Lactococcus lactis

<400> SEQUENCE: 183

Met Val Asp Ala Tyr Leu Asp Asn Asn Leu Gly Asp Asp Leu Met Ile
1               5                   10                  15

Arg Tyr Phe Ala Ser Tyr Phe Tyr Gln His Lys Ile Tyr Leu Val Glu
            20                  25                  30

Ser Arg Glu His Ile Arg Lys Thr Phe Tyr Asp Ile Pro Asn Ile Tyr
        35                  40                  45

Phe Tyr Ser Glu Glu Asp Tyr Lys Met Asn Glu Tyr Asp Phe Gln Leu
    50                  55                  60

His Val Thr Ile Gly Gly Ser Met Phe Ile Leu Asp Asp Phe Lys Lys
65                  70                  75                  80

Leu Ile Arg Phe Arg His Arg Ile Lys Asn Ser Arg Lys Ile Lys Lys
                85                  90                  95

Arg Asn Ile Pro Ser Ala Ile Ile Gly Cys Asn Leu Gly Pro Phe Asp
            100                 105                 110

Lys Arg Asn Phe Gly Leu Lys Leu Ala Lys Phe Glu Leu Lys Tyr Lys
        115                 120                 125

Asn Leu Val Thr Val Arg Asp Lys Gln Ser Lys Glu Leu Leu Leu Arg
    130                 135                 140

Gly Phe Lys Arg Lys Lys Ile Asn Ile Lys Leu Phe Pro Asp Ile Ile
145                 150                 155                 160
```

```
Phe Ser Lys Val Leu Tyr Lys Ser Ile Pro Lys Tyr Gly Leu Gly Met
                165                 170                 175

Thr Leu Ser Gln Val Phe Arg Val Thr Asn Val Glu Phe
            180                 185


<210> SEQ ID NO 184
<211> LENGTH: 337
<212> TYPE: PRT
<213> ORGANISM: Lactococcus lactis

<400> SEQUENCE: 184

Met Lys Asn Lys Phe Ser Ile Ile Val Pro Val Tyr Asn Gly Glu Ser
1               5                   10                  15

His Ile Lys Lys Cys Ile Asp Thr Leu Leu Lys Gln Thr Tyr Asn Asp
            20                  25                  30

Phe Glu Ile Ile Ile Ile Asn Asp Gly Ser Thr Asp Asp Thr Lys Ser
        35                  40                  45

Val Leu Thr Lys Phe Tyr Ala Lys Asn Leu Lys Val Lys Ile Val Asn
    50                  55                  60

Thr Ser Asn Lys Gly Val Ser Phe Ala Arg Asn Leu Gly Ile Asn Gln
65                  70                  75                  80

Ser Ser Gly Gln Tyr Leu Leu Phe Val Asp Ser Asp Asp Glu Leu Ser
                85                  90                  95

Ile Asn Ala Leu Lys Tyr Leu Ser Ile Met Leu Asn Lys Lys Asp Arg
            100                 105                 110

Asp Leu Ile Leu Phe Gly Phe Ser Leu Thr Gly Asp Asn Asn Arg Lys
        115                 120                 125

Asn Asp Thr Ser Ile Leu Lys Ser Ile Ala Asn Gln Asn Thr Asp Cys
    130                 135                 140

Lys Met Asn Ile Leu Lys Ser Ile Leu Ser Thr Lys Asn Asn Ile Leu
145                 150                 155                 160

Gly Tyr Val Trp Arg Ala Val Tyr Ser Leu Asp Phe Ile Lys Lys Asn
                165                 170                 175

Asn Ile Phe Phe Glu Thr His Leu Lys Ile Ser Glu Asp Tyr Leu Phe
            180                 185                 190

Leu Leu Gln Ser Val Glu His Ser Asn Asn Leu Phe Val Ile Thr Glu
        195                 200                 205

Glu Phe Tyr Lys Tyr Asn Leu Gly Glu Thr Ser Met Ser Asn Lys Phe
    210                 215                 220

Val Pro Thr Leu Leu Asn Asp Met Val Trp Val Asn Asn Trp Ile Glu
225                 230                 235                 240

Ser Asn Ile Leu Thr Val Tyr Pro Gln Phe Phe Val Gly Phe Asn Cys
                245                 250                 255

Leu Val Ala Asn Thr Tyr Ile Arg Tyr Val Gln Asn Ala Ile Arg Asn
            260                 265                 270

Lys Glu Glu Asn Phe Met Leu Lys Tyr Arg Glu Ile Lys Ile Asn Lys
        275                 280                 285

Arg Lys Tyr Asn Phe Gln Arg Ser Ile Asn Gln Val Ile Phe His Leu
    290                 295                 300

Asp Lys Phe Asp Phe Lys Ser Lys Ile Gly Val Ile Leu Phe Arg Ile
305                 310                 315                 320

His Leu Asp Ile Val Tyr Glu Leu Leu Phe Asn Ile Lys Glu Arg Lys
                325                 330                 335

Asn
```

<210> SEQ ID NO 185
<211> LENGTH: 384
<212> TYPE: PRT
<213> ORGANISM: Lactococcus lactis

<400> SEQUENCE: 185

```
Met Thr Asn Leu Asn Arg Lys Lys Phe Phe Ile Asn Phe Gln Ser Leu
1               5                   10                  15

Val Phe Phe Ile Leu Ile Ile Ile Tyr Gly Leu Thr Thr Lys Asn Val
            20                  25                  30

Met Gly Gly Ser Gly Ile Phe Ser Ile Asp Ser Ile Leu Lys Tyr Gly
        35                  40                  45

Ile Leu Phe Ile Cys Ile Ser Val Glu Gly Tyr Ile Phe Leu Lys Asn
    50                  55                  60

Gly Asn Glu Arg Arg Glu Thr Ser Glu Asn Tyr Asn Asn Phe Lys Tyr
65                  70                  75                  80

Tyr Phe Ile Ile Ile Thr Phe Leu Ser Leu Phe Ala Ser Phe Lys Gln
                85                  90                  95

Val His Phe Ser Phe Arg Thr Val Gln Ser Phe Ile Phe Ile Phe Ile
            100                 105                 110

Pro Met Leu Tyr Ser Tyr Leu Ile Leu Asn Asn Trp Thr Phe Arg Gln
        115                 120                 125

Ile Asn Phe Ser Met Lys Ile Ala Leu Phe Leu Ser Val Ile Glu Tyr
    130                 135                 140

Leu Phe Ser Ile Arg Met Gly Phe Ser Gln Ile Ile Ser Ser Leu Ala
145                 150                 155                 160

Ser Ile Asn Tyr Asn Asn Thr Asn Ala Ser Ala Leu Glu Ser Ser Thr
                165                 170                 175

Phe Ala Leu Leu Ser Leu Gly Phe Ala Ala Tyr Phe Gly Tyr Tyr Lys
            180                 185                 190

Lys Asn Phe Leu Cys Lys Ile Val Ser Leu Leu Phe Val Ile Met Thr
        195                 200                 205

Phe Lys Arg Val Ile Thr Leu Ser Gly Cys Ile Leu Val Ile Leu Gly
    210                 215                 220

Ile Leu Lys Ile Lys Asn Leu Arg Val Asn Arg Phe Phe Leu Ile Val
225                 230                 235                 240

Ser Thr Ile Thr Leu Val Ser Phe Ser Leu Ile Tyr Tyr Tyr Ser Ile
                245                 250                 255

Gln Pro Gln Asn Ile Leu Glu Ile Ser Glu Lys Ile Gly Phe Ser Ile
            260                 265                 270

Arg Asp Phe Ser Thr Asn Arg Thr Asp Arg Leu Ala Trp Leu Ser Met
        275                 280                 285

Thr Asp Phe Lys Ser Tyr Gly Leu Gly Ser Thr Thr Asp Phe Met Tyr
    290                 295                 300

Lys Leu Trp Gly Val Asp Leu Glu Met Asp Ile Val Gln Leu Ile Leu
305                 310                 315                 320

Glu Val Gly Ala Phe Gly Val Ile Val Phe Ile Tyr Phe Tyr Leu Arg
                325                 330                 335

Phe Ser Lys Ser Asn Leu Tyr Ala Phe Ser Phe Met Ala Leu Leu Leu
            340                 345                 350

Leu Asn Ser Ile Leu Ser Ser Gly Met Met Ser Thr Phe Ser Trp Ile
        355                 360                 365

Ile Ile Leu Ile Ala Met Ser Thr Ile Met Glu Tyr Lys Glu Gly Met
    370                 375                 380
```

<210> SEQ ID NO 186
<211> LENGTH: 161
<212> TYPE: PRT
<213> ORGANISM: Lactococcus lactis

<400> SEQUENCE: 186

```
Met Ile Phe Val Thr Val Gly Thr His Glu Gln Pro Phe Asn Arg Leu
1               5                   10                  15

Ile Gln Lys Ile Asp Glu Leu Val Arg Asp Gly Gln Ile Lys Asp Asp
            20                  25                  30

Val Phe Met Gln Ile Gly Tyr Ser Thr Tyr Glu Pro Lys Tyr Thr Lys
        35                  40                  45

Trp Ala Ser Val Ile Gly Tyr Asn Asp Met Thr Ala Tyr Phe Asn Lys
    50                  55                  60

Ala Asp Ile Val Ile Thr His Gly Gly Pro Ser Thr Tyr Met Gln Val
65                  70                  75                  80

Leu Gln His Gly Lys Ile Pro Ile Val Val Pro Arg Gln Glu Lys Phe
                85                  90                  95

Gly Glu His Ile Asn Asp His Gln Leu Arg Val Ser Lys Gln Val Ile
            100                 105                 110

Lys Lys Gly Tyr Pro Leu Ile Leu Cys Glu Asp Val Ser Ala Leu Lys
        115                 120                 125

Ile Cys Ile Glu Ser Ser Arg Ile Arg Thr Asp Glu Phe Ile Lys Ser
    130                 135                 140

Asn Asn Lys Asn Phe Ile Ser Asn Phe Lys Lys Ile Ile Ala Phe Glu
145                 150                 155                 160

Glu
```

<210> SEQ ID NO 187
<211> LENGTH: 149
<212> TYPE: PRT
<213> ORGANISM: Lactococcus lactis

<400> SEQUENCE: 187

```
Met Lys Ile Ala Leu Val Gly Ser Ser Gly Gly His Leu Thr His Leu
1               5                   10                  15

Tyr Leu Leu Lys Lys Phe Trp Glu Asn Glu Asp Arg Phe Trp Val Thr
            20                  25                  30

Phe Asp Lys Thr Asp Ala Lys Ser Ile Leu Lys Glu Glu Arg Phe Tyr
        35                  40                  45

Pro Cys Tyr Tyr Pro Thr Asn Arg Asn Val Lys Asn Thr Ile Lys Asn
    50                  55                  60

Thr Ile Leu Ala Phe Lys Ile Leu Arg Lys Glu Lys Pro Asp Leu Ile
65                  70                  75                  80

Ile Ser Ser Gly Ala Ala Val Ala Val Pro Phe Phe Trp Ile Gly Lys
                85                  90                  95

Leu Phe Gly Ala Lys Thr Val Tyr Ile Glu Ile Phe Asp Arg Ile Asp
            100                 105                 110

Lys Pro Thr Leu Thr Gly Lys Leu Val Tyr Pro Val Thr Asp Lys Phe
        115                 120                 125

Ile Val Gln Trp Glu Glu Leu Lys Lys Val Tyr Pro Lys Ala Ile Asn
    130                 135                 140

Leu Gly Gly Ile Phe
145
```

<210> SEQ ID NO 188
<211> LENGTH: 228
<212> TYPE: PRT
<213> ORGANISM: Lactococcus lactis

<400> SEQUENCE: 188

Met Glu Phe Phe Glu Asp Ala Ser Ser Pro Glu Ser Glu Glu Pro Lys
1               5                   10                  15

Leu Val Glu Leu Lys Asn Phe Ser Tyr Arg Glu Leu Ile Ile Lys Arg
            20                  25                  30

Ala Ile Asp Ile Leu Gly Gly Leu Ala Gly Ser Val Leu Phe Leu Ile
        35                  40                  45

Ala Ala Ala Leu Leu Tyr Val Pro Tyr Lys Met Ser Ser Lys Lys Asp
    50                  55                  60

Gln Gly Pro Met Phe Tyr Lys Gln Lys Arg Tyr Gly Lys Asn Gly Lys
65                  70                  75                  80

Ile Phe Tyr Ile Leu Lys Phe Arg Thr Met Ile Phe Asn Ala Glu Gln
                85                  90                  95

Tyr Leu Glu Leu Asn Pro Asp Val Lys Ala Ala Tyr His Ala Asn Gly
            100                 105                 110

Asn Lys Leu Glu Asn Asp Pro Arg Val Thr Lys Ile Gly Ser Phe Ile
        115                 120                 125

Arg Arg His Ser Ile Asp Glu Leu Pro Gln Phe Ile Asn Val Leu Lys
    130                 135                 140

Gly Asp Met Ala Leu Val Gly Pro Arg Pro Ile Leu Leu Phe Glu Ala
145                 150                 155                 160

Lys Glu Tyr Gly Glu Arg Leu Ser Tyr Leu Leu Met Cys Lys Pro Gly
                165                 170                 175

Ile Thr Gly Tyr Trp Thr Thr His Gly Arg Ser Lys Val Leu Phe Pro
            180                 185                 190

Gln Arg Ala Asp Leu Glu Leu Tyr Tyr Leu Gln Tyr His Ser Thr Lys
        195                 200                 205

Asn Asp Ile Lys Leu Leu Ser Leu Thr Ile Val Gln Ser Ile Asn Gly
    210                 215                 220

Ser Asp Ala Tyr
225

<210> SEQ ID NO 189
<211> LENGTH: 231
<212> TYPE: PRT
<213> ORGANISM: Lactococcus lactis

<400> SEQUENCE: 189

Met Ala Lys Asn Lys Arg Ser Ile Asp Asn Asn Arg Tyr Ile Ile Thr
1               5                   10                  15

Ser Val Asn Pro Gln Ser Pro Ile Ser Glu Gln Tyr Arg Thr Ile Arg
            20                  25                  30

Thr Thr Ile Asp Phe Lys Met Ala Asp Gln Gly Ile Lys Ser Phe Leu
        35                  40                  45

Val Thr Ser Ser Glu Ala Ala Ala Gly Lys Ser Thr Val Ser Ala Asn
    50                  55                  60

Ile Ala Val Ala Phe Ala Gln Gln Gly Lys Lys Val Leu Leu Ile Asp
65                  70                  75                  80

Gly Asp Leu Arg Lys Pro Thr Val Asn Ile Thr Phe Lys Val Gln Asn
                85                  90                  95

```
Arg Val Gly Leu Thr Asn Ile Leu Met His Gln Ser Ser Ile Glu Asp
            100                 105                 110

Ala Ile Gln Gly Thr Arg Leu Ser Glu Asn Leu Thr Ile Ile Thr Ser
        115                 120                 125

Gly Pro Ile Pro Pro Asn Pro Ser Glu Leu Leu Ala Ser Ser Ala Met
    130                 135                 140

Lys Asn Leu Ile Asp Ser Val Ser Asp Phe Phe Asp Val Val Leu Ile
145                 150                 155                 160

Asp Thr Pro Pro Leu Ser Ala Val Thr Asp Ala Gln Ile Leu Ser Ser
                165                 170                 175

Tyr Val Gly Gly Val Val Leu Val Val Arg Ala Tyr Glu Thr Lys Lys
            180                 185                 190

Glu Ser Leu Ala Lys Thr Lys Lys Met Leu Glu Gln Val Asn Ala Asn
        195                 200                 205

Ile Leu Gly Val Val Leu His Gly Val Asp Ser Ser Asp Ser Pro Ser
    210                 215                 220

Tyr Tyr Tyr Tyr Gly Val Glu
225                 230
```

<210> SEQ ID NO 190
<211> LENGTH: 225
<212> TYPE: PRT
<213> ORGANISM: Lactococcus lactis

<400> SEQUENCE: 190

```
Met Gln Glu Thr Gln Glu Gln Thr Ile Asp Leu Arg Gly Ile Phe Lys
1               5                   10                  15

Ile Ile Arg Lys Arg Leu Ser Leu Ile Leu Phe Ser Ala Leu Ile Val
            20                  25                  30

Thr Ile Leu Gly Ser Ile Tyr Thr Phe Phe Ile Ala Ser Pro Val Tyr
        35                  40                  45

Thr Ala Ser Thr Gln Leu Val Val Lys Leu Pro Asn Ser Asp Asn Ser
    50                  55                  60

Asp Ala Tyr Ala Gly Gln Val Ser Gly Asn Ile Gln Met Ala Asn Thr
65                  70                  75                  80

Ile Asn Gln Val Ile Val Ser Pro Val Ile Leu Asp Lys Val Gln Ser
                85                  90                  95

Asn Leu Asn Leu Ser Asp Asp Ser Phe Gln Lys Gln Val Thr Ala Ala
            100                 105                 110

Asn Gln Thr Asn Ser Gln Val Ile Thr Leu Thr Val Lys Tyr Ser Asn
        115                 120                 125

Pro Tyr Ile Ala Gln Lys Ile Ala Asp Glu Thr Ala Lys Ile Phe Ser
    130                 135                 140

Ser Asp Ala Ala Lys Leu Leu Asn Val Thr Asn Val Asn Ile Leu Ser
145                 150                 155                 160

Lys Ala Lys Ala Gln Thr Thr Pro Ile Ser Pro Lys Pro Lys Leu Tyr
                165                 170                 175

Leu Ala Ile Ser Val Ile Ala Gly Leu Val Leu Gly Leu Ala Ile Ala
            180                 185                 190

Leu Leu Lys Glu Leu Phe Asp Asn Lys Ile Asn Lys Glu Glu Asp Ile
        195                 200                 205

Glu Ala Leu Gly Leu Thr Val Leu Gly Val Thr Ser Leu Cys Ser Asn
    210                 215                 220

Glu
225
```

<210> SEQ ID NO 191
<211> LENGTH: 255
<212> TYPE: PRT
<213> ORGANISM: Lactococcus lactis

<400> SEQUENCE: 191

Met Met Lys Lys Gly Ile Phe Val Ile Thr Ile Val Ile Ser Ile Ala
1 5 10 15

Leu Ile Ile Gly Gly Phe Tyr Ser Tyr Asn Ser Arg Ile Asn Asn Leu
20 25 30

Ser Lys Ala Asp Lys Gly Lys Glu Val Val Lys Asn Ser Ser Glu Lys
35 40 45

Asn Gln Ile Asp Leu Thr Tyr Lys Lys Tyr Tyr Lys Asn Leu Pro Lys
50 55 60

Ser Val Gln Asn Lys Ile Asp Asp Ile Ser Ser Lys Asn Lys Glu Val
65 70 75 80

Thr Leu Thr Cys Ile Trp Gln Ser Asp Ser Val Ile Ser Glu Gln Phe
85 90 95

Gln Gln Asn Leu Gln Lys Tyr Tyr Gly Asn Lys Phe Trp Asn Ile Lys
100 105 110

Asn Ile Thr Tyr Asn Gly Glu Thr Ser Glu Gln Leu Leu Ala Glu Lys
115 120 125

Val Gln Asn Gln Val Leu Ala Thr Asn Pro Asp Val Val Leu Tyr Glu
130 135 140

Ala Pro Leu Phe Asn Asp Asn Gln Asn Ile Glu Ala Thr Ala Ser Trp
145 150 155 160

Thr Ser Asn Glu Gln Leu Ile Thr Asn Leu Ala Ser Thr Gly Ala Glu
165 170 175

Val Ile Val Gln Pro Ser Pro Pro Ile Tyr Gly Gly Val Val Tyr Pro
180 185 190

Val Gln Glu Glu Gln Phe Lys Gln Ser Leu Ser Thr Lys Tyr Pro Tyr
195 200 205

Ile Asp Tyr Trp Ala Ser Tyr Pro Asp Lys Asn Ser Asp Glu Met Lys
210 215 220

Gly Leu Phe Ser Asp Asp Gly Val Tyr Arg Thr Leu Asn Ala Ser Gly
225 230 235 240

Asn Lys Val Trp Leu Asp Tyr Ile Thr Lys Tyr Phe Thr Ala Asn
245 250 255

<210> SEQ ID NO 192
<211> LENGTH: 105
<212> TYPE: PRT
<213> ORGANISM: Lactococcus lactis

<400> SEQUENCE: 192

Met Asn Asn Leu Phe Tyr His Arg Leu Lys Glu Leu Val Glu Ser Ser
1 5 10 15

Gly Lys Ser Ala Asn Gln Ile Glu Arg Glu Leu Gly Tyr Pro Arg Asn
20 25 30

Ser Leu Asn Asn Tyr Lys Leu Gly Gly Glu Pro Ser Gly Thr Arg Leu
35 40 45

Ile Gly Leu Ser Glu Tyr Phe Asn Val Ser Pro Lys Tyr Leu Met Gly
50 55 60

Ile Ile Asp Glu Pro Asn Asp Ser Ser Ala Ile Asn Leu Phe Lys Thr
65 70 75 80

```
Leu Thr Gln Glu Glu Lys Lys Glu Met Phe Ile Ile Cys Gln Lys Trp
                85                  90                  95

Leu Phe Leu Glu Tyr Gln Ile Glu Leu
            100                 105


<210> SEQ ID NO 193
<211> LENGTH: 471
<212> TYPE: PRT
<213> ORGANISM: Lactococcus lactis

<400> SEQUENCE: 193

Met Gln Ile Ala Lys Asn Tyr Leu Tyr Asn Ala Ile Tyr Gln Val Phe
1               5                   10                  15

Ile Ile Ile Val Pro Leu Leu Thr Ile Pro Tyr Leu Ser Arg Ile Leu
            20                  25                  30

Gly Pro Ser Gly Ile Gly Ile Asn Ser Tyr Thr Asn Ser Ile Val Gln
        35                  40                  45

Tyr Phe Val Leu Phe Gly Ser Ile Gly Val Gly Leu Tyr Gly Asn Arg
    50                  55                  60

Gln Ile Ala Phe Val Arg Asp Asn Gln Val Lys Met Ser Lys Val Phe
65                  70                  75                  80

Tyr Glu Ile Phe Ile Leu Arg Leu Phe Thr Ile Cys Leu Ala Tyr Phe
                85                  90                  95

Leu Phe Val Ala Phe Leu Ile Ile Asn Gly Gln Tyr His Ala Tyr Tyr
            100                 105                 110

Leu Ser Gln Ser Ile Ala Ile Val Ala Ala Ala Phe Asp Ile Ser Trp
        115                 120                 125

Phe Phe Met Gly Ile Glu Asn Phe Lys Val Thr Val Leu Arg Asn Phe
    130                 135                 140

Ile Val Lys Leu Leu Ala Leu Phe Ser Ile Phe Leu Phe Val Lys Ser
145                 150                 155                 160

Tyr Asn Asp Leu Asn Ile Tyr Ile Leu Ile Thr Val Leu Ser Thr Leu
                165                 170                 175

Ile Gly Asn Leu Thr Phe Phe Pro Ser Leu His Arg Tyr Leu Val Lys
            180                 185                 190

Val Asn Tyr Arg Glu Leu Arg Pro Ile Lys His Leu Lys Gln Ser Leu
        195                 200                 205

Val Met Phe Ile Pro Gln Ile Ala Val Gln Ile Tyr Trp Val Leu Asn
    210                 215                 220

Lys Thr Met Leu Gly Ser Leu Asp Ser Val Thr Ser Ser Gly Phe Phe
225                 230                 235                 240

Asp Gln Ser Asp Lys Ile Val Lys Leu Val Leu Ala Ile Ala Thr Ala
                245                 250                 255

Thr Gly Thr Val Met Leu Pro Arg Val Ala Asn Ala Phe Ala His Arg
            260                 265                 270

Glu Tyr Ser Lys Ile Lys Glu Tyr Met Tyr Ala Gly Phe Ser Phe Val
        275                 280                 285

Ser Ala Ile Ser Ile Pro Met Met Phe Gly Leu Ile Ala Ile Thr Pro
    290                 295                 300

Lys Phe Val Pro Leu Phe Phe Thr Ser Gln Phe Ser Asp Val Ile Pro
305                 310                 315                 320

Val Leu Met Ile Glu Ser Ile Ala Ile Ile Phe Ile Ala Trp Ser Asn
                325                 330                 335

Ala Ile Gly Asn Gln Tyr Leu Leu Pro Thr Asn Gln Asn Lys Ser Tyr
```

```
            340                 345                 350

Thr Val Ser Val Ile Ile Gly Ala Ile Val Asn Leu Met Leu Asn Ile
        355                 360                 365

Pro Leu Ile Ile Tyr Leu Gly Thr Val Gly Ala Ser Ile Ala Thr Val
    370                 375                 380

Ile Ser Glu Met Ser Val Thr Val Tyr Gln Leu Phe Ile Ile His Lys
385                 390                 395                 400

Gln Leu Asn Leu His Thr Leu Phe Ser Asp Leu Ser Lys Tyr Leu Ile
                405                 410                 415

Ala Gly Leu Val Met Phe Leu Ile Val Phe Lys Ile Ser Leu Leu Thr
            420                 425                 430

Pro Thr Ser Trp Ile Phe Ile Leu Leu Glu Ile Thr Val Gly Ile Ile
        435                 440                 445

Ile Tyr Val Val Leu Leu Ile Phe Leu Lys Ala Glu Ile Ile Asn Lys
    450                 455                 460

Leu Lys Phe Ile Met His Lys
465                 470


<210> SEQ ID NO 194
<211> LENGTH: 331
<212> TYPE: PRT
<213> ORGANISM: Lactococcus lactis

<400> SEQUENCE: 194

Met Lys Lys Asn Val Leu Leu Ser Ile Ile Val Pro Ile Tyr Asn Val
1               5                   10                  15

Glu Lys Tyr Ile Gly Ser Leu Val Asn Ser Leu Val Lys Gln Thr Asn
            20                  25                  30

Lys Asn Phe Glu Val Ile Phe Ile Asp Asp Gly Ser Thr Asp Glu Ser
        35                  40                  45

Met Gln Ile Leu Lys Glu Ile Ile Ala Gly Ser Glu Gln Glu Phe Ser
    50                  55                  60

Leu Lys Leu Leu Gln Gln Val Asn Gln Gly Leu Ser Ser Ala Arg Asn
65                  70                  75                  80

Ile Gly Ile Leu Asn Ala Thr Gly Glu Tyr Ile Phe Phe Leu Asp Ser
                85                  90                  95

Asp Asp Glu Ile Glu Ile Asn Phe Val Glu Thr Ile Leu Thr Ser Cys
            100                 105                 110

Tyr Lys Tyr Ser Gln Pro Asp Thr Leu Ile Phe Asp Tyr Ser Ser Ile
        115                 120                 125

Asp Glu Phe Gly Asn Ala Leu Asp Ser Asn Tyr Gly His Gly Ser Ile
    130                 135                 140

Tyr Arg Gln Lys Asp Leu Cys Thr Ser Glu Gln Ile Leu Thr Ala Leu
145                 150                 155                 160

Tyr Lys Asp Glu Ile Pro Ile Thr Ala Trp Ser Phe Val Thr Lys Arg
                165                 170                 175

Ser Val Ile Glu Lys His Asn Leu Leu Phe Ser Val Gly Lys Lys Phe
            180                 185                 190

Glu Asp Asn Asn Phe Thr Pro Lys Val Phe Tyr Phe Ser Lys Asn Ile
        195                 200                 205

Gly Val Ile Ser Leu Arg Leu Tyr Arg Tyr Arg Lys Arg Ser Gly Ser
    210                 215                 220

Ile Met Ser Asn His Pro Glu Lys Phe Phe Ser Asp Asp Ala Ile Phe
225                 230                 235                 240
```

```
Val Thr Tyr Asp Leu Leu Asp Phe Tyr Asp Gln Tyr Lys Ile Arg Glu
                245                 250                 255

Leu Gly Ala Val Val Gly Lys Leu Val Met Thr Arg Leu Ala Phe Phe
            260                 265                 270

Pro Asp Ser Lys Lys Leu Tyr Asn Glu Leu Asn Pro Ile Ile Lys Lys
        275                 280                 285

Val Phe Lys Asp Tyr Ile Ser Ile Glu Lys Arg His Thr Lys Arg Ile
    290                 295                 300

Lys Met Tyr Val Lys Met Tyr Val Phe Ser Ser Tyr Val Gly Tyr Lys
305                 310                 315                 320

Leu Tyr Arg Leu Val Lys Gly Lys His Trp Lys
                325                 330


<210> SEQ ID NO 195
<211> LENGTH: 299
<212> TYPE: PRT
<213> ORGANISM: Lactococcus lactis

<400> SEQUENCE: 195

Met Lys Lys Lys Met Arg Leu Lys Val Leu Leu Ala Ser Thr Ala Thr
1               5                   10                  15

Ala Leu Leu Leu Leu Ser Gly Cys Gln Ser Asn Gln Thr Asp Gln Thr
            20                  25                  30

Val Ala Thr Tyr Ser Gly Gly Lys Val Thr Glu Ser Ser Phe Tyr Lys
        35                  40                  45

Glu Leu Lys Gln Ser Pro Thr Thr Lys Thr Met Leu Ala Asn Met Leu
    50                  55                  60

Ile Tyr Arg Ala Leu Asn His Ala Tyr Gly Lys Ser Val Ser Thr Lys
65                  70                  75                  80

Thr Val Asn Asp Ala Tyr Asp Ser Tyr Lys Gln Gln Tyr Gly Glu Asn
                85                  90                  95

Phe Asp Ala Phe Leu Ser Gln Asn Gly Phe Ser Arg Ser Ser Phe Lys
            100                 105                 110

Glu Ser Leu Arg Thr Asn Phe Leu Ser Glu Val Ala Leu Lys Lys Leu
        115                 120                 125

Lys Lys Val Ser Glu Ser Gln Leu Lys Ala Ala Trp Lys Thr Tyr Gln
    130                 135                 140

Pro Lys Val Thr Val Gln His Ile Leu Thr Ser Asp Glu Asp Thr Ala
145                 150                 155                 160

Lys Gln Val Ile Ser Asp Leu Ala Ala Gly Lys Asp Phe Ala Met Leu
                165                 170                 175

Ala Lys Thr Asp Ser Ile Asp Thr Ala Thr Lys Asp Asn Gly Gly Lys
            180                 185                 190

Ile Ser Phe Glu Leu Asn Asn Lys Thr Leu Asp Ala Thr Phe Lys Asp
        195                 200                 205

Ala Ala Tyr Lys Leu Lys Asn Gly Asp Tyr Thr Gln Thr Pro Val Lys
    210                 215                 220

Val Thr Asp Gly Tyr Glu Val Ile Lys Met Ile Asn His Pro Ala Lys
225                 230                 235                 240

Gly Thr Phe Thr Ser Ser Lys Lys Val Leu Thr Ala Ser Val Tyr Ala
                245                 250                 255

Lys Trp Ser Arg Asp Ser Ser Ile Met Gln Arg Val Ile Ser Gln Val
            260                 265                 270

Leu Lys Asn Gln His Val Thr Ile Lys Asp Lys Asp Leu Ala Asp Ala
        275                 280                 285
```

```
Leu Asp Ser Tyr Lys Lys Leu Ala Thr Thr Asn
    290                 295


<210> SEQ ID NO 196
<211> LENGTH: 2022
<212> TYPE: PRT
<213> ORGANISM: Lactococcus lactis

<400> SEQUENCE: 196

Met Gln Arg Lys Lys Lys Gly Leu Ser Phe Leu Leu Ala Gly Thr Val
1               5                   10                  15

Ala Leu Gly Ala Leu Ala Val Leu Pro Val Gly Glu Ile Gln Ala Lys
            20                  25                  30

Ala Ala Ile Ser Gln Gln Thr Lys Gly Ser Ser Leu Ala Asn Thr Val
        35                  40                  45

Thr Ala Ala Thr Ala Lys Gln Ala Ala Thr Asp Thr Thr Ala Ala Thr
    50                  55                  60

Thr Asn Gln Ala Ile Ala Thr Gln Leu Ala Ala Lys Gly Ile Asp Tyr
65                  70                  75                  80

Asn Lys Leu Asn Lys Val Gln Gln Gln Asp Ile Tyr Val Asp Val Ile
                85                  90                  95

Val Gln Met Ser Ala Ala Pro Ala Ser Glu Asn Gly Thr Leu Arg Thr
            100                 105                 110

Asp Tyr Ser Ser Thr Ala Glu Ile Gln Gln Glu Thr Asn Lys Val Ile
        115                 120                 125

Ala Ala Gln Ala Ser Val Lys Ala Ala Val Glu Gln Val Thr Gln Gln
    130                 135                 140

Thr Ala Gly Glu Ser Tyr Gly Tyr Val Val Asn Gly Phe Ser Thr Lys
145                 150                 155                 160

Val Arg Val Val Asp Ile Pro Lys Leu Lys Gln Ile Ala Gly Val Lys
                165                 170                 175

Thr Val Thr Leu Ala Lys Val Tyr Tyr Pro Thr Asp Ala Lys Ala Asn
            180                 185                 190

Ser Met Ala Asn Val Gln Ala Val Trp Ser Asn Tyr Lys Tyr Lys Gly
        195                 200                 205

Glu Gly Thr Val Val Ser Val Ile Asp Ser Gly Ile Asp Pro Thr His
    210                 215                 220

Lys Asp Met Arg Leu Ser Asp Asp Lys Asp Val Lys Leu Thr Lys Ser
225                 230                 235                 240

Asp Val Glu Lys Phe Thr Asp Thr Val Lys His Gly Arg Tyr Phe Asn
                245                 250                 255

Ser Lys Val Pro Tyr Gly Phe Asn Tyr Ala Asp Asn Asn Asp Thr Ile
            260                 265                 270

Thr Asp Asp Lys Val Asp Glu Gln His Gly Met His Val Ala Gly Ile
        275                 280                 285

Ile Gly Ala Asn Gly Thr Gly Asp Asp Pro Ala Lys Ser Val Val Gly
    290                 295                 300

Val Ala Pro Glu Ala Gln Leu Leu Ala Met Lys Val Phe Thr Asn Ser
305                 310                 315                 320

Asp Thr Ser Ala Thr Thr Gly Ser Asp Thr Leu Val Ser Ala Ile Glu
                325                 330                 335

Asp Ser Ala Lys Ile Gly Ala Asp Val Leu Asn Met Ser Leu Gly Ser
            340                 345                 350

Asp Ser Gly Asn Gln Thr Leu Glu Asp Pro Glu Ile Ala Ala Val Gln
```

```
        355                 360                 365

Asn Ala Asn Glu Ser Gly Thr Ala Ala Val Ile Ser Ala Gly Asn Ser
    370                 375                 380

Gly Thr Ser Gly Ser Ala Thr Glu Gly Val Asn Lys Asp Tyr Tyr Gly
385                 390                 395                 400

Leu Gln Asp Asn Glu Met Val Gly Thr Pro Gly Thr Ser Arg Gly Ala
                405                 410                 415

Thr Thr Val Ala Ser Ala Glu Asn Thr Asp Val Ile Thr Gln Ala Val
            420                 425                 430

Thr Ile Thr Asp Gly Thr Gly Leu Gln Leu Gly Pro Glu Thr Ile Gln
        435                 440                 445

Leu Ser Ser Asn Asp Phe Thr Gly Ser Phe Asp Gln Lys Lys Phe Tyr
    450                 455                 460

Val Val Lys Asp Ala Ser Gly Asn Leu Ser Lys Gly Lys Val Ala Asp
465                 470                 475                 480

Tyr Thr Ala Asp Ala Lys Gly Lys Ile Ala Ile Val Lys Arg Gly Glu
                485                 490                 495

Leu Thr Phe Asp Asp Lys Gln Lys Tyr Ala Gln Ala Ala Gly Ala Ala
            500                 505                 510

Gly Leu Ile Ile Val Asn Asn Asp Gly Thr Ala Thr Pro Val Thr Ser
        515                 520                 525

Met Ala Leu Thr Thr Thr Phe Pro Thr Phe Gly Leu Ser Ser Val Thr
    530                 535                 540

Gly Gln Lys Leu Val Asp Trp Val Thr Ala His Pro Asp Asp Ser Leu
545                 550                 555                 560

Gly Val Lys Ile Ala Leu Thr Leu Val Pro Asn Gln Lys Tyr Thr Glu
                565                 570                 575

Asp Lys Met Ser Asp Phe Thr Ser Tyr Gly Pro Val Ser Asn Leu Ser
            580                 585                 590

Phe Lys Pro Asp Ile Thr Ala Pro Gly Gly Asn Ile Trp Ser Thr Gln
        595                 600                 605

Asn Asn Asn Gly Tyr Thr Asn Met Ser Gly Thr Ser Met Ala Ser Pro
    610                 615                 620

Phe Ile Ala Gly Ser Gln Ala Leu Leu Lys Gln Ala Leu Asn Asn Lys
625                 630                 635                 640

Asn Asn Pro Phe Tyr Ala Tyr Tyr Lys Gln Leu Lys Gly Thr Ala Leu
                645                 650                 655

Thr Asp Phe Leu Lys Thr Val Glu Met Asn Thr Ala Gln Pro Ile Asn
            660                 665                 670

Asp Ile Asn Tyr Asn Asn Val Ile Val Ser Pro Arg Arg Gln Gly Ala
        675                 680                 685

Gly Leu Val Asp Val Lys Ala Ala Ile Asp Ala Leu Glu Lys Asn Pro
    690                 695                 700

Ser Thr Val Val Ala Glu Asn Gly Tyr Pro Ala Val Glu Leu Lys Asp
705                 710                 715                 720

Phe Thr Ser Thr Asp Lys Thr Phe Lys Leu Thr Phe Thr Asn Arg Thr
                725                 730                 735

Thr His Glu Leu Thr Tyr Gln Met Asp Ser Asn Thr Asp Thr Asn Ala
            740                 745                 750

Val Tyr Thr Ser Ala Thr Asp Pro Asn Ser Gly Val Leu Tyr Asp Lys
        755                 760                 765

Lys Ile Asp Gly Ala Ala Ile Lys Ala Gly Ser Asn Ile Thr Val Pro
    770                 775                 780
```

```
Ala Gly Lys Thr Ala Gln Ile Glu Phe Thr Leu Ser Leu Pro Lys Ser
785                 790                 795                 800

Phe Asp Gln Gln Gln Phe Val Glu Gly Phe Leu Asn Phe Lys Gly Ser
                805                 810                 815

Asp Gly Ser Arg Leu Asn Leu Pro Tyr Met Gly Phe Phe Gly Asp Trp
            820                 825                 830

Asn Asp Gly Lys Ile Val Asp Ser Leu Asn Gly Ile Thr Tyr Ser Pro
        835                 840                 845

Ala Gly Gly Asn Phe Gly Thr Val Pro Leu Leu Thr Asn Lys Asn Thr
    850                 855                 860

Gly Thr Gln Tyr Tyr Gly Gly Met Val Thr Asp Ala Asp Gly Asn Gln
865                 870                 875                 880

Thr Val Asp Asp Gln Ala Ile Ala Phe Ser Ser Asp Lys Asn Ala Leu
                885                 890                 895

Tyr Asn Asp Ile Ser Met Lys Tyr Tyr Leu Leu Arg Asn Ile Ser Asn
            900                 905                 910

Val Gln Val Asp Ile Leu Asp Gly Gln Gly Asn Lys Val Thr Thr Leu
        915                 920                 925

Ser Ser Ser Thr Asn Leu Thr Lys Thr Tyr Tyr Asn Ala His Ser Gln
    930                 935                 940

Gln Tyr Ile Tyr Tyr His Ala Pro Ala Trp Asp Gly Thr Tyr Tyr Asp
945                 950                 955                 960

Gln Arg Asp Gly Asn Ile Lys Thr Ala Asp Asp Gly Ser Tyr Thr Tyr
                965                 970                 975

Arg Ile Ser Gly Val Pro Glu Gly Gly Asp Lys Arg Gln Val Phe Asp
            980                 985                 990

Val Pro Phe Lys Leu Asp Ser Lys  Ala Pro Thr Val Arg  His Val Ala
        995                 1000                1005

Leu Ser  Ala Lys Thr Lys Asn  Gly Lys Thr Gln Tyr  Tyr Leu Thr
    1010                1015                1020

Ala Glu  Val Lys Asp Asp Leu  Ser Gly Leu Asp Ala  Thr Lys Ser
    1025                1030                1035

Val Lys  Thr Ala Ile Asn Glu  Val Thr Asn Leu Asp  Ala Thr Phe
    1040                1045                1050

Thr Asp  Ala Gly Thr Thr Ala  Asp Gly Tyr Thr Lys  Ile Glu Thr
    1055                1060                1065

Pro Leu  Ser Asp Glu Gln Ala  Gln Ala Leu Gly Asn  Gly Asp Asn
    1070                1075                1080

Ser Ala  Glu Leu Tyr Leu Thr  Asp Asn Ala Ser Asn  Ala Thr Asp
    1085                1090                1095

Gln Asp  Ala Ser Val Gln Lys  Pro Gly Ser Thr Ser  Phe Asp Leu
    1100                1105                1110

Ile Val  Asn Gly Ser Gly Ile  Pro Asp Lys Ile Ser  Ser Thr Thr
    1115                1120                1125

Thr Gly  Tyr Glu Ala Asn Thr  Gln Gly Gly Gly Thr  Tyr Thr Phe
    1130                1135                1140

Ser Gly  Thr Tyr Pro Ala Ala  Val Asp Gly Thr Tyr  Thr Asp Ala
    1145                1150                1155

Gln Gly  Lys Lys His Asp Leu  Asn Thr Thr Tyr Asp  Ala Ala Thr
    1160                1165                1170

Asn Ser  Phe Thr Ala Ser Met  Pro Val Thr Asn Ala  Asp Tyr Ala
    1175                1180                1185
```

```
Ala Gln Val Asp Leu Tyr Ala Asp Lys Ala His Thr Gln Leu Leu
    1190                1195                1200

Lys His Phe Asp Thr Lys Val Arg Leu Thr Ala Pro Thr Phe Thr
    1205                1210                1215

Asp Leu Lys Phe Asn Asn Gly Ser Asp Gln Thr Ser Glu Ala Thr
    1220                1225                1230

Ile Lys Val Thr Gly Thr Val Ser Ala Asp Thr Lys Thr Val Asn
    1235                1240                1245

Val Gly Asp Thr Val Ala Ala Leu Asp Ala Gln His His Phe Ser
    1250                1255                1260

Val Asp Val Pro Val Asn Tyr Gly Asp Asn Thr Ile Lys Val Ile
    1265                1270                1275

Ala Thr Asp Glu Asp Gly Asn Thr Thr Thr Glu Gln Lys Thr Ile
    1280                1285                1290

Thr Ser Ser Tyr Asp Pro Asp Met Leu Lys Asn Pro Val Thr Phe
    1295                1300                1305

Asp Gln Gly Val Thr Phe Gly Ser Asn Glu Phe Asn Ala Thr Ser
    1310                1315                1320

Ala Lys Phe Tyr Asp Pro Lys Thr Gly Ile Ala Thr Ile Thr Gly
    1325                1330                1335

Lys Val Lys His Pro Thr Thr Thr Leu Gln Val Asp Gly Lys Gln
    1340                1345                1350

Ile Pro Ile Lys Asp Asp Leu Thr Phe Ser Phe Thr Leu Asp Leu
    1355                1360                1365

Gly Thr Leu Gly Gln Lys Pro Phe Gly Val Val Val Gly Asp Thr
    1370                1375                1380

Thr Gln Asn Lys Thr Phe Gln Glu Ala Leu Thr Phe Ile Leu Asp
    1385                1390                1395

Ala Val Ala Pro Thr Leu Ser Leu Asp Ser Ser Thr Asp Ala Pro
    1400                1405                1410

Val Tyr Thr Asn Asp Pro Asn Phe Gln Ile Thr Gly Thr Ala Thr
    1415                1420                1425

Asp Asn Ala Gln Tyr Leu Ser Leu Ser Ile Asn Gly Ser Ser Val
    1430                1435                1440

Ala Ser Gln Tyr Ala Asp Ile Asn Ile Asn Ser Gly Lys Pro Gly
    1445                1450                1455

His Met Ala Ile Asp Gln Pro Val Lys Leu Leu Glu Gly Lys Asn
    1460                1465                1470

Val Leu Thr Val Ala Val Thr Asp Ser Glu Asp Asn Thr Thr Thr
    1475                1480                1485

Lys Asn Ile Thr Val Tyr Tyr Glu Pro Lys Lys Thr Leu Ala Ala
    1490                1495                1500

Pro Thr Val Thr Pro Ser Thr Thr Glu Pro Ala Gln Thr Val Thr
    1505                1510                1515

Leu Thr Ala Asn Ala Ala Ala Thr Gly Glu Thr Val Gln Tyr Ser
    1520                1525                1530

Ala Asp Gly Gly Lys Thr Tyr Gln Asp Val Pro Ala Ala Gly Val
    1535                1540                1545

Thr Ile Thr Ala Asn Gly Thr Phe Lys Phe Lys Ser Thr Asp Leu
    1550                1555                1560

Tyr Gly Asn Glu Ser Pro Ala Val Asp Tyr Val Val Thr Asn Ile
    1565                1570                1575

Lys Ala Asp Asp Pro Ala Gln Leu Gln Ala Ala Lys Gln Ala Leu
```

```
    1580                1585                1590

Thr Asn  Leu Ile Ala Ser Ala  Lys Thr Leu Ser Ala  Ser Gly Lys
    1595                1600                1605

Tyr Asp  Asp Ala Thr Thr Thr  Ala Leu Ala Ala Ala  Thr Gln Lys
    1610                1615                1620

Ala Gln  Thr Ala Leu Asp Gln  Thr Asn Ala Ser Val  Asp Ser Leu
    1625                1630                1635

Thr Gly  Ala Asn Arg Asp Leu  Gln Thr Ala Ile Asn  Gln Leu Ala
    1640                1645                1650

Ala Lys  Leu Pro Ala Asp Lys  Lys Thr Ser Leu Leu  Asn Gln Leu
    1655                1660                1665

Gln Ser  Val Lys Asp Ala Leu  Gly Thr Asp Leu Gly  Asn Gln Thr
    1670                1675                1680

Asp Pro  Ser Thr Gly Lys Thr  Phe Thr Ala Ala Leu  Asp Asp Leu
    1685                1690                1695

Val Ala  Gln Ala Gln Ala Gly  Thr Gln Thr Asp Asp  Gln Leu Gln
    1700                1705                1710

Ala Thr  Leu Ala Lys Ile Leu  Asp Glu Val Leu Ala  Lys Leu Ala
    1715                1720                1725

Glu Gly  Ile Lys Ala Ala Thr  Pro Ala Glu Val Gly  Asn Ala Lys
    1730                1735                1740

Asp Ala  Ala Thr Gly Lys Thr  Trp Tyr Ala Asp Ile  Ala Asp Thr
    1745                1750                1755

Leu Thr  Ser Gly Gln Ala Ser  Ala Asp Ala Ser Asp  Lys Leu Ala
    1760                1765                1770

His Leu  Gln Ala Leu Gln Ser  Leu Lys Thr Lys Val  Ala Ala Ala
    1775                1780                1785

Val Glu  Ala Asp Lys Thr Val  Gly Lys Gly Asp Asp  Thr Thr Gly
    1790                1795                1800

Thr Ser  Asp Lys Gly Ser Gly  Gln Gly Thr Pro Ala  Pro Ala Thr
    1805                1810                1815

Gly Asp  Thr Gly Lys Asp Lys  Gly Asp Glu Gly Ser  Gln Pro Ser
    1820                1825                1830

Ser Gly  Gly Asn Ile Pro Thr  Asn Pro Ala Thr Thr  Thr Ser Thr
    1835                1840                1845

Ser Ala  Asp Asp Thr Thr Asp  Arg Asn Gly Gln His  Thr Thr Gly
    1850                1855                1860

Thr Ser  Asp Lys Gly Gly Gly  Gln Gly Thr Pro Ala  Pro Ala Thr
    1865                1870                1875

Gly Asp  Thr Gly Lys Asp Lys  Gly Asp Glu Gly Ser  Gln Pro Ser
    1880                1885                1890

Ser Gly  Gly Asn Ile Pro Thr  Asn Pro Ala Thr Thr  Thr Ser Thr
    1895                1900                1905

Ser Ala  Asp Asp Thr Thr Asp  Arg Asn Gly Gln His  Thr Thr Gly
    1910                1915                1920

Thr Ser  Asp Lys Gly Gly Gly  Gln Gly Thr Pro Ala  Pro Ala Thr
    1925                1930                1935

Gly Asp  Thr Gly Lys Asp Lys  Gly Asp Glu Gly Ser  Gln Pro Ser
    1940                1945                1950

Ser Gly  Gly Asn Ile Pro Thr  Asn Pro Ala Thr Thr  Thr Ser Thr
    1955                1960                1965

Ser Thr  Asp Asp Thr Thr Asp  Arg Asn Gly Gln His  Thr Thr Gly
    1970                1975                1980
```

```
Lys Gly  Ala Leu Pro Lys Thr  Gly Glu Thr Thr Glu  Arg Pro Ala
    1985                 1990                 1995

Phe Gly  Phe Leu Gly Val Ile  Val Val Ile Leu Met  Gly Val Leu
    2000                 2005                 2010

Gly Leu  Lys Arg Lys Gln Arg  Glu Glu
    2015                 2020
```

<210> SEQ ID NO 197
<211> LENGTH: 193
<212> TYPE: PRT
<213> ORGANISM: Lactococcus lactis

<400> SEQUENCE: 197

```
Met Arg Ala Ala Glu Gly Leu Phe Val Tyr Asn Lys Thr Asn Phe His
1               5                   10                  15

Tyr Leu Pro Gln Asn Ile Ala Phe Ala Asp Phe Lys Ser Gly Lys Phe
            20                  25                  30

Ala Thr Ser Gly Met Ser Met Ile Leu Ile Asp Ser Val Asn His Arg
        35                  40                  45

Ile Leu Asp Val Met Lys Asp Arg Gly Ala Gly Gln Leu Arg Ala Tyr
    50                  55                  60

Phe Asn Gln Tyr Ser Pro Ser Ala Arg Ala Ala Val Lys Thr Ile Thr
65                  70                  75                  80

Val Asp Leu Phe Thr Pro Tyr Arg Ala Met Ile Lys Asp Leu Phe Pro
                85                  90                  95

Asn Ala Asn Ile Val Ala Asp Arg Phe His Val Val Thr Gln Ala Tyr
            100                 105                 110

Arg Glu Leu Asn Lys Val Arg Ile Ser Val Met Lys Gln Phe Gly Ser
        115                 120                 125

Asp Ser Lys Glu Tyr Arg Gln Leu Lys Arg Phe Trp Lys Leu Leu Met
    130                 135                 140

Lys His Glu Asn Ala Leu Asp Tyr Met Thr Ser Lys Asn Arg Ile Asn
145                 150                 155                 160

Phe Lys His Ala Tyr Leu Thr Asp Lys Glu Val Ile Asp Arg Leu Leu
                165                 170                 175

Ala Leu Ser Asp Glu Leu Arg Asp Ala Tyr Ala Phe Tyr Gln Val Ile
            180                 185                 190

Leu
```

<210> SEQ ID NO 198
<211> LENGTH: 86
<212> TYPE: PRT
<213> ORGANISM: Lactococcus lactis

<400> SEQUENCE: 198

```
Met Asp Asn Asp Ile Arg Ile Leu Ile Gly Leu Thr Asp Leu Asn Ile
1               5                   10                  15

Asp Phe Asp Ala Lys Ala Glu Gln His Phe Asn Glu Thr Asn Leu Asn
            20                  25                  30

Gly Thr Ala Pro Ile Thr Trp Asn Leu Leu Leu Thr Tyr Ala Thr Asn
        35                  40                  45

Cys Glu Lys Phe Gly Thr Pro Met Val His Asn Gly Ile Lys Met Val
    50                  55                  60

Thr His Lys Gly Pro Arg Ile Ala Phe Lys Phe Gln Asn Tyr Arg Ile
65                  70                  75                  80
```

```
Arg Lys Gln Lys Phe Leu
                85


<210> SEQ ID NO 199
<211> LENGTH: 165
<212> TYPE: PRT
<213> ORGANISM: Lactococcus lactis

<400> SEQUENCE: 199

Met Ile Glu Asn Thr Ile Asn Ile Ala Tyr Ala Arg Lys Phe Tyr Lys
1               5                   10                  15

Thr Lys Asp Tyr His Ser Phe Cys Asn Leu Ile Lys Gly Asn Lys Gly
            20                  25                  30

Leu Phe Gly Asn Lys Thr Val Asn Gln Lys Ala Asn Ile Ser Phe Val
        35                  40                  45

Lys Ser Glu Gly Glu Lys His Thr His Ile Tyr Leu Asp Tyr Gln Glu
    50                  55                  60

Thr Cys Lys Val Ala His Pro Asn Phe Leu Gln Leu Ile Asn Leu Leu
65                  70                  75                  80

Lys Asn Tyr Asp Pro Glu Phe Ser Glu Glu Lys Leu Pro Thr Phe Asp
                85                  90                  95

Leu Asn Asp Lys Ile Phe Gly Glu Tyr Glu Ile Lys Val Ile Pro Ile
            100                 105                 110

Ser Lys Thr Lys Ile Val Asn Thr Ile Asp Asp Val Met Asn Glu Ile
        115                 120                 125

Ala Lys Glu Ile Val Leu Lys Tyr Asn Gln Asp Met Phe Lys Val Thr
    130                 135                 140

Ser Lys Leu Gly Glu Ile Ser Leu Thr Pro Ile Gln Glu Lys Phe Asp
145                 150                 155                 160

Lys Leu Lys Asp Ile
                165


<210> SEQ ID NO 200
<211> LENGTH: 385
<212> TYPE: PRT
<213> ORGANISM: Lactococcus lactis

<400> SEQUENCE: 200

Met Ile Ile Pro Glu Lys Gln Asn Lys Gln Lys Gln Val Leu Thr Leu
1               5                   10                  15

Asn Glu Leu Glu Lys Arg Lys Val Val Glu His Asn Ala Leu Ile Gln
            20                  25                  30

Ser Val Ala Lys Met Gln Lys Thr Ala Leu Lys Met Phe Glu Leu Ala
        35                  40                  45

Val Ser Cys Ile Asp Thr Glu Glu Pro Pro Lys Asn Asn Thr Val Tyr
    50                  55                  60

Leu Ser Lys Ser Glu Leu Phe Lys Phe Phe Glu Val Ser Ser Ser Ser
65                  70                  75                  80

Lys His Ser Gln Phe Lys Glu Ala Val Asn Tyr Met Gln Lys Gln Ala
                85                  90                  95

Phe Phe Asn Ile Lys Ala Asp Lys Lys Leu Gly Ile Glu Tyr Glu Ser
            100                 105                 110

Ile Val Pro Ile Pro Tyr Val Lys Trp Asn Asp Tyr Asn Asp Glu Val
        115                 120                 125

Thr Ile Arg Phe Asp Gln Ala Ile Met Pro Tyr Leu Ile Asp Leu Lys
    130                 135                 140
```

-continued

```
Ala Glu Phe Thr Gln Tyr Lys Ile Ser Glu Leu Gln Lys Leu Asn Ser
145                 150                 155                 160

Lys Tyr Ser Ile Ile Leu Tyr Arg Trp Leu Ser Met Asn Tyr Asn Gln
                165                 170                 175

Tyr Glu His Tyr Ser Val Lys Gly Gly Arg Arg Ala Asp Gln Val Glu
            180                 185                 190

Ala Tyr Arg Thr Pro Ser Ile Lys Val Lys Glu Leu Arg Glu Ile Thr
        195                 200                 205

Asp Thr Ile Asn Glu His Gln His Phe Pro His Phe Glu Thr Arg Val
    210                 215                 220

Leu Lys Lys Ala Ile Glu Glu Ile Asn Ala His Thr Ser Phe Asn Val
225                 230                 235                 240

Thr Tyr Glu Lys Val Lys Lys Gly Arg Ser Ile Asp Ser Ile Val Phe
                245                 250                 255

His Ile Glu Lys Lys Arg Met Ala Asp Asp Asn Ser Tyr Lys Leu Glu
            260                 265                 270

Asp Lys Val Tyr Gln Glu Asp Lys Ala Arg Lys Ala Glu Thr Glu Lys
        275                 280                 285

Asp Leu Val Phe Gln Ala Met Gln Ser Pro Tyr Thr Arg Leu Leu Ile
    290                 295                 300

Glu Asn Met Phe Leu Asn Val Tyr Glu Thr Thr Asp Ser Gln Ile Met
305                 310                 315                 320

Ala Gly Leu Gln Lys Asn Val Tyr Pro Leu Tyr Asp Glu Leu Lys Glu
                325                 330                 335

Leu Arg Gly Leu Asn Gly Val Lys Asp His Leu Ser Tyr Val Ser Ser
            340                 345                 350

Lys Gln Glu Ala Tyr Ser Lys Arg Asn Val Ala Lys Tyr Leu Lys Lys
        355                 360                 365

Ala Ile Glu Gln Tyr Leu Pro Thr Val Lys Arg Gln Asp Leu Asn His
    370                 375                 380

Glu
385
```

<210> SEQ ID NO 201
<211> LENGTH: 208
<212> TYPE: PRT
<213> ORGANISM: Lactococcus lactis

<400> SEQUENCE: 201

```
Met Ser Glu Asp Leu Lys Thr Ile Lys Glu Leu Ala Asp Glu Leu Gly
1               5                   10                  15

Val Ser Lys Ser Tyr Val Asp Lys Ile Ile Arg Ile Leu Lys Leu His
            20                  25                  30

Thr Lys Leu Asp Lys Val Gly Asn Lys Tyr Val Ile Ser Lys Lys Gln
        35                  40                  45

Glu Lys Ser Ile Ile Thr Arg Ile Glu Asn Ser Lys Ser Thr Thr Glu
    50                  55                  60

Thr His Thr Glu Ser Thr Thr Gln Ser His Thr Lys Val Asp Ala Glu
65                  70                  75                  80

Val Asp Phe Leu Lys Glu Glu Ile Ala Tyr Leu Lys Ser Asn His Asp
                85                  90                  95

Lys Gln Leu Thr Asn Lys Asp Lys Gln Ile Glu Thr Leu Ser Asn Leu
            100                 105                 110

Leu Asp Gln Gln Gln Arg Leu Ala Leu Gln Asp Lys Lys Trp Leu Glu
        115                 120                 125
```

```
Glu Tyr Lys Ala Glu Ile Asn Asp Leu Lys Ala Leu Lys Met Pro Ser
    130                 135                 140

Glu Asp Thr Lys Glu Glu Gln Ser Asn Tyr Arg Ser Leu Glu Lys Glu
145                 150                 155                 160

Lys Asp Phe Val Gln Thr Ile Gln Glu Ser Tyr Glu Ser Glu Ile Lys
                165                 170                 175

Val Leu Asn Gln Lys Leu Ala Glu Gln Glu Glu Gln Ile Gln Glu Ile
            180                 185                 190

Gln Lys Glu Lys Glu Thr Lys Glu Lys Lys Trp Phe Gln Phe Trp Lys
        195                 200                 205


<210> SEQ ID NO 202
<211> LENGTH: 76
<212> TYPE: PRT
<213> ORGANISM: Lactococcus lactis

<400> SEQUENCE: 202

Met Ala Gln Thr Phe Asp Arg Lys Ile Leu Arg Ala Leu Gln Asp Asn
1               5                   10                  15

Gly Val Arg Glu Ile Arg Ala Tyr Glu Val Val Ser Lys Arg Leu Thr
            20                  25                  30

Ile Phe Gln Thr Asp Arg Gly Thr Phe Lys Tyr Ser Asp Ser Leu Tyr
        35                  40                  45

Arg Leu Val Ala Pro Arg Gln Glu Leu Trp Arg Asn Cys Thr Thr Gly
    50                  55                  60

Phe Ile Ser Glu Glu Lys Tyr His Phe Tyr Lys Lys
65                  70                  75


<210> SEQ ID NO 203
<211> LENGTH: 226
<212> TYPE: PRT
<213> ORGANISM: Lactococcus lactis

<400> SEQUENCE: 203

Met Asn His Phe Lys Gly Lys Gln Phe Lys Lys Asp Val Ile Ile Val
1               5                   10                  15

Ala Val Gly Tyr Tyr Leu Arg Tyr Asn Leu Ser Tyr Arg Glu Ile Gln
            20                  25                  30

Glu Leu Leu Tyr Asp Arg Gly Ile Asn Val Cys His Thr Thr Ile Tyr
        35                  40                  45

Arg Trp Val Gln Glu Tyr Ser Lys Val Leu Tyr His Leu Trp Lys Lys
    50                  55                  60

Lys Asn Arg Gln Ser Phe Tyr Ser Trp Lys Met Asp Glu Thr Tyr Ile
65                  70                  75                  80

Lys Ile Lys Gly Arg Trp His Tyr Leu Tyr Arg Ala Ile Asp Ala Asp
                85                  90                  95

Gly Leu Thr Leu Asp Ile Trp Leu Arg Lys Lys Arg Asp Thr Gln Ala
            100                 105                 110

Ala Tyr Ala Phe Leu Lys Arg Leu His Lys Gln Phe Gly Gln Pro Arg
        115                 120                 125

Val Ile Val Thr Asp Lys Ala Pro Ser Ile Gly Ser Ala Phe Arg Lys
    130                 135                 140

Leu Gln Ser Asn Gly Leu Tyr Thr Lys Thr Glu His Arg Thr Val Lys
145                 150                 155                 160

Tyr Leu Asn Asn Leu Ile Glu Gln Asp His Arg Pro Ile Lys Arg Arg
                165                 170                 175
```

```
Asn Lys Phe Tyr Arg Ser Leu Arg Thr Ala Ser Thr Thr Ile Lys Gly
            180                 185                 190

Met Glu Thr Ile Arg Gly Ile Tyr Lys Lys Asn Arg Arg Asn Gly Thr
        195                 200                 205

Leu Phe Gly Phe Ser Val Ser Thr Glu Ile Lys Val Leu Met Gly Ile
    210                 215                 220

Leu Ala
225


<210> SEQ ID NO 204
<211> LENGTH: 300
<212> TYPE: PRT
<213> ORGANISM: Lactococcus lactis

<400> SEQUENCE: 204

Met Glu Arg Lys Lys Lys Lys Lys Glu Asn Ile Trp Ala Ile Ile Val
1               5                   10                  15

Pro Ile Leu Ile Ile Ile Ser Leu Ile Gly Ala Trp Ala Tyr Ala Leu
            20                  25                  30

Arg Asp Ser Leu Ile Pro Asn Asp Tyr Thr Lys Thr Asn Ser Ser Asp
        35                  40                  45

Gln Pro Thr Lys Thr Ser Val Ser Asn Gly Tyr Val Glu Gln Lys Gly
    50                  55                  60

Val Glu Ala Ala Val Gly Ser Ile Ala Leu Val Asp Asp Ala Gly Val
65                  70                  75                  80

Pro Glu Trp Val Lys Val Pro Ser Lys Val Asn Leu Asp Lys Phe Thr
                85                  90                  95

Asp Leu Ser Thr Asn Asn Ile Thr Ile Tyr Arg Ile Asn Asn Pro Glu
            100                 105                 110

Val Leu Lys Thr Val Thr Asn Arg Thr Asp Gln Arg Met Lys Met Ser
        115                 120                 125

Glu Val Ile Ala Lys Tyr Pro Asn Ala Leu Ile Met Asn Ala Ser Ala
    130                 135                 140

Phe Asp Met Gln Thr Gly Gln Val Ala Gly Phe Gln Ile Asn Asn Gly
145                 150                 155                 160

Lys Leu Ile Gln Asp Trp Ser Pro Gly Thr Thr Thr Gln Tyr Ala Phe
                165                 170                 175

Val Ile Asn Lys Asp Gly Ser Cys Lys Ile Tyr Asp Ser Ser Thr Pro
            180                 185                 190

Ala Ser Thr Ile Ile Lys Asn Gly Gly Gln Gln Ala Tyr Asp Phe Gly
        195                 200                 205

Thr Ala Ile Ile Arg Asp Gly Lys Ile Gln Pro Ser Asp Gly Ser Val
    210                 215                 220

Asp Trp Lys Ile His Ile Phe Ile Ala Asn Asp Lys Asp Asn Asn Leu
225                 230                 235                 240

Tyr Ala Ile Leu Ser Asp Thr Asn Ala Gly Tyr Asp Asn Ile Met Lys
                245                 250                 255

Ser Val Ser Asn Leu Lys Leu Gln Asn Met Leu Leu Leu Asp Ser Gly
            260                 265                 270

Gly Ser Ser Gln Leu Ser Val Asn Gly Lys Thr Ile Val Ala Ser Gln
        275                 280                 285

Asp Asp Arg Ala Val Pro Asp Tyr Ile Val Met Lys
    290                 295                 300
```

<210> SEQ ID NO 205
<211> LENGTH: 279
<212> TYPE: PRT
<213> ORGANISM: Lactococcus lactis

<400> SEQUENCE: 205

```
Met Ala Gln Thr Ile Gln Thr Leu Ala Leu Asn Val Arg Leu Ser Cys
1               5                   10                  15

Gln Leu Leu Asp Val Pro Glu Ser Ser Tyr Tyr Glu Arg Ile Asn Arg
            20                  25                  30

His Pro Ser Lys Thr Gln Leu Arg Arg Gln Tyr Leu Ser Leu Lys Ile
        35                  40                  45

Ser Gln Leu Phe Asn Ala Asn Arg Gly Ile Tyr Gly Ala Pro Lys Ile
    50                  55                  60

His His Leu Leu Leu Lys Gln Gly Glu Lys Val Gly Leu Lys Leu Val
65                  70                  75                  80

Gln Lys Leu Met Lys Gln Leu Gln Leu Lys Ser Val Val Ile Lys Lys
                85                  90                  95

Phe Lys Pro Gly Tyr Ser Leu Ser Asp His Ile Asn Arg Lys Asn Leu
            100                 105                 110

Ile Gln Thr Glu Pro Thr Lys Lys Asn Lys Val Trp Ser Thr Asp Ile
        115                 120                 125

Thr Tyr Ile Pro Thr Gln Gln Gly Trp Ala Tyr Leu Ser Thr Ile Met
    130                 135                 140

Asp Arg Tyr Thr Lys Lys Val Ile Ala Trp Asp Leu Gly Lys Arg Met
145                 150                 155                 160

Thr Val Glu Leu Val Gln Arg Thr Leu Asn Lys Ala Ile Lys Ser Gln
                165                 170                 175

Asp Tyr Pro Glu Ala Val Ile Leu His Ser Asp Gln Gly Ser Gln Tyr
            180                 185                 190

Thr Ser Leu Glu Tyr Glu Glu Leu Leu Lys Tyr Tyr Gly Met Thr His
        195                 200                 205

Ser Phe Ser Arg Arg Gly Tyr Pro Tyr His Asn Ala Ser Leu Glu Ser
    210                 215                 220

Trp His Gly His Leu Lys Arg Glu Trp Val Tyr Gln Phe Lys Tyr Lys
225                 230                 235                 240

Asn Phe Glu Glu Ala Tyr Gln Ser Ile Phe Trp Tyr Ile Glu Ala Phe
                245                 250                 255

Tyr Asn Ser Lys Arg Ile His Gln Ser Leu Gly Tyr Leu Thr Pro Asn
            260                 265                 270

Gln Phe Glu Lys Val Ser Ala
        275
```

<210> SEQ ID NO 206
<211> LENGTH: 189
<212> TYPE: PRT
<213> ORGANISM: Lactococcus lactis

<400> SEQUENCE: 206

```
Met Val Asp Ala Tyr Leu Asp Asn Asn Leu Gly Asp Asp Leu Met Ile
1               5                   10                  15

Arg Tyr Phe Ala Ser Tyr Phe Tyr Gln His Lys Ile Tyr Leu Val Glu
            20                  25                  30

Ser Arg Glu His Ile Arg Lys Thr Phe Tyr Asp Ile Pro Asn Ile Tyr
        35                  40                  45

Phe Tyr Ser Glu Glu Asp Tyr Lys Met Asn Glu Tyr Asp Phe Gln Leu
```

```
    50                  55                  60

His Val Thr Ile Gly Gly Ser Met Phe Ile Leu Asp Asp Phe Lys Lys
65                  70                  75                  80

Leu Ile Arg Phe Arg His Arg Ile Lys Asn Ser Arg Lys Ile Lys Lys
                85                  90                  95

Arg Asn Ile Pro Ser Ala Ile Ile Gly Cys Asn Leu Gly Pro Phe Asp
            100                 105                 110

Lys Arg Asn Phe Gly Leu Lys Leu Ala Lys Phe Glu Leu Lys Tyr Lys
        115                 120                 125

Asn Leu Val Thr Val Arg Asp Lys Gln Ser Lys Glu Leu Leu Leu Arg
    130                 135                 140

Gly Phe Lys Arg Lys Lys Ile Asn Ile Lys Leu Phe Pro Asp Ile Ile
145                 150                 155                 160

Phe Ser Lys Val Leu Tyr Lys Ser Ile Pro Lys Tyr Gly Leu Gly Met
                165                 170                 175

Thr Leu Ser Gln Val Phe Arg Val Thr Asn Val Glu Phe
            180                 185
```

<210> SEQ ID NO 207
<211> LENGTH: 337
<212> TYPE: PRT
<213> ORGANISM: Lactococcus lactis

<400> SEQUENCE: 207

```
Met Lys Asn Lys Phe Ser Ile Ile Val Pro Val Tyr Asn Gly Glu Ser
1               5                   10                  15

His Ile Lys Lys Cys Ile Asp Thr Leu Leu Lys Gln Thr Tyr Asn Asp
            20                  25                  30

Phe Glu Ile Ile Ile Ile Asn Asp Gly Ser Thr Asp Asp Thr Lys Ser
        35                  40                  45

Val Leu Thr Lys Phe Tyr Ala Lys Asn Leu Lys Val Lys Ile Val Asn
    50                  55                  60

Thr Ser Asn Lys Gly Val Ser Phe Ala Arg Asn Leu Gly Ile Asn Gln
65                  70                  75                  80

Ser Ser Gly Gln Tyr Leu Leu Phe Val Asp Ser Asp Asp Glu Leu Ser
                85                  90                  95

Ile Asn Ala Leu Lys Tyr Leu Ser Ile Met Leu Asn Lys Lys Asp Arg
            100                 105                 110

Asp Leu Ile Leu Phe Gly Phe Ser Leu Thr Gly Asp Asn Asn Arg Lys
        115                 120                 125

Asn Asp Thr Ser Ile Leu Lys Ser Ile Ala Asn Gln Asn Thr Asp Cys
    130                 135                 140

Lys Met Asn Ile Leu Lys Ser Ile Leu Ser Thr Lys Asn Asn Ile Leu
145                 150                 155                 160

Gly Tyr Val Trp Arg Ala Val Tyr Ser Leu Asp Phe Ile Lys Lys Asn
                165                 170                 175

Asn Ile Phe Phe Glu Thr His Leu Lys Ile Ser Glu Asp Tyr Leu Phe
            180                 185                 190

Leu Leu Gln Ser Val Glu His Ser Asn Asn Leu Phe Val Ile Thr Glu
        195                 200                 205

Glu Phe Tyr Lys Tyr Asn Leu Gly Glu Thr Ser Met Ser Asn Lys Phe
    210                 215                 220

Val Pro Thr Leu Leu Asn Asp Met Val Trp Val Asn Asn Trp Ile Glu
225                 230                 235                 240
```

Ser Asn Ile Leu Thr Val Tyr Pro Gln Phe Phe Val Gly Phe Asn Cys
245 250 255

Leu Val Ala Asn Thr Tyr Ile Arg Tyr Val Gln Asn Ala Ile Arg Asn
260 265 270

Lys Glu Glu Asn Phe Met Leu Lys Tyr Arg Glu Ile Lys Ile Asn Lys
275 280 285

Arg Lys Tyr Asn Phe Gln Arg Ser Ile Asn Gln Val Ile Phe His Leu
290 295 300

Asp Lys Phe Asp Phe Lys Ser Lys Ile Gly Val Ile Leu Phe Arg Ile
305 310 315 320

His Leu Asp Ile Val Tyr Glu Leu Leu Phe Asn Ile Lys Glu Arg Lys
325 330 335

Asn

<210> SEQ ID NO 208
<211> LENGTH: 384
<212> TYPE: PRT
<213> ORGANISM: Lactococcus lactis

<400> SEQUENCE: 208

Met Thr Asn Leu Asn Arg Lys Lys Phe Phe Ile Asn Phe Gln Ser Leu
1 5 10 15

Val Phe Phe Ile Leu Ile Ile Ile Tyr Gly Leu Thr Thr Lys Asn Val
20 25 30

Met Gly Gly Ser Gly Ile Phe Ser Ile Asp Ser Ile Leu Lys Tyr Gly
35 40 45

Ile Leu Phe Ile Cys Ile Ser Val Glu Gly Tyr Ile Phe Leu Lys Asn
50 55 60

Gly Asn Glu Arg Arg Glu Thr Ser Glu Asn Tyr Asn Asn Phe Lys Tyr
65 70 75 80

Tyr Phe Ile Ile Ile Thr Phe Leu Ser Leu Phe Ala Ser Phe Lys Gln
85 90 95

Val His Phe Ser Phe Arg Thr Val Gln Ser Phe Ile Phe Ile Phe Ile
100 105 110

Pro Met Leu Tyr Ser Tyr Leu Ile Leu Asn Asn Trp Thr Phe Arg Gln
115 120 125

Ile Asn Phe Ser Met Lys Ile Ala Leu Phe Leu Ser Val Ile Glu Tyr
130 135 140

Leu Phe Ser Ile Arg Met Gly Phe Ser Gln Ile Ile Ser Ser Leu Ala
145 150 155 160

Ser Ile Asn Tyr Asn Asn Thr Asn Ala Ser Ala Leu Glu Ser Ser Thr
165 170 175

Phe Ala Leu Leu Ser Leu Gly Phe Ala Ala Tyr Phe Gly Tyr Tyr Lys
180 185 190

Lys Asn Phe Leu Cys Lys Ile Val Ser Leu Leu Phe Val Ile Met Thr
195 200 205

Phe Lys Arg Val Ile Thr Leu Ser Gly Cys Ile Leu Val Ile Leu Gly
210 215 220

Ile Leu Lys Ile Lys Asn Leu Arg Val Asn Arg Phe Phe Leu Ile Val
225 230 235 240

Ser Thr Ile Thr Leu Val Ser Phe Ser Leu Ile Tyr Tyr Tyr Ser Ile
245 250 255

Gln Pro Gln Asn Ile Leu Glu Ile Ser Glu Lys Ile Gly Phe Ser Ile
260 265 270

```
Arg Asp Phe Ser Thr Asn Arg Thr Asp Arg Leu Ala Trp Leu Ser Met
        275                 280                 285

Thr Asp Phe Lys Ser Tyr Gly Leu Gly Ser Thr Thr Asp Phe Met Tyr
    290                 295                 300

Lys Leu Trp Gly Val Asp Leu Glu Met Asp Ile Val Gln Leu Ile Leu
305                 310                 315                 320

Glu Val Gly Ala Phe Gly Val Ile Val Phe Ile Tyr Phe Tyr Leu Arg
                325                 330                 335

Phe Ser Lys Ser Asn Leu Tyr Ala Phe Ser Phe Met Ala Leu Leu Leu
            340                 345                 350

Leu Asn Ser Ile Leu Ser Ser Gly Met Met Ser Thr Phe Ser Trp Ile
        355                 360                 365

Ile Ile Leu Ile Ala Met Ser Thr Ile Met Glu Tyr Lys Glu Gly Met
    370                 375                 380


<210> SEQ ID NO 209
<211> LENGTH: 245
<212> TYPE: PRT
<213> ORGANISM: Lactococcus lactis

<400> SEQUENCE: 209

Met Lys Lys Leu Lys Ile Ser Val Ile Ile Arg Thr Tyr Asn Glu Val
1               5                   10                  15

Lys His Ile Gly Glu Val Leu Lys Ser Leu Thr Asp Gln Thr Tyr Leu
            20                  25                  30

Asn His Glu Ile Ile Ile Val Asp Ser Gly Ser Val Asp Gly Thr Leu
        35                  40                  45

Asp Ile Ile Glu Arg Tyr Pro Val Lys Leu Val Ser Ile Asn Lys Glu
    50                  55                  60

Asp Phe Asn Tyr Ser Tyr Ala Ser Asn Val Gly Val Gln Asn Ser Ser
65                  70                  75                  80

Gly Asp Ile Val Cys Phe Leu Ser Gly His Ser Val Pro Val Tyr Lys
                85                  90                  95

Asn Tyr Leu Glu Lys Ile Asn Glu Ile Phe Gln Glu Thr Glu Ile Gly
            100                 105                 110

Ala Cys Tyr Gly Glu Val Ile Ala Leu Pro Asp Gly Ser Ile Thr Glu
        115                 120                 125

Lys Ile Phe Asn Arg Ile Gly Tyr Leu Lys Ser Lys Leu Ser Leu Asn
    130                 135                 140

Asn Lys Arg Phe Phe Leu Glu Asn Lys Ile His Pro Gly Ile Phe Ser
145                 150                 155                 160

Cys Ser Asn Ala Cys Ala Arg Lys Lys Leu Leu Leu Lys Tyr Pro Phe
                165                 170                 175

Lys Val Glu Leu Gly His Gly Gly Glu Asp Val Glu Val Ala Tyr Arg
            180                 185                 190

Ile Ile Gln Asp Gly Tyr Phe Val Ala Lys Ser Val Glu Leu Leu Val
        195                 200                 205

Met His Ser His Gly Ser Ser Leu Lys Lys Phe Ile Lys Glu Tyr Lys
    210                 215                 220

Ala Trp Gly Lys Met Tyr Glu Asp Val Leu Lys Phe Ile Lys Lys Asn
225                 230                 235                 240

Asn Asp Lys Ser Gln
                245


<210> SEQ ID NO 210
```

<211> LENGTH: 161
<212> TYPE: PRT
<213> ORGANISM: Lactococcus lactis

<400> SEQUENCE: 210

Met Ile Phe Val Thr Val Gly Thr His Glu Gln Pro Phe Asn Arg Leu
1 5 10 15

Ile Gln Lys Ile Asp Glu Leu Val Arg Asp Gly Gln Ile Lys Asp Asp
20 25 30

Val Phe Met Gln Ile Gly Tyr Ser Thr Tyr Glu Pro Lys Tyr Thr Lys
35 40 45

Trp Ala Ser Val Ile Gly Tyr Asn Asp Met Thr Ala Tyr Phe Asn Lys
50 55 60

Ala Asp Ile Val Ile Thr His Gly Gly Pro Ser Thr Tyr Met Gln Val
65 70 75 80

Leu Gln His Gly Lys Ile Pro Ile Val Val Pro Arg Gln Glu Lys Phe
85 90 95

Gly Glu His Ile Asn Asp His Gln Leu Arg Val Ser Lys Gln Val Ile
100 105 110

Lys Lys Gly Tyr Pro Leu Ile Leu Cys Glu Asp Val Ser Ala Leu Lys
115 120 125

Ile Cys Ile Glu Ser Ser Arg Ile Arg Thr Asp Glu Phe Ile Lys Ser
130 135 140

Asn Asn Lys Asn Phe Ile Ser Asn Phe Lys Lys Ile Ile Ala Phe Glu
145 150 155 160

Glu

<210> SEQ ID NO 211
<211> LENGTH: 149
<212> TYPE: PRT
<213> ORGANISM: Lactococcus lactis

<400> SEQUENCE: 211

Met Lys Ile Ala Leu Val Gly Ser Ser Gly Gly His Leu Thr His Leu
1 5 10 15

Tyr Leu Leu Lys Lys Phe Trp Glu Asn Glu Asp Arg Phe Trp Val Thr
20 25 30

Phe Asp Lys Thr Asp Ala Lys Ser Ile Leu Lys Glu Glu Arg Phe Tyr
35 40 45

Pro Cys Tyr Tyr Pro Thr Asn Arg Asn Val Lys Asn Thr Ile Lys Asn
50 55 60

Thr Ile Leu Ala Phe Lys Ile Leu Arg Lys Glu Lys Pro Asp Leu Ile
65 70 75 80

Ile Ser Ser Gly Ala Ala Val Ala Val Pro Phe Phe Trp Ile Gly Lys
85 90 95

Leu Phe Gly Ala Lys Thr Val Tyr Ile Glu Ile Phe Asp Arg Ile Asp
100 105 110

Lys Pro Thr Leu Thr Gly Lys Leu Val Tyr Pro Val Thr Asp Lys Phe
115 120 125

Ile Val Gln Trp Glu Glu Leu Lys Lys Val Tyr Pro Lys Ala Ile Asn
130 135 140

Leu Gly Gly Ile Phe
145

<210> SEQ ID NO 212
<211> LENGTH: 228

<212> TYPE: PRT
<213> ORGANISM: Lactococcus lactis

<400> SEQUENCE: 212

Met Glu Phe Phe Glu Asp Ala Ser Ser Pro Glu Ser Glu Glu Pro Lys
1               5                   10                  15

Leu Val Glu Leu Lys Asn Phe Ser Tyr Arg Glu Leu Ile Ile Lys Arg
            20                  25                  30

Ala Ile Asp Ile Leu Gly Gly Leu Ala Gly Ser Val Leu Phe Leu Ile
        35                  40                  45

Ala Ala Ala Leu Leu Tyr Val Pro Tyr Lys Met Ser Ser Lys Lys Asp
    50                  55                  60

Gln Gly Pro Met Phe Tyr Lys Gln Lys Arg Tyr Gly Lys Asn Gly Lys
65                  70                  75                  80

Ile Phe Tyr Ile Leu Lys Phe Arg Thr Met Ile Phe Asn Ala Glu Gln
                85                  90                  95

Tyr Leu Glu Leu Asn Pro Asp Val Lys Ala Ala Tyr His Ala Asn Gly
            100                 105                 110

Asn Lys Leu Glu Asn Asp Pro Arg Val Thr Lys Ile Gly Ser Phe Ile
        115                 120                 125

Arg Arg His Ser Ile Asp Glu Leu Pro Gln Phe Ile Asn Val Leu Lys
    130                 135                 140

Gly Asp Met Ala Leu Val Gly Pro Arg Pro Ile Leu Leu Phe Glu Ala
145                 150                 155                 160

Lys Glu Tyr Gly Glu Arg Leu Ser Tyr Leu Leu Met Cys Lys Pro Gly
                165                 170                 175

Ile Thr Gly Tyr Trp Thr Thr His Gly Arg Ser Lys Val Leu Phe Pro
            180                 185                 190

Gln Arg Ala Asp Leu Glu Leu Tyr Tyr Leu Gln Tyr His Ser Thr Lys
        195                 200                 205

Asn Asp Ile Lys Leu Leu Ser Leu Thr Ile Val Gln Ser Ile Asn Gly
    210                 215                 220

Ser Asp Ala Tyr
225

<210> SEQ ID NO 213
<211> LENGTH: 254
<212> TYPE: PRT
<213> ORGANISM: Lactococcus lactis

<400> SEQUENCE: 213

Met Ile Asp Ile His Cys His Ile Leu Pro Gly Ile Asp Asp Gly Ala
1               5                   10                  15

Lys Thr Ser Gly Asp Thr Leu Thr Met Leu Lys Ser Ala Ile Asp Glu
            20                  25                  30

Gly Ile Thr Thr Ile Thr Ala Thr Pro His His Asn Pro Gln Phe Asn
        35                  40                  45

Asn Glu Ser Pro Leu Ile Leu Lys Lys Val Lys Glu Val Gln Asn Ile
    50                  55                  60

Ile Asp Glu His Gln Leu Pro Ile Glu Val Leu Pro Gly Gln Glu Val
65                  70                  75                  80

Arg Ile Tyr Gly Asp Leu Leu Lys Glu Phe Ser Glu Gly Lys Leu Leu
                85                  90                  95

Thr Ala Ala Gly Thr Ser Ser Tyr Ile Leu Ile Glu Phe Pro Ser Asn
            100                 105                 110

```
His Val Pro Ala Tyr Ala Lys Glu Leu Phe Tyr Asn Ile Lys Leu Glu
        115                 120                 125

Gly Leu Gln Pro Ile Leu Val His Pro Glu Arg Asn Ser Gly Ile Ile
    130                 135                 140

Glu Asn Pro Asp Ile Leu Phe Asp Phe Ile Glu Gln Gly Val Leu Ser
145                 150                 155                 160

Gln Ile Thr Ala Ser Ser Val Thr Gly His Phe Gly Lys Lys Ile Gln
                165                 170                 175

Lys Leu Ser Phe Lys Met Ile Glu Asn His Leu Thr His Phe Val Ala
            180                 185                 190

Ser Asp Ala His Asn Val Thr Ser Arg Ala Phe Lys Met Lys Glu Ala
        195                 200                 205

Phe Glu Ile Ile Glu Asp Ser Tyr Gly Ser Asp Val Ser Arg Met Phe
    210                 215                 220

Gln Asn Asn Ala Glu Ser Val Ile Leu Asn Glu Ser Phe Tyr Gln Glu
225                 230                 235                 240

Lys Pro Thr Lys Ile Lys Thr Lys Lys Leu Leu Gly Leu Phe
                245                 250


<210> SEQ ID NO 214
<211> LENGTH: 231
<212> TYPE: PRT
<213> ORGANISM: Lactococcus lactis

<400> SEQUENCE: 214

Met Ala Lys Asn Lys Arg Ser Ile Asp Asn Asn Arg Tyr Ile Ile Thr
1               5                   10                  15

Ser Val Asn Pro Gln Ser Pro Ile Ser Glu Gln Tyr Arg Thr Ile Arg
            20                  25                  30

Thr Thr Ile Asp Phe Lys Met Ala Asp Gln Gly Ile Lys Ser Phe Leu
        35                  40                  45

Val Thr Ser Ser Glu Ala Ala Ala Gly Lys Ser Thr Val Ser Ala Asn
    50                  55                  60

Ile Ala Val Ala Phe Ala Gln Gln Gly Lys Lys Val Leu Leu Ile Asp
65                  70                  75                  80

Gly Asp Leu Arg Lys Pro Thr Val Asn Ile Thr Phe Lys Val Gln Asn
                85                  90                  95

Arg Val Gly Leu Thr Asn Ile Leu Met His Gln Ser Ser Ile Glu Asp
            100                 105                 110

Ala Ile Gln Gly Thr Arg Leu Ser Glu Asn Leu Thr Ile Ile Thr Ser
        115                 120                 125

Gly Pro Ile Pro Pro Asn Pro Ser Glu Leu Leu Ala Ser Ser Ala Met
    130                 135                 140

Lys Asn Leu Ile Asp Ser Val Ser Asp Phe Phe Asp Val Val Leu Ile
145                 150                 155                 160

Asp Thr Pro Pro Leu Ser Ala Val Thr Asp Ala Gln Ile Leu Ser Ser
                165                 170                 175

Tyr Val Gly Gly Val Val Leu Val Val Arg Ala Tyr Glu Thr Lys Lys
            180                 185                 190

Glu Ser Leu Ala Lys Thr Lys Lys Met Leu Glu Gln Val Asn Ala Asn
        195                 200                 205

Ile Leu Gly Val Val Leu His Gly Val Asp Ser Ser Asp Ser Pro Ser
    210                 215                 220

Tyr Tyr Tyr Tyr Gly Val Glu
225                 230
```

<210> SEQ ID NO 215
<211> LENGTH: 225
<212> TYPE: PRT
<213> ORGANISM: Lactococcus lactis

<400> SEQUENCE: 215

```
Met Gln Glu Thr Gln Glu Gln Thr Ile Asp Leu Arg Gly Ile Phe Lys
1               5                   10                  15

Ile Ile Arg Lys Arg Leu Ser Leu Ile Leu Phe Ser Ala Leu Ile Val
            20                  25                  30

Thr Ile Leu Gly Ser Ile Tyr Thr Phe Phe Ile Ala Ser Pro Val Tyr
        35                  40                  45

Thr Ala Ser Thr Gln Leu Val Val Lys Leu Pro Asn Ser Asp Asn Ser
    50                  55                  60

Asp Ala Tyr Ala Gly Gln Val Ser Gly Asn Ile Gln Met Ala Asn Thr
65                  70                  75                  80

Ile Asn Gln Val Ile Val Ser Pro Val Ile Leu Asp Lys Val Gln Ser
                85                  90                  95

Asn Leu Asn Leu Ser Asp Asp Ser Phe Gln Lys Gln Val Thr Ala Ala
            100                 105                 110

Asn Gln Thr Asn Ser Gln Val Ile Thr Leu Thr Val Lys Tyr Ser Asn
        115                 120                 125

Pro Tyr Ile Ala Gln Lys Ile Ala Asp Glu Thr Ala Lys Ile Phe Ser
    130                 135                 140

Ser Asp Ala Ala Lys Leu Leu Asn Val Thr Asn Val Asn Ile Leu Ser
145                 150                 155                 160

Lys Ala Lys Ala Gln Thr Thr Pro Ile Ser Pro Lys Pro Lys Leu Tyr
                165                 170                 175

Leu Ala Ile Ser Val Ile Ala Gly Leu Val Leu Gly Leu Ala Ile Ala
            180                 185                 190

Leu Leu Lys Glu Leu Phe Asp Asn Lys Ile Asn Lys Glu Glu Asp Ile
        195                 200                 205

Glu Ala Leu Gly Leu Thr Val Leu Gly Val Thr Ser Leu Cys Ser Asn
    210                 215                 220

Glu
225
```

<210> SEQ ID NO 216
<211> LENGTH: 255
<212> TYPE: PRT
<213> ORGANISM: Lactococcus lactis

<400> SEQUENCE: 216

```
Met Met Lys Lys Gly Ile Phe Val Ile Thr Ile Val Ile Ser Ile Ala
1               5                   10                  15

Leu Ile Ile Gly Gly Phe Tyr Ser Tyr Asn Ser Arg Ile Asn Asn Leu
            20                  25                  30

Ser Lys Ala Asp Lys Gly Lys Glu Val Val Lys Asn Ser Ser Glu Lys
        35                  40                  45

Asn Gln Ile Asp Leu Thr Tyr Lys Lys Tyr Tyr Lys Asn Leu Pro Lys
    50                  55                  60

Ser Val Gln Asn Lys Ile Asp Asp Ile Ser Ser Lys Asn Lys Glu Val
65                  70                  75                  80

Thr Leu Thr Cys Ile Trp Gln Ser Asp Ser Val Ile Ser Glu Gln Phe
                85                  90                  95
```

```
Gln Gln Asn Leu Gln Lys Tyr Tyr Gly Asn Lys Phe Trp Asn Ile Lys
            100                 105                 110

Asn Ile Thr Tyr Asn Gly Glu Thr Ser Glu Gln Leu Leu Ala Glu Lys
        115                 120                 125

Val Gln Asn Gln Val Leu Ala Thr Asn Pro Asp Val Val Leu Tyr Glu
    130                 135                 140

Ala Pro Leu Phe Asn Asp Asn Gln Asn Ile Glu Ala Thr Ala Ser Trp
145                 150                 155                 160

Thr Ser Asn Glu Gln Leu Ile Thr Asn Leu Ala Ser Thr Gly Ala Glu
                165                 170                 175

Val Ile Val Gln Pro Ser Pro Pro Ile Tyr Gly Gly Val Val Tyr Pro
            180                 185                 190

Val Gln Glu Glu Gln Phe Lys Gln Ser Leu Ser Thr Lys Tyr Pro Tyr
        195                 200                 205

Ile Asp Tyr Trp Ala Ser Tyr Pro Asp Lys Asn Ser Asp Glu Met Lys
    210                 215                 220

Gly Leu Phe Ser Asp Asp Gly Val Tyr Arg Thr Leu Asn Ala Ser Gly
225                 230                 235                 240

Asn Lys Val Trp Leu Asp Tyr Ile Thr Lys Tyr Phe Thr Ala Asn
                245                 250                 255


<210> SEQ ID NO 217
<211> LENGTH: 105
<212> TYPE: PRT
<213> ORGANISM: Lactococcus lactis

<400> SEQUENCE: 217

Met Asn Asn Leu Phe Tyr His Arg Leu Lys Glu Leu Val Glu Ser Ser
1               5                   10                  15

Gly Lys Ser Ala Asn Gln Ile Glu Arg Glu Leu Gly Tyr Pro Arg Asn
            20                  25                  30

Ser Leu Asn Asn Tyr Lys Leu Gly Gly Glu Pro Ser Gly Thr Arg Leu
        35                  40                  45

Ile Gly Leu Ser Glu Tyr Phe Asn Val Ser Pro Lys Tyr Leu Met Gly
    50                  55                  60

Ile Ile Asp Glu Pro Asn Asp Ser Ser Ala Ile Asn Leu Phe Lys Thr
65                  70                  75                  80

Leu Thr Gln Glu Glu Lys Lys Glu Met Phe Ile Ile Cys Gln Lys Trp
                85                  90                  95

Leu Phe Leu Glu Tyr Gln Ile Glu Leu
            100                 105


<210> SEQ ID NO 218
<211> LENGTH: 191
<212> TYPE: PRT
<213> ORGANISM: Lactococcus lactis

<400> SEQUENCE: 218

Met Ser Val Ser Ile Ile Asp Ser Phe Pro Ile Pro Leu Cys Gln Pro
1               5                   10                  15

Ile Arg Asn Phe Arg Ser Lys Gly Leu Gly Asp Tyr Ala Asn Val Gly
            20                  25                  30

Tyr Asn Ala Thr Lys Gly Gln Tyr Phe Tyr Gly Cys Lys Cys His Ala
        35                  40                  45

Leu Val Ser Glu Ser Gly Tyr Val Ile Asp Tyr Thr Ile Thr Pro Ala
    50                  55                  60
```

Ser Met Ala Asp Ser Ser Met Thr Glu Glu Val Leu Ser Gln Phe Gly
65 70 75 80

Thr Pro Thr Val Leu Gly Asp Met Gly Tyr Leu Gly Gln Ser Leu His
85 90 95

Asp Arg Leu Glu Leu Lys Gly Ile Asp Leu Met Thr Pro Val Arg Lys
100 105 110

Asn Met Lys Gln Lys Lys Ile Leu Phe Pro Asn Phe Ser Lys Arg Arg
115 120 125

Lys Val Ile Glu Arg Val Phe Ser Phe Leu Thr Asn Leu Gly Ala Glu
130 135 140

Arg Cys Lys Ser Arg Ser Pro Gln Gly Phe Gln Leu Lys Leu Glu Met
145 150 155 160

Ile Leu Leu Ala Tyr Ser Leu Leu Leu Lys Ser Ala Lys Ser Leu Glu
165 170 175

Pro Glu Thr Leu Arg Tyr Ser Ile Gly Tyr Gln Val Met Ala Lys
180 185 190

<210> SEQ ID NO 219
<211> LENGTH: 127
<212> TYPE: PRT
<213> ORGANISM: Lactococcus lactis

<400> SEQUENCE: 219

Met Thr Ile Lys Asn Lys Lys Asp Leu Ser Ser Ser Ile Glu Gln Leu
1 5 10 15

Glu Lys Ala Ile Asn Gln Gln Glu Thr Ile Leu Lys Lys Phe Asp Asn
20 25 30

Glu Gln Leu Asp Phe Glu Gln Ile Lys Lys Leu Glu Asn Leu Leu Ile
35 40 45

Gln Glu Arg Glu Lys Ala Lys Gln Val Gln Ile Lys Ile Asn Arg Ser
50 55 60

Val Leu Gln Asn Asn Ser Glu Asn Tyr Lys Glu Arg Lys Lys Arg Thr
65 70 75 80

Arg Gln Leu Ile Gln Lys Gly Ala Leu Leu Glu Lys Tyr Leu Glu Ala
85 90 95

Lys His Leu Thr Val Asp Glu Thr Glu Gln Leu Leu Gln Ile Phe Ala
100 105 110

Asn Met Ile Asn Lys Pro Glu Leu Leu Val Asn Phe Ile Gly Lys
115 120 125

<210> SEQ ID NO 220
<211> LENGTH: 196
<212> TYPE: PRT
<213> ORGANISM: Lactococcus lactis

<400> SEQUENCE: 220

Met Val Gln Gln Ile Val Leu Pro Ile Lys Asp Ser Asn Ile Leu Lys
1 5 10 15

Met Val Gln Asp Thr Leu Leu Asp Ser Phe Arg Ala Gly Arg Arg Asn
20 25 30

Tyr Thr Ile Phe Gln Val Gly Lys Ala Thr Leu Leu Arg Val Ser Asp
35 40 45

Val Met Lys Leu Lys Lys Thr Asp Val Phe Asn Ser Asp Gly Thr Val
50 55 60

Lys Gln Thr Ala Phe Ile His Asp Gln Lys Thr Gly Lys Ala Asn Thr
65 70 75 80

Leu Tyr Leu Lys Pro Val Gln Gln Asp Leu Val Val Tyr His Asp Trp
85 90 95

Met Val Gln Gln Asn Leu Asn Ser Glu Trp Leu Phe Pro Ser Thr Ser
100 105 110

Arg Pro Asp Arg Pro Ile Thr Glu Lys Gln Phe Tyr Lys Ile Met Ala
115 120 125

Arg Val Gly Asp Leu Leu Ser Ile Asn Tyr Leu Gly Thr His Thr Met
130 135 140

Arg Lys Thr Gly Ala Tyr Arg Val Tyr Thr Gln Ser Asn Tyr Asn Ile
145 150 155 160

Gly Leu Val Ile His Leu Leu Asn His Ser Ser Glu Ala Met Thr Leu
165 170 175

Thr Tyr Leu Gly Leu Asp Gln Ala Ser Arg Glu Thr Met Leu Asp Gln
180 185 190

Ile Asp Phe Gly
195

<210> SEQ ID NO 221
<211> LENGTH: 121
<212> TYPE: PRT
<213> ORGANISM: Lactococcus lactis

<400> SEQUENCE: 221

Met Asp Gln Lys Glu Val Ser Gln Asn Gln Thr Lys Tyr Ile Gln Phe
1 5 10 15

Arg Leu Ser Glu Glu Gln Tyr Asn Lys Leu Lys Ile Ser Gly Glu Thr
20 25 30

Tyr Gly Leu Ser Pro Asn Leu Tyr Ala Lys Lys Leu Ala Gln Lys Ser
35 40 45

His Leu Lys Lys Pro Tyr Leu Glu His Asp Gln Ala Lys Ser Leu Leu
50 55 60

Leu Glu Leu Ser Lys Gln Gly Thr Asn Leu Asn Gln Ile Ala Lys Lys
65 70 75 80

Leu Asn Gln Phe Asp Arg Met Asp Asn Gln Asp Lys Glu Leu Ile Glu
85 90 95

Ala Leu Arg Tyr Thr Tyr Gly Val Leu Ala Gln Ala Gln Lys Gly Tyr
100 105 110

Gln Glu Leu Trp Gln Gln Leu Gln Lys
115 120

<210> SEQ ID NO 222
<211> LENGTH: 410
<212> TYPE: PRT
<213> ORGANISM: Lactococcus lactis

<400> SEQUENCE: 222

Met Ala Thr Ile Ala Lys Ile Ser Asn Gly Ala Ser Ala Ala Ser Ala
1 5 10 15

Leu Asn Tyr Ala Leu Gly Gln Asp Arg Pro Met His Glu Lys Thr Glu
20 25 30

Gln Trp Leu Gln Asp His Gln Leu Glu Arg Pro Val Glu Leu Thr Asn
35 40 45

Cys Arg Ala Val Ala Val Gly Gly Thr Asn Gly Ile Asp Pro Phe Ile
50 55 60

Ala Lys Glu Gln Phe Asp Val Val Arg Gln Leu His Asn Gln Thr Lys
65 70 75 80

```
Glu Ser Asn Gln Val Met Arg Ile Thr Gln Ser Phe Ala Leu Asp Glu
                85                  90                  95

Leu Asn Pro Lys Val Gln Lys Asp Trp Gln Lys Ala Asn Asp Leu Gly
            100                 105                 110

Val Glu Leu Ala Glu Asn Leu Tyr Pro Asn His Gln Ser Ala Val Tyr
        115                 120                 125

Thr His Leu Asp Gly Lys Asn His Val Leu His Asn His Ile Ile Val
    130                 135                 140

Asn Lys Val Asn Leu Glu Thr Gly Lys Lys Leu Arg Glu Gln Lys Gly
145                 150                 155                 160

Glu Ser Val Gln Arg Ala Arg Glu Met Asn Asp Arg Leu Ala Ser Arg
                165                 170                 175

Glu Asn Trp His Ile Leu Glu Pro Pro Lys Glu Arg Gln Thr Glu Thr
            180                 185                 190

Glu Lys Glu Leu Ile Ala Lys Asn Glu Tyr Ser Tyr Met Asp Asp Leu
        195                 200                 205

Arg Glu Arg Ile Asn Lys Ser Leu Gln Asp Val Ser Val Ser Ser Tyr
    210                 215                 220

Glu Thr Phe Lys Glu Arg Leu Ser Asp Asn Gly Val Ile Leu Ser Glu
225                 230                 235                 240

Arg Gly Gln Thr Phe Ser Tyr Ala Phe Leu Asp Ala Asn Asn Lys Gln
                245                 250                 255

Arg Arg Ala Arg Glu Thr Arg Leu Gly Ser Asp Phe Gly Lys Glu Thr
            260                 265                 270

Ile Leu His Glu Leu Glu Asn Arg Ala Arg Gln Asn Glu Phe Ser Ala
        275                 280                 285

Val Glu Gln Arg Glu Pro Ala Ile Thr Pro Leu Glu Arg Asp Thr Gln
    290                 295                 300

Gln Arg Glu Ser Glu Ile Val Ser Leu Glu Gln Ala Ile Glu Pro Arg
305                 310                 315                 320

Lys Ser Glu Ala Leu Lys Arg Glu Ser Lys Ile Asn Arg Phe Ile Asp
                325                 330                 335

Thr Ile Lys Gln Phe Ala Gly Arg Val Pro Glu Leu Thr Gln Arg Val
            340                 345                 350

Thr Arg Lys Leu Lys Gln Thr Lys Asp Lys Ile Leu Asp Asp Phe Glu
        355                 360                 365

Arg Arg Phe Ser Lys Asp Met Lys Asn Tyr Glu Gln Glu Gln Gln Lys
    370                 375                 380

Ser Leu Glu Lys Gln Ala Asn Arg Asp Val Gln Ser Glu Lys Lys Pro
385                 390                 395                 400

Thr Lys Asp His Asp Arg Gly Met Ser Arg
                405                 410


<210> SEQ ID NO 223
<211> LENGTH: 207
<212> TYPE: PRT
<213> ORGANISM: Lactococcus lactis

<400> SEQUENCE: 223

Met Asn Lys Asp Glu Gln Leu Val Val Gln Val Leu Asn Ala Tyr Lys
1               5                   10                  15

Asn Gly Lys Ile Asp Phe Ser Asn Val Pro Glu Leu Asp Arg Leu Val
            20                  25                  30

Arg Gln Glu Val Asn Lys Asp Phe Arg Asp Tyr Gln Glu Lys Ile Glu
```

```
        35                  40                  45

Ala Val Ala Asn Gln Lys Ile Glu Ser Ala Ile Gln Glu Gln Leu His
    50                  55                  60

Arg Leu Glu Ala Glu Asn Leu Lys Ala Thr Ile Leu Lys Asp Ile Gln
65                  70                  75                  80

Val Glu Lys Gln Ala Leu Leu Ala Leu Lys Lys Glu Leu Asn Glu Gln
                85                  90                  95

Lys Glu Gln Ile Lys Ala Asp Arg Lys Arg Glu Ile Val Glu Arg Tyr
            100                 105                 110

Gly Ile Leu Ile Ala Asn Ile Val Cys Leu Phe Cys Phe Leu Val Val
        115                 120                 125

Gly Ile Leu Ile Gly Arg Trp Ile Tyr Lys Gly Ile Trp Asp Gly Trp
    130                 135                 140

Gly Leu His Ile Leu Tyr Asp Thr Val Met Glu Ile Lys Pro Lys His
145                 150                 155                 160

Pro Tyr Gly Ala Val Ile Leu Gly Leu Gly Gly Phe Gly Leu Ile Gly
                165                 170                 175

Ala Gly Ile Tyr Gly Ser Phe Arg Leu Met Tyr Thr Ala Ser Thr Trp
            180                 185                 190

Phe Asp Gln Arg Pro Lys Ile Phe Lys Arg Ile Phe Pro Lys Lys
        195                 200                 205


<210> SEQ ID NO 224
<211> LENGTH: 200
<212> TYPE: PRT
<213> ORGANISM: Lactococcus lactis

<400> SEQUENCE: 224

Met Val Leu Asp Asn Lys Leu Gly Leu Thr Asn Ser Ala Glu Leu Ala
1               5                   10                  15

Lys Gln Glu Glu Leu Leu Thr Lys Lys Arg Ala Lys Glu Leu Phe Glu
            20                  25                  30

Ser Gly Lys Ile Glu Asp Leu Glu Ile Gly Thr Phe Gln Gly Leu Ser
        35                  40                  45

Asp Ile His Gln Phe Leu Phe Gln Asp Ile Tyr Asp Phe Ala Gly Lys
    50                  55                  60

Ile Arg Glu Val Asn Ile Ala Lys Gly Asn Phe Gln Phe Ala Pro Arg
65                  70                  75                  80

Ile Phe Leu Ala Gln Thr Leu Glu Tyr Ile Asp Lys Leu Pro Gln Glu
                85                  90                  95

Thr Phe Asp Glu Ile Ile Asp Lys Tyr Ser Asp Met Asn Val Ala His
            100                 105                 110

Pro Phe Arg Glu Gly Asn Gly Arg Ala Thr Arg Ile Trp Leu Asp Leu
        115                 120                 125

Ile Leu Lys Asn Lys Leu His Lys Ile Val Asp Trp Asn Gln Ile Asp
    130                 135                 140

Lys Asp Glu Tyr Leu Asn Ala Met Ile Arg Ser Thr Val Ser Thr Asn
145                 150                 155                 160

Glu Leu Lys Tyr Leu Ile Gln Lys Ala Leu Thr Asp Asp Leu Gly Lys
                165                 170                 175

Glu Gln Phe Phe Lys Gly Ile Asp Ala Ser Tyr Tyr Tyr Glu Gly Tyr
            180                 185                 190

Tyr Glu Ile Lys Thr Glu Asp Leu
        195                 200
```

<210> SEQ ID NO 225
<211> LENGTH: 383
<212> TYPE: PRT
<213> ORGANISM: Lactococcus lactis

<400> SEQUENCE: 225

Met Ser Ile Ile Thr Glu Phe Glu Lys Asn Gln Lys Gln Val Lys Ala
1 5 10 15

Leu Asn Glu Leu Ser Lys Arg Lys Val Val Glu His Asn Ser Leu Ile
20 25 30

Thr Ser Ile Ala Lys Met Asp Lys Thr Pro Leu Lys Met Phe Glu Leu
35 40 45

Ala Val Ser Cys Ile Asn Thr Glu Ala Pro Pro Lys Asp His Thr Val
50 55 60

Tyr Leu Ser Lys Thr Glu Leu Phe Ala Phe Phe Lys Val Ser Asp Asn
65 70 75 80

Asp Lys His Ser Arg Phe Lys Gln Ala Val Glu Asn Met Gln Lys Gln
85 90 95

Ala Phe Phe Lys Ile Gln Glu Lys Lys Glu Tyr Gly Phe Glu Phe Glu
100 105 110

Asn Ile Val Pro Ile Pro Tyr Val Lys Trp Ala Asp Tyr His Asp Glu
115 120 125

Val Thr Ile Arg Phe Ser Pro Glu Ile Met Pro Tyr Leu Ile Asn Leu
130 135 140

Lys Gln Asn Phe Thr Gln His Ala Leu Ser Asp Ile Ala Glu Leu Asn
145 150 155 160

Ser Lys Tyr Ser Ile Ile Leu Tyr Arg Trp Leu Ser Met Asn Tyr Asn
165 170 175

Gln Tyr Glu His Tyr Ser Ala Lys Gly Gly Arg Arg Glu Glu Gln Val
180 185 190

Glu Thr Tyr Arg Asn Pro Ser Ile Ser Ile Arg Glu Leu Arg Glu Met
195 200 205

Thr Asp Thr Met Lys Asp Tyr Pro Arg Phe Gln Ser Leu Glu Ser Tyr
210 215 220

Ile Ile Lys Asn Ser Leu Lys Glu Ile Asn Glu His Thr Ser Phe Lys
225 230 235 240

Val Thr Tyr Glu Lys Val Lys Lys Gly Arg Ser Ile Asn Ser Ile Val
245 250 255

Phe His Ile Thr Lys Lys Arg Arg Ala Asp Asp Asn Ser Tyr Lys Leu
260 265 270

Glu Asp Lys Val Tyr Gln Lys Ala Lys Val Gln Lys Glu Gln Lys Glu
275 280 285

Asn Leu Leu Tyr Ala Glu Ala Met Gln Ser Lys Tyr Thr Lys Leu Leu
290 295 300

Leu Glu His Phe Leu Leu Ser Pro Tyr Glu Met Thr Asn Pro Ala Thr
305 310 315 320

Met Ala Gly Leu Gln Arg Asn Val Tyr Pro Lys Tyr Asp Glu Leu Lys
325 330 335

Asp Leu Met Gly Ile Asp Gly Val Lys Lys His Leu Ser Tyr Ile Tyr
340 345 350

Asp Lys Gln Glu Pro Tyr Ser Lys Gly Asn Ile Ala Lys Tyr Leu Lys
355 360 365

Lys Ala Ile Glu Gln Tyr Leu Pro Thr Val Lys Arg Arg Gly Leu
370 375 380

<210> SEQ ID NO 226
<211> LENGTH: 206
<212> TYPE: PRT
<213> ORGANISM: Lactococcus lactis

<400> SEQUENCE: 226

```
Met Ser Asp Asn Leu Lys Thr Ile Lys Glu Leu Ala Asp Glu Leu Gly
1               5                   10                  15

Val Ser Lys Thr Ala Ile Asn Lys Lys Val Thr Asp Arg Glu Arg Lys
            20                  25                  30

Leu Trp Phe Ser Lys Ile Gly Asn Lys Phe Val Ile Asn Glu Asp Gly
        35                  40                  45

Gln Lys Ser Ile Lys Arg Met Phe Glu Gly Leu Thr Glu Asn Gln Glu
    50                  55                  60

Ser Gln Thr Glu Asn Leu Glu Gln Lys Pro Asn Ser Gln Thr Glu Asn
65                  70                  75                  80

Phe Arg Asn Asn Asn Glu Ser Asn Ala Asp Ile Lys Tyr Ile Leu Asp
                85                  90                  95

Ile Ile Glu Tyr Gln Lys Glu Gln Ile Lys Asp Leu Gln Asn Thr Lys
            100                 105                 110

Asp Glu Gln Phe Lys Gln Leu Ser Asn Met Gln Asn Leu Leu Asp Gln
        115                 120                 125

Gln Gln Arg Leu Ala Leu Gln Asp Lys Lys Leu Leu Glu Glu Tyr Lys
    130                 135                 140

Ser Glu Asn Asp Arg Leu Lys Val Leu Lys Met Pro Ser Gln Glu Thr
145                 150                 155                 160

Lys Glu Glu Gln Ala Asn Ile Gln Pro Gln Glu Glu Leu Glu Thr Leu
                165                 170                 175

Lys Glu Gln Thr Arg Ala Leu Asn Asp Lys Ile Lys Gly Gln Glu Glu
            180                 185                 190

Leu Asn Asn Lys Ser Ser Lys Lys Trp Tyr Gln Phe Trp Lys
        195                 200                 205
```

<210> SEQ ID NO 227
<211> LENGTH: 103
<212> TYPE: PRT
<213> ORGANISM: Lactococcus lactis

<400> SEQUENCE: 227

```
Met Phe Ser Tyr Ile Tyr Ile Ile Leu Ser Tyr Asn Thr Ile Lys Val
1               5                   10                  15

Lys Glu Val Leu Lys Phe Glu Tyr Arg Ile Cys Thr Ser Phe Asn Trp
            20                  25                  30

Thr Ser Lys Phe Ala Glu Glu Met Lys Thr Cys Phe Phe Asn Ser Gly
        35                  40                  45

Phe Lys Phe Lys Asn Phe Lys Gly Leu Asp Asn Arg Asn Ala Lys Glu
    50                  55                  60

Lys Ser Glu Leu Ile Ser Glu Ala Glu Val Val Ile Leu Ala Gly Gly
65                  70                  75                  80

His Val Pro Thr Gln Asn Ile Phe Phe Gln Gln Ile Asn Leu Lys Asn
                85                  90                  95

Met Ser Pro Val Arg Ile Phe
            100
```

<210> SEQ ID NO 228

<211> LENGTH: 471
<212> TYPE: PRT
<213> ORGANISM: Lactococcus lactis

<400> SEQUENCE: 228

```
Met Gln Ile Ala Lys Asn Tyr Leu Tyr Asn Ala Ile Tyr Gln Val Phe
1               5                   10                  15

Ile Ile Ile Val Pro Leu Leu Thr Ile Pro Tyr Leu Ser Arg Ile Leu
            20                  25                  30

Gly Pro Ser Gly Ile Gly Ile Asn Ser Tyr Thr Asn Ser Ile Val Gln
        35                  40                  45

Tyr Phe Val Leu Phe Gly Ser Ile Gly Val Gly Leu Tyr Gly Asn Arg
    50                  55                  60

Gln Ile Ala Phe Val Arg Asp Asn Gln Val Lys Met Ser Lys Val Phe
65                  70                  75                  80

Tyr Glu Ile Phe Ile Leu Arg Leu Phe Thr Ile Cys Leu Ala Tyr Phe
                85                  90                  95

Leu Phe Val Ala Phe Leu Ile Ile Asn Gly Gln Tyr His Ala Tyr Tyr
            100                 105                 110

Leu Ser Gln Ser Ile Ala Ile Val Ala Ala Ala Phe Asp Ile Ser Trp
        115                 120                 125

Phe Phe Met Gly Ile Glu Asn Phe Lys Val Thr Val Leu Arg Asn Phe
    130                 135                 140

Ile Val Lys Leu Leu Ala Leu Phe Ser Ile Phe Leu Phe Val Lys Ser
145                 150                 155                 160

Tyr Asn Asp Leu Asn Ile Tyr Ile Leu Ile Thr Val Leu Ser Thr Leu
                165                 170                 175

Ile Gly Asn Leu Thr Phe Phe Pro Ser Leu His Arg Tyr Leu Val Lys
            180                 185                 190

Val Asn Tyr Arg Glu Leu Arg Pro Ile Lys His Leu Lys Gln Ser Leu
        195                 200                 205

Val Met Phe Ile Pro Gln Ile Ala Val Gln Ile Tyr Trp Val Leu Asn
    210                 215                 220

Lys Thr Met Leu Gly Ser Leu Asp Ser Val Thr Ser Ser Gly Phe Phe
225                 230                 235                 240

Asp Gln Ser Asp Lys Ile Val Lys Leu Val Leu Ala Ile Ala Thr Ala
                245                 250                 255

Thr Gly Thr Val Met Leu Pro Arg Val Ala Asn Ala Phe Ala His Arg
            260                 265                 270

Glu Tyr Ser Lys Ile Lys Glu Tyr Met Tyr Ala Gly Phe Ser Phe Val
        275                 280                 285

Ser Ala Ile Ser Ile Pro Met Met Phe Gly Leu Ile Ala Ile Thr Pro
    290                 295                 300

Lys Phe Val Pro Leu Phe Phe Thr Ser Gln Phe Ser Asp Val Ile Pro
305                 310                 315                 320

Val Leu Met Ile Glu Ser Ile Ala Ile Ile Phe Ile Ala Trp Ser Asn
                325                 330                 335

Ala Ile Gly Asn Gln Tyr Leu Leu Pro Thr Asn Gln Asn Lys Ser Tyr
            340                 345                 350

Thr Val Ser Val Ile Ile Gly Ala Ile Val Asn Leu Met Leu Asn Ile
        355                 360                 365

Pro Leu Ile Ile Tyr Leu Gly Thr Val Gly Ala Ser Ile Ala Thr Val
    370                 375                 380

Ile Ser Glu Met Ser Val Thr Val Tyr Gln Leu Phe Ile Ile His Lys
```

```
385                 390                 395                 400

Gln Leu Asn Leu His Thr Leu Phe Ser Asp Leu Ser Lys Tyr Leu Ile
                405                 410                 415

Ala Gly Leu Val Met Phe Leu Ile Val Phe Lys Ile Ser Leu Leu Thr
            420                 425                 430

Pro Thr Ser Trp Ile Phe Ile Leu Leu Glu Ile Thr Val Gly Ile Ile
        435                 440                 445

Ile Tyr Val Val Leu Leu Ile Phe Leu Lys Ala Glu Ile Ile Asn Lys
    450                 455                 460

Leu Lys Phe Ile Met His Lys
465                 470


<210> SEQ ID NO 229
<211> LENGTH: 332
<212> TYPE: PRT
<213> ORGANISM: Lactococcus lactis

<400> SEQUENCE: 229

Met Asn Leu Phe Gly Asp Ser Asp Tyr Leu Glu Lys Leu Ser Ser Lys
1               5                   10                  15

Gly Asp Pro Leu Glu Arg Leu Glu Lys Val Val Asp Phe Glu Cys Phe
            20                  25                  30

Arg Pro Thr Leu Asn Arg Ile Phe Lys Tyr Asp Leu Lys Asn Lys Ser
        35                  40                  45

His Gly Gly Arg Pro Pro Tyr Asp Leu Val Leu Met Leu Lys Ile Leu
    50                  55                  60

Ile Leu Gln Arg Leu Tyr Asn Leu Ser Asp Asp Ala Met Glu Tyr Gln
65                  70                  75                  80

Met Ile Asp Arg Ile Ser Phe Arg Arg Phe Leu Lys Ile Asp Asp Lys
                85                  90                  95

Val Pro Asp Ala Lys Thr Ile Trp Asn Phe Arg Asn Gln Leu Ser Lys
            100                 105                 110

Ser Asn Arg Gly Asn Trp Leu Phe Ser Ala Phe Gln Glu Lys Leu Glu
        115                 120                 125

Ser Gln Gly Met Ile Ala His Lys Gly Gln Ile Val Asp Ala Thr Phe
    130                 135                 140

Ile Glu Ala Pro Lys Gln Arg Asn Pro Lys Asp Glu Asn Glu Leu Ile
145                 150                 155                 160

Lys Ala Asn Arg Val Pro Val Asn Trp Thr Lys Asn Lys Arg Ala Gln
                165                 170                 175

Lys Asp Thr Ala Ala Arg Trp Thr Ile Lys Gly Asn Glu Arg His Tyr
            180                 185                 190

Gly Tyr Lys Asn His Ile Ala Ile Asp Thr Lys Ser Lys Phe Val Lys
        195                 200                 205

Asn Tyr Gln Thr Thr Pro Ala Asn Val His Asp Ser Gln Val Ile Gly
    210                 215                 220

Val Leu Val Asp Pro Asp Glu Ile Thr Leu Ala Asp Ser Ala Tyr Gln
225                 230                 235                 240

Asn Lys Ala Thr Pro Lys Gly Ala Glu Leu Phe Thr Phe Leu Lys Asn
                245                 250                 255

Thr Arg Ser Lys Ser Leu Lys Ala Asp Asp Lys Met Phe Asn Lys Ile
            260                 265                 270

Ile Ser Lys Ile Arg Val Arg Ile Glu His Val Phe Gly Phe Val Glu
        275                 280                 285
```

```
Asn Ser Met His Gly Ser Ser Leu Arg Ser Ile Gly Phe Asp Arg Ala
    290                 295                 300

Val Leu Asn Thr Asp Leu Thr Asn Leu Thr Tyr Asn Leu Leu Arg His
305                 310                 315                 320

Glu Gln Val Lys Arg Leu Asn Leu Lys Thr Trp Arg
                325                 330


<210> SEQ ID NO 230
<211> LENGTH: 189
<212> TYPE: PRT
<213> ORGANISM: Lactococcus lactis

<400> SEQUENCE: 230

Met Arg Lys Tyr Met Ile Tyr Leu Ser Ser Leu Leu Val Thr Phe Ile
1               5                   10                  15

Leu Ser Tyr Ala Thr Ile Thr Trp Leu Ile Met Pro Val Leu Thr Arg
            20                  25                  30

Tyr Gln Ser Leu Ala Arg Leu Ile Asn His Phe Asp Tyr Thr Ala Leu
        35                  40                  45

Thr Leu Ile Leu Leu Leu Thr Leu Ile Ile Trp Leu Phe Gly Ile Gln
    50                  55                  60

Tyr His Leu Lys His Phe Ser Val Ile Tyr Leu Tyr Leu Ala Phe Ser
65                  70                  75                  80

Val Tyr Leu Leu Leu Leu Phe Met Val Ile Phe Asn Lys Thr Thr Asp
                85                  90                  95

Phe Gln Ala Ile Ser Leu Asn Pro Phe Asp Phe Ile Lys Ala Asp Thr
            100                 105                 110

Arg Thr Ile Gln Glu Ala Val Leu Asn Ile Ile Tyr Phe Ile Pro Leu
        115                 120                 125

Gly Gly Leu Tyr Cys Ile Asn Thr Asp Phe Lys Gln Phe Val Ile Ile
    130                 135                 140

Ser Leu Val Thr Leu Leu Gly Ile Glu Thr Ile Gln Phe Ile Phe Tyr
145                 150                 155                 160

Leu Gly Thr Phe Ala Ile Ser Asp Ile Ile Leu Asn Phe Leu Gly Cys
                165                 170                 175

Leu Ile Gly Tyr Tyr Cys Cys Trp Glu Ile Lys Lys Ser
            180                 185


<210> SEQ ID NO 231
<211> LENGTH: 152
<212> TYPE: PRT
<213> ORGANISM: Lactococcus lactis

<400> SEQUENCE: 231

Met Asp Glu Thr Tyr Ile Lys Ile Lys Gly Arg Gly His Tyr Leu Tyr
1               5                   10                  15

Arg Thr Ile Asp Ala Asp Gly Leu Thr Leu Asp Ile Trp Leu Arg Lys
            20                  25                  30

Lys Arg Asp Thr Gln Ala Ala Tyr Ala Phe Leu Lys Arg Leu His Lys
        35                  40                  45

Gln Phe Gly Glu Pro Lys Ala Ile Val Thr Asp Lys Ala Pro Ser Leu
    50                  55                  60

Gly Ser Ala Phe Arg Lys Leu Gln Ser Val Gly Leu Tyr Thr Lys Thr
65                  70                  75                  80

Glu His Arg Thr Val Lys Tyr Leu Asn Asn Leu Ile Glu Gln Asp His
                85                  90                  95
```

```
Arg Pro Ile Lys Arg Arg Asn Lys Phe Tyr Gln Ser Leu Arg Thr Ala
            100                 105                 110

Ser Ser Thr Ile Lys Gly Met Glu Thr Leu Arg Gly Ile Tyr Lys Asn
        115                 120                 125

Asn Arg Arg Asn Gly Thr Leu Phe Gly Phe Ser Val Ser Thr Glu Ile
    130                 135                 140

Lys Val Leu Met Gly Ile Thr Ala
145                 150


<210> SEQ ID NO 232
<211> LENGTH: 331
<212> TYPE: PRT
<213> ORGANISM: Lactococcus lactis

<400> SEQUENCE: 232

Met Lys Lys Asn Val Leu Leu Ser Ile Ile Val Pro Ile Tyr Asn Val
1               5                   10                  15

Glu Lys Tyr Ile Gly Ser Leu Val Asn Ser Leu Val Lys Gln Thr Asn
            20                  25                  30

Lys Asn Phe Glu Val Ile Phe Ile Asp Asp Gly Ser Thr Asp Glu Ser
        35                  40                  45

Met Gln Ile Leu Lys Glu Ile Ile Ala Gly Ser Glu Gln Glu Phe Ser
    50                  55                  60

Leu Lys Leu Leu Gln Gln Val Asn Gln Gly Leu Ser Ser Ala Arg Asn
65                  70                  75                  80

Ile Gly Ile Leu Asn Ala Thr Gly Glu Tyr Ile Phe Phe Leu Asp Ser
                85                  90                  95

Asp Asp Glu Ile Glu Ile Asn Phe Val Glu Thr Ile Leu Thr Ser Cys
            100                 105                 110

Tyr Lys Tyr Ser Gln Pro Asp Thr Leu Ile Phe Asp Tyr Ser Ser Ile
        115                 120                 125

Asp Glu Phe Gly Asn Ala Leu Asp Ser Asn Tyr Gly His Gly Ser Ile
    130                 135                 140

Tyr Arg Gln Lys Asp Leu Cys Thr Ser Glu Gln Ile Leu Thr Ala Leu
145                 150                 155                 160

Tyr Lys Asp Glu Ile Pro Ile Thr Ala Trp Ser Phe Val Thr Lys Arg
                165                 170                 175

Ser Val Ile Glu Lys His Asn Leu Leu Phe Ser Val Gly Lys Lys Phe
            180                 185                 190

Glu Asp Asn Asn Phe Thr Pro Lys Val Phe Tyr Phe Ser Lys Asn Ile
        195                 200                 205

Gly Val Ile Ser Leu Arg Leu Tyr Arg Tyr Arg Lys Arg Ser Gly Ser
    210                 215                 220

Ile Met Ser Asn His Pro Glu Lys Phe Phe Ser Asp Asp Ala Ile Phe
225                 230                 235                 240

Val Thr Tyr Asp Leu Leu Asp Phe Tyr Asp Gln Tyr Lys Ile Arg Glu
                245                 250                 255

Leu Gly Ala Val Val Gly Lys Leu Val Met Thr Arg Leu Ala Phe Phe
            260                 265                 270

Pro Asp Ser Lys Lys Leu Tyr Asn Glu Leu Asn Pro Ile Ile Lys Lys
        275                 280                 285

Val Phe Lys Asp Tyr Ile Ser Ile Glu Lys Arg His Thr Lys Arg Ile
    290                 295                 300

Lys Met Tyr Val Lys Met Tyr Val Phe Ser Ser Tyr Val Gly Tyr Lys
305                 310                 315                 320
```

Leu Tyr Arg Leu Val Lys Gly Lys His Trp Lys
325 330

<210> SEQ ID NO 233
<211> LENGTH: 226
<212> TYPE: PRT
<213> ORGANISM: Lactococcus lactis

<400> SEQUENCE: 233

Met Asn His Phe Lys Gly Lys Gln Phe Lys Lys Asp Val Ile Ile Val
1 5 10 15

Ala Val Gly Tyr Tyr Leu Arg Tyr Asn Leu Ser Tyr Arg Glu Val Gln
20 25 30

Glu Leu Leu Tyr Asp Arg Gly Ile Asn Val Cys His Thr Thr Ile Tyr
35 40 45

Arg Trp Val Gln Glu Tyr Ser Lys Val Leu Tyr Asp Leu Cys Lys Lys
50 55 60

Lys Asn Arg Gln Ser Phe Tyr Ser Trp Lys Met Asp Glu Thr Tyr Ile
65 70 75 80

Lys Ile Lys Gly Arg Trp His Tyr Leu Tyr Arg Ala Ile Asp Ala Asp
85 90 95

Gly Leu Thr Leu Asp Ile Trp Leu Gln Lys Lys Arg Asp Thr Gln Ala
100 105 110

Ala Tyr Ala Phe Leu Lys Arg Leu His Lys Gln Phe Gly Glu Pro Lys
115 120 125

Ala Ile Val Thr Asp Lys Ala Pro Ser Leu Gly Ser Ala Phe Arg Lys
130 135 140

Leu Gln Ser Val Gly Leu Tyr Thr Lys Thr Glu His Arg Thr Val Lys
145 150 155 160

Tyr Leu Asn Asn Leu Ile Glu Gln Asp His Trp Pro Ile Lys Arg Arg
165 170 175

Asn Lys Phe Tyr Gln Ser Leu Arg Thr Ala Ser Ser Thr Ile Lys Gly
180 185 190

Met Glu Thr Leu Arg Gly Ile Tyr Lys Asn Asn Arg Arg Asn Gly Thr
195 200 205

Leu Phe Gly Phe Ser Val Ser Thr Glu Ile Lys Val Leu Met Gly Ile
210 215 220

Thr Ala
225

<210> SEQ ID NO 234
<211> LENGTH: 84
<212> TYPE: PRT
<213> ORGANISM: Lactococcus lactis

<400> SEQUENCE: 234

Met Gln Gln Asn Leu Leu Lys Tyr Tyr Gly Met Thr His Ser Phe Ser
1 5 10 15

Arg Arg Gly Tyr Pro Tyr His Asn Ala Ser Leu Glu Ser Trp His Gly
20 25 30

His Leu Lys Arg Glu Trp Val Tyr Gln Phe Lys Tyr Lys Asn Phe Glu
35 40 45

Glu Ala Tyr Gln Ser Ile Phe Trp Tyr Ile Glu Ala Phe Tyr Asn Ser
50 55 60

-continued

```
Lys Arg Ile His Gln Ser Leu Gly Tyr Leu Thr Pro Asn Gln Phe Glu
65                  70                  75                  80

Lys Val Ser Ala
```